(12) United States Patent
Nakajima et al.

(10) Patent No.: US 7,880,013 B2
(45) Date of Patent: Feb. 1, 2011

(54) THIAZOLE DERIVATIVES

(75) Inventors: Takao Nakajima, Fujisawa (JP);
Masamori Sugawara, Mishima (JP);
Yuji Nomoto, Sunto-gun (JP); Noriaki Uesaka, Sunto-gun (JP); Yoshisuke Nakasato, Susono (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 12/766,986

(22) Filed: Apr. 26, 2010

(65) Prior Publication Data

US 2010/0256361 A1 Oct. 7, 2010

Related U.S. Application Data

(62) Division of application No. 10/584,633, filed as application No. PCT/JP2004/019778 on Dec. 24, 2004, now Pat. No. 7,718,808.

(30) Foreign Application Priority Data

Dec. 26, 2003 (JP) ............................. 2003-432777

(51) Int. Cl.
A61K 31/427 (2006.01)
C07D 417/14 (2006.01)

(52) U.S. Cl. .................. 548/195; 546/270.7; 544/333; 514/256; 514/342; 514/371

(58) Field of Classification Search ................ 548/195; 546/270.7
See application file for complete search history.

(56) References Cited

U.S. PATENT DOCUMENTS

| | | | |
|---|---|---|---|
| 4,766,137 A | 8/1988 | Carenzi et al. | |
| 4,766,138 A | 8/1988 | Carenzi et al. | |
| 5,128,340 A | 7/1992 | Rae et al. | |
| 5,189,049 A | 2/1993 | Frehel et al. | |
| 5,314,889 A | 5/1994 | Boigegrain et al. | |
| 5,464,847 A | 11/1995 | Courtemanche et al. | |
| 5,856,347 A | 1/1999 | Hashiguchi et al. | |
| 6,414,011 B1 | 7/2002 | Hogenkamp et al. | |
| 6,436,966 B1 | 8/2002 | Ohkawa et al. | |
| 6,489,476 B1 | 12/2002 | Dang et al. | |
| 6,596,744 B2 | 7/2003 | Wagle et al. | |
| 6,605,629 B1 | 8/2003 | Momose et al. | |
| 6,649,641 B2 | 11/2003 | Behrens et al. | |
| 6,756,360 B1 | 6/2004 | Erion et al. | |
| 6,962,933 B1 | 11/2005 | Ohkawa et al. | |
| 6,965,033 B2 | 11/2005 | Jiang et al. | |
| 7,101,899 B1 | 9/2006 | Ohkawa et al. | |
| 7,495,018 B2 | 2/2009 | Ohkawa et al. | |
| 2002/0119970 A1 | 8/2002 | Wagle et al. | |
| 2003/0018022 A1 | 1/2003 | Collins et al. | |
| 2003/0073728 A1 | 4/2003 | van Poelje et al. | |
| 2003/0105143 A1 | 6/2003 | Ammendola et al. | |
| 2003/0130296 A1 | 7/2003 | Bauer et al. | |
| 2003/0158199 A1 | 8/2003 | Stieber et al. | |
| 2003/0195231 A1 | 10/2003 | Takemoto et al. | |
| 2004/0038990 A1 | 2/2004 | Guba et al. | |
| 2004/0039035 A1 | 2/2004 | Collins et al. | |
| 2004/0053973 A1 | 3/2004 | Ohkawa et al. | |
| 2004/0053982 A1 | 3/2004 | Press et al. | |
| 2004/0063765 A1 | 4/2004 | Ammendola et al. | |
| 2004/0082626 A1 | 4/2004 | Takemoto et al. | |
| 2004/0097555 A1 | 5/2004 | Ohkawa et al. | |
| 2004/0122016 A1 | 6/2004 | Cao et al. | |
| 2004/0142988 A1 | 7/2004 | Sugiyama et al. | |
| 2004/0192743 A1 | 9/2004 | Mjalli et al. | |
| 2004/0235914 A1 | 11/2004 | Ammendola et al. | |
| 2005/0004134 A1 | 1/2005 | Tsutsumi et al. | |
| 2005/0080113 A1 | 4/2005 | Ohkawa et al. | |

(Continued)

FOREIGN PATENT DOCUMENTS

EP 1 354 603 10/2003

(Continued)

OTHER PUBLICATIONS

Saldabol, et al., "Thiocyanation, Halogenation, Dehalogenation, Transhalogenation and Nitration of 2-Substituted 4-(2-furyl) Thiazoles", Chemistry of Heterocyclic Compounds, vol. 38, No. 7 (2002) 873-81.

(Continued)

Primary Examiner—Laura L. Stockton
(74) Attorney, Agent, or Firm—Fitzpatrick, Cella, Harper & Scinto

(57) ABSTRACT

(Wherein n is an integer of from 0 to 3; $R^1$ is substituted or unsubstituted cycloalkyl, substituted or unsubstituted aryl, a substituted or unsubstituted alicyclic heterocyclic group, or a substituted or unsubstituted aromatic heterocyclic group; $R^2$ is halogen, substituted or unsubstituted lower alkyl, substituted or unsubstituted aryl, a substituted or unsubstituted alicyclic heterocyclic group, a substituted or unsubstituted aromatic heterocyclic group, —$COR^8$, or the like; $R^3$ and $R^4$ may be the same or different, and each represents a hydrogen atom, substituted or unsubstituted lower alkyl, substituted or unsubstituted aralkyl, —$COR^{12}$, or the like)

For example, provided are adenosine $A_{2A}$ receptor antagonists comprising, as the active ingredient, a thiazole derivative represented by a general formula (I), or a pharmaceutically acceptable salt thereof, and the like.

(I)

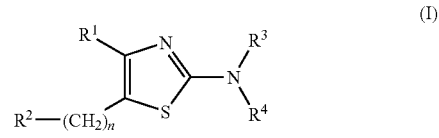

15 Claims, No Drawings

U.S. PATENT DOCUMENTS

| | | |
|---|---|---|
| 2005/0090534 A1 | 4/2005 | Sakai et al. |
| 2005/0153977 A1 | 7/2005 | Sugasawa et al. |
| 2005/0176789 A1 | 8/2005 | Hadida Ruah et al. |
| 2005/0182104 A1 | 8/2005 | Baltzer et al. |
| 2005/0234116 A1 | 10/2005 | Sugiyama et al. |
| 2006/0015494 A1 | 1/2006 | Keating et al. |
| 2006/0035944 A1 | 2/2006 | Muto et al. |
| 2006/0247233 A1 | 11/2006 | Dodic et al. |
| 2008/0051436 A1 | 2/2008 | Baltzer et al. |
| 2008/0234233 A1 | 9/2008 | Muto et al. |

FOREIGN PATENT DOCUMENTS

| | | |
|---|---|---|
| JP | 05-345772 | 12/1993 |
| JP | 10-087490 | 4/1998 |
| JP | 11-209284 | 8/1999 |
| JP | 2000-302680 | 10/2000 |
| JP | 2002-053566 | 2/2002 |
| JP | 2002-302488 | 10/2002 |
| JP | 2003-335680 | 11/2003 |
| WO | 93/21168 | 10/1993 |
| WO | 97/03058 | 1/1997 |
| WO | 98/57937 | 12/1998 |
| WO | 99/64418 | 12/1999 |
| WO | 02/079204 | 10/2002 |
| WO | 02/094264 | 11/2002 |
| WO | 02/094798 | 11/2002 |
| WO | 03/015777 | 2/2003 |
| WO | 03/062233 | 7/2003 |
| WO | 03/093250 | 11/2003 |
| WO | 2006/032273 | 3/2006 |

OTHER PUBLICATIONS

Khimiko-Farmatsevticheskii Zhurnal, vol. 8 (1974) 25-29.

Closier, et al., "Nitrofuryl heterocyclics", J. Med. Chem., vol. 13, No. 4 (1970) 638-40.

Ya, et al, "The bromination of 2-amino-and 2-acetylamino-4-(2-furyl)- thiazoles", Khimiya Geterotsiklicheskikh Soedinenii, vol. 5, No. 3 (1969) 498-500.

Kreutzberger, et al., "Synthese and antiparkinsonwirkung von N-phenyl-N'-(2-Thiazolyl Harnstoffen", Phosphorus and Sulfur, vol. 40, No. 3-4 (1988) 123-28.

Joshi, et al., Chem. Abs., vol. 57 (1962) 10831.

Sherman et al., "4-(5-Nitro-2-furyl)thiazoles", J. Org. Chem., vol. 27, No. 4 (1962) 1351-55.

THIAZOLE DERIVATIVES

This application is a division of application Ser. No.10/584,633 filed Jun. 26, 2006, (now U.S. Pat. No. 7,718,808 issued May 18, 2010), which in turn is an application filed under 35 U.S.C. §371 based upon application No. PCT/JP04/019778 filed Dec. 24, 2004.

TECHNICAL FIELD

The present invention relates to, for example, adenosine $A_{2A}$ receptor antagonists comprising a thiazole derivative or a pharmaceutically acceptable salt thereof as the active ingredient, etc.

BACKGROUND ART

It is known that adenosine ranges broadly in a living body and exhibits various physiological actions on the central nervous system, the cardiac muscle, the kidney, the lung, the smooth muscle and the like via its receptor. Four subtypes of adenosine receptors, $A_1$, $A_{2A}$, $A_{2B}$ and $A_3$ have heretofore been known. The respective subtype-selective receptor antagonists and agonists are expected to exhibit their pharmaceutical effects based on the physiological meanings of the subtype and on the biological distribution thereof. Among them, the $A_{2A}$ receptors are localized in the brain, especially in the corpus striatum thereof and as one of its functions, the inhibition of neurotransmitter release is reported (*European Journal of Pharmacology*, Vol. 168, p. 285, 1989). Accordingly, antagonists to the adenosine $A_{2A}$ receptor may be expected as agents for preventing and/or treating diseases associated with adenosine $A_{2A}$ receptor, such as Parkinson's disease, Alzheimer's disease, progressive supranuclear palsy, AIDS encephalopathy, Transmissible spongiform encephalopathy, multiple sclerosis, amyotrophic lateral sclerosis, Huntington's chorea, multiple system atrophy, cerebral ischemia, attention deficit hyperactivity disorder, sleep disorder, ischemic cardiopathy, intermittent claudication, diabetes, anxiety disorders (e.g., panic attack and panic disorder, phobia, obsessive-compulsive disorder, posttraumatic stress disorder, acute stress disorder, generalized anxiety disorder, anxiety physical symptoms or substance-caused), mood disorders (e.g., depression, dysthymic disorder, mood-circulatory disorder), restless legs syndrome (RLS), drug dependence (e.g., alcohol dependence), eating disorder, epilepsy, migraine and chronic musculoskeletal system pain.

On the other hand, a large number of compounds having thiazole skeleton are known (for example, see U.S. Pat. Nos. 5,314,889 and 5,189,049; Japanese Patent Application No. 335680/2003, Japanese Published Unexamined Patent Application No. 53566/2002, Japanese Patent Application Nos. 209284/1999 and 087490/1998; WO93/21168, WO96/16650, WO97/03058, WO01/52847, WO01/53267, WO01/74811, WO02/053156, WO02/053161, WO02/094798, WO03/000257, WO03/062215, WO03/062233, WO03/072554, WO03/075923, WO2004/002481, WO2004/014884, WO2004/041813 and the like); and as thiazole derivatives having adenosine receptor antagonism, known are thiazole derivatives having adenosine $A_3$ receptor antagonism (see WO99/21555 and Japanese Published Unexamined Patent Application No. 114779/2001), thiazole derivatives having adenosine $A_{2B}$ receptor antagonism and adenosine $A_3$ receptor antagonism (see WO99/64418 and US Patent Application Publication No. 2004-0053982), and thiazole derivatives having adenosine $A_1$ receptor antagonism and adenosine $A_{2A}$ receptor antagonism (see WO03/039451).

Further, thiazole derivatives having furyl group at the 4 position thereof are known (see U.S. Pat. No. 6,489,476; WO02/03978, WO01/47935, WO00/38666, WO00/14095; *Chemistry of Heterocyclic Compounds*, 2002, Vol. 38, p. 873; *Khimiko-Farmatsevticheskii Zhurnal*, 1974, Vol. 8, p. 25; *Journal of Medicinal Chemistry*, 1970, Vol. 13, p. 638; *Khimiya Geterotsiklicheskikh Soedinenii*, 1969, Vol. 3, p. 498; *Journal of Organic Chemistry*, 1962, Vol. 27, p. 1351).

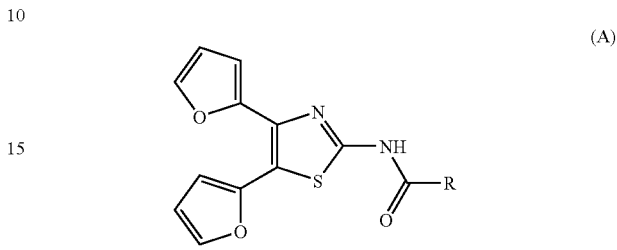

(A)

(Wherein R represents phenylmethyl, 2-furyl, 4-fluorophenyl, 2-fluorophenyl, 2,4-dichlorophenyl, 4-nitrophenyl, 2-nitrophenyl, 4-bromophenyl, 3-bromophenyl, 2-bromophenyl, 2-chlorophenyl, 3-bromo-2-methoxyphenyl, 4-tert-butylphenyl, 3-methylphenyl, 4-methylphenyl, 4-methoxyphenyl, 2-methoxyphenyl or phenyl.)

Also, thiazole derivatives represented the above-described general formula (A) are registered as a chemical library in CAS REGISTRY Database (Registry Nos. 341929-13-3, 341929-11-1, 341929-09-7, 341929-07-5, 341929-05-3, 341929-04-2, 341929-02-0, 341929-00-8, 341928-98-1, 341928-96-9, 341928-94-7, 341928-92-5, 341928-90-3, 341928-88-9, 341928-86-7, 341928-84-5, 341928-82-3 and 341928-80-1).

DISCLOSURE OF THE INVENTION

An object of the present invention is to provide, for example, adenosine $A_{2A}$ receptor antagonists comprising a thiazole derivative or a pharmaceutically acceptable salt thereof as the active ingredient, and thiazole derivatives or pharmaceutically acceptable salts thereof which have an adenosine $A_{2A}$ receptor antagonism and are useful for preventing and/or treating diseases associated with adenosine $A_{2A}$ receptor.

The invention relates to the following (1) to (118):

(1) An adenosine $A_{2A}$ receptor antagonist comprising, as the active ingredient, a thiazole derivative represented by a general formula (I):

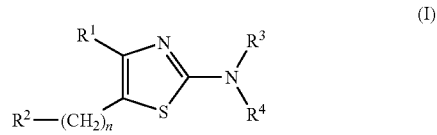

(I)

{wherein;
n represents an integer of from 0 to 3;
$R^1$ represents substituted or unsubstituted cycloalkyl,
substituted or unsubstituted aryl,
a substituted or unsubstituted alicyclic heterocyclic group, or
a substituted or unsubstituted aromatic heterocyclic group;
$R^2$ represents a halogen, substituted or unsubstituted lower alkyl,
substituted or unsubstituted lower alkenyl,
substituted or unsubstituted lower alkynyl,
substituted or unsubstituted cycloalkyl,
substituted or unsubstituted aryl,
substituted or unsubstituted aralkyl,
a substituted or unsubstituted alicyclic heterocyclic group,
a substituted or unsubstituted aromatic heterocyclic group,
substituted or unsubstituted alicyclic heterocyclic-alkyl,
substituted or unsubstituted aromatic heterocyclic-alkyl,
—$NR^5R^6$ (wherein
  $R^5$ and $R^6$ may be the same or different, and each represents
    a hydrogen atom,
    substituted or unsubstituted lower alkyl,
    substituted or unsubstituted lower alkenyl,
    substituted or unsubstituted lower alkynyl,
    substituted or unsubstituted lower alkanoyl,
    substituted or unsubstituted cycloalkyl,
    substituted or unsubstituted aryl,
    substituted or unsubstituted aralkyl,
    a substituted or unsubstituted alicyclic heterocyclic group,
    a substituted or unsubstituted aromatic heterocyclic group,
    substituted or unsubstituted alicyclic heterocyclic-alkyl, or substituted or unsubstituted aromatic heterocyclic-alkyl),
—$OR^7$ (wherein
  $R^7$ represents a hydrogen atom,
    substituted or unsubstituted lower alkyl,
    substituted or unsubstituted lower alkanoyl,
    substituted or unsubstituted cycloalkyl,
    substituted or unsubstituted aryl,
    substituted or unsubstituted aralkyl,
    a substituted or unsubstituted alicyclic heterocyclic group,
    a substituted or unsubstituted aromatic heterocyclic group,
    substituted or unsubstituted alicyclic heterocyclic-alkyl, or
    substituted or unsubstituted aromatic heterocyclic-alkyl), or
—$COR^8$ [wherein
  $R^8$ represents a hydrogen atom,
    substituted or unsubstituted lower alkyl,
    substituted or unsubstituted lower alkenyl,
    substituted or unsubstituted lower alkynyl,
    substituted or unsubstituted cycloalkyl,
    substituted or unsubstituted aryl,
    substituted or unsubstituted aralkyl,
    a substituted or unsubstituted alicyclic heterocyclic group,
    a substituted or unsubstituted aromatic heterocyclic group,
    substituted or unsubstituted alicyclic heterocyclic-alkyl,
    substituted or unsubstituted aromatic heterocyclic-alkyl,
    —$NR^9R^{10}$ (wherein
      $R^9$ and $R^{10}$ may be the same or different, and each represent
        a hydrogen atom,
        substituted or unsubstituted lower alkyl,
        substituted or unsubstituted lower alkenyl,
        substituted or unsubstituted lower alkynyl,
        substituted or unsubstituted lower alkanoyl,
        substituted or unsubstituted lower alkoxy,
        substituted or unsubstituted cycloalkyl,
        substituted or unsubstituted aryl,
        substituted or unsubstituted aralkyl,
        a substituted or unsubstituted alicyclic heterocyclic group,
        a substituted or unsubstituted aromatic heterocyclic group,
        substituted or unsubstituted alicyclic heterocyclic-alkyl, or
        substituted or unsubstituted aromatic heterocyclic-alkyl), or
    —$OR^{11}$ (wherein
      $R^{11}$ represents a hydrogen atom,
        substituted or unsubstituted lower alkyl,
        substituted or unsubstituted lower alkenyl,
        substituted or unsubstituted lower alkynyl,
        substituted or unsubstituted cycloalkyl,
        substituted or unsubstituted aryl,
        substituted or unsubstituted aralkyl,
        a substituted or unsubstituted alicyclic heterocyclic group,
        a substituted or unsubstituted aromatic heterocyclic group,
        substituted or unsubstituted alicyclic heterocyclic-alkyl, or
        substituted or unsubstituted aromatic heterocyclic-alkyl)]; and
$R^3$ and $R^4$ may be the same or different, and each represents
  a hydrogen atom,
  substituted or unsubstituted lower alkyl,
  substituted or unsubstituted lower alkenyl,
  substituted or unsubstituted lower alkynyl,
  substituted or unsubstituted aralkyl,
  substituted or unsubstituted alicyclic heterocyclic-alkyl,
  substituted or unsubstituted aromatic heterocyclic-alkyl,
  —$COR^{12}$ [wherein
    $R^{12}$ represents a hydrogen atom,
      substituted or unsubstituted lower alkyl,
      substituted or unsubstituted lower alkenyl,
      substituted or unsubstituted lower alkynyl,
      substituted or unsubstituted cycloalkyl,
      substituted or unsubstituted aryl,
      substituted or unsubstituted aralkyl,
      a substituted or unsubstituted alicyclic heterocyclic group,
      a substituted or unsubstituted aromatic heterocyclic group,
      substituted or unsubstituted alicyclic heterocyclic-alkyl,
      substituted or unsubstituted aromatic heterocyclic-alkyl,
      —$NR^{13}R^{14}$ (wherein
        $R^{13}$ and $R^{14}$ may be the same or different, and each represents
          a hydrogen atom,
          substituted or unsubstituted lower alkyl,
          substituted or unsubstituted lower alkenyl,
          substituted or unsubstituted lower alkynyl,
          substituted or unsubstituted lower alkanoyl,
          substituted or unsubstituted lower alkoxy,
          substituted or unsubstituted cycloalkyl,
          substituted or unsubstituted aryl,
          substituted or unsubstituted aralkyl,
          a substituted or unsubstituted alicyclic heterocyclic group, a substituted or unsubstituted aromatic heterocyclic group,
substituted or unsubstituted alicyclic heterocyclic-alkyl, or
substituted or unsubstituted aromatic heterocyclic-alkyl), or
—$OR^{15}$ (wherein
$R^{15}$ represents a hydrogen atom,
substituted or unsubstituted lower alkyl,
substituted or unsubstituted lower alkenyl,
substituted or unsubstituted lower alkynyl,
substituted or unsubstituted cycloalkyl,
substituted or unsubstituted aryl,
substituted or unsubstituted aralkyl,
a substituted or unsubstituted alicyclic heterocyclic group,
a substituted or unsubstituted aromatic heterocyclic group,
substituted or unsubstituted alicyclic heterocyclic-alkyl, or
substituted or unsubstituted aromatic heterocyclic-alkyl)];
provided that,
when $R^1$ is substituted or unsubstituted phenyl and n is 0, then $R^2$ is not substituted or unsubstituted 6-oxo-1,6-dihydropyridazin-3-yl},
or a pharmaceutically acceptable salt thereof.

(2) The adenosine $A_{2A}$ receptor antagonist according to the above (1), wherein $R^1$ is substituted or unsubstituted aryl, or a substituted or unsubstituted aromatic heterocyclic group.

(3) The adenosine $A_{2A}$ receptor antagonist according to the above (1), wherein $R^1$ is a substituted or unsubstituted aromatic heterocyclic group.

(4) The adenosine $A_{2A}$ receptor antagonist according to the above (1), wherein $R^1$ is a substituted or unsubstituted monocyclic aromatic heterocyclic group.

(5) The adenosine $A_{2A}$ receptor antagonist according to the above (1), wherein $R^1$ is a substituted or unsubstituted 5-membered aromatic heterocyclic group.

(6) The adenosine $A_{2A}$ receptor antagonist according to the above (1), wherein $R^1$ is a substituted or unsubstituted 5-membered aromatic heterocyclic group containing at least one oxygen atom.

(7) The adenosine $A_{2A}$ receptor antagonist according to the above (1), wherein $R^1$ is substituted or unsubstituted furyl.

(8) The adenosine $A_{2A}$ receptor antagonist according to any one of the above (1) to (7), wherein n is 0.

(9) The adenosine $A_{2A}$ receptor antagonist according to any one of the above (1) to (8), wherein $R^2$ is substituted or unsubstituted lower alkyl, substituted or unsubstituted aryl, a substituted or unsubstituted alicyclic heterocyclic group, a substituted or unsubstituted aromatic heterocyclic group, substituted or unsubstituted alicyclic heterocyclic-alkyl, substituted or unsubstituted aromatic heterocyclic-alkyl, or —$COR^8$ (wherein $R^8$ has the same meaning as defined above).

(10) The adenosine $A_{2A}$ receptor antagonist according to any one of the above (1) to (8), wherein $R^2$ is substituted or unsubstituted aryl.

(11) The adenosine $A_{2A}$ receptor antagonist according to any one of the above (1) to (8), wherein $R^2$ is a substituted or unsubstituted alicyclic heterocyclic group, or a substituted or unsubstituted aromatic heterocyclic group.

(12) The adenosine $A_{2A}$ receptor antagonist according to any one of the above (1) to (8), wherein $R^2$ is a substituted or unsubstituted alicyclic heterocyclic group.

(13) The adenosine $A_{2A}$ receptor antagonist according to any one of the above (1) to (8), wherein $R^2$ is a substituted or unsubstituted aromatic heterocyclic group.

(14) The adenosine $A_{2A}$ receptor antagonist according to any one of the above (1) to (8), wherein $R^2$ is —$COR^8$ (wherein $R^8$ has the same meaning as defined above).

(15) The adenosine $A_{2A}$ receptor antagonist according to any one of the above (1) to (9) and (14), wherein $R^8$ is a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted alicyclic heterocyclic group, a substituted or unsubstituted aromatic heterocyclic group, substituted or unsubstituted alicyclic heterocyclic-alkyl, or substituted or unsubstituted aromatic heterocyclic-alkyl.

(16) The adenosine $A_{2A}$ receptor antagonist according to any one of the above (1) to (9) and (14), wherein $R^8$ is substituted or unsubstituted cycloalkyl, substituted or unsubstituted aryl, a substituted or unsubstituted alicyclic heterocyclic group, or a substituted or unsubstituted aromatic heterocyclic group.

(17) The adenosine $A_{2A}$ receptor antagonist according to any one of the above (1) to (9) and (14), wherein $R^8$ is substituted or unsubstituted aryl, a substituted or unsubstituted alicyclic heterocyclic group, or a substituted or unsubstituted aromatic heterocyclic group.

(18) The adenosine $A_{2A}$ receptor antagonist according to any one of the above (1) to (9) and (14), wherein $R^8$ is substituted or unsubstituted aryl.

(19) The adenosine $A_{2A}$ receptor antagonist according to any one of the above (1) to (9) and (14), wherein $R^8$ is a substituted or unsubstituted aromatic heterocyclic group.

(20) The adenosine $A_{2A}$ receptor antagonist according to any one of the above (1) to (9) and (14), wherein $R^8$ is a substituted or unsubstituted alicyclic heterocyclic group.

(21) The adenosine $A_{2A}$ receptor antagonist according to any one of the above (1) to (9) and (14), wherein $R^8$ is a substituted or unsubstituted alicyclic heterocyclic group containing at least one oxygen atom.

(22) The adenosine $A_{2A}$ receptor antagonist according to any one of the above (1) to (21), wherein $R^3$ is a hydrogen atom.

(23) The adenosine $A_{2A}$ receptor antagonist according to any one of the above (1) to (21), wherein $R^3$ is lower alkyl or aralkyl.

(24) The adenosine $A_{2A}$ receptor antagonist according to the above (22) or (23), wherein $R^4$ is —$COR^{12}$ (wherein $R^{12}$ has the same meaning as defined above).

(25) The adenosine $A_{2A}$ receptor antagonist according to the above (22) or (23), wherein $R^4$ is —$COR^{12a}$ (wherein $R^{12a}$ is substituted or unsubstituted lower alkyl, substituted or unsubstituted lower alkoxy, substituted or unsubstituted cycloalkyl, substituted or unsubstituted aryl, substituted or unsubstituted aralkyl, a substituted or unsubstituted alicyclic heterocyclic group, a substituted or unsubstituted aromatic heterocyclic group, substituted or unsubstituted alicyclic heterocyclic-alkyl, or substituted or unsubstituted aromatic heterocyclic-alkyl).

(26) The adenosine $A_{2A}$ receptor antagonist according to the above (22) or (23), wherein $R^4$ is —$COR^{12b}$ (wherein $R^{12b}$ is substituted or unsubstituted phenyl, or a substituted or unsubstituted aromatic heterocyclic group).

(27) The adenosine $A_{2A}$ receptor antagonist according to the above (22) or (23), wherein $R^4$ is —$COR^{12c}$ (wherein $R^{12c}$ is substituted or unsubstituted alicyclic heterocyclic-methyl, or substituted or unsubstituted aromatic heterocyclic-methyl).

(28) The adenosine $A_{2A}$ receptor antagonist according to the above (27), wherein $R^{12c}$ is substituted or unsubstituted alicyclic heterocyclic-methyl.

(29) The adenosine $A_{2A}$ receptor antagonist according to the above (22) or (23), wherein $R^4$ is —$COR^{12d}$ (wherein $R^{12d}$ is substituted or unsubstituted aryl, a substituted or unsubstituted alicyclic heterocyclic group, or a substituted or unsubstituted aromatic heterocyclic group).

(30) The adenosine $A_{2A}$ receptor antagonist according to the above (29), wherein $R^{12d}$ is a substituted or unsubstituted alicyclic heterocyclic group.

(31) The adenosine $A_{2A}$ receptor antagonist according to the above (22) or (23), wherein $R^4$ is —$COR^{12e}$ (wherein $R^{12e}$ is substituted or unsubstituted lower alkoxy).

(32) The adenosine $A_{2A}$ receptor antagonist according to the above (22) or (23), wherein $R^4$ is —$COR^{12f}$ [wherein $R^{12f}$ is —$NR^{13}R^{14}$ (wherein $R^{13}$ and $R^{14}$ have the same meanings as defined above, respectively)].

(33) The adenosine $A_{2A}$ receptor antagonist according to the above (32), wherein $R^{13}$ is a hydrogen atom.

(34) The adenosine $A_{2A}$ receptor antagonist according to the above (22) or (23), wherein $R^4$ is —$COR^{12g}$ [wherein $R^{12g}$ is substituted or unsubstituted lower alkyl, substituted or unsubstituted lower alkoxy, substituted or unsubstituted cycloalkyl, substituted or unsubstituted aryl (provided that the "site to be substituted by the substituent in the substituted aryl" does not neighbor on the "site at which —CO— bonds to $R^{12g}$ in —$COR^{12g}$"), substituted or unsubstituted aralkyl (provided that the "site to be substituted by the substituent in the aryl moiety of the substituted aralkyl" does not neighbor on the "site at which the alkyl moiety of the aralkyl bonds to the aryl moiety thereof"), a substituted or unsubstituted alicyclic heterocyclic group, a substituted or unsubstituted aromatic heterocyclic group (provided that the "site to be substituted by the substituent in the substituted aromatic heterocyclic group" does not neighbor on the "site at which —CO— bonds to $R^{12g}$ in —$COR^{12g}$"), substituted or unsubstituted alicyclic heterocyclic-alkyl, or substituted or unsubstituted aromatic heterocyclic-alkyl (provided that the "site to be substituted by the substituent in the aromatic heterocyclic moiety of the substituted aromatic heterocyclic-alkyl" does not neighbor on the "site at which the alkyl moiety of the aromatic heterocyclic-alkyl bonds to the aromatic heterocyclic moiety thereof")].

(35) The adenosine $A_{2A}$ receptor antagonist according to any one of the above (1) to (21), wherein $R^3$ and $R^4$ may be the same or different, and each represents —$COR^{12}$ (wherein $R^{12}$ has the same meaning as defined above).

(36) The adenosine $A_{2A}$ receptor antagonist according to any one of the above (1) to (21), wherein $R^3$ and $R^4$ may be the same or different, and each represents —$COR^{12a}$ (wherein $R^{12a}$ has the same meaning as defined above).

(37) The adenosine $A_{2A}$ receptor antagonist according to any one of the above (1) to (21), wherein $R^3$ and $R^4$ may be the same or different, and each represents —$COR^{12b}$ (wherein $R^{12b}$ has the same meaning as defined above).

(38). The adenosine $A_{2A}$ receptor antagonist according to any one of the above (1) to (21), wherein $R^3$ and $R^4$ may be the same or different, and each represents —$COR^{12c}$ (wherein $R^{12c}$ has the same meaning as defined above).

(39) The adenosine $A_{2A}$ receptor antagonist according to any one of the above (1) to (21), wherein $R^3$ and $R^4$ may be the same or different, and each represents —$COR^{12d}$ (wherein $R^{12d}$ has the same meaning as defined above).

(40) The adenosine $A_{2A}$ receptor antagonist according to any one of the above (1) to (21), wherein $R^3$ and $R^4$ may be the same or different, and each represents —$COR^{12e}$ (wherein $R^{12e}$ has the same meaning as defined above).

(41) The adenosine $A_{2A}$ receptor antagonist according to any one of the above (1) to (21), wherein $R^3$ and $R^4$ may be the same or different, and each represents —$COR^{12f}$ (wherein $R^{12f}$ has the same meaning as defined above).

(42) The adenosine $A_{2A}$ receptor antagonist according to any one of the above (1) to (21), wherein $R^3$ and $R^4$ may be the same or different, and each represents —$COR^{12g}$ (wherein $R^{12g}$ has the same meaning as defined above).

(43) The adenosine $A_{2A}$ receptor antagonist according to the above (1), wherein n is 0; $R^1$ is a substituted or unsubstituted 5-membered aromatic heterocyclic group containing at least one oxygen atom; and $R^2$ is —$COR^{8a}$ (wherein $R^{8a}$ represents a substituted or unsubstituted alicyclic heterocyclic group).

(44) The adenosine $A_{2A}$ receptor antagonist according to the above (43), wherein $R^1$ is substituted or unsubstituted furyl.

(45) The adenosine $A_{2A}$ receptor antagonist according to the above (43) or (44), wherein $R^{8a}$ is a substituted or unsubstituted alicyclic heterocyclic group containing at least one oxygen atom.

(46) The adenosine $A_{2A}$ receptor antagonist according to any one of the above (1) to (21) and (43) to (45), wherein $R^3$ is a hydrogen atom; and $R^4$ is substituted or unsubstituted lower alkyl, substituted or unsubstituted aralkyl, or substituted or unsubstituted aromatic heterocyclic-alkyl.

(47) The adenosine $A_{2A}$ receptor antagonist according to any one of the above (1) to (21) and (43) to (45), wherein $R^3$ is a hydrogen atom; and $R^4$ is lower alkyl, aralkyl, or aromatic heterocyclic-alkyl.

(48) The adenosine $A_{2A}$ receptor antagonist according to any one of the above (1) to (21) and (43) to (45), wherein $R^3$ is a hydrogen atom; and $R^4$ is lower alkyl, or aralkyl.

(49) The adenosine $A_{2A}$ receptor antagonist according to any one of the above (1) to (21) and (43) to (45), wherein $R^3$ and $R^4$ may be the same or different, and each represents substituted or unsubstituted lower alkyl, substituted or unsubstituted aralkyl, or substituted or unsubstituted aromatic heterocyclic-alkyl.

(50) An agent for treating and/or preventing diseases associated with adenosine $A_{2A}$ receptor comprising, as the active ingredient, a thiazole derivative according to any one of the above (1) to (49), or a pharmaceutically acceptable salt thereof.

(51) The agent for treating and/or preventing according to the above (50), wherein the disease associated with adenosine $A_{2A}$ receptor is Parkinson's disease.

(52) A thiazole derivative represented by a formula (IA):

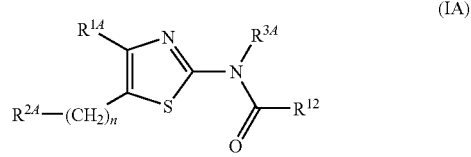

(IA)

[wherein
$R^{1A}$ represents a substituted or unsubstituted 5-membered aromatic heterocyclic group containing at least one oxygen atom (excluding a group selected from 5-phosphonofuran-2-yl and 5-nitrofuran-2-yl);

9

$R^{12}$ and n have the same meanings as defined above, respectively;

$R^{3A}$ represents a hydrogen atom;
  substituted or unsubstituted lower alkyl,
  substituted or unsubstituted lower alkenyl,
  substituted or unsubstituted lower alkynyl,
  substituted or unsubstituted aralkyl,
  substituted or unsubstituted alicyclic heterocyclic-alkyl, substituted or unsubstituted aromatic heterocyclic-alkyl, or
  —$COR^{12A}$ (wherein $R^{12A}$ have the same meaning as that of $R^{12}$); and $R^{2A}$ represents substituted or unsubstituted lower alkyl,
  substituted or unsubstituted lower alkenyl,
  substituted or unsubstituted lower alkynyl,
  substituted or unsubstituted cycloalkyl;
  substituted or unsubstituted aryl,
  substituted or unsubstituted aralkyl,
  a substituted or unsubstituted alicyclic heterocyclic group,
  a substituted or unsubstituted aromatic heterocyclic group (excluding 2-furyl),
  substituted or unsubstituted alicyclic heterocyclic-alkyl, substituted or unsubstituted aromatic heterocyclic-alkyl,
  —$NR^5R^6$ (wherein $R^5$ and $R^6$ have the same meanings as defined above, respectively),
  —$OR^7$ (wherein $R^7$ has the same meaning as defined above), or
  —$COR^8$ (wherein $R^8$ has the same meaning as defined above)], or a pharmaceutically acceptable salt thereof.

(53) The thiazole derivative according to the above (52), wherein $R^{1A}$ is substituted or unsubstituted furyl, or a pharmaceutically acceptable salt thereof.

(54) The thiazole derivative according to the above (52) or (53), wherein n is 0, or a pharmaceutically acceptable salt thereof.

(55) The thiazole derivative according to any one of the above (52) to (54), wherein $R^{2A}$ is substituted or unsubstituted lower alkyl, substituted or unsubstituted aryl, a substituted or unsubstituted alicyclic heterocyclic group, a substituted or unsubstituted aromatic heterocyclic group, substituted or unsubstituted alicyclic heterocyclic-alkyl, substituted or unsubstituted aromatic heterocyclic-alkyl, or —$COR^8$ (wherein $R^8$ has the same meaning as defined above), or a pharmaceutically acceptable salt thereof.

(56) The thiazole derivative according to any one of the above (52) to (54), wherein $R^{2A}$ is substituted or unsubstituted aryl, or a pharmaceutically acceptable salt thereof.

(57) The thiazole derivative according to any one of the above (52) to (54), wherein $R^{2A}$ is a substituted or unsubstituted alicyclic heterocyclic group, or a substituted or unsubstituted aromatic heterocyclic group, or a pharmaceutically acceptable salt thereof.

(58) The thiazole derivative according to any one of the above (52) to (54), wherein $R^{2A}$ is a substituted or unsubstituted alicyclic heterocyclic group, or a pharmaceutically acceptable salt thereof.

(59) The thiazole derivative according to any one of the above (52) to (54), wherein $R^{2A}$ is a substituted or unsubstituted aromatic heterocyclic group, or a pharmaceutically acceptable salt thereof.

(60) The thiazole derivative according to any one of the above (52) to (54), wherein $R^{2A}$ is —$COR^8$ (wherein $R^8$ has the same meaning as defined above), or a pharmaceutically acceptable salt thereof.

10

(61) The thiazole derivative according to the above (60), wherein $R^8$ is a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted alicyclic heterocyclic group, a substituted or unsubstituted aromatic heterocyclic group, substituted or unsubstituted alicyclic heterocyclic-alkyl, or substituted or unsubstituted aromatic heterocyclic-alkyl, or a pharmaceutically acceptable salt thereof.

(62) The thiazole derivative according to the above (60), wherein $R^8$ is substituted or unsubstituted cycloalkyl, substituted or unsubstituted aryl, a substituted or unsubstituted alicyclic heterocyclic group, or a substituted or unsubstituted aromatic heterocyclic group, or a pharmaceutically acceptable salt thereof.

(63) The thiazole derivative according to the above (60), wherein $R^8$ is substituted or unsubstituted aryl, a substituted or unsubstituted alicyclic heterocyclic group, or a substituted or unsubstituted aromatic heterocyclic group, or a pharmaceutically acceptable salt thereof.

(64) The thiazole derivative according to the above (60), wherein $R^8$ is substituted or unsubstituted aryl, or a pharmaceutically acceptable salt thereof.

(65) The thiazole derivative according to the above (60), wherein $R^8$ is a substituted or unsubstituted aromatic heterocyclic group, or a pharmaceutically acceptable salt thereof.

(66) The thiazole derivative according to the above (60), wherein $R^8$ is a substituted or unsubstituted alicyclic heterocyclic group, or a pharmaceutically acceptable salt thereof.

(67) The thiazole derivative according to the above (60), wherein $R^8$ is a substituted or unsubstituted alicyclic heterocyclic group containing at least one oxygen atom, or a pharmaceutically acceptable salt thereof.

(68) The thiazole derivative according to the above (60), wherein $R^8$ is substituted or unsubstituted lower alkyl, substituted or unsubstituted lower alkenyl, substituted or unsubstituted lower alkynyl, substituted or unsubstituted cycloalkyl, substituted or unsubstituted aryl, a substituted or unsubstituted alicyclic heterocyclic group, or a substituted or unsubstituted aromatic heterocyclic group (excluding a substituted or unsubstituted heterocyclic group having a nitrogen atom and bonding to —CO— of —$COR^8$ via the nitrogen atom thereof), or a pharmaceutically acceptable salt thereof.

(69) The thiazole derivative according to the above (68), wherein $R^8$ is a substituted or unsubstituted aromatic heterocyclic group, or a pharmaceutically acceptable salt thereof.

(70) The thiazole derivative according to the above (68), wherein $R^8$ is a substituted or unsubstituted alicyclic heterocyclic group, or a pharmaceutically acceptable salt thereof.

(71) The thiazole derivative according to the above (68), wherein $R^8$ is a substituted or unsubstituted alicyclic heterocyclic group containing at least one oxygen atom, or a pharmaceutically acceptable salt thereof.

(72) The thiazole derivative according to any one of the above (52) to (71), wherein $R^{3A}$ is a hydrogen atom, or a pharmaceutically acceptable salt thereof.

(73) The thiazole derivative according to any one of the above (52) to (71), wherein $R^{3A}$ is lower alkyl or aralkyl, or a pharmaceutically acceptable salt thereof.

(74) The thiazole derivative according to any one of the above (52) to (71), wherein $R^{3A}$ is —$COR^{12A}$ (wherein $R^{12A}$ has the same meaning as defined above), or a pharmaceutically acceptable salt thereof.

(75) The thiazole derivative according to the above (74), wherein $R^{12A}$ is substituted or unsubstituted lower alkyl, substituted or unsubstituted lower alkoxy, substituted or unsubstituted cycloalkyl, substituted or unsubstituted aryl, substituted or unsubstituted aralkyl, a substituted or unsubstituted alicyclic heterocyclic group, a substituted or unsubstituted aromatic heterocyclic group, substituted or unsubstituted alicyclic heterocyclic-alkyl, or substituted or unsubstituted aromatic heterocyclic-alkyl, or a pharmaceutically acceptable salt thereof.

(76). The thiazole derivative according to the above (74), wherein $R^{12A}$ is substituted or unsubstituted phenyl, or a substituted or unsubstituted aromatic heterocyclic group, or a pharmaceutically acceptable salt thereof.

(77) The thiazole derivative according to the above (74), wherein $R^{12A}$ is substituted or unsubstituted alicyclic heterocyclic-methyl, or substituted or unsubstituted aromatic heterocyclic-methyl, or a pharmaceutically acceptable salt thereof.

(78) The thiazole derivative according to the above (74), wherein $R^{12A}$ is substituted or unsubstituted alicyclic heterocyclic-methyl, or a pharmaceutically acceptable salt thereof.

(79) The thiazole derivative according to the above (74), wherein $R^{12A}$ is substituted or unsubstituted aryl, a substituted or unsubstituted alicyclic heterocyclic group, or a substituted or unsubstituted aromatic heterocyclic group, or a pharmaceutically acceptable salt thereof.

(80) The thiazole derivative according to the above (74), wherein $R^{12A}$ is a substituted or unsubstituted alicyclic heterocyclic group, or a pharmaceutically acceptable salt thereof.

(81) The thiazole derivative according to the above (74), wherein $R^{12A}$ is substituted or unsubstituted lower alkoxy, or a pharmaceutically acceptable salt thereof.

(82) The thiazole derivative according to the above (74), wherein $R^{12A}$ is $-NR^{13A}R^{14A}$ (wherein $R^{13A}$ and $R^{14A}$ have the same meanings as $R^{13}$ and $R^{14}$ defined above, respectively), or a pharmaceutically acceptable salt thereof.

(83) The thiazole derivative according to the above (82), wherein $R^{13A}$ is a hydrogen atom, or a pharmaceutically acceptable salt thereof.

(84) The thiazole derivative according to the above (74), wherein $R^{12A}$ is substituted or unsubstituted lower alkyl, substituted or unsubstituted lower alkoxy, substituted or unsubstituted cycloalkyl, substituted or unsubstituted aryl (provided that the "site to be substituted by the substituent in the substituted aryl" does not neighbor on the "site at which —CO— bonds to $R^{12A}$ in —COR$^{12A}$") substituted or unsubstituted aralkyl (provided that the "site to be substituted by the substituent in the aryl moiety of the substituted aralkyl" does not neighbor on the "site at which the alkyl moiety of the aralkyl bonds to the aryl moiety thereof"), a substituted or unsubstituted alicyclic heterocyclic group, a substituted or unsubstituted aromatic heterocyclic group (provided that the "site to be substituted by the substituent in the substituted aromatic heterocyclic group" does not neighbor on the "site at which —CO— bonds to $R^{12A}$ in —COR$^{12A}$"), substituted or unsubstituted alicyclic heterocyclic-alkyl, or substituted or unsubstituted aromatic heterocyclic-alkyl (provided that the "site to be substituted by the substituent in the aromatic heterocyclic moiety of the substituted aromatic heterocyclic-alkyl" does not neighbor on the "site at which the alkyl moiety of the aromatic heterocyclic-alkyl bonds to the aromatic heterocyclic moiety thereof"), or a pharmaceutically acceptable salt thereof.

(85) The thiazole derivative according to any one of the above (52) to (84), wherein $R^{12}$ is substituted or unsubstituted lower alkyl, substituted or unsubstituted lower alkoxy, substituted or unsubstituted cycloalkyl, substituted or unsubstituted aryl, substituted or unsubstituted aralkyl, a substituted or unsubstituted alicyclic heterocyclic group, a substituted or unsubstituted aromatic heterocyclic group, substituted or unsubstituted alicyclic heterocyclic-alkyl, or substituted or unsubstituted aromatic heterocyclic-alkyl, or a pharmaceutically acceptable salt thereof.

(86) The thiazole derivative according to any one of the above (52) to (84), wherein $R^{12}$ is substituted or unsubstituted phenyl, or a substituted or unsubstituted aromatic heterocyclic group, or a pharmaceutically acceptable salt thereof.

(87) The thiazole derivative according to any one of the above (−52) to (84), wherein $R^{12}$ is substituted or unsubstituted alicyclic heterocyclic-methyl, or substituted or unsubstituted aromatic heterocyclic-methyl, or a pharmaceutically acceptable salt thereof.

(88) The thiazole derivative according to any one of the above (52) to (84), wherein $R^{12}$ is substituted or unsubstituted alicyclic heterocyclic-methyl, or a pharmaceutically acceptable salt thereof.

(89) The thiazole derivative according to any one of the above (52) to (84), wherein $R^{12}$ is substituted or unsubstituted aryl, a substituted or unsubstituted alicyclic heterocyclic group, or a substituted or unsubstituted aromatic heterocyclic group, or a pharmaceutically acceptable salt thereof.

(90) The thiazole derivative according to any one of the above (52) to (84), wherein $R^{12}$ is a substituted or unsubstituted alicyclic heterocyclic group, or a pharmaceutically acceptable salt thereof.

(91) The thiazole derivative according to any one of the above (52) to (84), wherein $R^{12}$ is substituted or unsubstituted lower alkoxy, or a pharmaceutically acceptable salt thereof.

(92) The thiazole derivative according to any one of the above (52) to (84), wherein $R^{12}$ is $NR^{13}R^{14}$ (wherein $R^{13}$ and $R^{14}$ have the same meanings as defined above, respectively), or a pharmaceutically acceptable salt thereof.

(93) The thiazole derivative according to the above (92), wherein $R^{13}$ is a hydrogen atom, or a pharmaceutically acceptable salt thereof.

(94) The thiazole derivative according to any one of the above (52) to (84), wherein $R^{12}$ is substituted or unsubstituted lower alkyl, substituted or unsubstituted lower alkoxy, substituted or unsubstituted cycloalkyl, substituted or unsubstituted aryl (provided that the "site to be substituted by the substituent in the substituted aryl" does not neighbor on the "site at which —CO— bonds to $R^{12}$ in —COR$^{12}$"), substituted or unsubstituted aralkyl (provided that the "site to be substituted by the substituent in the aryl moiety of the substituted aralkyl" does not neighbor on the "site at which the alkyl moiety of the aralkyl bonds to the aryl moiety thereof"), a substituted or unsubstituted alicyclic heterocyclic group, a substituted or unsubstituted aromatic heterocyclic group (provided that the "site to be substituted by the substituent in the substituted aromatic heterocyclic group" does not neighbor on the "site at which —CO— bonds to $R^{12}$ in —COR$^{12}$"), substituted or unsubstituted alicyclic heterocyclic-alkyl, or substituted or unsubstituted aromatic heterocyclic-alkyl (provided that the "site to be substituted by the substituent in the aromatic heterocyclic moiety of the substituted aromatic heterocyclic-alkyl" does not neighbor on the "site at which the alkyl moiety of the aromatic heterocyclic-alkyl bonds to the aromatic heterocyclic moiety thereof"), or a pharmaceutically acceptable salt thereof.

(95) A thiazole derivatives represented by a formula (IB):

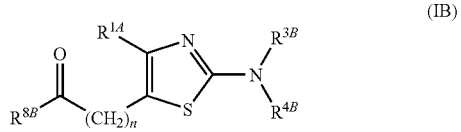

(wherein
n and $R^{1A}$ have the same meanings as defined above, respectively;
$R^{3B}$ represents a hydrogen atom,
substituted or unsubstituted lower alkyl,
substituted or unsubstituted lower alkenyl,
substituted or unsubstituted lower alkynyl,
substituted or unsubstituted aralkyl,
substituted or unsubstituted alicyclic heterocyclic-alkyl, or
substituted or unsubstituted aromatic heterocyclic-alkyl;
$R^{4B}$ represents substituted or unsubstituted lower alkyl,
substituted or unsubstituted lower alkenyl,
substituted or unsubstituted lower alkynyl,
substituted or unsubstituted aralkyl,
substituted or unsubstituted alicyclic heterocyclic-alkyl, or
substituted or unsubstituted aromatic heterocyclic-alkyl;
and
$R^{8B}$ represents a hydrogen atom,
substituted or unsubstituted lower alkyl,
substituted or unsubstituted lower alkenyl,
substituted or unsubstituted lower alkynyl,
substituted or unsubstituted cycloalkyl,
substituted or unsubstituted aryl,
substituted or unsubstituted aralkyl,
a substituted or unsubstituted alicyclic heterocyclic group,
a substituted or unsubstituted aromatic heterocyclic group,
substituted or unsubstituted alicyclic heterocyclic-alkyl, or
substituted or unsubstituted aromatic heterocyclic-alkyl), or a pharmaceutically acceptable salt thereof.

(96) The thiazole derivative according to the above (95), wherein $R^{1A}$ is substituted or unsubstituted furyl, or a pharmaceutically acceptable salt thereof.

(97) The thiazole derivative according to the above (95) or (96), wherein n is 0, or a pharmaceutically acceptable salt thereof.

(98) The thiazole derivative according to any one of the above (95) to (97), wherein $R^{8B}$ is a substituted or unsubstituted alicyclic heterocyclic group, or a pharmaceutically acceptable salt thereof.

(99) The thiazole derivative according to any one of the above (95) to (97), wherein $R^{8B}$ is a substituted or unsubstituted alicyclic heterocyclic group containing at least one oxygen atom, or a pharmaceutically acceptable salt thereof.

(100) The thiazole derivative according to any one of the above (95) to (97), wherein $R^{8B}$ is substituted or unsubstituted tetrahydropyranyl, or a pharmaceutically acceptable salt thereof.

(101) The thiazole derivative according to any one of the above (95) to (100), wherein $R^{3B}$ is a hydrogen atom, or a pharmaceutically acceptable salt thereof.

(102) The thiazole derivative according to the above (101), wherein $R^{4B}$ is lower alkyl, aralkyl or aromatic heterocyclic-aralkyl, or a pharmaceutically acceptable salt thereof.

(103) The thiazole derivative according to the above (101), wherein $R^{4B}$ is lower alkyl or aralkyl, or a pharmaceutically acceptable salt thereof.

(104) A pharmaceutical composition comprising, as the active ingredient, a thiazole derivative according to any one of the above (52) to (103), or a pharmaceutically acceptable salt thereof.

(105) An adenosine $A_{2A}$ receptor antagonist comprising, as the active ingredient, a thiazole derivative according to any one of the above (52) to (103), or a pharmaceutically acceptable salt thereof.

(106) An agent for treating and/or preventing diseases associated with adenosine $A_{2A}$ receptor comprising, as the active ingredient, a thiazole derivative according to any one of the above (52) to (103), or a pharmaceutically acceptable salt thereof.

(107) An agent for treating and/or preventing central nervous system diseases comprising, as the active ingredient, a thiazole derivative according to any one of the above (52) to (103), or a pharmaceutically acceptable salt thereof.

(108) An agent for treating and/or preventing Parkinson's disease comprising, as the active ingredient, a thiazole derivative according to any one of the above (52) to (103), or a pharmaceutically acceptable salt thereof.

(109) A method for treating and/or preventing diseases associated with adenosine $A_{2A}$ receptor, which comprises administering an effective amount of a thiazole derivative represented by a general formula (I):

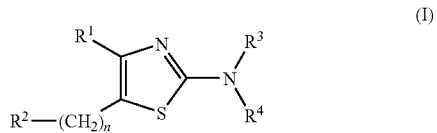

(wherein n, $R^1$, $R^2$, $R^3$ and $R^4$ have the same meanings as defined above, respectively), or a pharmaceutically acceptable salt thereof.

(110) A method for treating and/or preventing Parkinson's disease, which comprises administering an effective amount of a thiazole derivative according to any one of the above (52) to (103), or a pharmaceutically acceptable salt thereof.

(111) A method for treating and/or preventing diseases associated with adenosine $A_{2A}$ receptor, which comprises administering an effective amount of a thiazole derivative according to any one of the above (52) to (103), or a pharmaceutically acceptable salt thereof.

(112) A method for treating and/or preventing central nervous system diseases, which comprises administering an effective amount of a thiazole derivative according to any one of the above (52) to (103), or a pharmaceutically acceptable salt thereof.

(113) Use of a thiazole derivative represented by a general formula (I):

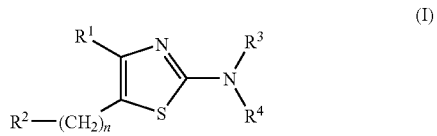

(wherein n, $R^1$, $R^2$, $R^3$ and $R^4$ have the same meanings as defined above, respectively) or a pharmaceutically acceptable salt thereof for the manufacture of an agent, for treating and/or preventing diseases associated with adenosine $A_{2A}$ receptor.

(114) Use of a thiazole derivative represented by a general formula (I):

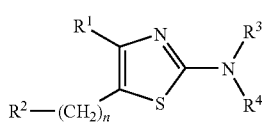

(wherein n, $R^1$, $R^2$, $R^3$ and $R^4$ have the same meanings as defined above, respectively) or a pharmaceutically acceptable salt thereof, for the manufacture of an adenosine $A_{2A}$ receptor antagonist.

(115) Use of a thiazole derivative according to any one of the above (52) to (103) or a pharmaceutically acceptable salt thereof for the manufacture of an agent for treating and/or preventing Parkinson's disease.

(116) Use of a thiazole derivative according to any one of the above (52) to (103) or a pharmaceutically acceptable salt thereof for the manufacture of an agent for treating and/or preventing diseases associated with adenosine $A_{2A}$ receptor.

(117) Use of a thiazole derivative according to any one of the above (52) to (103) or a pharmaceutically acceptable salt thereof for the manufacture of an agent for treating and/or preventing central nervous system diseases.

(118) Use of a thiazole derivative according to any one of the above (52) to (103) or a pharmaceutically acceptable salt thereof for the manufacture of an adenosine $A_{2A}$ receptor antagonist.

Hereinafter, the compounds represented by general formula (I) are referred to as Compounds (I), and the same applies to compounds of other formula numbers.

In the definition of each group in general formula (I), general formula (IA) and general formula (IB):

(i) Examples of the lower alkyl moiety of the lower alkyl, the lower alkoxy and the lower alkanoyl include linear or branched alkyl having 1 to 10 carbon atoms, such as methyl, ethyl, propyl, isopropyl, butyl, isobutyl, sec-butyl, tert-butyl, pentyl, isopentyl, neopentyl, hexyl, heptyl, octyl, nonyl and decyl.

(ii) Examples of the lower alkenyl include linear or branched alkenyl having 2 to 10 carbon atoms, such as vinyl, allyl, 1-propenyl, butenyl, pentenyl, hexenyl, heptenyl, octenyl, nonenyl and decenyl.

(iii) Examples of the lower alkynyl include a linear or branched alkynyl having 2 to 10 carbon atoms, such as ethynyl, propynyl, butynyl, pentynyl, hexynyl, heptynyl, octynyl, nonynyl and decynyl.

(iv) Examples of the cycloalkyl include a cycloalkyl having 3 to 8 carbon atoms, such as cyclopropyl, cyclobutyl, cyclopentyl, cyclohexyl, cycloheptyl and cyclooctyl.

(v) Examples of the aryl moiety of the aryl and the aralkyl include aryl having 6 to 10 carbon atoms, such as phenyl and naphthyl.

(vi) Examples of the aromatic heterocyclic moiety of the aromatic heterocyclic group, the aromatic heterocyclic-alkyl and the aromatic heterocyclic-methyl include 5-membered or 6-membered monocyclic aromatic heterocyclic groups containing at least one atom selected from a nitrogen atom, an oxygen atom and a sulfur atom; or bicyclic or tricyclic condensed-ring aromatic heterocyclic groups containing at least one atom selected from a nitrogen atom, an oxygen atom and a sulfur atom in which 4- to 8-membered rings are condensed; such as includes furyl, thienyl, pyrrolyl, pyridyl, N-oxopyridyl, pyrazinyl, imidazolyl, pyrazolyl, triazolyl, thiazolyl, isothiazolyl, thiadiazolyl, oxazolyl, isoxazolyl, oxadiazolyl, pyrimidinyl, pyridazinyl, indolyl, isoindolyl, benzothienyl, benzofuranyl, benzothiazolyl, benzimidazolyl, benzothiadiazolyl, benzotriazolyl, quinolyl, isoquinolyl, quinazolinyl and furo[2,3-b]pyridyl.

(vii) Examples of the monocyclic aromatic heterocyclic group include the 5-membered or 6-membered monocyclic aromatic heterocyclic groups described in the above examples of the aromatic heterocyclic group (vi), such as furyl, thienyl, pyrrolyl, pyridyl, N-oxopyridyl, pyrazinyl, imidazolyl, pyrazolyl, triazolyl, thiazolyl, isothiazolyl, thiadiazolyl, oxazolyl, isoxazolyl, oxadiazolyl, pyrimidinyl and pyridazinyl.

(viii) Examples of the 5-membered aromatic heterocyclic group include the 5-membered monocyclic aromatic heterocyclic groups described in the above examples of the monocyclic aromatic heterocyclic group (vii), such as furyl, thienyl, pyrrolyl, imidazolyl, pyrazolyl, triazolyl, thiazolyl, isothiazolyl, thiadiazolyl, oxazolyl, isoxazolyl and oxadiazolyl.

(ix) Examples of the 5-membered aromatic heterocyclic group containing at least one oxygen atom include the 5-membered monocyclic aromatic heterocyclic groups containing at least one oxygen atom of the 5-membered monocyclic aromatic heterocyclic groups described in the above examples of the 5-membered aromatic heterocyclic group (viii), such as furyl, oxazolyl, isoxazolyl and oxadiazolyl.

(x) Examples of the alicyclic heterocyclic moiety of the alicyclic heterocyclic group, the alicyclic heterocyclic-alkyl and the alicyclic heterocyclic-methyl include 3-membered to 6-membered monocyclic alicyclic heterocyclic groups containing at least one atom selected from a nitrogen atom, an oxygen atom and a sulfur atom; or bicyclic or tricyclic condensed-ring alicyclic heterocyclic groups containing at least one atom selected from a nitrogen atom, an oxygen atom and a sulfur atom in which 4- to 8-membered rings are condensed; such as pyrrolidinyl, imidazolidinyl, thiazolidinyl, piperidinyl, piperazinyl, morpholinyl, thiomorpholinyl, piperidino, morpholino, thiomorpholino, oxazolinyl, dioxolanyl, dioxanyl, dioxepanyl, dihydropyridyl, tetrahydropyridyl, pyranyl, dihydropyranyl, tetrahydropyranyl, tetrahydroisoquinolinyl, tetrahydroquinolinyl, indolinyl, isoindolinyl, dihydropyridazinyl, oxiranyl, oxetanyl, oxolanyl, thiolanyl, thianyl, aziridinyl, azetidinyl, azolidinyl, perhydroxazepinyl, perhydrothiazepinyl, perhydroazepinyl, perhydroazocinyl, perhydrodiazepinyl, succinimido, phthalimido, glutarimido, 1,3-benzodioxolyl, 1,4-benzodioxanyl, 3,4-dihydro-2H-1,5-benzodioxepinyl, 1,4-dioxaspiro[4.5]decanyl, 1,4-dioxa-8-azaspiro[4.5]decanyl, octahydropyrrolo[1,2-a]pyrazinyl, octahydropyrazino[2,1-c][1,4]oxazinyl and octahydropyrazino[2,1-c][1,4]thiazinyl.

(xi) Examples of the alicyclic heterocyclic group containing at least one oxygen atom include the alicyclic heterocyclic groups containing at least one oxygen atom described in the above examples of the alicyclic heterocyclic group (x), such as morpholinyl, morpholino, oxazolinyl, dioxolanyl, dioxanyl, dioxepanyl, pyranyl, dihydropyranyl, tetrahydropyranyl, oxiranyl, oxetanyl, oxolanyl, perhydroxazepinyl, 1,3-benzodioxolyl, 1,4-benzodioxanyl, 3,4-dihydro-2H-1,5-benzodioxepinyl, 1,4-dioxaspiro[4.5]decanyl, 1,4-dioxa-8-azaspiro[4.5]decanyl and octahydropyrazino[2,1-c][1,4]oxazinyl.

(xii) Examples of the heterocyclic group having a nitrogen atom and bonding to —CO— of —$COR^8$ via the nitrogen atom include 5-membered or 6-membered monocyclic heterocyclic groups containing at least one nitrogen atom (the monocyclic heterocyclic groups may contain any other nitrogen atom, oxygen atom or sulfur atom); or bicyclic or tricyclic condensed-ring heterocyclic groups containing at least one nitrogen atom in which 3- to 8-membered rings are condensed (the condensed-ring heterocyclic groups may contain any other nitrogen atom, oxygen atom or sulfur atom); such as 1-pyrrolyl, 1-pyrrolidinyl, morpholino, thiomorpholino, 1-pyrazolidinyl, piperidino, 1-piperazinyl, 1-homopiperazinyl, 1-aziridinyl, 1-azetidinyl, 1-azolidinyl, 1-perhydroazepinyl and 1-perhydroazocinyl.

(xiii) Examples of the alkylene moiety of the aralkyl, the aromatic heterocyclic-alkyl and the alicyclic heterocyclic-alkyl include linear or branched alkylene having 1 to 10 carbon atoms, such as one produced by each removing one hydrogen atom from groups described in the above examples of lower alkyl (i).

(xiv) The halogen means each atom of fluorine, chlorine, bromine and iodine.

(xv) Examples of the substituents (A) in the substituted lower alkyl include 1 to 3 substituents which may be the same or different, such as halogen, hydroxy, nitro, azido, amino, cyano, carboxy, formyl, substituted or unsubstituted lower alkoxy, substituted or unsubstituted lower alkanoyloxy, substituted or unsubstituted lower alkylsulfanyl, substituted or unsubstituted lower alkylamino, substituted or unsubstituted di(lower alkyl)amino, substituted or unsubstituted adamantylamino, substituted or unsubstituted cycloalkyl, substituted or unsubstituted aryloxy and substituted or unsubstituted heterocyclic-oxy.

In the examples of the substituents (A), examples of the substituents (a) in the substituted lower alkoxy, the substituted lower alkanoyloxy, the substituted lower alkylsulfanyl, the substituted lower alkylamino and the substituted di(lower alkyl)amino include 1 to 3 substituents which may be the same or different, such as halogen, hydroxy, hydroxyimino, methoxyimino, nitro, azido, amino, cyano, carboxy, cycloalkyl, substituted or unsubstituted lower alkoxy, substituted or unsubstituted lower alkanoyloxy, substituted or unsubstituted lower alkylamino, substituted or unsubstituted di(lower alkyl)amino, substituted or unsubstituted aryl, a substituted or unsubstituted alicyclic heterocyclic group, a substituted or unsubstituted aromatic heterocyclic group, aryloxy and heterocyclic-oxy.

In the examples of the substituents (a), examples of the substituents (b) in the substituted lower alkoxy, the substituted lower alkanoyloxy, the substituted lower alkylamino and the substituted di(lower alkyl)amino include 1 to 3 substituents which may be the same or different, such as halogen, hydroxy, amino, lower alkoxy, lower alkylamino, di(lower alkyl)amino, aryl, an alicyclic heterocyclic group and an aromatic heterocyclic group.

In the examples of the substituents (a), examples of the substituents (c) in the substituted aryl and the substituted aromatic heterocyclic group include 1 to 3 substituents which may be the same or different, such as the groups described in the examples of the substituents (b), and lower alkyl.

In the examples of the substituents (a), examples of the substituents (d) in the substituted alicyclic heterocyclic group include 1 to 3 substituents which may be the same or different, such as the groups described in the examples of the substituents (b), lower alkyl and oxo.

In the examples of the substituents (A), examples of the substituents (e) in the substituted adamantylamino include 1 to 3 substituents which may be the same or different, such as lower alkyl, lower alkoxy, hydroxy, oxo and formyl.

In the examples of the substituents (A), examples of the substituents (f) in the substituted cycloalkyl include 1 to 3 substituents which may be the same or different, such as the groups in the examples of the substituents (a), lower alkyl, oxo and formyl.

In the examples of the substituents (A), examples of the substituents (g) in the substituted aryloxy and the substituted heterocyclic-oxy include 1 to 3 substituents which may be the same or different, such as halogen, hydroxy, nitro, azido, amino, cyano, carboxy, formyl, substituted or unsubstituted lower alkyl, substituted or unsubstituted lower alkanoyl, cycloalkyl, lower alkoxy, lower alkylsulfanyl, lower alkylsulfonyl, lower alkoxycarbonyl, lower alkylaminocarbonyl, di(lower alkyl)aminocarbonyl, lower alkylamino, di(lower alkyl)amino, aryl, an alicyclic heterocyclic group, an aromatic heterocyclic group, aryloxy and heterocyclic-oxy.

In the examples of the substituents (g), examples of the substituents in the substituted lower alkyl and the substituted lower alkanoyl include 1 to 3 substituents which may be the same or different, such as the groups described in the examples of the substituents (b).

In the examples of the substituents (A), the substituents (a), the substituents (b), the substituents (c), the substituents (d), the substituents (e), the substituents (f) and the substituents (g), examples of the lower alkyl moiety of the lower alkyl, the lower alkoxy, the lower alkanoyl, the lower alkanoyloxy, the lower alkylsulfanyl, the lower alkylsulfonyl, the lower alkoxycarbonyl, the lower alkylaminocarbonyl, the di(lower alkyl)aminocarbonyl, the lower alkylamino and the di(lower alkyl)amino; the cycloalkyl; the aryl moiety of the aryl and the aryloxy; the alicyclic heterocyclic group; the aromatic heterocyclic group; and the halogen have the same meanings as the lower alkyl (i), the cycloalkyl (iv), the aryl (v), the alicyclic heterocyclic group (x), the aromatic heterocyclic group (vi) and the halogen (xiv) defined above, respectively; the heterocyclic moiety of the heterocyclic-oxy includes the groups described in the above examples of the alicyclic heterocyclic group (x), aromatic heterocyclic group (vi) and the like; and the two lower alkyl moieties of the di(lower alkyl)aminocarbonyl and the di(lower alkyl)amino may be the same or different.

(xvi) Examples of the substituents (B) in the substituted lower alkanoyl, the substituted lower alkenyl, the substituted lower alkynyl and the substituted lower alkoxy include 1 to 3 substituents which may be the same or different, such as the groups described in the examples of the substituents (A), substituted or unsubstituted aryl, a substituted or unsubstituted alicyclic heterocyclic group, and a substituted or unsubstituted aromatic heterocyclic group.

In the examples of the substituents (B), examples of the substituents (h) in the substituted aryl and the substituted aromatic heterocyclic group include 1 to 3 substituents which may be the same or different, such as the groups described in the examples of the substituents (a) and lower alkyl.

In the examples of the substituents (B), examples of the substituents (j) in the substituted alicyclic heterocyclic group include 1 to 3 substituents which may be the same or different, such as the groups described in the examples of the substituents (a), lower alkyl, oxo and formyl.

In the examples of the substituents (B), the substituents (h) and the substituents (j), the lower alkyl, the aryl, the alicyclic heterocyclic group and the aromatic heterocyclic group have the same meanings as the lower alkyl (i), the aryl (v), the alicyclic heterocyclic group (x) and the aromatic heterocyclic group (vi) defined above, respectively.

(xvii) Examples of the substituents (C) in the substituted cycloalkyl include 1 to 3 substituents which may be the same or different, such as the groups described in the examples of the substituents (A), lower alkyl and oxo.

In the examples of the substituents (C), the lower alkyl has the same meaning as the lower alkyl (i) defined above.

(xviii) Examples of the substituents (D) in the substituted aryl, the substituted phenyl, the substituted aralkyl, the substituted aromatic heterocyclic group, the substituted monocyclic aromatic heterocyclic group, the substituted 5-membered aromatic heterocyclic group, the substituted 5-membered aromatic heterocyclic group containing at least one oxygen atom, the substituted furyl, the substituted heterocyclic group having a nitrogen atom and bonding to —CO— of —COR$^8$ via the nitrogen atom, the substituted 6-oxo-1,6-dihydropyridazin-3-yl, the substituted aromatic heterocyclic-alkyl and the substituted aromatic heterocyclic-methyl include 1 to 4 substituents which may be the same or different, such as halogen, hydroxy, nitro, azido, amino, cyano, carboxy, formyl, substituted or unsubstituted lower alkyl, substituted or unsubstituted lower alkanoyl, substituted or unsubstituted lower alkenyl, substituted or unsubstituted lower alkynyl, substituted or unsubstituted cycloalkyl, substituted or unsubstituted lower alkoxy, substituted or unsubstituted lower alkanoyloxy, substituted or unsubstituted lower alkylamino, substituted or unsubstituted di(lower alkyl)amino, substituted or unsubstituted lower alkylsulfanyl, substituted or unsubstituted lower alkylsulfonyl, sulfamoyl, substituted or unsubstituted lower alkylaminosulfonyl, substituted or unsubstituted di(lower alkyl)aminosulfonyl, substituted or unsubstituted lower alkoxycarbonyl, substituted or unsubstituted lower alkylaminocarbonyl, substituted or unsubstituted di(lower alkyl)aminocarbonyl, heterocyclic-carbonyl, substituted or unsubstituted aryl, a substituted or unsubstituted alicyclic heterocyclic group, a substituted or unsubstituted aromatic heterocyclic group, substituted or unsubstituted aryloxy, substituted or unsubstituted heterocyclic-oxy and tri(lower alkyl)silyl.

In the examples of the substituents (D), examples of the substituents in the substituted lower alkyl, the substituted lower alkenyl, the substituted lower alkynyl, the substituted lower alkanoyl the substituted lower alkoxy, the substituted lower alkanoyloxy, the substituted lower alkylamino, the substituted di(lower alkyl)amino, the substituted lower alkylsulfanyl, the substituted lower alkylsulfonyl, the substituted lower alkylaminosulfonyl, the substituted di(lower alkyl)aminosulfonyl, the substituted lower alkoxycarbonyl the substituted lower alkylaminocarbonyl and the substituted di(lower alkyl)aminocarbonyl include 1 to 3 substituents which may be the same or different, such as the groups described in the examples of the substituents (a).

In the examples of the substituents (D), examples of the substituents in the substituted aryl, the substituted aryloxy, the substituted aromatic heterocyclic group and the substituted heterocyclic-oxy include 1 to 3 substituents which may be the same or different, such as the groups described in the examples of the substituents (g).

In the examples of the substituents (D), examples of the substituents (k) in the substituted cycloalkyl and the substituted alicyclic heterocyclic group include 1 to 3 substituents which may be the same or different, such as the groups described in the examples of the substituents (a), lower alkyl and oxo.

In the examples of the substituents (D) and the substituents (k), the lower alkyl moiety of the lower alkyl, the lower alkanoyl, the lower alkoxy, the lower alkanoyloxy, the lower alkylamino, the di(lower alkyl)amino, the lower alkylsulfanyl, the lower alkylsulfonyl, the lower alkylaminosulfonyl, the di(lower alkyl)aminosulfonyl, the lower alkoxycarbonyl, the lower alkylaminocarbonyl, the di(lower alkyl)aminocarbonyl and the tri(lower alkyl)silyl; the lower alkenyl; the lower alkynyl; the cycloalkyl; the aryl moiety of the aryl and the aryloxy; the alicyclic heterocyclic group; the aromatic heterocyclic group and the halogen have the same meanings as the lower alkyl (i), the lower alkenyl (ii), the lower alkynyl (iii), the cycloalkyl (iv), the aryl (v), the alicyclic heterocyclic group (x), the aromatic the heterocyclic group (vi) and the halogen (xiv), defined above, respectively; the heterocyclic moiety of the heterocyclic-carbonyl and the heterocyclic-oxy includes the groups described in the examples of the above-described alicyclic heterocyclic group (x) and aromatic heterocyclic group (vi), and the like; the two lower alkyl moieties of the di(lower alkyl)amino, the di(lower alkyl)aminocarbonyl and the di(lower alkyl)aminosulfonyl may be the same or different; and the three lower alkyl moieties of the tri(lower alkyl)silyl may be the same or different.

(xix) Examples of the substituents (E) in the substituted alicyclic heterocyclic group, the substituted alicyclic heterocyclic group containing at least one oxygen atom, the substituted tetrahydropyranyl, the substituted alicyclic heterocyclic-alkyl and the substituted alicyclic heterocyclic-methyl include 1 to 3 substituents which may be the same or different, such as the groups described in the examples of the substituents (D) and oxo.

Examples of the pharmaceutically acceptable salt of Compound (I) includes pharmaceutically acceptable acid addition salts, metal salts, ammonium salts, organic amine addition salts, amino acid addition salts. Examples of the pharmaceutically acceptable acid addition salts of Compounds (I) include inorganic acid addition salts such as hydrochloride, sulfate, nitrate and phosphate, and organic acid addition salts such as acetate, maleate, fumarate and citrate. Examples of the pharmaceutically acceptable metal salts include alkali metal salts such as sodium salt and potassium salt, alkaline earth metal salts such as magnesium salt and calcium salt, aluminum salt, and zinc salt. Examples of the pharmaceutically acceptable ammonium salts include ammonium and tetramethylammonium. Examples of the pharmaceutically acceptable organic amine addition salts include an addition salt of morpholine or piperidine. Examples of the pharmaceutically acceptable amino acid addition salts include an addition salt of lysine, glycine, phenylalanine, aspartic acid or glutamic acid.

Examples of diseases associated with adenosine $A_{2A}$ receptor, which can be treated and/or prevented by the adenosine $A_{2A}$ receptor antagonist of the present invention, include Parkinson's disease, Alzheimer's disease, progressive supranuclear palsy, AIDS encephalopathy, Transmissible spongiform encephalopathy, multiple sclerosis, amyotrophic lateral sclerosis, Huntington's chorea, multiple system atrophy, cerebral ischemia, attention deficit hyperactivity disorder, sleep disorder, ischemic cardiopathy, intermittent claudication, diabetes, anxiety disorders (e.g., panic attack and panic disorder, phobia, obsessive-compulsive disorder, posttraumatic stress disorder, acute stress disorder, generalized anxiety disorder, anxiety physical symptoms or substance-caused), mood disorders (e.g., depression, dysthymic disorder, mood-circulatory disorder), restless legs syndrome (RLS), drug dependence (e.g., alcohol dependence), eating disorder, epilepsy, migraine, chronic musculoskeletal system pain and the like.

The processes for preparing Compounds (I) are described below.

In the following production processes, when the defined groups undergo changes under the reaction conditions or are not suitable to carry out the processes, desired compounds can be produced by methods generally used in synthetic organic chemistry, such as protection of functional groups, removal of protecting groups and the like [e.g. T. W. Greene, Protective Groups in Organic Synthesis, third edition, John Wiley & Sons Inc. (1999)] If necessary, the order of reaction steps such as introduction of a substituent may be changed.

Compounds (I) can be produced according to the following processes.

<Production Method 1>

Among Compounds (I), Compounds (Ia) in which $R^3$ and $R^4$ are hydrogen atoms; Compounds (Ib) in which $R^3$ is a hydrogen atom, and $R^4$ is substituted or unsubstituted lower alkyl, substituted or unsubstituted lower alkenyl, substituted or unsubstituted lower alkynyl, substituted or unsubstituted aralkyl, substituted or unsubstituted aromatic heterocyclic-alkyl or —$COR^{12}$ (wherein $R^{12}$ has the same meaning as defined above); and Compounds (Ic) in which $R^3$ and $R^4$ may be the same or different, and each represents substituted or unsubstituted lower alkyl, substituted or unsubstituted lower alkenyl, substituted or unsubstituted lower alkynyl, substituted or unsubstituted aralkyl, substituted or unsubstituted aromatic heterocyclic-alkyl or —$COR^{12}$ (wherein $R^{12}$ has the same meaning as defined above) can be produced, for example, according to the method described in Japanese Published Unexamined Patent Application Nos. 155871/1993, 193281/1999 or the like, or methods similar thereto. Briefly, they can be produced according to the following steps:

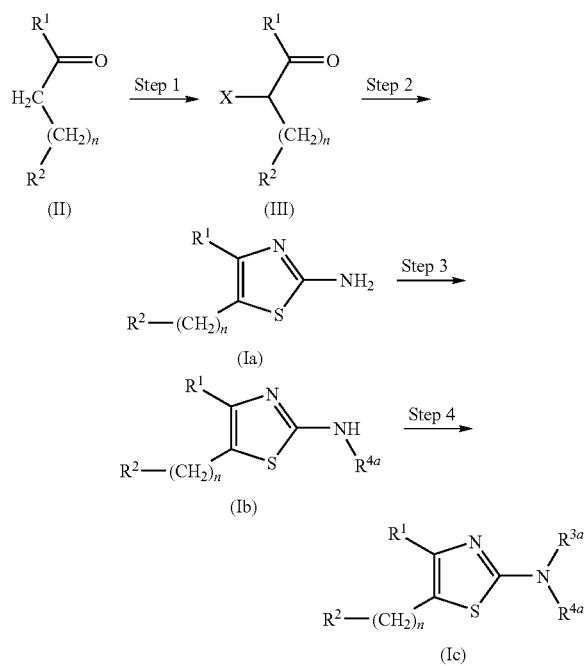

[In the formulae, $R^1$, $R^2$ and n have the same meanings as defined above, respectively; X represents a chlorine atom, a bromine atom or an iodine atom; $R^{3a}$ and $R^{4a}$ may be the same or different in the definition of the above $R^3$ and $R^4$, and each represents substituted or unsubstituted lower alkyl, substituted or unsubstituted lower alkenyl, substituted or unsubstituted lower alkynyl, substituted or unsubstituted aralkyl, substituted or unsubstituted aromatic heterocyclic-alkyl, or —$COR^{12}$ (wherein $R^{12}$ has the same meaning as defined above).]

Step 1:

Compound (III) can be produced by reacting Compound (II), which is commercially available or which can be obtained, for example, according to the method described in WO03/35639, Japanese Published Unexamined Patent Application No. 193281/1999 or the like, or methods similar thereto, with 1 to 200 equivalents, preferably 1 to 5 equivalents of a halogenating agent in the absence of a solvent or in an inert solvent to the reaction, at a temperature between −30° C. and 150° C., preferably at a temperature between 0° C. and 100° C., for 5 minutes to 48 hours.

Examples of the halogenating agent include chlorine, bromine, iodine, N,N,N,N-tetra-n-butylammonium tribromide and pyridinium tribromide.

The inert solvent to the reaction is not specifically limited, and examples thereof include acetone, 1,4-dioxane, acetonitrile, chloroform, dichloromethane, tetrahydrofuran (THF), ethyl acetate, N,N-dimethylformamide (DMF), acetic acid and water. These can be used herein either singly or in a combination.

Step 2:

Compound (Ia) can be produced by reacting Compound (III) with 1 to 20 equivalents of thiourea in an inert solvent to the reaction at a temperature between −30° C. and 150° C., preferably at a temperature between room temperature and 100° C., for 5 minutes to 48 hours.

The inert solvent to the reaction is not specifically limited, and examples thereof include toluene, hexane, THF, DMF, ethanol and acetonitrile. These can be used herein either singly or in a combination.

Step 3:

Compound (Ib) can be produced by reacting Compound (III) with 1 to 100 equivalents of $R^{4a}X^1$ (wherein $R^{4a}$ has the same meaning as defined above, $X^1$ has the same meaning as X defined above), in the absence of a solvent or in an inert solvent to the reaction, optionally in the presence of 1 to 100 equivalents of a base, at a temperature between −30° C. and 150° C. for 5 minutes to 48 hours.

The inert solvent to the reaction is not specifically limited, and examples thereof include acetonitrile, dichloromethane, 1,2-dichloroethane, chloroform, 1,2-dimethoxyethane, DMF, N,N-dimethylacetamide (DMA), 1,4-dioxane, THF, diethyl ether, diisopropyl ether, benzene, toluene, xylene, pyridine, N,N-dimethylimidazolidinone (DMI), N-methylpyrrolidone (NMP) and sulforane. These can be used herein either singly or in a combination.

Examples of the base include pyridine, triethylamine, diisopropylethylamine, N-methylmorpholine, N-methylpiperidine, 1,8-diazabicyclo[5.4.0]undec-7-ene (DBU), N,N-dimethylaminopyridine (DMAP), potassium acetate, potassium carbonate, cesium carbonate, sodium carbonate, sodium hydrogencarbonate, sodium hydroxide, lithium hydroxide, potassium hydroxide and potassium phosphate. These may be used herein either singly in a combination of two or more.

Step 4:

Compound (Ic) can be produced by reacting Compound (Ib) with 1 to 100 equivalents of $R^{3a}X^2$ (wherein $R^{3a}$ has the same meaning as defined above, $X^2$ has the same meaning as X defined above), in the absence of a solvent or in an inert solvent to the reaction, optionally in the presence of 1 to 100 equivalents of a base, at a temperature between −30° C. and 150° C. for 5 minutes to 48 hours.

The inert solvent to the reaction is not specifically limited, and examples thereof include acetonitrile, dichloromethane, 1,2-dichloroethane, chloroform, 1,2-dimethoxyethane, DMF, DMA, 1,4-dioxane, THF, diethyl ether, diisopropyl ether, benzene, toluene, xylene, pyridine, DMI, NMP and sulforane. These can be used herein either singly or in a combination.

Examples of the base include pyridine, triethylamine, diisopropylethylamine, N-methylmorpholine, N-methylpiperidine, DBU, DMAP, potassium acetate, potassium carbonate, cesium carbonate, sodium carbonate, sodium hydrogencarbonate, sodium hydroxide, lithium hydroxide, potassium hydroxide and potassium phosphate. These may be used herein either singly in a combination of two or more.

<Production Method 2>

Among Compounds (I), Compounds (Ib-i) in which $R^3$ is a hydrogen atom and $R^4$ is —$COR^{12}$ (wherein $R^{12}$ has the same meaning as defined above) can also be produced according to the following step:

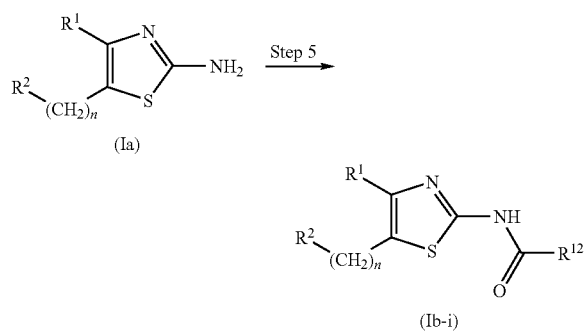

(In the formulae, $R^1$, $R^2$, $R^{12}$ and n have the same meanings as defined above, respectively.)

Step 5:

Compound (Ib-i) can be produced by reacting Compound (Ia) with 1 to 100 equivalents of $(R^{12}CO)_2O$ (wherein $R^{12}$ has the same meaning as defined above) or $R^{12}COCl$ (wherein $R^{12}$ has the same meaning as defined above), in the absence of a solvent or in an inert solvent to the reaction, optionally in the presence of 1 to 100 equivalents of a base, at a temperature between −30° C. and 150° C. for 5 minutes to 48 hours.

The inert solvent to the reaction is not specifically limited, and examples thereof include acetonitrile, dichloromethane, 1,2-dichloroethane, chloroform, 1,2-dimethoxyethane, DMF, DMA, 1,4-dioxane, THF, diethyl ether, diisopropyl ether, benzene, toluene, xylene, pyridine, DMI, NMP and sulforane. These can be used herein either singly or in a combination.

Examples of the base include pyridine, triethylamine, diisopropylethylamine, N-methylmorpholine, N-methylpiperidine; DBU, DMAP, potassium acetate, potassium carbonate, cesium carbonate, sodium carbonate, sodium hydrogencarbonate, sodium hydroxide, lithium hydroxide, potassium hydroxide and potassium phosphate. These may be used herein either singly in a combination of two or more.

As another method for it, Compound (Ib-i) can also be produced by reacting Compound (Ia) with 1 to 50 equivalents of $R^{12}COOH$ (wherein $R^{12}$ has the same meaning as defined above) in an inert solvent to the reaction, in the presence of 1 to 30 equivalents of a condensing agent, optionally in the presence of 1 to 30 equivalents of an appropriate additive, at a temperature between −30° C. and 100° C. for 5 minutes to 48 hours.

The inert solvent to the reaction is not specifically limited, and examples thereof include acetonitrile, dichloromethane, 1,2-dichloroethane, chloroform, 1,2-dimethoxyethane, DMF, DMA, 1,4-dioxane, THF, diethyl ether, diisopropyl ether, benzene, toluene, xylene, pyridine, DMI, NMP, sulforane and water. These can be used herein either singly or in a combination.

Examples of the condensing agent include dicyclohexylcarbodiimide (DCC), diisopropylcarbodiimide, N-(3-dimethylaminopropyl)-N'-ethylcarbodiimide (EDC), EDC hydrochloride, benzotriazol-1-yl-tris(dimethylamino)phosphonium hexafluorophosphate (BOP), benzotriazol-1-yl-tripyrrolidinophosphonium hexafluorophosphate (PyBOP) and diphenylphosphorylazide (DPPA).

Examples of the additive include 1-hydroxybenzotriazole hydrate and triethylamine. These can be used herein either singly or in a combination.

<Production Method 3>

Among Compounds (I), Compounds (Ib-ii) in which $R^3$ is a hydrogen atom, and $R^4$ is —$COR^{12h}$ [wherein $R^{12h}$ is in the definition of the above $R^{12}$ and represents a substituted or unsubstituted alicyclic heterocyclic group having a nitrogen atom and bonding to —CO— of —$COR^{12}$ via the nitrogen atom, —$NR^{13}R^{14}$ (wherein $R^{13}$ and $R^{14}$ have the same meaning as defined above, respectively) or —$OR^{15}$ (wherein $R^{15}$ has the same meaning as defined above)] can be produced according to the following steps:

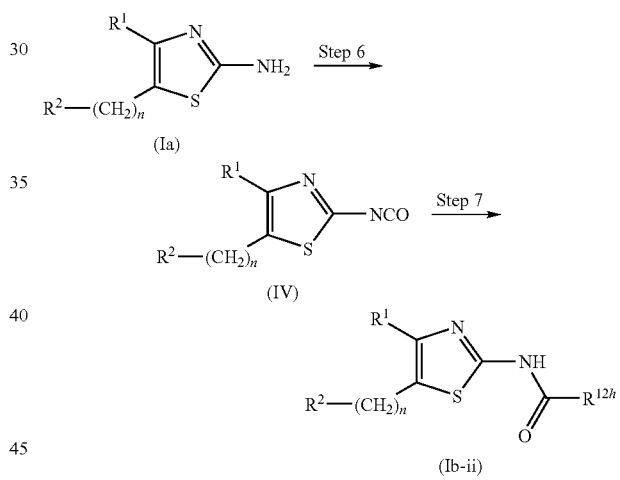

(In the formulae, $R^1$, $R^2$, $R^{12h}$ and n have the same meanings as defined above, respectively.)

Step 6:

Compound (IV) can be prepared from Compound (Ia) according to the method described in *Lecture of Experimental Chemistry* (4th ed.), Vol. 20, pp. 473-483, by the Chemical Society of Japan, Maruzen, 1992, or methods similar thereto.

Briefly, Compound (IV) can be produced by reacting Compound (Ia) with 1 to 20 equivalents of phosgene or a phosgene equivalent in the absence of a solvent or in an inert solvent to the reaction, optionally in the presence of 1 to 100 equivalents of a base, at a temperature of from −30° C. and 150° C. for 5 minutes to 72 hours.

The inert solvent to the reaction is not specifically limited, and examples thereof include acetonitrile, methanol, ethanol, dichloromethane, chloroform, 1,2-dichloroethane, 1,2-dimethoxyethane, DMF, DMA, 1,4-dioxane, THF, diethyl ether, diisopropyl ether, benzene, toluene, xylene, DMI, NMP, sulforane and water. These can be used herein either singly or in a combination. Among those, DMF or DMA is preferred.

Examples of the phosgene equivalent include triphosgene and 1,1'-dicarbonylimidazole (CDI).

Examples of the base include triethylamine, diisopropylethylamine, DBU, potassium carbonate and sodium hydroxide.

Step 7:

Compound (Ib-ii) may be produced by reacting Compound (IV) with 1 to 200 equivalents of $HR^{12h}$ (wherein $R^{12h}$ has the same meaning as defined above), in the absence of a solvent or in an inert solvent to the reaction, optionally in the presence of 1 to 100 equivalents of a base, at a temperature between −30° C. and 150° C. for 5 minutes to 72 hours.

The inert solvent to the reaction is not specifically limited, and examples thereof include acetonitrile, dichloromethane, chloroform, 1,2-dichloroethane, 1,2-dimethoxyethane, DMF, DMA, 1,4-dioxane, THF, diethyl ether, diisopropyl ether, benzene, toluene, xylene, DMI, NMP, sulforane and water. These can be used herein either singly or in a combination. Among those, DMF or DMA is preferred.

Examples of the base include triethylamine, diisopropylethylamine and DBU.

<Production Method 4>

Among Compounds (I), Compounds (Id) in which n is 0 and $R^2$ is $R^{2a}$ [$R^{2a}$ is in the definition of the above $R^2$, and represents a substituted or unsubstituted alicyclic heterocyclic group having a nitrogen atom and bonding to the thiazole ring via the nitrogen atom, or —$NR^5R^6$ (wherein $R^5$ and $R^6$ have the same meanings as defined above, respectively)] can be produced according to the following steps:

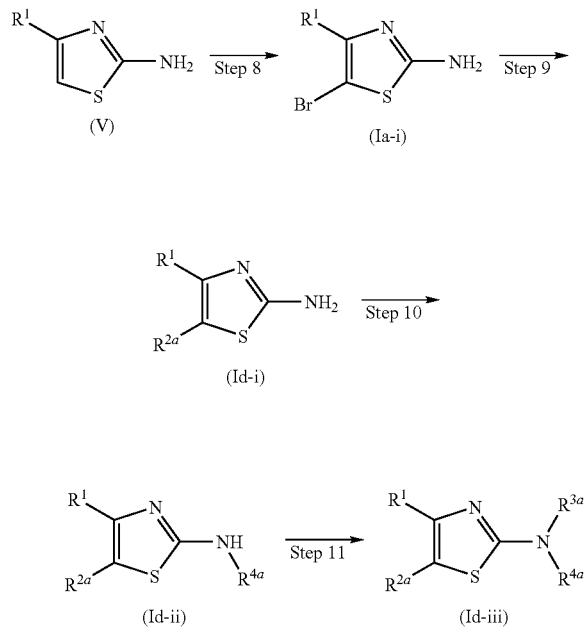

(In the formulae, $R^1$, $R^{2a}$, $R^{3a}$ and $R^{4a}$ have the same meanings as defined above, respectively.)

Step 8:

Compound (Ia-i) can be produced, for example, according to the method described in *J. Chem. Soc.*, p. 114, 1947 or methods similar thereto, by using Compound (V) which is commercially available or which can be obtained, for example, according to the method described in *J. Am. Chem. Soc.*, Vol. 72, p. 3722, 1953 or methods similar thereto.

Briefly, Compound (Ia-i) can be produced by reacting Compound (V) with 1 to 20 equivalents of a brominating agent in an inert solvent to the reaction at a temperature between −30° C. and the boiling point of the solvent used, for 5 minutes to 48 hours.

The inert solvent to the reaction is not specifically limited, and examples thereof include dichloromethane, chloroform and 1,2-dichloroethane. These can be used herein either singly or in a combination.

Examples of the brominating agent include N-bromosuccinimide, bromine and N,N,N,N-tetra-n-butylammonium bromide.

Step 9:

Among Compounds (Id), Compounds (Id-i) in which $R^3$ and $R^4$ are hydrogen atoms can be produced according to, for example, the method described in EP518731 or methods similar thereto, by using Compound (Ia-i).

Briefly, Compound (Id-i) can be produced by reacting Compound (Ia-i) with 1 to 200 equivalents of $HR^{2a}$ (wherein $R^{2a}$ has the same meaning as defined above) in the absence of a solvent or in an inert solvent to the reaction, optionally in the presence of 1 to 100 equivalents of a base, at a temperature between −30° C. and 150° C. for 5 minutes to 72 hours.

The inert solvent to the reaction is not specifically limited, and examples thereof include acetonitrile, methanol, ethanol, dichloromethane, chloroform, 1,2-dichloroethane, 1,2-dimethoxyethane, DMF, DMA, 1,4-dioxane, THF, diethyl ether, diisopropyl ether, benzene, toluene, xylene, DMI, NMP, sulforane and water. These can be used herein either singly or in a combination. Among those, DMF or DMA is preferred.

Examples of the base include triethylamine, diisopropylethylamine, DBU, potassium carbonate and sodium hydroxide.

Step 10:

Among Compounds (Id), Compounds (Id-ii) in which $R^3$ is a hydrogen atom and $R^4$ is $R^{4a}$ ($R^{4a}$ has the same meaning as defined above) can be produced in a manner similar to that in Step 3 of Production Method 1, by using Compound (Id-i).

Step 11:

Among Compounds (Id), Compounds (Id-iii) in which $R^3$ and $R^4$ are $R^{3a}$ ($R^{3a}$ has the same meaning as defined above) and $R^{4a}$ ($R^{4a}$ has the same meaning as defined above), respectively, can be produced in a manner similar to that in Step 4 of Production Method 1, by using Compound (Id-ii).

<Production Method 5>

Among Compounds (I), Compounds (Ie) in which n is 0 and $R^2$ is formyl, and Compounds (If) in which n is 1 and $R^2$ is —$NR^5R^6$ (wherein $R^5$ and $R^6$ have the same meanings as defined above, respectively) can be produced according to the following steps:

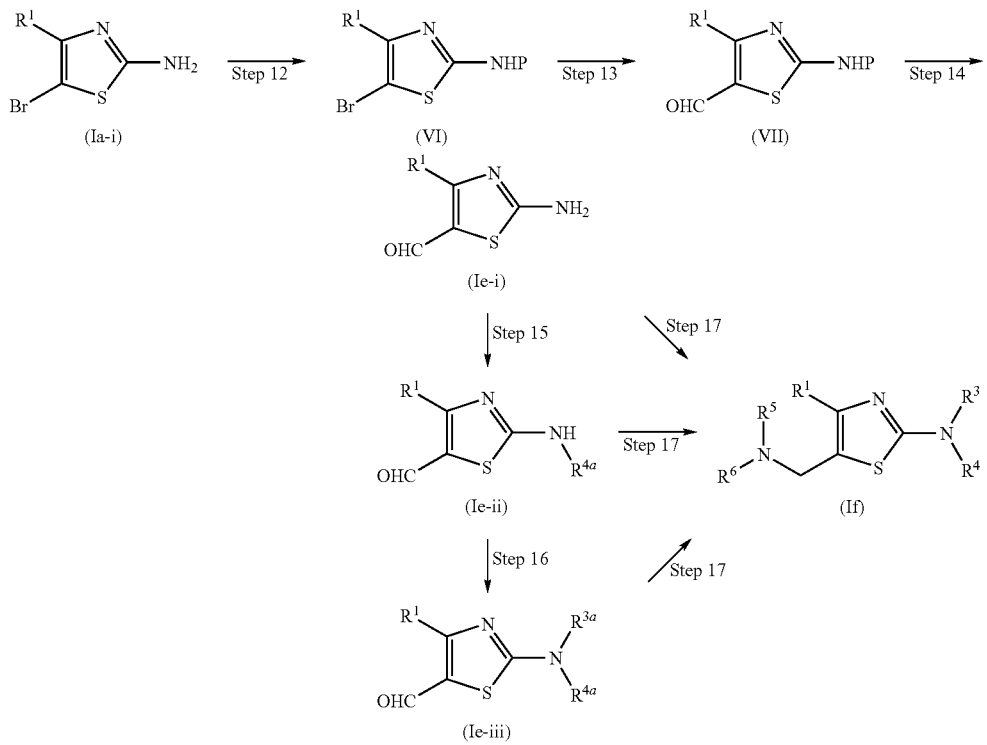

(In the formulae, $R^1$, $R^3$, $R^4$, $R^{3a}$, $R^{4a}$, $R^5$ and $R^6$ have the same meanings as defined above, respectively; p represents a protective group, and examples of the protective group include tert-butoxycarbonyl (Boc group), benzyloxycarbonyl (Z group), benzyl, acetyl or benzoyl.)

Step 12:

Compound (VI) can be produced in a manner similar to methods for introducing a protective group into an amino group, for example, as described in *Protective Groups in Organic Synthesis*, by T. W. Greene, John Wiley & Sons Inc., 1981, by using Compound (Ia-i) obtained in Step 8 of Production Method 4.

For example, among Compounds (VI), Compounds (VI-i) in which P is Boc group can be produced by reacting Compound (Ia-i) with 1 to 30 equivalents of di-tert-butyl dicarbonate in an inert solvent to the reaction, optionally in the presence of 1 to 30 equivalents of a base, at a temperature between −30° C. and the boiling point of the solvent used, for 5 minutes to 48 hours.

The inert solvent to the reaction is not specifically limited, and examples thereof include 1,2-dimethoxyethane, DMF, dioxane, THF, diethyl ether, diisopropyl ether, dichloromethane, chloroform, 1,2-dichloroethane, benzene, toluene, xylene, pyridine, NMP, DMI, sulforane and water. These can be used herein either singly or in a combination.

Examples of the base include pyridine, triethylamine, diisopropylamine, DBU, DMAP, N-methylmorpholine, N-methylpiperidine, potassium acetate, potassium carbonate, cesium carbonate, sodium carbonate, sodium hydrogencarbonate, sodium hydroxide, lithium hydroxide, potassium hydroxide and potassium phosphate. These may be used herein either singly or in a combination of two or more.

Step 13:

Compound (VII) can be produced by reacting Compound (VI) with 1 to 100 equivalents of a formylating agent in an inert solvent to the reaction in the presence of 1 to 20 equivalents of a base, at a temperature between −78° C. and room temperature, for 5 minutes to 48 hours.

The inert solvent to the reaction is not specifically limited, and examples thereof include THF, diethyl ether, 1,4-dioxane, 1,2-dimethoxyethane and hexane. These can be used herein either singly or in a combination.

Examples of the formylating agent include DMF, N-methyl-N-phenylformamide, N-methyl-N-(2-pyridyl)formamide and morpholinoformamide. Among those, DMF is preferred.

Examples of the base include lithium diisopropylamide, lithium bis(trimethylsilyl)amide, methyllithium, n-butyllithium, lithium hydride, sodium hydride, potassium hydride, methylmagnesium bromide, ethylmagnesium bromide and isopropylmagnesium chloride. These may be used herein either singly in a combination of two or more.

Step 14:

Among Compounds (Ie), Compounds (Ie-i) in which $R^3$ and $R^4$ are hydrogen atoms can be produced in a manner similar to methods for removing a protective group, for example, as described in Protective Groups in Organic Synthesis, by T. W. Greene, John Wiley & Sons Inc., 1981, by using Compound (VII).

For example, when P is Boc group, Compound (Ie-i) can be produced by reacting Compound (VII) with 1 equivalent to a large excessive, amount of an acid in the absence of a solvent or in an inert solvent to the reaction, at a temperature between −30° C. and 150° C. for 5 minutes to 48 hours.

The inert solvent to the reaction is not specifically limited, and examples thereof include dichloromethane, chloroform, 1,2-dichloroethane, methanol, ethanol, THF, ethyl acetate and water. These can be used herein either singly or in a combination.

Examples of the acid include trifluoroacetic acid, hydrochloric acid and sulfuric acid.

Step 15:

Among Compounds (Ie), Compounds (Ie-ii) in which $R^3$ is a hydrogen atom and $R^4$ is $R^{4a}$ ($R^{4a}$ has the same meaning as defined above) can be produced in a manner similar to that in Step 3 of Production Method 1, by using Compound (Ie-i).

Step 16:

Among Compounds (Ie), Compounds (Ie-iii) in which $R^3$ is $R^{3a}$ ($R^{3a}$ has the same meaning as defined above) and $R^4$ is $R^{1a}$ ($R^{4a}$ has the same meaning as defined above) can be produced in a manner similar to that in Step 4 of Production Method 1, by using Compound (Ie-ii).

Step 17:

Compound (If) can be produced by reacting Compound (Ie-i), Compound (Ie-ii) or Compound (Ie-iii) with 1 to 200 equivalents of $HNR^5R^6$ (wherein $R^5$ and $R^6$ have the same meanings as defined above, respectively) in an inert solvent to the reaction in the presence of 1 to 50 equivalents of a reducing agent, at a temperature between −30° C. and the boiling point of the solvent used, for 5 minutes to 48 hours.

Examples of the reducing agent include sodium triacetoxyborohydride, sodium borohydride and sodium cyanoborohydride. Among those, sodium triacetoxyborohydride is preferred.

The inert solvent to the reaction is not specifically limited, and examples thereof include methanol, ethanol, dichloromethane, chloroform, 1,2-dichloroethane, THF, 1,4-dioxane, diethyl ether, diisopropyl ether, benzene, toluene, xylene, DMF and water. These can be used herein either singly or in a combination.

<Production Method 6>

Among Compounds (I), Compounds (Ih) in which $R^2$ is —COOH, and Compounds (Ii) in which $R^2$ is —COR$^{8b}$ [wherein $R^{8b}$ is in the definition of the above $R^8$, and represents a substituted or unsubstituted alicyclic heterocyclic group having a nitrogen atom and bonding to —CO— of —COR$^8$ via the nitrogen atom, or —NR$^9$R$^{10}$ (wherein $R^9$ and $R^{10}$ have the same meanings as defined above, respectively)] can be produced according to the following steps:

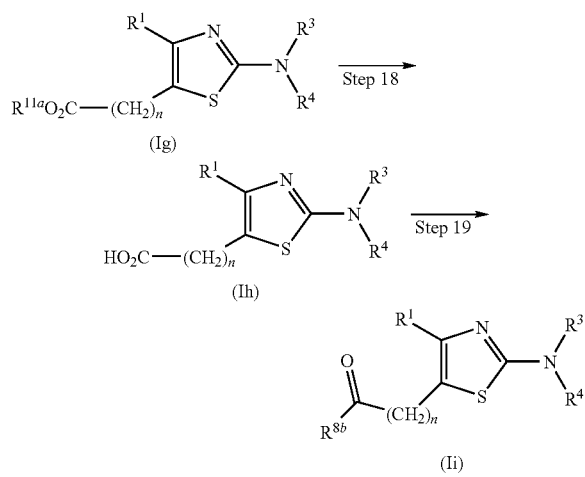

(In the formulae, $R^1$, $R^3$, $R^4$, $R^3$ and n have the same meanings as defined above, respectively; $R^{11a}$ is in the definition of the above $R^{11}$, and represents lower alkyl or benzyl.)

Step 18:

Compound (Ih) can be produced for example, in a manner similar to methods for removing a protective group as described in Protective Groups in Organic Synthesis, by T. W. Greene, John Wiley & Sons Inc., 1981, by using Compound (Ig) in which $R^2$ is —COOR$^{11a}$ (wherein $R^{11a}$ has the same meaning as defined above) among Compounds (I) obtained according to Production Method 1.

For example, when $R^{11a}$ is methyl or ethyl, Compound (Ih) can be produced by treating Compound (Ig) with 1 equivalent to a large excessive amount of a base in a solvent containing water, at a temperature between 0° C. and the boiling point of the solvent used for 5 minutes to 48 hours.

The solvent is not specifically limited, and examples thereof include methanol, ethanol, propanol, THF, 1,4-dioxane, 1,2-dimethoxyethane, toluene, dichloromethane and DMF. These can be used herein either singly or in a combination.

Examples of the base include sodium hydroxide, potassium hydroxide and lithium hydroxide.

Further, for example, when $R^{11a}$ is tert-butyl, Compound (Ih) can be produced by treating Compound (Ig) with 1 equivalent to a large excessive amount of an acid in the absence of a solvent or in an inert solvent to the reaction, at a temperature between −30° C. and 100° C. for 5 minutes to 48 hours.

The inert solvent to the reaction is not specifically limited, and examples thereof include methanol, ethanol, propanol, THF, 1,4-dioxane, 1,2-dimethoxyethane, toluene, ethyl acetate, dichloromethane, DMF and water. These can be used herein either singly or in a combination.

Examples of the acid include trifluoroacetic acid, hydrochloric acid and sulfuric acid.

Step 19:

Compound (Ii) can be produced by reacting Compound (Ih) with 1 to 100 equivalents of $HR^{8b}$ (wherein $R^{8b}$ has the same meaning as defined above) in the absence of a solvent or in an inert solvent to the reaction in the presence of 1 to 30 equivalents of an appropriate condensing agent and optionally in the presence of 1 to 30 equivalents of an appropriate additive, at a temperature between −30° C. and 100° C. for 5 minutes to 72 hours.

The solvent is not specifically limited, and examples thereof include acetonitrile, dichloromethane, 1,2-dichloroethane, chloroform, 1,2-dimethoxyethane, DMF, DMA, 1,4-dioxane, THF, diethyl ether, diisopropyl ether, benzene, toluene, xylene, pyridine, DMI, NMP, sulforane and water. These can be used herein either singly or in a combination.

Examples of the condensing agent include DCC, diisopropylcarbodiimide, EDC, EDC hydrochloride, BOP, PyBOP and DPPA.

Examples of the additive include 1-hydroxybenzotriazole hydrate and triethylamine, and these be used herein either singly or in a combination.

<Production Method 7>

Among Compounds (I), Compounds (Ij) in which $R^2$ is —COR$^{8c}$ (wherein $R^{8c}$ is in the definition of the above $R^8$, and represents substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted alicyclic heterocyclic group, substituted or unsubstituted alicyclic heterocyclicalkyl, a substituted or unsubstituted aromatic heterocyclic group, or substituted or unsubstituted aromatic heterocyclicalkyl) can be produced according to the following steps:

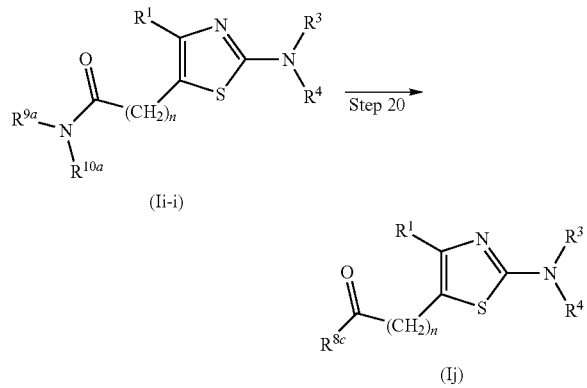

(In the formulae, $R^1$, $R^3$, $R^4$, $R^{8c}$ and n have the same meanings as defined above, respectively; $R^{9a}$ represents the same lower alkoxy as above; and $R^{10a}$ represents the same lower alkyl as defined above.)

Step 20:

Compound (Ij) can be produced by reacting Compound (Ii-i) obtained in Production Method 6 with 1 to 50 equivalents of $R^{8c}M$ (wherein $R^{8c}$ has the same meaning as defined above; M represents a metal group of MgCl, MgBr, MgI, Li, $ZnCH_3$, $ZnCH_2CH_3$, $Ti(OCH(CH_3)_2)_2$ or the like), in an inert solvent to the reaction at a temperature between $-78°$ C. and the boiling point of the solvent used for 5 minutes to 48 hours.

The inert solvent to the reaction is not specifically limited, and examples thereof include diethyl ether, THF, 1,4-dioxane, 1,2-dimethoxyethanea and toluene. These can be used herein either singly or in a combination.

<Production Method 8>

Among Compounds (I), Compounds (Ij-i) in which n is 0 and $R^2$ is $—COR^{8c}$ (wherein $R^{8c}$ has the same meaning as defined above) can be produced according to the following steps:

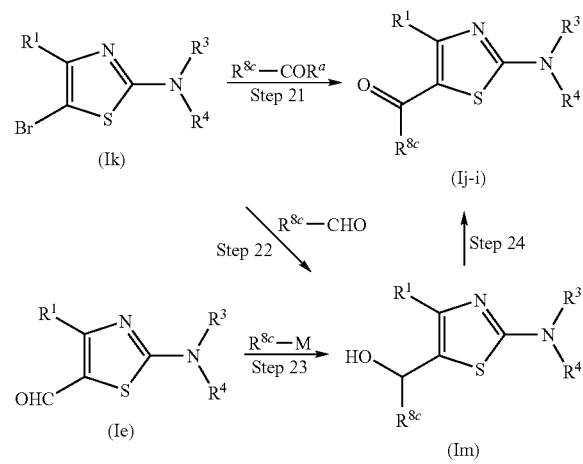

[In the formulae, $R^1$, $R^3$, $R^4$, $R^{8c}$ and M have the same meanings as defined above, respectively; $R^a$ has the same lower alkoxy as defined above, or represents $—NR^{b1}R^{b2}$ (wherein $R^{b1}$ and $R^{b2}$ may be the same or different, and each represents the same lower alkyl as defined above or the same lower alkoxy as defined above).]

Step 21:

Compound (Ij-i) can be produced by reacting Compound (Ik) with 1 to 100 equivalents of $R^{8c}—COR^a$ in an inert solvent to the reaction in the presence of 1 to 20 equivalents of a base, at a temperature between $-78°$ C. and room temperature for 5 minutes to 48 hours.

Compounds (Ia-i) obtained in Step 8 of Production Method 4; or compounds obtained from Compound (Ia-i) in a manner similar to that in Step 3 of Production Method 1 or in Step 3 and Step 4 of Production Method 1 are used as the starting Compound (Ik).

The inert solvent to the reaction is not specifically limited, and examples thereof include THF, diethyl ether, 1,4-dioxane, 1,2-dimethoxyethane and hexane. These can be used herein either singly or in a combination.

Examples of the base include lithium diisopropylamide, lithium bis(trimethylsilyl)amide, methyllithium, n-butyllithium, lithium hydride, sodium hydride, potassium hydride, methylmagnesium bromide, ethylmagnesium bromide and isopropylmagnesium chloride. These may be used herein either singly in a combination of two or more.

Step 22:

Compound (Im) can be produced by reacting Compound (Ik) with 1 to 100 equivalents of $R^{8a}CHO$ in an inert solvent to the reaction in the presence of 1 to 20 equivalents of a base at a temperature between $-78°$ C. and room temperature for 5 minutes to 48 hours.

The inert solvent to the reaction is not specifically limited, and examples thereof include THF, diethyl ether, 1,4-dioxane, 1,2-dimethoxyethane and hexane. These can be used herein either singly or in a combination.

Examples of the base include lithium diisopropylamide, lithium bis(trimethylsilyl)amide, methyllithium, n-butyllithium, lithium hydride, sodium hydride, potassium hydride, methylmagnesium bromide, ethylmagnesium bromide and isopropylmagnesium chloride. These may be used herein either singly in a combination of two or more can be used a mixture with Step 23:

Compound (Im) can also be produced by reacting Compound (Ie) obtained in Production Method 5, with 1 to 50 equivalents of $R^{8c}M$ (wherein $R^{8c}$ and M have the same meanings as defined above, respectively) in an inert solvent to the reaction at a temperature between $-78°$ C. and the boiling point of the solvent used, for 5 minutes to 48 hours.

The inert solvent to the reaction is not specifically limited, and examples thereof include diethyl ether, THF, 1,4-dioxane, 1,2-dimethoxyethane and toluene. These can be used herein either singly or in a combination.

Step 24:

Compound (Ij-i) can be produced by treating Compound (Im) with 1 to 100 equivalents of an oxidizing agent in the absence of a solvent or a solvent inert to the reaction at a temperature between $-78°$ C. and the boiling point of the solvent used, for 5 minutes to 48 hours.

The inert solvent to the reaction is not specifically limited, and examples thereof include acetonitrile, dichloromethane, 1,2-dichloroethane, chloroform, 1,2-dimethoxyethane, DMF, DMA, 1,4-dioxane, THF, diethyl ether, diisopropyl ether, benzene, toluene, xylene, pyridine, DMI, NMP, sulforane and water. These can be used herein either singly or in a combination.

Examples of the oxidizing agent include chromic acid, pyridinium chlorochromate (PCC), pyridinium dichromate (PDC), dimethylsulfoxide (DMSO)-oxalyl chloride, DMSO-dicyclohexylimide (DCC), tetrapropylammonium perruthenate (TPAP), Dess-Martin reagent (DMP: 1,1,1-triacetoxy-1,1-dihydro-1,2-benziodoxol-3(1H)-one, *Lecture of Experimental Chemistry,* 5th Ed., Vol. 15, p. 27, by the Chemical Society of Japan, Maruzen, 2003), 2-iodoxylbenzoic acid (IBX), 2,2,6,6-tetramethylpiperidine-N-oxide (TEMPO) and manganese dioxide.

Further, the transformation of the functional group contained in $R^1$, $R^2$, $R^3$ or $R^4$ in Compounds (I) can be carried out according to any known methods other than the above-described steps (for example, methods described in Comprehensive Organic Transformations, by R. C. Larock, 1989) or methods similar thereto.

By appropriately combining the above-described processes and the like, Compounds (I) having desired functional groups at desired positions can be obtained.

The intermediates and the desired compounds in the above-described production processes can be isolated and purified by appropriately combining separation and purification methods conventionally used in synthetic organic chemistry, for example, filtration, extraction, washing, drying, concentration, recrystallization, and various kinds of chromatography. The intermediates can also be subjected to the subsequent reactions without purification.

For some of Compounds (I), there may exist stereoisomers such as regioisomers, geometrical isomers, optical isomers, tautomers, and all possible isomers including them and mixtures thereof can be used for the adenosine $A_{2A}$ receptor antagonists of the present invention.

When it is desired to obtain a salt of Compound (I), in the case where Compound (I) is produced in the form of the salt, it can be purified as such, but where it is produced in the free state, it can be converted into a salt by dissolving or suspending it in an appropriate solvent and then adding an acid or a base thereto.

Further, Compounds (I) and pharmaceutically acceptable salts thereof may exist in the form of adducts with water or various solvents, and these adducts can also be used for the adenosine $A_{2A}$ receptor antagonist of the present invention.

Specific examples of Compounds (I) obtained in the present invention are shown in Table 1 to Table 8. However, the compounds usable in the present invention or the compounds of the present invention should not be limited to these.

TABLE 1

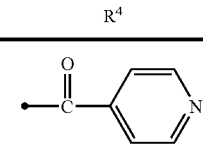

TABLE 2

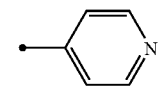

TABLE 2-continued
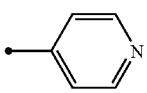
(I)
| Compound No. | R² | R⁴ |
|---|---|---|
| 5 | 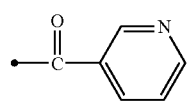 | 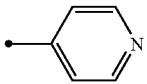 |
| 6 | 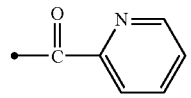 | 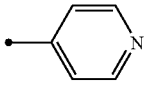 |
| 7 | 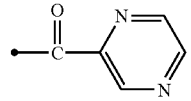 | 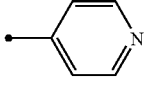 |
| 8 | 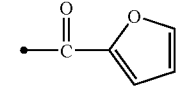 | 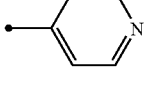 |
| 9 | 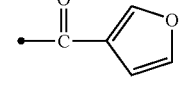 | 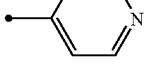 |
| 10 | 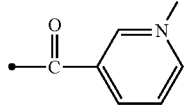 | 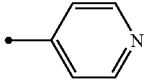 |
| 11 | 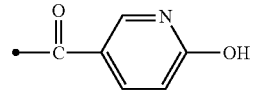 | 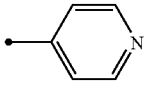 |
| 12 | 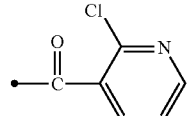 | 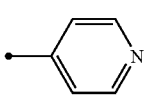 |
| 13 | 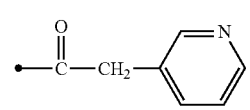 | 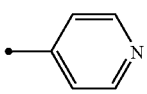 |
| 14 | 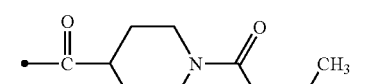 |  |
| 15 | 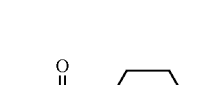 | |

TABLE 2-continued
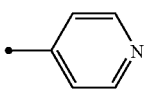
(I)
| Compound No. | R² | R⁴ |
|---|---|---|
| 16 | 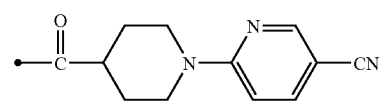 | 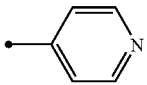 |
| 17 | 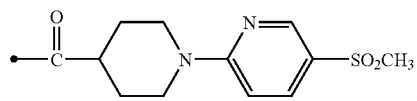 | 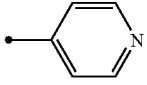 |
| 18 | 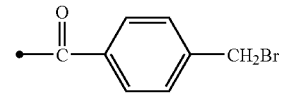 | 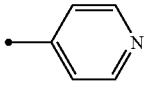 |
| 19 | 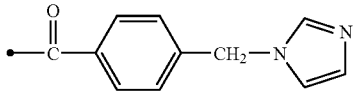 | 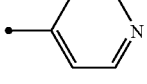 |
| 20 | 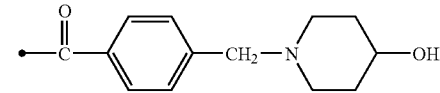 | 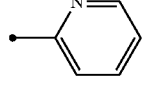 |
| 21 | 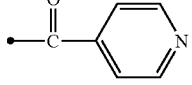 | 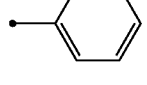 |
| 22 | 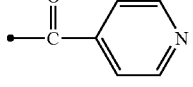 | 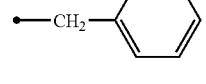 |
| 23 | 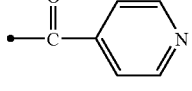 | 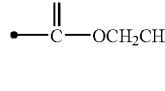 |
| 24 | 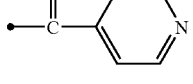 | 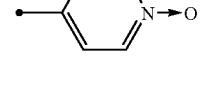 |
| 25 | 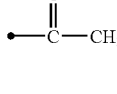 |  |
| 26 | —CH₃ | 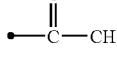 |
| 27 | 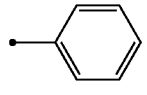 | 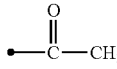 |

TABLE 2-continued

Structure (I): 4-(furan-2-yl)-N-R⁴-thiazol-2-amine with R² at 5-position

| Compound No. | R² | R⁴ |
|---|---|---|
| 28 | phenyl | –C(=O)–cyclohexyl |
| 29 | morpholin-4-yl | –C(=O)–(pyridin-4-yl) |
| 30 | morpholin-4-yl | –C(=O)–CH₃ |
| 31 | morpholin-4-yl | –C(=O)–(pyridin-3-yl) |
| 32 | morpholin-4-yl | –C(=O)–(6-chloropyridin-3-yl) |
| 33 | morpholin-4-yl | –C(=O)–(6-(2-hydroxyethylamino)pyridin-3-yl) |
| 34 | morpholin-4-yl | –C(=O)–(6-morpholin-4-yl-pyridin-3-yl) |
| 35 | morpholin-4-yl | –C(=O)–(6-(4-methylpiperazin-1-yl)pyridin-3-yl) |
| 36 | morpholin-4-yl | –C(=O)–(6-(chloromethyl)pyridin-3-yl) |
| 37 | morpholin-4-yl | –C(=O)–(6-(imidazol-1-ylmethyl)pyridin-3-yl) |
| 38 | morpholin-4-yl | –C(=O)–(6-((4-hydroxypiperidin-1-yl)methyl)pyridin-3-yl) |
| 39 | morpholin-4-yl | –C(=O)–(2-chloropyridin-4-yl) |

TABLE 2-continued
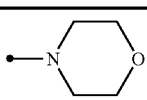
(I)
| Compound No. | R² | R⁴ |
|---|---|---|
| 40 | 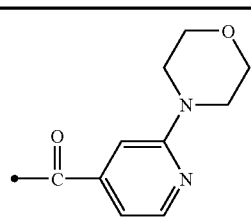 | 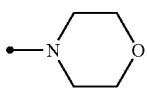 |
| 41 | 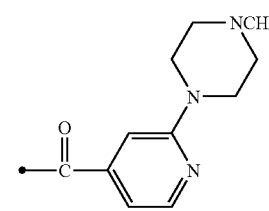 | 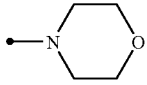 |
| 42 | 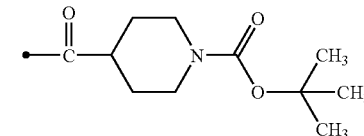 | 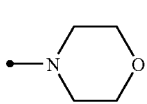 |
| 43 | 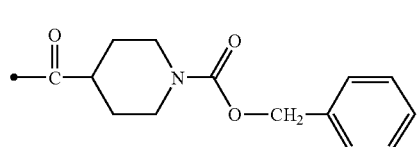 | 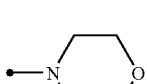 |
| 44 | 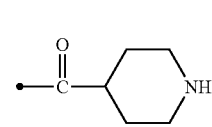 | 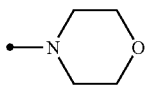 |
| 45 | 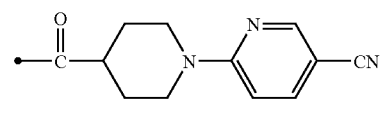 | 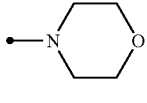 |
| 46 | 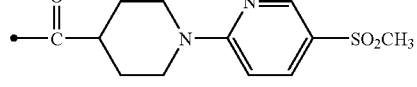 | 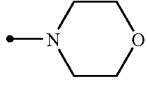 |
| 47 | 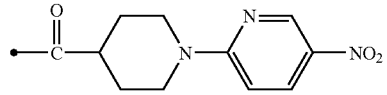 | 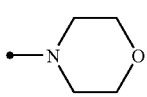 |
| 48 | 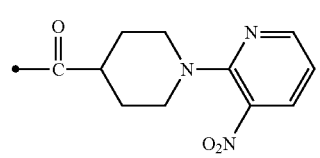 |  |

TABLE 2-continued

Structure (I): 4-(furan-2-yl)-thiazole with R² at 5-position and NH-R⁴ at 2-position.

| Compound No. | R² | R⁴ |
|---|---|---|
| 49 | morpholin-4-yl | -C(O)-[piperidin-4-yl]-N-(pyrimidin-2-yl) |
| 50 | morpholin-4-yl | -C(O)-[piperidin-4-yl]-N-(pyrazin-2-yl) |
| 51 | morpholin-4-yl | -C(O)-[piperidin-4-yl]-N-(6-chloropyrimidin-4-yl) |
| 52 | morpholin-4-yl | -C(O)-[piperidin-4-yl]-N-(pyrimidin-4-yl) |
| 53 | morpholin-4-yl | -C(O)-[piperidin-4-yl]-N-(6-chloropyridazin-3-yl) |
| 54 | morpholin-4-yl | -C(O)-[piperidin-4-yl]-N-COCH$_3$ |
| 55 | morpholin-4-yl | -C(O)-[piperidin-4-yl]-N-CON(CH$_3$)$_2$ |
| 56 | morpholin-4-yl | -C(O)-[piperidin-4-yl]-N-C(O)-morpholin-4-yl |
| 57 | morpholin-4-yl | -C(O)-[piperidin-4-yl]-N-SO$_2$CH$_3$ |
| 58 | morpholin-4-yl | -C(O)-[piperidin-4-yl]-N-SO$_2$N(CH$_3$)$_2$ |
| 59 | morpholin-4-yl | -C(O)-C$_6$H$_4$-CH$_2$Br (para) |

TABLE 2-continued

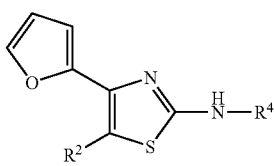
(I)

| Compound No. | R² | R⁴ |
|---|---|---|
| 60 | morpholin-4-yl | —C(O)—C₆H₄—CH₂—(imidazol-1-yl) |
| 61 | morpholin-4-yl | —C(O)—C₆H₄—CH₂—N(4-hydroxypiperidin-1-yl) |
| 62 | morpholin-4-yl | —C(O)—C₆H₄—CH₂—(morpholin-4-yl) |
| 63 | morpholin-4-yl | —C(O)—C₆H₄—CH₂—N(CH₃)CH₂CH₂OCH₃ |
| 64 | morpholin-4-yl | —C(O)—C₆H₄—CH₂—(2-oxopiperidin-1-yl) |
| 65 | morpholin-4-yl | —C(O)—C₆H₄—CH₂—(2-oxopyridin-1-yl) |
| 66 | 4-methylpiperazin-1-yl | —C(O)-(pyridin-4-yl) |
| 67 | 4-ethylpiperazin-1-yl | —C(O)-(pyridin-4-yl) |
| 68 | 4-benzylpiperazin-1-yl | —C(O)-(pyridin-4-yl) |
| 69 | thiomorpholin-4-yl | —C(O)-(pyridin-4-yl) |
| 70 | 1-oxothiomorpholin-4-yl | —C(O)-(pyridin-4-yl) |

TABLE 2-continued

Structure (I): 4-(furan-2-yl)-thiazole with R² at 5-position and NH-R⁴ at 2-position.

| Compound No. | R² | R⁴ |
|---|---|---|
| 71 | thiomorpholine-1,1-dioxide-4-yl (N-linked) | C(=O)-(pyridin-4-yl) |
| 72 | piperidin-1-yl | C(=O)-(pyridin-4-yl) |
| 73 | 2-methylpiperidin-1-yl | C(=O)-(pyridin-4-yl) |
| 74 | 4-oxopiperidin-1-yl | C(=O)-(pyridin-4-yl) |
| 75 | 3,4-dihydroisoquinolin-2(1H)-yl | C(=O)-(pyridin-4-yl) |
| 76 | —N(CH₃)₂ | C(=O)-(pyridin-4-yl) |
| 77 | —N(CH₃)CH₂CH₂OCH₃ | C(=O)-(pyridin-4-yl) |
| 78 | —N(CH₃)CH₂CH₂-(pyridin-2-yl) | C(=O)-(pyridin-4-yl) |
| 79 | 4-benzylpiperazin-1-yl | C(=O)—CH₃ |
| 80 | piperazin-1-yl | C(=O)—CH₃ |
| 81 | 3,4-dihydroisoquinolin-2(1H)-yl | C(=O)—CH₃ |

TABLE 2-continued
(I)
| Compound No. | R² | R⁴ |
|---|---|---|
| 82 | 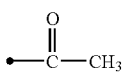 | 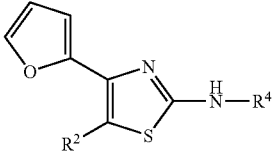 |
| 83 | 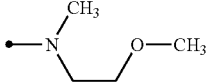 | 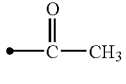 |
| 84 | 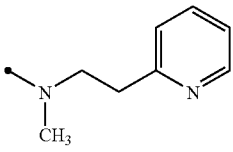 | 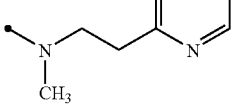 |
| 85 | —CHO | 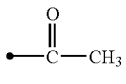 |
| 86 | 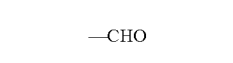 | 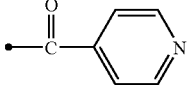 |
| 87 | 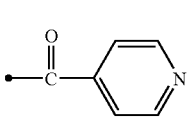 | 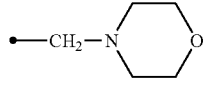 |
| 88 | 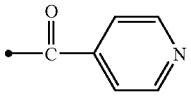 |  |
| 89 | 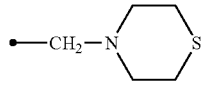 | 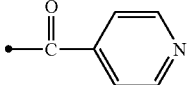 |
| 90 | 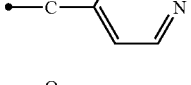 | 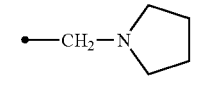 |
| 91 | 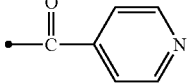 | 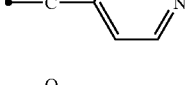 |
| 92 | —CHO | 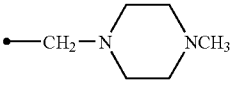 |

TABLE 2-continued (I)

| Compound No. | R² | R⁴ |
|---|---|---|
| 93 | —CH₂—N(morpholine) | —C(O)—OC(CH₃)₃ |
| 94 | —CH₂—N(morpholine) | —C(O)-(3-pyridyl) |
| 95 | —C(O)—OH | —C(O)-(4-pyridyl) |
| 96 | —C(O)—N(morpholine) | —C(O)-(4-pyridyl) |
| 97 | —C(O)—N(CH₃)₂ | —C(O)-(4-pyridyl) |
| 98 | —C(O)—N(OCH₃)(CH₃) | —C(O)-(4-pyridyl) |
| 99 | —C(O)-phenyl | —C(O)-(4-pyridyl) |

TABLE 3

(I)

| Compound No. | R² | R⁴ | Z |
|---|---|---|---|
| 100 | —N(morpholine) | —C(O)-(4-pyridyl) | —Br |

TABLE 4

(I)

| Compound No. | R² | R⁴ |
|---|---|---|
| 101 | 4-pyridyl | benzoyl (C(=O)-phenyl) |
| 102 | 4-pyridyl | 4-fluorobenzoyl |
| 103 | 4-pyridyl | 4-methoxybenzoyl |
| 104 | 4-pyridyl | pivaloyl (C(=O)-C(CH₃)₃) |
| 105 | 4-pyridyl | 2-methoxypyridine-4-carbonyl |
| 106 | 4-pyridyl | 2-(4-methoxybenzyloxy)pyridine-4-carbonyl |
| 107 | 4-pyridyl | 2-(chloromethyl)pyridine-4-carbonyl |
| 108 | 4-pyridyl | 2-(1H-imidazol-1-ylmethyl)pyridine-4-carbonyl |
| 109 | 4-pyridyl | 2-{[(2-(dimethylamino)ethyl)(methyl)amino]methyl}pyridine-4-carbonyl |

TABLE 4-continued (I)

| Compound No. | R² | R⁴ |
|---|---|---|
| 110 | 3-pyridyl | -C(O)-(2-((N-methyl-N-(2-methoxyethyl)amino)methyl)pyridin-4-yl) |
| 111 | 4-pyridyl | -C(O)-(2-((4-hydroxypiperidin-1-yl)methyl)pyridin-4-yl) |
| 112 | 4-pyridyl | -C(O)-(2-oxo-1,2-dihydropyridin-4-yl) |
| 113 | 4-pyridyl | -C(O)-(1-benzyl-2-oxo-1,2-dihydropyridin-4-yl) |
| 114 | 3-methylpyridin-4-yl | -C(O)-(pyridin-4-yl) |
| 115 | 2-furyl | -C(O)-phenyl |
| 116 | 2-thienyl | -C(O)-phenyl |
| 117 | 1-methylindol-2-yl | -C(O)-phenyl |
| 118 | 2-methylphenyl | -C(O)-(pyridin-4-yl) |

TABLE 4-continued
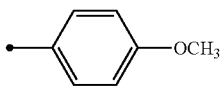
(I)
| Compound No. | R² | R⁴ |
|---|---|---|
| 119 | 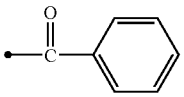 | 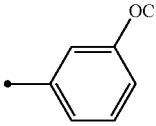 |
TABLE 5
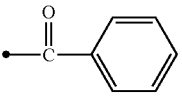
(I)
| Compound No. | R² | R⁴ |
|---|---|---|
| 120 | 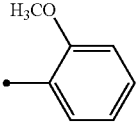 | 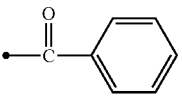 |
| 121 | 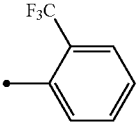 | 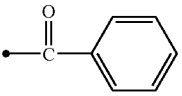 |
| 122 | 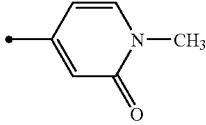 | 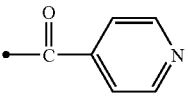 |
| 123 | 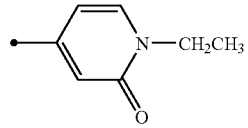 | 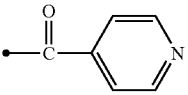 |
| 124 | 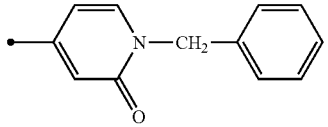 | 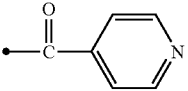 |
| 125 | | |

TABLE 5-continued
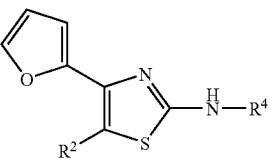
(I)
| Compound No. | R² | R⁴ |
|---|---|---|
| 126 | 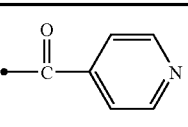 | 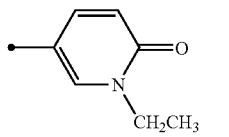 |
| 127 | 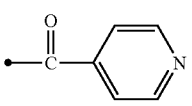 | 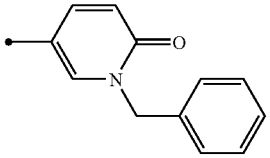 |
| 128 | 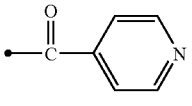 | 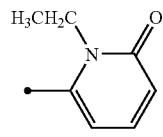 |
| 129 | 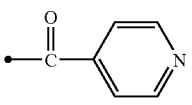 | 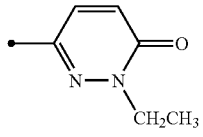 |
| 130 | 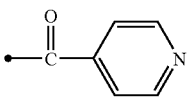 | 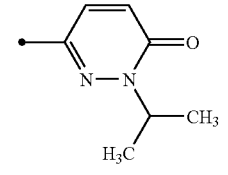 |
| 131 | 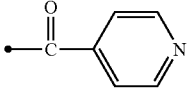 | 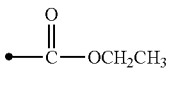 |
| 132 | 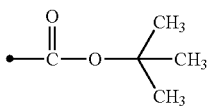 | 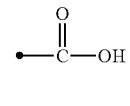 |
| 133 | 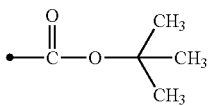 | 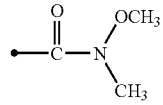 |
| 134 | 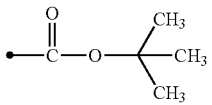 | |

TABLE 5-continued
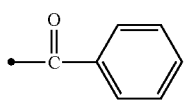
(I)
| Compound No. | R² | R⁴ |
|---|---|---|
| 135 | 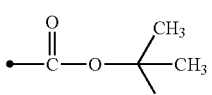 | 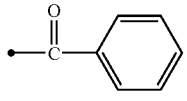 |
| 136 | 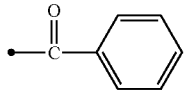 | —H |
| 137 | 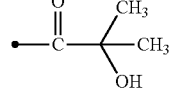 | 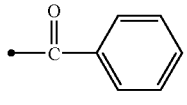 |
| 138 | 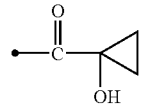 | 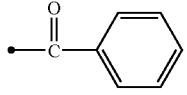 |
| 139 | 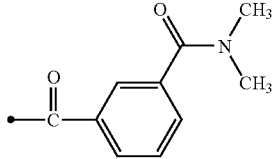 | 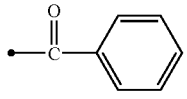 |
| 140 | 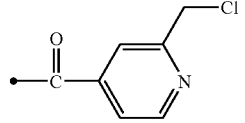 | 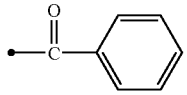 |
| 141 | 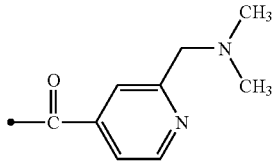 | 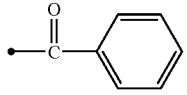 |
| 142 | 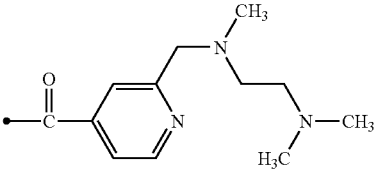 | 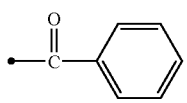 |
| 143 | 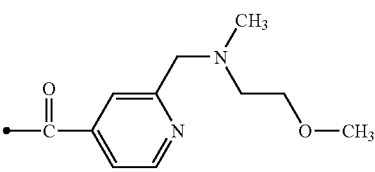 | |

TABLE 5-continued
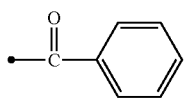
(I)
| Compound No. | R² | R⁴ |
|---|---|---|
| 144 | 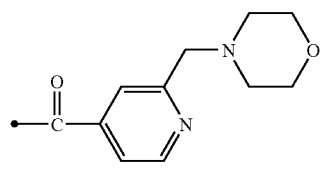 | 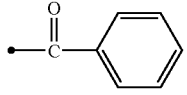 |
| 145 | 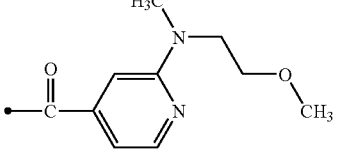 | 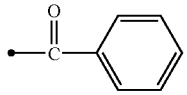 |
| 146 | 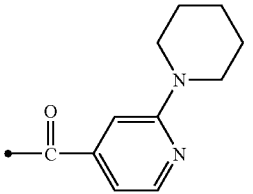 | 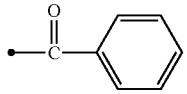 |
| 147 | 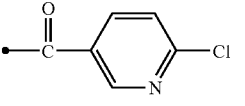 | 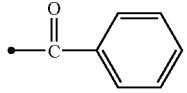 |
| 148 | 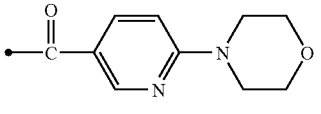 | 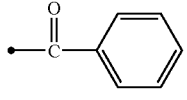 |
| 149 | 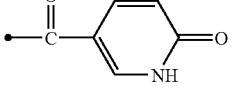 | 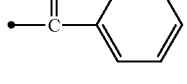 |
| 150 | 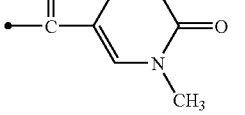 | 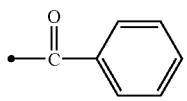 |
| 151 | 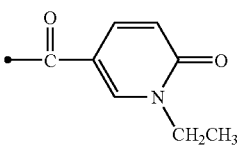 | |

TABLE 5-continued
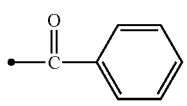
(I)
| Compound No. | R² | R⁴ |
|---|---|---|
| 152 | 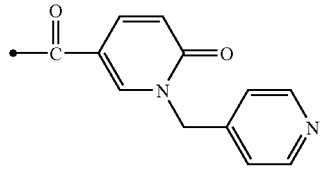 | 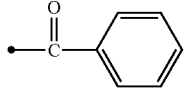 |
| 153 | 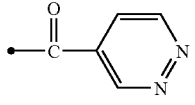 | 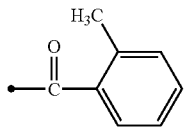 |
| 154 | 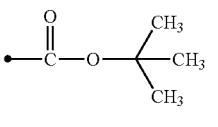 | 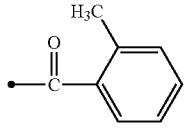 |
| 155 | 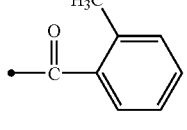 | —H |
| 156 | 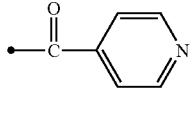 | 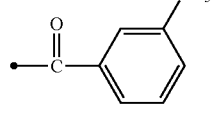 |
| 157 | 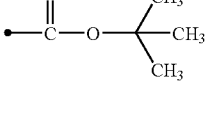 | 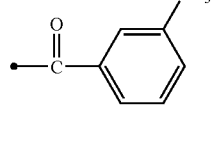 |
| 158 | 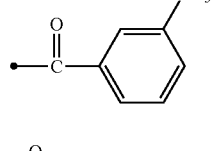 | —H |
| 159 | 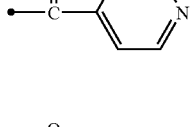 | 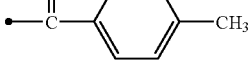 |
| 160 | 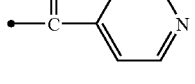 | |

TABLE 5-continued

| Compound No. | R² | R⁴ |
|---|---|---|
| 161 | 2-methoxybenzoyl | -C(=O)O-C(CH₃)₃ |
| 162 | 2-methoxybenzoyl | —H |
| 163 | 2-methoxybenzoyl | isonicotinoyl (4-pyridyl-C(=O)-) |
| 164 | 3-methoxybenzoyl | isonicotinoyl |
| 165 | 4-methoxybenzoyl | isonicotinoyl |
| 166 | 2-fluorobenzoyl | -C(=O)O-C(CH₃)₃ |
| 167 | 2-fluorobenzoyl | —H |
| 168 | 2-fluorobenzoyl | isonicotinoyl |
| 169 | 3-fluorobenzoyl | isonicotinoyl |
| 170 | 4-fluorobenzoyl | isonicotinoyl |

TABLE 5-continued
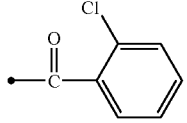
(I)
| Compound No. | R² | R⁴ |
|---|---|---|
| 171 | 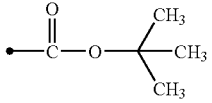 | 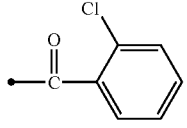 |
| 172 | 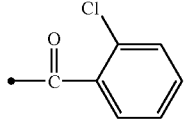 | —H |
| 173 | 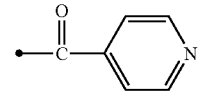 | 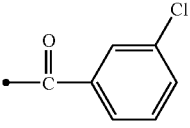 |
| 174 | 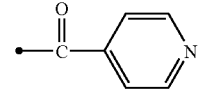 | 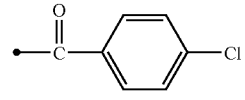 |
| 175 | 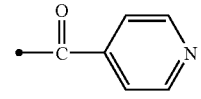 | 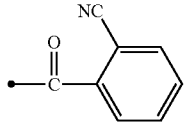 |
| 176 | 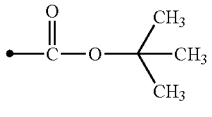 | 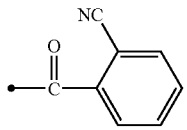 |
| 177 | 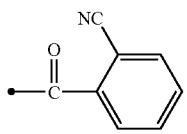 | —H |
| 178 | 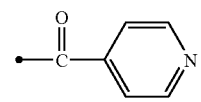 | 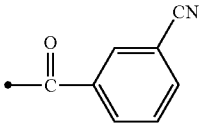 |
| 179 | 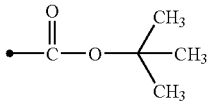 | |

TABLE 5-continued
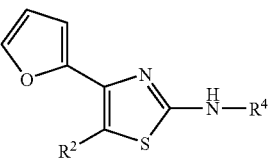
(I)
| Compound No. | R² | R⁴ |
|---|---|---|
| 180 | 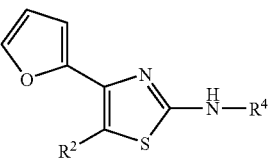 | —H |
| 181 | 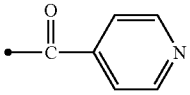 | 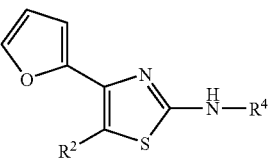 |
| 182 | 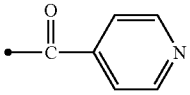 | 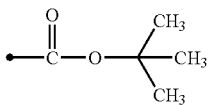 |
| 183 | 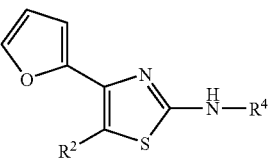 | —H |
| 184 | 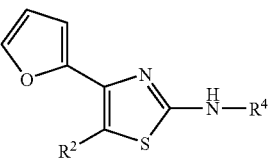 | 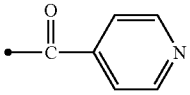 |
| 185 | 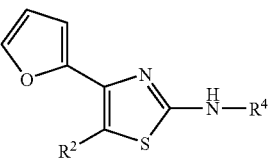 | 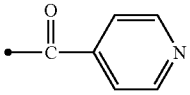 |
| 186 | 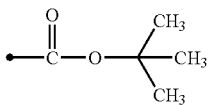 | —H |
| 187 | 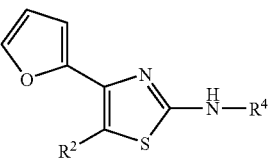 | 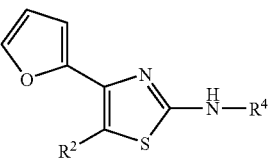 |
| 188 | 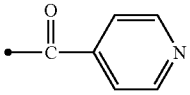 | 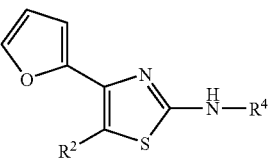 |
| 189 | 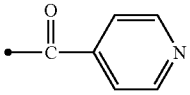 | 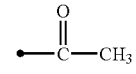 |
| 190 | 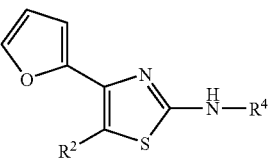 | 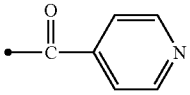 |

TABLE 5-continued (I)

| Compound No. | R² | R⁴ |
|---|---|---|
| 191 | –C(O)-(2-pyridyl) | –C(O)-cyclopropyl |
| 192 | –C(O)-(2-pyridyl) | –C(O)-(1-methylcyclopropyl) |
| 193 | –C(O)-(2-pyridyl) | –C(O)-cyclobutyl |
| 194 | –C(O)-(2-pyridyl) | –C(O)-(tetrahydropyran-4-yl) |
| 195 | –C(O)-(2-pyridyl) | –C(O)-(1-(tert-butoxycarbonyl)piperidin-4-yl) |
| 196 | –C(O)-(2-pyridyl) | –C(O)-(piperidin-4-yl) |
| 197 | –C(O)-(2-pyridyl) | –C(O)-(1-((pyridin-3-yl)methyl)piperidin-4-yl) |
| 198 | –C(O)-(2-pyridyl) | –C(O)-(1-((pyridin-4-yl)methyl)piperidin-4-yl) |
| 199 | –C(O)-(2-pyridyl) | –C(O)-phenyl |
| 200 | –C(O)-(2-pyridyl) | –C(O)-(2-methoxyphenyl) |
| 201 | –C(O)-(2-pyridyl) | –C(O)-(3-methoxyphenyl) |

TABLE 5-continued
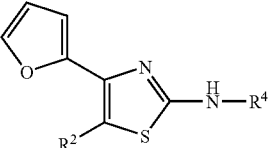
(I)
| Compound No. | R² | R⁴ |
|---|---|---|
| 202 | 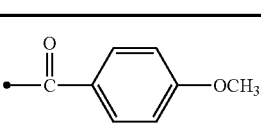 | 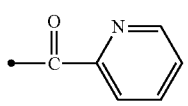 |
| 203 | 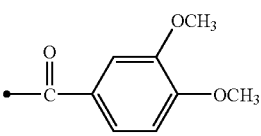 | 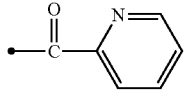 |
| 204 | 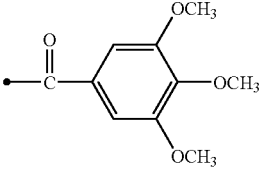 | 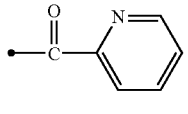 |
| 205 | 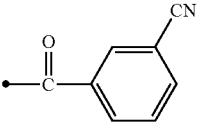 | 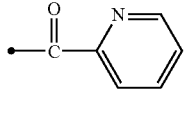 |
| 206 | 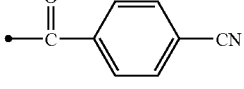 | 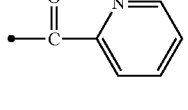 |
| 207 | 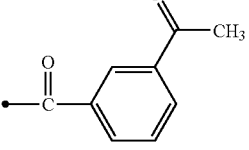 | 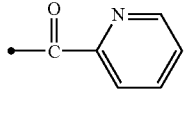 |
| 208 | 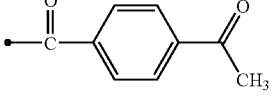 | 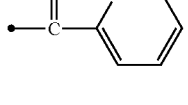 |
| 209 | 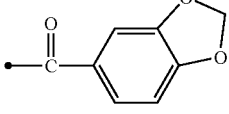 | 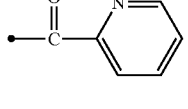 |
| 210 | 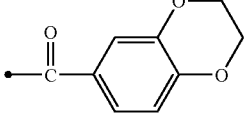 | |

TABLE 5-continued
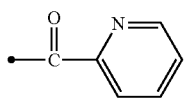
(I)
| Compound No. | R² | R⁴ |
|---|---|---|
| 211 | 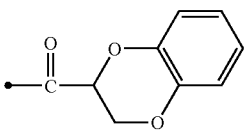 | 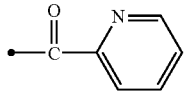 |
| 212 | 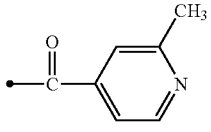 | 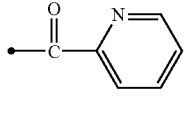 |
| 213 | 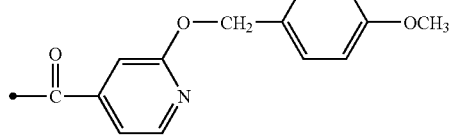 | 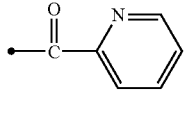 |
| 214 | 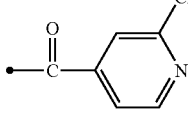 | 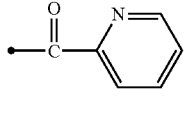 |
| 215 | 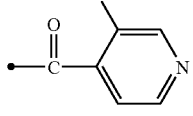 | 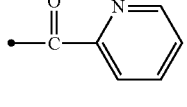 |
| 216 | 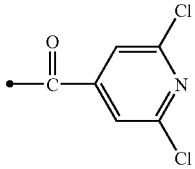 | 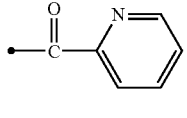 |
| 217 | 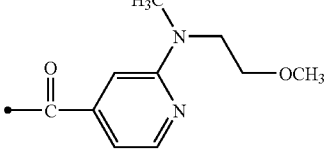 | 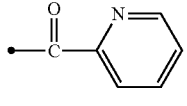 |
| 218 | 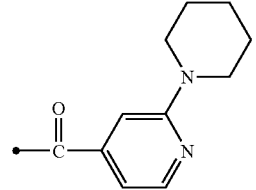 | |

TABLE 5-continued (I)

| Compound No. | R² | R⁴ |
|---|---|---|
| 219 | −C(O)−(2-pyridyl) | −C(O)−(2-morpholino-pyridin-4-yl) |
| 220 | −C(O)−(2-pyridyl) | −C(O)−(3-pyridyl) |
| 221 | −C(O)−(2-pyridyl) | −C(O)−(2-methylpyridin-3-yl) |
| 222 | −C(O)−(2-pyridyl) | −C(O)−(6-methylpyridin-3-yl) |
| 223 | −C(O)−(2-pyridyl) | −C(O)−(5-methylpyridin-3-yl) |
| 224 | −C(O)−(2-pyridyl) | −C(O)−(2,6-dimethoxypyridin-3-yl) |
| 225 | −C(O)−(2-pyridyl) | −C(O)−(6-chloropyridin-3-yl) |
| 226 | −C(O)−(2-pyridyl) | −C(O)−(5-bromopyridin-3-yl) |
| 227 | −C(O)−(2-pyridyl) | −C(O)−(pyridazin-4-yl) |
| 228 | −C(O)−(2-pyridyl) | −C(O)−(2-methylpyrimidin-5-yl) |

TABLE 5-continued
(I)
| Compound No. | R² | R⁴ |
|---|---|---|
| 229 | 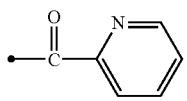 | 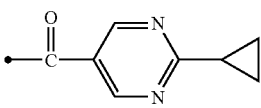 |
| 230 | 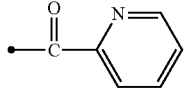 | 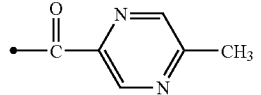 |
| 231 | 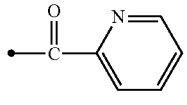 | 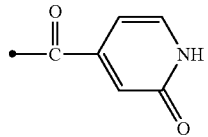 |
| 232 | 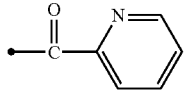 | 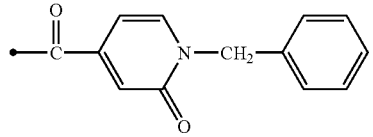 |
| 233 | 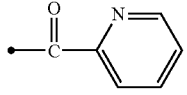 | 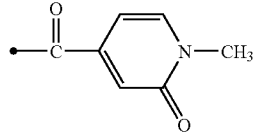 |
| 234 | 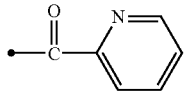 | 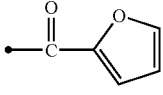 |
| 235 | 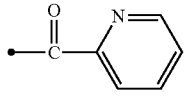 | 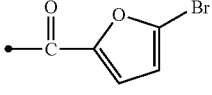 |
| 236 | 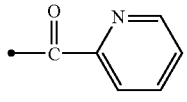 | 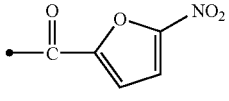 |
| 237 | 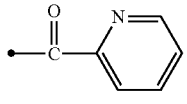 | 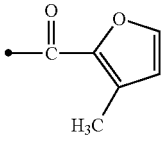 |
| 238 | 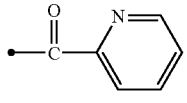 | 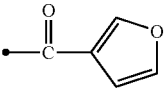 |

TABLE 5-continued
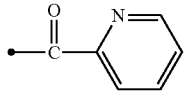
(I)
| Compound No. | R² | R⁴ |
|---|---|---|
| 239 | 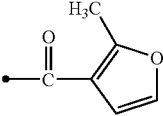 | 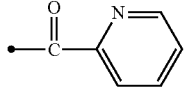 |
| 240 | 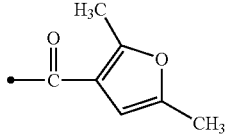 | 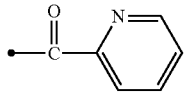 |
| 241 | 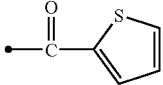 | 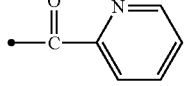 |
| 242 | 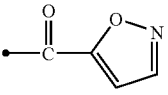 | 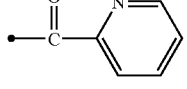 |
| 243 | 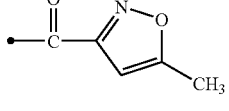 | 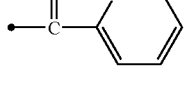 |
| 244 | 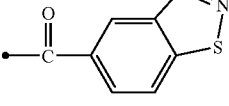 | 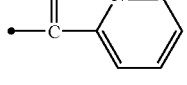 |
| 245 | 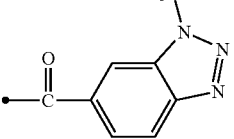 | 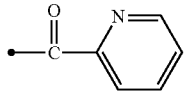 |
| 246 | 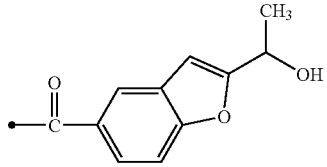 | 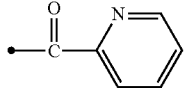 |
| 247 | 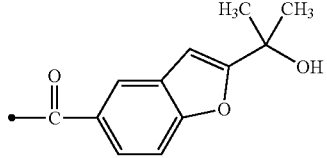 | |

TABLE 5-continued
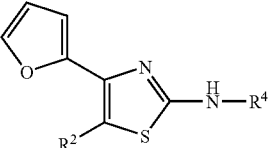
(I)
| Compound No. | R² | R⁴ |
|---|---|---|
| 248 | 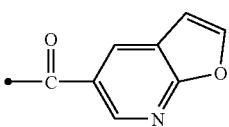 | 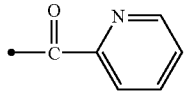 |
| 249 | 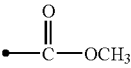 | 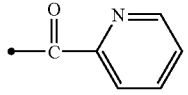 |
| 250 |  | 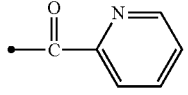 |
| 251 | 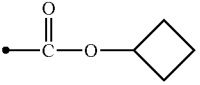 | 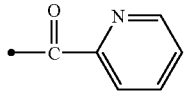 |
| 252 | 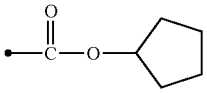 | 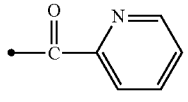 |
| 253 | 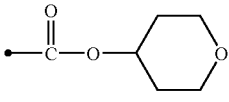 | 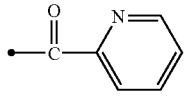 |
| 254 | 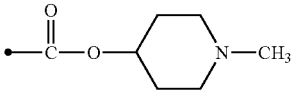 | 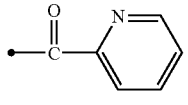 |
| 255 | 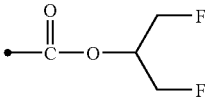 | 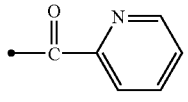 |
| 256 | 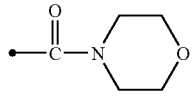 | 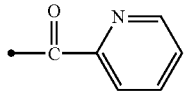 |
| 257 | 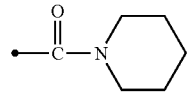 | 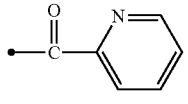 |
| 258 | 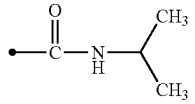 |  |

TABLE 5-continued
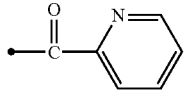
(I)
| Compound No. | R² | R⁴ |
|---|---|---|
| 259 | 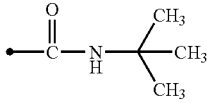 | 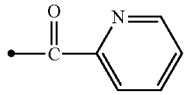 |
| 260 | 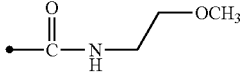 | 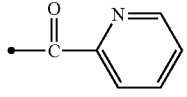 |
| 261 | 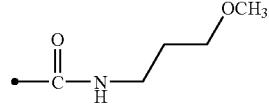 | 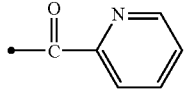 |
| 262 | 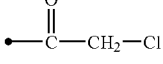 | 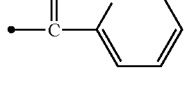 |
| 263 | 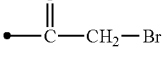 | 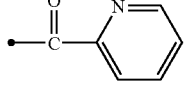 |
| 264 | 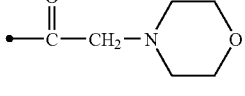 | 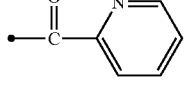 |
| 265 | 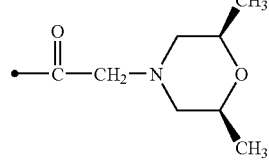 | 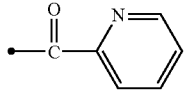 |
| 266 | 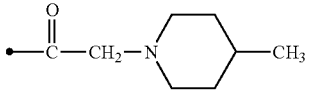 | 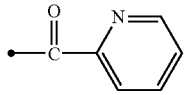 |
| 267 | 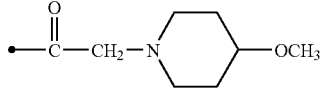 | 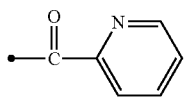 |
| 268 | 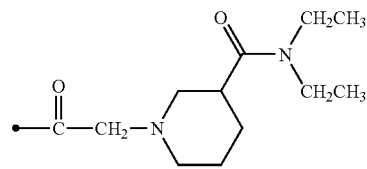 | |

TABLE 5-continued
(I)
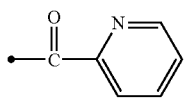
| Compound No. | R² | R⁴ |
|---|---|---|
| 269 | 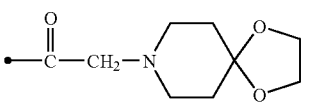 | 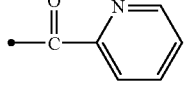 |
| 270 | 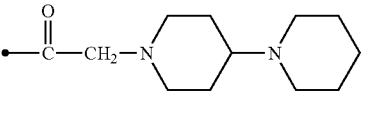 | 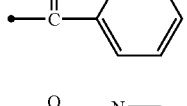 |
| 271 | 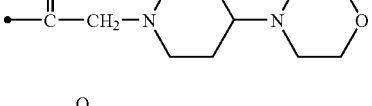 | 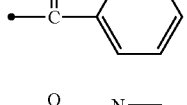 |
| 272 | 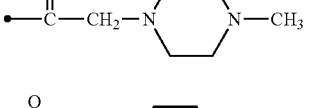 | 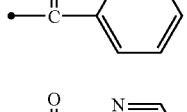 |
| 273 | 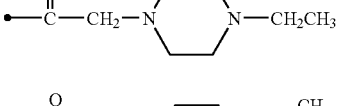 | 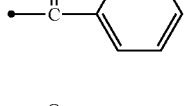 |
| 274 | 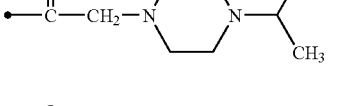 | 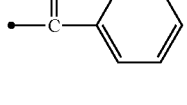 |
| 275 | 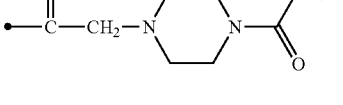 | 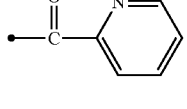 |
| 276 | 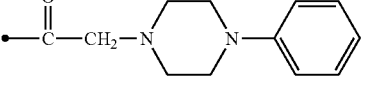 | 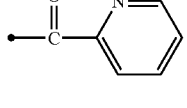 |
| 277 | 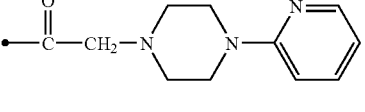 | 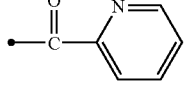 |
| 278 | 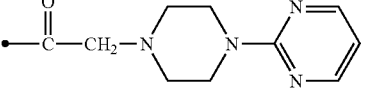 | 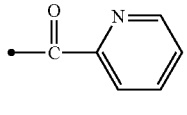 |
| 279 | 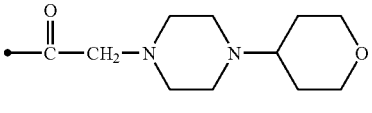 | |

TABLE 5-continued
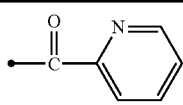
(I)
| Compound No. | R² | R⁴ |
|---|---|---|
| 280 | 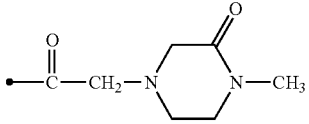 | 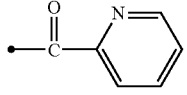 |
| 281 | 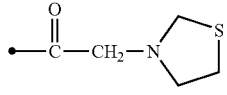 | 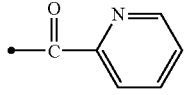 |
| 282 | 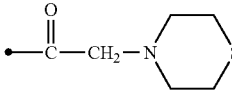 | 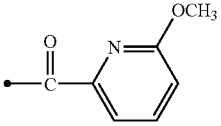 |
| 283 | 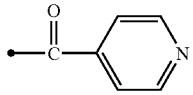 | 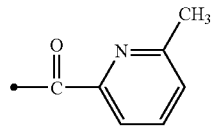 |
| 284 | 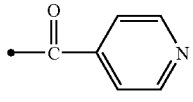 | 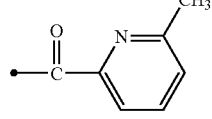 |
| 285 | 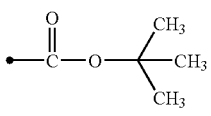 | 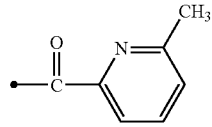 |
| 286 | 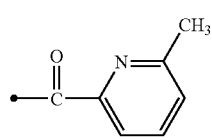 | —H |
| 287 | 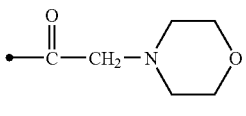 | 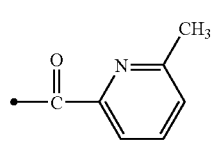 |
| 288 | 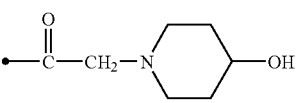 | 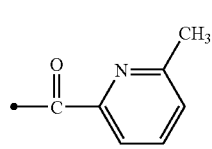 |
| 289 | 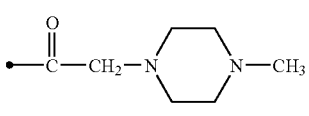 |  |

TABLE 5-continued (I)

| Compound No. | R² | R⁴ |
|---|---|---|
| 290 | -C(=O)-(6-methylpyridin-2-yl) | -C(=O)-CH₂-N(piperazine)N-CH₂CH₃ |
| 291 | -C(=O)-(6-methylpyridin-2-yl) | -C(=O)-CH₂-N(piperazine)N-C(=O)CH₃ |
| 292 | -C(=O)-(6-methylpyridin-2-yl) | -C(=O)-CH₂-N(piperazine)N-(pyridin-2-yl) |
| 293 | -C(=O)-(6-methylpyridin-2-yl) | -C(=O)-CH₂-N(piperidine)-N(morpholine) |
| 294 | -C(=O)-(5-methylpyridin-2-yl) | -C(=O)-(pyridin-4-yl) |
| 295 | -C(=O)-(4-methylpyridin-2-yl) | -C(=O)-(pyridin-4-yl) |
| 296 | -CH(OH)-(5-methoxypyridin-2-yl) | -C(=O)-O-C(CH₃)₃ |
| 297 | -C(=O)-(5-methoxypyridin-2-yl) | -C(=O)-O-C(CH₃)₃ |
| 298 | -C(=O)-(5-methoxypyridin-2-yl) | —H |
| 299 | -C(=O)-(5-methoxypyridin-2-yl) | -C(=O)-(pyridin-4-yl) |

TABLE 5-continued
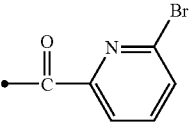
(I)
| Compound No. | R² | R⁴ |
|---|---|---|
| 300 | 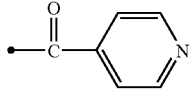 | 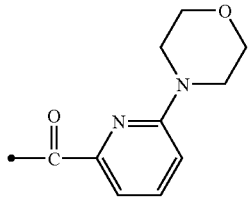 |
| 301 | 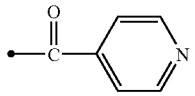 | 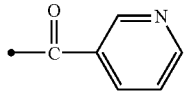 |
| 302 | 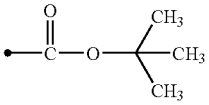 | 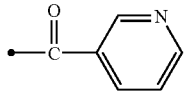 |
| 303 | 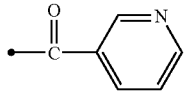 | —H |
| 304 | 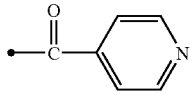 | 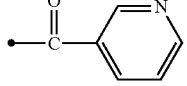 |
| 305 | 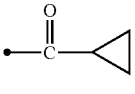 | 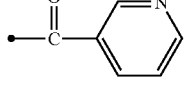 |
| 306 |  | 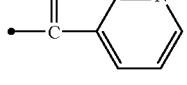 |
| 307 | 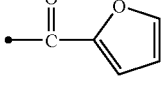 | 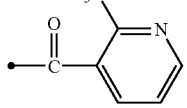 |
| 308 | 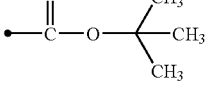 | 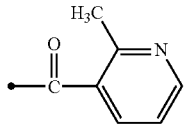 |
| 309 |  | —H |

TABLE 5-continued

Structure (I): 4-(furan-2-yl)-thiazole with R² at 5-position and NH-R⁴ at 2-position.

| Compound No. | R² | R⁴ |
|---|---|---|
| 310 | 2-methylpyridin-3-yl carbonyl | pyridin-4-yl carbonyl |
| 311 | 6-methylpyridin-3-yl carbonyl | tert-butoxycarbonyl |
| 312 | 6-methylpyridin-3-yl carbonyl | —H |
| 313 | 6-methylpyridin-3-yl carbonyl | pyridin-4-yl carbonyl |
| 314 | 6-methylpyridin-3-yl carbonyl | 4-cyanobenzoyl |
| 315 | 6-methylpyridin-3-yl carbonyl | furan-2-yl carbonyl |
| 316 | 6-methylpyridin-3-yl carbonyl | furan-3-yl carbonyl |
| 317 | 6-methoxypyridin-3-yl carbonyl | tert-butoxycarbonyl |
| 318 | 6-methoxypyridin-3-yl carbonyl | —H |
| 319 | 6-methoxypyridin-3-yl carbonyl | pyridin-4-yl carbonyl |
| 320 | 6-chloropyridin-3-yl carbonyl | tert-butoxycarbonyl |

TABLE 5-continued (I)

[Structure: 4-(furan-2-yl)-thiazole with R² at 5-position and NH-R⁴ at 2-position]

| Compound No. | R² | R⁴ |
|---|---|---|
| 321 | -C(=O)-(6-chloropyridin-3-yl) | —H |
| 322 | -C(=O)-(6-chloropyridin-3-yl) | -C(=O)-(pyridin-4-yl) |
| 323 | -C(=O)-(6-(dimethylamino)pyridin-3-yl) | -C(=O)-(pyridin-4-yl) |
| 324 | -C(=O)-(6-morpholinopyridin-3-yl) | -C(=O)-(pyridin-4-yl) |
| 325 | -C(=O)-(6-(4-methylpiperazin-1-yl)pyridin-3-yl) | -C(=O)-(pyridin-4-yl) |
| 326 | -C(=O)-(6-(4-hydroxypiperidin-1-yl)pyridin-3-yl) | -C(=O)-(pyridin-4-yl) |
| 327 | -C(=O)-(pyridin-4-yl) | -C(=O)-O-C(CH₃)₃ |
| 328 | -C(=O)-(pyridin-4-yl) | —H |
| 329 | -C(=O)-(pyridin-4-yl) | -C(=O)-(pyridin-4-yl) |
| 330 | -C(=O)-(2-methylpyridin-4-yl) | -C(=O)-O-C(CH₃)₃ |
| 331 | -C(=O)-(2-methylpyridin-4-yl) | —H |

TABLE 5-continued (I)

| Compound No. | R² | R⁴ |
|---|---|---|
| 332 | 4-C(=O)-(2-methylpyridin-4-yl) | 4-C(=O)-pyridin-4-yl |
| 333 | 4-C(=O)-(2-methylpyridin-4-yl) | 4-C(=O)-(2-methylpyridin-4-yl) |
| 334 | 4-C(=O)-(2-methoxypyridin-4-yl) | -C(=O)-O-C(CH₃)₃ |
| 335 | 4-C(=O)-(2-methoxypyridin-4-yl) | —H |
| 336 | 4-C(=O)-(2-methoxypyridin-4-yl) | -C(=O)-pyridin-4-yl |
| 337 | 4-C(=O)-(2-morpholinopyridin-4-yl) | -C(=O)-O-C(CH₃)₃ |
| 338 | 4-C(=O)-(2-morpholinopyridin-4-yl) | —H |
| 339 | 4-C(=O)-(2-morpholinopyridin-4-yl) | -C(=O)-pyridin-4-yl |

TABLE 5-continued (I) Structure: 4-(furan-2-yl)-thiazol-2-amine core with R² at 5-position and NH-R⁴ at 2-position.

| Compound No. | R² | R⁴ |
|---|---|---|
| 340 | -C(O)-(furan-2-yl) | -C(O)-O-C(CH₃)₃ |
| 341 | -C(O)-(furan-2-yl) | —H |
| 342 | -C(O)-(furan-2-yl) | -C(O)-(pyridin-4-yl) |
| 343 | -C(O)-(5-methylfuran-2-yl) | -C(O)-(pyridin-4-yl) |
| 344 | -C(O)-(furan-3-yl) | -C(O)-O-C(CH₃)₃ |
| 345 | -C(O)-(furan-3-yl) | —H |
| 346 | -C(O)-(furan-3-yl) | -C(O)-(pyridin-4-yl) |
| 347 | -C(O)-(thiophen-2-yl) | -C(O)-(pyridin-4-yl) |
| 348 | -C(O)-(thiazol-2-yl) | -C(O)-(pyridin-4-yl) |
| 349 | -C(O)-(5-methylthiazol-2-yl) | -C(O)-(pyridin-4-yl) |
| 350 | -C(O)-(4-methylthiazol-2-yl) | -C(O)-(pyridin-4-yl) |

TABLE 5-continued
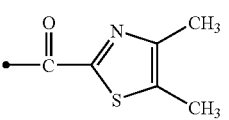
(I)
| Compound No. | R² | R⁴ |
|---|---|---|
| 351 | 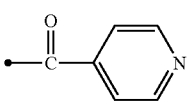 | 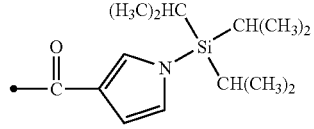 |
| 352 | 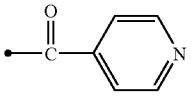 | 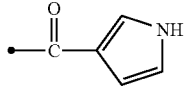 |
| 353 | 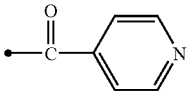 | 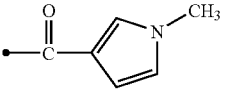 |
| 354 | 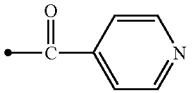 | 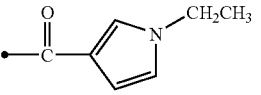 |
| 355 | 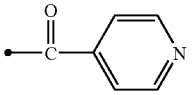 | 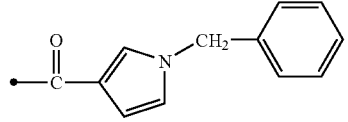 |
| 356 | 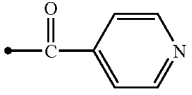 | 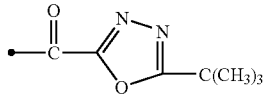 |
| 357 | 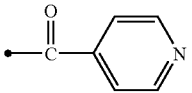 | 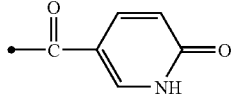 |
| 358 | 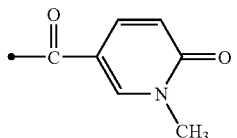 | —H |
| 359 | 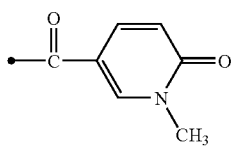 | —H |
| 360 | 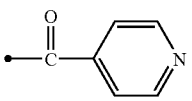 |  |

TABLE 5-continued
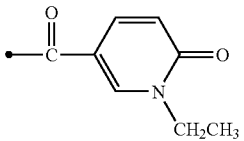
(I)
| Compound No. | R² | R⁴ |
|---|---|---|
| 361 | 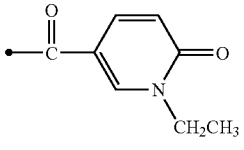 | —H |
| 362 | 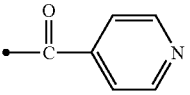 | 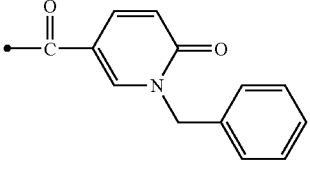 |
| 363 | 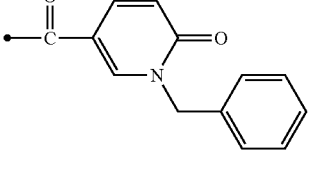 | —H |
| 364 | 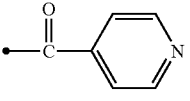 | 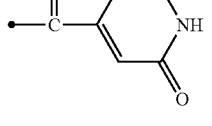 |
| 365 | 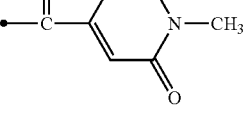 | —H |
| 366 | 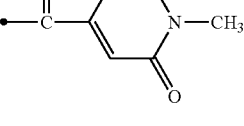 | —H |
| 367 | 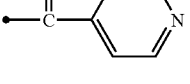 | 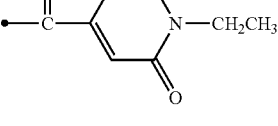 |
| 368 |  | —H |

TABLE 5-continued (I)

| Compound No. | R² | R⁴ |
|---|---|---|
| 369 | 4-(1-ethyl-2-oxo-1,2-dihydropyridine)carbonyl | 4-pyridylcarbonyl |
| 370 | 4-(1-benzyl-2-oxo-1,2-dihydropyridine)carbonyl | —H |
| 371 | 4-(1-benzyl-2-oxo-1,2-dihydropyridine)carbonyl | 4-pyridylcarbonyl |
| 372 | pyrazinylcarbonyl | —C(O)O—C(CH₃)₃ |
| 373 | pyrazinylcarbonyl | —H |
| 374 | pyrazinylcarbonyl | 4-pyridylcarbonyl |
| 375 | pyrimidinylcarbonyl | 4-pyridylcarbonyl |
| 376 | pyridazinylcarbonyl | 4-pyridylcarbonyl |
| 377 | —C(O)CH₃ | 4-pyridylcarbonyl |
| 378 | —C(O)CF₃ | —C(O)O—C(CH₃)₃ |
| 379 | —C(O)CF₃ | —H |

TABLE 5-continued

Structure (I): 4-(furan-2-yl)-thiazole with R² at 5-position and NH-R⁴ at 2-position.

| Compound No. | R² | R⁴ |
|---|---|---|
| 380 | -C(=O)-CF₃ | -C(=O)-(pyridin-4-yl) |
| 381 | -C(=O)-CH₂CH₃ | -C(=O)-(pyridin-4-yl) |
| 382 | -C(=O)-CH₂CH₂CH₃ | -C(=O)-(pyridin-4-yl) |
| 383 | -C(=O)-CH₂CH₂CH₃ | -C(=O)-O-C(CH₃)₃ |
| 384 | -C(=O)-CH₂CH₂CH₃ | —H |
| 385 | -C(=O)-CH₂CH₂CH₃ | -C(=O)-cyclopropyl |
| 386 | -C(=O)-CH₂CH₂CH₃ | -C(=O)-(furan-2-yl) |
| 387 | -C(=O)-CH₂CH₂CH₃ | -C(=O)-(2-(chloromethyl)pyridin-4-yl) |
| 388 | -C(=O)-CH₂CH₂CH₃ | -C(=O)-(2-(methoxymethyl)pyridin-4-yl) |
| 389 | -C(=O)-CH₂CH₂CH₃ | -C(=O)-(2-((2-(dimethylamino)ethoxy)methyl)pyridin-4-yl) |
| 390 | -C(=O)-CH₂CH₂CH₃ | -C(=O)-CH₂-morpholin-4-yl |

TABLE 5-continued
(I)
| Compound No. | R² | R⁴ |
|---|---|---|
| 391 | 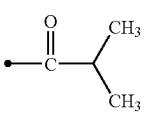 | 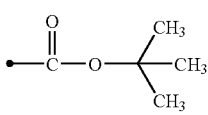 |
| 392 | 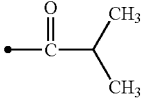 | —H |
| 393 | 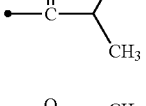 | 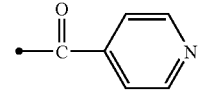 |
| 394 | 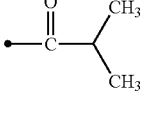 | 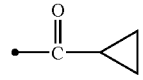 |
| 395 | 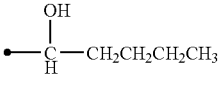 | 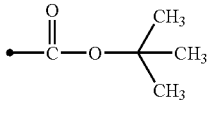 |
| 396 | 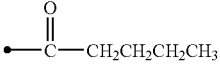 | 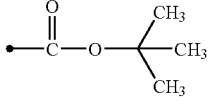 |
| 397 | 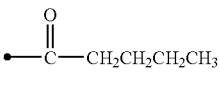 | —H |
| 398 | 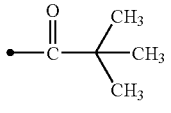 | 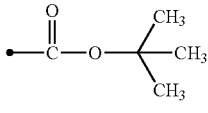 |
| 399 | 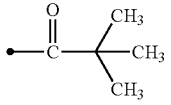 | —H |
| 400 | 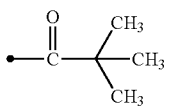 | 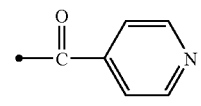 |
| 401 | 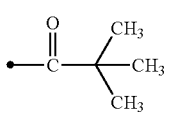 | 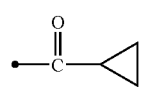 |

TABLE 5-continued
(I)
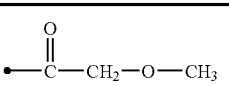
| Compound No. | R² | R⁴ |
|---|---|---|
| 402 | •—C(=O)—CH₂—O—CH₃ | •—C(=O)—O—C(CH₃)₃ |
| 403 | •—C(=O)—CH₂—O—CH₃ | —H |
| 404 | •—C(=O)—CH₂—O—CH₃ | •—C(=O)-(6-chloropyridin-3-yl) |
| 405 | •—C(=O)—CH₂—O—CH₃ | •—C(=O)-(4-fluorophenyl) |
| 406 | •—C(=O)—CH₂—O—CH₂CH₃ | •—C(=O)—O—C(CH₃)₃ |
| 407 | •—C(=O)—CH₂—O—CH₂CH₃ | —H |
| 408 | •—C(=O)—CH=CH₂ | •—C(=O)—O—C(CH₃)₃ |
| 409 | •—C(=O)—CH₂CH₂—O—CH₃ | •—C(=O)—O—C(CH₃)₃ |
| 410 | •—C(=O)—CH₂CH₂—O—CH₃ | —H |
| 411 | •—C(=O)—CH₂CH₂—O—CH₂CH₃ | •—C(=O)—O—C(CH₃)₃ |
| 412 | •—C(=O)—CH₂CH₂—O—CH₂CH₃ | —H |
| 413 | •—C(=O)—C≡C—CH₂—OCH₃ | •—C(=O)-(pyridin-4-yl) |

TABLE 5-continued (I)

Structure: 4-(furan-2-yl)-thiazole with R² at 5-position and NH-R⁴ at 2-position

| Compound No. | R² | R⁴ |
|---|---|---|
| 414 | −C(=O)−C≡C−CH₂−OCH₃ | −C(=O)−O−C(CH₃)₃ |
| 415 | −C(=O)−CH₂CH₂CH₂−OCH₃ | −C(=O)−O−C(CH₃)₃ |
| 416 | −C(=O)−CH₂CH₂CH₂−OCH₃ | −H |
| 417 | −C(=O)−cyclopropyl | −C(=O)−(4-pyridyl) |
| 418 | −C(=O)−cyclopropyl | −C(=O)−O−C(CH₃)₃ |
| 419 | −C(=O)−cyclopropyl | −H |
| 420 | −C(=O)−cyclopropyl | −C(=O)−(2-methoxyphenyl) |
| 421 | −C(=O)−cyclopropyl | −C(=O)−CH₂−N(morpholino) |
| 422 | −C(=O)−cyclobutyl | −C(=O)−O−C(CH₃)₃ |
| 423 | −C(=O)−cyclobutyl | −H |
| 424 | −C(=O)−cyclobutyl | −C(=O)−(4-pyridyl) |
| 425 | −C(=O)−cyclobutyl | −C(=O)−(2-furyl) |

TABLE 5-continued (I)

[Structure: 4-(furan-2-yl)thiazole with R² at 5-position and NH-R⁴ at 2-position]

| Compound No. | R² | R⁴ |
|---|---|---|
| 426 | –C(=O)–cyclobutyl | –C(=O)–C₆H₄–CN (4-cyanophenyl) |
| 427 | –C(=O)–cyclobutyl | –C(=O)–cyclopropyl |
| 428 | –CH(OH)–(3-methyloxetan-3-yl) | –C(=O)–O–C(CH₃)₃ |
| 429 | –C(=O)–(3-methyloxetan-3-yl) | –C(=O)–O–C(CH₃)₃ |
| 430 | –C(=O)–(3-methyloxetan-3-yl) | —H |
| 431 | –C(=O)–cyclopentyl | –C(=O)–(pyridin-4-yl) |
| 432 | –C(=O)–cyclopentyl | –C(=O)–O–C(CH₃)₃ |
| 433 | –C(=O)–cyclopentyl | —H |
| 434 | –C(=O)–cyclopentyl | –C(=O)–cyclopropyl |
| 435 | –C(=O)–cyclopentyl | –C(=O)–morpholin-4-yl |
| 436 | –CH(OH)–cyclohexyl | –C(=O)–O–C(CH₃)₃ |

TABLE 5-continued (I)

[Structure: 4-(furan-2-yl)-thiazole with R² at 5-position and NH-R⁴ at 2-position]

| Compound No. | R² | R⁴ |
|---|---|---|
| 437 | −C(=O)−cyclohexyl | −C(=O)−O−C(CH₃)₃ |
| 438 | −C(=O)−cyclohexyl | −H |
| 439 | −C(=O)−cyclohexyl | −C(=O)−(4-pyridyl) |
| 440 | −C(=O)−(4-methoxycyclohexyl) | −C(=O)−O−C(CH₃)₃ |
| 441 | −C(=O)−(4-methoxycyclohexyl) | −H |
| 442 | −C(=O)−(4-methoxycyclohexyl) | −C(=O)−(4-pyridyl) |
| 443 | −C(=O)−(4-methoxycyclohexyl) | −C(=O)−(4-cyanophenyl) |
| 444 | −C(=O)−(4-hydroxycyclohexyl) | −H |
| 445 | −C(=O)−(1,4-dioxaspiro[4.5]decan-8-yl) | −C(=O)−O−C(CH₃)₃ |
| 446 | −C(=O)−(1,4-dioxaspiro[4.5]decan-8-yl) | −H |
| 447 | −C(=O)−(4-oxocyclohexyl) | −H |
| 448 | −C(=O)−(4-oxocyclohexyl) | −C(=O)−(4-pyridyl) |

TABLE 5-continued
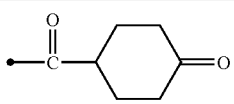
(I)
| Compound No. | R² | R⁴ |
|---|---|---|
| 449 | 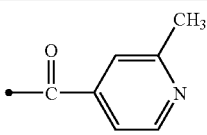 | 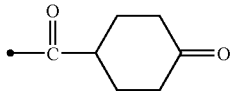 |
| 450 | 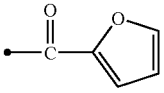 | 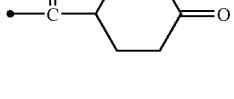 |
| 451 | 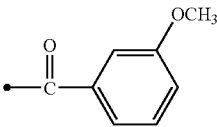 | 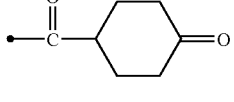 |
| 452 | 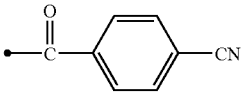 | 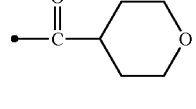 |
| 453 | 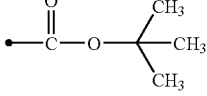 | 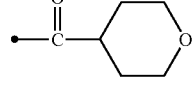 |
| 454 | 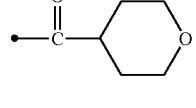 | —H |
| 455 | 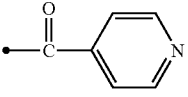 | 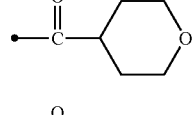 |
| 456 | 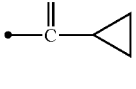 | 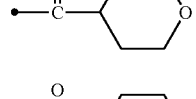 |
| 457 | 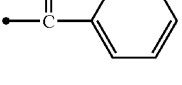 | 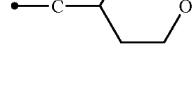 |
| 458 | 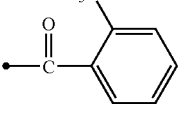 | 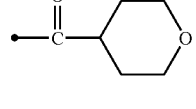 |
| 459 | 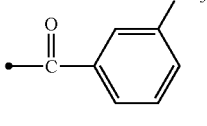 |  |

TABLE 5-continued (I)

| Compound No. | R² | R⁴ |
|---|---|---|
| 460 | –C(O)–(tetrahydropyran-4-yl) | –C(O)–(4-CH₃-C₆H₄) |
| 461 | –C(O)–(tetrahydropyran-4-yl) | –C(O)–(2-OCH₃-C₆H₄) |
| 462 | –C(O)–(tetrahydropyran-4-yl) | –C(O)–(3-OCH₃-C₆H₄) |
| 463 | –C(O)–(tetrahydropyran-4-yl) | –C(O)–(4-OCH₃-C₆H₄) |
| 464 | –C(O)–(tetrahydropyran-4-yl) | –C(O)–(3-N(CH₃)₂-C₆H₄) |
| 465 | –C(O)–(tetrahydropyran-4-yl) | –C(O)–(4-N(CH₃)₂-C₆H₄) |
| 466 | –C(O)–(tetrahydropyran-4-yl) | –C(O)–(2-F-C₆H₄) |
| 467 | –C(O)–(tetrahydropyran-4-yl) | –C(O)–(3-F-C₆H₄) |
| 468 | –C(O)–(tetrahydropyran-4-yl) | –C(O)–(4-F-C₆H₄) |
| 469 | –C(O)–(tetrahydropyran-4-yl) | –C(O)–(2-Cl-C₆H₄) |

TABLE 5-continued
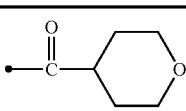
(I)
| Compound No. | R² | R⁴ |
|---|---|---|
| 470 | 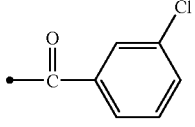 | 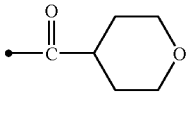 |
| 471 | 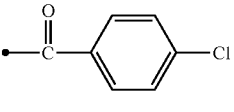 | 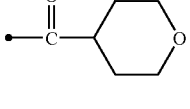 |
| 472 | 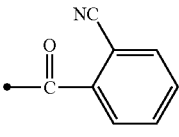 | 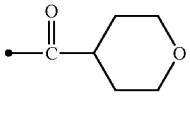 |
| 473 | 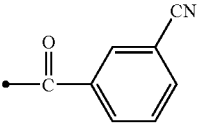 | 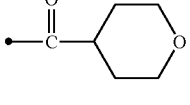 |
| 474 | 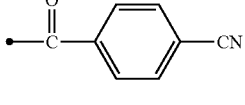 | 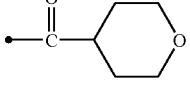 |
| 475 | 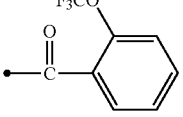 | 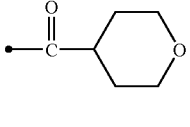 |
| 476 | 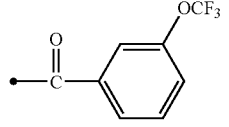 | 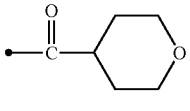 |
| 477 | 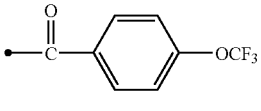 | 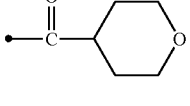 |
| 478 | 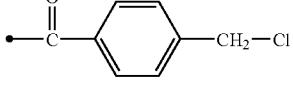 | 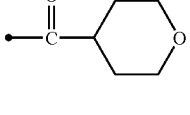 |
| 479 | 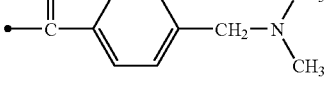 | 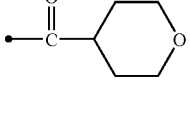 |
| 480 | 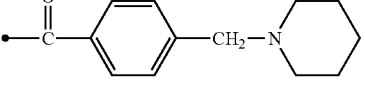 | |

TABLE 5-continued

| Compound No. | R² | R⁴ |
|---|---|---|
| 481 | —C(O)-(tetrahydropyran-4-yl) | —C(O)-C₆H₄-4-CH₂-N(piperidin-4-ol) |
| 482 | —C(O)-(tetrahydropyran-4-yl) | —C(O)-C₆H₄-4-CH₂-N(morpholine) |
| 483 | —C(O)-(tetrahydropyran-4-yl) | —C(O)-(2,3-dimethoxyphenyl) |
| 484 | —C(O)-(tetrahydropyran-4-yl) | —C(O)-(2,4-dimethoxyphenyl) |
| 485 | —C(O)-(tetrahydropyran-4-yl) | —C(O)-(2,5-dimethoxyphenyl) |
| 486 | —C(O)-(tetrahydropyran-4-yl) | —C(O)-(2,6-dimethoxyphenyl) |
| 487 | —C(O)-(tetrahydropyran-4-yl) | —C(O)-(3,4-dimethoxyphenyl) |
| 488 | —C(O)-(tetrahydropyran-4-yl) | —C(O)-(3,5-dimethoxyphenyl) |
| 489 | —C(O)-(tetrahydropyran-4-yl) | —C(O)-(2,3-difluorophenyl) |

TABLE 5-continued (I)

| Compound No. | R² | R⁴ |
|---|---|---|
| 490 | -C(O)-tetrahydropyran-4-yl | -C(O)-(2,4-difluorophenyl) |
| 491 | -C(O)-tetrahydropyran-4-yl | -C(O)-(2,5-difluorophenyl) |
| 492 | -C(O)-tetrahydropyran-4-yl | -C(O)-(2,6-difluorophenyl) |
| 493 | -C(O)-tetrahydropyran-4-yl | -C(O)-(3,4-difluorophenyl) |
| 494 | -C(O)-tetrahydropyran-4-yl | -C(O)-(3,5-difluorophenyl) |
| 495 | -C(O)-tetrahydropyran-4-yl | -C(O)-(2,3-dihydro-1,4-benzodioxin-5-yl) |
| 496 | -C(O)-tetrahydropyran-4-yl | -C(O)-(1,3-benzodioxol-5-yl) |
| 497 | -C(O)-tetrahydropyran-4-yl | -C(O)-(2,2-difluoro-1,3-benzodioxol-4-yl) |

TABLE 5-continued

| Compound No. | R² | R⁴ |
|---|---|---|
| 498 | tetrahydropyran-4-yl-C(=O)- | 2,2-difluoro-benzo[1,3]dioxol-5-yl-C(=O)- |
| 499 | tetrahydropyran-4-yl-C(=O)- | 2-chloropyridin-4-yl-C(=O)- |
| 500 | tetrahydropyran-4-yl-C(=O)- | 2-methylpyridin-4-yl-C(=O)- |
| 501 | tetrahydropyran-4-yl-C(=O)- | pyridin-3-yl-C(=O)- |
| 502 | tetrahydropyran-4-yl-C(=O)- | 6-chloropyridin-3-yl-C(=O)- |
| 503 | tetrahydropyran-4-yl-C(=O)- | 6-morpholinopyridin-3-yl-C(=O)- |
| 504 | tetrahydropyran-4-yl-C(=O)- | 6-methylpyridin-3-yl-C(=O)- |
| 505 | tetrahydropyran-4-yl-C(=O)- | 6-trifluoromethylpyridin-3-yl-C(=O)- |
| 506 | tetrahydropyran-4-yl-C(=O)- | 5-methylpyridin-3-yl-C(=O)- |
| 507 | tetrahydropyran-4-yl-C(=O)- | pyridin-2-yl-C(=O)- |

TABLE 5-continued (I)

| Compound No. | R² | R⁴ |
|---|---|---|
| 508 | -C(O)-(tetrahydropyran-4-yl) | -C(O)-(2-methylpyrimidin-5-yl) |
| 509 | -C(O)-(tetrahydropyran-4-yl) | -C(O)-(pyrazin-2-yl) |
| 510 | -C(O)-(tetrahydropyran-4-yl) | -C(O)-(5-methylpyrazin-2-yl) |
| 511 | -C(O)-(tetrahydropyran-4-yl) | -C(O)-(furan-2-yl) |
| 512 | -C(O)-(tetrahydropyran-4-yl) | -C(O)-(5-methylfuran-2-yl) |
| 513 | -C(O)-(tetrahydropyran-4-yl) | -C(O)-(5-formylfuran-2-yl) |
| 514 | -C(O)-(tetrahydropyran-4-yl) | -C(O)-(5-(CH=N-OH)furan-2-yl) |
| 515 | -C(O)-(tetrahydropyran-4-yl) | -C(O)-(5-cyanofuran-2-yl) |
| 516 | -C(O)-(tetrahydropyran-4-yl) | -C(O)-(furan-3-yl) |
| 517 | -C(O)-(tetrahydropyran-4-yl) | -C(O)-(thiophen-2-yl) |
| 518 | -C(O)-(tetrahydropyran-4-yl) | -C(O)-(thiophen-3-yl) |
| 519 | -C(O)-(tetrahydropyran-4-yl) | -C(O)-(1-methylpyrazol-4-yl) |

TABLE 5-continued

Structure (I): 4-(furan-2-yl)-thiazole with R² at 5-position and NH-R⁴ at 2-position.

| Compound No. | R² | R⁴ |
|---|---|---|
| 520 | -C(=O)-(tetrahydropyran-4-yl) | -C(=O)-(1-ethyl-1H-pyrazol-4-yl) |
| 521 | -C(=O)-(tetrahydropyran-4-yl) | -C(=O)-(1-phenyl-1H-pyrazol-4-yl) |
| 522 | -C(=O)-(tetrahydropyran-4-yl) | -C(=O)-(isoxazol-5-yl) |
| 523 | -C(=O)-(tetrahydropyran-4-yl) | -C(=O)-(tetrahydrofuran-2-yl) |
| 524 | -C(=O)-(tetrahydropyran-4-yl) | -C(=O)-(tetrahydrofuran-3-yl) |
| 525 | -C(=O)-(tetrahydropyran-4-yl) | -C(=O)-CH₂-(tetrahydropyran-4-yl) |
| 526 | -C(=O)-(tetrahydropyran-4-yl) | -C(=O)-CH₂-C₆H₅ |
| 527 | -C(=O)-(tetrahydropyran-4-yl) | -C(=O)-CH₂-CH₂-C₆H₅ |
| 528 | -C(=O)-(tetrahydropyran-4-yl) | -C(=O)-CH=CH-C₆H₅ |
| 529 | -C(=O)-(tetrahydropyran-4-yl) | -C(=O)-CH₂-O-C₆H₅ |
| 530 | -C(=O)-(tetrahydropyran-4-yl) | -C(=O)-CH₂-O-CH₃ |

TABLE 5-continued (I)

| Compound No. | R² | R⁴ |
|---|---|---|
| 531 | —C(O)-(tetrahydropyran-4-yl) | —C(O)—CH₂—Br |
| 532 | —C(O)-(tetrahydropyran-4-yl) | —C(O)—CH₂—O—CH₂CH₃ |
| 533 | —C(O)-(tetrahydropyran-4-yl) | —C(O)—CH₂—N(CH₃)₂ |
| 534 | —C(O)-(tetrahydropyran-4-yl) | —C(O)—CH₂—N(CH₃)(CH₂CH₂OCH₃) |
| 535 | —C(O)-(tetrahydropyran-4-yl) | —C(O)—CH₂—N(CH₂CH₂OCH₃)₂ |
| 536 | —C(O)-(tetrahydropyran-4-yl) | —C(O)—CH₂-(pyrrolidin-1-yl) |
| 537 | —C(O)-(tetrahydropyran-4-yl) | —C(O)—CH₂-((2S)-2-(methoxymethyl)pyrrolidin-1-yl) |
| 538 | —C(O)-(tetrahydropyran-4-yl) | —C(O)—CH₂-((2R)-2-(methoxymethyl)pyrrolidin-1-yl) |
| 539 | —C(O)-(tetrahydropyran-4-yl) | —C(O)—CH₂-(3-(dimethylamino)pyrrolidin-1-yl) |
| 540 | —C(O)-(tetrahydropyran-4-yl) | —C(O)—CH₂-(isoindolin-2-yl) |

TABLE 5-continued

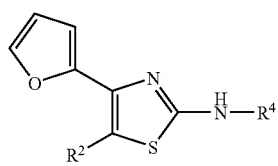

(I)

| Compound No. | R² | R⁴ |
|---|---|---|
| 541 | •—C(=O)—(tetrahydropyran-4-yl) | •—C(=O)—CH₂—N(thiazolidine) |
| 542 | •—C(=O)—(tetrahydropyran-4-yl) | •—C(=O)—CH₂—N(piperidine) |
| 543 | •—C(=O)—(tetrahydropyran-4-yl) | •—C(=O)—CH₂—N(piperidine-4-OH) |
| 544 | •—C(=O)—(tetrahydropyran-4-yl) | •—C(=O)—CH₂—N(piperidine-3-OH) |
| 545 | •—C(=O)—(tetrahydropyran-4-yl) | •—C(=O)—CH₂—N(piperidine-4-OCH₃) |
| 546 | •—C(=O)—(tetrahydropyran-4-yl) | •—C(=O)—CH₂—N(piperidine-4-CH₃,4-OH) |
| 547 | •—C(=O)—(tetrahydropyran-4-yl) | •—C(=O)—CH₂—N(piperidine-3-CH₂OH) |
| 548 | •—C(=O)—(tetrahydropyran-4-yl) | •—C(=O)—CH₂—N(piperidine-4-CH₂OH) |
| 549 | •—C(=O)—(tetrahydropyran-4-yl) | •—C(=O)—CH₂—N(piperidine-4-C(CH₃)₂OH) |
| 550 | •—C(=O)—(tetrahydropyran-4-yl) | •—C(=O)—CH₂—N(piperidine-4-CH₂C(CH₃)₂OH) |
| 551 | •—C(=O)—(tetrahydropyran-4-yl) | •—C(=O)—CH₂—N(piperidine-4-pyrrolidin-1-yl) |

TABLE 5-continued (I)

| Compound No. | R² | R⁴ |
|---|---|---|
| 552 | —C(O)-(tetrahydropyran-4-yl) | —C(O)—CH₂—N(piperidin-1-yl)(piperidin-4-yl) |
| 553 | —C(O)-(tetrahydropyran-4-yl) | —C(O)—CH₂—N(piperidin-1-yl)(4-morpholinyl) |
| 554 | —C(O)-(tetrahydropyran-4-yl) | —C(O)—CH₂—N(1,4-dioxa-8-azaspiro[4.5]decan-8-yl) |
| 555 | —C(O)-(tetrahydropyran-4-yl) | —C(O)—CH₂—N(4-cyanopiperidin-1-yl) |
| 556 | —C(O)-(tetrahydropyran-4-yl) | —C(O)—CH₂—N(4,4-difluoropiperidin-1-yl) |
| 557 | —C(O)-(tetrahydropyran-4-yl) | —C(O)—CH₂—N(1,2,3,6-tetrahydropyridin-1-yl) |
| 558 | —C(O)-(tetrahydropyran-4-yl) | —C(O)—CH₂—N(morpholin-4-yl) |
| 559 | —C(O)-(tetrahydropyran-4-yl) | —C(O)—CH₂—N(2,6-dimethylmorpholin-4-yl) |
| 560 | —C(O)-(tetrahydropyran-4-yl) | —C(O)—CH₂—N(4-Boc-piperazin-1-yl) |
| 561 | —C(O)-(tetrahydropyran-4-yl) | —C(O)—CH₂—N(piperazin-1-yl) |
| 562 | —C(O)-(tetrahydropyran-4-yl) | —C(O)—CH₂—N(4-methylpiperazin-1-yl) |

TABLE 5-continued

| Compound No. | R² | R⁴ |
|---|---|---|
| 563 | -C(=O)-(tetrahydropyran-4-yl) | -C(=O)-CH₂-N(piperazine)N-CH(CH₃)₂ |
| 564 | -C(=O)-(tetrahydropyran-4-yl) | -C(=O)-CH₂-N(piperazine)N-C(=O)-O-CH₂CH₃ |
| 565 | -C(=O)-(tetrahydropyran-4-yl) | -C(=O)-CH₂-N(piperazine)N-CH₂-C(CH₃)₂-OH |
| 566 | -C(=O)-(tetrahydropyran-4-yl) | -C(=O)-CH₂-N(piperazine)N-CH₂-C(CH₃)₂-O-CH₃ |
| 567 | -C(=O)-(tetrahydropyran-4-yl) | -C(=O)-CH₂-N(piperazine)N-CH₂-(1-methoxycyclopropyl) |
| 568 | -C(=O)-(tetrahydropyran-4-yl) | -C(=O)-CH₂-N(octahydropyrrolo[1,2-a]pyrazine with OCH₃) |
| 569 | -C(=O)-(tetrahydropyran-4-yl) | -C(=O)-CH₂-N(octahydropyrrolo[1,2-a]pyrazine with OH) |
| 570 | -C(=O)-(tetrahydropyran-4-yl) | -C(=O)-CH₂-N(octahydropyrazino[2,1-c][1,4]thiazine) |
| 571 | -C(=O)-(tetrahydropyran-4-yl) | -C(=O)-CH₂-N(piperazine)N-(tetrahydropyran-4-yl) |
| 572 | -C(=O)-(tetrahydropyran-4-yl) | -C(=O)-CH₂-N(oxo-hexahydropyrazino[2,1-c][1,4]oxazine) |

TABLE 5-continued

| Compound No. | R² | R⁴ |
|---|---|---|
| 573 | -C(=O)-tetrahydropyran-4-yl | -C(=O)-CH₂-N(hexahydropyrazino[2,1-c]morpholine) |
| 574 | -C(=O)-tetrahydropyran-4-yl | -C(=O)-CH₂-N(4-methyl-3-oxopiperazin-1-yl) |
| 575 | -C(=O)-tetrahydropyran-4-yl | -C(=O)-CH₂-N(1,4-oxazepan-4-yl) |
| 576 | -C(=O)-tetrahydropyran-4-yl | -C(=O)-CH₂-N(4-methyl-1,4-diazepan-1-yl) |
| 577 | -C(=O)-tetrahydropyran-4-yl | -C(=O)-CH₂-NH-(adamantan-1-yl) |
| 578 | -C(=O)-tetrahydropyran-4-yl | -C(=O)-CH₂-NH-(3-hydroxyadamantan-1-yl) |
| 579 | -C(=O)-tetrahydropyran-4-yl | -C(=O)-CH₂-N(imidazol-1-yl) |
| 580 | -C(=O)-tetrahydropyran-4-yl | -C(=O)-CH₂-N(2-methylimidazol-1-yl) |
| 581 | -C(=O)-tetrahydropyran-4-yl | -C(=O)-O-CH₂CH₃ |
| 582 | -C(=O)-(4-methyltetrahydropyran-4-yl) | -C(=O)-O-C(CH₃)₃ |

TABLE 5-continued (I)

| Compound No. | R² | R⁴ |
|---|---|---|
| 583 | 4-methyl-tetrahydropyran-4-yl carbonyl | —H |
| 584 | 4-methoxy-tetrahydropyran-4-yl carbonyl (H₃CO) | —C(=O)—O—C(CH₃)₃ |
| 585 | 4-methoxy-tetrahydropyran-4-yl carbonyl (H₃CO) | —H |
| 586 | (hydroxy)(tetrahydrothiopyran-4-yl)methyl | —C(=O)—O—C(CH₃)₃ |
| 587 | tetrahydrothiopyran-4-yl carbonyl | —C(=O)—O—C(CH₃)₃ |
| 588 | tetrahydrothiopyran-4-yl carbonyl | —H |
| 589 | tetrahydrothiopyran-4-yl carbonyl | pyridin-4-yl carbonyl |
| 590 | tetrahydrothiopyran-4-yl carbonyl | 2-methylpyrimidin-5-yl carbonyl |
| 591 | (1-oxo-tetrahydrothiopyran-4-yl) carbonyl | —C(=O)—O—C(CH₃)₃ |
| 592 | (1-oxo-tetrahydrothiopyran-4-yl) carbonyl | —H |
| 593 | (1,1-dioxo-tetrahydrothiopyran-4-yl) carbonyl | —C(=O)—O—C(CH₃)₃ |

TABLE 5-continued
(I)
[Structure: furan-thiazole core with R² and NH-R⁴ substituents]
| Compound No. | R² | R⁴ |
|---|---|---|
| 594 | ●—C(=O)—[cyclohexyl-SO₂ ring] | —H |
| 595 | ●—CH(OH)—CH₂—Ph | ●—C(=O)—O—C(CH₃)₃ |
| 596 | ●—C(=O)—CH₂—Ph | ●—C(=O)—O—C(CH₃)₃ |
| 597 | ●—C(=O)—CH₂—Ph | —H |
| 598 | ●—CH(OH)—CH₂—(2-OCH₃-C₆H₄) | ●—C(=O)—O—C(CH₃)₃ |
| 599 | ●—C(=O)—CH₂—(2-OCH₃-C₆H₄) | ●—C(=O)—O—C(CH₃)₃ |
| 600 | ●—C(=O)—CH₂—(2-OCH₃-C₆H₄) | —H |
TABLE 6
(I)
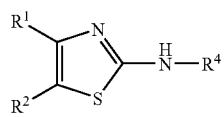
| Compound No. | R¹ | R² | R⁴ |
|---|---|---|---|
| 601 | ●—(5-CH₃-furan-2-yl) | ●—(pyridin-4-yl) | ●—C(=O)—(pyridin-4-yl) |

TABLE 6-continued

| Compound No. | R¹ | R² | R⁴ |
|---|---|---|---|
| 602 | 3-methylfuran-2-yl | pyridin-4-yl | pyridine-4-carbonyl |
| 603 | 3-phenylfuran-2-yl | pyridin-4-yl | pyridine-4-carbonyl |
| 604 | 3-(pyridin-4-yl)furan-2-yl | pyridin-4-yl | pyridine-4-carbonyl |
| 605 | furan-3-yl | pyridin-4-yl | pyridine-4-carbonyl |
| 606 | furan-3-yl | pyridine-2-carbonyl | tert-butoxycarbonyl |
| 607 | furan-3-yl | pyridine-2-carbonyl | —H |
| 608 | furan-3-yl | pyridine-2-carbonyl | pyridine-4-carbonyl |
| 609 | furan-3-yl | tetrahydropyran-4-carbonyl | tert-butoxycarbonyl |
| 610 | furan-3-yl | tetrahydropyran-4-carbonyl | —H |
| 611 | furan-3-yl | tetrahydropyran-4-carbonyl | cyclopropanecarbonyl |

TABLE 6-continued
(I)
| Compound No. | R¹ | R² | R⁴ |
|---|---|---|---|
| 612 | 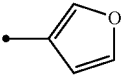 | 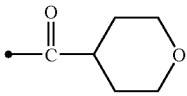 | 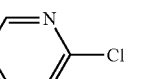 |
| 613 | 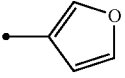 | 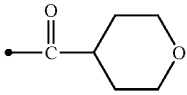 | 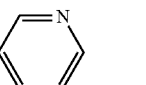 |
| 614 | 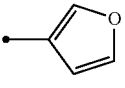 | 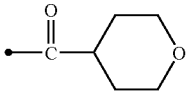 | 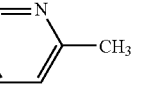 |
| 615 | 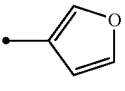 | 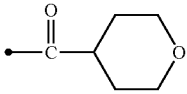 | 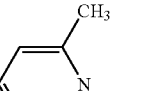 |
| 616 | 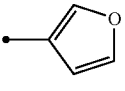 | 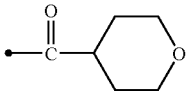 | 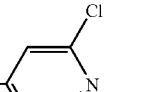 |
| 617 | 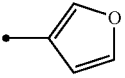 | 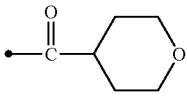 | 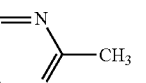 |
| 618 | 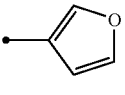 | 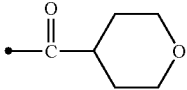 | 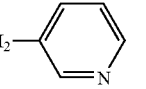 |
| 619 | 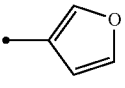 | 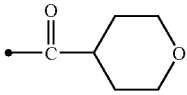 | 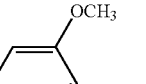 |
| 620 | 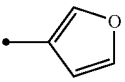 | 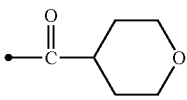 | 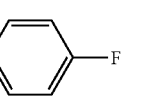 |
| 621 | 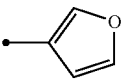 | 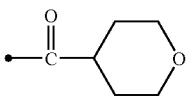 | 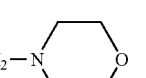 |

TABLE 7

(I)

Structure: 2-furyl group attached to thiazole at 4-position; R² at 5-position; 2-amino group with R³ and R⁴ substituents.

| Compound No. | R² | R³ | R⁴ |
|---|---|---|---|
| 622 | —C(=O)-cyclopentyl | —C(=O)-cyclopropyl | —C(=O)-cyclopropyl |
| 623 | —C(=O)—CH₂—OCH₂CH₃ | —CH₃ | —C(=O)—O—C(CH₃)₃ |
| 624 | —C(=O)—CH₂—OCH₂CH₃ | —H | —CH₃ |
| 625 | —C(=O)-(tetrahydropyran-4-yl) | —H | —CH₂—C₆H₅ |
| 626 | —C(=O)-(tetrahydropyran-4-yl) | —H | —CH₃ |
| 627 | —C(=O)-(tetrahydropyran-4-yl) | —H | —C(CH₃)₃ |
| 628 | —C(=O)-(tetrahydropyran-4-yl) | —H | —C(CH₃)₂—CH₂—C(CH₃)₃ |
| 629 | 4-hydroxy-1-methylpiperidin-4-yl | —H | —C(=O)—C₆H₅ |

TABLE 8

(I)

Structure: thiazole with R¹ at 4-position, R² at 5-position, 2-NH—R⁴.

| Compound No. | R¹ | R² | R⁴ |
|---|---|---|---|
| 630 | 2-pyridyl | —C(=O)-(2-pyridyl) | —H |

TABLE 8-continued structure (I): R¹ and R² on a thiazole ring, with 2-amino substituent N(H)—R⁴

| Compound No. | R¹ | R² | R⁴ |
|---|---|---|---|
| 631 | 2-pyridyl | –C(O)–(2-pyridyl) | –C(O)–(pyridyl) |
| 632 | phenyl | –C(O)–(2-pyridyl) | –C(O)–O–C(CH₃)₃ |
| 633 | phenyl | –C(O)–(2-pyridyl) | –H |
| 634 | phenyl | –C(O)–(2-pyridyl) | –C(O)–(4-pyridyl) |

Pharmacological activities of typical Compounds (I) are illustrated below referring to Test Examples.

TEST EXAMPLE 1

Binding Activity to Adenosine Receptor (Adenosine $A_{2A}$ Receptor Binding Test)

This test was carried but in a similar manner to a Bruns et al's method (*Molecular Pharmacology*, Vol. 29, p. 331, 1986).

Corpus striatum of rats (SD rat, by Nippon SLC) was suspended in 50 mL of an ice-cooled 50 mmol/L tris(hydroxymethyl)aminomethane hydrochloride (Tris-HCl) buffer (pH 7.7) using a polytron homogenizer (by Kinematica). The resulting homogenate was centrifuged (48,000× g, 20 minutes), and the resulting precipitate was again suspended by adding the same amount of a 50 mmol/L Tris-HCl buffer, followed by centrifugation under the same condition. The resulting final precipitate was suspended by adding a 50 mmol/L Tris-HCl buffer [containing 10 mmol/L magnesium chloride, adenosine deaminase 0.02 units/mg tissue (by Sigma)] so that the tissue concentration was 5 mg (wet weight)/mL.

To 100 μL of the above purified tissue suspension, were added 80 μL (final concentration 6.0 mmol/L) of tritium-labeled CGS-21680 {³H-2-[p-(2-carboxyethyl)phenethylamino]-5'-(N-ethylcarboxamido)-adenosine: 40 curies/mmol; by New England Nuclear [*The Journal of Pharmacology and Experimental Therapeutics*, Vol. 251, p. 888, 1989]} and 20 μL of a test compound solution ($10^{-7}$ mol/L; a solution of a test compound in DMSO was diluted with Tris-HCl buffer). The resulting mixture was allowed to stand at 25° C. for 120 minutes, followed by rapid suction filtration through a glass fiber paper filter (GF/C; by Whatman). The filter was immediately washed three times with 200 μL of an ice-cooled 50 mmol/L Tris-HCl buffer. The glass fiber paper filter was transferred into a vial, Microscinti (by Perkin Elmer) was added thereto, and the radioactivity level was measured with Topcount (by Perkin Elmer).

The inhibition rate of the test compound to the adenosine $A_{2A}$ receptor binding (³H-CGS21680 binding) was calculated according to the following formula.

$$\text{Inhibition rate (\%)} = \left(1 - \frac{\text{Amount of binding in the presence of test compound} - \text{Amount of non-specific binding}}{\text{Amount of total binding} - \text{Amount of non-specific binding}}\right) \times 100$$

Amount of total binding means the ³H-CGS21680 binding radioactivity content in the absence of the test compound. Amount of non-specific binding means the ³H-CGS21680 binding radioactivity content in the presence of 100 μmol/L cyclopentyladenosine (CPA; by Sigma). Amount of binding in the presence of test compound means the ³H-CGS21680 binding radioactivity content in the presence of $10^{-7}$ mol/L of the test compound.

The results are shown in Table 9.

TABLE 9

| Compound No. | Rat Adenosine $A_{2A}$ Receptor Binding Inhibition rate (%) ($10^{-7}$ mol/L) |
|---|---|
| 1 | 90 |
| 4 | 95 |
| 5 | 100 |
| 8 | 100 |

TABLE 9-continued

| Compound No. | Rat Adenosine $A_{2A}$ Receptor Binding Inhibition rate (%) ($10^{-7}$ mol/L) |
|---|---|
| 9 | 100 |
| 11 | 100 |
| 19 | 90 |
| 23 | 85 |
| 24 | 88 |
| 41 | 92 |
| 46 | 95 |
| 87 | 100 |
| 94 | 100 |
| 99 | 98 |
| 131 | 99 |
| 149 | 91 |
| 170 | 87 |
| 187 | 86 |
| 191 | 98 |
| 206 | 95 |
| 228 | 84 |
| 234 | 100 |
| 249 | 85 |
| 348 | 100 |
| 431 | 98 |
| 455 | 100 |
| 456 | 94 |
| 462 | 99 |
| 468 | 93 |
| 502 | 90 |
| 504 | 100 |
| 511 | 88 |
| 515 | 95 |
| 558 | 92 |

Table 9 indicates that Compounds (I) have a strong adenosine $A_{2A}$ receptor antagonism. Therefore, it was suggested that pharmaceutical composition comprising Compound (I) as the active ingredient is effective for diseases associated with adenosine $A_{2A}$ receptor [for example, central nervous system disorders such as Parkinson's disease, Alzheimer's disease, progressive supranuclear palsy, AIDS encephalopathy, Transmissible spongiform encephalopathy, multiple sclerosis, amyotrophic lateral sclerosis, Huntington's chorea, multiple system atrophy, cerebral ischemia, attention deficit hyperactivity disorder, sleep disorder, intermittent claudication, diabetes, anxiety disorders (e.g., panic attack and panic disorder, phobia, obsessive-compulsive disorder, posttraumatic stress disorder, acute stress disorder, generalized anxiety disorder, anxiety physical symptoms or substance-caused), mood disorders (e.g., depression, dysthymic disorder, mood-circulatory disorder), restless legs syndrome (RLS), drug dependence (e.g., alcohol dependence), eating disorder, epilepsy, migraine and chronic musculoskeletal system pain; ischemic cardiopathy such as myocardial infarction and cerebral infarction].

TEST EXAMPLE 2

Effect in Parkinson's Disease Model
[1-methyl-4-phenyl-1,2,3,6-tetrahydropyridine (MPTP)-treated Common Marmoset]

Parkinson's disease is a disorder based on the degeneration and lack of dopaminergic neurons in the nigro-striatal pathway. In the primates, treatment with a dopamine neurotoxin, that is MPTP, causes selective degeneration and lack of the dopaminergic neurons in the nigro-striatal pathway and causes a symptom such as akinesia and muscular rigidity. The MPTP-treated primate is known as a Parkinson's disease model (*Proceedings of the National Academy of Science USA*, Vol. 80, p. 4546, 1983). Also, common marmoset belongs to Anthropoidea, and is known to have parkinsonism caused by MPTP like others of Anthropoidea (*Neuroscience Letter*, Vol. 57, p. 37, 1985).

The experiment was carried out using four male and female common marmosets of 2 or 3 years old (body weight, 300 to 375 g, by Nippon Clea) per group. MPTP (by RBI) was dissolved in a physiological saline for injection (by Otsuka Pharmaceutical), and hypodermically administered to the common marmosets in a dose of 2.0 mg/kg, once a day for 5 days. Six weeks or more after the administration, animals showing chronic parkinsonian symptoms were used in the test. The test compound was used as a suspension in an aqueous solution containing 0.3% Tween 80 and 10% sucrose. One hour before the administration of the test compound, the animals to be tested were put into an observation cage (equipped with a spontaneous locomotor activity measuring apparatus) to adopt them to the environment. The motor disability of the animals before the administration of the test compound was scored, and this was compared with the motor disability score after orally administration of the test compound (Compound 1) in a dose of 10 mg/kg. As, the parkinsonian symptoms, the motor disabilities were scored at intervals of 30 minutes for 8 hours, by observation through a one-way viewing window. The spontaneous locomotor activity was measured at intervals of 30 minutes for 12 hours by a computer-controlled automatic measuring apparatus. The parkinsonian symptoms were scored on the basis of the rating scale of each observation item as shown below, and the total of the points were used as the score of each individual.

Table 10 shows the relationship between the observation items and the score.

TABLE 10

| Observation Items | Score | | | | |
|---|---|---|---|---|---|
| | 0 | 1 | 2 | 3 | 4 |
| Alertness | Normal | Reduced | Sleepy | | |
| Checking Movement | Present | Reduced | Absent | | |
| Attention Blinking | Normal | Abnormal | | | |
| Posture | Normal | | Abnormal; in Trunk, Tail or Limbs (each 1 point) | | Grossly Abnormal |
| Balance | Normal | Impaired | Unstable | Falls | |
| Reactivity | Normal | Reduced | Slow | Absent | |
| Vocalization | Normal | Reduced | Absent | | |
| Total | | | 0-17 points | | |

The results were judged by comparing the average scores of the parkinsonian symptoms in 4 animals per group between before and after administration of Compound 1 (significance test: Wilcoxon Rank Sum test).

As a result, it was confirmed that Compound 1 is effective for remission of the parkinsonian symptoms in the above-described test, and indicates that Compounds (I) are effective for preventing and/or treating Parkinson's disease.

Although Compounds (I) or pharmaceutically acceptable salts thereof can be administered as such, it is generally preferred to offer them in the form of various pharmaceutical preparations. Such pharmaceutical preparations are to be used in animals and humans.

The pharmaceutical preparations of the present invention can comprise Compounds (I) or pharmaceutically acceptable salts thereof as the active ingredient alone or in combination with any other active ingredients for the therapy. These pharmaceutical preparations may be produced by any methods well known in the technical field of pharmaceutics by mixing the active ingredient with one or more pharmaceutically acceptable carriers.

It is desirable to select a route of administration that is most effective for the therapy, examples thereof being oral administration or parenteral administration such as intravenous administration.

Examples of the dosage form include tablets and injections.

Preparations suitable for oral administration such as tablets can be produced using, for example, excipients (e.g., lactose and mannitol), disintegrators (e.g., starch), lubricants (e.g., magnesium stearate), binders (e.g., hydroxypropyl cellulose), surfactants (e.g., fatty acid esters) and plasticizers (e.g., glycerin).

Preparations suitable for parenteral administration preferably comprise a sterilized aqueous preparation containing an active compound which is isotonic to the recipient's blood. In the case of an injection, for example, a solution for injection is prepared using a carrier comprising a saline solution, a glucose solution, or a mixture of a saline solution and a glucose solution.

The parenteral preparations may also comprise one or more auxiliary components selected from the excipients, disintegrators, lubricants, binders, surfactants and plasticizers described in the above description of oral preparations and diluents, antiseptics, flavors, etc.

In the case of the above-described applications, in general, Compounds (I) or pharmaceutically acceptable salts thereof may be administered systemically or locally, and orally or parenterally. The dose and the administration frequency may vary, depending on the administration form, on the age and the body weight of the patient, and on the property and the seriousness of the symptom to be treated. In the case of oral administration, in general, it may be administered once to a few times a day in a dose of 0.01 to 1000 mg/adult, preferably 0.05 to 500 mg/adult. In the case of parenteral administration such as intravenous administration, in general, it may be administered once to a few times a day or continuously administered in a mode of intravenous administration for 1 to 24 hours a day, in a dose of 0.001 to 1000 mg/adult, preferably 0.01 to 300 mg/adult. However, the dose and the administration frequency may vary depending on various conditions mentioned above.

BEST MODE FOR CARRYING OUT THE INVENTION

The invention is described in detail with reference to the following Examples, Reference Examples and Formulation Examples.

The proton nuclear magnetic resonance spectrum ($^1$H NMR) used in Examples is determined at 270 MHz or 300 MHz. Some compounds could not show an exchangeable proton in some conditions. The signal multiplicity expression is an ordinary one, for which "br" indicates an apparently broad signal.

Example 1

N-[4-(2-Furyl)-5-(4-pyridyl)thiazol-2-yl]pyridine-4-carboxamide (Compound 1)

Compound a (1.70 g, 7.00 mmol) obtained in Reference Example 1 was dissolved in DMA (14 mL), and isonicotinoyl chloride hydrochloride (2.49 g, 14.0 mmol) and triethylamine (1.95 mL, 14.0 mmol) were added thereto, followed by stirring at room temperature for 4 hours. Aqueous saturated sodium hydrogencarbonate solution was added to the reaction mixture, and the precipitated solid was collected by filtration. The resulting solid was washed successively with water and ethanol, and the entitled Compound 1 (2.19 g, 90%) was obtained as pale brown crystals.

$^1$H NMR (DMSO-d$_6$, δ ppm): 6.61 (dd, J=1.8, 3.3 Hz, 1H), 6.74 (dd, J=0.7, 3.3 Hz, 1H), 7.46 (dd, J=1.5, 4.6 Hz, 2H), 7.67 (dd, J=0.7, 1.8 Hz, 1H), 8.02 (dd, J=1.5, 4.6 Hz, 2H), 8.63 (dd, J=1.5, 4.6 Hz, 2H), 8.83 (dd, J=1.5, 4.6 Hz, 2H).

ESIMS m/z: [M+H]$^+$ 349.

Example 2

N-[4-(2-Furyl)-5-(4-pyridyl)thiazol-2-yl]acetamide (Compound 2)

Compound a (729 mg, 3.00 mmol) obtained in Reference Example 1 was dissolved in DMA (15 mL), and acetyl chloride (0.43 mL, 6.00 mmol) was added thereto, followed by stirring at 80° C. for 3 hours. Aqueous saturated sodium hydrogencarbonate solution was added to the reaction mixture, and the precipitated solid was collected by filtration to afford the entitled Compound 2 (620 mg, 72%).

$^1$H NMR (DMSO-d$_6$, δ ppm) 2.20 (s, 3H), 6.58 (dd, J=1.8, 3.3 Hz, 1H), 6.68 (dd, J=0.7, 3.3 Hz, 1H), 7.42 (dd, J=1.5, 4.5 Hz, 2H), 7.62 (dd, J=0.7, 1.8 Hz, 1H), 8.58 (dd, J=1.5, 4.5 Hz, 2H), 12.50 (br s, 1H).

ESIMS m/z: [M+H]$^+$ 286.

Example 3

N-[4-(2-Furyl)-5-(4-pyridyl)thiazol-2-yl]methoxyacetamide (Compound 3)

Compound a (300 mg, 1.23 mmol) obtained in Reference Example 1 was dissolved in DMF (17 mL), and methoxyacetic acid (0.19 mL, 2.46 mmol), EDC hydrochloride (472 mg, 2.46 mmol) and 1-hydroxybenzotriazole monohydrate (377 mg, 2.46 mmol) were added thereto, followed by stirring at 50° C. for 3 hours. Water was added to the reaction mixture, and the precipitated solid was collected by filtration to afford the entitled Compound 3 (142 mg, 36%).

$^1$H NMR (DMSO-d$_6$, δ ppm): 3.34 (s, 3H), 4.20 (s, 2H), 6.59 (dd, J=1.8, 3.3 Hz, 1H), 6.70 (d, J=3.3 Hz, 1H), 7.43 (d, J=6.1 Hz, 2H), 7.65 (d, J=1.8 Hz, 1H), 8.61 (d, J=6.1 Hz, 2H), 12.5 (br s, 1H).

APCIMS m/z: [M+H]$^+$ 315.

Example 4

N-[4-(2-Furyl)-5-(4-pyridyl)thiazol-2-yl]cyclohexanecarboxamide (Compound 4)

In a manner similar to that in Example 1, by using cyclohexanecarbonyl chloride (0.22 mL, 0.82 mmol) in place of isonicotinoyl chloride hydrochloride, the entitled Compound 4 (261 mg, 90%) was obtained from Compound a (200 mg, 0.82 mmol) obtained in Reference Example 1.

$^1$H NMR (DMSO-d$_6$, δ ppm): 1.24-1.86, (10H, m), 2.50-2.56 (m, 1H), 6.58 (dd, J=1.8, 3.3 Hz, 1H), 6.69 (d, J=3.3 Hz, 1H), 7.41 (d, J=6.0 Hz, 2H), 7.64 (d, J=1.8 Hz, 1H), 8.56 (d, J=6.0 Hz, 2H), 12.4 (br s, 1H).

ESIMS m/z: [M+H]$^+$ 354.

Example 5

N-[4-(2-Furyl)-5-(4-pyridyl)thiazol-2-yl]pyridine-3-carboxamide (Compound 5)

In a manner similar to that in Example 3, by using nicotinic acid (303 mg, 2.46 mmol) in place of methoxyacetic acid, the entitled Compound 5 (230 mg, 54%) was obtained from Compound a (300 mg, 1.23 mmol) obtained in Reference Example 1.

$^1$H NMR (DMSO-d$_6$, δ ppm): 6.61 (dd, J=1.8, 3.3 Hz, 1H), 6.75 (d, J=3.3 Hz, 1H), 7.48 (d, J=6.1 Hz, 2H), 7.59-7.63 (m, 1H), 7.67-7.68 (m, 1H), 8.44-8.48 (m, 1H), 8.64 (d, J=6.1 Hz, 2H), 8.81-8.83 (m, 1H), 9.24-9.25 (m, 1H).

APCIMS m/z: [M+H]$^+$ 349.

Example 6

N-[4-(2-Furyl)-5-(4-pyridyl)thiazol-2-yl]pyridine-2-carboxamide (Compound 6)

In a manner similar to that in Example 3, by using picolinic acid (303 mg, 2.46 mmol) in place of methoxyacetic acid, the entitled Compound 6 (154 mg, 36%) was obtained from Compound a (300 mg, 1.23 mmol) obtained in Reference Example 1.

$^1$H NMR (DMSO-d$_6$, δ ppm): 6.61 (dd, J=1.8, 3.3 Hz, 1H), 6.77 (d, J=3.3 Hz, 1H), 7.47 (dd, J=1.7, 4.4 Hz, 2H), 7.68 (d, J=1.8 Hz, 1H), 7.72-7.76 (m, 1H), 8.09-8.21 (m, 2H), 8.63 (dd, J=1.7, 4.4 Hz, 2H), 8.78-8.80 (m, 1H), 12.4 (br s, 1H).

APCIMS m/z: [M+H]$^+$ 349.

Example 7

N-[4-(2-Furyl)-5-(4-pyridyl)thiazol-2-yl]pyrazine-2-carboxamide (Compound 7)

In a manner similar to that in Example 3, by using pyrazine-2-carboxylic acid (305 mg, 2.46 mmol) in place of methoxyacetic acid, the entitled Compound 7 (182 mg, 42%) was obtained from Compound a (300 mg, 1.23 mmol) obtained in Reference Example 1.

$^1$H NMR (DMSO-d$_6$, δ ppm): 6.58 (dd, J=1.8, 3.3 Hz, 1H), 6.74 (d, J=3.3, Hz, 1H), 7.45 (d, J=6.1 Hz, 2H), 7.66 (d, J=1.8 Hz, 1H), 8.61 (d, J=6.1 Hz, 2H), 8.83-8.84 (m, 1H), 8.94-8.95 (m, 1H), 9.30-9.31 (m, 1H), 12.85 (br s, 1H).

APCIMS m/z: [M+H]$^+$ 350.

Example 8

N-[4-(2-Furyl)-5-(4-pyridyl)thiazol-2-yl]furan-2-carboxamide (Compound 8)

In a manner similar to that in Example 3, by using furan-2-carboxylic acid (276 mg, 2.46 mmol) in place of methoxyacetic acid, the entitled Compound 8 (126 mg, 30%) was obtained from Compound a (300 mg, 1.23 mmol) obtained in Reference Example 1.

$^1$H NMR (DMSO-d$_6$, δ ppm): 6.60 (dd, J=1.8, 3.3 Hz, 1H), 6.74 (d, J=3.3 Hz, 1H), 6.77 (dd, J=1.7, 3.5 Hz, 1H), 7.45 (d, J=6.0 Hz, 2H), 7.67 (d, J=1.8 Hz, 1H), 7.76 (d, J=3.5 Hz, 1H), 8.05 (d, J=1.7 Hz, 1H), 8.62 (d, J=6.0 Hz, 2H), 13.02 (br s, 1H).

APCIMS m/z: [M+H]$^+$ 338.

Example 9

N-[4-(2-Furyl)-5-(4-pyridyl)thiazol-2-yl]furan-3-carboxamide (Compound 9)

In a manner similar to that in Example 3, by using furan-3-carboxylic acid (276 mg, 2.46 mmol) in place of methoxyacetic acid, the entitled Compound 9 (47.9 mg, 12%) was obtained from Compound a (300 mg, 1.23 mmol) obtained in Reference Example 1.

$^1$H NMR (DMSO-d$_6$, δ ppm): 6.59 (dd, J=1.8, 3.3 Hz, 1H), 6.71 (d, J=3.3 Hz, 1H), 7.12-7.13 (m, 1H), 7.42-7.44 (m, 2H), 7.65 (d, J=1.8 Hz, 1H), 7.85-7.86 (m, 1H), 8.30-8.62 (m, 3H), 12.84 (br s, 1H).

APCIMS m/z: [M+H]$^+$ 338.

Example 10

N-[4-(2-Furyl)-5-(4-pyridyl)thiazol-2-yl]-1-oxopyridine-3-carboxamide (Compound 10)

In a manner similar to that in Example 3, by using nicotinic acid N-oxide (342 mg, 2.46 mmol) in place of methoxyacetic acid, the entitled Compound 10 (60.1 mg, 13%) was obtained from Compound a (300 mg, 1.23 mmol) obtained in Reference Example 1.

$^1$H NMR (DMSO-d$_6$, δ ppm): 6.62 (dd, J=1.7, 3.5 Hz, 1H), 6.77 (dd, J=0.7, 3.5 Hz, 1H), 7.53 (dd, J=1.7, 4.6 Hz, 2H), 7.58-7.63 (m, 1H), 7.68 (dd, J=0.7, 1.7 Hz, 1H), 7.96-7.99 (m, 1H), 8.44-8.46 (m, 1H), 8.66 (dd, J=1.7, 4.6 Hz, 2H), 8.83-8.84 (m, 1H).

APCIMS m/z: [M+H]$^+$ 365.

Example 11

N-[4-(2-Furyl)-5-(4-pyridyl)thiazol-2-yl]-2-hydroxypyridine-5-carboxamide (Compound 11)

In a manner similar to that in Example 3, by using 6-hydroxynicotinic acid (342 mg, 2.46 mmol) in place of methoxyacetic acid, the entitled Compound 11 (38.2 mg, 8%) was obtained from Compound a (300 mg, 1.23 mmol) obtained in Reference Example 1.

$^1$H NMR (DMSO-d$_6$, δ ppm): 6.42 (d, J=9.7 Hz, 1H), 6.58 (dd, J=1.7, 3.3 Hz, 1H), 6.70 (d, J=3.3 Hz, 1H), 7.42 (d, J=6.1 Hz, 2H), 7.64 (d, J=1.7 Hz, 1H), 8.03 (dd, J=2.8, 9.7 Hz, 1H), 8.42 (d, J=2.8 Hz, 1H), 8.59 (d, J=6.1 Hz, 2H).

APCIMS m/z: [M+H]$^+$ 365.

Example 12

2-Chloro-N-[4-(2-furyl)-5-(4-pyridyl)thiazol-2-yl]pyridine-3-carboxamide (Compound 12)

In a manner similar to that in Example 3, by using 2-chloronicotinic acid (388 mg, 2.46 mmol) in place of methoxyacetic acid, the entitled Compound 12 (60.3 mg, 13%) was obtained from Compound a (300 mg, 1.23 mmol) obtained in Reference Example 1.

¹H NMR (DMSO-d₆, δ ppm): 6.58 (dd, J=1.8, 3.3 Hz, 1H), 6.71 (d, J=3.3 Hz, 1H), 7.47 (d, J=6.1 Hz, 2H), 7.58 (dd, J=4.8, 7.5 Hz, 1H), 7.65 (d, J=1.8 Hz, 1H), 8.17 (dd, J=1.8, 7.5 Hz, 1H), 8.57 (dd, J=1.8, 4.8 Hz, 1H), 8.62 (d, J=6.1 Hz, 2H), 13.28 (br s, 1H).
APCIMS m/z: [M+H]⁺ 383.

Example 13

N-[4-(2-Furyl)-5-(4-pyridyl)thiazol-2-yl]-(3-pyridyl)acetamide (Compound 13)

In a manner similar to that in Example 3, by using 3-pyridylacetic acid hydrochloride (427 mg, 2.46 mmol) in place of methoxyacetic acid, the entitled Compound 13 (20.2 mg, 4%) was obtained from Compound a (300 mg, 1.23 mmol) obtained in Reference Example 1.
¹H NMR (DMSO-d₆, δ ppm): 4.02 (s, 2H), 6.59 (dd, J=1.8, 3.3 Hz, 1H), 6.71 (d, J=3.3 Hz, 1H), 7.28-7.32 (m, 1H), 7.42 (m, 3H), 7.65 (d, J=1.8 Hz, 1H), 7.76-7.81 (m, 1H), 8.50-8.52 (m, 1H), 8.60 (dd, J=1.8, 4.4 Hz, 2H), 12.8 (br s, 1H).
APCIMS m/z: [M+H]⁺ 363.

Example 14

1-(tert-Butoxycarbonyl)-N-[4-(2-furyl)-5-(4-pyridyl)thiazol-2-yl]piperidine-4-carboxamide (Compound 14)

Compound a (2.00 g, 8.22 mmol) obtained in Reference Example 1,1-(tert-butoxycarbonyl)piperidine-4-carboxylic acid (5.94 g, 25.9 mmol) and PyBOP (14.1 g, 27.1 mmol) were dissolved in DMF (32 mL), and triethylamine (7.56 mL, 54.3 mmol) was added thereto, followed by stirring at 60° C. for 4 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting solid was reslurried with ethanol to afford the entitled Compound 14 (1.88 g, 50%).
¹H NMR (DMSO-d₆, δ ppm): 1.41 (s, 9H), 1.41-1.57 (m, 2H), 1.81-1.85 (m, 2H), 2.65-2.80 (m, 3H), 3.94-3.99 (m, 2H), 6.58 (dd, J=1.7, 3.5 Hz, 1H), 6.69 (dd, J=0.7, 3.5 Hz, 1H), 7.41 (dd, J=1.6, 4.4 Hz, 2H), 7.64 (dd, J=0.7, 1.7 Hz, 1H), 8.60 (dd, J=1.6, 4.4 Hz, 2H), 12.56 (br s, 1H).
APCIMS m/z: [M+H]⁺ 455.

Example 15

N-[4-(2-Furyl)-5-(4-pyridyl)thiazol-2-yl]piperidine-4-carboxamide (Compound, 15)

Compound 14 (1.80 g, 3.96 mmol) was dissolved in dichloromethane (20 mL), and trifluoroacetic acid (20 mL) was added thereto, followed by stirring at room temperature for 30 minutes. The reaction mixture was concentrated under reduced pressure, and water was added to the resulting residue, followed by adding a 10 mol/L aqueous solution of sodium hydroxide to adjust the pH to 12. The precipitated solid was collected by filtration to afford the entitled Compound 15 (1.17 g, 84%).
¹H NMR (DMSO-d₆, δ ppm): 1.46-1.60 (m, 2H), 1.74 (d, J=10.2 Hz, 2H), 2.40-2.55 (m, 3H), 2.90 (d, J=12.4 Hz, 2H), 6.58 (dd, J=1.6, 3.2 Hz, 1H), 6.68 (dd, J=0.8, 3.2 Hz, 1H), 7.40 (dd, J=1.6, 4.6 Hz, 2H), 7.63 (d, J=0.8, 1.6 Hz, 1H), 8.59 (dd, J=1.6, 4.6 Hz, 2H)
APCIMS m/z: [M+H]⁺ 355. .

Example 16

1-(5-Cyanopyridin-2-yl)-N-[4-(2-furyl)-5-(4-pyridyl)thiazol-2-yl]piperidine-4-carboxamide (Compound 16)

Compound 15 (177 mg, 0.50 mmol), 2-chloro-5-cyanopyridine (104 mg, 0.75 mmol) and potassium carbonate (207 mg, 1.50 mmol) were dissolved in NMP (4 mL), followed by stirring overnight under heating and reflux. The reaction mixture was allowed to cool down to room temperature, then poured into water, and the deposited precipitate was collected by filtration. The resulting precipitate was purified through silica gel column chromatography (chloroform:methanol=17:3) to afford the entitled Compound 16 (114 mg, 50%).
¹H NMR (DMSO-d₆, δ ppm): 1.55-1.68 (m, 2H), 1.91-1.96 (m, 2H), 2.85-2.90 (m, 1H), 3.02-3.10 (m, 2H), 4.42-4.52 (m, 2H), 6.59 (dd, J=1.9, 3.5 Hz, 1H), 6.69 (dd, J=0.8, 3.5 Hz, 1H), 6.97 (d, J=9.2 Hz, 1H), 7.41 (dd, J=1.6, 4.6 Hz, 2H), 7.64 (dd, J=0.8, 1.9 Hz, 1H), 7.84 (dd, J=2.4, 9.2 Hz, 1H), 8.48 (d, J=2.4 Hz, 1H), 8.59 (dd, J=1.6, 4.6 Hz, 2H), 12.60 (br s, 1H).
APCIMS m/z: [M+H]⁺ 457.

Example 17

N-[4-(2-Furyl)-5-(4-pyridyl)thiazol-2-yl]-1-[5-(methanesulfonyl)pyridin-2-yl]piperidine-4-carboxamide (Compound 17)

In a manner similar to that in Example 16, by using 2-chloro-5-(methanesulfonyl)pyridine (144 mg, 0.75 mmol) obtained according to the method described in WO02/51836 in place of 2-chloro-5-cyanopyridine, the entitled Compound 17 (94.3 mg, 37%) was obtained from Compound 15 (177 mg, 0.50 mmol).
¹H NMR (DMSO-d₆, δ ppm): 1.55-1.69 (m, 2H), 1.91-1.97 (m, 2H), 2.86-2.91 (m, 1H), 3.03-3.21 (m, 2H), 3.23 (s, 3H), 4.45-4.55 (m, 2H), 6.59 (dd, J=1.6, 3.5 Hz, 1H), 6.70 (dd, J=0.8, 3.5 Hz, 1H), 7.01 (d, J=9.2 Hz, 1H), 7.41 (dd, J=1.6, 4.6 Hz, 2H), 7.64 (dd, J=0.8, 1.6 Hz, 1H), 7.88 (dd, J=3.0, 9.2 Hz, 1H), 8.50 (d, J=3.0 Hz, 1H), 8.59 (dd, J=1.6, 4.6 Hz, 2H), 12.61 (br s, 1H).
APCIMS m/z: [M+H]⁺ 510.

Example 18

4-(Bromomethyl)-N-[4-(2-furyl)-5-(4-pyridyl)thiazol-2-yl]benzamide (Compound 18)

4-(Bromomethyl)benzoic acid (1.12 g, 5.20 mmol) was dissolved in toluene (80 mL), and thionyl chloride (7.59 mL, 104 mmol) was added thereto, followed by stirring under heating and reflux for 5 hours. The reaction mixture was concentrated under reduced pressure, and the resulting residue was dissolved in THF (50 mL). Compound a (1.00 g, 4.11 mmol) obtained in Reference Example 1, triethylamine (0.86 mL, 6.17 mmol) and N,N-dimethylaminopyridine (97.6 mg, 0.800 mmol) were added thereto, followed by stirring under heating and reflux for 1 hour. The reaction mixture was allowed to cool down to room temperature, and the precipitated solid was collected by filtration, followed by washing with diethyl ether to afford the entitled Compound 18 (2.28 g, 100%).
¹H NMR (DMSO-d₆, δ ppm): 4.86 (s, 2H), 6.60 (dd, J=1.9, 3.5 Hz, 1H), 6.74 (dd, J=0.5, 3.5 Hz, 1H), 7.46 (dd, J=1.6, 4.3

Hz, 2H), 7.62 (d, J=8.4 Hz, 2H), 7.67 (dd, J=0.5, 1.9 Hz, 1H), 8.14 (dd, J=1.6, 4.3 Hz, 2H), 8.62 (d, J=8.4 Hz, 2H).

Example 19

N-[4-(2-Furyl)-5-(4-pyridyl)thiazol-2-yl]-4-(imidazol-1-ylmethyl)benzamide (Compound 19)

Compound 18 (880 mg, 2.00 mmol) was suspended in NMP (10 mL), and imidazole (408 mg, 6.00 mmol) was added thereto, followed by stirring at 65° C. for 2 hours. The reaction mixture was allowed to cool down to room temperature and then poured into water, and the deposited precipitate was collected by filtration. The resulting precipitate was purified through silica gel column chromatography (chloroform:methanol=17:3) to afford the entitled Compound 19 (538 mg, 63%).

$^1$H NMR (DMSO-$d_6$, δ ppm): 5.23 (s, 2H), 6.42 (dd, J=1.9, 3.2 Hz, 1H), 6.57 (dd, J=0.8, 3.2 Hz, 1H), 6.93 (m, 1H), 7.17 (m, 1H), 7.28 (d, J=8.4 Hz, 2H), 7.36 (dd, J=0.8, 1.9 Hz, 1H), 7.42 (dd, J=1.6, 4.6 Hz, 2H), 7.60 (m, 1H), 7.96 (d, J=8.4 Hz, 2H), 8.65 (dd, J=1.6, 4.6 Hz, 2H), 10.15 (br s, 1H).

APCIMS m/z: [M+H]$^+$ 428.

Example 20

N-[4-(2-Furyl)-5-(4-pyridyl)thiazol-2-yl]-4-[(4-hydroxypiperidino)methyl]benzamide dihydrochloride (Compound 20)

In a manner similar to that in Example 19, by using 4-hydroxypiperidine (607 mg, 6.00 mmol) in place of imidazole, a free form of the entitled Compound was obtained. The resulting free form was treated with an ethyl acetate solution of 4 mol/L hydrogen chloride to afford the entitled Compound 20 (512 mg, 48%).

$^1$H NMR (DMSO-$d_6$, δ ppm): 1.38-1.42 (m, 2H), 1.69-1.73 (m, 2H), 2.03-2.18 (m, 2H), 2.65-2.70 (m, 3H), 3.40-3.50 (m, 2H), 4.55 (d, J=4.0 Hz, 1H), 6.60 (dd, J=1.9, 3.5 Hz, 1H), 6.74; (dd, J=0.8, 3.5 Hz, 1H), 7.45 (dd, J=1.6, 4.6 Hz, 2H), 7.47 (d, J=8.4 Hz, 2H), 7.67 (dd, J=0.8, 1.9 Hz, 1H), 8.10 (d, J=8.4 Hz, 2H), 8.62 (dd, J=1.6, 4.6 Hz, 2H), 12.97 (br s, 1H).

APCIMS m/z: [M+H]$^+$ 461.

Example 21

N-[4-(2-Furyl)-5-(2-pyridyl)thiazol-2-yl]pyridine-4-carboxamide (Compound 21)

In a manner similar to that in Example 1, the entitled Compound 21 (157 mg, 90%) was obtained from Compound b (122 mg, 0.50 mmol) obtained in Reference Example 2 in place of Compound a.

$^1$H NMR (DMSO-$d_6$, δ ppm): 6.65 (dd, J=1.8, 3.3 Hz, 1H), 6.84 (d, J=3.3 Hz, 1H), 7.31-7.35 (m, 1H), 7.50-7.53 (m, 1H), 7.74 (d, J=1.8 Hz, 1H), 7.78-7.83 (m, 1H), 8.00 (d, J=4.8 Hz, 2H), 8.60-8.62 (m, 1H), 8.81 (d, J=4.8 Hz, 2H), 13.2 (br s, 1H).

APCIMS m/z: [M+H]$^+$ 349.

Example 22

N-[4-(2-Furyl)-5-phenylthiazol-2-yl]pyridine-4-carboxamide (Compound 22)

In a manner similar to that in Example 1, by using Compound c (300 mg, 1.24 mmol) obtained in Reference Example 3 in place of Compound a, the entitled Compound 22 (372 mg, 86%) was obtained.

$^1$H NMR (DMSO-$d_6$, δ ppm): 6.53-6.55 (m, 2H), 7.43-7.46 (m, 5H), 7.61 (dd, J=0.7, 1.8 Hz, 1H), 8.02 (dd, J=1.7, 4.5 Hz, 2H), 8.82 (dd, J=1.7, 4.5 Hz, 2H), 13.23 (br s, 1H).

ESIMS m/z: [M+H]$^+$ 348.

Example 23

N-[5-Benzyl-4-(2-furyl)thiazol-2-yl]pyridine-4-carboxamide (Compound 23)

In a manner similar to that in Example 1, the entitled Compound 23 (99.4 mg, 31%) was obtained from Compound d (300 mg, 0.89 mmol) obtained in Reference Example 4 in place of Compound a.

$^1$H NMR (DMSO-$d_6$, δ ppm): 4.39 (s, 2H), 6.34 (dd, J=1.8, 3.5 Hz, 1H), 6.50 (d, J=3.5 Hz, 1H), 7.26-7.36 (m, 6H), 7.63 (dd, J=1.7, 4.5 Hz, 2H), 8.71 (dd, J=1.7, 4.5 Hz, 2H), 10.90 (br s, 1H).

ESIMS m/z: [M−H]$^-$ 360.

Example 24

N-(5-(Ethoxycarbonyl)-4-(2-furyl)thiazol-2-yl]pyridine-4-carboxamide (Compound 24)

In a manner similar to that in Example 1, the entitled Compound 24, (1.15 g, 53%) was obtained from Compound e (2.00 g, 6.27 mmol) obtained in Reference Example 5 in place of Compound a.

$^1$H NMR (DMSO-$d_6$, δ ppm): 1.41 (t, J=7.2 Hz, 3H), 4.39 (q, J=7.2 Hz, 2H), 6.52 (dd, J=1.7, 3.5 Hz, 1H), 7.47 (d, J=1.7 Hz, 1H), 7.73 (dd, J=1.5, 4.4 Hz, 2H), 7.79 (d, J=3.5 Hz, 1H), 8.71 (dd, J=1.5, 4.4 Hz, 2H).

ESIMS m/z: [M−H]$^-$ 342.

Example 25

N-[4-(2-Furyl)-5-(1-oxopyridin-4-yl)thiazol-2-yl]acetamide (Compound 25)

Compound 2 (550 mg, 1.92 mmol) was suspended in dichloromethane (30 mL), and m-chloroperbenzoic acid (531 mg, 2.51 mmol) was added thereto, followed by stirring at room temperature for 1 hour. An aqueous solution of sodium thiosulfate was added to the reaction mixture, followed by stirring for 30 minutes, and then the solvent was distilled away under reduced pressure. A saturated aqueous solution of sodium hydrogencarbonate was added to the resulting residue, and the precipitated crystals were collected by filtration. The resulting crystals were washed successively with water and ethanol to afford the entitled Compound 25 (517 mg, 89%) as a yellow solid.

$^1$H NMR (DMSO-$d_6$, δ ppm): 2.18 (s, 3H), 6.59 (dd, J=1.8, 3.3 Hz, 1H), 6.71 (dd, J=0.7, 3.3 Hz, 1H), 7.44 (dd, J=1.5, 4.6 Hz, 2H), 7.66 (dd, J=0.7, 1.8 Hz, 1H), 8.22 (dd, J=1.5, 4.6 Hz, 2H), 12.5 (br s, 1H).

ESIMS m/z: [M+H]$^+$ 302.

Example 26

N-[4-(2-Furyl)-5-methylthiazol-2-yl]acetamide (Compound 26)

In a manner similar to that in Example 2, the entitled Compound 26 (206 mg, 80%) was obtained from Compound f (207 mg, 1.15 mmol) obtained in Reference Example 6 in place of Compound a.

$^1$H NMR (DMSO-$d_6$, δ ppm): 2.03 (s, 3H), 2.55 (s, 3H), 6.46 (dd, J=1.8, 3.3 Hz, 1H), 6.56 (d, J=3.3 Hz, 1H), 7.45 (d, J=1.8 Hz, 1H).

APCIMS m/z: [M+H]$^+$ 223.

Example 27

N-[4-(2-Furyl)-5-phenylthiazol-2-yl]acetamide (Compound 27)

In a manner similar to that in Example 2, the entitled Compound 27 (277 mg, 78%) was obtained from Compound c (300 mg, 1.24 mmol) obtained in Reference Example 3 in place of Compound a.

$^1$H NMR (DMSO-$d_6$, δ ppm): 2.17 (s, 3H), 6.47-6.57 (m, 2H), 7.35-7.49 (m, 5H), 7.57 (d, J=1.8 Hz, 1H), 12.37 (br s, 1H).

APCIMS m/z: [M+H]$^+$ 285.

Example 28

N-[4-(2-Furyl)-5-phenylthiazol-2-yl]cyclohexanecarboxamide (Compound 28)

In a manner similar to that in Example 4, the entitled Compound 28 (332 mg, 76%) was obtained from Compound c (300 mg, 1.24 mmol) obtained in Reference Example 3 in place of Compound a.

$^1$H NMR (DMSO-$d_6$, δ ppm): 1.24-1.86 (m, 10H), 2.50-2.56 (m, 1H), 6.51 (s, 2H), 7.42 (br s, 5H), 7.57 (s, 1H), 12.30 (s, 1H).

APCIMS m/z: [M+H]$^+$ 353.

Example 29

N-[4-(2-Furyl)-5-morpholinothiazol-2-yl]pyridine-4-carboxamide (Compound 29)

Step 1:

Compound g (250 mg, 1.02 mmol) obtained in Reference Example 7 was dissolved in DMF (4 mL), and morpholine (0.440 mL, 5.10 mmol) was added thereto, followed by stirring at 100° C. for 6 hours. The reaction mixture was allowed to cool down, and water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford 2-amino-4-(2-furyl)-5-morpholinothiazole (135 mg, 52%).

$^1$H NMR (CDCl$_3$, δ ppm): 2.86-2.89 (m, 4H), 3.84-3.87 (m, 4H), 4.94 (br s, 2H), 6.47 (dd, J=1.8, 3.3 Hz, 1H), 6.85 (dd, J=0.8, 3.3 Hz, 1H), 7.42 (dd, J=0.8, 1.8 Hz, 1H).

Step 2:

In a manner similar to that in Example 1, the entitled Compound 29 (175 mg, 60%) was obtained from 2-amino-4-(2-furyl)-5-morpholinothiazole (206 mg, 0.82 mmol) obtained in Step 1 in place of Compound a.

$^1$H NMR (CDCl$_3$, δ ppm): 3.02-3.05 (m, 4H), 3.89-3.92 (m, 4H), 6.43 (dd, J=1.8, 3.3 Hz, 1H), 6.82 (dd, J=0.8, 3.3 Hz, 1H), 7.31 (dd, J=0.8, 1.8 Hz, 1H), 7.68 (dd, J=1.5, 4.5 Hz, 2H), 8.76 (dd, J=1.5, 4.5 Hz, 2H), 10.56 (br s, 1H).

ESIMS m/z: [M−H]$^-$ 355.

Example 30

N-[4-(2-Furyl)-5-morpholinothiazol-2-yl]acetamide (Compound 30)

In a manner similar to that in Example 2, the entitled Compound 30 (136 mg, 92%) was obtained from 2-amino-4-(2-furyl)-5-morpholinothiazole (127 mg, 0.51 mmol) obtained in Step 1 of Example 29 in place of Compound a obtained in Reference Example 1.

$^1$H NMR (CDCl$_3$, δ ppm): 2.17 (s, 3H), 2.98-3.01 (m, 4H), 3.86 (m, 4H), 6.50 (dd, J=1.7, 3.3 Hz, 1H), 6.85 (d, J=3.3 Hz, 1H), 7.44 (d, J=1.7 Hz, 1H), 9.25 (br s, 1H).

ESIMS m/z: [M+H]$^+$ 294

Example 31

N-[4-(2-Furyl)-5-morpholinothiazol-2-yl]pyridine-3-carboxamide (Compound 31)

In a manner similar to that in Example 1, by using nicotinoyl chloride hydrochloride (356 mg, 2.00 mmol) in place of isonicotinoyl chloride hydrochloride and using 2-amino-4-(2-furyl)-5-morpholinothiazole (251 mg, 1.00 mmol) obtained in Step 1 of Example 29 in place of Compound a obtained in Reference Example 1, the entitled Compound 31 (216 mg, 61%) was obtained.

$^1$H NMR (CDCl$_3$, δ ppm): 3.04 (t, J=4.6 Hz, 4H), 3.90 (t, J=4.6 Hz, 4H), 6.33 (dd, J=1.9, 3.5 Hz, 1H), 6.85 (d, J=3.5 Hz, 1H), 7.39 (d, J=1.9 Hz, 1H), 7.45 (dd, J=4.9, 7.8 Hz, 1H), 8.21 (ddd, J=1.9, 2.2, 7.8 Hz, 1H), 8.81 (dd, J=1.9, 4.9 Hz, 1H), 9.14 (d, J=2.2 Hz, 1H).

APCIMS m/z: [M+H]$^+$ 357.

Example 32

2-Chloro-N-[4-(2-furyl)-5-morpholinothiazol-2-yl]pyridine-5-carboxamide (Compound 32)

2-Amino-4-(2-furyl)-5-morpholinothiazole (2.15 g, 8.57 mmol) obtained in Step 1 of Example 29 was dissolved in pyridine (25 mL), and 6-chloronicotinoyl chloride (1.81 g, 10.3 mmol) and N,N-dimethylaminopyridine (105 mg, 0.86 mmol) were added thereto. The mixture was stirred at room temperature for 10 hours, and then the solvent was distilled away under reduced pressure. The resulting residue was purified through silica gel column chromatography (hexane:ethyl acetate=1:1 to 1:2) to afford the entitled Compound 32 (1.96 g, 59%).

$^1$H NMR (CDCl$_3$, δ ppm): 3.04 (t, J=4.3 Hz, 4H), 3.90 (t, J=4.3 Hz, 4H), 6.41 (dd, J=1.6, 3.5 Hz, 1H), 6.79 (d, J=3.5 Hz, 1H), 7.23 (d, J=1.6 Hz, 1H), 7.36 (d, J=8.4 Hz, 1H), 8.11 (dd, J=2.2, 8.4 Hz, 1H), 8.84 (d, J=2.2 Hz, 1H).

Example 33

N-[4-(2-Furyl)-5-morpholinothiazol-2-yl]-2-[(2-hydroxyethyl)amino]pyridine-5-carboxamide (Compound 33)

Compound 32 (391 mg, 1.00 mmol) was dissolved in 1,4-dioxane (4 mL), and ethanolamine (0.300 mL, 5.00 mmol) was added thereto, followed by stirring overnight under heating and reflux. The reaction mixture was concentrated under reduced pressure, and a saturated aqueous solution of sodium chloride and chloroform were added to the resulting residue, and the precipitated solid was collected by filtration to afford the entitled Compound 33 (244 mg, 59%).

$^1$H NMR (DMSO-$d_6$, δ ppm): 2.91 (t, J=4.4 Hz, 4H), 3.30-3.43 (m, 2H), 3.51-3.54 (m, 2H), 3.78 (t, J=4.4 Hz, 4H), 4.74 (m, 1H), 6.55 (d, J=8.9 Hz, 1H), 6.60 (dd, J=1.9, 3.2 Hz, 1H), 6.81 (dd, J=0.8, 3.2 Hz, 1H), 7.36 (t, J=8.1 Hz, 1H), 7.68 (dd, J=0.8, 1.9 Hz, 1H), 8.00 (dd, J=2.2, 8.9 Hz, 1H), 8.75 (d, J=2.2 Hz, 1H).

APCIMS m/z: [M+H]$^+$ 416.

Example 34

N-[4-(2-Furyl)-5-morpholinothiazol-2-yl]-2-morpholinopyridine-5-carboxamide (Compound 34)

Compound 32 (391 mg, 1.00 mmol) was dissolved in 1,4-dioxane (10 mL), and morpholine (0.44 mL, 5.00 mmol) was added thereto, followed by stirring under heating and reflux for 10 hours. The reaction mixture was concentrated under reduced pressure, and a saturated aqueous solution of sodium chloride was added to the resulting residue, followed by extraction with chloroform. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=19:1) to afford the entitled Compound 34 (372 mg, 84%).

$^1$H NMR (CDCl$_3$, δ ppm): 3.02 (t, J=4.6 Hz, 4H), 3.68 (t, J=4.7 Hz, 4H), 3.82 (t, J=4.7 Hz, 4H), 3.89 (t, J=4.6 Hz, 4H), 6.51 (dd, J=1.9, 3.5 Hz, 1H), 6.66 (d, J=9.2 Hz, 1H), 6.88 (d, J=3.5 Hz, 1H), 7.45 (d, J=1.9 Hz, 1H), 7.98 (dd, J=2.4, 9.2 Hz, 1H), 8.72 (d, J=2.4 Hz, 1H).

APCIMS m/z: [M+H]$^+$ 442.

Example 35

N-[4-(2-Furyl)-5-morpholinothiazol-2-yl]-2-(4-methylpiperazin-1-yl)pyridine-5-carboxamide (Compound 35)

Compound 32 (391 mg, 1.00 mmol) was dissolved in 1,4-dioxane (10 mL), and 1-methylpiperazine (0.56 mL, 5.00 mmol) was added thereto, followed by stirring under heating and reflux for 10 hours. The reaction mixture was concentrated under reduced pressure, a saturated aqueous solution of sodium chloride was added to the resulting residue, followed by extraction with chloroform. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol:28% aqueous ammonia=10:1:1) to afford the entitled Compound 35 (454 mg, 100%).

$^1$H NMR (CDCl$_3$, δ ppm): 2.36 (s, 3H), 2.52 (t, J=4.9 Hz, 4H), 3.02 (t, J=4.6 Hz, 4H), 3.74 (t, J=4.9 Hz, 4H), 3.89 (t, J=4.6 Hz, 4H), 6.51 (dd, J=1.9, 3.2 Hz, 1H), 6.66 (d, J=9.4 Hz, 1H), 6.87 (d, J=3.2 Hz, 1H), 7.45 (d, J=1.9 Hz, 1H), 7.95 (dd, J=2.4, 9.4 Hz, 1H), 8.70 (d, J=2.4 Hz, 1H).

APCIMS m/z: [M+H]$^+$ 455.

Example 36

2-Chloromethyl-N-[4-(2-furyl)-5-morpholinothiazol-2-yl]pyridine-5-carboxamide (Compound 36)

Step 1:

Methyl 6-chloromethylnicotinate (1.30 g, 7.00 mmol) obtained according to the method described in WO02/92455 was added to 2 mol/L hydrochloric acid, followed by stirring under heating and reflux for 5 hours. The reaction mixture was allowed to cool down to room temperature, and the precipitated solid was collected by filtration to afford 6-chloromethylnicotinic acid (539 mg, 45%).

$^1$H NMR (DMSO-$d_6$, δ ppm): 4.87 (s, 2H), 7.70 (d, J=8.1 Hz, 1H), 8.32 (dd, J=2.2, 8.1 Hz 1H), 9.04 (d, J=2.2 Hz, 1H).

Step 2:

6-Chloromethylnicotinic acid (172 mg, 1.00 mmol) obtained in Step 1,2-amino-4-(2-furyl)-5-morpholinothiazole (251 mg, 1.00 mmol) obtained in Step 1 of Example 29 and PyBOP (572 mg, 1.10 mmol) were dissolved in DMF (4 mL), and triethylamine (0.307 mL, 2.20 mmol) was added thereto, followed by stirring at room temperature for 2 hours. The reaction mixture was poured into water, followed by extraction with ethyl acetate. The organic layer was washed with a saturated aqueous solution of sodium chloride and dried over anhydrous magnesium sulfate, and then the solvent was distilled away under the reduced pressure. The resulting residue was purified through silica gel column chromatography (hexane:ethyl acetate=2:1 to 1:3) to afford the entitled Compound 36 (194 mg, 48%).

$^1$H NMR (CDCl$_3$, δ ppm): 3.04 (t, J=4.6 Hz, 4H), 3.85 (t, J=4.6 Hz, 4H), 4.64 (s, 2H), 6.28 (dd, J=2.2, 3.5 Hz, 1H), 6.69 (dd, J=0.8, 3.5 Hz, 1H), 7.05 (dd, J=0.8, 2.2 Hz, 1H), 7.42 (d, J=8.4 Hz, 1H), 8.12 (dd, J=2.4, 8.4 Hz, 1H), 8.98 (d, J=2.4 Hz, 1H), 12.26 (br s, 1H).

Example 37

N-[4-(2-Furyl)-5-morpholinothiazol-2-yl]-2-(imidazol-1-ylmethyl)pyridine-5-carboxamide (Compound 37)

Compound 36 (97.1 mg, 0.240 mmol) was dissolved in DMF (2.5 mL), imidazole (49.0 mg, 0.721 mmol) was added thereto, followed by stirring at 95° C. for 2 hours. The reaction mixture was poured into water, followed by extraction with ethyl acetate. The organic layer was washed with a saturated aqueous solution of sodium chloride and dried over anhydrous magnesium sulfate, and then the solvent was distilled away under the reduced pressure. The resulting residue was purified through silica gel column chromatography (chloroform:methanol=17:3) to afford the entitled Compound 37 (58.0 mg, 55%).

$^1$H NMR (CDCl$_3$, δ ppm): 3.02 (t, J=4.6 Hz, 4H), 3.90 (t, J=4.6 Hz, 4H), 5.31 (s, 2H), 6.42 (dd, J=1.9, 3.2 Hz, 1H), 6.80 (d, J=3.2 Hz, 1H), 6.97 (d, J=8.1 Hz, 1H), 6.96-6.70 (m, 1H), 7.15-7.19 (m, H), 7.28 (d, J=1.9 Hz, 1H), 7.62-7.66 (m, 1H), 8.15 (dd, J=2.2, 8.1 Hz, 1H), 9.09 (d, J=2.2 Hz, 1H)

APCIMS m/z: [M+H]$^+$ 437. .

Example 38

N-[4-(2-Furyl)-5-morpholinothiazol-2-yl]-2-(4-hydroxypiperidinomethyl)pyridine-5-carboxamide (Compound 38)

In a manner similar to that in Example 37, by using 4-hydroxypiperidine and 1,4-dioxane in place of imidazole and DMF, respectively, the entitled Compound 38 (66.2 mg, 59%) was obtained from Compound 36 (96.8 mg, 0.239 mmol).
$^1$H NMR (CDCl$_3$, δ ppm): 1.59-1.72 (m, 4H), 1.92-2.00 (m, 2H), 2.15-2.30 (m, 1H), 2.75-2.80 (m, 2H), 3.03 (t, J=4.6 Hz, 4H), 3.73 (s, 2H), 3.96 (t, J=4.6 Hz, 4H), 6.47 (dd, J=1.9, 3.5 Hz, 1H), 6.85 (dd, J=0.8, 3.5 Hz, 1H), 7.38 (dd, J=0.8, 1.9 Hz, 1H), 7.60 (d, J=7.7 Hz, 1H), 8.18 (dd, J=2.2, 7.7 Hz, 1H), 9.06 (d, J=2.2 Hz, 1H).
APCIMS m/z: [M+H]$^+$ 470.

Example 39

2-Chloro-N-[4-(2-furyl)-5-morpholinothiazol-2-yl]pyridine-4-carboxamide (Compound 39)

2-Chloroisonicotinic acid (5.00 g, 31.7 mmol) was added to thionyl chloride (40 mL), followed by stirring under heating and reflux for 2 hours. The reaction mixture was concentrated under reduced pressure, and the resulting residue was dissolved in dichloromethane (1 mL). The resulting solution was added to a pyridine (16 ml) solution of 2-amino-4-(2-furyl)-5-morpholinothiazole (880 mg, 5.00 mmol) obtained in Step 1 of Example 29, and then N,N-dimethylaminopyridine (48.8 mmol, 0.400 mmol) was added thereto, followed by stirring at room temperature for 1 hour. The reaction mixture was concentrated under reduced pressure, and the resulting residue was purified through silica gel column chromatography (hexane:ethyl acetate=1:3 to ethyl acetate) to afford the entitled Compound 39 (1.05.g, 66%)
$^1$H NMR (CDCl$_3$, δ ppm): 3.03 (t, J=4.6 Hz, 4H), 3.60 (t, J=4.6 Hz, 4H), 6.52 (dd, J=1.6, 3.5 Hz, 1H), 6.88 (dd, J=0.8, 3.5 Hz, 1H), 6.95 (dd, J=1.4, 5.1 Hz, 1H), 7.10-7.12 (m, 1H), 7.46 (dd, J=0.8, 1.6 Hz, 1H), 8.35 (dd, J=0.8, 5.1 Hz, 1H), 9.33 (br s, 1H).

Example 40

N-[4-(2-Furyl)-5-morpholinothiazol-2-yl]-2-morpholinopyridine-4-carboxamide (Compound 40)

Compound 39 (391 mg, 1.00 mmol) was dissolved in NMP (10 mL), morpholine (1.05 mL, 12.0 mmol) was added thereto, followed by stirring at 150° C. for 8 hours. The reaction mixture was purified through silica gel column chromatography (hexane:ethyl acetate=2:1 to 1:3) to afford the entitled Compound 40 (118 mg, 27%).
$^1$H NMR (CDCl$_3$, δ ppm): 3.03 (t, J=4.6 Hz, 4H), 3.58 (t, J=4.9 Hz, 4H), 3.84 (t, J=4.9 Hz, 4H), 3.88 (t, J=4.6 Hz, 4H), 6.50 (dd, J=1.9, 3.5 Hz, 1H), 6.86 (d, J=3.5 Hz, 1H), 6.94 (dd, J=1.6, 5.1 Hz, 1H), 7.09 (d, J=1.6 Hz, 1H), 7.42 (d, J=1.9 Hz, 1H), 8.33 (d, J=5.1 Hz, 1H).
APCIMS m/z: [M+H]$^+$ 442.

Example 41

N-[4-(2-Furyl)-5-morpholinothiazol-2-yl]-2-(4-methylpiperazin-1-yl)pyridine-4-carboxamide (Compound 41)

Compound 39 (391 mg, 1.00 mmol) was dissolved in NMP (10 mL), and 1-methylpiperazine (1.11 mL, 10.0 mmol) was added thereto, followed by stirring overnight at 150° C. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=19:1) to afford the entitled Compound 41 (22.2 mg, 5%).
$^1$H NMR (CDCl$_3$, δ ppm): 2.37 (s, 3H), 2.55 (t, J=4.9 Hz, 4H), 3.03 (t, J=4.6 Hz, 4H), 3.66 (t, J=4.9 Hz, 4H), 3.90 (t, J=4.6 Hz, 4H), 6.51 (dd, J=1.9, 3.2 Hz, 1H), 6.87 (dd, J=0.8, 3.2 Hz, 1H), 6.90 (dd, J=1.3, 5.1 Hz, 1H), 7.11 (d, J=1.3 Hz, 1H), 7.44 (dd, J=0.8, 1.9 Hz, 1H), 8.32 (d, J=5.1 Hz, 1H), 9.50 (br s, 1H).
APCIMS m/z: [M+H]$^+$ 455.

Example 42

1-(tert-Butoxycarbonyl)-N-[4-(2-furyl)-5-morpholinothiazol-2-yl]piperidine-4-carboxamide (Compound 42)

2-Amino-4-(2-furyl)-5-morpholinothiazole (3.58 g, 14.3 mmol) obtained in Step 1 of Example 29, 1-(tert-butoxycarbonyl)-4-piperidinecarboxylic acid (3.27 g, 14.3 mmol) and PyBOP (8.16 g, 15.7 mmol) were dissolved in DMF (30 mL), and triethylamine (4.37 mL, 31.4 mmol) was added thereto, followed by stirring overnight at room temperature. The reaction mixture was poured into water, followed by extraction with ethyl acetate. The organic layer was washed successively with 1 mol/L hydrochloric acid, a saturated aqueous solution of sodium hydrogencarbonate and a saturated aqueous solution of sodium chloride, and dried over anhydrous magnesium sulfate, and then the solvent was distilled away under reduced pressure. The resulting residue was purified through silica gel column chromatography (hexane:ethyl acetate=1:1) to afford the entitled Compound 42 (4.52 g, 68%).
$^1$H NMR (CDCl$_3$, δ ppm): 1.45 (s, 9H), 1.60-1.80 (m, 4H), 2.20-2.28 (m, 1H), 2.49-2.58 (m, 2H), 3.00 (t, J=4.6 Hz, 4H), 3.88 (t, J=4.6 Hz, 4H), 3.95-4.15 (m, 2H), 6.52 (dd, J=1.9, 3.5 Hz, 1H), 6.90 (d, J=3.5 Hz, 1H), 7.43 (d, J=1.9 Hz, 1H), 10.28 (br s, 1H).
APCIMS m/z: [M+H]$^+$ 463.

Example 43

1-(Benzyloxycarbonyl)-N-[4-(2-furyl)-5-morpholinothiazol-2-yl]piperidine-4-carboxamide (Compound 43)

1-Benzyloxycarbonylpiperidine-4-carboxylic acid (5.00 g, 19.0 mmol) was dissolved in dichloromethane (80 mL), and thionyl chloride (6.93 mL, 95.0 mmol) and DMF (0.15 mL, 1.90 mmol) were added thereto, followed by 178, stirring under heating and reflux for 3 hours. The reaction mixture was concentrated under reduced pressure, and the resulting residue was dissolved in dichloromethane (2 mL). The resulting solution was added to a solution of 2-amino-4-(2-furyl)-5-morpholinothiazole (2.01 g, 8.00 mmol) in pyridine (32 mL) obtained in Step 1 of Example 29, and then N,N-dimethylaminopyridine (97.6 mg, 0.800 mmol) was added thereto, followed by stirring at room temperature for 1 hour.

The solvent was distilled away under reduced pressure, and the resulting residue was purified through silica gel column chromatography (hexane:ethyl acetate=1:1 to 1:3) to afford the entitled Compound 43 (4.96 g, 100%).

$^1$H NMR (CDCl$_3$, δ ppm): 1.61-1.78 (m, 4H), 2.30-2.38 (m, 1H), 2.70-2.78 (m, 2H), 2.98 (t, J=4.6 Hz, 4H), 3.88 (t, J=4.6 Hz, 4H), 4.13-4.23 (m, 2H), 5.12 (s, 2H), 6.51 (dd, J=1.6, 3.2 Hz, 1H), 6.87 (d, J=3.2 Hz, 1H), 7.29-7.36 (m, 5H), 7.44 (d, J=1.6 Hz, 1H), 9.71 (br s, 1H).

APCIMS m/z: [M+H]$^+$ 497.

Example 44

N-[4-(2-Furyl)-5-morpholinothiazol-2-yl]piperidine-4-carboxamide (Compound 44)

Compound 43 (4.71 g, 9.50 mmol) was dissolved in dichloromethane (100 mL), and dimethyl sulfide (29.4 mL, 400 mmol) and boron trifluoride-diethyl ether complex (24.6 mL, 200 mmol) were added thereto, followed by stirring overnight at room temperature. The reaction mixture was poured into 28% aqueous ammonia, followed by extraction with chloroform. The organic layer was washed with a saturated aqueous solution of sodium chloride and dried over anhydrous magnesium sulfate, and then the solvent was distilled away under reduced pressure to afford the entitled Compound 44 (1.36 g, 38%).

$^1$H NMR (DMSO-d$_6$, δ ppm): 1.43-1.57 (m, 2H), 1.67-1.71 (m, 2H), 2.40-2.60 (m, 3H), 2.88 (t, J=4.6 Hz, 4H), 2.95-3.00 (m, 2H), 3.77 (t, J=4.6 Hz, 4H), 6.59 (dd, J=1.9, 3.2 Hz, 1H), 6.77 (dd, J=0.8, 3.2 Hz, 1H), 7.67 (dd, J=0.8, 1.9 Hz, 1H).

APCIMS m/z: [M+H]$^+$ 363.

Example 45

1-(5-Cyanopyridin-2-yl)-N-[4-(2-furyl)-5-morpholinothiazol-2-yl]piperidine-4-carboxamide (Compound 45)

Compound 44 (181 mg, 0.50 mmol), 2-chloro-5-cyanopyridine (104 mg, 0.75 mmol) and potassium carbonate (207 mg, 1.50 mmol) were suspended in 1,4-dioxane (4 mL), followed by stirring overnight under heating and reflux. The insoluble was removed through filtration, the filtrate was distilled away under reduced pressure, and the resulting residue was purified through silica gel column chromatography (chloroform:methanol=20:1) to afford the entitled Compound 45 (158 mg, 68%).

$^1$H NMR (CDCl$_3$, δ ppm): 1.70-1.95 (m, 4H), 2.40-2.55 (m, 1H), 2.85-2.95 (m, 2H), 2.99 (t, J=4.6 Hz, 4H), 3.88 (t, J=4.6 Hz, 4H), 4.35-4.45 (m, 2H), 6.52 (dd, J=1.9, 3.5 Hz, 1H), 6.60 (d, J=9.4 Hz, 1H), 6.87 (dd, J=0.8, 3.5 Hz, 1H), 7.45 (dd, J=0.8, 1.9 Hz, 1H), 7.61 (dd, J=2.2, 9.4 Hz, 1H), 8.40 (d, J=2.2 Hz, 1H), 9.76 (br s, 1H).

APCIMS m/z: [M+H]$^+$ 465.

Example 46

N-[4-(2-Furyl)-5-morpholinothiazol-2-yl]-1-[5-(methanesulfonyl)pyridin-2-yl]piperidine-4-carboxamide (Compound 46)

In a manner similar to that in Example 45, by using 2-chloro-5-(methanesulfonyl)pyridine (144 mg, 0.75 mmol) obtained according to the method described in WO02/51836 in place of 2-chloro-5-cyanopyridine, the entitled Compound 46 (83.3 mg, 32%) was obtained from Compound 44 (181 mg, 0.50 mmol).

$^1$H NMR (CDCl$_3$, δ ppm): 1.70-1.90 (m, 2H), 1.90-2.00 (m, 2H), 2.45-2.55 (m, 1H), 2.99 (t, J=4.7 Hz, 4H), 3.04 (s, 3H), 3.05-3.10 (m, 2H), 3.88 (t, J=4.7 Hz, 4H), 4.41-4.51 (m, 2H), 6.52 (dd, J=1.9, 3.2 Hz, 1H), 6.63 (d, J=9.2 Hz, 1H), 6.87 (d, J=3.2 Hz, 1H), 7.45 (d, J=1.9 Hz, 1H), 7.87 (dd, J=2.4, 9.2 Hz, 1H), 8.63 (d, J=2.4 Hz, 1H), 9.51 (br s, 1H).

APCIMS m/z: [M+H]$^+$ 518.

Example 47

N-[4-(2-Furyl)-5-morpholinothiazol-2-yl]-1-(5-nitropyridin-2-yl)piperidine-4-carboxamide (Compound 47)

In a manner similar to that in Example 45, by using 2-chloro-5-nitropyridine (238 mg, 1.50 mmol) in place of 2-chloro-5-cyanopyridine, the entitled Compound 47 (78.5 mg, 41%) was obtained from Compound 44 (145 mg, 0.400 mmol).

$^1$H NMR (CDCl$_3$, δ ppm): 1.75-1.95 (m, 4H), 2.40-2.55 (m, 1H), 2.90-3.00 (m, 2H), 3.00 (t, J=4.6 Hz, 4H), 3.80-3.90 (m, 2H), 3.89 (t, J=4.6 Hz, 4H), 6.52 (dd, J=1.9, 3.5 Hz, 1H), 6.76 (dd, J=4.6, 8.1 Hz, 1H), 6.88 (dd, J=0.8, 3.5 Hz, 1H), 7.45 (dd, J=0.8, 1.9 Hz, 1H), 8.13 (dd, J=1.8, 8.1 Hz, 1H), 8.32 (dd, J=1.8, 4.6 Hz, 1H), 9.70 (br s, 1H).

APCIMS m/z: [M+H]$^+$ 485.

Example 48

N-[4-(2-Furyl)-5-morpholinothiazol-2-yl]-1-(3-nitropyridin-2-yl)piperidine-4-carboxamide (Compound 48)

In a manner similar to that in Example 45, by using 2-chloro-3-nitropyridine (238 mg, 1.50 mmol) in place of 2-chloro-5-cyanopyridine, the entitled Compound 48 (76.0 mg, 39%) was obtained from Compound 44 (145 mg, 0.400 mmol).

$^1$H NMR (CDCl$_3$, δ ppm): 2.37 (m, 1H), 2.54 (t, J=4.9 Hz, 4H), 3.03 (t, J=4.6 Hz, 4H), 3.66 (t, J=4.9 Hz, 4H), 3.89 (t, J=4.6 Hz, 4H), 6.50 (dd, J=1.6, 3.2 Hz, 1H), 6.86 (dd, J=0.8, 1.6 Hz, 1H), 6.89 (dd, J=1.6, 5.1 Hz, 1H), 7.10 (d, J=1.6 Hz, 1H), 7.43 (dd, J=0.8, 1.6 Hz, 1H), 8.31 (d, J=5.1 Hz, 1H), 9.50 (br s, 1H).

APCIMS m/z: [M+H]$^+$ 485.

Example 49

N-[4-(2-Furyl)-5-morpholinothiazol-2-yl]-1-(2-pyrimidinyl)piperidine-4-carboxamide (Compound 49)

In a manner similar to that in Example 45, by using 2-chloropyrimidine (172 mg, 1.50 mmol) in place of 2-chloro-5-cyanopyridine, the entitled Compound 49 (87.5 mg, 50%) was obtained from Compound 44 (145 mg, 0.40 mmol).

$^1$H NMR (CDCl$_3$, δ ppm): 1.72-1.78 (m, 2H), 1.85-1.95 (m, 2H), 2.40-2.50 (m, 1H), 2.83-2.89 (m, 2H), 2.99 (t, J=4.6 Hz, 4H), 3.88 (t, J=4.6 Hz, 4H), 4.72-4.80 (m, 2H), 6.49 (t, J=4.9 Hz, 2H), 6.51 (dd, J=1.6, 3.5 Hz, 1H), 6.87 (dd, J=0.8, 3.5 Hz, 1H), 7.45 (dd, J=0.8, 1.6 Hz, 1H), 8.30 (d, J=4.9 Hz, 1H), 9.54 (br s, 1H).

APCIMS m/z: [M+H]$^+$ 441.

Example 50

N-[4-(2-Furyl)-5-morpholinothiazol-2-yl]-1-(2-pyrazinyl)piperidine-4-carboxamide (Compound 50)

In a manner similar to that in Example 45, by using 2-chloropyrazine (0.69 mL, 0.75 mmol) in place of 2-chloro-5-cyanopyridine, the entitled Compound 50 (37.5 mg, 17%) was obtained from Compound 44 (181 mg, 0.5 mmol).

$^1$H NMR (DMSO-$d_6$, δ ppm): 2.91 (t, J=4.6 Hz, 4H), 3.30-3.40 (m, 4H), 3.45-3.50 (m, 2H), 3.55-3.65 (m, 2H), 3.78 (t, J=4.6 Hz, 4H), 4.72-4.76 (m, 1H), 6.55 (d, J=9.2 Hz, 1H), 6.60 (dd, J=1.9, 3.2 Hz, 1H), 6.82 (dd, J=0.8, 3.2 Hz, 1H), 7.68 (dd, J=0.8, 1.9 Hz, 1H), 8.01 (dd, J=2.4, 9.2 Hz, 1H), 8.75 (d, J=2.4 Hz, 1H), 12.26 (br s, 1H).

APCIMS m/z: [M+H]$^+$ 441.

Example 51

1-(6-Chloropyrimidin-4-yl)-N-[4-(2-furyl)-5-morpholinothiazol-2-yl]piperidine-4-carboxamide (Compound 51)

In a manner similar to that in Example 45, by using 4,6-dichloropyrimidine (298 mg, 2.00 mmol) in place of 2-chloro-5-cyanopyridine, the entitled Compound 51 (356 mg, 75%) was obtained from Compound 44 (361 mg, 1.00 mmol).

$^1$H NMR (CDCl$_3$, δ ppm): 1.70-1.90 (m, 4H), 2.40-2.55 (m, 1H), 2.84-2.93 (m, 2H), 2.99 (t, J=4.6 Hz, 4H), 3.88 (t, J=4.6 Hz, 4H), 4.28-4.38 (m, 2H), 6.50 (s, 1H), 6.53 (dd, J=1.9, 3.5 Hz, 1H), 6.88 (d, J=3.5 Hz, 1H), 7.45 (d, J=1.9 Hz, 1H), 8.37 (s, 1H), 10.24 (br s, 1H).

APCIMS m/z: [$^{35}$ClM+H]$^+$ 475, [$^{37}$ClM+H]$^+$ 477.

Example 52

N-[4-(2-Furyl)-5-morpholinothiazol-2-yl]-1-(4-pyrimidinyl)piperidine-4-carboxamide (Compound 52)

Compound 51 (300 mg, 0.63 mmol) was dissolved in ethanol (10 mL), and 10% palladium-carbon (500 mg) was added thereto, followed by stirring in an atmosphere of hydrogen at room temperature for 4 hours. The reaction mixture was filtered through Celite, and the filtrate was distilled away under reduced pressure to afford the entitled Compound 52 (213 mg, 77%).

$^1$H NMR (CDCl$_3$, δ ppm): 1.70-1.90 (m, 2H), 1.90-2.05 (m, 2H), 2.45-2.55 (m, 1H), 2.99 (t, J=4.6 Hz, 4H), 3.00-3.05 (m, 2H), 3.88 (t, J=4.6 Hz, 4H), 4.37-4.47 (m, 2H), 6.50-6.54 (m, 2H), 6.86 (d, J=3.2 Hz, 1H), 7.45 (d, J=1.6 Hz, 1H), 8.21 (d, J=6.2 Hz, 1H), 8.60 (s, 1H), 9.20 (br s, 1H).

APCIMS m/z: [M+H]$^+$ 441.

Example 53

1-(6-Chloropyridazin-3-yl)-N-[4-(2-furyl)-5-morpholinothiazol-2-yl]piperidine-4-carboxamide (Compound 53)

In a manner similar to that in Example 45, by using 3,6-dichloropyridazine (298 mg, 2.00 mmol) in place of 2-chloro-5-cyanopyridine, the entitled Compound 53 (299 mg, 63%) was obtained from Compound 44 (361 mg, 1.00 mmol).

$^1$H NMR (CDCl$_3$, δ ppm): 1.70-2.00 (m, 4H), 2.45-2.55 (m, 1H), 2.90-3.05 (m, 2H), 2.99 (t, J=4.6 Hz, 4H), 3.88 (t, J=4.6 Hz, 4H), 4.29-4.39 (m, 2H, 2H), 6.52 (dd, J=1.6, 3.5 Hz, 1H), 6.87 (dd, J=3.5 Hz, 1H), 6.91 (d, J=9.4 Hz, 1H), 7.21 (d, J=9.4 Hz, 1H), 7.45 (d, J=1.6 Hz, 1H), 9.56 (br s, 1H).

APCIMS m/z: [$^{35}$ClM+H]$^+$ 475, [$^{37}$ClM+H]$^+$ 477.

Example 54

1-Acetyl-N-[4-(2-furyl)-5-morpholinothiazol-2-yl]piperidine-4-carboxamide (Compound 54)

Compound 44 (145 mg, 0.400 mmol) was dissolved in pyridine (5 mL), acetic anhydride (0.19 mL, 2.00 mmol) was added thereto, followed by stirring at room temperature for 2 hours. The reaction mixture was concentrated under reduced pressure, and the resulting residue was purified through silica gel column chromatography (ethyl acetate:methanol=9:1) to afford the entitled Compound 54 (40.0 mg, 25%).

$^1$H NMR (CDCl$_3$, δ ppm): 1.60-1.95 (m, 4H), 2.11 (s, 3H), 2.40-2.55 (m, 1H), 2.60-2.80 (m, 1H), 2.98 (t, J=4.6 Hz, 4H), 3.00-3.15 (m, 1H), 3.88 (t, J=4.6 Hz, 4H), 3.88-3.95 (m, 1H), 4.57 (d, J=13.5 Hz, 1H), 6.51 (dd, J=1.9, 3.5 Hz, 1H), 6.86 (dd, J=0.8, 3.5 Hz, 1H), 7.45 (dd, J=0.8, 1.9 Hz, 1H), 9.18 (br s, 1H).

APCIMS m/z: [M+H]$^+$ 405.

Example 55

1-(N,N-Dimethylcarbamoyl)-N-[4-(2-furyl)-5-morpholinothiazol-2-yl]piperidine-4-carboxamide (Compound 55)

Step 1:

A mixture of ethyl isonipecotinate (1.54 mL, 10.0 mmol), triethylamine (4.18 mL, 30.0 mmol) and N,N-dimethylcarbamoyl chloride (2.20 mL, 24.0 mmol) was stirred overnight at room temperature. 28% aqueous ammonia was added to the reaction mixture, followed by stirring at room temperature for 10 minutes, and then extracted with chloroform. The organic layer was washed successively with 1 mol/L hydrochloric acid, a saturated aqueous solution of sodium hydrogencarbonate and a saturated aqueous solution of sodium chloride, and dried over anhydrous magnesium sulfate, and then the solvent was distilled away under reduced pressure. The resulting residue was purified through silica gel column chromatography (chloroform:ethyl acetate=1:1) to afford ethyl 1-(N,N-dimethylcarbamoyl)piperidine-4-carboxylate (2.28 g, 100%).

$^1$H NMR (CDCl$_3$, δ ppm): 1.26 (t, J=6.9 Hz, 3H), 1.65-1.76 (m, 2H), 1.85-1.94 (m, 2H), 2.41-2.8.5 (m, 1H), 2.77-2.85 (m, 2H), 2.83 (s, 6H), 3.59-3.65 (m, 2H), 4.14 (q, J=6.9 Hz, 2H).

Step 2:

Ethyl 1-(N,N-dimethylcarbamoyl)piperidine-4-carboxylate (2.28 g, 10.0 mmol) obtained in Step 1 was dissolved in a mixed solvent of methanol (30 mL) and water (10 mL), lithium hydroxide monohydrate (2.10 g, 50.0 mmol) was added thereto, followed by stirring at room temperature for 30 minutes. The reaction mixture was concentrated under reduced pressure, and 6 mol/L hydrochloric acid was added to the resulting residue to adjust the pH to 1, followed by extraction with chloroform. The organic layer was dried over anhydrous magnesium sulfate, and then the solvent was distilled away under reduced pressure to afford 1-(N,N-dimethylcarbamoyl)piperidine-4-carboxylic acid (830 mg, 42%).

$^1$H NMR (CDCl$_3$, δ ppm): 1.68-1.79 (m, 2H), 1.91-1.97 (m, 2H), 2.46-2.54 (m, 1H), 2.80-2.85 (m, 2H), 2.82 (s, 6H), 3.58-3.66 (m, 2H).

Step 3:

1-(N,N-dimethylcarbamoyl)piperidine-4-carboxylic acid (300 mg, 1.50 mmol) obtained in Step 2 was dissolved in dichloromethane (15 mL), and thionyl chloride (0.547 mL, 7.50 mmol) was added thereto, followed by stirring under heating and reflux for 1 hour. The reaction mixture was concentrated under reduced pressure, and the resulting residue was dissolved in chloroform (5 mL). The resulting solution was added to a pyridine (10 mL) solution of 2-amino-4-(2-furyl)-5-morpholinothiazole (126 mg, 0.50 mmol) obtained in Step 1 of Example 29, followed by stirring at room temperature for 1 hour. The reaction mixture was concentrated under reduced pressure, and the resulting residue was purified through silica gel column chromatography (ethyl acetate:methanol=9:1) to afford the entitled Compound 55 (171 mg, 81%).

$^1$H NMR (CDCl$_3$, δ ppm): 1.60-1.95 (m, 4H), 2.35-2.50 (m, 1H), 2.70-2.80 (m, 2H), 2.83 (s, 6H), 3.00 (t, J=4.3 Hz, 4H), 3.68 (d, J=13.5 Hz, 2H), 3.88 (t, J=4.3 Hz, 4H), 6.51 (dd, J=1.6, 3.2 Hz, 1H), 6.86 (dd, J=0.5, 3.2 Hz, 1H), 7.44 (dd, J=0.5, 1.6 Hz, 1H), 9.54 (br s, 1H).

APCIMS m/z: [M+H]$^+$ 434.

Example 56

N-[4-(2-Furyl)-5-morpholinothiazol-2-yl]-1-morpholinocarbonylpiperidine-4-carboxamide (Compound 56)

In a manner similar to that in Example 55, by using morpholinocarbonyl chloride in place of N,N-dimethylcarbamoyl chloride, the entitled Compound 56 (167 mg, 72%) was obtained from 2-amino-4-(2-furyl)-5-morpholinothiazole (126 mg, 0.50 mmol) obtained in Step 1 of Example 29.

$^1$H NMR (CDCl$_3$, δ ppm): 1.60-1.90 (m, 4H), 2.30-2.50 (m, 1H), 2.65-2.85 (m, 2H), 2.99 (t, J=4.3 Hz, 4H), 3.26 (t, J=4.3 Hz, 4H), 3.68 (t, J=4.3 Hz, 4H), 3.66-3.76 (m, 2H), 3.88 (t, J=4.3 Hz, 4H), 6.51 (dd, J=1.9, 3.5 Hz, 1H), 6.87 (d, J=3.5 Hz, 1H), 7.44 (d, J=1.9 Hz, 1H), 9.73 (br s, 1H).

APCIMS m/z: [M+H]$^+$ 476.

Example 57

N-[4-(2-Furyl)-5-morpholinothiazol-2-yl]-1-methanesulfonylpiperidine-4-carboxamide (Compound 57)

In a manner similar to that in Example 55, by using methanesulfonyl chloride in place of N,N-dimethylcarbamoyl chloride, the entitled Compound 57 (123 mg, 56%) was obtained from 2-amino-4-(2-furyl)-5-morpholinothiazole (126 mg, 0.50 mmol) obtained in Step 1 of Example 29.

$^1$H NMR (CDCl$_3$, δ ppm): 1.80-2.00 (m, 4H), 2.35-2.50 (m, 1H), 2.70-2.85 (m, 2H), 2.80 (s, 3H), 2.99 (t, J=4.3 Hz, 4H), 3.76 (ddd, J=3.8, 3.8, 14.6 Hz, 2H), 3.88 (t, J=4.3 Hz, 4H), 6.52 (dd, J=1.9, 3.5 Hz, 1H), 6.87 (d, J=3.5 Hz, 1H), 7.45 (d, J=1.9 Hz, 1H), 9.67 (br s, 1H).

APCIMS m/z: [M+H]$^+$ 441.

Example 58

1-(N,N-Dimethylsulfamoyl)-N-[4-(2-furyl)-5-morpholinothiazol-2-yl]piperidine-4-carboxamide (Compound 58)

In a manner similar to that in Example 55, by using N,N-dimethylsulfamoyl chloride in place of N,N-dimethylcarbamoyl chloride, the entitled Compound 58 (103 mg, 44%) was obtained from 2-amino-4-(2-furyl)-5-morpholinothiazole (126 mg, 0.50 mmol) obtained in Step 1 of Example 29.

$^1$H NMR (CDCl$_3$, δ ppm): 1.70-1.95 (m, 4H), 2.25-2.45 (m, 1H), 2.70-2.85 (m, 2H), 2.83 (s, 6H), 2.99 (t, J=4.6 Hz, 4H), 3.78 (ddd, J=3.8, 3.8, 14.8 Hz, 2H), 3.89 (t, J=4.6 Hz, 4H), 6.52 (dd, J=1.9, 3.2 Hz, 1H), 6.87 (d, J=3.2 Hz, 1H), 7.44 (d, J=1.9 Hz, 1H), 9.75 (br s, 1H).

APCIMS m/z: [M+H]$^+$ 470.

Example 59

4-Bromomethyl-N-[4-(2-furyl)-5-morpholinothiazol-2-yl]benzamide (Compound 59)

4-Bromomethylbenzoic acid (2.24 g, 10.4 mmol) was dissolved in toluene (80 mL), and thionyl chloride (7.59 mL, 104 mmol) was added thereto, followed by stirring under heating and reflux for 6 hours. The reaction mixture was concentrated under reduced pressure. The resulting residue was dissolved in THF (50 mL), and 2-amino-4-(2-furyl)-5-morpholinothiazole (2.00 g, 7.97 mmol) obtained in Step 1 of Example 29, triethylamine (1.67 mL, 12.0 mmol) and N,N-dimethylaminopyridine (97.6 mg, 0.800 mmol) were added thereto, followed by stirring under heating and reflux for 1 hour. The reaction mixture was allowed to cool down to room temperature, and then a 10% aqueous solution of sodium carbonate was added thereto, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:ethyl acetate=9:1) to afford the entitled Compound 59 (3.29 g, 92%).

$^1$H NMR (CDCl$_3$, δ ppm): 3.03 (t, J=4.6 Hz, 4H), 3.89 (t, J=4.6 Hz, 4H), 4.59 (s, 2H), 6.40 (dd, J=1.6, 3.2 Hz, 1H), 6.79 (d, J=3.2 Hz, 1H), 7.25 (d, J=1.6 Hz, 1H), 7.43 (dd, J=2.2, 8.6 Hz, 2H), 7.83 (dd, J=2.2, 8.6 Hz, 2H), 10.56 (br s, 1H).

Example 60

N-[4-(2-Furyl)-5-morpholinothiazol-2-yl]-4-(imidazol-1-ylmethyl)benzamide (Compound 60)

Compound 59 (448 mg, 1.00 mmol) was dissolved in DMF (4 mL), imidazole (204 mg, 3.00 mmol) was added thereto, followed by stirring at 65° C. for 2 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=20:1) to afford the entitled Compound 60 (348 mg, 80%).

$^1$H NMR (CDCl$_3$, δ ppm): 3.03 (t, J=4.6 Hz, 4H), 3.90 (t, J=4.6 Hz, 4H), 5.23 (s, 2H), 6.52 (dd, J=1.9, 3.2 Hz, 1H), 6.88 (d, J=3.2 Hz, 1H), 6.93 (s, 1H), 7.15 (s, 1H), 7.28 (d, J=8.4 Hz, 2H), 7.45 (d, J=1.9 Hz, 1H), 7.61 (s, 1H), 7.90 (d, J=8.4 Hz, 2H), 9.45 (br s, 1H).

APCIMS m/z: [M+H]$^+$ 436.

Example 61

N-[4-(2-Furyl)-5-morpholinothiazol-2-yl]-4-[4-(hydroxypiperidino)methyl]benzamide (Compound 61)

In a manner similar to that in Example 60, by using 4-hydroxypiperidine and 1,4-dioxane in place of imidazole and DMF, respectively, the entitled Compound 61 (351 mg, 75%) was obtained from Compound 59 (448 mg, 1.00 mmol).

$^1$H NMR (CDCl$_3$, δ ppm): 1.50-1.70 (m, 3H), 1.88-1.93 (m, 2H), 2.14-2.22 (m, 2H), 2.72-2.76 (m, 2H), 3.03 (t, J=4.5 Hz, 4H), 3.55 (s, 2H), 3.70-3.75 (m, 1H), 3.90 (t, J=4.5 Hz, 4H), 6.49 (dd, J=1.9, 3.2 Hz, 1H), 6.86 (d, J=3.2 Hz, 1H), 7.41 (d, J=1.9 Hz, 1H), 7.46 (d, J=8.1 Hz, 2H), 7.86 (d, J=8.1 Hz, 2H), 9.70 (br s, 1H).

APCIMS m/z: [M+H]$^+$ 469.

Example 62

N-[4-(2-Furyl)-5-morpholinothiazol-2-yl]-4-(morpholinomethyl)benzamide (Compound 62)

In a manner similar to that in Example 60, by using morpholine and 1,4-dioxane in place of imidazole and DMF, respectively, the entitled Compound 62 (36.5 mg, 8%) was obtained from Compound 59 (448 mg, 1.00 mmol).

$^1$H NMR (CDCl$_3$, δ ppm): 2.46 (t, J=4.6 Hz, 4H), 3.03 (t, J=4.6 Hz, 4H), 3.57 (s, 2H), 3.73 (t, J=4.6 Hz, 4H), 3.90 (t, J=4.6 Hz, 4H), 6.50 (dd, J=1.6, 3.5 Hz, 1H), 6.87 (dd, J=0.8, 3.5 Hz, 1H), 7.44 (dd, J=0.8, 1.6 Hz, 1H), 7.49 (d, J=8.1 Hz, 2H), 7.86 (d, J=8.1 Hz, 2H), 9.51 (br s, 1H).

APCIMS m/z: [M+H]$^+$ 455.

Example 63

N-[4-(2-Furyl)-5-morpholinothiazol-2-yl]-4-{[N-(2-methoxyethyl)-N-methylamino]methyl}benzamide (Compound 63)

In a manner similar to that in Example 60, by using N-(2-methoxyethyl)-N-methylamine and 1,4-dioxane in place of imidazole and DMF, respectively, the entitled Compound 63 (173 mg, 38%) was obtained from Compound 59 (448 mg, 1.00 mmol).

$^1$H NMR (DMSO-d$_6$, δ ppm): 2.74 (s, 3H), 2.94 (t, J=4.6 Hz, 4H), 3.16-3.30 (m, 2H), 3.31 (s, 3H), 3.70-3.73 (m, 2H), 3.79 (t, J=4.6 Hz, 4H), 4.36 (d, J=13.5 Hz, 1H), 4.48 (d. J=13.5 Hz, 1H), 6.62 (dd, J=1.6, 3.2 Hz, 1H), 6.84 (d, J=3.2 Hz, 1H), 7.70 (d, J=3.2 Hz, 1H), 7.73 (d, J=8.1 Hz, 2H), 8.18 (d, J=8.1 Hz, 2H).

APCIMS m/z: [M+H]$^+$ 457.

Example 64

N-[4-(2-Furyl)-5-morpholinothiazol-2-yl]-4-[2-(oxopiperidino)methyl]benzamide (Compound 64)

Step 1:

60% sodium hydride (600 mg, 15.0 mmol) was suspended in DMF (30 mL), 2-piperidone (1.49 g, 15.0 mmol) was added thereto, followed by stirring at room temperature for 30 minutes. A solution of methyl 4-bromomethylbenzoate (2.29 g, 10.0 mmol) in DMF (10 mL) was added to the reaction mixture, followed by stirring at room temperature for 3 hours. The reaction mixture was poured into a saturated aqueous solution of sodium chloride, followed by extraction with ethyl acetate. The organic layer was dried over anhydrous magnesium sulfate, and then the solvent was distilled away under reduced pressure. The resulting residue was purified through silica gel column chromatography (ethyl acetate: methanol=9:1) to afford methyl 4-[(2-oxopiperidino)methyl] benzoate (2.47 g 100%).

$^1$H NMR (CDCl$_3$, δ ppm): 1.74-1.85 (m, 4H), 2.46-2.51 (m, 2H), 3.20-3.22 (m, 2H), 3.91 (s, 3H), 4.64 (s, 2H), 7.31 (d, J=8.0 Hz, 2H), 8.00 (d, J=8.0 Hz, 2H).

Step 2:

Methyl 4-[(2-oxopiperidino)methyl]benzoate (2.47 g, 10.0 mmol) obtained in Step 1 was dissolved in a mixed solvent of methanol (30 mL) and water (10 mL), and lithium hydroxide monohydrate (2.10 g, 50.0 mmol) was added thereto, followed by stirring at room temperature for 30 minutes. The reaction mixture was concentrated under reduced pressure, and 6 mol/L hydrochloric acid was added to the resulting residue to adjust the pH to 1, followed by extraction with chloroform. The organic layer was dried over anhydrous magnesium sulfate, and then the solvent was distilled away under reduced pressure to afford 4-[(2-oxopiperidino)methyl]benzoic acid (629 mg. 27%).

$^1$H NMR (DMSO-d$_6$, δ ppm): 1.69-1.75 (m, 4H), 2.27-2.34 (m, 2H), 3.14-3.22 (m, 2H), 4.56 (s, 2H), 7.31 (d, J=8.4 Hz, 2H), 7.90 (d, J=8.4 Hz, 2H).

Step 3:

4-[(2-Oxopiperidino)methyl]benzoic acid (233 mg, 1.00 mmol) obtained in Step 2 was dissolved in dichloromethane (10 mL), and thionyl chloride (5 mL) was added thereto, followed by stirring under heating and reflux for 1 hour. The reaction mixture was concentrated under reduced pressure, and the resulting residue was dissolved in chloroform (5 mL). The resulting solution was added to a solution of 2-amino-4-(2-furyl)-5-morpholinothiazole (126 mg, 0.50 mmol) in pyridine (10 mL) obtained in Step 1 of Example 29, followed by stirring at room temperature for 1 hour. The reaction mixture was concentrated under reduced pressure, and the resulting residue was purified through silica gel column chromatography (chloroform:methanol=20:1) to afford the entitled Compound 64 (68.3 mg, 29%).

$^1$H NMR (CDCl$_3$, δ ppm): 1.81-1.84 (m, 4H), 2.48-2.51 (m, 2H), 3.03 (t, J=4.6 Hz, 4H), 3.22-3.26 (m, 2H), 3.90 (t, J=4.6 Hz, 4H), 4.66 (s, 2H), 6.51 (dd, J=1.9, 3.5 Hz, 1H), 6.88 (dd, J=0.5, 3.5 Hz, 1H), 7.45 (dd, J=0.5, 1.9 Hz, 1H), 7.67 (d, J=13.5 Hz, 2H), 7.87 (d, J=13.5 Hz, 2H), 9.45 (br s, 1H).

APCIMS m/z: [M+H]$^+$ 467.

Example 65

N-[4-(2-Furyl)-5-morpholinothiazol-2-yl]-4-[(2-oxo-1,2-dihydropyridin-1-yl)methyl]benzamide (Compound 65)

In a manner similar to that in Example 64, by using 2-hydroxypyridine in place of 2-piperidone, the entitled Compound 65 (66.2 mg, 29%) was obtained from 2-amino-4-(2-furyl)-5-morpholinothiazole (126 mg, 0.50 mmol) obtained in Step 1 of Example 29.

$^1$H NMR (CDCl$_3$, δ ppm): 3.02 (t, J=4.6 Hz, 4H), 3.89 (t, J=4.6 Hz, 4H), 5.21 (s, 2H), 6.20 (ddd, J=1.4, 6.5, 6.5 Hz, 1H), 6.51 (dd, J=1.9, 3.5 Hz, 1H), 6.65 (dd, J=1.4, 8.6 Hz, 1H), 6.87 (dd, J=0.8, 3.5 Hz, 1H), 7.28 (dd, J=2.2, 6.5 Hz, 1H), 7.36 (ddd, J=2.2, 6.5, 8.6 Hz, 1H), 7.43 (d, J=8.4 Hz, 2H), 7.45 (dd, J=0.8, 1.9 Hz, 1H), 7.88 (d, J=8.4 Hz, 2H), 9.44 (br s, 1H)

APCIMS m/z: [M+H]$^+$ 463. .

Example 66

N-[4-(2-Furyl)-5-(4-methylpiperazin-1-yl)thiazol-2-yl]pyridine-4-carboxamide (Compound 66)

In a manner similar to that in Example 29, by using 1-methylpiperazine (0.51 mL, 4.56 mmol) in place of morpholine, the entitled Compound 66 (108 mg, 32%) was obtained from Compound g (224 mg, 0.91 mmol) obtained in Reference Example 7.
$^1$H NMR (CDCl$_3$, δ ppm): 2.47 (s, 3H), 2.70-2.81 (m, 4H), 3.10-3.19 (m, 4H), 6.40 (dd, J=1.8, 3.3 Hz, 1H), 6.76 (d, J=3.3 Hz, 1H), 7.28 (d, J=1.8 Hz, 1H), 7.66 (d, J=6.1 Hz, 2H), 8.74 (d, J=6.1 Hz, 2H).
APCIMS m/z: [M+H]$^+$ 370.

Example 67

N-[5-(4-Ethylpiperazin-1-yl)-4-(2-furyl)thiazol-2-yl]pyridine-4-carboxamide (Compound 67)

In a manner similar to that in Example 29, by using 1-ethylpiperazine (1.18 mL, 8.50 mmol) in place of morpholine, the entitled Compound 67 (319 mg, 49%) was obtained from Compound g (417 mg, 1.70 mmol) obtained in Reference Example 7.
$^1$H NMR (CDCl$_3$, δ ppm): 1.14 (t, J=7.2 Hz, 3H), 2.52 (dd, J=7.2, 14.5 Hz, 2H), 2.64-2.68 (m, 4H), 3.07-3.10 (m, 4H), 6.42 (dd, J=1.8, 3.3 Hz, 1H), 6.80 (dd, J=0.6, 3.3 Hz, 1H), 7.29 (dd, J=0.6, 1.8 Hz, 1H), 7.67 (dd, J=1.7, 4.4 Hz, 2H), 8.76 (dd, J=1.7, 4.4 Hz, 2H).
APCIMS m/z: [M+H]$^+$ 384.

Example 68

N-[5-(4-Benzylpiperazin-1-yl)-4-(2-furyl)thiazol-2-yl]pyridine-4-carboxamide (Compound 68)

Step 1:
In a manner similar to that in Step 1 of Example 29, by using 1-benzylpiperazine (3.46 mL, 19.9 mmol) in place of morpholine, 2-amino-5-(4-benzylpiperazin-1-yl)-4-(2-furyl)thiazole (1.09 g, 78%) was obtained from Compound g (1.00 g, 4.08 mmol) obtained in Reference Example 7.
$^1$H NMR (CDCl$_3$, δ ppm): 2.60-2.63 (m, 4H), 2.88-2.91 (m, 4H), 3.57 (s, 2H), 4.91 (br s, 2H), 6.46 (dd, J=1.8, 3.5 Hz, 1H), 6.85 (dd, J=0.9, 3.5 Hz, 1H), 7.26-7.34 (m, 5H), 7.40 (dd, J=0.9, 1.8 Hz, 1H).

Step 2:
In a manner similar to that in Example 1, the entitled Compound 68 (359 mg, 55%) was obtained from 2-amino-5-(4-benzylpiperazin-1-yl)-4-(2-furyl)thiazole (500 mg, 1.46 mmol) obtained in Step 1, in place of Compound a.
$^1$H NMR (CDCl$_3$, δ ppm): 2.70-2.88 (m, 4H), 3.09-3.23 (m, 4H), 3.74 (s, 2H), 6.41 (dd, J=1.8, 3.3 Hz, 1H), 6.75 (d, J=3.3 Hz, 1H), 7.30-7.43 (m, 6H), 7.67 (d, J=6.2 Hz, 2H), 8.75 (d, J=6.2 Hz, 2H).
ESIMS m/z: [M+H]$^+$ 446.

Example 69

N-[4-(2-Furyl)-5-thiomorpholinothiazol-2-yl]pyridine-4-carboxamide (Compound 69)

In a manner similar to that in Example 29, by using thiomorpholine (1.03 mL, 10.2 mmol) in place of morpholine, the entitled Compound 69 (593 mg, 78%) was obtained from Compound g (500 mg, 2.04 mmol) obtained in Reference Example 7.
$^1$H NMR (CDCl$_3$, δ ppm): 2.84-2.87 (m, 4H), 3.25-3.28 (m, 4H), 6.45 (dd, J=1.8, 3.5 Hz, 1H), 6.81 (d, J=3.5 Hz, 1H), 7.34 (d, J=1.8 Hz, 1H), 7.69 (dd, J=1.7, 4.6 Hz, 2H), 8.78 (dd, J=1.7, 4.6 Hz, 2H), 10.2 (br-s, 1H).
APCIMS m/z: [M+H]$^+$ 373.

Example 70

N-[4-(2-Furyl)-5-(1-oxothiomorpholino)thiazol-2-yl]pyridine-4-carboxamide (Compound 70)

Step 1:
2-Amino-4-(2-furyl)-5-thiomorpholinothiazole (972 mg, 3.64 mmol) obtained as the intermediate in Example 69 was dissolved in dichloromethane (18 mL), m-chloroperbenzoic acid (1.32 g, 7.63 mmol) was added thereto, followed by stirring at room temperature for 1 hour. Water was added to the reaction mixture, followed by extraction with chloroform. The organic layer was dried over anhydrous magnesium sulfate, and then the solvent was distilled away under reduced pressure. The resulting residue was purified through silica gel column chromatography (chloroform:methanol=50:1) to afford 2-amino-4-(2-furyl)-5-(1-oxothiomorpholino)thiazole (724 mg, 70%).

Step 2:
In a manner similar to that in Example 1, the entitled Compound 70 (752 mg, 76-%) was obtained from 2-amino-4-(2-furyl)-5-(1-oxothiomorpholino)thiazole (724 mg, 2.55 mmol) obtained in Step 1, in place of Compound a.
$^1$H NMR (DMSO-d$_6$, δ ppm): 2.93-3.33 (m, 8H), 6.61 (dd, J=1.8, 3.3 Hz, 1H), 6.88 (d, J=3.3 Hz, 1H), 7.70 (d, J=1.8 Hz, 1H), 7.97 (d, J=6.2 Hz, 2H), 8.79 (d, J=6.2 Hz, 2H).
APCIMS m/z: [M+H]$^+$ 389.

Example 71

N-[5-(1,1-Dioxothiomorpholino)-4-(2-furyl)thiazol-2-yl]pyridine-4-carboxamide (Compound 71)

In a manner similar to that in Step 1 of Example 70, the entitled Compound 71 (365 mg, 48%) was obtained from Compound 69 in place of 2-amino-4-(2-furyl)-5-thiomorpholinothiazole.
$^1$H NMR (CDCl$_3$, δ ppm): 3.21-3.24 (m, 4H), 3.52-3.56 (m, 4H), 6.47 (dd, J=1.8, 3.3 Hz, 1H), 6.74 (d, J=3.3 Hz, 1H), 7.42 (d, J=1.8 Hz, 1H), 7.76 (d, J=6.1 Hz, 2H), 8.80 (d, J=6.1 Hz, 2H).
APCIMS m/z: [M+H]$^+$ 405.

Example 72

N-[4-(2-Furyl)-5-piperidinothiazol-2-yl]pyridine-4-carboxamide (Compound 72)

In a manner similar to that in Example 29, by using piperidine (0.740 mL, 7.44 mmol) in place of morpholine, the entitled Compound-72 (354 mg, 67%) was obtained from Compound g (365 mg, 1.49 mmol) obtained in Reference Example 7.
$^1$H NMR (CDCl$_3$, δ ppm): 1.59-1.62 (m, 2H), 1.72-1.79 (m, 4H), 2.92-2.96 (m, 4H), 6.34 (dd, J=1.8, 3.3 Hz, 1H), 6.72 (d, =3.3 Hz, 1H), 7.14 (d, J=1.8 Hz, 1H), 7.65 (d, J=6.1 Hz, 2H), 8.67 (d, J=6.1 Hz, 2H)
APCIMS m/z: [M−H]$^-$ 353. .

Example 73

N-[4-(2-Furyl)-5-(2-methylpiperidino)thiazol-2-yl]pyridine-4-carboxamide (Compound 73)

In a manner similar to that in Example 29, by using 2-methylpiperidine (0.750 mL, 6.35 mmol) in place of morpholine, the entitled Compound 73 (155 mg, 33%) was obtained from Compound g (312 mg, 1.27 mmol) obtained in Reference Example 7.

$^1$H NMR (CDCl$_3$, δ ppm): 1.00-1.02 (m, 3H), 1.40-1.51 (m, 2H), 1.66-1.83 (m, 4H), 2.65-2.80 (m, 2H), 3.07-3.11 (m, 1H), 6.29 (dd, J=1.8, 3.3 Hz, 1H), 6.94 (d, J=3.3 Hz, 1H), 7.08 (d, J=1.8 Hz, 1H), 7.65 (d, J=6.1 Hz, 2H), 8.63 (d, J=6.1 Hz, 2H).

APCIMS m/z: [M−H]$^-$ 367.

Example 74

N-[4-(2-Furyl)-5-(4-oxopiperidino)thiazol-2-yl]pyridine-4-carboxamide (Compound 74)

Step 1:

In a manner similar to that in Step 1 of Example 29, by using 1,4-dioxa-8-azaspiro[4.5]decane (3.82 mL, 29.8 mmol) in place of morpholine, 2-amino-5-(1,4-dioxa-8-azaspiro[4.5]decan-8-yl)-4-(2-furyl)thiazole (1.54 g, 84%) was obtained from Compound g (1.46 g, 5.96 mmol) obtained in Reference Example 7.

Step 2:

2-Amino-5-(1,4-dioxa-8-azaspiro[4.5]decan-8-yl)-4-(2-furyl)thiazole (1.00 g, 3.25 mmol) obtained in Step 1 was dissolved in THF (10 mL), 2 mol/L hydrochloric acid (5 mL) was added thereto, followed by stirring under heating and reflux for 4 hours. The reaction mixture was neutralized with a saturated aqueous solution of sodium hydrogencarbonate, followed by extraction with ethyl acetate. The organic layer was dried over anhydrous magnesium sulfate, and then the solvent was distilled away under reduced pressure. The resulting residue was purified through silica gel column chromatography (hexane:ethyl acetate=1:1) to afford 2-amino-4-(2-furyl)-5-(4-oxopiperidino)thiazole (151 mg, 18%).

Step 3:

In a manner similar to that in Example 1, the entitled Compound 74 (151 mg, 72%) was obtained from 2-amino-4-(2-furyl)-5-(4-oxopiperidino)thiazole (151 mg, 0.54 mmol) obtained in Step 2, in place of Compound a.

$^1$H NMR (CDCl$_3$, δ ppm): 2.62-2.71 (m, 4H), 3.36-3.40 (m, 4H), 6.44 (dd, J=1.8, 3.3 Hz, 1H), 6.83 (d, J=3.3 Hz, 1H), 7.29 (d, J=1.8 Hz, 1H), 7.70 (d, J=6.2 Hz, 2H), 8.76 (d, J=6.2 Hz, 2H), 10.81 (br s, 1H).

APCIMS m/z: [M−H]$^-$ 367.

Example 75

N-[4-(2-Furyl)-5-(1,2,3,4-tetrahydroisoquinolin-2-yl)thiazol-2-yl]pyridine-4-carboxamide (Compound 75)

Step 1:

In a manner similar to that in Step 1 of Example 29, by using 1,2,3,4-tetrahydroisoquinoline (1.28 mL, 10.2 mmol) in place of morpholine, 2-amino-4-(2-furyl)-5-(1,2,3,4-tetrahydroisoquinolin-2-yl)thiazole (524 mg, 86%) was obtained from Compound g (500 mg, 2.04 mmol) obtained in Reference Example 7.

$^1$H NMR (CDCl$_3$, δ ppm): 3.04-3.08 (m, 2H), 3.17-3.21 (m, 2H), 4.08 (s, 2H), 4.86 (br s, 2H), 6.40 (dd, J=1.8, 3.3 Hz, 1H), 6.80 (dd, J=0.7, 3.3 Hz, 1H), 7.05-7.20 (m, 4H), 7.40 (dd, J=0.7, 1.8 Hz, 1H).

Step 2:

In a manner similar to that in Example 1, the entitled Compound 75 (133 mg, 39%) was obtained from 2-amino-4-(2-furyl)-5-(1,2,3,4-tetrahydroisoquinolin-2-yl)thiazole (250 mg, 0.84 mmol) obtained in Step 1, in place of Compound a.

$^1$H NMR (CDCl$_3$, δ ppm): 3.09-3.03 (m, 2H), 3.33-3.37 (m, 2H), 4.24 (s, 2H), 6.41 (dd, J=1.8, 3.3 Hz, 1H), 6.79 (d, J=3.3 Hz, 1H), 7.09-7.26 (m, 4H), 7.34 (d, J=1.8 Hz, 1H), 7.73 (d, J=6.1 Hz, 2H), 8.80 (d, J=6.1 Hz, 2H).

ESIMS m/z: [M−H]$^-$ 401.

Example 76

N-[5-Dimethylamino-4-(2-furyl)thiazol-2-yl]pyridine-4-carboxamide (Compound 76)

In a manner similar to that in Example 29, by using a methanol solution (1.53 mL, 3.06 mmol) of 2 mol/L dimethylamine in place of morpholine, the entitled Compound 76 (79.2 mg, 41%) was obtained from Compound g (150,mg, 0.61 mmol) obtained in Reference Example 7.

$^1$H NMR (CDCl$_3$, δ ppm): 2.80 (s, 6H), 6.41 (dd, J=1.8, 3.3 Hz, 1H), 6.74 (d, J=3.3 Hz, 1H), 7.31 (d, J=1.8 Hz, 1H), 7.71 (d, J=6.2 Hz, 2H), 8.75 (d, J=6.2 Hz, 2H).

APCIMS m/z: [M+H]$^+$ 315.

Example 77

N-{4-(2-Furyl)-5-[N-(2-methoxyethyl)-N-methylamino]thiazol-2-yl}pyridine-4-carboxamide (Compound 77)

Step 1:

In a manner similar to that in Step 1 of Example 29, by using N-(2-methoxyethyl)-N-methylamine (909 mg, 10.2 mmol) in place of morpholine, 2-amino-4-(2-furyl)-5-[N-(2-methoxyethyl)-N-methylamino]thiazole (363 mg, 70%) was obtained from Compound g (500 mg, 2.04 mmol) obtained in Reference Example 7.

$^1$H NMR (CDCl$_3$, δ ppm): 2.90 (s, 3H), 3.22-3.25 (m, 2H), 3.31 (s, 3H), 3.51-3.54 (m, 2H), 6.40 (dd, J=1.8, 3.3 Hz, 1H), 6.80 (dd, J=0.7, 3.3 Hz, 1H), 7.05 (br s, 2H), 7.40 (dd, J=0.7, 1.8 Hz, 1H).

Step 2:

In a manner similar to that in Example 1, the entitled Compound 77 (195 mg, 88%) was obtained from 2-amino-4-(2-furyl)-5-[N-(2-methoxyethyl)-N-methylamino]thiazole (150 mg, 0.62 mmol) obtained in Step 1, in place of Compound a.

$^1$H NMR (CDCl$_3$, δ ppm): 2.90 (s, 3H), 3.22-3.25 (m, 2H), 3.31 (s, 3H), 3.51-3.54 (m, 2H), 6.49 (dd, J=1.8, 3.3 Hz, 1H), 6.93 (d, J=3.3 Hz, 1H), 7.46 (d, J=1.8 Hz, 1H), 8.02 (d, J=6.2 Hz, 2H), 8.84 (d, J=6.2 Hz, 2H).

APCIMS m/z: [M+H]$^+$ 359.

Example 78

N-{4-(2-Furyl)-5-{N-methyl-N-[2-(2-pyridyl)ethyl]amino}thiazol-2-yl}pyridine-4-carboxamide (Compound 78)

Step 1:
In a manner similar to that in Step 1 of Example 29, by using N-methyl-N-[2-(2-pyridyl)ethyl]amine (1.41 mL, 10.2 mmol) in place of morpholine, 2-amino-4-(2-furyl)-5-{N-methyl-N-[2-(2-pyridyl)ethyl]amino}thiazole (349 mg, 57%) was obtained from Compound g (500 mg, 2.04 mmol) obtained in Reference Example 7.

$^1$H NMR (CDCl$_3$, δ ppm): 2.70 (s, 3H), 2.95-3.00 (m, 2H), 3.20-3.25 (m, 2H), 5.03 (br s, 2H), 6.36 (dd, J=1.8, 3.3 Hz, 1H), 6.57 (dd, J=0.7, 3.3 Hz, 1H), 7.00-7.10 (m, 2H), 7.37 (dd, J=0.7, 1.8 Hz, 1H), 7.45-7.51 (m, 1H), 8.50-8.52 (m, 1H).

Step 2:
In a manner similar to that in Example 1, the entitled Compound 78 (143 mg, 53%) was obtained from –2-amino-4-(2-furyl)-5-{N-methyl-N-[2-(2-pyridyl)ethyl]amino}thiazole (200 mg, 0.67 mmol) obtained in Step 1, in place of Compound a.

$^1$H NMR (CDCl$_3$, δ ppm): 2.83 (s, 3H), 3.01-3.07 (m, 2H), 3.41-3.46 (m, 2H), 6.38 (dd, J=1.8, 3.5 Hz, 1H), 6.58 (d, J=3.5 Hz, 1H), 7.03-7.12 (m, 2H), 7.35 (d, J=1.8 Hz, 1H), 7.49-7.55 (m, 1H), 7.72 (d, J=6.1 Hz, 2H), 8.51-8.53 (m, 1H), 8.82 (d, J=6.1 Hz, 2H).

ESIMS m/z: [M+H]$^+$ 406.

Example 79

N-[5-(4-Benzylpiperazin-1-yl)-4-(2-furyl)thiazol-2-yl]acetamide (Compound 79)

In a manner similar to that in Example 2, the entitled Compound 79; (550 mg, 77%) was obtained from 2-amino-5-(4-benzylpiperazin-1-yl)-4-(2-furyl)thiazole (458 mg, 1.87 mmol) obtained in Step 1 of Example 68, in place of Compound a.

$^1$H NMR (DMSO-d$_6$, δ ppm): 1.99 (s, 3H), 2.63-2.66 (m, 4H), 3.01-3.04 (m, 4H), 3.59 (s, 2H), 6.49 (dd, J=1.8, 3.3 Hz, 1H), 6.85 (d, J=3.3 Hz, 1H), 7.23-7.40 (m, 6H), 10.9 (br-s, 1H).

ESIMS m/z: [M+H]$^+$ 383.

Example 80

N-[4-(2-Furyl)-5-(piperazin-1-yl)thiazol-2-yl]acetamide fumarate (Compound 80)

Compound 79 (274 mg, 0.72 mmol) was dissolved in methanol (7 mL), and 10% palladium-carbon (274 mg) was added thereto, followed by stirring in an atmosphere of hydrogen at 50° C. for 24 hours. The reaction mixture was filtered through Celite, and the resulting filtrate was concentrated to afford a free form of the entitled Compound. The resulting free form was dissolved in ethanol (5 mL), fumaric acid (83.0 mg, 0.51 mmol) was added thereto, and the precipitated solid was collected by filtration to afford the entitled Compound 80 (40.1 mg, 14%).

$^1$H NMR (CDCl$_3$, δ ppm): 2.10 (s, 3H), 2.97-3.06 (m, 4H), 3.14-3.21 (m, 4H), 6.58 (dd, J=1.8, 3.3 Hz, 1H), 6.54 (s, 2H), 6.79 (d, J=3.3 Hz, 1H), 7.67 (d, J=1.8 Hz, 1H).

APCIMS m/z: [M+H]$^+$ 293.

Example 81

N-[4-(2-Furyl)-5-(1,2,3,4-tetrahydroisoquinolin-2-yl)thiazol-2-yl]acetamide (Compound 81)

In a manner similar to that in Example 2, the entitled Compound 81 (225 mg, 74%) was obtained from 2-amino-4-(2-furyl)-5-(1,2,3,4-tetrahydroisoquinolin-2-yl)thiazole (267 mg, 0.89 mmol) obtained in Step 1 of Example 75, in place of Compound a.

$^1$H NMR (DMSO-d$_6$, δ ppm): 2.11 (s, 3H), 2.98-3.02 (m, 2H), 3.21-3.25 (m, 2H), 4.13 (s, 2H), 6.55 (dd, J=1.8, 3.3 Hz, 1H), 6.67 (dd, J=0.8, 3.3 Hz, 1H), 7.10-7.19 (m, 4H), 7.67 (dd, J=0.8, 1.8 Hz, 1H), 12.08 (br s, 1H).

ESIMS m/z: [M+H]$^+$ 340.

Example 82

N-[5-(1,4-Dioxa-8-azaspiro[4.5]decan-8-yl)-4-(2-furyl)thiazol-2-yl]acetamide (Compound 82)

In a manner similar to that in Example 2, the entitled Compound 82 (488 mg, 84%) was obtained from 2-amino-5-(1,4-dioxa-8-azaspiro[4.5]decan-8-yl)-4-(2-furyl)thiazole (510 mg, 1.66 mmol) obtained in Step 1 of Example 74, in place of Compound a.

$^1$H NMR (CDCl$_3$, δ ppm): 1.87-1.91 (m, 4H), 2.14 (s, 3H), 3.05-3.09 (m, 4H), 3.98 (s, 4H), 6.47 (dd, J=1.8, 3.3 Hz, 1H), 6.80 (dd, J=0.7, 3.3 Hz, 1H), 7.39 (dd, J=0.7, 1.8 Hz, 1H), 10.61 (br s, 1H).

APCIMS m/z: [M+H]$^+$ 350.

Example 83

N-{4-(2-Furyl)-5-[N-(2-methoxyethyl)-N-methylamino]thiazol-2-yl}acetamide 0.5 fumarate (Compound 83)

In a manner similar to that in Example 2, a free form of the entitled Compound was obtained from 2-amino-4-(2-furyl)-5-[N-(2-methoxyethyl)-N-methylamino]thiazole (160 mg, 0.63 mmol) obtained in Step 1 of Example 77, in place of Compound a. The resulting free form was dissolved in ethanol (5 mL), and fumaric acid (146 mg, 1.26 mmol) was added thereto, and the precipitated solid was collected by filtration to afford the entitled Compound 83 (39.8 mg, 18%).

$^1$H NMR (DMSO-d$_6$, δ ppm): 2.09 (s, 3H), 2.72 (s, 3H), 3.03-3.07 (m, 2H), 3.19 (s, 3H), 3.41-3.45 (m, 2H), 6.56 (dd, J=1.8, 3.3 Hz, 1H), 6.60 (s, 1H), 6.77 (dd, J=0.7, 3.3 Hz, 1H), 7.64 (dd, J=0.7, 1.8 Hz, 1H), 12.08 (br s, 1H).

APCIMS m/z: [M+H]$^+$ 296.

Example 84

N-{4-(2-Furyl)-5-{N-methyl-N-[2-(2-pyridyl)ethyl]amino}thiazol-2-yl}acetamide fumarate (Compound 84)

In a manner similar to that in Example 2, a free form of the entitled Compound was obtained from 2-amino-4-(2-furyl)-5-{N-methyl-N-[2-(2-pyridyl)ethyl]amino}thiazole (108 mg, 0.36 mmol) obtained in Step 1 of Example 78, in place of Compound a. In a manner similar to that in Example 83, the entitled Compound 84 (20.2 mg, 12%) was obtained from the free form thereof.

¹H NMR (DMSO-d₆, δ ppm): 2.11 (s, 3H), 2.76 (s, 3H), 2.92 (t, J=7.1 Hz, 2H), 3.27 (t, J=7.1 Hz, 2H), 6.28-6.29 (m, 2H), 7.16-7.23 (m, 2H), 7.61-7.67 (m, 2H), 8.43-8.56 (m, 1H).

ESIMS m/z: [M+H]⁺ 343.

Example 85

N-[5-Formyl-4-(2-furyl)thiazol-2-yl]pyridine-4-carboxamide (Compound 85)

Compound i (684 mg, 3.52 mmol) obtained in Reference Example 9 was dissolved in DMF (17 mL), and isonicotinic acid (867 mg, 7.04 mmol), EDC hydrochloride (1.35 g, 7.04 mmol) and 1-hydroxybenzotriazole monohydrate (1.08 g, 7.04 mmol) were added thereto, followed by stirring at 50° C. for 3 hours. Water was added to the reaction mixture, and the precipitated crystals were collected by filtration to afford the entitled Compound 85 (546 mg, 52%).

¹H NMR (DMSO-d₆, δ ppm): 6.77 (dd, J=1.7, 3.5 Hz, 1H), 7.18 (dd, J=0.7, 3.5 Hz, 1H), 8.00-8.03 (m, 3H), 8.84 (dd, J=1.7, 4.6 Hz, 2H), 10.46 (s, 1H), 13.60 (br s, 1H).

Example 86

N-[4-(2-Furyl)-5-(morpholinomethyl)thiazol-2-yl]pyridine-4-carboxamide (Compound 86)

Compound 85 (250 mg, 0.836 mmol) was dissolved in 1,2-dichloroethane (4 mL), and morpholine (0.15 mL, 1.67 mmol) and sodium triacetoxyborohydride (531 mg, 2.51 mmol) were added thereto, followed by stirring overnight at room temperature. Water was added to the reaction mixture, followed by extraction with chloroform. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=30:1) to afford the entitled Compound 86 (302 mg, 98%).

¹H NMR (DMSO-d₆, δ ppm): 3.31-3.34 (m, 4H), 3.59-3.62 (m, 4H), 3.95 (s, 2H), 6.62 (dd, J=1.8, 3.3 Hz, 1H), 6.75 (dd, J=0.9, 3.3 Hz, 1H), 7.79 (dd, J=0.9, 1.8 Hz, 1H), 7.99 (dd, J=1.7, 4.4 Hz, 2H), 8.81 (dd, J=1.7, 4.4 Hz, 2H), 13.02 (br s, 1H)

ESIMS m/z: [M−H]⁺ 371.

Example 87

N-[4-(2-Furyl)-5-(thiomorpholinomethyl)thiazol-2-yl]pyridine-4-carboxamide (Compound 87)

In a manner similar to that in Example 86, by using thiomorpholine (0.170 mL, 1.67 mmol) in place of morpholine, the entitled Compound 87 (272 mg, 84%) was obtained from Compound 85 (250 mg, 0.836 mmol).

¹H NMR (CDCl₃, δ ppm): 2.71-2.74 (m, 4H), 2.86-2.89 (m, 4H), 3.94 (s, 2H), 6.40 (dd, J=1.8, 3.3 Hz, 1H), 6.56 (dd, J=0.7, 3.3 Hz, 1H), 7.38 (dd, J=0.7, 1.8 Hz, 1H), 7.71 (dd, J=1.8, 4.4 Hz, 2H), 8.77 (dd, J=1.8, 4.4 Hz, 2H), 10.61 (br s, 1H).

APCIMS m/z: [M+H]⁺ 387.

Example 88

N-[4-(2-Furyl)-5-(pyrrolidin-1-ylmethyl)thiazol-2-yl]pyridine-4-carboxamide (Compound 88)

In a manner similar to that in Example 86, by using pyrrolidine (0.141 mL, 1.67 mmol) in place of morpholine, the entitled Compound 88 (249 mg, 84%) was obtained from Compound 85 (250 mg, 0.836 mmol).

¹H NMR (CDCl₃, δ ppm): 1.80-1.84 (m, 4H), 2.65-2.72 (m, 4H), 4.05 (s, 2H), 6.42 (dd, J=1.8, 3.3 Hz, 1H), 6.59 (d, J=3.3 Hz, 1H), 7.40 (d, J=1.8 Hz, 1H), 7.70 (d, J=6.1 Hz, 2H), 8.76 (d, J=6.1 Hz, 2H).

APCIMS m/z: [M+H]⁺ 355.

Example 89

N-[4-(2-Furyl)-5-(4-methylpiperazin-1-ylmethyl)thiazol-2-yl]pyridine-4-carboxamide (Compound 89)

In a manner similar to that in Example 86, by using 1-methylpiperazine (0.152 mL, 1.34 mmol) in place of morpholine, the entitled Compound 89 (142 mg, 55%) was obtained from Compound 85 (200 mg, 0.669 mmol).

¹H NMR (CD₃OD, δ ppm): 2.98 (s, 3H), 3.37-3.72 (m, 8H), 4.77 (s, 2H), 6.61 (dd, J=1.8, 3.3 Hz, 1H), 6.96 (d, J=3.3 Hz, 1H), 7.74 (d, J=1.8 Hz, 1H), 8.58 (d, J=6.1 Hz, 2H), 9.09 (d, J=6.1 Hz, 2H).

APCIMS m/z: [M+H]⁺ 384.

Example 90

N-[4-(2-Furyl)-5-(octahydropyrazino[2,1-c][1,4]oxazin-8-ylmethyl)thiazol-2-yl]pyridine-4-carboxamide (Compound 90)

In a manner similar to that in Example 86, by using octahydropyrazino[2,1-c][1,4]oxazine (300 mg, 2.11 mmol) obtained according to the method described in EP 472826, in place of morpholine, the entitled Compound 90 (212 mg, 47%) was obtained from Compound 85 (316 mg, 1.05 mmol).

¹H NMR (CDCl₃, δ ppm): 1.91-1.98 (m, 1H), 2.37-2.50 (m, 4H), 2.64-2.78 (m, 3H), 2.96-2.99 (m, 1H), 3.20-3.27 (m, 1H), 3.63-3.69 (m, 2H), 3.82-3.84 (m, 1H), 3.92 (s, 2H), 6.41 (dd, J=1.8, 3.3 Hz, 1H), 6.59 (d, J=3.3 Hz, 1H), 7.39 (d, J=1.8 Hz, 1H), 7.70 (d, J=6.1 Hz, 2H), 8.78 (d, J=6.1 Hz, 2H).

APCIMS m/z: [M+H]⁺ 426.

Example 91

N-(4-(2-Furyl)-5-[(2-morpholinoethylamino)methyl]thiazol-2-yl)pyridine-4-carboxamide dihydrochloride (Compound 91)

In a manner similar to that in Example 86, by using N-(2-aminoethyl)morpholine (0.180 mL, 1.34 mmol) in place of morpholine, a free form of the entitled Compound was obtained from Compound 85 (200 mg, 0.669 mmol). The resulting free form was dissolved in ethanol (4 mL), an ethyl acetate solution (0.30 mL) of 4 mol/L hydrogen chloride was added thereto, and the precipitated solid was collected by filtration to afford the entitled Compound 91 (40.3 mg, 12%).

¹H NMR (CD₃OD, δ ppm): 3.10-3.39 (m, 6H), 3.56-3.65 (m, 2H), 3.87-3.94 (m, 4H), 4.80 (s, 2H), 6.63 (dd, J=1.8, 3.3 Hz, 1H), 6.98 (d, J=3.3 Hz, 1H), 7.76 (d, J=1.8 Hz, 1H), 8.10 (d, J=6.1 Hz, 2H), 8.86 (d, J=6.1 Hz, 2H).

APCIMS m/z: [M+H]⁺ 414.

Example 92

2-(tert-Butoxycarbonylamino)-5-formyl-4-(2-furyl)thiazole (Compound 92)

Compound h (3.10 g, 8.98 mmol) obtained in Reference Example 8 was dissolved in THF (45 mL), and a 1.58 mol/L solution of n-butyllithium in n-hexane (14.2 mL, 22.5 mmol) was added thereto in a stream of argon at −78° C. The mixture was stirred at −78° C. for 10 minutes, and then DMF (14.2 mL, 183 mmol) was added dropwise thereto, followed by stirring at room temperature for 1 hour. A saturated aqueous solution of ammonium chloride was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=4:1) to afford the entitled Compound 92 (1.50 g, 57%).

$^1$H NMR (CDCl$_3$, δ ppm): 1.50 (s, 9H), 6.57 (dd, J=1.8, 3.4 Hz, 1H), 6.99 (dd, J=0.8, 3.4 Hz, 1H), 7.60 (dd, J=0.8, 1.8 Hz, 1H), 8.95 (br s, 1H), 10.52 (s, 1H).

Example 93

2-(tert-Butoxycarbonylamino)-4-(2-furyl)-5-morpholinomethylthiazole (Compound 93)

Compound 92 (1.58 g, 5.37 mmol) and morpholine (0.64 mL, 10.7 mmol) were dissolved in 1,2-dichloroethane (26 mL), and sodium triacetoxyborohydride (3.41 g, 16.1 mmol) was added thereto, followed by stirring overnight at room temperature. Water was added to the reaction mixture, followed by extraction with chloroform. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=30:1) to afford the entitled Compound 93 (1.15 g, 57%).

$^1$H NMR (CDCl$_3$, δ ppm): 1.50 (s, 9H), 2.56-2.60 (m, 4H), 3.70-3.74 (m, 4H), 3.90 (s, 2H), 6.47 (dd, J=1.8, 3.3 Hz, 1H), 6.63 (dd, J=0.7, 3.3 Hz, 1H), 7.46 (dd, J=0.7, 1.8 Hz, 1H).

Example 94

N-[4-(2-Furyl)-5-(morpholinomethyl)thiazol-2-yl]pyridine-3-carboxamide (Compound 94)

Step 1:

Compound 93 (1.15 g, 0.32 mmol) was dissolved in trifluoroacetic acid (12 mL), followed by stirring at room temperature for 30 minutes. The reaction mixture was concentrated under reduced pressure, and aqueous 1 mol/L sodium hydroxide solution and a mixed solvent (4:1) of chloroform and 2-propanol were added to the resulting residue, and the organic layer was separated. The organic layer was dried over anhydrous magnesium sulfate, and then the solvent was distilled away under reduced pressure to afford 2-amino-4-(2-furyl)-5-(morpholinomethyl)thiazole (835 mg, 100%).

$^1$H NMR (CD$_3$OD, δ ppm): 2.50-2.53 (m, 4H), 3.65-3.68 (m, 4H), 3.83 (s, 2H), 6.47 (dd, J=1.8, 3.3 Hz, 1H), 6.61 (dd, J=0.7, 3.3 Hz, 1H), 7.52 (dd, J=0.7, 1.8 Hz, 1H).

Step 2:

2-Amino-4-(2-furyl)-5-(morpholinomethyl)thiazole (225 mg, 0.85 mmol) obtained in Step 1 was dissolved in DMF (4 mL), and nicotinoyl chloride hydrochloride (302 mg, 1.70 mmol) and triethylamine (0.24 mL, 1.70 mmol) were added thereto, followed by stirring at room temperature for 4 hours. A saturated aqueous solution of sodium hydrogencarbonate was added to the reaction mixture, followed by extraction with ethyl acetate. The organic layer was dried over anhydrous magnesium sulfate, and then the solvent was distilled away under reduced pressure. The resulting residue was purified through silica gel column chromatography (hexane:ethyl acetate 1:1) to afford the entitled Compound 94 (73.0 mg, 23%).

$^1$H NMR (CDCl$_3$, δ ppm): 2.60-2.63 (m, 4H), 3.74-3.77 (m, 4H), 3.94 (s, 2H), 6.42 (dd, J=1.8, 3.3 Hz, 1H), 6.61 (d, J=3.3 Hz, 1H), 7.41 (d, J=1.8 Hz, 1H), 7.42-7.44 (m, 1H), 8.24-8.28 (m, 1H), 8.78-8.83 (m, 1H), 9.18-9.19 (m, 1H).

APCIMS m/z: [M−H]$^-$ 369.

Example 95

N-[5-Carboxy-4-(2-furyl)thiazol-2-yl]pyridine-4-carboxamide (Compound 95)

Compound 24 (840 mg, 2.45 mmol) was dissolved in THF (5 mL) and methanol (5 mL), and a 4 mol/L aqueous sodium hydroxide solution (3 mL) was added thereto, followed by stirring at 60° C. for 2 hours. The reaction mixture was allowed to cool down, and neutralized with 2 mol/L hydrochloric acid added thereto. The precipitated solid was collected by filtration to afford the entitled Compound 95 (411 mg, 53%).

$^1$H NMR (DMSO-d$_6$, δ ppm): 6.68 (dd, J=1.8, 3.5 Hz, 1H), 7.61 (dd, J=1.0, 3.5 Hz, 1H), 7.86 (dd, J=1.0, 1.8 Hz, 1H), 8.20 (dd, J=1.7, 4.8 Hz, 2H), 8.94 (dd, J=1.7, 4.8 Hz, 2H).

Example 96

N-[4-(2-Furyl)-5-morpholinocarbonylthiazol-2-yl]pyridine-4-carboxamide (Compound 96)

Compound 95 (410 mg, 1.30 mmol), morpholine (0.141 mL, 1.60 mmol), EDC hydrochloride (500 mg, 2.60 mmol), 1-hydroxybenzotriazole monohydrate (400 mg, 2.60 mmol) and triethylamine (0.36 mL, 2.60 mmol) were dissolved in DMF (5 mL), followed by stirring at room temperature for 3 hours. Water was added to the reaction mixture, followed by extraction with chloroform. The organic layer was washed with a saturated aqueous solution of sodium chloride and dried over anhydrous magnesium sulfate, and then the solvent was distilled away under reduced pressure. The resulting residue was recrystallized from ethanol to afford the entitled Compound 96 (159 mg, 34%) as colorless crystals.

$^1$H NMR (DMSO-d$_6$, δ ppm): 3.59-3.68 (m, 8H), 6.39 (dd, J=1.8, 3.3 Hz, 1H), 6.67 (dd, J=0.7, 3.3 Hz, 1H), 7.27 (dd, J=0.7, 1.8 Hz, 1H), 7.78 (dd, J=1.6, 4.5 Hz, 2H), 8.81 (dd, J=1.6, 4.5 Hz, 2H), 10.82 (br s, 1H).

ESIMS m/z: [M−H]$^-$ 383.

Example 97

N-[5-(N,N-Dimethylcarbamoyl)-4-(2-furyl)thiazol-2-yl]pyridine-4-carboxamide (Compound 97)

In a manner similar to that in Example 96, by using a 2 mol/L solution of dimethylamine (0.420 mL, 0.850 mmol) in methanol in place of morpholine, the entitled Compound 97 (85.1 mg, 31%) was obtained from Compound 95 (250 mg, 0.794 mmol).

$^1$H NMR (DMSO-$d_6$, δ ppm): 2.81 (s, 3H), 3.01 (s, 3H), 6.62 (dd, J=1.8, 3.3 Hz, 1H), 6.74 (dd, J=0.7, 3.3 Hz, 1H), 7.77 (dd, J=0.7, 1.8 Hz, 1H), 7.94 (d, J=6.1 Hz, 2H), 8.81 (d, J=6.1 Hz, 2H).

ESIMS m/z; [M−H]$^+$ 343.

Example 98

N-[4-(2-Furyl)-5-(N-methoxy-N-methylcarbamoyl) thiazol-2-yl]pyridine-4-carboxamide (Compound 98)

In a manner similar to that in Example 96, by using N,O-dimethylhydroxyamine hydrochloride (810 mg, 8.30 mmol) in place of morpholine, the entitled Compound 98 (1.20 g, 81%) was obtained from Compound 95 (1.31 g, 4.15 mmol).

$^1$H NMR (CDCl$_3$, δ ppm): 3.38 (s, 3H), 3.70 (s, 3H), 6.40 (dd, J=1.8, 3.5 Hz, 1H), 7.03 (dd, J=0.7, 3.5 Hz, 1H), 7.37 (dd, J=0.7, 1.8 Hz, 1H), 7.75 (dd, J=1.7, 4.6 Hz, 2H), 8.82 (dd, J=1.7, 4.6 Hz, 2H).

Example 99

N-[5-Benzoyl-4-(2-furyl)thiazol-2-yl]pyridine-4-carboxamide (Compound 99)

Compound 98 (354 mg, 0.989 mmol) was dissolved in THF (5 mL), and a diethyl ether solution of 3 mol/L phenylmagnesium bromide (1.32 mL, 3.96 mmol) was added thereto under ice-cooling, followed by stirring at room temperature for 1 hour. A saturated aqueous solution of ammonium chloride was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was reslurried with ethanol to afford the entitled Compound 99 (220 mg, 59%) as pale yellow crystals.

$^1$H NMR (CDCl$_3$, δ ppm): 6.52 (dd, J=1.8, 3.5 Hz, 1H), 6.96 (dd, J=0.7, 3.5 Hz 1H), 7.44-7.49 (m, 2H), 7.50 (dd, J=0.7, 1.8 Hz, 1H), 7.58-7.63 (m, 1H), 7.72-7.75 (m, 2H), 8.03 (dd, J=1.7, 4.4 Hz, 2H), 8.84 (dd, J=1.7, 4.4 Hz, 2H).

ESIMS m/z: [M+H]$^+$ 376.

Example 100

N-[4-(5-Bromofuran-2-yl)-5-morpholinothiazol-2-yl]pyridine-4-carboxamide (Compound 100)

In a manner similar to that in Example 29, the entitled Compound 100 (156 mg, 31%) was obtained from Compound j (379 mg, 1.17 mmol) obtained in Reference Example 10, in place of Compound g obtained in Reference Example 7.

$^1$H NMR (CDCl$_3$, δ ppm): 3.01-3.05 (m, 4H), 3.88-3.91 (m, 4H), 6.36 (d, J=3.3 Hz, 1H), 6.77 (d, J=3.3 Hz, 1H), 7.72 (dd, J=1.5, 4.4 Hz, 2H), 8.80 (dd, J=1.5, 4.4 Hz, 2H), 10.31 (br s, 1H)

APCIMS m/z: [$^{79}$BrM+H]$^+$ 435, [$^{81}$BrM+H]$^+$ 437.

Example 101

N-[4-(2-Furyl)-5-(4-pyridyl)thiazol-2-yl]benzamide (Compound 101)

In a manner similar to that in Example 2, by using benzoyl chloride (0.160 mL, 1.39 mmol) in place of acetyl chloride, the entitled Compound 101 (183 mg, 64%) was obtained as a pale yellow solid from Compound a (200 mg, 0.820 mmol) obtained in Reference Example 1.

$^1$H NMR (DMSO-$d_6$, δ ppm): 6.60 (dd, J=1.6, 3.2 Hz, 1H), 6.74 (d, J=3.2 Hz, 1H), 7.45 (d, J=6.2 Hz, 2H), 7.51-7.61 (m, 2H), 7.61-7.70 (m, 2H), 8.09-8.18 (m, 2H), 8.62 (d, J=6.2 Hz, 2H), 13.01 (br s, 1H).

APCIMS m/z: [M+H]$^+$ 248.

m.p.: 270-300° C. (decomposition).

Example 102

4-Fluoro-N-[4-(2-furyl)-5-(4-pyridyl)thiazol-2-yl]benzamide (Compound 102)

In a manner similar to that in Example 2, by using 4-fluorobenzoyl chloride (0.170 mL, 1.39 mmol) in place of acetyl chloride, the entitled Compound 102 (94.1 mg, 31%) was obtained as a pale yellow solid from Compound a (200 mg, 0.820 mmol) obtained in Reference Example 1.

$^1$H NMR (DMSO-$d_6$, δ ppm): 6.60 (dd, J=1.6, 3.2 Hz, 1H), 6.73 (d, J=3.2 Hz, 1H), 7.40 (dd, J=8.9, 8.9 Hz, 2H), 7.45 (d, J=6.2 Hz, 2H), 7.67 (d, J=1.6 Hz, 1H), 8.22 (dd, J=5.4, 8.9 Hz, 2H), 8.62 (d, J=6.2 Hz, 2H), 13.07 (br s, 1H).

APCIMS m/z: [M+H]$^+$ 366.

m.p.: 270-300° C. (decomposition).

Example 103

N-[4-(2-Furyl)-5-(4-pyridyl)thiazol-2-yl]-4-methoxybenzamide (Compound 103)

In a manner similar to that in Example 2, by using 4-methoxybenzoyl chloride (0.150 mL, 1.39 mmol) in place of acetyl chloride, the entitled Compound 103 (133 mg, 43%) was obtained as a pale yellow solid from Compound a (200 mg, 0.820 mmol) obtained in Reference Example 1.

$^1$H NMR (DMSO-$d_6$, δ ppm): 3.86 (s, 3H), 6.61 (dd, J=1.9, 3.2 Hz, 1H), 6.7.3 (dd, J=0.8, 3.2 Hz, 1H), 7.09 (d, J=8.9 Hz, 2H), 7.44 (d, J=6.2 Hz, 2H), 7.67 (dd, J=0.8, 1.9 Hz, 1H), 8.15 (d, J=8.9 Hz, 2H), 8.62 (d, J=6.2 Hz, 2H), 12.86 (br s, 1H).

APCIMS m/z: [M+H]$^+$ 378.

m.p.: 235-245° C.

Example 104

N-[4-(2-Furyl)-5-(4-pyridyl)thiazol-2-yl]-2,2-dimethylpropanamide (Compound 104)

In a manner similar to that in Example 2, by using pivaloyl chloride (0.170 mL, 1.39 mmol) in place of acetyl chloride, the entitled Compound 104 (107 mg, 40%) was obtained as a white solid from Compound a (200 mg, 0.820 mmol) obtained in Reference Example 1.

$^1$H NMR (DMSO-$d_6$, δ ppm): 1.27 (s, 9H), 6.58 (dd, J=1.6, 3.2 Hz, 1H), 6.70 (d, J=3.2 Hz, 1H), 7.40 (d, J=5.9 Hz, 2H), 7.64 (d, J=1.6 Hz, 1H), 8.60 (d, J=5.9 Hz, 2H), 12.19 (br-s, 1H).

APCIMS m/z: [M+H]$^+$ 328.

m.p.: 240-241° C.

Example 105

N-[4-(2-Furyl)-5-(4-pyridyl)thiazol-2-yl]-2-methoxypyridine-4-carboxamide (Compound 105)

In a manner similar to that in Example 42, by using Compound k obtained in Reference Example 11 in place of 1-(tert-butoxycarbonyl)piperidine-4-carboxylic acid, the entitled Compound 105 (1.93 g, 85%) was obtained from Compound a (1.46 g, 6.00 mmol) obtained in Reference Example 1, in place of 2-amino-4-(2-furyl)-5-morpholinothiazole.

$^1$H NMR (DMSO-$d_6$, δ ppm): 3.94 (s, 3H), 6.56 (dd, J=1.9, 3.5 Hz, 1H), 6.69 (dd, J=0.8, 3.5 Hz, 1H), 7.43 (dd, J=1.6, 4.6 Hz, 2H), 7.46 (dd, J=0.5, 1.3 Hz, 1H), 7.57 (dd, J=1.3, 5.4 Hz, 1H), 8.36 (dd, J=0.5, 5.4 Hz, 1H), 8.61 (dd, J=1.6, 4.6 Hz, 2H), 12.96 (br s, 1H).

APCIMS m/z; [M+H]$^+$ 379.

m.p.: 285-288° C.

Example 106

N-[4-(2-Furyl)-5-(4-pyridyl)thiazol-2-yl]-2-(4-methoxybenzyloxy)pyridine-4-carboxamide (Compound 106)

In a manner similar to that in Example 42, by using Compound l obtained in Reference Example 12 in place of 1-(tert-butoxycarbonyl)piperidine-4-carboxylic acid, the entitled Compound 106 (2.41 g, 83%) was obtained from Compound a (1.46 g, 6.00 mmol) obtained in Reference Example 1, in place of 2-amino-4-(2-furyl)-5-morpholinothiazole.

$^1$H NMR (DMSO-$d_6$, δ ppm): 3.76 (s, 3H), 5.35 (s, 2H), 6.60 (dd, J=1.6, 3.2 Hz, 1H), 6.74 (d, J=3.2 Hz, 1H), 6.95 (d, J=8.7 Hz, 2H), 7.42 (d, J=8.7 Hz, 2H), 7.47 (dd, J=1.6, 4.6 Hz, 2H), 7.48-7.50 (m, 1H), 7.59 (dd, J=1.1, 5.1 Hz, 1H), 7.67-7.68 (m, 1H), 8.40 (d, J=5.1 Hz, 1H), 8.63 (dd, J=1.6, 4.6 Hz, 2H), 13.29 (br s, 1H).

APCIMS m/z: [M+H]$^+$ 485.

Example 107

2-(Chloromethyl)-N-[4-(2-furyl)-5-(4-pyridyl)thiazol-2-yl]pyridine-4-carboxamide (Compound 107)

In a manner similar to that in Example 3, by using 2-(chloromethyl)isonicotinic acid (2.12 g, 12.3 mmol) obtained according to the method described in WO03/043636 in place of methoxyacetic acid, the entitled Compound 107 (1.75 g, 71%) was obtained from Compound a (1.50 g, 6.17 mmol) obtained in Reference Example 1.

$^1$H NMR (DMSO-$d_6$, δ ppm): 4.90 (s, 2H), 6.61 (dd, J=1.8, 3.5 Hz, 1H), 6.75 (d, J=3.5 Hz, 1H), 7.47 (d, J=6.1 Hz, 2H), 7.68 (d, J=1.8 Hz, 1H), 8.01 (d, J=5.1 Hz, 1H), 8.18 (s, 1H), 8.63 (d, J=6.1 Hz, 2H), 8.81 (d, J=5.1 Hz, 1H).

Example 108

N-[4-(2-Furyl)-5-(4-pyridyl)thiazol-2-yl]-2-(imidazol-1-ylmethyl)pyridine-4-carboxamide (Compound 108)

Compound 107 (150 mg, 0.387 mmol) was dissolved in DMF (2 ml), and imidazole (129 mg, 1.89 mmol) was added thereto, followed by stirring at 90° C. for 3 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=30:1) to afford the entitled Compound 108 (120 mg, 74%).

$^1$H NMR (DMSO-$d_6$, δ ppm): 5.43 (s, 2H), 6.61 (dd, J=1.8, 3.3 Hz, 1H), 6.75 (d, J=3.3 Hz, 1H), 6.98 (s, 1H), 7.23 (s, 1H), 7.46 (d, J=6.2 Hz, 2H), 7.68 (d, J=1.8 Hz, 1H), 7.81 (s, 1H), 7.85 (s, 1H), 7.97 (d, J=5.1 Hz, 1H), 8.63 (d, J=6.2 Hz, 2H), 8.79 (d, J=5.1 Hz, 1H).

APCIMS m/z: [M+H]$^+$ 429.

m.p.: 239-250° C.

Example 109

2-{N-[2-(Dimethylamino)ethyl]-N-methylaminomethyl}-N-[4-(2-furyl)-5-(4-pyridyl)thiazol-2-yl]pyridine-4-carboxamide (Compound 109)

Compound 107 (150 mg, 0.387 mmol) was dissolved in N,N,N'-trimethylethylenediamine (1 mL), followed by stirring at 60° C. for 4 hours. The reaction mixture was concentrated under reduced pressure. The resulting residue was purified through silica gel column chromatography (chloroform:methanol=20:1) and then crystallized from diisopropyl ether to afford the entitled Compound 109 (70 mg, 40%) as a white solid.

$^1$H NMR (CDCl$_3$, δ ppm): 2.30 (s, 6H), 2.35 (s, 3H), 2.50-2.54 (m, 2H), 3.81 (s, 2H), 6.46 (dd, J=1.7, 3.2 Hz, 1H), 6.65 (d, J=3.2 Hz, 1H), 7.38 (d, J=1.7 Hz, 1H), 7.42 (d, J=6.2 Hz, 2H), 7.81 (d, J=5.1 Hz, 1H), 8.37 (s, 1H), 8.64 (d, J=6.2 Hz, 2H), 8.75 (d, J=5.1 Hz, 1H).

APCIMS m/z: [M+H]$^+$ 463.

m.p.: 203-205° C.

Example 110

N-[4-(2-Furyl)-5-(4-pyridyl)thiazol-2-yl]-2-[N-(2-methoxyethyl)-N-methylaminomethyl]pyridine-4-carboxamide (Compound 110)

In a manner similar to that in Example 109, by using N-(2-methoxyethyl)-N-methylamine (1 mL) in place of N,N,N'-trimethylethylenediamine, the entitled Compound 110 (137 mg, 81%) was obtained from Compound 107 (150 mg, 0.387 mmol).

$^1$H NMR (CDCl$_3$, δ ppm): 2.42 (s, 3H), 2.69 (t, J=5.1 Hz, 2H), 3.51 (s, 3H), 3.59 (t, J=5.1 Hz, 2H), 3.85 (s, 2H), 6.43 (dd, J=1.8, 3.3 Hz, 1H), 6.61 (d, J=3.3 Hz, 1H), 7.35 (d, J=1.8 Hz, 1H), 7.43 (d, J=6.1 Hz, 2H), 7.76 (d, J=5.1 Hz, 1H), 8.20 (s, 2H), 8.65 (d, J=6.1 Hz, 2H), 8.75 (d, J=5.1 Hz, 1H).

APCIMS m/z: [M+H]$^+$ 450.

m.p.: 195-197° C.

Example 111

N-[4-(2-Furyl)-5-(4-pyridyl)thiazol-2-yl]-2-(4-hydroxypiperidinomethyl)pyridine-4-carboxamide (Compound 111)

In a manner similar to that in Example 108, by using 4-hydroxypiperidine in place of imidazole, the entitled Compound 111 (92.0 mg, 53%) was obtained from Compound 107.

$^1$H NMR (DMSO-$d_6$, δ ppm): 0.84-0.89 (m, 4H), 1.24-1.37 (m, 4H), 1.60-1.68 (m, 1H), 4.14 (s, 2H), 6.60 (dd, J=1.8, 3.3 Hz, 1H), 6.75 (d, J=3.3 Hz, 1H), 7.47 (d, J=1.8 Hz, 1H), 7.69

(d, J=6.1 Hz, 2H), 7.91 (d, J=5.1 Hz, 1H), 8.05 (s, 1H), 8.62 (s, J=6.1 Hz, 2H), 8.73 (d, J=5.1 Hz, 1H).
APCIMS m/z: [M+H]$^+$ 462.
m.p.: 203-208° C.

Example 112

N-[4-(2-Furyl)-5-(4-pyridyl)thiazol-2-yl]-2-oxo-1,2-dihydropyridine-4-carboxamide (Compound 112)

Compound 106 (2.10 g, 4.33 mmol) and anisole (4.72 mL, 43.4 mmol) were suspended in trifluoroacetic acid (7 mL), followed by stirring at 65° C. for 30 minutes. A saturated aqueous solution of sodium hydrogencarbonate was added to the reaction mixture to adjust the pH to 8, and the precipitated solid was collected by filtration. The resulting solid was purified through silica gel column chromatography (chloroform:methanol=4:1) to afford the entitled Compound 112 (1.07 g, 68%).

$^1$H NMR (DMSO-d$_6$, δ ppm): 6.66 (dd, J=1.6, 3.2 Hz, 1H), 6.73 (d, J=3.2 Hz, 1H), 7.00-7.05 (m, 2H), 7.45 (dd, J=1.6, 4.0 Hz, 2H), 7.54 (d, J=7.0 Hz, 1H), 7.67 (d, J=1.6 Hz, 1H), 8.62 (dd, J=1.6, 4.0 Hz, 2H), 11.98 (br s, 1H), 13.17 (br s, 1H).
APCIMS m/z: [M+H]$^+$ 365.
m.p. 277-281° C.

Example 113

1-Benzyl-N-[4-(2-furyl)-5-(4-pyridyl)thiazol-2-yl]-2-oxo-1,2-dihydropyridine-4-carboxamide (Compound 113)

Compound 112 (146 mg, 0.400 mmol) was dissolved in DMF (2 mL), 60% sodium hydride (35.2 mg, 0.880 mmol) was added thereto, followed by stirring at room temperature for 30 minutes. Benzyl bromide (0.0523 mL, 0.440 mmol) was added dropwise to the reaction mixture, followed by stirring overnight at room temperature. The reaction mixture was poured into water, and 1 mol/L hydrochloric acid was added thereto to adjust the pH to 7, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=99:1) to afford the entitled Compound 113 (25.0 mg, 14%).

$^1$H NMR (DMSO-d$_6$, δ ppm): 5.15 (s, 2H), 6.60 (dd, J=1.6, 3.2 Hz, 1H), 6.73 (d, J=3.2 Hz, 1H), 6.76 (dd, J=1.9, 7.0 Hz, 1H), 7.16 (d, J=1.9 Hz, 1H), 7.17-7.39 (m, 5H), 7.45 (dd, J=1.6, 4.3 Hz, 2H), 7.67 (d, J=1.6 Hz, 1H), 7.99 (d, J=7.0 Hz, 1H), 8.62 (dd, J=1.6, 4.3 Hz, 2H), 13.22 (br s, 1H).
APCIMS m/z: [M+H]$^+$ 455.
m.p.: 244-248° C.

Example 114

N-[4-(2-Furyl)-5-(3-methylpyridin-4-yl)thiazol-2-yl]pyridine-4-carboxamide (Compound 114)

In a manner similar to that in Example 3, by using isonicotinic acid in place of methoxyacetic acid, the entitled Compound 114 (502 mg, 73%) was obtained from Compound m (514 mg, 2.00 mmol) obtained in Reference Example 13, in place of Compound a.

$^1$H NMR (DMSO-d$_6$, δ ppm): 2.08 (s, 3H), 6.49 (dd, J=0.5, 3.2 Hz, 1H), 6.53 (dd, J=1.9, 3.2 Hz, 1H), 7.38 (d, J=4.9 Hz, 1H), 7.59 (dd, J=0.5, 1.9 Hz, 1H), 8.03 (dd, J=1.6, 6.2 Hz, 2H), 8.49 (d, J=4.9 Hz, 1H), 8.58 (s, 1H), 8.83 (dd, J=1.6, 6.2 Hz, 2H), 13.37 (br s, 1H).
APCIMS m/z: [M+H]$^+$ 363.

Example 115

N-[4,5-Di(2-furyl)thiazol-2-yl]benzamide (Compound 115)

Compound n (300 mg, 0.760 mmol) obtained in Reference Example 14, tributyl(2-furyl)stannane (0.720 mL, 2.28 mmol), silver oxide (0.180 g, 0.760 mmol) and tetrakis(triphenylphosphine)palladium (0.130 g, 0.114 mmol) were suspended in DMF (7.6 mL), followed by stirring at 60° C. for 2 hours and at 100° C. for 15 minutes. The reaction mixture was cooled with ice, ethyl acetate was added thereto, and the precipitated silver oxide was collected by filtration. The filtrate was concentrated under reduced pressure. A 10% aqueous solution (35 mL) of potassium fluoride was added to the resulting residue, followed by stirring at room temperature for 10 minutes, and then extracted with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=10:1 to 5:1) to afford the entitled Compound 114 (20.6 mg, 8%).

$^1$H NMR (CDCl$_3$, δ ppm): 6.48 (dd, J=1.9, 3.5 Hz, 1H), 6.52 (dd, J=1.9, 3.5 Hz, 1H), 6.77 (dd, J=0.8, 3.5 Hz, 1H), 6.80 (dd, J=0.8, 3.5 Hz, 1H), 7.47-7.66 (m, 3H), 7.49 (dd, J=0.8, 1.9 Hz, 1H), 7.51 (dd, J=0.8, 1.9 Hz, 1H), 7.90-7.97 (m, 2H), 9.59 (br s, 1H).
m.p.: 156-157° C.

Example 116

N-[4-(2-Furyl)-5-(2-thienyl)thiazol-2-yl]benzamide (Compound 116)

In a manner similar to that in Example 115, by using tributyl(2-thienyl)stannane (0.240 mL, 0.750 mmol) in place of tributyl(2-furyl)stannane, the entitled Compound 115 (98.9 mg, 100%) was obtained from Compound n (100 mg, 0.250 mmol) obtained in Reference Example 14.

$^1$H NMR, (CDCl$_3$, δ ppm): 6.33 (dd, J=1.8, 3.3 Hz, 1H), 6.46 (dd, J=3.3 Hz, 1H), 7.11 (dd, J=3.7, 5.1 Hz, 1H), 7.27 (dd, J=1.5, 3.7 Hz, 1H), 7.34 (d, J=1.8 Hz, 1H), 7.41 (dd, J=1.5, 5.1 Hz, 1H), 7.43-7.53 (m, 2H), 7.54-7.62 (m, 1H), 7.86-7.94 (m, 2H), 9.59 (br s, 1H).
APCIMS m/z: [M+H]$^+$ 353.

Example 117

N-[4-(2-Furyl)-5-(1-methylindol-2-yl)thiazol-2-yl]benzamide (Compound 117)

In a manner similar to that in Example 115, by using tributyl(1-methylindol-2-yl)stannane (1.37 mL, 3.78 mmol) in place of tributyl(2-furyl)stannane, the entitled Compound 117 (395 mg, 78%) was obtained as a pale yellow solid from Compound n (500 mg, 1.26 mmol) obtained in Reference Example 14.

$^1$H NMR (CDCl$_3$, δ ppm): 3.55 (s, 3H), 6.05 (d, J=3.5 Hz, 1H), 6.29 (dd, J=1.6, 3.5 Hz, 1H), 6.73 (s, 1H), 7.14-7.22 (m, 1H), 7.24-7.41 (m, 2H), 7.35 (d, J=1.6 Hz, 1H), 7.50-7.71 (m, 4H), 7.91-7.97 (m, 2H), 9.76 (br s, 1H).
m.p. 195-196° C.

Example 118

N-[4-(2-Furyl)-5-(2-methylphenyl)thiazol-2-yl]pyridine-4-carboxamide (Compound 118)

In a manner similar to that in Example 3, by using isonicotinic acid in place of methoxyacetic acid, the entitled Compound 118 (482 mg, 67%) was obtained from Compound o (512 mg, 2.00 mmol) obtained in Reference Example 15, in place of Compound a.

$^1$H NMR (DMSO-d$_6$, δ ppm): 2.09 (s, 3H), 6.18 (d, J=3.2 Hz, 1H), 6.46 (dd, J=1.9, 3.2 Hz, 1H), 7.28-7.40 (m, 4H), 7.57 (d, J=1.9 Hz, 1H), 8.01 (dd, J=1.4, 5.9 Hz, 2H), 8.82 (dd, J=1.4, 5.9 Hz, 2H), 12.27 (br s, 1H).

APCIMS m/z: [M+H]$^+$ 362.

Example 119

N-[4-(2-Furyl)-5-(4-methoxyphenyl)thiazol-2-yl]benzamide (Compound 119)

In a manner similar to that in Example 115, by using tributyl(4-methoxyphenyl)stannane (1.15 mL, 3.78 mmol) in place of tributyl(2-furyl)stannane, the entitled Compound 119 (137 mg, 29%) was obtained as a pale yellow solid from Compound n (500 mg, 1.26 mmol) obtained in Reference Example 14.

$^1$H NMR (CDCl$_3$, δ ppm): 3.87 (s, 3H), 6.32 (dd, J=0.8, 3.5 Hz, 1H), 6.34 (dd, J=1.9, 3.5 Hz, 1H), 6.96 (d, J=8.9 Hz, 2H), 7.37 (dd, J=0.8, 1.9 Hz, 1H), 7.43 (d, J=8.9 Hz, 2H), 7.48-7.57 (m, 2H), 7.58-7.66 (m, 1H), 7.90-7.97 (m, 2H), 9.61 (br s, 1H).

APCIMS m/z: [M+H]$^+$ 377.

m.p.:90-98° C.

Example 120

N-[4-(2-Furyl)-5-(3-methoxyphenyl)thiazol-2-yl]benzamide (Compound 120)

In a manner similar to that in Example 115, by using tributyl(3-methoxyphenyl)stannane (1.40 mL, 3.78 mmol) in place of tributyl(2-furyl)stannane, the entitled Compound 120 (245 mg, 52%) was obtained as a pale yellow solid from Compound n (500 mg, 1.26 mmol) obtained in Reference Example 14.

$^1$H NMR (CDCl$_3$, δ ppm): 3.82 (s, 3H), 6.31 (dd, J=1.6, 3.3 Hz, 1H), 6.36 (d, J=3.3 Hz, 1H), 6.95 (dd, J=2.5, 8.2 Hz, 1H), 7.05 (dd, J=2.5, 2.5 Hz, 1H), 7.10 (dd, J=2.5, 7.5 Hz, 1H), 7.32 (d, J=1.6 Hz, 1H), 7.34 (dd, J=7.5, 8.2 Hz, 1H), 7.45-7.54 (m, 2H), 7.56-7.63 (m, 1H), 7.89-7.95 (m, 2H), 8.74 (br s, 1H).

APCIMS m/z: [M+H]$^+$ 377.

Example 121

N-[4-(2-Furyl)-5-(2-methoxyphenyl)thiazol-2-yl]benzamide (Compound 121)

In a manner similar to that in Example 115, by using tributyl(2-methoxyphenyl)stannane (1.49 mL, 4.53 mmol) in place of tributyl(2-furyl)stannane, the entitled Compound 121 (181 mg, 33%) was obtained from Compound n (600 mg, 1.51 mmol) obtained in Reference Example 14.

$^1$H NMR (CDCl$_3$, δ ppm): 3.77 (s, 3H), 6.08 (d, J=3.3 Hz, 1H), 6.17 (dd, J=1.8, 3.3 Hz, 1H), 6.96-7.06 (m, 2H), 7.15 (d, J=1.8 Hz, 1H), 7.34-7.55 (m, 5H), 7.86-7.92 (m, 2H), 10.91 (br s, 1H).

APCIMS m/z: [M+H]$^+$ 377.

Example 122

N-[4-(2-Furyl)-5-(2-trifluoromethylphenyl)thiazol-2-yl]benzamide (Compound 122)

In a manner similar to that in Example 115, by using tributyl(2-trifluoromethylphenyl)stannane (1.41 mL, 3.78 mmol) in place of tributyl(2-furyl)stannane, the entitled Compound 122 (313 mg, 60%) was obtained as a pale yellow solid from Compound n (500 mg, 1.26 mmol) obtained in Reference Example 14.

$^1$H NMR (CDCl$_3$, δ ppm): 5.88 (dd, J=0.8, 3.2 Hz, 1H), 6.25 (dd, J=1.9, 3.2 Hz, 1H), 7.26 (dd, J=0.8, 1.9 Hz, 1H), 7.46-7.67 (m, 6H), 7.81-7.87 (m, 1H), 7.91-7.97 (m, 2H), 9.72 (br s, 1H).

m.p.: 205-206° C.

Example 123

N-[4-(2-Furyl)-5-(1-methyl-2-oxo-1,2-dihydropyridine-4-yl)thiazol-2-yl]pyridine-4-carboxamide (Compound 123)

Step 1:

Compound p (259 mg, 1.00 mmol) obtained in Reference Example 16 was suspended in methanol (4 mL), a 28% solution of sodium methoxide (385 mg, 2.00 mmol) in methanol was added thereto, followed by stirring for 30 minutes. Further, methyl iodide (0.185 mL, 3.00 mmol) was added to the reaction mixture, followed by stirring overnight, and the reaction mixture was concentrated under reduced pressure. The resulting residue was purified through silica gel column chromatography (chloroform:methanol=9:1) to afford 2-amino-4-(2-furyl)-5-(1-methyl-2-oxo-1,2-dihydropyridin-4-yl)thiazole (222 mg, 81%) as a yellow solid.

$^1$H NMR (DMSO-d$_6$, δ ppm): 3.39 (s, 3H), 6.02 (dd, J=2.1, 7.1 Hz, 1H), 6.24 (d, J=2.1 Hz, 1H), 6.56 (dd, J=1.7, 3.3 Hz), 6.63 (dd, J=0.8, 3.3 Hz, 1H), 7.42 (br s, 2H), 7.59 (d, J=7.1 Hz, 1H), 7.65 (dd, J=0.8, 1.7 Hz, 1H).

APCIMS m/z: [M+H]$^+$ 274.

Step 2:

2-Amino-4-(2-furyl)-5-(1-methyl-2-oxo-1,2-dihydropyridin-4-yl)thiazole (222 mg, 0.812 mmol) obtained in Step 1 was dissolved in DMF (4 mL), and isonicotinic acid (199 mg, 1.62 mmol), PyBOP (926 mg, 1.78 mmol) and triethylamine (0.497 mL, 3.56 mmol) were added thereto, followed by stirring at 80° C. for 1 hour. The reaction mixture was poured into water, and the precipitated solid was collected by filtration. The resulting solid was purified through silica gel column chromatography (chloroform:methanol=17:3), followed by reslurrying with methanol to afford the entitled Compound 123 (158 mg, 52%) as a pale yellow solid.

$^1$H NMR (DMSO-d$_6$, δ ppm): 3.46 (s, 3H), 6.21 (dd, J=1.6, 7.0 Hz, 1H), 6.46 (d, J=1.6 Hz, 1H), 6.62 (dd, J=1.9, 3.5 Hz, 1H), 6.77 (dd, J=0.8, 3.5 Hz, 1H), 7.74 (d, J=7.0 Hz, 1H), 7.74 (dd, J=0.8, 1.9 Hz, 1H), 8.01 (dd, J=1.6, 4.6 Hz, 2H), 8.82 (dd, J=1.6, 4.6 Hz, 2H), 13.35 (br s, 1H).

APCIMS m/z: [M+H]$^+$ 379.

m.p.: 280-282° C.

Example 124

N-[5-(1-Ethyl-2-oxo-1,2-dihydropyridin-4-yl)-4-(2-furyl)thiazol-2-yl]pyridine-4-carboxamide (Compound 124)

Step 1:

In a manner similar to that in Step 1 of Example 123, by using ethyl iodide in place of methyl iodide, 2-amino-5-(1-ethyl-2-oxo-1,2-dihydropyridin-4-yl)-4-(2-furyl)thiazole (0.185 mg, 3.00 mmol) was obtained from Compound p (259 mg, 1.00 mmol) obtained in Reference Example 16.

$^1$H NMR (DMSO-$d_6$, δ ppm): 1.21 (t, J=7.1 Hz, 3H), 3.67 (q, J=7.1 Hz, 2H), 6.04 (dd, J=2.0, 7.1 Hz, 1H), 6.24 (d, J=2.0 Hz, 1H), 6.56 (dd, J=1.8, 3.4 Hz, 1H), 6.63 (dd, J=0.9, 3.4 Hz, 1H), 7.43 (br s, 2H), 7.60 (d, J=7.1 Hz, 1H), 7.66 (dd, J=0.9, 1.8 Hz, 1H).

APCIMS m/z: [M+H]$^+$ 288.

Step 2:

2-Amino-5-(1-ethyl-2-oxo-1,2-dihydropyridin-4-yl)-4-(2-furyl)thiazole (167 mg, 0.582 mmol) obtained in Step 1 was dissolved in DMF (8 mL), and isonicotinic acid (143 mg, 1.16 mmol), PyBOP (664 mg, 1.28 mmol) and triethylamine (0.356 mL, 2.55 mmol) were added thereto, followed by stirring at 80° C. for 1 hour. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=17:1), followed by reslurrying with a mixed solvent of methanol and diethyl ether to afford the entitled Compound 124 (83.5 mg, 37%) as a pale brown solid.

$^1$H NMR (DMSO-$d_6$, δ ppm): 1.25 (t, J=7.0 Hz, 3H), 3.93 (q, J=7.0 Hz, 2H), 6.23 (dd, J=1.9, 7.0 Hz, 1H), 6.44 (d, J=1.9 Hz, 1H), 6.62 (dd, J=1.9, 3.2 Hz, 1H), 6.76 (dd, J=0.8, 3.2 Hz, 1H), 7.74 (d, J=7.0 Hz, 1H), 7.74 (dd, J=0.8, 1.9 Hz, 1H), 8.01 (dd, J=1.6, 4.3 Hz, 2H), 8.82 (dd, J=1.6, 4.3 Hz, 2H), 13.36 (br s, 1H).

APCIMS m/z: [M+H]$^+$ 393.

m.p.: 245-248° C.

Example 125

N-[5-(1-Benzyl-2-oxo-1,2-dihydropyridin-4-yl)-4-(2-furyl)thiazol-2-yl]pyridine-4-carboxamide (Compound 125)

Step 1:

In a manner similar to that in Step 1 of Example 123, by using benzyl bromide in place of methyl iodide, 2-amino-5-(1-benzyl-2-oxo-1,2-dihydropyridin-4-yl)-4-(2-furyl)thiazole (289 mg, 83%) was obtained from Compound p (259 mg, 1.00 mmol) obtained in Reference Example 16.

$^1$H NMR (DMSO-$d_6$, δ ppm): 5.02 (s, 2H), 6.07 (dd, J=2.1, 7.2 Hz, 1H), 6.28 (d, J=2.1 Hz, 1H), 6.56 (dd, J=1.8, 3.3 Hz, 1H), 6.64 (d, J=3.3 Hz, 1H), 7.25-7.39 (m, 5H), 7.46 (br s, 2H), 7.66 (d, J=1.8 Hz, 1H), 7.69 (d, J=7.2 Hz, 1H).

APCIMS m/z: [M+H]$^+$ 350.

Step 2:

In a manner similar to that in Step 2 of Example 124, the entitled Compound 125 (42.6 mg, 11%) was obtained as a pale brown solid from 2-amino-5-(1-benzyl-2-oxo-1,2-dihydropyridin-4-yl)-4-(2-furyl)thiazole (289 mg, 0.827 mmol) obtained in Step 1, in place of 2-amino-5-(1-ethyl-2-oxo-1,2-dihydropyridin-4-yl)-4-(2-furyl)thiazole.

$^1$H NMR (DMSO-$d_6$, δ ppm): 5.13 (s, 2H), 6.26 (dd, J=1.9, 7.0 Hz, 1H), 6.50 (d, J=1.9 Hz, 1H), 6.62 (dd, J=1.9, 3.2 Hz, 1H), 6.77 (dd, J=0.5, 3.2 Hz, 1H), 7.25-7.45 (m, 5H), 7.74 (dd, J=0.5, 1.9 Hz, 1H), 7.83 (d, J=7.0 Hz, 1H), 8.01 (dd, J=1.6, 5.9 Hz, 2H), 8.81 (dd, J=1.6, 5.9 Hz, 2H), 13.36 (br s, 1H).

APCIMS m/z: [M+H]$^+$ 455.

m.p.: 137-140° C.

Example 126

N-[4-(2-Furyl)-5-(1-methyl-2-oxo-1,2-dihydropyridin-5-yl)thiazol-2-yl]pyridine-4-carboxamide (Compound 126)

Step 1:

Compound q (259 mg, 1.00 mmol) obtained in Reference Example 17 and sodium methoxide (119 mg, 2.20 mmol) were suspended in methanol (6mL), followed by stirring at room temperature for 40 minutes. Further, methyl iodide (0.218 mL, 3.50 mmol) was added to the reaction mixture, followed by stirring overnight, and the reaction mixture was concentrated under reduced pressure. The resulting residue was purified through silica gel column chromatography (chloroform:methanol=4:1) to afford 2-amino-4-(2-furyl)-5-(1-methyl-2-oxo-1,2-dihydropyridin-5-yl)thiazole (203 mg, 74%) as a pale brown solid.

$^1$H NMR (DMSO-$d_6$, δ ppm): 3.44 (s, 3H), 6.38 (d, J=9.2 Hz, 1H), 6.48 (m, 2H), 7.15 (br s, 2H), 7.34 (dd, J=2.6, 9.2 Hz, 1H), 7.53-7.57 (m, 1H), 7.92 (d, J=2.6 Hz, 1H).

APCIMS m/z: [M+H]$^+$ 274.

Step 2:

2-Amino-4-(2-furyl)-5-(1-methyl-2-oxo-1,2-dihydropyridin-5-yl)thiazole (200 mg, 0.732 mmol) obtained in Step 1 was dissolved in DMF (4 mL), and isonicotinic acid (180 mg, 1.46 mmol), PyBOP (838 mg, 1.61 mmol) and triethylamine (0.449 mL, 3.21 mmol) were added thereto, followed by stirring at 80° C. for 1 hour. The reaction mixture was poured into water, and the precipitated solid was collected by filtration. The resulting solid was purified through silica gel column chromatography (chloroform:methanol=17:1), followed by reslurrying with methanol to afford the entitled Compound 111 (155 mg, 56%) as a pale yellow solid.

$^1$H NMR (DMSO-$d_6$, δ ppm): 3.49 (s, 3H), 6.46 (d, J=9.4 Hz, 1H), 6.57 (dd, J=1.9, 3.5 Hz, 1H), 6.66 (dd, J=0.8, 3.5 Hz, 1H), 7.44 (dd, J=2.7, 9.4 Hz, 1H), 7.67 (dd, J=0.8, 1.9 Hz, 1H), 8.00 (d, J=2.7 Hz, 1H), 8.01 (dd, J=1.6, 4.3 Hz, 2H), 8.20 (dd, J=1.6, 4.3 Hz, 2H), 13.22 (br s, 1H).

APCIMS m/z: [M+H]$^+$ 379.

m.p.: 294-295° C.

Example 127

N-[5-(1-Ethyl-2-oxo-1,2-dihydropyridin-5-yl)-4-(2-furyl)thiazol-2-yl]pyridine-4-carboxamide (Compound 127)

Step 1:

In a manner similar to that in Step 1 of Example 126, by using ethyl iodide in place of methyl iodide, 2-amino-5-(1-ethyl-2-oxo-1,2-dihydropyridin-5-yl)-4-(2-furyl)thiazole (287 mg, 100%) was obtained from Compound q (259 mg, 1.00 mmol) obtained in Reference Example 17.

¹H NMR (DMSO-d₆, δ ppm): 1.22 (t, J=7.1 Hz, 3H), 3.92 (q, J=7.1 Hz, 2H), 6.38 (d, J=9.4 Hz, 1H), 6.45-6.50 (m, 2H), 7.16 (br s, 2H), 7.34 (dd, J=2.6, 9.4 Hz, 1H) 7.53-7.57 (m, 1H), 7.82 (d, J=2.6 Hz, 1H).

APCIMS m/z: [M+H]⁺ 288.

Step 2:

2-Amino-5-(1-ethyl-2-oxo-1,2-dihydropyridin-5-yl)-4-(2-furyl)thiazole (287 mg, 1.00 mmol) obtained in Step 1 was dissolved in DMF (4 mL), and isonicotinic acid (246 mg, 2.00 mmol), PyBOP (1.14 g, 2.20 mmol) and triethylamine (0.613 mL, 4.40 mmol) were added thereto, followed by stirring at 80° C. for 1 hour. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=17:1), followed by reslurrying with a mixed solvent of methanol and diethyl ether to afford the entitled Compound 127 (99.0 mg, 25%) as a pale brown solid.

¹H NMR (DMSO-d₆, δ ppm): 1.26 (t, J=7.0 Hz, 3H), 3.97 (q, J=7.0 Hz, 2H), 6.45 (d, J=9.2 Hz, 1H), 6.58 (dd, J=1.6, 3.2 Hz, 1H), 6.66 (d, J=3.2 Hz, 1H), 7.45 (dd, J=2.7, 9.2 Hz, 1H), 7.68 (d, J=1.6 Hz, 1H), 8.00 (d, J=2.7 Hz, 1H), 8.04 (dd, J=1.6, 4.3 Hz, 2H), 8.84 (dd, J=1.6, 4.3 Hz, 2H), 13.24 (br s, 1H).

APCIMS m/z: [M+H]⁺ 393.

m.p.: 285-289° C.

Example 128

N-[5-(1-Benzyl-2-oxo-1,2-dihydropyridin-5-yl)-4-(2-furyl)thiazol-2-yl]pyridine-4-carboxamide (Compound 128)

Step 1:

In a manner similar to that in Step 1 of Example 126, by using benzyl bromide in place of methyl iodide, 2-amino-5-(1-benzyl-2-oxo-1,2-dihydropyridin-5-yl)-4-(2-furyl)thiazole (349 mg, 100%) was obtained from Compound q (259 mg, 1.00 mmol) obtained in Reference Example 17.

Step 2:

2-Amino-5-(1-benzyl-2-oxo-1,2-dihydropyridin-5-yl)-4-(2-furyl)thiazole (349 mg, 1.00 mmol) obtained in Step 1 was dissolved in DMF (4 mL), and isonicotinic acid (246 mg, 2.00 mmol), PyBOP (1.14 g, 2.20 mmol) and triethylamine (0.613 mL, 4.40 mmol) were added thereto, followed by stirring at 80° C. for 1 hour. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=17:1), followed by reslurrying with a mixed solvent of methanol and diethyl ether to afford the entitled Compound 128 (128 mg, 28%) as a pale brown solid.

¹H NMR (DMSO-d₆, δ ppm): 5.16 (s, 2H), 6.51 (d, J=9.2 Hz, 1H), 6.54 (dd, J=1.6, 3.5 Hz, 1H), 6.63 (dd, J=0.8, 3.5 Hz, 1H), 7.26-7.44 (m, 5H), 7.49 (dd, J=2.4, 9.2 Hz, 1H), 7.51 (dd, J=0.8, 1.9 Hz, 1H), 8.00 (dd, J=1.6, 4.6 Hz, 2H), 8.11 (d, J=2.4 Hz, 1H), 8.81 (dd, J=1.6, 4.6 Hz, 2H), 13.25 (br s, 1H).

APCIMS m/z: [M+H]⁺ 455.

m.p.: 215-218° C.

Example 129

N-[5-(1-Ethyl-6-oxo-1,6-dihydropyridin-2-yl)-4-(2-furyl)thiazol-2-yl]pyridine-4-carboxamide (Compound 129)

Compound r (660 mg, 2.30 mmol) obtained in Reference Example 18 was dissolved in DMF (8 mL), and isonicotinic acid (1.70 g, 13.8 mmol), EDC hydrochloride (2.64 g, 13.8 mmol) and 1-hydroxybenzotriazole monohydrate (2.11 g, 6.66 mmol) were added thereto, followed by stirring at 80° C. for 3 hours. The reaction mixture was poured into water, and the precipitated solid was collected by filtration. The resulting solid was purified through silica gel column chromatography (chloroform:methanol=19:1), followed by reslurrying with a mixed solvent of methanol and diethyl ether to afford the entitled Compound 129 (442 mg, 49%) as a pale brown solid.

¹H NMR (CDCl₃, δ ppm): 1.16 (t, J=6.5 Hz, 3H), 3.22 (q, J=6.5 Hz, 2H), 6.32 (dd, J=1.4, 6.8 Hz, 1H), 6.38-6.42 (m, 2H), 6.75 (dd, J=1.4, 9.2 Hz, 1H), 7.33-7.40 (m, 2H), 7.81 (dd, J=1.6, 4.6 Hz, 2H), 8.88 (dd, J=1.6, 4.6 Hz, 2H)

APCIMS m/z: [M+H]⁺ 393.

m.p.:>300° C.

Example 130

N-[5-(1-Ethyl-6-oxo-1,6-dihydropyridazin-3-yl)-4-(2-furyl)thiazol-2-yl]pyridine-4-carboxamide (Compound 130)

In a manner similar to that in Example 3, by using isonicotinic acid in place of methoxyacetic acid, the entitled Compound 130 (200 mg, 87%) was obtained from Compound s (186 mg, 0.588 mmol) obtained in Reference Example 19, in place of Compound a.

¹H NMR (CDCl₃, δ ppm): 1.43 (t, J=7.1 Hz, 3H), 4.27 (q, J=7.1 Hz, 2H), 6.40 (dd, J=1.8, 3.3 Hz, 1H), 6.63 (d, J=3.3 Hz, 1H), 6.91 (d, J=9.6 Hz, 1H), 7.34 (d, J=9.6 Hz, 1H), 7.35 (d, J=1.8 Hz, 1H), 7.77 (d, J=6.1 Hz, 2H), 8.80 (d, J=6.1 Hz, 2H).

APCIMS m/z: [M+H]⁺ 394.

m.p.: 235-239° C.

Example 131

N-[4-(2-Furyl)-5-(1-isopropyl-6-oxo-1,6-dihydropyridazin-3-yl)thiazol-2-yl]pyridine-4-carboxamide (Compound 131)

In a manner similar to that in Example 3, by using isonicotinic acid in place of methoxyacetic acid, the entitled Compound 131 (157 mg, 72%) was obtained from Compound t (162 mg, 0.539 mmol) obtained in Reference Example 20, in place of Compound a.

¹H NMR (DMSO-d₆, δ ppm): 1.32-1.34 (m, 6H), 5.17-5.22 (m, 1H), 6.66 (dd, J=1.8, 3.3 Hz, 1H), 6.85 (d, J=3.3 Hz, 1H), 6.96 (d, J=9.7 Hz, 1H), 7.45 (d, J=9.7 Hz, 1H), 7.78 (d, J=1.8 Hz, 1H), 8.03 (d, J=4.5 Hz, 2H), 8.85 (d, J=4.5 Hz, 2H), 13.3 (s, 1H).

APCIMS m/z: [M+H]⁺ 408.

m.p.: 190-194° C.

Example 132

Ethyl 2-(tert-butoxycarbonylamino)-4-(2-furyl)thiazole-5-carboxylate (Compound 132)

In a manner similar to that in Reference Example 8, the entitled Compound 132 (5.12 g, 74%) was obtained from Compound e (4.89 g, 20.5 mmol) obtained in Reference Example 5, in place of Compound g obtained in Reference Example 7.

$^1$H NMR (CDCl$_3$, δ ppm): 1.37 (t, J=7.0 Hz, 3H), 1.46 (s, 9H), 4.35 (q, J=7.0 Hz, 2H), 6.55 (dd, J=1.6, 3.5 Hz, 1H), 7.52 (dd, J=0.3, 1.6 Hz, 1H), 7.79 (dd, J=0.3, 3.5 Hz, 1H), 9.43 (br s, 1H).

ESIMS m/z: [M+H]$^+$ 339.

Example 133

2-(tert-Butoxycarbonylamino)-4-(2-furyl)thiazole-5-carboxylic acid (Compound 133)

In a manner similar to that in Example 95, the entitled Compound 133 (4.65 g, 99%) was obtained from Compound 132 (5.12 g, 15.1 mmol), in place of Compound 24.

$^1$H NMR (DMSO-d$_6$, δ ppm): 1.50 (s, 9H), 6.61 (dd, J=1.9, 3.2 Hz, 1H), 7.55 (dd, J=0.8, 3.2 Hz, 1H), 7.76 (dd, J=0.8, 1.9 Hz, 1H), 12.00 (br s, 1H).

APCIMS m/z: [M+H]$^+$ 311.

Example 134

2-(tert-Butoxycarbonylamino)-4-(2-furyl)-N-methoxy-N-methylthiazole-5-carboxamide (Compound 134)

In a manner similar to that in Example 96, by using N,O-dimethylhydroxyamine hydrochloride in place of morpholine, the entitled Compound 134 (2.59 g, 49%) was obtained from Compound 133 (4.65 g, 15.0 mmol), in place of Compound 95.

$^1$H NMR (CDCl$_3$, δ ppm): 1.46 (s, 9H), 3.34 (s, 3H), 3.67 (s, 3H), 6.47 (dd, J=1.6, 3.5 Hz, 1H), 7.04 (dd, J=0.8, 3.5 Hz, 1H), 7.47 (dd, J=0.8, 1.6 Hz, 1H), 9.23 (br s, 1H).

Example 135 tert-Butyl N-[5-benzoyl-4-(2-furyl)thiazol-2-yl]carbamate (Compound 135)

Compound 134 (10.7 g, 30.3 mmol) was dissolved in THF (240 ml), and a THF solution of 2.0 mol/L phenylmagnesium chloride (60.6 mL, 121 mmol) was added thereto at 0° C. in an atmosphere of argon, followed by stirring at room temperature for 2 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=3:1) to afford the entitled Compound 135 (6.18 g, 55%).

$^1$H NMR (CDCl$_3$, δ ppm): 1.49 (s, 9H), 6.38 (dd, J=1.8, 3.5 Hz, 1H), 7.10 (d, J=3.5 Hz, 1H), 7.27 (d, J=1.8 Hz, 1H), 7.36-7.53 (m, 3H), 7.76-7.78 (m, 2H).

Example 136

2-Amino-4-(2-furyl)thiazol-5-yl phenyl ketone (Compound 136)

Compound 135 (6.18 g, 16.7 mmol) was dissolved in trifluoroacetic acid (17 mL), followed by stirring at room temperature for 1 hour. The reaction mixture was concentrated under reduced pressure, ethyl acetate and a saturated aqueous solution of sodium hydrogencarbonate were added to the residue, and the organic layer was separated. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:4) to afford the entitled Compound 136 (4.39 g, 97%).

$^1$H NMR (DMSO-d$_6$, δ ppm): 6.40 (dd, J=1.8, 3.5 Hz, 1H), 6.80 (dd, J=0.7, 3.5 Hz, 1H), 7.30 (dd, J=0.7, 1.8 Hz, 1H), 7.31-7.37 (m, 2H), 7.44-7.55 (m, 3H), 8.00 (s, 2H).

Example 137

N-[5-Benzoyl-4-(2-furyl)thiazol-2-yl]-2-hydroxy-2-methylpropanamide (Compound 137)

Compound 136 (150 mg, 0.555 mmol) was dissolved in DMF (2.5 mL), and 2-hydroxy-2-methylpropanoic acid (116 mg, 1.11 mmol), EDC hydrochloride (313 mg, 1.11 mmol) and 1-hydroxybenzotriazole monohydrate (170 mg, 1.11 mmol) were added thereto, followed by stirring at 50° C. for 3 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 137 (158 mg, 80%).

$^1$H NMR (CDCl$_3$, δ ppm): 1.63 (s, 6H), 6.44 (dd, J=1.8, 3.5 Hz, 1H), 7.21 (dd, J=0.7, 3.5 Hz, 1H), 7.38 (dd, J=0.7, 1.8 Hz, 1H), 7.39-7.53 (m, 3H), 7.78-7.82 (m, 2H), 10.6 (s, 1H).

APCIMS m/z: [M+H]$^+$ 357.

m.p.: 153-154° C.

Example 138

N-[5-Benzoyl-4-(2-furyl)thiazol-2-yl]-1-hydroxycyclopropanecarboxamide (Compound 138)

In a manner similar to that in Example 137, by using 1-hydroxycyclopropanecarboxylic acid in place of 2-hydroxy-2-methylpropanoic acid, the entitled Compound 138 (151 mg, 77%) was obtained from Compound 136 (150 mg, 0.555 mmol).

$^1$H NMR (CDCl$_3$, δ ppm): 1.26-1.32 (m, 2H), 1.51-1.56 (m, 2H), 6.41 (dd, J=1.8, 3.5 Hz, 1H), 7.13 (dd, J=0.7, 3.5 Hz, 1H), 7.34 (dd, J=0.7, 1.8 Hz, 1H), 7.37-7.42 (m, 2H), 7.49-7.52 (m, 1H), 7.77-7.80 (m, 2H), 10.31 (s, 1H).

APCIMS m/z: [M+H]$^+$ 355.

m.p.: 202-205° C.

Example 139

N-[5-Benzoyl-4-(2-furyl)thiazol-2-yl]-3-(N,N-dimethylcarbamoyl)benzamide (Compound 139)

Step 1:

Methyl isophthalate (2.00 g, 11.1 mmol) was dissolved in THF (60 mL), and a 2.0 mol/L solution of dimethylamine (11.1 ml, 22.2 mmol) in methanol, EDC hydrochloride (4.27 g, 22.2 mmol) and 1-hydroxybenzotriazole monohydrate (3.40 g, 22.2 mmol) were added thereto, followed by stirring at room temperature for 2 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:3) to afford methyl 3-(N,N-dimethylcarbamoyl)benzoate (2.30 g, 100%).

Step 2:

Methyl 3-(N,N-dimethylcarbamoyl)benzoate (2.30 g, 11.1 mmol) obtained in Step 1 was dissolved in a mixed solvent (1:1) (50 mL) of methanol and water, and lithium hydroxide monohydrate (932 mg, 22.2 mmol) was added thereto, followed by stirring at room temperature for 1 hour. 3 mol/L hydrochloric acid was added to the reaction mixture to adjust the pH to 3, and the precipitated solid was collected by filtration to afford 3-(N,N-dimethylcarbamoyl)benzoic acid (2.12 g, 99%).

$^1$H NMR (DMSO-$d_6$, δ ppm): 2.89 (s, 3H), 2.97 (s, 3H), 7.36-7.37 (m, 2H), 7.89-7.95 (m, 2H).

Step 3:

In a manner similar to that in Example 137, by using 3-(N,N-dimethylcarbamoyl)benzoic acid obtained in Step 2 in place of 2-hydroxy-2-methylpropanoic acid, the entitled Compound 139 (138 mg, 46%) was obtained from Compound 136 (184 mg, 0.680 mmol).

$^1$H NMR (DMSO-$d_6$, δ ppm): 2.94 (s, 3H), 3.02 (s, 3H), 6.50 (dd, J=1.8, 3.5 Hz, 1H), 6.94 (dd, J=0.8, 3.5 Hz, 1H), 7.45-7.49 (m, 3H), 7.56-7.73 (m, 5H), 8.16-8.20 (m, 2H).

APCIMS m/z: [M+H]$^+$ 386.

m.p.: 222-224° C.

Example 140

2-Chloromethyl-N-[5-benzoyl-4-(2-furyl)thiazol-2-yl]pyridine-4-carboxamide (Compound 140)

In a manner similar to that in Example 137, by using 2-chloromethylisonicotinic acid obtained according to the method described in WO03/043636 in place of 2-hydroxy-2-methylpropanoic acid, the entitled Compound 140 (712 mg, 91%) was obtained from Compound 136 (500 mg, 1.85 mmol).

$^1$H NMR (CDCl$_3$, δ ppm): 4.69 (s, 2H), 6.22 (dd, J=1.7, 3.3 Hz, 1H), 6.97 (d, J=3.3 Hz, 1H), 7.12 (d, J=1.7 Hz, 1H), 7.39-7.64 (m, 4H), 7.81-7.85 (m, 3H), 8.66-8.68 (m, 1H).

Example 141

N-[5-Benzoyl-4-(2-furyl)thiazol-2-yl]-2-(dimethylaminomethyl)pyridine-4-carboxamide (Compound 141)

Compound 140 (100 mg, 0.236 mmol) was dissolved in a methanol solution (2 mL) of 2.0 mol/L dimethylamine, followed by stirring overnight. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford the entitled Compound 141 (42.0 mg, 41%).

$^1$H NMR (CDCl$_3$, δ ppm): 2.30 (s, 6H), 3.65 (s, 2H), 6.30 (dd, J=1.8, 3.3 Hz, 1H), 7.06 (d, J=3.3 Hz, 1H), 7.21 (d, J=1.8 Hz, 1H), 7.39-7.44 (m, 2H), 7.52-7.57 (m, 1H), 7.65 (dd, J=1.5, 5.0 Hz, 1H), 7.80 (d, J=1.5 Hz, 1H), 7.81-7.87 (m, 2H), 8.72 (d, J=5.0 Hz, 1H).

APCIMS m/z: [M+H]$^+$ 433.

m.p.: 205-209° C.

Example 142

N-[5-Benzoyl-4-(2-furyl)thiazol-2-yl]-2-[N-(2-dimethylaminoethyl)-N-methylaminomethyl]pyridine-4-carboxamide (Compound 142)

In a manner similar to that in Example 141, by using N,N,N'-trimethylethylenediamine in place of the 2.0 mol/L solution of dimethylamine in methanol, the entitled Compound 142 (90.7 mg, 46%) was obtained from Compound 140 (170 mg, 0.401 mmol).

$^1$H NMR (DMSO-$d_6$, δ ppm): 2.31 (s, 3H), 2.48 (s, 3H), 2.49 (s, 3H), 2.70 (t, J=6.2 Hz, 2H), 2.84 (t, J=6.2 Hz, 2H), 3.78 (s, 2H), 6.42 (dd, J=1.9, 3.2 Hz, 1H), 6.88 (dd, J=0.8, 3.2 Hz, 1H), 7.35-7.44 (m, 3H), 7.47-7.55 (m, 1H), 7.64-7.69 (m, 2H), 7.88 (dd, J=1.9, 5.1 Hz, 1H), 8.06 (m, 1H), 8.62 (dd, J=0.8, 5.1 Hz, 1H).

APCIMS m/z: [M+H]$^+$ 490.

Example 143

N-[5-Benzoyl-4-(2-furyl)thiazol-2-yl]-2-[N-(2-methoxyethyl)-N-methylaminomethyl]pyridine-4-carboxamide dihydrochloride (Compound 143)

In a manner similar to that in Example 141, by using N-(2-methoxyethyl)-N-methylethylenediamine in place of the 2.0 mol/L solution of dimethylamine in methanol, a free form of the entitled Compound was obtained from Compound 140 (170 mg, 0.401 mmol). The resulting free form was treated with 4 mol/L hydrogen chloride in ethyl acetate to afford the entitled Compound 143 (182 mg, 83%).

$^1$H NMR (DMSO-$d_6$, δ ppm): 2.87 (s, 3H), 3.31 (s, 3H), 3.41 (t, J=5.4 Hz, 2H), 3.77 (t, J=5.4 Hz, 2H), 4.59 (s, 2H), 6.48 (dd, J=1.6, 3.2 Hz, 1H), 6.89 (dd, J=0.8, 3.2 Hz 1H), 7.41-7.49 (m, 3H), 7.55-7.61 (m, 1H), 7.70-7.76 (m, 2H), 8.11 (dd, J=1.6, 5.1 Hz, 1H), 8.21 (d, J=1.6 Hz, 1H), 8.90 (d, J=5.1 Hz, 1H).

APCIMS m/z: [M+H]$^+$ 477.

Example 144

N-[5-Benzoyl-4-(2-furyl)thiazol-2-yl]-2-(morpholinomethyl)pyridine-4-carboxamide (Compound 144)

In a manner similar to that in Example 141, by using morpholine in place of the 2.0 mol/L solution of dimethylamine in methanol, the entitled Compound 144 (52.0 mg, 49%) was obtained from Compound 140 (100 mg, 0.236 mmol).

$^1$H NMR (CDCl$_3$, δ ppm): 2.52-2.53 (m, 4H), 3.71 (s, 2H), 3.72-3.75 (m, 4H), 6.29 (dd, J=1.8, 3.5 Hz, 1H), 7.04 (d, J=3.5 Hz, 1H), 7.21 (d, J=1.8 Hz, 1H), 7.39-7.45 (m, 2H), 7.53-7.58 (m, 1H), 7.62 (dd, J=1.8, 5.1 Hz, 1H), 7.80 (d, J=1.8 Hz, 1H), 7.83-7.87 (m, 2H), 8.72 (d, J=5.1 Hz, 1H).

APCIMS m/z: [M+H]$^+$ 475.

m.p.: 212-213° C.

Example 145

N-[5-Benzoyl-4-(2-furyl)thiazol-2-yl]-2-[N-(2-methoxyethyl)-N-methylamino]pyridine-4-carboxamide (Compound 145)

In a manner similar to that in Example 137, by using 2-[N-(2-methoxyethyl)-N-methylamino]pyridine-4-carboxylic acid in place of 2-hydroxy-2-methylpropanoic acid, the entitled Compound 145 (40.0 mg, 23%) was obtained from Compound 136 (100 mg, 0.370 mmol).

$^1$H NMR (DMSO-d$_6$, δ ppm): 3.13 (s, 3H), 3.35 (s, 3H), 3.59 (t, J=5.5 Hz, 2H), 3.79 (t, J=5.5 Hz, 2H), 6.35 (dd, J=1.8, 3.5 Hz, 1H), 6.89 (dd, J=1.3, 5.1 Hz, 1H), 7.01 (d, J=1.8 Hz, 1H), 7.07 (d, J=3.5 Hz, 1H), 7.38-7.43 (m, 2H), 7.51-7.56 (m, 1H), 7.79-7.82 (m, 2H), 8.06 (d, J=1.3 Hz, 1H), 8.26 (d, J=5.1 Hz, 1H), 10.70 (br s, 1H).

APCIMS m/z: [M+H]$^+$ 463.

m.p.: 145-147° C.

Example 146

N-[5-Benzoyl-4-(2-furyl)thiazol-2-yl]-2-piperidinopyridine-4-carboxamide (Compound 146)

In a manner similar to that in Example 137, by using 2-piperidinoisonicotinic acid in place of 2-hydroxy-2-methylpropanoic acid, the entitled Compound 146 (89.0 mg, 52%) was obtained from Compound 136 (100 mg, 0.370 mmol).

$^1$H NMR (DMSO-d$_6$, δ ppm): 1.55-1.64 (m, 6H), 3.61-3.65 (m, 4H), 6.51 (dd, J=1.8, 3.5 Hz, 1H), 6.96 (d, J=3.5 Hz, 1H), 7.12 (d, J=5.0 Hz, 1H), 7.43-7.51 (m, 4H), 7.58-7.63 (m, 1H), 7.72-7.74 (m, 2H), 8.27 (d, J=5.0 Hz, 1H), 13.38 (br s, 1H).

APCIMS m/z: [M+H]$^+$ 459.

m.p.: 195-198° C.

Example 147

2-Chloro-N-[5-benzoyl-4-(2-furyl)thiazol-2-yl]pyridine-5-carboxamide (Compound 147)

In a manner similar to that in Example 137, by using 6-chloronitocinic acid in place of 2-hydroxy-2-methylpropanoic acid, the entitled Compound 147 (583 mg, 77%) was obtained from Compound 136 (500 mg, 1.85 mmol).

$^1$H NMR (CDCl$_3$, δ ppm): 6.31 (dd, J=1.8, 3.3 Hz, 1H), 7.02 (d, J=3.3 Hz, 1H), 7.21 (d, J=1.8 Hz, 1H), 7.39-7.46 (m, 3H), 7.52-7.57 (m, 1H), 7.79-7.82 (m, 2H), 8.16 (dd, J=2.6, 8.1 Hz, 1H), 8.93 (d, J=2.6 Hz, 1H).

Example 148

N-[5-Benzoyl-4-(2-furyl)thiazol-2-yl]-2-morpholino-5-pyridinecarboxamide (Compound 148)

Compound 147 (100 mg, 0.244 mmol) was dissolved in morpholine (1 mL), followed by stirring at 80° C. for 1 hour. Water was added to the reaction system, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane: ethyl acetate=1:1) to afford the entitled Compound 148 (81.0 mg, 72%).

$^1$H NMR (CDCl$_3$, δ ppm): 3.67-3.70 (m, 4H), 3.80-3.83 (m, 4H), 6.37 (dd, J=1.8, 3.7 Hz, 1H), 6.62 (d, J=9.2 Hz, 1H), 7.14 (d, J=3.7 Hz, 1H), 7.30 (d, J=1.8 Hz, 1H), 7.38-7.43 (m, 2H), 7.51-7.56 (m, 1H), 7.80-7.83 (m, 2H), 7.97 (dd, J=2.6, 9.2 Hz, 1H), 8.73 (d, J=2.6 Hz, 1H), 10.02 (br s, 1H).

APCIMS m/z: [M+H]$^+$ 461.

Example 149

N-[5-Benzoyl-4-(2-furyl)thiazol-2-yl]-2-oxo-1,2-dihydropyridine-5-carboxamide (Compound 147)

In a manner similar to that in Example 137, by using 6-hydroxynicotinic acid in place of 2-hydroxy-2-methylpropanoic acid, the entitled Compound 149 (180 mg, 25%) was obtained from Compound 136 (500 mg, 1.85 mmol).

$^1$H NMR (DMSO-d$_6$, δ ppm): 6.41 (d, J=9.7 Hz, 1H), 6.48 (dd, J=1.8, 3.5 Hz, 1H), 6.93 (d, J=3.5 Hz, 1H), 7.41-7.46 (m, 3H), 7.55-7.60 (m, 1H), 7.68-7.70 (m, 2H), 8.02 (dd, J=2.8, 9.7 Hz, 1H), 8.44 (d, J=2.8 Hz, 1H).

APCIMS m/z: [M+H]$^+$ 392.

m.p.: >300° C.

Example 150

N-[5-Benzoyl-4-(2-furyl)thiazol-2-yl]-1-methyl-2-oxo-1,2-dihydropyridine-5-carboxamide (Compound 150)

Compound 149 (100 mg, 0.255 mmol) was dissolved in DMF (1.2 mL), and 55% sodium hydride (22.0 mg, 0.511 mmol) and methyl iodide (0.0159 mL, 0.255 mmol) were added thereto, followed by stirring at room temperature for 3 hours. Water was added to the reaction mixture, followed by extraction with chloroform. The organic layer was washed with a saturated aqueous solution of sodium chloride and dried over anhydrous magnesium sulfate, and then the solvent was distilled away under reduced pressure. The resulting residue was reslurried with diisopropyl ether to afford the entitled Compound 150 (71.0 mg, 68%).

$^1$H NMR (DMSO-d$_6$, δ ppm): 3.99 (s, 3H), 6.45 (dd, J=1.8, 3.5 Hz, 1H), 6.91 (d, J=3.5 Hz, 1H), 7.38-7.43 (m, 3H), 7.51-7.57 (m, 1H), 7.65-7.67 (m, 2H), 7.94 (d, J=5.0 Hz, 1H), 8.09 (s, 1H), 8.71 (d, J=5.0 Hz, 1H).

APCIMS m/z: [M+H]$^+$ 406.

m.p.: 220-225° C.

Example 151

N-[5-Benzoyl-4-(2-furyl)thiazol-2-yl]-1'-ethyl-2-oxo-1,2-dihydropyridine-5-carboxamide (Compound 151)

In a manner similar to that in Example 137, by using Compound u obtained in Reference Example 21 in place of 2-hydroxy-2-methylpropanoic acid, the entitled Compound 151 (70.0 mg, 45%) was obtained from Compound-136 (100 mg, 0.370 mmol).

$^1$H NMR (DMSO-d$_6$, δ ppm): 1.36 (t, J=7.1 Hz, 3H), 4.00 (q, J=7.1 Hz, 2H), 6.27 (dd, J=1.8, 3.3 Hz, 1H), 6.50 (d, J=9.5 Hz, 1H), 6.95 (d, J=3.3 Hz, 1H), 7.17 (d, J=1.8 Hz, 1H), 7.37-7.42 (m, 2H), 7.50-7.56 (m, 1H), 7.69 (dd, J=2.6, 9.5 Hz, 1H), 7.78-7.82 (m, 2H), 8.23 (d, J=2.6 Hz, 1H), 11.28 (br s, 1H).

APCIMS m/z: [M+H]$^+$ 420.

m.p.: 109-114° C.

Example 152

N-[5-Benzoyl-4-(2-furyl)thiazol-2-yl]-2-oxo-1-(pyridin-4-ylmethyl)-1,2-dihydropyridine-5-carboxamide (Compound 152)

In a manner similar to that in Example 137, by using Compound v obtained in Reference Example 22 in place of 2-hydroxy-2-methylpropanoic acid, the entitled Compound 152 (75.0 mg, 42%) was obtained from Compound 136 (100 mg, 0.370 mmol).

$^1$H NMR (DMSO-d$_6$, δ ppm): 5.22 (s, 2H), 6.49 (dd, J=1.8, 3.5 Hz, 1H), 6.55 (d, J=9.6 Hz, 1H), 6.92 (d, J=3.5 Hz, 1H), 7.28 (d, J=5.9 Hz, 2H), 7.41-7.47 (m, 3H), 7.56-7.61 (m, 1H), 7.68-7.72 (m, 2H), 8.10 (dd, J=2.5, 9.6 Hz, 1H), 8.54 (d, J=5.9 Hz, 2H), 8.91 (d, J=2.5 Hz, 1H), 13.01 (br s, 1H).

APCIMS m/z; [M+H]$^+$ 483.

m.p.: 270-275° C.

Example 153

N-[5-Benzoyl-4-(2-furyl)thiazol-2-yl]pyridazine-4-carboxamide (Compound 153)

In a manner similar to that in Example 137, by using pyridazine-4-carboxylic acid in place of 2-hydroxy-2-propanoic acid, the entitled Compound 153 (154 mg, 74%) was obtained from Compound 136 (150 mg, 0.555 mmol).

$^1$H NMR (DMSO-d$_6$, δ ppm): 6.49 (dd, J=1.8, 3.5 Hz, 1H), 6.94 (d, J=3.5 Hz, 1H), 7.41-7.47 (m, 3H), 7.56-7.59 (m, 1H), 7.69-7.72 (m, 2H), 8.22-8.25 (m, 1H), 9.51-9.53 (m, 1H), 9.71-9.73 (m, 1H).

APCIMS m/z: [M+H]$^+$ 377.

m.p.: 225-248° C.

Example 154 tert-Butyl N-[4-(2-furyl)-5-(2-methylbenzoyl)thiazol-2-yl]carbamate (Compound 154)

Step 1:

Phenol (2.00 g, 12.3 mmol) was dissolved in THF (40 mL), 55% sodium hydride (1.02 g, 23.4 mmol) was added thereto at 0° C., followed by stirring at 0° C. for 30 minutes.

A solution (10 mL) of 2-methylbenzoyl chloride (4.16 mL) in THF was added dropwise to the reaction mixture, followed by stirring overnight at room temperature. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=9:1) to afford phenyl 2-methylbenzoate (2.88 g, 64%).

$^1$H NMR (CDCl$_3$, δ ppm): 2.68 (s, 3H), 7.15-7.35 (m, 5H), 7.37-7.51 (m, 3H), 8.16 (dd, J=1.9, 5.1 Hz, 1H).

APCIMS m/z: [M+H]$^+$ 213.

Step 2:

Compound h (520 mg, 1.51 mmol) obtained in Reference Example 8 was dissolved in THF (4 mL), and a 1.58 mol/L solution of n-butyllithium in n-hexane (2.10 mL, 3.32 mmol) was added thereto in a stream of argon at −78° C., followed by stirring at −78° C. for 10 minutes. A solution (4 mL) of phenyl 2-methylbenzoate (960 mg, 4.52 mmol) in THF obtained in Step 1 was added dropwise to the reaction mixture, followed by stirring at room temperature for 1 hour. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=3:2) to afford the entitled Compound 154 (250 mg, 43%).

$^1$H NMR (CDCl$_3$, δ ppm): 1.48 (s, 9H), 2.42 (s, 3H), 6.45 (dd, J=1.6, 3.5 Hz, 1H), 7.13-7.40 (m, 5H), 7.50-7.55 (m, 1H), 8.86 (br s, 1H).

APCIMS m/z: [M+H]$^+$ 385.

Example 155

2-Amino-4-(2-furyl)thiazol-5-yl 2-methylphenyl ketone (Compound 155)

In a manner similar to that in Example 136, the entitled Compound 155 (132 mg, 30%) was obtained from Compound 154 (250 mg, 0.650 mmol) in place of Compound 135.

$^1$H NMR (DMSO-d$_6$, δ ppm): 2.37 (s, 3H), 6.40 (dd, J=1.6, 3.2 Hz, 1H), 7.05-7.30 (m, 4H), 7.39 (dd, J=0.5, 1.6 Hz, 1H), 8.05 (br s, 2H).

APCIMS m/z: [M+H]$^+$ 285.

Example 156

N-[4-(2-Furyl)-5-(2-methylbenzoyl)thiazol-2-yl]pyridine-4-carboxamide (Compound 156)

In a manner similar to that in Example 3, by using isonicotinic acid in place of methoxyacetic acid, followed by reslurrying with ethanol, the entitled Compound 156 (120 mg, 55%) was obtained as a pale brown solid from Compound 155 (160 mg, 0.561 mmol) in place of Compound a.

$^1$H NMR (DMSO-d$_6$, δ ppm): 2.31 (s, 3H), 6.52 (dd, J=1.9, 3.5 Hz, 1H), 6.95 (d, J=3.5 Hz, 1H), 7.30-7.45 (m, 2H), 7.51 (d, J=1.9 Hz, 1H), 7.52-7.55 (m, 2H), 8.02 (dd, J=1.6, 4.6 Hz, 2H), 8.83 (dd, J=1.6, 4.6 Hz, 2H), 13.58 (br s, 1H).

APCIMS m/z: [M+H]$^+$ 390.

Example 157 tert-Butyl N-[4-(2-furyl)-5-(3-methylbenzoyl)thiazol-2-yl]carbamate (Compound 157)

In a manner similar to that in Example 154, by using 3-methylbenzoyl chloride in place of 2-methylbenzoyl chloride, the entitled Compound 157 (180 mg, 31%) was obtained from Compound h (520 mg, 1.51 mmol) obtained in Reference Example 8.

$^1$H NMR (CDCl$_3$, δ ppm): 1.52 (s, 9H), 2.35 (s, 3H), 6.39 (dd, J=1.9, 3.5 Hz, 1H), 7.09 (d, J=3.5 Hz, 1H), 7.26-7.33 (m, 3H), 7.53-7.59 (m, 2H), 8.55 (br s, 1H).

APCIMS m/z: [M+H]$^+$ 385.

Example 158

2-Amino-4-(2-furyl)thiazol-5-yl 3-methylphenyl ketone (Compound 158)

In a manner similar to that in Example 136, the entitled Compound 158 (133 mg, 100%) was obtained from Compound 157 (180 mg, 0.468 mmol in place of Compound 135.

$^1$H NMR (DMSO-d$_6$, δ ppm): 2.25 (s, 3H), 6.41 (dd, J=1.6, 3.2 Hz, 1H), 6.80 (d, J=3.2 Hz, 1H), 7.18-7.36 (m, 6H), 7.98 (br s, 2H).

APCIMS m/z: [M+H]$^+$ 285.

Example 159

N-[4-(2-Furyl)-5-(3-methylbenzoyl)thiazol-2-yl] pyridine-4-carboxamide (Compound 159)

In a manner similar to that in Example 3, by using isonicotinic acid in place of methoxyacetic acid, followed by reslurrying with ethanol, the entitled Compound 159 (97.0 mg, 51%) was obtained as a pale yellow solid from Compound 158 (133 mg, 0.468 mmol) in place of Compound a.

$^1$H NMR (DMSO-d$_6$, δ ppm): 2.35 (s, 3H), 6.54 (dd, J=1.6, 3.5 Hz, 1H), 7.17-7.21 (m, 1H), 7.23 (dd, J=0.8, 3.5 Hz, 1H), 7.30-7.43 (m, 3H), 7.62 (dd, J=0.8, 1.6 Hz, 1H), 8.00 (dd, J=1.6, 4.6 Hz, 2H), 8.83 (dd, J=1.6, 4.6 Hz, 2H), 13.61 (br s, 1H).

APCIMS m/z: [M+H]$^+$ 390.

Example 160

N-[4-(2-Furyl)-5-(4-methylbenzoyl)thiazol-2-yl] pyridine-4-carboxamide (Compound 160)

In a manner similar to that in Example 99, by using a 1.0 mol/L solution of p-tolylmagnesium bromide in THF in place of phenylmagnesium bromide, followed by reslurrying with a mixed solvent of methanol and diethyl ether, the entitled Compound 160 (113 mg, 52%) was obtained as a pale yellow solid from Compound 98 (200 mg, 0.558 mmol).

$^1$H NMR (DMSO-d$_6$, δ ppm): 2.37 (s, 3H), 6.53 (dd, J=1.8, 3.3 Hz, 1H), 6.95 (d, J=3.3 Hz, 1H), 7.28 (d, J=8.1 Hz, 2H), 7.54 (d, J=1.8 Hz, 1H), 7.66 (d, J=8.1 Hz, 2H), 8.03 (dd, J=1.5, 4.5 Hz, 2H), 8.84 (dd, J=1.5, 4.5 Hz, 2H), 13.58 (br s, 1H).

APCIMS m/z: [M+H]$^+$ 390.

Example 161 tert-Butyl N-[4-(2-furyl)-5-(2-methoxybenzoyl)thiazol-2-yl]carbamate (Compound 161)

In a manner similar to that in Example 154, by using 2-methoxybenzoyl chloride in place of 2-methylbenzoyl chloride, the entitled Compound 161 (360 mg, 67%) was obtained from Compound h (520 mg, 1.51 mmol) obtained in Reference Example 8.

$^1$H NMR (CDCl$_3$, δ ppm): 1.48 (s, 9H), 3.74 (s, 3H), 6.45 (dd, J=1.9, 3.5 Hz, 1H), 6.83-6.92 (m, 1H), 6.97 (ddd, J=0.8, 7.3, 7.3 Hz, 1H), 7.35-7.37 (m, 1H), 7.39-7.43 (m, 2H), 7.54-7.57 (m, 1H), 8.78 (br s, 1H).

APCIMS m/z: [M+H]$^+$ 401.

Example 162

2-Amino-4-(2-furyl)thiazol-5-yl 2-methoxyphenyl ketone (Compound 162)

In a manner similar to that in Example 136, the entitled Compound 162 (223 mg, 73%) was obtained from Compound 161 (360 mg, 1.01 mmol) in place of Compound 135.

$^1$H NMR (DMSO-d$_6$, δ ppm): 3.64 (s, 3H), 6.42 (dd, J=1.6, 3.2 Hz, 1H), 6.88-7.04 (m, 3H), 7.19-7.23 (m, 1H), 7.30-7.40 (m, 1H), 7.41-7.43 (m, 1H), 7.97 (br s, 2H).

APCIMS m/z: [M+H]$^+$ 301.

Example 163

N-[4-(2-Furyl)-5-(2-methoxybenzoyl)thiazol-2-yl] pyridine-4-carboxamide (Compound 163)

In a manner similar to that in Example 3, by using isonicotinic acid in place of methoxyacetic acid, followed by reslurrying with ethanol, the entitled Compound 163 (220 mg, 73%) was obtained as a pale yellow solid from Compound 162 (223 mg, 0.741 mmol) in place of Compound a.

$^1$H NMR (DMSO-d$_6$, δ ppm): 3.67 (s, 3H), 6.56 (dd, J=1.6, 3.2 Hz, 1H), 7.03 (dd, J=7.5, 7.5 Hz, 1H), 7.09 (d, J=8.6 Hz 1H), 7.28 (dd, J=0.5, 3.2 Hz, 1H), 7.40 (dd, J=1.6, 7.5 Hz, 1H), 7.50 (ddd, J=1.6, 7.5, 8.6 Hz, 1H), 7.53 (dd, J=0.5, 1.6 Hz, 1H), 8.00 (dd, J=1.6, 4.3 Hz, 2H), 8.82 (dd, J=1.6, 4.3 Hz, 2H), 13.55 (br s, 1H).

APCIMS m/z: [M+H]$^+$ 406.

Example 164

N-[4-(2-Furyl)-5-(3-methoxybenzoyl)thiazol-2-yl] pyridine-4-carboxamide (Compound 164)

In a manner similar to that in Example 99, by using a 1.0 mol/L solution of m-methoxyphenylmagnesium bromide in THF in place of phenylmagnesium bromide, followed by reslurrying with a mixed solvent of ethanol and diethyl ether, the entitled Compound 164 (165 mg, 72%) was obtained as a pale brown solid from Compound 98 (200 mg, 0.558 mmol).

$^1$H NMR (DMSO-d$_6$, δ ppm): 3.75 (s, 3H), 6.53 (dd, J=1.6, 3.5 Hz, 1H), 6.97 (dd, J=0.5, 3.5 Hz, 1H), 7.17 (ddd, J=1.1, 2.7, 7.5 Hz, 1H), 7.22-7.32 (m, 2H), 7.30-7.40 (m, 1H), 7.52 (dd, J=0.5, 1.6 Hz, 1H), 8.03 (dd, J=1.6, 4.6 Hz, 2H), 8.84 (dd, J=1.6, 4.6 Hz, 2H), 13.59 (br s, 1H).

APCIMS m/z: [M+H]$^+$ 406.

Example 165

N-[4-(2-Furyl)-5-(4-methoxybenzoyl)thiazol-2-yl] pyridine-4-carboxamide (Compound 165)

In a manner similar to that in Example 99, by using a 0.5 mol/L solution of p-methoxyphenylmagnesium bromide in THF in place of phenylmagnesium bromide, followed by reslurrying with a mixed solvent of ethanol and diethyl ether, the entitled Compound 165 (121 mg, 53%) was obtained as a pale brown solid from Compound 98 (200 mg, 0.558 mmol).

¹H NMR (DMSO-d₆, δ ppm): 3.09 (s, 3H), 6.53 (dd, J=1.6, 3.5 Hz, 1H), 6.89 (dd, J=0.8, 3.5 Hz, 1H), 7.00 (dd, J=2.2, 8.9 Hz, 2H), 7.55 (dd, J=0.8, 1.6 Hz, 1H), 7.76 (dd, J=2.2, 8.9 Hz, 2H), 8.03 (dd, J=1.6, 4.6 Hz, 2H), 8.84 (dd, J=1.6, 4.6 Hz, 2H), 13.54 (br s, 1H).
APCIMS m/z: [M+H]⁺ 406.

Example 166 tert-Butyl N-[5-(2-fluorobenzoyl)-4-(2-furyl)thiazol-2-yl]carbamate (Compound 166)

In a manner similar to that in Example 154, by using 2-fluorobenzoyl chloride in place of 2-methylbenzoyl chloride, the entitled Compound 166 (360 mg, 62%) was obtained from Compound h (520 mg, 1.51 mmol) obtained in Reference Example 8.
¹H NMR (CDCl₃, δ ppm): 1.51 (s, 9H), 6.43 (dd, J=1.6, 3.5 Hz, 1H), 7.06 (ddd, J=1.1, 8.7, 9.5 Hz, 1H), 7.18 (ddd, J=1.1, 7.6, 7.6 Hz, 1H), 7.35 (d, J=3.5 Hz, 1H), 7.39-7.48 (m, 2H), 7.53 (ddd, J=1.6, 7.6, 7.6 Hz, 1H), 8.56 (br s, 1H).
APCIMS m/z: [M+H]⁺ 389.

Example 167

2-Amino-4-(2-furyl)thiazol-5-yl 2-fluorophenyl ketone (Compound 167)

In a manner similar to that in Example 136, the entitled Compound 167 (190 mg, 92%) was obtained from Compound 166 (280 mg, 0.722 mmol) in place of Compound 135.
¹H NMR (DMSO-d₆, δ ppm): 6.40 (dd, J=1.9, 3.5 Hz, 1H), 6.88 (dd, J=0.8, 3.5 Hz, 1H), 7.14 (d, J=8.1 Hz, 1H), 7.18 (dd, J=3.0, 3.8 Hz, 1H), 7.34 (dd, J=0.8, 1.9 Hz, 1H), 7.36-7.49 (m, 2H), 8.17 (br s, 2H).
APCIMS m/z: [M+H]⁺ 289.

Example 168

N-[5-(2-Fluorobenzoyl)-4-(2-furyl)thiazol-2-yl]pyridine-4-carboxamide (Compound 168)

In a manner similar to that in Example 3, by using isonicotinic acid in place of methoxyacetic acid, followed by reslurrying with diethyl ether, the entitled Compound 168 (207 mg, 80%) was obtained as a pale brown solid from Compound 167 (190 mg, 0.659 mmol) in place of Compound a.
¹H NMR (DMSO-d₆, δ ppm): 6.46 (dd, J=1.9, 3.2 Hz, 1H), 7.15-7.25 (m, 3H), 7.36-7.46 (m, 2H), 7.49 (dd, J=0.8, 1.9 Hz, 1H), 7.96 (d, J=5.4 Hz, 2H), 8.63 (d, J=5.4 Hz, 2H).
APCIMS m/z: [M+H]⁺ 394

Example 169

N-[5-(3-Fluorobenzoyl)-4-(2-furyl)thiazol-2-yl]pyridine-4-carboxamide (Compound 169)

In a manner similar to that in Example 99, by using a 0.5 mol/L solution of m-fluorophenylmagnesium bromide in THF in place of phenylmagnesium bromide, followed by reslurrying with diethyl ether, the entitled Compound 169 (70.0 mg, 32%) was obtained as a pale yellow solid from Compound 98 (200 mg, 0.558 mmol).
¹H NMR (DMSO-d₆, δ ppm): 6.53 (dd, J=1.8, 3.6 Hz, 1H), 6.97 (d, J=3.6 Hz, 1H), 7.40-7.55 (m, 5H), 8.03 (dd, J=1.5, 4.2 Hz, 2H), 8.84 (dd, J=1.5, 4.2 Hz, 2H), 13.64 (br s, 1H).
ESIMS m/z: [M+H]⁺ 394.

Example 170

N-[5-(4-Fluorobenzoyl)-4-(2-furyl)thiazol-2-yl]pyridine-4-carboxamide (Compound 170)

In a manner similar to that in Example 99, by using a 1.0 mol/L solution of p-fluorophenylmagnesium bromide in THF in place of phenylmagnesium bromide, followed by reslurrying with a mixed solvent of ethanol and diethyl ether, the entitled Compound 170 (132 mg, 60%) was obtained as a yellow solid from Compound 98 (200 mg, 0.558 mmol).
¹H NMR (DMSO-d₆, δ ppm): 6.53 (dd, J=1.6, 3.5 Hz, 1H), 6.92 (dd, J=0.8, 3.5 Hz, 1H), 7.28 (ddd, J=1.9, 8.9, 8.9 Hz, 2H), 7.51 (dd, J=0.8, 1.6 Hz, 1H), 7.81 (ddd, J=1.9, 5.4, 8.9 Hz, 2H), 8.03 (dd, J=1.9, 4.6 Hz, 2H), 8.84 (dd, J=1.9, 4.6 Hz, 2H), 13.60 (br s, 1H).
ESIMS m/z: [M+H]⁺ 394.

Example 171 tert-Butyl N-[5-(2-chlorobenzoyl)-4-(2-furyl)thiazol-2-yl]carbamate (Compound 171)

In a manner similar to that in Example 154, by using 2-chlorobenzoyl chloride in place of 2-methylbenzoyl chloride, the entitled Compound 166 (290 mg, 48%) was obtained from Compound h (520 mg, 1.51 mmol) obtained in Reference Example 8.
¹H NMR (CDCl₃, δ ppm): 1.48 (s, 9H), 6.48 (dd, J=1.6, 3.2 Hz, 1H), 7.20-7.42 (m, 6H), 7.68 (d, J=1.6 Hz, 1H), 8.87 (br s, 1H).
APCIMS m/z: [³⁵ClM+H]⁺ 405, [³⁷ClM+H]⁺ 407.

Example 172

2-Amino-4-(2-furyl)thiazol-5-yl, 2-chlorophenyl ketone (Compound 172)

In a manner similar to that in Example 136, the entitled Compound 172 (161 mg, 73%) was obtained from Compound 171 (290 mg, 0.716 mmol) in place of Compound 135.
¹H NMR (DMSO-d₆, δ ppm): 6.42 (dd, J=1.6, 3.2 Hz, 1H), 7.03 (d, J=3.2 Hz, 1H), 7.26-7.47 (m, 5H), 8.19 (br s, 2H).
APCIMS m/z: [³⁵ClM+H]⁺ 305, [³⁷ClM+H]⁺ 307.

Example 173

N-[5-(2-Chlorobenzoyl)-4-(2-furyl)thiazol-2-yl]pyridine-4-carboxamide (Compound 173)

In a manner similar to that in Example 3, by using isonicotinic acid in place of methoxyacetic acid, followed by reslurrying with a mixed solvent of ethanol and diethyl ether, the entitled Compound 173 (110 mg, 50%) was obtained as a pale brown solid from Compound 172 (161 mg, 0.529 mmol) in place of Compound a.
¹H NMR (DMSO-d₆, δ ppm): 6.58 (dd, J=1.6, 3.5 Hz, 1H), 7.36 (dd, J=0.8, 3.5 Hz, 1H), 7.42 (ddd, J=3.2, 6.5, 7.8 Hz, 1H), 7.51-7.59 (m, 3H), 7.65 (dd, J=0.8, 1.6 Hz, 1H), 8.00 (dd, J=1.6, 4.6 Hz, 2H), 8.83 (dd, J=1.6, 4.6 Hz, 2H), 13.69 (br s, 1H)
APCIMS m/z: [³⁵ClM+H]⁺ 410, [³⁷ClM+H]⁺ 412. .

Example 174

N-[5-(3-Chlorobenzoyl)-4-(2-furyl)thiazol-2-yl]pyridine-4-carboxamide (Compound 174)

In a manner similar to that in Example 99, by using a 0.5 mol/L solution of m-chlorophenylmagnesium bromide in THF in place of phenylmagnesium bromide, followed by reslurrying with a mixed solvent of ethanol and diethyl ether, the entitled Compound 174 (124 mg, 54%) was obtained as a yellow solid from Compound 98 (200 mg, 0.558 mmol).

$^1$H NMR (DMSO-$d_6$, δ ppm): 6.53 (dd, J=1.6, 3.5 Hz, 1H), 6.98 (d, J=3.5 Hz 1H), 7.44-7.51 (m, 2H), 7.63 (d, J=1.6 Hz, 1H), 7.65-7.69 (m, 2H), 8.03 (dd, J=1.6, 4.6 Hz, 2H), 8.84 (dd, J=1.6, 4.6 Hz, 2H), 13.63 (br s, 1H)

ESIMS m/z: [$^{35}$ClM+H]$^+$ 410, [$^{37}$ClM+H]$^+$ 412.

Example 175

N-[5-(4-Chlorobenzoyl)-4-(2-furyl)thiazol-2-yl]pyridine-4-carboxamide (Compound 175)

In a manner similar to that in Example 99, by using a 1.0 mol/L solution of p-chlorophenylmagnesium bromide in THF in place of phenylmagnesium bromide, followed by reslurrying with a mixed solvent of ethanol and diethyl ether, the entitled Compound 175 (141 mg, 61%) was obtained as a yellow solid from Compound 98 (200 mg, 0.558 mmol).

$^1$H NMR (DMSO-$d_6$, δ ppm): 6.54 (dd, J=1.8, 3.6 Hz, 1H), 6.95 (d, J=3.6 Hz, 1H), 7.52 (d, J=1.8 Hz, 1H), 7.52 (d, J=8.4 Hz, 2H), 7.73 (d, J=8.4 Hz, 2H), 8.03 (d, J=6.0 Hz, 2H), 8.84 (d, J=6.0 Hz, 2H), 13.63 (br s, 1H).

ESIMS m/z: [$^{35}$ClM−H]$^-$ 408, [$^{37}$ClM−H]$^-$ 410.

Example 176 tert-Butyl N-[5-(2-cyanobenzoyl)-4-(2-furyl)thiazol-2-yl]carbamate (Compound 176)

Step 1:

2-Cyanobenzoic acid (1.00 g, 6.80 mmol), phenol (576 mg, 6.12 mmol) and PyBOP (3.90 g, 7.48 mmol) were dissolved in DMF (12 mL), and triethylamine (2.10 mL, 15.0 mmol) was added thereto, followed by stirring at room temperature for 4 hours. The reaction mixture was poured into water, followed by extraction with ethyl acetate. The organic layer was washed successively with a saturated aqueous solution of sodium hydrogencarbonate and a saturated aqueous solution of sodium chloride and dried over anhydrous magnesium sulfate, and then the solvent was distilled away under reduced pressure. The resulting residue was purified through silica gel column chromatography (hexane:ethyl acetate=3:2) to afford phenyl 2-cyanobenzoate (1.24 g, 82%).

$^1$H NMR (DMSO-$d_6$, δ ppm): 7.31-7.39 (m, 3H), 7.41-7.55 (m, 2H), 7.90-7.97 (m, 2H), 8.08-8.14 (m, 1H), 8.33-8.38 (m, 1H).

ESIMS m/z: [M+H]$^+$ 224.

Step 2:

Compound h (520 mg, 1.51 mmol) obtained in Reference Example 8 was dissolved in THF (4 mL), a 1.58 mol/L solution of n-butyllithium in n-hexane (2.10 mL, 3.32 mmol) was added thereto in a stream of argon at −78° C., followed by stirring at −78° C. for 10 minutes. A solution (4 ml) of phenyl 2-cyanobenzoate (1.00 g, 4.52 mmol) in THF obtained in Step 1 was added dropwise to the reaction mixture, followed by stirring at room temperature for 1 hour. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=3:2) to afford the entitled Compound 176 (355 mg, 60%).

$^1$H NMR (CDCl$_3$, δ ppm): 1.52 (s, 9H), 6.39 (dd, J=1.9, 3.5 Hz, 1H), 7.19-7.22 (m, 1H), 7.26-7.28 (m, 1H), 7.50-7.65 (m, 3H), 7.67-7.75 (m, 1H), 8.54 (br s, 1H).

APCIMS m/z: [M+H]$^+$ 396.

Example 177

2-Amino-4-(2-furyl)thiazol-5-yl 2-cyanophenyl ketone (Compound 177)

In a manner similar to that in Example 136, the entitled Compound 177 (157 mg, 59%) was obtained from Compound 176 (355 mg, 0.900 mmol) in place of Compound 135.

$^1$H NMR (DMSO-$d_6$, δ ppm): 6.38 (dd, J=1.9, 3.5 Hz, 1H), 6.80 (dd, J=0.8, 3.5 Hz, 1H), 7.22 (dd, J=0.8, 1.9 Hz, 1H), 7.47-7.52 (m, 1H), 7.55-7.60 (m, 2H), 7.83-7.88 (m, 1H), 8.29 (br s, 2H).

APCIMS m/z: [M+H]$^+$ 296.

Example 178

N-[5-(2-Cyanobenzoyl)-4-(2-furyl)thiazol-2-yl]pyridine-4-carboxamide (Compound 178)

In a manner similar to that in Example 3, by using isonicotinic acid in place of methoxyacetic acid, followed by reslurrying with methanol, the entitled Compound 178 (90.6 mg, 43%) was obtained as a yellow solid from Compound 177 (157 mg, 0.532 mmol) in place of Compound a.

$^1$H NMR (DMSO-$d_6$, δ ppm): 6.50 (dd, J=1.6, 3.5 Hz, 1H), 7.04 (dd, J=0.8, 3.5 Hz, 1H), 7.45 (dd, J=0.8, 1.6 Hz, 1H), 7.67-7.73 (m, 3H), 7.95-8.00 (m, 1H), 8.03 (dd, J=1.6, 4.3 Hz, 2H), 8.84 (dd, J=1.6, 4.3 Hz, 2H), 13.70 (br s, 1H).

APCIMS m/z: [M+H]$^+$ 401.

Example 179 tert-Butyl N-[5-(3-cyanobenzoyl)-4-(2-furyl)thiazol-2-yl]carbamate (Compound 179)

In a manner similar to that in Example 176, by using 3-cyanobenzoic acid in place of 2-cyanobenzoic acid, the entitled Compound 179 (290 mg, 48%) was obtained from Compound h (520 mg, 1.51 mmol) obtained in Reference Example 8.

$^1$H NMR (CDCl$_3$, δ ppm): 1.54 (s, 9H), 6.40 (dd, J=1.9, 3.5 Hz, 1H), 7.05 (d, J=3.5 Hz, 1H), 7.18 (d, J=1.9 Hz, 1H), 7.50 (dd, J=7.8, 7.8 Hz, 1H), 7.75 (ddd, J=1.3, 1.3, 7.8 Hz, 1H), 7.94 (ddd, J=1.3, 1.3, 7.8 Hz, 1H), 7.95-7.99 (m, 1H), 8.51 (br s, 1H).

APCIMS m/z: [M+H]$^+$ 396.

Example 180

2-Amino-4-(2-furyl)thiazol-5-yl 3-cyanophenyl ketone (Compound 180)

In a manner similar to that in Example 136, the entitled Compound 180 (155 mg, 72%) was obtained from Compound 179 (290 mg, 0.733 mmol) in place of Compound 135.

$^1$H NMR (DMSO-$d_6$, δ ppm): 6.41 (dd, J=1.9, 3.5 Hz, 1H), 6.78 (dd, J=0.8, 3.5 Hz, 1H), 7.27 (dd, J=0.8, 1.9 Hz, 1H), 7.54 (dd, J=7.8, 7.8 Hz, 1H), 7.79 (ddd, J=1.3, 1.3, 7.8 Hz, 1H), 7.85 (dd, J=1.3, 1.3 Hz, 1H), 7.89 (ddd, J=1.3, 1.3, 7.8 Hz, 1H), 8.17 (br s, 2H).

APCIMS m/z: [M+H]$^+$ 296.

Example 181

N-[5-(3-Cyanobenzoyl)-4-(2-furyl)thiazol-2-yl]pyridine-4-carboxamide (Compound 181)

In a manner similar to that in Example 3, by using isonicotinic acid in place of methoxyacetic acid, followed by reslurrying with a mixed solvent of ethanol and diethyl ether, the entitled Compound 181 (110 mg, 50%) was obtained as a pale brown solid from Compound 180 (161 mg, 0.529 mmol) in place of Compound a.

$^1$H NMR (DMSO-$d_6$, δ ppm): 6.51 (dd, J=1.9, 3.5 Hz, 1H), 6.96 (d, J=3.5 Hz, 1H), 7.46 (d, J=1.9 Hz, 1H), 7.65 (dd, J=7.8, 7.8 Hz, 1H), 7.96-8.08 (m, 5H), 8.84 (d, J=5.9 Hz, 2H), 13.66 (br s, 1H).

APCIMS m/z: [M+H]$^+$ 401.

Example 182 tert-Butyl N-[5-(4-cyanobenzoyl)-4-(2-furyl)thiazol-2-yl]carbamate (Compound 182)

In a manner similar to that in Example 176, by using 4-cyanobenzoic acid in place of 2-cyanobenzoic acid, the entitled Compound 182 (321 mg, 54. %) was obtained from Compound h (520 mg, 1.51 mmol) obtained in Reference Example 8.

$^1$H NMR (CDCl$_3$, δ ppm): 1.51 (s, 9H), 6.39 (dd, J=1.9, 3.5 Hz, 1H), 7.07 (d, J=3.5, Hz, 1H), 7.17 (d, J=1.9 Hz, 1H), 7.65 (dd, J=1.9, 8.6 Hz, 2H), 7.79 (dd, J=1.9, 8.6 Hz, 2H), 8.79 (br s, 1H).

APCIMS m/z: [M+H]$^+$ 396.

Example 183

2-Amino-4-(2-furyl)thiazol-5-yl 4-cyanophenyl ketone (Compound 183)

In a manner similar to that in Example 136, the entitled Compound 183 (161 mg, 73%) was obtained from Compound 182 (290 mg, 0.716 mmol) in place of Compound 135.

$^1$H NMR (DMSO-$d_6$, δ ppm): 6.41 (dd, J=1.6, 3.2 Hz, 1H), 6.90 (dd, J=0.5, 3.2 Hz, 1H), 7.27 (dd, J=0.5, 1.6 Hz, 1H), 7.62 (dd, J=1.9, 8.1 Hz, 2H), 7.78 (dd, J=1.9, 8.1 Hz, 2H), 8.18 (br s, 2H).

APCIMS m/z: [M+H]$^+$ 296.

Example 184

N-[5-(4-Cyanobenzoyl)-4-(2-furyl)thiazol-2-yl]pyridine-4-carboxamide (Compound 184)

In a manner similar to that in Example 3, by using isonicotinic acid in place of methoxyacetic acid, followed by reslurrying with a mixed solvent of ethanol and diethyl ether, the entitled Compound 181 (130 mg, 77%) was obtained from Compound 183 (129 mg, 0.438 mmol) in place of Compound a.

$^1$H NMR (DMSO-$d_6$, δ ppm): 6.52 (dd, J=1.9, 3.5 Hz, 1H), 6.98 (dd, J=0.8, 3.5 Hz, 1H), 7.46 (dd, J=0.8, 1.9 Hz, 1H), 7.82 (dd, J=2.2, 8.6 Hz, 2H), 7.91 (dd, J=2.2, 8.6 Hz, 2H), 8.03 (dd, J=1.9, 4.6 Hz, 2H), 8.84 (dd, J=1.9, 4.6 Hz, 2H), 13.67 (br s, 1H).

ESIMS m/z: [M+H]$^+$ 401.

Example 185 tert-Butyl N-[4-(2-furyl)-5-(pyridin-2-ylcarbonyl)thiazol-2-yl]carbamate (Compound 185)

Step 1:

Picolinic acid (1.00 g, 8.12 mmol) was dissolved in DMF (40 mL), and N,O-dimethylhydroxylamine hydrochloride (1.58 g, 16.2 mmol), EDC hydrochloride (3.12 g, 16.2 mmol), 1-hydroxybenzotriazole monohydrate (2.48 mg, 16.2 mmol) and triethylamine (2.25 ml, 16.2 mmol) were added thereto, followed by stirring at 50° C. for 3 hours. A saturated aqueous solution of sodium hydrogencarbonate was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:4) to afford N-methoxy-N-methylpyridine-2-carboxamide (988 mg, 73%).

$^1$H NMR (CDCl$_3$, δ ppm): 3.39 (s, 3H), 3.73 (s, 3H), 7.32-7.37 (m, 1H), 7.60-7.68 (m, 1H), 7.73-7.80 (m, 1H), 8.59-8.61 (m, 1H).

Step 2:

Compound h (500 mg, 1.45 mmol) obtained in Reference Example 8 was dissolved in THF (7.5 mL), and a 1.58 mol/L solution of n-butyllithium in n-hexane (2.02 mL, 3.19 mmol) was added thereto in a stream of argon at −78° C., and the reaction mixture was stirred at −78° C. for 15 minutes. N-methoxy-N-methyl-2-pyridinecarboxamide (723 mg, 4.35 mmol) obtained in Step 1 was added to the reaction mixture, followed by stirring at room temperature for 1.5 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 185 (286 mg, 53%).

$^1$H NMR (CDCl$_3$, δ ppm): 1.46 (s, 9H), 6.53 (dd, J=1.8, 3.7 Hz, 1H), 7.43-7.47 (m, 1H), 7.48 (d, J=1.8 Hz, 1H), 7.84 (d, J=3.7 Hz, 1H), 7.84-7.89 (m, 1H), 8.14-8.17 (m, 1H), 8.70-8.71 (m, 1H).

Example 186

2-Amino-4-(2-furyl)thiazol-5-yl 2-pyridyl ketone (Compound 186)

Compound 185 (286 mg, 0.770 mmol) was dissolved in trifluoroacetic acid (2 mL), followed by stirring at room temperature for 1 hour. The reaction mixture was concentrated under reduced pressure, and ethyl acetate and a saturated aqueous solution of sodium hydrogencarbonate were added to the resulting residue, and the organic layer was separated. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:4) to afford the entitled Compound 186 (208 mg, 99%).

$^1$H NMR (CDCl$_3$, δ ppm): 6.03 (br s, 2H), 6.53 (dd, J=1.8, 3.5 Hz, 1H), 7.43-7.46 (m, 1H), 7.51 (d, J=1.8 Hz, 1H), 7.86-7.89 (m, 1H), 7.95 (d, J=3.5 Hz, 1H), 8.14-8.17 (m, 1H), 8.60-8.61 (m, 1H).

Example 187

N-[4-(2-Furyl)-5-(pyridin-2-ylcarbonyl)thiazol-2-yl]pyridine-4-carboxamide (Compound 187)

Compound 186 (209 mg, 0.770 mmol) was dissolved in DMF (4 mL), and isonicotinic acid (190 mg, 1.54 mmol), EDC hydrochloride (296 mg, 1.54 mmol) and 1-hydroxybenzotriazole monohydrate (236 mg, 1.54 mmol) were added thereto, followed by stirring at 50° C. for 3 hours. Water was added to the reaction mixture, and the precipitated solid was collected by filtration, followed by reslurrying with ethanol to afford the entitled Compound 187 (211 mg, 72%) as a yellow solid.

$^1$H NMR (DMSO-d$_6$, δ ppm): 6.65 (dd, J=1.7, 3.5 Hz, 1H), 7.47 (d, J=3.5 Hz, 1H), 7.67-7.71 (m, 1H), 7.73 (d, J=1.7 Hz, 1H), 8.05 (d, J=6.1 Hz, 2H), 8.09-8.11 (m, 2H), 8.71-8.74 (m, 1H), 8.84 (d, J=6.1 Hz, 2H), 13.5 (br s, 1H).

APCIMS m/z: [M+H]$^+$ 377.

m.p.: 218-227° C.

Example 188

N-[4-(2-Furyl)-5-(pyridin-2-ylcarbonyl)thiazol-2-yl]acetamide (Compound 188)

Compound 186 (300 mg, 1.11 mmol) was dissolved in pyridine (3.7 mL), and acetyl chloride (0.130 mL, 1.89 mmol) and N,N-dimethylaminopyridine (6.75 mg, 0.0553 mmol) were added thereto, followed by stirring at room temperature for 3 hours. The reaction mixture was concentrated under reduced pressure, and the resulting residue was purified through silica gel column chromatography (hexane:ethyl acetate=2:1) to afford the entitled Compound 188 (233 mg, 67%) as a pale yellow solid.

$^1$H NMR (CDCl$_3$, δ ppm): 2.20 (s, 3H), 6.57 (dd, J=1.8, 3.6 Hz, 1H), 7.49 (dd, J=7.2, 11.3 Hz, 1H), 7.54 (d, J=1.8 Hz, 1H), 7.85 (d, J=3.6 Hz, 1H), 7.90 (dd, J=11.3, 11.5 Hz, 1H), 8.19 (d, J=11.5 Hz, 1H), 8.74 (d, J=7.2 Hz, 1H), 9.72 (br s, 1H).

APCIMS m/z: [M+H]$^+$ 314.

m.p.: 216-217° C.

Example 189

N-[4-(2-Furyl)-5-(pyridin-2-ylcarbonyl)thiazol-2-yl]butanamide (Compound 189)

In a manner similar to that in Example 188, by using butyryl chloride (0.200 mL, 1.89 mmol) in place of acetyl chloride, the entitled Compound 189 (297 mg, 78%) was obtained from Compound 186 (288 mg, 1.11 mmol) as a pale yellow solid.

$^1$H NMR (CDCl$_3$, δ ppm): 0.98 (t, J=7.3 Hz, 3H), 1.68-1.84 (m, 2H), 2.37 (t, J=7.3 Hz, 2H), 6.57 (dd, J=1.9, 3.5 Hz, 1H), 7.49 (dd, J=4.9, 7.6 Hz, 1H), 7.53 (d, J=1.9 Hz, 1H), 7.86 (d, J=3.5 Hz, 1H), 7.89 (dd, J=7.6, 7.8 Hz, 1H), 8.19 (d, J=7.8 Hz, 1H), 8.73 (d, J=4.9 Hz, 1H), 9.60 (br s, 1H).

APCIMS m/z: [M+H]$^+$ 342.

m.p.: 148-149° C.

Example 190

N-[4-(2-Furyl)-5-(pyridin-2-ylcarbonyl)thiazol-2-yl]-2,2-dimethylpropanamide (Compound 190)

In a manner similar to that in Example 188, by using pivaloyl chloride (0.230 mL, 1.89 mmol) in place of acetyl chloride, the entitled Compound 190 (380 mg, 96%) was obtained from Compound 186 (300 mg, 1.11 mmol) as a pale yellow solid.

$^1$H NMR (CDCl$_3$, δ ppm): 1.36 (s, 9H), 6.58 (dd, J=1.6, 3.2 Hz, 1H), 7.48 (dd, J=4.9, 7.6 Hz; 1H), 7.57 (d, J=1.6 Hz, 1H), 7.89 (dd, J=7.6, 8.1 Hz, 1H), 7.92 (d, J=3.2 Hz, 1H), 8.19 (d, J=8.1 Hz, 1H), 8.74 (d, J=4.9 Hz, 1H), 9.10 (br s, 1H).

APCIMS m/z: [M+H]$^+$ 356.

m.p.: 186-187° C.

Example 191

N-[4-(2-Furyl)-5-(pyridin-2-ylcarbonyl)thiazol-2-yl]cyclopropanecarboxamide (Compound 191)

In a manner similar to that in Example 188, by using cyclopropanecarbonyl chloride (0.170 mL, 1.89 mmol) in place of acetyl chloride, the entitled Compound 191 (405 mg, 100%) was obtained from Compound 186 (300 mg, 1.11 mmol) as a pale yellow solid.

$^1$H NMR (CDCl$_3$, δ ppm): 0.82-0.92 (m, 2H), 1.12-1.21 (m, 2H), 1.37-1.48 (m, 1H), 6.55 (dd, J=1.6, 3.5 Hz, 1H), 7.46 (dd, J=4.9, 7.6 Hz, 1H), 7.53 (dd, J=0.8, 1.6 Hz, 1H), 7.88 (dd, J=7.6, 7.8 Hz, 1H), 7.89 (dd, J=0.8, 1.6 Hz, 1H), 8.17 (d, J=7.8 Hz, 1H), 8.7 (d, J=4.9 Hz, 1H), 10.91 (br s, 1H).

APCIMS m/z: [M+H]$^+$ 340.

m.p.: 191-192° C.

Example 192

N-[4-(2-Furyl)-5-(pyridin-2-ylcarbonyl)thiazol-2-yl]-1-methylcyclopropanecarboxamide (Compound 192)

In a manner similar to that in Example 187, by using 1-methylcyclopropanecarboxylic acid (221 mg, 2.22 mmol) in place of isonicotinic acid, the entitled Compound 192 (305 mg, 78%) was obtained from Compound 186 (300 mg, 1.11 mmol) as a pale yellow solid.

¹H NMR (DMSO-d$_6$, δ ppm): 0.77-0.84 (m, 2H), 1.25-1.31 (m, 2H), 1.44 (s, 3H), 6.61 (dd, J=1.9, 3.5 Hz, 1H), 7.39 (dd, J=0.5, 3.5 Hz, 1H), 7.60-7.69 (m, 1H), 7.68 (dd, J=0.5, 1.9 Hz, 1H), 8.01-8.10 (m, 2H), 8.64-8.69 (m, 1H), 12.14 (br s, 1H).

APCIMS m/z: [M+H]$^+$ 354.

m.p.: 195-196° C.

Example 193

N-[4-(2-Furyl)-5-(pyridin-2-ylcarbonyl)thiazol-2-yl]cyclobutanecarboxamide (Compound 193)

In a manner similar to that in Example 188, by using cyclobutanecarbonyl chloride (0.210 mL, 1.89 mmol) in place of acetyl chloride, the entitled Compound 193 (348 mg, 89%) was obtained from Compound 186 (300 mg, 1.11 mmol) as a pale yellow solid.

¹H NMR (CDCl$_3$, δ ppm): 1.77-2.38 (m, 6H), 3.33-3.48 (m, 1H), 6.61 (dd, J=1.6, 3.2 Hz, 1H), 7.40 (d, J=3.2 Hz, 1H), 7.61-7.71 (m, 1H), 7.67 (d, J=1.6 Hz, 1H), 8.01-8.10 (m, 2H), 8.68 (d, J=4.6 Hz, 1H), 12.56 (br s, 1H).

APCIMS m/z: [M+H]$^+$ 354.

m.p.: 165-170° C.

Example 194

N-[4-(2-Furyl)-5-(pyridin-2-ylcarbonyl)thiazol-2-yl]tetrahydropyran-4-carboxamide (Compound 194)

In a manner similar to that in Example 187, by using 4-tetrahydropyrancarboxylic acid (288 mg, 2.22 mmol) in place of isonicotinic acid, the entitled Compound 194 (169 mg, 39%) was obtained from Compound 186 (300 mg, 1.11 mmol) as a pale yellow solid.

¹H NMR (CDCl$_3$, δ ppm): 1.62-1.98 (m, 4H), 2.44-2.64 (m, 1H), 3.33-3.46 (m, 2H), 3.95-4.07 (m, 2H), 6.57 (dd, J=1.9, 3.8 Hz, 1H), 7.48 (ddd, J=1.1, 4.9, 7.6 Hz, 1H), 7.54 (dd, J=1.6, 1.9 Hz, 1H), 7.88 (ddd, J=1.6, 7.6, 7.8 Hz, 1H), 7.88 (dd, J=1.6, 3.8 Hz, 1H), 8.19 (ddd, J=0.8, 1.1, 7.8 Hz, 1H), 8.72 (ddd, J=0.8, 1.6, 4.9 Hz, 1H), 9.67 (br s, 1H).

APCIMS m/z: [M+H]$^+$ 384.

m.p.: 234-235° C.

Example 195

1-(tert-Butoxycarbonyl)-N-[4-(2-furyl)-5-(pyridin-2-ylcarbonyl)thiazol-2-yl]piperidine-4-carboxamide (Compound 195)

In a manner similar to that in Example 187, by using 1-(tert-butoxycarbonyl)piperidine-4-carboxylic acid (5.07 g, 22.2 mmol) in place of isonicotinic acid, the entitled Compound 195 (5.58 g, 100%) was obtained from Compound 186 (3.00 g, 11.1 mmol) as a pale yellow oily substance.

¹H NMR (DMSO-d$_6$, δ ppm): 1.30-1.59 (m, 2H), 1.41 (s, 9H), 1.81-1.93 (m, 2H), 2.67-2.89 (m, 3H), 3.92-4.11 (m, 2H), 6.62 (dd, J=1.6, 3.2. Hz, 1H), 7.42 (dd, J=0.5, 3.2 Hz, 1H), 7.62-7.71 (m, 1H), 7.68 (d, J=1.6 Hz, 1H), 8.02-8.10 (m, 2H), 8.66-8.70 (m, 1H), 12.76 (br s, 1H).

Example 196

N-[4-(2-Furyl)-5-(pyridin-2-ylcarbonyl)thiazol-2-yl]piperidine-4-carboxamide (Compound 196)

In a manner similar to that in Example 15, the entitled Compound 196 (4.25 g, 100%) was obtained as a reddish brown solid from Compound 195 (5.82 g, 11.1 mmol) in place of Compound 14.

¹H NMR (DMSO-d$_6$, δ ppm): 1.74-1.92 (m, 2H), 1.98-2.12 (m, 2H), 2.79-3.02 (m, 3H), 3.29-3.40 (m, 2H), 6.62 (dd, J=1.6, 3.5 Hz, 1H), 7.42 (d, J=3.5 Hz, 1H), 7.63-7.70 (m, 1H), 7.68 (d, J=1.6 Hz, 1H), 8.02-8.11 (m, 2H), 8.66-8.70 (m, 1H).

Example 197

N-[4-(2-Furyl)-5-(pyridin-2-ylcarbonyl)thiazol-2-yl]-1-(pyridin-3-ylmethyl)piperidine-4-carboxamide (Compound 197)

In a manner similar to that in Example 86, by using 3-pyridinecarbaldehyde (0.370 mL, 3.90 mmol) in place of Compound 85, the entitled Compound 197 (89.9 mg, 24%) was obtained as a pale yellow solid from Compound 196 (300 mg, 0.780 mmol) in place of morpholine.

¹H NMR (DMSO-d$_6$, δ ppm): 1.57-1.75 (m, 2H), 1.77-1.89 (m, 2H), 1.94-2.07 (m, 2H), 2.38-2.68 (m, 1H), 2.79-2.91 (m, 2H), 3.52 (s, 2H), 6.61 (dd, J=1.6, 3.2 Hz, 1H), 7.36 (dd, J=4.9, 7.8 Hz, 1H), 7.41 (d, J=3.2 Hz, 1H), 7.64 (dd, J=4.6, 4.6 Hz, 1H), 7.67 (d, J=1.6 Hz, 1H), 7.72 (d, J=7.8 Hz, 1H), 8.03-8.09 (m, 2H), 8.47 (d, J=4.9 Hz, 1H), 8.50 (s, 1H), 8.67 (d, J=4.6 Hz, 1H), 12.67 (br s, 1H).

APCIMS m/z: [M+H]$^+$ 474.

m.p.: 208-209° C.

Example 198

N-[4-(2-Furyl)-5-(pyridin-2-ylcarbonyl)thiazol-2-yl]-1-(pyridin-4-ylmethyl)piperidine-4-carboxamide (Compound 198)

In a manner similar to that in Example 86, by using 4-pyridinecarbaldehyde (0.37 mL, 3.90 mmol) in place of Compound 85, the entitled Compound 198 (114 mg, 31%) was obtained as a pale yellow solid from Compound 196 (300 mg, 0.785 mmol) in place of morpholine.

¹H NMR (DMSO-d$_6$, δ ppm): 1.61-1.79 (m, 2H), 1.89-1.92 (m, 2H), 1.96-2.08 (m, 2H), 2.41-2.63 (m, 1H), 2.79-2.88 (m, 2H), 3.52 (s, 2H), 6.61 (dd, J=1.8, 3.3 Hz, 1H), 7.33 (d, J=5.7 Hz, 2H), 7.42 (d, J=3.3 Hz, 1H), 7.66 (dd, J=3.9, 4.8 Hz, 1H), 7.68 (d, J=1.8 Hz, 1H), 8.05-8.10 (m, 2H), 8.51 (d, J=5.7 Hz, 2H), 8.69 (d, J=4.8 Hz, 1H), 12.71 (br s, 1H).

APCIMS m/z: [M+H]$^+$ 474.

m.p.: 240-241° C.

Example 199

N-[4-(2-Furyl)-5-(pyridin-2-ylcarbonyl)thiazol-2-yl]benzamide (Compound 199)

In a manner similar to that in Example 188, by using benzoyl chloride (0.210 mL, 1.89 mmol) in place of acetyl chloride, the entitled Compound 199 (388 mg, 93%) was obtained as a pale yellow solid from Compound 186 (288 mg, 1.11 mmol).

¹H NMR (CDCl₃, δ ppm): 6.58 (dd, J=1.9, 3.8 Hz, 1H), 7.48-7.59 (m, 4H), 7.60-7.69 (m, 1H), 7.87-8.00 (m, 4H), 8.22 (d, J=7.6 Hz, 1H), 8.78 (d, J=4.9 Hz, 1H), 9.79 (br s, 1H).
APCIMS m/z: [M+H]⁺ 376.
m.p.: 165-171° C.

Example 200

N-[4-(2-Furyl)-5-(pyridin-2-ylcarbonyl)thiazol-2-yl]-2-methoxybenzamide (Compound 200)

In a manner similar to that in Example 188, by using 2-methoxybenzoyl chloride (0.0930 mL, 0.629 mmol) in place of acetyl chloride, the entitled Compound 200 (183 mg, 100%) was obtained as a pale yellow solid from Compound 186 (100 mg, 0.370 mmol).
¹H NMR (CDCl₃, δ ppm): 4.13 (s, 3H), 6.57 (dd, J=1.6, 3.5 Hz, 1H), 7.08 (d, J=8.4 Hz, 1H), 7.16 (dd, J=6.8, 7.8 Hz, 1H), 7.48 (ddd, J=1.4, 4.9, 7.6 Hz, 1H), 7.56 (d, J=1.6 Hz, 1H), 7.58 (ddd, J=1.9, 6.8, 7.8 Hz, 1H), 7.81 (d, J=3.5 Hz, 1H), 7.89 (ddd, J=1.6, 7.6, 7.8 Hz, 1H), 8.17 (ddd, J=0.8, 1.4, 7.8 Hz, 1H), 8.31 (dd, J=1.9, 7.8 Hz, 1H), 8.75 (ddd, J=0.8, 1.6, 4.9 Hz, 1H), 11.44 (br s, 1H).
APCIMS m/z: [M+H]⁺ 406.
m.p.: 205-208° C.

Example 201

N-[4-(2-Furyl)-5-(pyridin-2-ylcarbonyl)thiazol-2-yl]-3-methoxybenzamide (Compound 201)

In a manner similar to that in Example 188, by using 3-methoxybenzoyl chloride (0.260 mL, 1.89 mmol) in place of acetyl chloride, the entitled Compound 201 (311 mg, 69%) was obtained as a pale yellow solid from Compound 186 (300 mg, 1.11 mmol).
¹H NMR (CDCl₃, δ ppm): 3.88 (s, 3H), 6.56 (dd, J=1.9, 3.8 Hz, 1H), 7.16 (ddd, J=1.4, 2.4, 5.6 Hz, 1H), 7.43 (dd, J=5.6, 5.6 Hz, 1H), 7.46-7.57 (m, 3H), 7.54 (dd, J=0.8, 1.9 Hz, 1H), 7.87-7.95 (m, 1H), 7.91 (dd, J=0.8, 3.8 Hz, 1H), 8.22 (d, J=7.8 Hz, 1H), 8.77 (d, J=4.9 Hz, 1H), 9.85 (br s, 1H).
APCIMS m/z: [M+H]⁺ 406.
m.p.: 165-166° C.

Example 202

N-[4-(2-Furyl)-5-(pyridin-2-ylcarbonyl)thiazol-2-yl]-4-methoxybenzamide (Compound 202)

In a manner similar to that in Example 188, by using 4-methoxybenzoyl chloride (320 mg, 1.89 mmol) in place of acetyl chloride, the entitled Compound 202 (254 mg, 56%) was obtained as a pale yellow solid from Compound 186 (300 mg, 1.11 mmol).
¹H NMR (CDCl₃, δ ppm): 3.90 (s, 3H), 6.57 (dd, J=1.9, 3.8 Hz, 1H), 7.02 (d, J=8.6 Hz, 2H), 7.50 (dd, J=4.9, 7.8 Hz, 1H), 7.54 (d, J=1.9 Hz, 1H), 7.86-7.97 (m, 2H), 7.93 (d, J=8.6 Hz, 2H), 8.21 (d, J=7.8 Hz, 1H), 8.77 (d, J=4.9 Hz, 1H), 9.75 (br s, 1H).
APCIMS m/z: [M+H]⁺ 406.
m.p.: 187-188° C.

Example 203

N-[4-(2-Furyl)-5-(pyridin-2-ylcarbonyl)thiazol-2-yl]-3,4-dimethoxybenzamide (Compound 203)

In a manner similar to that in Example 187, by using 3,4-dimethoxybenzoic acid (368 mg, 2.22 mmol) in place of isonicotinic acid, the entitled Compound 203 (181 mg, 37%) was obtained as a pale yellow solid from Compound 186 (300 mg, 1.11 mmol).
¹H NMR (DMSO-d₆, δ ppm): 3.86 (s, 3H), 3.88 (s, 3H), 6.63 (dd, J=1.9, 3.5 Hz, 1H), 7.14 (d, J=8.4 Hz, 1H), 7.44 (d, J=3.5 Hz, 1H), 7.64-7.72 (m, 1H), 7.70 (d, J=1.9 Hz, 1H), 7.82 (d, J=2.2 Hz, 1H), 7.85 (dd, J=2.2, 8.4 Hz, 1H), 8.06-8.11 (m, 2H), 8.68-8.73 (m, 1H), 13.04 (br s, 1H).
APCIMS m/z: [M+H]⁺ 436.
m.p.: 169-170° C.

Example 204

N-[4-(2-Furyl)-5-(pyridin-2-ylcarbonyl)thiazol-2-yl]-3,4,5-trimethoxybenzamide (Compound 204)

In a manner similar to that in Example 188, by using 3,4,5-benzoyl chloride (434 mg, 1.89 mmol) in place of acetyl chloride, the entitled Compound 204 (526 mg, 100%) was obtained as a pale yellow solid from Compound 186 (300 mg, 1.11 mmol).
¹H NMR (DMSO-d₆, δ ppm): 3.77 (s, 3H), 3.90 (s, 6H), 6.64 (dd, J=1.6, 3.2 Hz, 1H), 7.47 (d, J=3.2 Hz, 1H), 7.58 (s, 2H), 7.65-7.73 (m, 1H), 7.72 (d, J=1.6 Hz, 1H), 8.04-8.12 (m, 2H), 8.69-8.74 (m, 1H), 13.16 (br s, 1H).
APCIMS m/z: [M+H]⁺ 466.
m.p.: 172-180° C. (decomposition).

Example 205

3-Cyano-N-[4-(2-furyl)-5-(pyridin-2-ylcarbonyl)thiazol-2-yl]benzamide (Compound 205)

In a manner similar to that in Example 188, by using 3-cyanobenzoyl chloride (364 mg, 2.21 mmol) in place of acetyl chloride, the entitled Compound 205 (241 mg, 46%) was obtained as a pale yellow solid from Compound 186 (350 mg, 1.30 mmol).
¹H NMR (CDCl₃, δ ppm): 6.50 (dd, J=1.6, 3.2 Hz, 1H), 7.46 (d, J=1.6 Hz, 1H), 7.52 (ddd, J=1.1, 4.9, 7.6 Hz, 1H), 7.62 (dd, J=8.0, 8.1 Hz, 1H), 7.86 (d, J=8.0 Hz, 1H), 7.88 (d, J=3.2 Hz, 1H), 7.92 (ddd, J=1.6, 7.6, 7.8 Hz, 1H), 8.13 (d, J=8.1 Hz, 1H), 8.22 (ddd, J=0.8, 1.1, 7.8 Hz, 1H), 8.26 (s, 1H), 8.78 (ddd, J=0.8, 1.6, 4.9 Hz, 1H).
APCIMS m/z: [M+H]⁺ 401.
m.p.: 234-237° C.

Example 206

4-Cyano-N-[4-(2-furyl)-5-(pyridin-2-ylcarbonyl)thiazol-2-yl]benzamide (Compound 206)

In a manner similar to that in Example 188, by using 4-cyanobenzoyl chloride (31.1 mg, 1.89 mmol) in place of acetyl chloride, the entitled Compound 206 (231 mg, 52%) was obtained as a pale yellow solid from Compound 186 (300 mg, 1.11 mmol).
¹H NMR (CDCl₃, δ ppm): 6.51 (dd, J=1.6, 3.5 Hz, 1H), 7.45 (d, J=1.6 Hz, 1H), 7.53 (dd, J=4.6, 7.6 Hz, 1H), 7.79 (d, J=8.1 Hz, 2H), 7.85 (d, J=3.5 Hz, 1H), 7.93 (dd, J=7.6, 8.1 Hz, 1H), 8.03 (d, J=8.1 Hz, 2H), 8.24 (d, J=8.1 Hz, 1H), 8.78 (d, J=4.6 Hz, 1H), 10.50 (br s, 1H).
APCIMS m/z: [M+H]⁺ 401.
m.p.: 232-235° C.

Example 207

3-Acetyl-N-[4-(2-furyl)-5-(pyridin-2-ylcarbonyl)thiazol-2-yl]benzamide (Compound 207)

In a manner similar to that in Example 187, by using 3-acetylbenzoic acid (363 mg, 2.22 mmol) in place of isonicotinic acid, the entitled Compound 207 (479 mg, 100%) was obtained as a pale yellow solid from Compound 186 (300 mg, 1.11 mmol).

$^1$H NMR (DMSO-$d_6$, δ ppm): 2.70 (s, 3H), 6.64 (dd, J=1.3, 3.5 Hz, 1H), 7.46 (d, J=3.5 Hz, 1H), 7.63-7.78 (m, 3H), 8.03-8.13 (m, 2H), 8.20 (d, J=7.0 Hz, 1H), 8.37 (d, J=6.8 Hz, 1H), 8.68-8.74 (m, 1H), 8.77 (s, 1H), 13.43 (br s, 1H).

APCIMS m/z: [M+H]$^+$ 418.

m.p.: 168-169° C.

Example 208

4-Acetyl-N-[4-(2-furyl)-5-(pyridin-2-ylcarbonyl)thiazol-2-yl]benzamide (Compound 208)

In a manner similar to that in Example 187, by using 4-acetylbenzoic acid (182 mg, 2.22 mmol) in place of isonicotinic acid, the entitled Compound 208 (422 mg, 91%) was obtained as a pale yellow solid from Compound 186 (300 mg, 1.11 mmol).

$^1$H NMR (DMSO-$d_6$, δ ppm): 2.66 (s, 3H), 6.64 (dd, J=1.6, 3.2 Hz, 1H), 7.46 (d, J=3.2 Hz, 1H), 7.65-7.75 (m, 1H), 7.72 (d, J=1.6 Hz, 1H), 8.04-8.14 (m, 2H), 8.11 (d, J=8.4 Hz, 2H), 8.28 (d, J=8.4 Hz, 2H), 8.69-8.75 (m, 1H), 13.40 (br s, 1H).

APCIMS m/z: [M+H]$^+$ 418.

m.p.: 204-206° C.

Example 209

N-[4-(2-Furyl)-5-(pyridin-2-ylcarbonyl)thiazol-2-yl]-3,4-methylenedioxybenzamide (Compound 209)

In a manner similar to that in Example 187, by using 3,4-methylenedioxybenzoic acid (367 mg, 2.22 mmol) in place of isonicotinic acid, the entitled Compound 209 (369 mg, 79%) was obtained as a pale yellow solid from Compound 186 (300 mg, 1.11 mmol).

$^1$H NMR (DMSO-$d_6$, δ ppm): 6.17 (s, 2H), 6.63 (dd, J=1.6, 3.5 Hz, 1H), 7.09 (d, J=8.4 Hz, 1H), 7.44 (dd, J=0.8, 3.5 Hz, 1H), 7.64-7.72 (m, 1H), 7.70 (dd, J=0.8, 1.6 Hz, 1H), 7.73 (d, J=1.9 Hz, 1H), 7.82 (dd, J=1.9, 8.4 Hz, 1H), 8.05-8.11 (m, 2H), 8.68-8.73 (m, 1H), 12.99 (br s, 1H).

APCIMS m/z: [M+H]$^+$ 420.

m.p.: 235-236° C.

Example 210

N-[4-(2-Furyl)-5-(pyridin-2-ylcarbonyl)thiazol-2-yl]-1,4-benzodioxane-6-carboxamide (Compound 210)

In a manner similar to that in Example 187, by using 1,4-benzodioxane-6-carboxylic acid (398 mg, 2.22 mmol) in place of isonicotinic acid, the entitled Compound 210 (412 mg, 86%) was obtained as a pale yellow solid from Compound 186 (300 mg, 1.11 mmol).

$^1$H NMR (DMSO-$d_6$, δ ppm): 4.28-4.38 (m, 4H), 6.63 (dd, J=1.9, 3.5 Hz, 1H), 7.02 (d, J=8.6 Hz, 1H), 7.44 (dd, J=0.5, 3.5 Hz, 1H), 7.63-7.73 (m, 1H), 7.71 (dd, J=0.5, 1.9 Hz, 1H), 7.74 (dd, J=2.2, 8.6 Hz, 1H), 7.77 (d, J=2.2 Hz, 1H), 8.03-8.11 (m, 2H), 8.68-8.73 (m, 1H), 13.00 (br s, 1H).

APCIMS m/z: [M+H]$^+$ 434.

m.p.: 189-191° C.

Example 211

N-[4-(2-Furyl)-5-(pyridin-2-ylcarbonyl)thiazol-2-yl]-1,4-benzodioxane-2-carboxamide (Compound 211)

In a manner similar to that in Example 187, by using 1,4-benzodioxane-2-carboxylic acid (398 mg, 2.22 mmol) in place of isonicotinic acid, the entitled Compound 211 (394 mg, 82%) was obtained as a pale yellow solid from Compound 186 (300 mg, 1.11 mmol).

$^1$H NMR (DMSO-$d_6$, δ ppm): 4.44 (dd, J=3.0, 12.2 Hz, 1H), 4.53 (dd, J=3.8, 12.2 Hz, 1H), 5.24 (dd, J=3.0, 3.8 Hz, 1H), 6.63 (dd, J=1.9, 3.5 Hz, 1H), 6.84-6.95 (m, 3H), 6.99-7.05 (m, 1H), 7.46 (dd, J=0.8, 3.5 Hz, 1H), 7.62-7.69 (m, 1H), 7.71 (dd, J=0.8, 1.9 Hz, 1H), 8.02-8.11 (m, 2H), 8.66-8.70 (m, 1H), 13.10 (br s, 1H).

APCIMS m/z: [M+H]$^+$ 434.

m.p.: 103-104° C.

Example 212

N-[4-(2-Furyl)-5-(pyridin-2-ylcarbonyl)thiazol-2-yl]-2-methylpyridine-4-carboxamide (Compound 212)

In a manner similar to that in Example 187, by using 2-methylisonicotinic acid (384 mg, 2.22 mmol) in place of isonicotinic acid, the entitled Compound 212 (186 mg, 43%) was obtained as a pale yellow solid from Compound 186 (300 mg, 1.11 mmol).

$^1$H NMR (DMSO-$d_6$, δ ppm): 2.59 (s, 3H), 6.65 (dd, J=1.9, 3.5 Hz, 1H), 7.46 (dd, J=0.8, 3.5 Hz, 1H), 7.66-7.75 (m, 1H), 7.73 (dd, J=0.8, 1.9 Hz, 1H), 7.85 (dd, J=1.1, 5.1 Hz, 1H), 7.94 (d, J=1.1 Hz, 1H), 8.05-8.14 (m, 2H), 8.69 (d, J=5.1 Hz, 1H), 8.69-8.74 (m, 1H), 13.43 (br s, 1H).

APCIMS m/z: [M+H]$^+$ 391.

m.p.: 187-188° C.

Example 213

N-[4-(2-Furyl)-5-(pyridin-2-ylcarbonyl)thiazol-2-yl]-2-(4-methoxybenzyloxy)pyridine-4-carboxamide (Compound 213)

Compound 186 (600 mg, 2.22 mmol) was dissolved in DMF (11 mL), and Compound 1 (1.43 mg, 5.53 mmol) obtained in Reference Example 12, N,N-diisopropylethylamine (2.34 mL, 13.3 mmol) and PyBOP (4.03 g, 7.74 mmol) were added thereto, followed by stirring at 50° C. for 10 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography to afford the entitled Compound 213 (912 mg, 81%) as a pale yellow oily substance.

$^1$H NMR (DMSO-$d_6$, δ ppm): 3.78 (s, 3H), 5.31 (s, 2H), 6.42 (dd, J=1.8, 3.6 Hz, 1H), 6.86 (d, J=8.9 Hz, 2H), 7.21 (dd, J=1.0, 1.6 Hz, 1H), 7.31 (dd, J=1.6, 5.4 Hz, 1H), 7.35 (d, J=8.9 Hz, 2H), 7.36 (dd, J=0.7, 1.8 Hz, 1H), 7.51 (ddd, J=1.2, 4.8, 7.6 Hz, 1H), 7.70 (dd, J=0.7, 3.6 Hz, 1H), 7.91 (ddd, J=1.8, 7.6, 7.9 Hz, 1H), 8.04 (br s, 1H), 8.19 (ddd, J=1.0, 1.2, 7.9 Hz, 1H), 8.27 (dd, J=1.0, 5.4 Hz, 1H), 8.77 (ddd, J=1.0, 1.8, 4.8 Hz, 1H).

Example 214

2-Chloro-N-[4-(2-furyl)-5-(pyridin-2-ylcarbonyl)thiazol-2-yl]pyridine-4-carboxamide (Compound 214)

In a manner similar to that in Example 187, by using 2-chloroisonicotinic acid (348 mg, 2.22 mmol) in place of isonicotinic acid, the entitled Compound 214 (270 mg, 59%) was obtained as a pale yellow solid from Compound 186 (300 mg, 1.11 mmol).
$^1$H NMR (DMSO-$d_6$, δ ppm): 6.65 (dd, J=1.6, 3.2 Hz, 1H), 7.47 (d, J=3.2 Hz, 1H), 7.66-7.73 (m, 1H), 7.74 (d, J=1.6 Hz, 1H), 8.04 (dd, J=1.6, 5.4 Hz, 1H), 8.08-8.14 (m, 2H), 8.20 (d, J=1.6 Hz, 1H), 8.68 (d, J=5.4 Hz, 1H), 8.70-8.75 (m, 1H), 13.57 (br s, 1H).
APCIMS m/z: [$^{35}$ClM+H]$^+$ 411, [$^{37}$ClM+H]$^+$ 413.
m.p.: 219-225° C.

Example 215

3-Chloro-N-[4-(2-furyl)-5-(pyridin-2-ylcarbonyl)thiazol-2-yl]pyridine-4-carboxamide (Compound 215)

In a manner similar to that in Example 187, by using 3-chloroisonicotinic acid (348 mg, 2.22 mmol) in place of isonicotinic acid, the entitled Compound 215 (452 mg, 99%) was obtained as a pale yellow solid from Compound 186 (300 mg, 1.11 mmol).
$^1$H NMR (DMSO-$d_6$, δ ppm): 6.64 (dd, J=1.6, 3.5 Hz, 1H), 7.46 (d, J=3.5 Hz, 1H), 7.65-7.74 (m, 1H), 7.73 (d, J=1.6 Hz, 1H), 7.78 (d, J=4.9 Hz, 1H), 8.06-8.17 (m, 2H), 8.72 (d, J=4.9 Hz, 1H), 8.72-8.76 (m, 1H), 8.84 (s, 1H), 13.57 (br s, 1H).
APCIMS m/z: [$^{35}$ClM+H]$^+$ 411, [$^{37}$ClM+H]$^+$ 413.
m.p.: 206-207° C.

Example 216

2,6-Dichloro-N-[4-(2-furyl)-5-(pyridin-2-ylcarbonyl)thiazol-2-yl]pyridine-4-carboxamide (Compound 216)

In a manner similar to that in Example 187, by using 2,6-dichloroisonicotinic acid (424 mg, 2.22 mmol) in place of isonicotinic acid, the entitled Compound 216 (402 mg, 81%) was obtained as a pale yellow solid from Compound 186 (300 mg, 1.11 mmol).
$^1$H NMR (DMSO-$d_6$, δ ppm): 6.65 (dd, J=1.6, 3.5 Hz, 1H), 7.48 (d, J=0.5 Hz, 1H), 7.66-7.72 (m, 1H), 7.74 (d, J=0.5 Hz, 1H), 8.05-8.15 (m, 2H), 8.19 (s, 2H), 8.69-8.75 (m, 1H), 13.59 (br s, 1H).
APCIMS m/z: [$^{35}$Cl$^{35}$ClM+H]$^+$ 445, [$^{35}$Cl $^{37}$ClM+H]$^+$ 447.
m.p.: 254-258° C.

Example 217

N-[4-(2-Furyl)-5-(pyridin-2-ylcarbonyl)thiazol-2-yl]-2-[N-(2-methoxyethyl)-N-methylamino]pyridine-4-carboxamide (Compound 217)

In a manner similar to that in Example 187, by using 2-[N-(2-methoxyethyl)-N-methylamino]pyridine-4-carboxylic acid (465 mg, 2.22 mmol) in place of isonicotinic acid, the entitled Compound 217 (273 mg, 59%) was obtained as a pale yellow solid from Compound 186 (300 mg, 1.11 mmol).
$^1$H NMR (CDCl$_3$, δ ppm): 3.17 (s, 3H), 3.34 (s, 3H), 3.61 (t, J=5.4 Hz, 2H), 3.82 (t, J=5.4 Hz, 2H), 6.56 (dd, J=1.9, 3.8 Hz, 1H), 6.91 (d, J=5.1 Hz, 1H), 7.04-7.08 (m, 1H), 7.50 (ddd, J=1.6, 4.9, 7.3 Hz, 1H), 7.54 (d, J=1.9 Hz, 1H), 7.90 (ddd, J=1.6, 7.3, 7.8 Hz, 1H), 7.91 (d, J=3.8 Hz, 1H), 8.21 (d, J=7.8 Hz, 1H), 8.29 (d, J=5.1 Hz, 1H), 8.75 (dd, J=1.6, 4.9 Hz, 1H).
APCIMS m/z: [M+H]$^+$ 464.
m.p.: 114-117° C.

Example 218

N-[4-(2-Furyl)-5-(pyridin-2-ylcarbonyl)thiazol-2-yl]-2-piperidinopyridine-4-carboxamide (Compound 218)

In a manner similar to that in Example 187, by using 2-piperidinopyridine-4-carboxylic acid (456 mg, 2.22 mmol) in place of isonicotinic acid, the entitled Compound 218 (300 mg, 59%) was obtained as a pale yellow solid from Compound 186 (300 mg, 1.11 mmol).
$^1$H NMR (CDCl$_3$, δ ppm): 1.50-1.82 (m, 6H), 3.53-3.80 (m, 4H), 6.55 (dd, J=1.9, 3.8 Hz, 1H), 6.88 (d, J=5.1 Hz, 1H), 7.14 (s, 1H), 7.50 (ddd, J=1.4, 4.9, 7.8 Hz, 1H), 7.52 (dd, J=0.5, 1.9 Hz, 1H), 7.90 (ddd, J=1.9, 7.8, 7.8 Hz, 1H), 7.90 (dd, J=0.5, 3.8 Hz, 1H), 8.21 (ddd, J=0.8, 1.4, 7.8 Hz, 1H), 8.29 (d, J=5.1 Hz, 1H), 8.75 (ddd, J=0.8, 1.9, 4.9 Hz, 1H), 9.97 (br s, 1H).
APCIMS m/z: [M+H]$^+$ 460.
m.p.: 136-141° C.

Example 219

N-[4-(2-Furyl)-5-(pyridin-2-ylcarbonyl)thiazol-2-yl]-2-morpholinopyridine-4-carboxamide (Compound 219)

In a manner similar to that in Example 187, by using 2-morpholinopyridine-4-carboxylic acid (461 mg, 2.22 mmol) in place of isonicotinic acid, the entitled Compound 219 (233 mg, 45%) was obtained as a pale yellow solid from Compound 186 (300 mg, 1.11 mmol).
$^1$H NMR (CDCl$_3$, δ ppm): 3.59-3.67 (m, 4H), 3.79-3.87 (m, 4H), 6.57 (dd, J=1.6, 3.5 Hz, 1H), 7.04 (d, J=4.6 Hz, 1H), 7.21 (s, 1H), 7.52 (dd, J=4.9, 7.6 Hz, 1H), 7.56 (d, J=1.6 Hz, 1H), 7.92 (ddd, J=1.9, 7.6, 7.8 Hz, 1H), 7.95 (d, J=3.5 Hz, 1H), 8.22 (d, J=7.8 Hz, 1H), 8.35 (d, J=4.6 Hz, 1H), 8.76 (dd, J=1.9, 4.9 Hz, 1H).
APCIMS m/z: [M+H]$^+$ 462.
m.p.: 216-217° C.

Example 220

N-[4-(2-Furyl)-5-(pyridin-2-ylcarbonyl)thiazol-2-yl]pyridine-3-carboxamide (Compound 220)

In a manner similar to that in Example 188, by using nicotinoyl chloride hydrochloride (394 mg, 2.22 mmol) in place of acetyl chloride, the entitled Compound 220 (252 mg, 60%) was obtained as a pale yellow solid from Compound 186 (300 mg, 1.11 mmol).

¹H NMR (DMSO-d₆, δ ppm): 6.65 (dd, J=1.9, 3.5 Hz, 1H), 7.48 (d, J=3.5 Hz, 1H), 7.62 (dd, J=5.1, 8.1 Hz, 1H), 7.66-7.73 (m, 1H), 7.73 (d, J=1.9 Hz, 1H), 8.05-8.14 (m, 2H), 8.50 (ddd, J=1.4, 2.2, 8.1 Hz, 1H), 8.71-8.75 (m, 1H), 8.83 (dd, J=1.4, 5.1 Hz, 1H), 9.28 (d, J=2.2 Hz, 1H), 13.43 (br s, 1H).
APCIMS m/z: [M+H]⁺ 377.

Example 221

N-[4-(2-Furyl)-5-(pyridin-2-ylcarbonyl)thiazol-2-yl]-2-methylpyridine-3-carboxamide (Compound 221)

In a manner similar to that in Example 187, by using 2-methylnicotinic acid (303 mg, 2.22 mmol) in place of isonicotinic acid, the entitled Compound 221 (316 mg, 73%) was obtained as a pale yellow solid from Compound 186 (300 mg, 1.11 mmol).
¹H NMR (DMSO-d₆, δ ppm): 2.63 (s, 3H), 6.63 (dd, J=1.9, 3.5 Hz, 1H), 7.38 (dd, J=4.9, 7.8 Hz, 1H), 7.44 (dd, J=0.8, 3.5 Hz, 1H), 7.65-7.73 (m 1H), 7.71 (dd, J=0.8, 1.9 Hz, 1H), 8.04-8.14 (m, 2H), 8.05 (dd, J=1.6, 7.8 Hz, 1H), 8.61 (dd, J=1.6, 4.9 Hz, 1H), 8.71-8.75 (m 1H), 12.67 (br s, 1H).
APCIMS m/z: [M+H]⁺ 391.
m.p.: 186-187° C.

Example 222

N-[4-(2-Furyl)-5-(pyridin-2-ylcarbonyl)thiazol-2-yl]-2-methylpyridine-5-carboxamide (Compound 222)

In a manner similar to that in Example 187, by using 6-methylnicotinic acid (303 mg, 2.22 mmol) in place of isonicotinic acid, the entitled Compound 222 (326 mg, 75%) was obtained as a pale yellow solid from Compound 186 (300 mg, 1.11 mmol).
¹H NMR (DMSO-d₆, δ ppm): 2.58 (s, 3H), 6.64 (dd, J=1.6, 3.5 Hz, 1H), 7.46 (d, J=7.8 Hz, 1H), 7.46 (dd, J=0.8, 3.5 Hz, 1H), 7.65-7.74 (m, 1H), 7.72 (dd, J=0.8, 1.6 Hz, 1H), 8.04-8.13 (m, 2H), 8.38 (dd, J=2.4, 7.8 Hz, 1H), 8.69-8.74 (m, 1H), 9.17 (d, J=2.4 Hz, 1H), 13.31 (br s, 1H).
APCIMS m/z: [M+H]⁺ 391.
m.p.: 210-215° C.

Example 223

N-[4-(2-Furyl)-5-(pyridine-2-ylcarbonyl)thiazol-2-yl]-5-methylpyridine-3-carboxamide (Compound 223)

In a manner similar to that in Example 187, by using 5-methylnicotinic acid (303 mg, 2.22 mmol) in place of isonicotinic acid, the entitled Compound 223 (391 mg, 90%) was obtained as a pale yellow solid from Compound 186 (300 mg, 1.11 mmol).
¹H NMR (DMSO-d₆, δ ppm): 2.41 (s, 3H), 6.64 (dd, J=1.9, 3.5 Hz, 1H), 7.46 (dd, J=0.8, 3.5 Hz, 1H), 7.65-7.75 (m, 1H), 7.73 (dd, J=0.8, 1.9 Hz, 1H), 8.05-8.14 (m, 2H), 8.33 (dd, J=1.4, 1.9 Hz, 1H), 8.67 (d, J=1.4 Hz, 1H), 8.70-8.73 (m, 1H), 9.08 (d, J=1.9 Hz, 1H), 13.35 (br s, 1H).
APCIMS m/z: [M+H]⁺ 391.
m.p.: 245-248° C.

Example 224

N-[4-(2-Furyl)-5-(pyridin-2-ylcarbonyl)thiazol-2-yl]-2,6-dimethoxypyridine-3-carboxamide (Compound 224)

In a manner similar to that in Example 187, by using 2,6-dimethoxynicotinic acid (405 mg, 2.22 mmol) in place of isonicotinic acid, the entitled Compound 224 (484 mg, 100%) was obtained as a pale yellow solid from Compound 186 (300 mg, 1.11 mmol).
¹H NMR (DMSO-d₆, δ ppm): 3.97 (s, 3H), 4.09 (s, 3H), 6.58 (d, J=8.6 Hz, 1H), 6.63 (dd, J=1.9, 3.2 Hz 1H), 7.45 (d, J=3.2 Hz, 1H), 7.64-7.71 (m, 1H), 7.71 (d, J=1.9 Hz, 1H), 8.03-8.12 (m, 2H), 8.18 (d, J=8.6 Hz, 1H), 8.69-8.73 (m, 1H), 11.97 (br s, 1H).
APCIMS m/z: [M+H]⁺ 437.
m.p.: 201-202° C.

Example 225

2-Chloro-N-[4-(2-furyl)-5-(pyridin-2-ylcarbonyl)thiazol-2-yl]pyridine-5-carboxamide (Compound 225)

In a manner similar to that in Example 187, by using 6-chloronicotinic acid (348 mg, 2.22 mmol) in place of isonicotinic acid, the entitled Compound 225 (298 mg, 65%) was obtained as a pale yellow solid from Compound 186 (300 mg, 1.11 mmol).
¹H NMR (DMSO-d₆, δ ppm): 6.64 (dd, J=1.6, 3.2 Hz, 1H), 7.47 (d, J=3.2 Hz, 1H), 7.65-7.74 (m, 1H), 7.72 (d, J=1.6 Hz, 1H), 7.76 (d, J=8.4 Hz, 1H), 8.04-8.14 (m, 2H), 8.52 (dd, J=2.4, 8.4 Hz, 1H), 8.70-8.74 (m, 1H), 9.12 (d, J=2.4 Hz, 1H), 13.47 (br s, 1H).
m.p.: 136-138° C.

Example 226

5-Bromo-N-[4-(2-furyl)-5-(pyridin-2-ylcarbonyl)thiazol-2-yl]pyridine-3-carboxamide (Compound 226)

In a manner similar to that in Example 187, by using 5-bromonicotinic acid (446 mg, 2.22 mmol) in place of isonicotinic acid, the entitled Compound 226 (303 mg, 60%) was obtained as a pale yellow solid from Compound 186 (300 mg, 1.11 mmol).
¹H NMR (DMSO-d₆, δ ppm): 6.65 (dd, J=1.9, 3.8 Hz, 1H), 7.48 (dd, J=0.8, 3.8 Hz, 1H), 7.65-7.72 (m, 1H), 7.73 (dd, J=0.8, 1.9 Hz, 1H), 8.06-8.15 (m, 2H), 8.71-8.77 (m, 1H), 8.75 (dd, J=1.9, 2.2 Hz, 1H), 8.97 (d, J=2.2 Hz, 1H), 9.22 (d, J=1.9 Hz, 1H), 13.46 (br s, 1H).
APCIMS m/z: [⁷⁹BrM+H]⁺ 455, [⁸¹BrM+H]⁺ 457.
m.p.: 259-262° C.

Example 227

N-[4-(2-Furyl)-5-(pyridin-2-ylcarbonyl)thiazol-2-yl]pyridazine-4-carboxamide (Compound 227)

In a manner similar to that in Example 187, by using pyridazine-4-carboxylic acid (274 mg, 2.22 mmol) in place of isonicotinic acid, the entitled Compound 227 (275 mg, 90%) was obtained as a pale yellow solid from Compound 186 (300 mg, 1.11 mmol).
¹H NMR (DMSO-d₆, δ ppm): 6.66 (dd, J=1.9, 3.5 Hz, 1H), 7.51 (d, J=3.5 Hz, 1H), 7.66-7.73 (m, 1H), 7.75 (d, J=1.9 Hz, 1H), 8.05-8.16 (m, 2H), 8.30 (dd, J=2.4, 5.4 Hz, 1H), 8.71-8.77 (m, 1H), 9.56 (dd, J=1.1, 5.4 Hz, 1H), 9.78 (dd, J=1.1, 2.4 Hz, 1H), 13.73 (br s, 1H).

Example 228

N-[4-(2-Furyl)-5-pyridin-2-ylcarbonyl)thiazol-2-yl]-2-methylpyrimidine-5-carboxamide (Compound 228)

Compound 186 (50.0 mg, 0.18 mmol) was dissolved in DMF (0.9 mL), and diisopropylethylamine (0.0500 mL, 0.270 mmol) and a 0.5 mol/L solution of 2-methylpyrimidine-5-carboxylic acid triethylamine salt (0.560 mL, 0.280 mmol) in DMF obtained according to the method described in Synthesis, p. 720, 2002, and PyBOP (144 mg, 0.280 mmol) were added thereto under ice-cooling, followed by stirring at 50° C. for 2 hours. To the reaction mixture, diisopropylethylamine, 2-methylpyrimidine-5-carboxylic acid triethylamine and PyBOP, respectively the same amount as added previously, were added to the reaction mixture, followed by stirring at 70° C. for 1.5 hours. Again, the same amount of diisopropylethylamine, 2-methylpyrimidine-5-carboxylic acid triethylamine salt and PyBOP as added previously were added thereto, followed by stirring at 80° C. for 1.5 hours. The reaction mixture was allowed to cool down, water was added thereto, and the precipitated solid was collected by filtration. The resulting solid was purified through silica gel column chromatography (chloroform:methanol=30:1) to afford the entitled Compound 228 (66.9 mg, 95%) as pale yellow crystals. Next, the same process as above was repeated to afford Compound 228. The obtained Compound 228 (14.3 g) was dissolved in a mixed solvent (4:1, 1.80 L) of ethanol and water under heating and reflux. The resulting solution was allowed to cool down to room temperature, and the precipitated crystals were collected by filtration to afford the entitled Compound 228 (11.3 g, recrystallization yield 79%).

$^1$H NMR (DMSO-$d_6$, δ ppm): 2.73 (s, 3H), 6.65 (dd, J=1.6, 3.5 Hz, 1H), 7.50 (dd, J=0.8, 3.5 Hz, 1H), 7.66-7.73 (m, 1H), 7.74 (dd, J=0.8, 1.6 Hz, 1H), 8.05-8.15 (m, 2H), 8.70-8.75 (m, 1H), 9.32 (s, 2H), 13.51 (br s, 1H).

APCIMS m/z: [M+H]$^+$ 392.

m.p.: 255-265° C. (decomposition).

Example 229

2-Cyclopropyl-N-[4-(2-furyl)-5-(pyridin-2-ylcarbonyl)thiazol-2-yl]pyrimidine-5-carboxamide (Compound 229)

In a manner similar to that in Example 228, by using a 0.5 mol/L solution of 2-cyclopropylpyrimidine-5-carboxylic acid triethylamine salt (4.86 mL, 2.43 mmol) in DMF obtained according to the method described in Synthesis, p. 720, 2002, in place of 2-methylpyrimidine-5-carboxylic acid triethylamine salt, the entitled Compound 229 (217 mg, 96%) was obtained as a pale yellow solid from Compound 186 (200 mg, 0.57 mmol).

$^1$H NMR (DMSO-$d_6$, δ ppm): 1.09-1.24 (m, 4H), 2.27-2.39 (m, 1H), 6.64 (dd, J=1.6, 3.5 Hz, 1H), 7.49 (d, J=3.5 Hz, 1H), 7.65-7.73 (m, 1H), 7.73 (d, J=1.6 Hz, 1H), 8.04-8.15 (m, 2H), 8.70-8.75 (m, 1H), 9.26 (s, 2H).

APCIMS m/z: [M+H]$^+$ 418.

m.p.: 150-154° C.

Example 230

N-[4-(2-Furyl)-5-(pyridine-2-ylcarbonyl)thiazol-2-yl]-5-methylpyrazine-2-carboxamide (Compound 230)

In a manner similar to that in Example 187, by using 5-methylpyrazine-2-carboxylic acid (186 mg, 1.34 mmol) in place of isonicotinic acid, the entitled Compound 230 (284 mg, 100%) was obtained as a pale yellow solid from Compound 186 (250 mg, 0.67 mmol).

$^1$H NMR (DMSO-$d_6$, δ ppm): 2.65 (s, 3H), 6.63 (dd, J=1.6, 3.2 Hz, 1H), 7.41 (d, J=3.2 Hz, 1H), 7.66-7.74 (m, 1H), 7.71 (d, J=1.6 Hz, 1H), 8.07-8.14 (m, 2H), 8.69-8.74 (m, 1H), 8.75 (s, 1H), 9.22 (s, 1H), 12.94 (br s, 1H).

APCIMS m/z: [M+H]$^+$ 392.

m.p.: 208-209° C.

Example 231

N-[4-(2-Furyl)-5-(pyridin-2-ylcarbonyl)thiazol-2-yl]-2-oxo-1,2-dihydropyridine-4-carboxamide (Compound 231)

Compound 213 (912 mg, 1.78 mmol) was dissolved in trifluoroacetic acid (3.6 mL), followed by stirring at room temperature for 30 minutes. The reaction mixture was concentrated under reduced pressure, and the resulting residue was reslurried with ethyl acetate to afford the entitled Compound 231 (469 mg, 67%) as a pale yellow solid.

$^1$H NMR (DMSO-$d_6$, δ ppm): 6.64 (dd, J=1.9, 3.5 Hz, 1H), 6.69 (dd, J=1.9, 6.8 Hz, 1H), 7.09 (d, J=1.9 Hz, 1H), 7.46 (d, J=3.5 Hz, 1H), 7.56 (d, J=6.8 Hz, 1H), 7.65-7.75 (m, 1H), 7.73 (d, J=1.9 Hz, 1H), 8.04-8.15 (m, 2H), δ 8.68-8.77 (m, 1H), 13.27 (br s, 1H).

APCIMS m/z: [M+H]$^+$ 393.

m.p.: 170-180° C. (decomposition)

Example 232

1-Benzyl-N-[4-(2-furyl)-5-(pyridin-2-ylcarbonyl)thiazol-2-yl]-2-oxo-1,2-dihydropyridine-4-carboxamide (Compound 232)

In a manner similar to that in Example 187, by using Compound w (341 mg, 1.48 mmol) obtained in Reference Example 23 in place of isonicotinic acid, the entitled Compound 232 (269 mg, 75%) was obtained as a pale yellow solid from Compound 186 (202 mg, 0.740 mmol).

$^1$H NMR (DMSO-$d_6$, δ ppm): 5.12 (s, 2H), 6.64 (dd, J=1.9, 3.5 Hz, 1H), 6.78 (dd, J=1.6, 7.3 Hz, 1H), 7.20 (d, J=1.6 Hz, 1H), 7.28-7.41 (m, 5H), 7.45 (dd, J=0.5, 3.5 Hz, 1H), 7.65-7.74 (m, 1H), 7.72 (dd, J=0.5, 1.9 Hz, 1H), 8.00 (d, J=7.3 Hz, 1H), 8.04-8.13 (m, 2H), 8.69-8.74 (m, 1H), 13.35 (br s, 1H).

APCIMS m/z: [M+H]$^+$ 483.

m.p.: 269-270° C.

Example 233

N-[4-(2-Furyl)-5-(pyridin-2-ylcarbonyl)thiazol-2-yl]-1-methyl-2-oxo-1,2-dihydropyridine-4-carboxamide (Compound 233)

In a manner similar to that in Example 187, by using Compound x (190 mg, 1.24 mmol) obtained in Reference Example 24 in place of isonicotinic acid, the entitled Com- APCIMS m/z: [M+H]$^+$ 378.

m.p.: 270-274° C.

pound 233 (233 mg, 92%) was obtained as a pale yellow solid from Compound 186 (168 mg, 0.620 mmol).

$^1$H NMR (DMSO-$d_6$, δ ppm): 3.54 (s, 3H), 6.64 (dd, J=1.9, 3.5 Hz, 1H), 6.74 (dd, J=2.2, 7.0 Hz, 1H), 7.15 (d, J=2.2 Hz, 1H), 7.46 (dd, J=0.8, 3.5 Hz, 1H), 7.65-7.72 (m, 1H), 7.73 (dd, J=0.8, 1.9 Hz, 1H), 7.88 (d, J=7.0 Hz, 1H), 8.04-8.14 (m, 2H), 8.70-8.74 (m, 1H), 13.36 (br s, 1H).

APCIMS m/z: [M+H]$^+$ 407.

m.p.: 280-285° C.

Example 234

N-[4-(2-Furyl)-5-(pyridin-2-ylcarbonyl)thiazol-2-yl]furan-2-carboxamide (Compound 234)

In a manner similar to that in Example 188, by using 2-furoyl chloride (0.190 mL, 1.89 mmol) in place of acetyl chloride, the entitled Compound 234 (196 mg, 48%) was obtained as a pale yellow solid from Compound 186 (300 mg, 1.11 mmol).

$^1$H NMR (CDCl$_3$, δ ppm): 6.57 (dd, J=1.9, 3.8 Hz, 1H), 6.62 (dd, J=1.9, 3.8 Hz, 1H), 7.41 (dd, J=0.8, 3.8 Hz, 1H), 7.49 (ddd, J=1.4, 4.9, 7.6 Hz, 1H), 7.56 (dd, J=0.8, 1.9 Hz, 1H), 7.59 (dd, J=0.8, 1.9 Hz, 1H), 7.89 (ddd, J=1.9, 7.6, 8.1 Hz, 1H), 7.92 (dd, J=0.8, 3.8 Hz, 1H), 8.19 (ddd, J=0.8, 1.4, 8.1 Hz, 1H), 8.74 (ddd, J=0.8, 1.9, 4.9 Hz, 1H), 10.11 (br s, 1H).

APCIMS m/z: [M+H]$^+$ 366.

m.p.: 184-185° C.

Example 235

5-Bromo-N-[4-(2-furyl)-5-(pyridin-2-ylcarbonyl)thiazol-2-yl]furan-2-carboxamide (Compound 235)

In a manner similar to that in Example 187, by using 5-bromofuran-2-carboxylic acid (422 mg, 2.22 mmol) in place of isonicotinic acid, the entitled Compound 235 (366 mg, 75%) was obtained as a pale yellow solid from Compound 186 (300 mg, 1.11 mmol).

$^1$H NMR (DMSO-$d_6$, δ ppm): 6.63 (dd, J=1.9, 3.5 Hz, 1H), 6.92 (d, J=3.5 Hz, 1H), 7.45 (dd, J=0.5, 3.5 Hz, 1H), 7.64-7.73 (m, 1H), 7.70 (dd, J=0.5, 1.9 Hz, 1H), 7.81 (d, J=3.5 Hz, 1H), 8.03-8.13 (m, 2H), 8.67-8.72 (m, 1H), 13.23 (br s, 1H).

APCIMS m/z: [$^{79}$BrM+H]$^+$ 444, [$^{81}$BrM+H]$^+$ 446.

m.p.: 211-212° C.

Example 236

N-[4-(2-Furyl)-5-(pyridin-2-ylcarbonyl)thiazol-2-yl]-5-nitrofuran-2-carboxamide (Compound 236)

In a manner similar to that in Example 187, by using 5-nitrofuran-2-carboxylic acid (347 mg, 2.22 mmol) in place of isonicotinic acid, the entitled Compound 236 (334 mg, 73%) was obtained as a pale yellow solid from Compound 1.86 (300 mg, 1.11 mmol).

$^1$H NMR (DMSO-$d_6$, δ ppm): 6.65 (dd, J=1.6, 3.5 Hz, 1H), 7.48 (dd, J=0.5, 1.6 Hz, 1H), 7.66-7.74 (m, 1H), 7.73 (dd, J=0.5, 1.6 Hz, 1H), 7.85 (d, J=4.1 Hz, 1H), 7.98 (d, J=4.1 Hz, 1H), 8.05-8.14 (m, 2H), 8.69-8.73 (m, 1H), 13.72 (br s, 1H).

APCIMS m/z: [M+H]$^+$ 411.

m.p.: 278-283° C. (decomposition)

Example 237

N-[4-(2-Furyl)-5-(pyridin-2-ylcarbonyl)thiazol-2-yl]-3-methylfuran-2-carboxamide (Compound 237)

In a manner similar to that in Example 187, by using 3-methylfuran-2-carboxylic acid (279 mg, 2.22 mmol) in place of isonicotinic acid, the entitled Compound 237 (377 mg, 90%) was obtained as a pale yellow solid from Compound 186 (300 mg, 1.11 mmol).

$^1$H NMR (DMSO-$d_6$, δ ppm): 2.40 (s, 3H), 6.62 (dd, J=1.9, 3.5 Hz, 1H), 6.67 (d, J=1.6 Hz, 1H), 7.40 (dd, J=0.5, 3.5 Hz, 1H), 7.62-7.72 (m, 1H), 7.70 (dd, J=0.5, 1.9 Hz, 1H), 7.88 (d, J=1.6 Hz, 1H), 8.03-8.11 (m, 2H), 8.69-8.73 (m, 1H), 12.87 (br s, 1H).

APCIMS m/z: [M+H]$^+$ 380.

m.p.: 174-176° C.

Example 238

N-[4-(2-Furyl)-5-(pyridin-2-ylcarbonyl)thiazol-2-yl]furan-3-carboxamide (Compound 238)

In a manner similar to that in Example 188, by using 3-furoyl chloride (248 mg, 1.89 mmol) in place of acetyl chloride, the entitled Compound 238 (241 mg, 59%) was obtained as a pale yellow solid from Compound 186 (300 mg, 1.11 mmol).

$^1$H NMR (DMSO-$d_6$, δ ppm): 6.63 (dd, J=1.6, 3.2 Hz, 1H), 7.14 (d, J=1.9 Hz, 1H), 7.44 (d, J=3.2 Hz, 1H), 7.67 (ddd, J=2.3, 4.6, 4.9 Hz, 1H), 7.69 (d, J=1.6 Hz, 1H), 7.87 (dd, J=1.9, 1.9 Hz, 1H), 8.03-8.11 (m, 2H), 8.64-8.68 (m, 1H), 8.69 (d, J=4.6 Hz, 1H), 13.00 (br s, 1H).

APCIMS m/z: [M+H]$^+$ 366.

m.p.: 187-189° C.

Example 239

N-[4-(2-Furyl)-5-(pyridin-2-ylcarbonyl)thiazol-2-yl]-2-methylfuran-3-carboxamide (Compound 239)

In a manner similar to that in Example 187, by using 2-methylfuran-3-carboxylic acid (279 mg, 2.22 mmol) in place of isonicotinic acid, the entitled Compound 239 (329 mg, 78%) was obtained as a pale yellow solid from Compound 186 (300 mg, 1.11 mmol).

$^1$H NMR (DMSO-$d_6$, δ ppm): 2.63 (s, 3H), 6.63 (dd, J=1.6, 3.5 Hz, 1H), 7.37 (d, J=2.2 Hz, 1H), 7.44 (dd, J=1.0, 3.5 Hz, 1H), 7.64-7.75 (m, 1H), 7.65 (d, J=2.2 Hz, 1H), 7.70 (dd, J=1.0, 1.6 Hz, 1H), 8.03-8.11 (m, 2H), 8.69-8.74 (m, 1H), 12.74 (br s, 1H).

APCIMS m/z: [M+H]$^+$ 380.

m.p.: 183-186° C.

Example 240

N-[4-(2-Furyl)-5-(pyridin-2-ylcarbonyl)thiazol-2-yl]-2,5-dimethylfuran-3-carboxamide (Compound 240)

In a manner similar to that in Example 187, by using 2,5-dimethylfuran-3-carboxylic acid (310 mg, 2.22 mmol) in place of isonicotinic acid, the entitled Compound 240 (290 mg, 66%) was obtained as a pale yellow solid from Compound 186 (300 mg, 1.11 mmol).

$^1$H NMR (DMSO-$d_6$, δ ppm): 2.27 (s, 3H), 2.58 (s, 3H), 6.62 (dd, J=1.9, 3.5 Hz, 1H), 6.96 (s, 1H), 7.44 (dd, J=0.5, 3.5

Hz, 1H), 7.62-7.72 (m, 1H), 7.70 (dd, J=0.5, 1.9 Hz, 1H), 8.03-8.11 (m, 2H), 8.69-8.73 (m, 1H), 12.65 (br s, 1H).
APCIMS m/z: [M+H]+ 394.
m.p.: 195-198° C.

Example 241

N-[4-(2-Furyl)-5-(pyridin-2-ylcarbonyl)thiazol-2-yl]thiophene-2-carboxamide (Compound 241)

In a manner similar to that in Example 188, by using 2-thiophenecarbonyl chloride (0.200 mL, 1.89 mmol) in place of acetyl chloride, the entitled Compound 241 (357 mg, 84%) was obtained as a pale yellow solid from Compound 186 (300 mg, 1.11 mmol).
$^1$H NMR (CDCl$_3$, δ ppm): 6.55 (dd, J=1.9, 3.5 Hz, 1H), 7.16 (dd, J=4.1, 5.1 Hz, 1H), 7.49 (ddd, J=1.1, 4.9, 7.6 Hz, 1H), 7.53 (dd, J=1.1, 1.9 Hz, 1H), 7.66 (d, J=5.1 Hz, 1H), 7.74 (dd, J=1.1, 3.5 Hz, 1H), 7.89 (ddd, J=1.6, 7.6, 7.6 Hz, 1H), 7.92 (d, J=4.1 Hz, 1H), 8.19 (ddd, J=0.8, 1.1, 7.6 Hz, 1H), 8.75 (ddd, J=0.8, 1.6, 4.9 Hz, 1H).
APCIMS m/z: [M+H]+ 382.
m.p.: 197-199° C.

Example 242

N-[4-(2-Furyl)-5-(pyridin-2-ylcarbonyl)thiazol-2-yl]isoxazole-5-carboxamide (Compound 242), In a manner similar to that in Example 188, by using 5-isoxazolecarbonyl chloride (0.240 mg, 1.89 mmol) in place of acetyl chloride, the entitled Compound 242 (333 mg, 82%) was obtained as a brown solid from Compound 186 (300 mg, 1.11 mmol).
$^1$H NMR (DMSO-d$_6$, δ ppm): 6.64 (dd, J=1.9, 3.5 Hz, 1H), 7.46 (d, J=3.5 Hz, 1H), 7.61 (d, J=1.9 Hz, 1H), 7.69 (ddd, J=2.4, 4.9, 6.5 Hz, 1H), 7.72 (d, J=1.9 Hz, 1H), 8.05-8.15 (m, 2H), 8.72 (d, J=4.9 Hz, 1H), 8.88 (d, J=1.9 Hz, 1H).
APCIMS m/z: [M+H]+ 367.
m.p.: 223-230° C.

Example 243

N-[4-(2-Furyl)-5-(pyridin-2-ylcarbonyl)thiazol-2-yl]-5-methylisoxazole-3-carboxamide (Compound 243)

In a manner similar to that in Example 187, by using 5-methylisoxazole-3-carboxylic acid (281 mg, 2.22 mmol) in place of isonicotinic acid, the entitled Compound 243 (277 mg, 66%) was obtained as a pale yellow solid from Compound 186 (300 mg, 1.11 mmol).
$^1$H NMR (DMSO-d$_6$, δ ppm): 2.53 (s, 3H), 6.63 (dd, J=1.6, 3.5 Hz, 1H), 6.90 (s, 1H), 7.42 (dd, J=0.5, 3.5 Hz, 1H), 7.65-7.74 (m, 1H), 7.72 (dd, J=0.5, 1.6 Hz, 1H), 8.04-8.13 (m, 2H), 8.68-8.74 (m, 1H), 13.47 (br s, 1H).
APCIMS m/z: [M+H]+ 381.
m.p.: 209-213° C.

Example 244

N-[4-(2-Furyl)-5-(pyridin-2-ylcarbonyl)thiazol-2-yl]-1,2,3-benzothiadiazole-5-carboxamide (Compound 244)

In a manner similar to that in Example 187, by using 1,2,3-benzothiadiazole-5-carboxylic acid (399 mg, 2.22 mmol) in place of isonicotinic acid, the entitled Compound 244 (400 mg, 83%) was obtained as a pale yellow solid from Compound 186 (300 mg, 1.11 mmol).
$^1$H NMR (DMSO-d$_6$, δ ppm): 6.65 (dd, J=1.6, 3.2 Hz, 1H), 7.48 (dd, J=0.5, 3.2 Hz, 1H), 7.66-7.73 (m, 1H), 7.74 (dd, J=0.5, 1.6 Hz, 1H), 8.05-8.15 (m, 2H), 8.47 (dd, J=1.6, 8.6 Hz, 1H), 8.60 (dd, J=0.8, 8.6 Hz, 1H), 8.72-8.77 (m, 1H), 9.56 (dd, J=0.8, 1.6 Hz, 1H), 13.58 (br s, 1H).
APCIMS m/z: [M+H]+ 434.
m.p.: 213-218° C.

Example 245

N-[4-(2-Furyl)-5-(pyridin-2-ylcarbonyl)thiazol-2-yl]-1-methyl-1H-benzotriazole-6-carboxamide (Compound 24.5)

In a manner similar to that in Example 187, by using 1-methyl-1H-benzotriazole-6-carboxylic acid (392 mg, 2.22 mmol) in place of isonicotinic acid, the entitled Compound 245 (574 mg, 100%) was obtained as a pale yellow solid from Compound 186 (300 mg, 1.11 mmol).
$^1$H NMR (DMSO-d$_6$, δ ppm): 4.37 (s, 3H), 6.64 (dd, J=1.6, 3.5 Hz, 1H), 7.46 (d, J=3.5 Hz, 1H), 7.65-7.74 (m, 1H), 7.72 (d, J=1.6 Hz, 1H), 8.03 (d, J=8.6 Hz, 1H), 8.07-8.13 (m, 2H), 8.29 (dd, J=1.4, 8.6 Hz, 1H), 8.70-8.75 (m, 1H), 8.97 (d, J=1.4 Hz, 1H), 13.38 (br s, 1H).
APCIMS m/z: [M+H]+ 431.
m.p.: 230-231° C.

Example 246

N-[4-(2-Furyl)-5-(pyridin-2-ylcarbonyl).thiazol-2-yl]-2-(1-hydroxyethyl)-1-benzofuran-5-carboxamide (Compound 246)

In a manner similar to that in Example 187, by using 2-(1-hydroxyethyl)-1-benzofuran-5-carboxylic acid (304 mg, 1.48 mmol) obtained according to the method described in *Tetrahedron Letters*, Vol. 38, p. 2311, 1997, in place of isonicotinic acid, the entitled Compound 246 (303 mg, 89%) was obtained as a pale yellow solid from Compound 186 (200 mg, 0.740 mmol).
$^1$H NMR (DMSO-d$_6$, δ ppm): 1.50 (d, J=6.6 Hz, 3H), 4.89 (dq, J=5.3, 6.6 Hz, 1H), 5.63 (d, J=5.3 Hz, 1H), 6.64 (dd, J=1.6, 3.2 Hz, 1H), 6.88 (s, 1H), 7.45 (d, J=3.2 Hz, 1H), 7.65-7.75 (m, 1H), 7.72 (d, J=7.8 Hz, 1H), 7.72 (d, J=1.6 Hz, 1H), 8.07-8.14 (m, 2H), 8.11 (dd, J=1.6, 7.8 Hz, 1H), 8.49 (d, J=1.6 Hz, 1H), 8.70-8.75 (m, 1H), 13.19 (br s, 1H).
APCIMS m/z: [M+H]+ 460.
m.p.: 246-249° C.

Example 247

N-[4-(2-Furyl)-5-(pyridin-2-ylcarbonyl)thiazol-2-yl]-2-(1-hydroxy-1-methylethyl)-1-benzofuran-5-carboxamide (Compound 247)

In a manner similar to that in Example 187, by using 2-(1-hydroxy-1-methylethyl)-1-benzofuran-5-carboxylic acid (260 mg, 1.16 mmol) obtained according to the method described in Tetrahedron Letters, Vol. 38, p. 2311, 1997, in place of isonicotinic acid, the entitled Compound 247 (274 mg, 100%) was obtained as a pale yellow solid from Compound 186 (157 mg, 0.580 mmol).
$^1$H NMR (DMSO-d$_6$, δ ppm): 1.55 (s, 6H), 5.52 (br s, 1H), 6.64 (dd, J=1.6, 3.2 Hz, 1H), 6.84 (s, 1H), 7.45 (d, J=3.2 Hz, 1H), 7.65-7.75 (m, 1H), 7.71 (d, J=8.9 Hz, 1H), 7.72 (d, J=1.6 Hz, 1H), 8.04-8.12 (m, 2H), 8.09 (dd, J=1.4, 8.9 Hz, 1H), 8.48 (d, J=1.4 Hz, 1H), 8.69-8.74 (m, 1H), 13.19 (br s, 1H).
APCIMS m/z: [M+H]$^+$ 474.
m.p.: 230-231° C.

Example 248

N-[4-(2-Furyl)-5-(pyridin-2-ylcarbonyl)thiazol-2-yl]furo[2,3-b]pyridine-5-carboxamide (Compound 248)

In a manner similar to that in Example 187, by using furo[2,3-b]pyridine-5-carboxylic acid (178 mg, 1.08 mmol) obtained according to the method described in *Tetrahedron Letters*, Vol. 35, p. 9355, 1994, in place of isonicotinic acid, the entitled Compound 248 (209 mg, 93%) was obtained as a pale yellow solid from Compound 186 (200 mg, 0.540 mmol).
$^1$H NMR (DMSO-d$_6$, δ ppm): 6.65 (dd, J=1.9, 3.5 Hz, 1H), 7.21 (d, J=2.4 Hz, 1H), 7.47 (d, J=3.5 Hz, 1H), 7.65-7.75 (m, 1H), 7.73 (d, J=1.9 Hz, 1H), 8.05-8.14 (m, 2H), 8.28 (d, J=2.4 Hz, 1H), 8.70-8.76 (m, 1H), 8.89 (d, J=1.9 Hz, 1H), 9.07 (d, J=1.9 Hz, 1H).
APCIMS m/z: [M+H]$^+$ 417.
m.p.: 234-235° C.

Example 249

Methyl N-[4-(2-furyl)-5-(pyridin-2-ylcarbonyl)thiazol-2-yl]carbamate (Compound 249)

In a manner similar to that in Example 188, by using methyl chloroformate (0.450 mL, 5.67 mmol) in place of acetyl chloride, the entitled Compound 249 (157 mg, 43%) was obtained as a pale yellow solid from Compound 186 (300 mg, 1.11 mmol).
$^1$H NMR (CDCl$_3$, δ ppm): 3.85 (s, 3H), 6.56 (dd, J=1.6, 3.2 Hz, 1H), 7.44-7.53 (m, 2H), 7.82-7.93 (m, 2H), 8.19 (d, J=7.8 Hz, 1H), 8.71 (d, J=4.5 Hz, 1H), 8.98 (br s, 1H).
APCIMS m/z: [M+H]$^+$ 330.

Example 250

Ethyl N-[4-(2-furyl)-5-(pyridin-2-ylcarbonyl)thiazol-2-yl]carbamate (Compound 250)

In a manner similar to that in Example 188, by using ethyl chloroformate (0.360 mL, 3.78 mmol) in place of acetyl chloride, the entitled Compound 250 (248 mg, 65%) was obtained as a pale yellow solid from Compound 186 (300 mg, 1.11 mmol).
$^1$H NMR (CDCl$_3$, δ ppm): 1.30 (t, J=7.0 Hz, 3H), 4.28 (q, J=7.0 Hz, 2H), 6.55 (dd, J=1.9, 3.5 Hz, 1H), 7.48 (ddd, J=0.8, 4.6, 7.6 Hz, 1H), 7.51 (dd, J=0.8, 1.9 Hz, 1H), 7.85 (dd, J=0.8, 3.5 Hz, 1H), 7.89 (ddd, J=1.9, 7.6, 7.8 Hz, 1H), 8.19 (ddd, J=0.8, 0.8, 7.8 Hz, 1H), 8.71 (ddd, J=0.8, 1.9, 4.6 Hz, 1H), 9.24 (br s, 1H).
APCIMS m/z: [M+H]$^+$ 344.
m.p.: 158-159° C.

Example 251

Cyclobutyl N-[4-(2-furyl)-5-(pyridin-2-ylcarbonyl)thiazol-2-yl]carbamate (Compound 251)

Compound y (249 mg, 0.839 mmol) obtained in Reference Example 25 was suspended in THF (4 mL), and cyclobutanol (0.328 mL, 4.20 mmol) was added thereto, followed by stirring for 30 minutes. The reaction mixture was concentrated under reduced pressure, and the resulting residue was purified through silica gel column chromatography (hexane:ethyl acetate=2:1) to afford the entitled Compound 251 (137 mg, 44%) as a pale yellow solid.
$^1$H NMR (CDCl$_3$, δ ppm): 1.54-1.90 (m, 2H), 2.04-2.22 (m, 2H), 2.32-2.46 (m, 2H), 5.01-5.15 (m, 1H), 6.57 (dd, J=1.8, 3.5 Hz, 1H), 7.49 (ddd, J=1.0, 4.8, 7.6 Hz, 1H), 7.54 (d, J=1.8 Hz, 1H), 7.90 (ddd, J=1.6, 7.6, 7.9 Hz, 1H), 7.91 (d, J=3.5 Hz, 1H), 8.19 (ddd, J=0.9, 1.0, 7.9 Hz, 1H), 8.72 (ddd, J=0.9, 1.6, 4.8 Hz, 1H).
APCIMS m/z: [M+H]$^+$ 370.
m.p.: 152-153° C.

Example 252

Cyclopentyl N-[4-(2-furyl)-5-(pyridin-2-ylcarbonyl)thiazol-2-yl]carbamate (Compound 252)

In a manner similar to that in Example 251, by using cyclopentanol (0.305 mL, 3.37 mmol) in place of cyclobutanol, the entitled Compound 252 (87.3 mg, 23%) was obtained as a pale yellow solid from Compound y (200 mg, 0.670 mmol) obtained in Reference Example 25.
$^1$H NMR (CDCl$_3$, δ ppm): 1.55-2.01 (m, 8H), 5.25-5.35 (m, 1H), 6.57 (dd, J=1.6, 3.5 Hz, 1H), 7.49 (ddd, J=1.2, 4.6, 7.4 Hz, 1H), 7.54 (dd, J=0.7, 1.6 Hz, 1H), 7.90 (ddd, J=1.7, 7.4, 7.9 Hz, 1H), 7.90 (dd, J=0.7, 3.5 Hz, 1H), 8.19 (ddd, J=1.0, 1.2, 7.9 Hz, 1H), 8.72 (ddd, J=1.0, 1.7, 4.6 Hz, 1H).
APCIMS m/z: [M+H]$^+$ 384.
m.p.: 162-163° C.

Example 253

4-Tetrahydropyranyl N-[4-(2-furyl)-5-(pyridin-2-ylcarbonyl)thiazol-2-yl]carbamate (Compound 253)

In a manner similar to that in Example 251, by using tetrahydropyran-4-ol (0.321 mL, 3.37 mmol) in place of cyclobutanol, the entitled Compound 253 (52.0 mg, 19%) was obtained as a pale yellow solid from Compound y (200 mg, 0.670 mmol) obtained in Reference Example 25.
$^1$H NMR (CDCl$_3$, δ ppm): 1.71-1.86 (m, 2H), 1.97-2.09 (m, 2H), 3.51-3.62 (m 2H), 3.89-4.00 (m, 2H), 5.01-5.12 (m, 1H), 6.58 (dd, J=1.8, 3.5 Hz, 1H), 7.50 (ddd, J=1.3, 4.8, 7.6 Hz, 1H), 7.56 (dd, J=0.7, 1.8 Hz, 1H), 7.91 (d, J=0.7, 3.5 Hz, 1H), 7.92 (ddd, J=1.7, 7.6, 7.9 Hz, 1H), 8.21 (ddd, J=0.8, 1.3, 7.9 Hz, 1H), 8.72 (ddd, J=0.8, 1.7, 4.8 Hz, 1H).
APCIMS m/z: [M+H]$^+$ 400.
m.p.: 144-145° C.

Example 254

1-Methylpiperidin-4-yl N-[4-(2-furyl)-5-(pyridin-2-ylcarbonyl)thiazol-2-yl]carbamate (Compound 254)

In a manner similar to that in Example 251, by using 1-methylpiperidin-4-ol (581 mg, 5.05 mmol) in place of cyclobutanol, the entitled Compound 254 (167 mg, 40%) was obtained as a pale yellow solid from Compound y (300' mg, 1.01 mmol) obtained in Reference Example 25.
$^1$H NMR (DMSO-d$_6$, δ ppm): 1.59-1.74 (m, 2H), 1.87-1.99 (m, 2H), 2.11-2.25 (m, 2H), 2.19 (s, 3H), 2.59-2.70 (m, 2H), 4.70-4.81 (m, 1H), 6.61 (dd, J=1.6, 3.2 Hz, 1H), 7.41 (dd, J=0.5, 3.2 Hz, 1H), 7.60-7.70 (m, 1H), 7.68 (dd, J=0.5, 1.6 Hz, 1H), 8.03-8.08 (m, 2H), 8.64-8.69 (m, 1H).

APCIMS m/z: [M+H]$^+$ 413.
m.p.: 222-225° C.

Example 255

2-Fluoro-1-(fluoromethyl)ethyl N-[4-(2-furyl)-5-(pyridin-2-ylcarbonyl)thiazol-2-yl]carbamate (Compound 255)

In a manner similar to that in Example 251, by using 1,3-difluoropropan-2-ol (0.322 mL, 4.21 mmol) in place of cyclobutanol, the entitled Compound 255 (93.2 mg, 28%) was obtained as a pale yellow solid from Compound y (250 mg, 0.841 mmol) obtained in Reference Example 25.
$^1$H NMR (CDCl$_3$, δ ppm): 4.56-4.61 (m, 2H), 4.73-4.79 (m, 2H), 5.21-5.43 (m, 1H), 6.58 (dd, J=1.8, 3.6 Hz, 1H), 7.51 (ddd, J=1.3, 4.8, 7.6 Hz, 1H), 7.56 (dd, J=0.7, 1.8 Hz, 1H), 7.90 (ddd, J=1.5, 7.6, 8.1 Hz, 1H), 7.90 (dd, J=0.7, 3.6 Hz, 1H), 8.22 (ddd, J=0.8, 1.3, 8.1 Hz, 1H), 8.73 (ddd, J=0.8, 1.5, 4.8 Hz, 1H).
APCIMS m/z: [M+H]$^+$ 394.
m.p.: 158-159° C.

Example 256

N-[4-(2-Furyl)-5-(pyridin-2-ylcarbonyl)thiazol-2-yl]morpholine-4-carboxamide (Compound 256)

Compound 186 (100 mg, 0.369 mmol) was suspended in dichloromethane (3.7 mL), and carbonyldiimidazole (89.7 mg, 554 mmol) was added thereto at room temperature, followed by stirring for 12 hours at room temperature. The reaction mixture was concentrated under reduced pressure, and the resulting residue was dissolved in THF (3.7 mL). Morpholine (0.0484 mL, 554 mmol) was added to the resulting solution, followed by stirring for 2 hours at room temperature. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol 20:1) to afford the entitled Compound 256 (93.9 mg, 66%) as a pale yellow solid.
$^1$H NMR (CDCl$_3$, δ ppm): 3.51-3.59 (m, 4H), 3.68-3.75 (m, 4H), 6.58 (dd, J=1.8, 3.6 Hz, 1H), 7.48 (ddd, J=1.2, 4.8, 7.6 Hz, 1H), 7.55 (d, J=1.8 Hz, 1H), 7.89 (ddd, J=1.7, 7.6, 7.9 Hz, 1H), 7.96 (d, J=3.6 Hz, 1H), 8.18 (ddd, J=0.8, 1.2, 7.9 Hz, 1H), 8.74 (ddd, J=0.8, 1.7, 4.8 Hz, 1H).
APCIMS m/z: [M+H]$^+$ 385.
m.p.: 144-145° C.

Example 257

N-[4-(2-Furyl)-5-(pyridin-2-ylcarbonyl)thiazol-2-yl]piperidine-1-carboxamide (Compound 257)

Compound y (130 mg, 0.437 mmol) obtained in Reference Example 25 was suspended in THF (4.4 mL), and piperidine (64.9 mL, 0.656 mmol) was added thereto, followed by stirring at room temperature for 20 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 257 (66.5 mg, 40%) as a pale yellow solid.
$^1$H NMR (CDCl$_3$, δ ppm): 1.57-1.71 (m, 6H), 3.48-3.56 (m, 4H), 6.57 (dd, J=1.7, 3.5 Hz, 1H), 7.46 (ddd, J=1.0, 4.6, 7.6 Hz, 1H), 7.55 (d, J=1.7 Hz, 1H), 7.88 (ddd, J=1.7, 7.6, 7.9 Hz, 1H), 7.94 (d, J=3.5 Hz, 1H), 8.17 (ddd, J=1.0, 1.1, 7.9 Hz, 1H), 8.73 (ddd, J=1.1, 1.7, 4.6 Hz, 1H).
APCIMS m/z: [M+H]$^+$ 383.
m.p.: 182-185° C.

Example 258

N-[4-(2-Furyl)-5-(pyridin-2-ylcarbonyl)thiazol-2-yl]-N'-isopropylurea (Compound 258)

In a manner similar to that in Example 257, by using isopropylamine (0.0900 mL, 1.01 mmol) in place of piperidine, the entitled Compound 258 (134 mg, 56%) was obtained as a pale yellow solid from Compound y (200 mg, 0.670 mmol) obtained in Reference Example 25.
$^1$H NMR (DMSO-d$_6$, δ ppm): 1.51 (d, J=6.5 Hz, 3H), 3.30 (d, J=6.5 Hz, 3H), 3.75-3.87 (m, 1H), 6.50 (br d, J=7.3 Hz, 1H), 6.58 (dd, J=1.9, 3.5 Hz, 1H), 7.37 (dd, J=0.8, 3.5 Hz, 1H), 7.59-7.66 (m, 1H), 7.63 (dd, J=0.8, 1.9 Hz, 1H), 7.99-8.08 (m, 2H), 8.62-8.66 (m, 1H), 10.90 (br s, 1H).
APCIMS m/z: [M+H]$^+$ 357.
m.p.: 182-186° C.

Example 259

N-tert-Butyl-N'-[4-(2-furyl)-5-pyridin-2-ylcarbonyl)thiazol-2-yl]urea (Compound 259)

In a manner similar to that in Example 257, by using tert-butylamine (0.130 mL, 1.26 mmol) in place of piperidine, the entitled Compound 259 (187 mg, 46%) was obtained as a pale yellow solid from Compound y (250 mg, 0.840 mmol) obtained in Reference Example 25.
$^1$H NMR (DMSO-d$_6$, δ ppm): 1.33 (s, 9H), 6.49 (br s, 1H), 6.59 (dd, J=1.9, 3.5 Hz, 1H), 7.40 (dd, J=0.8, 3.5 Hz, 1H), 7.59-7.62 (m, 1H), 7.65 (dd, J=0.8, 1.9 Hz, 1H), 8.00-8.09 (m, 2H), 8.65-8.69 (m, 1H), 10.71 (br s, 1H).
APCIMS m/z: [M+H]$^+$ 371.
m.p.: 123-124° C.

Example 260

N-[4-(2-Furyl)-5-(pyridin-2-ylcarbonyl)thiazol-2-yl]-N'-(2-methoxyethyl)urea (Compound 260)

In a manner similar to that in Example 257, by using 2-methoxyethylamine (0.0790 mL, 1.01 mmol) in place of piperidine, the entitled Compound 260 (142 mg, 57%) was obtained as a pale yellow solid from Compound y (200 mg, 0.670 mmol) obtained in Reference Example 25.
$^1$H NMR (DMSO-d$_6$, δ ppm): 3.27-3.38 (m, 2H), 3.29 (s, 3H), 3.42 (t, J=4.9 Hz, 2H), 6.59 (dd, J=1.9, 3.5 Hz, 1H), 6.74 (t, J=5.4 Hz, 1H), 7.38 (dd, J=0.5, 3.5 Hz, 1H), 7.59-7.66 (m, 1H), 7.63 (dd, J=0.5, 1.9 Hz, 1H), 8.00-8.09 (m, 2H), 8.01-8.07 (m, 1H), 11.09 (br s, 1H).
APCIMS m/z: [M+H]$^+$ 373.
m.p.: 150-151° C.

Example 261

N-[4-(2-Furyl)-5-(pyridin-2-ylcarbonyl)thiazol-2-yl]-N'-(3-methoxypropyl)urea (Compound 261)

In a manner similar to that in Example 257, by using 3-methoxypropylamine (0.102 mL, 1.01 mmol) in place of piperidine, the entitled Compound 261 (145 mg, 56%) was obtained as a pale yellow solid from Compound y (200 mg, 0.670 mmol) obtained in Reference Example 25.

$^1$H NMR (DMSO-$d_6$, δ ppm): 1.65-1.76 (m, 2H), 3.17-3.26 (m, 2H), 3.25 (s, 3H), 3.37 (t, J=6.2 Hz, 2H), 6.58 (dd, J=1.6, 3.2 Hz, 1H), 6.67 (t, J=6.3 Hz, 1H), 7.38 (dd, J=0.8, 3.2 Hz, 1H), 7.59-7.66 (m, 1H), 7.63 (dd, J=0.8, 1.6 Hz, 1H), 7.99-8.08 (m 2H), 8.62-8.66 (m, 1H), 11.18 (br s, 1H).

APCIMS m/z: [M+H]$^+$ 387.

m.p.: 169-170° C.

Example 262

2-Chloro-N-[4-(2-furyl)-5-(pyridin-2-ylcarbonyl)thiazol-2-yl]acetamide (Compound 262)

Compound 186 (0.900 g, 2.42 mmol) was dissolved in THF (10 mL), and N,N-dimethylaminopyridine (29.6 mg, 0.242 mmol), triethylamine (0.740 mL, 5.32 mmol) and chloroacetyl chloride (0.390 mL, 4.84 mmol) were added thereto under ice-cooling, followed by stirring at room temperature for 2 hours. Further, triethylamine (0.740 mL, 5.32 mmol) and chloroacetyl chloride (0.390 mL, 4.84 mmol) were added to the reaction mixture under ice-cooling, followed by stirring for 1 hour at room temperature. Water and a saturated aqueous solution of sodium hydrogencarbonate were added to the reaction mixture, and the precipitated solid was collected by filtration. The resulting solid was purified through silica gel column chromatography (hexane:ethyl acetate=2:1) to afford the entitled Compound 262 (0.810 g, 96%) as pale yellow crystals.

$^1$H NMR (CDCl$_3$, δ ppm): 4.30 (s, 2H), 6.57 (dd, J=1.6, 3.5 Hz, 1H), 7.49 (ddd, J=1.1, 4.6, 7.6 Hz, 1H), 7.55 (dd, J=0.8, 1.6 Hz, 1H), 7.85 (dd, J=0.8, 3.5 Hz, 1H), 7.89 (ddd, J=1.9, 7.6, 8.1 Hz, 1H), 8.19 (ddd, J=1.0, 1.1, 8.1 Hz, 1H), 8.72 (ddd, J=1.0, 1.9, 4.6 Hz, 1H), 10.10 (br s, 1H).

APCIMS m/z: [$^{35}$ClM+H]$^+$ 348, [$^{37}$CM+H]$^+$ 350.

m.p.: 184-185° C.

Example 263

2-Bromo-N-[4-(2-furyl)-5-(pyridin-2-ylcarbonyl)thiazol-2-yl]acetamide (Compound 263)

In a manner similar to that in Example 262, by using bromoacetyl bromide in place of chloroacetyl chloride, the entitled Compound 263 (230 mg, 72%) was obtained as a pale yellow solid from Compound 186 (300 mg, 1.11 mmol).

$^1$H NMR (CDCl$_3$, δ ppm): 4.05 (s, 2H), 6.56 (dd, J=1.6, 3.5 Hz, 1H), 7.46 (ddd, J=1.4, 4.6, 7.6 Hz, 1H), 7.52 (dd, J=0.8, 1.6 Hz, 1H), 7.78 (dd, J=0.8, 3.5 Hz, 1H), 7.89 (ddd, J=1.9, 7.6, 7.8 Hz, 1H), 8.17 (ddd, J=0.8, 1.4, 7.8 Hz, 1H), 8.71 (ddd, J=0.8, 1.6, 4.6 Hz, 1H).

Example 264

N-[4-(2-Furyl)-5-(pyridin-2-ylcarbonyl)thiazol-2-yl]morpholinoacetamide (Compound 264)

Compound 263 (196 mg, 0.49 mmol) was dissolved in THF (3.3 mL), morpholine (0.128 mL, 1.47 mmol) was added thereto, followed by stirring at room temperature for 1 hour. The reaction mixture was concentrated under reduced pressure, and the resulting residue was recrystallized from a mixed solvent (5:1) of hexane and acetone to afford the entitled Compound 264 (139 mg, 71%) as a pale yellow solid.

$^1$H NMR (DMSO-$d_6$, δ ppm): 2.48-2.62 (m, 4H), 3.36 (s, 2H), 3.58-3.64 (m, 4H), 6.62 (dd, J=1.9, 3.5 Hz, 1H), 7.41 (dd, J=0.8, 3.5 Hz, 1H), 7.63-7.70 (m, 1H), 7.68 (dd, J=0.8, 1.9 Hz, 1H), 8.05-8.10 (m, 2H), 8.66-8.70 (m, 1H).

APCIMS m/z: [M+H]$^+$ 399.

m.p.: 170-171° C.

Example 265

2-(cis-2,6-Dimethylmorpholino)-N-[4-(2-furyl)-5-(pyridin-2-ylcarbonyl)thiazol-2-yl]acetamide (Compound 265)

In a manner similar to that in Example 264, by using cis-2,6-dimethylmorpholine in place of morpholine, the entitled Compound 265 (361 mg, 98%) was obtained as pale yellow crystals from Compound 262 (300 mg, 0.860 mmol) in place of Compound 263.

$^1$H NMR (DMSO-$d_6$, δ ppm): 1.05 (d, J=6.3 Hz, 6H), 1.84-1.97 (m, 2H), 2.74-2.82 (m, 2H), 3.34 (s, 2H), 3.55-3.68 (m, 2H), 6.61 (dd, J=1.6, 3.5 Hz, 1H), 7.40 (d, J=3.5. Hz, 1H), 7.71-7.79 (m, 2H), 8.03-8.08 (m, 2H), 8.64-8.70 (m, 1H).

APCIMS m/z: [M+H]$^+$ 427.

m.p.: 188-191° C.

Example 266

N-[4-(2-Furyl)-5-(pyridin-2-ylcarbonyl)thiazol-2-yl]-2-(4-methylpiperidino)acetamide (Compound 276)

In a manner similar to that in Example 264, by using 4-methylpiperidine in place of morpholine, the entitled Compound 266 (297 mg, 84%) was obtained as pale yellow crystals from Compound 262 (300 mg, 0.860 mmol) in place of Compound 263.

$^1$H NMR (DMSO-$d_6$, δ ppm): 0.90 (d, J=6.1 Hz, 3H), 1.10-1.41 (m, 3H), 1.52-1.63 (m, 2H), 2.13-2.24 (m, 2H), 2.80-2.90 (m, 2H), 3.33 (s, 2H), 6.62 (dd, J=1.6, 3.5 Hz, 1H), 7.41 (d, J=3.5 Hz, 1H), 7.63-7.71 (m, 2H), 8.02-8.11 (m, 2H), 8.66-8.70 (m, 1H).

APCIMS m/z: [M+H]$^+$ 411.

m.p.: 104-106° C.

Example 267

N-[4-(2-Furyl)-5-(pyridin-2-ylcarbonyl)thiazol-2-yl]-2-(4-methoxypiperidino)acetamide hydrochloride (Compound 267)

In a manner similar to that in Example 264, by using 4-methoxypiperidine (0.280 mL, 2.28 mmol) in place of morpholine, a free form of the entitled Compound (299 mg, 92%) was obtained as pale yellow crystals from Compound 263 (300 mg, 0.760 mmol). The resulting free form (227 mg, 0.531 mmol) was dissolved in ethanol (2.3 mL), a 4 mol/L solution of hydrogen chloride (0.15 mL, 0.584 mmol) in ethyl acetate was added thereto, followed by stirring at room temperature for 30 minutes. The precipitated solid was collected by filtration to afford the entitled Compound 267 (187 mg, 76%) as pale yellow crystals.

$^1$H NMR (DMSO-$d_6$, δ ppm): 1.62-2.24 (m, 4H), 3.13-3.68 (m, 8H), 4.33 (s, 2H), 6.65 (dd, J=1.6, 3.5 Hz, —1H), 7.47 (d, J=3.5 Hz, 1H), 7.66-7.74 (m, 1H), 7.73 (d, J=1.6 Hz, 1H), 8.05-8.15 (m, 2H), 8.68-8.73 (m, 1H).

APCIMS m/z: [M+H]$^+$ 427.

m.p.: 220-232° C. (decomposition)

Example 268

2-[3-(N,N-Diethylcarbamoyl)piperidino]-N-[4-(2-furyl)-5-(pyridin-2-ylcarbonyl)thiazol-2-yl]acetamide hydrochloride (Compound 268)

In a manner similar to that in Example 264, by using 3-(N,N-diethylcarbamoyl)piperidine in place of morpholine, a free form of the entitled Compound (426 mg, 100%) was obtained as pale yellow crystals from Compound 262 (300 mg, 0.860 mmol) in place of Compound 263. The resulting free form (341 mg, 0.688 mmol) was dissolved in ethanol (3.4 mL), a 4 mol/L solution of hydrogen chloride (0.19 mL, 0.757 mmol) in ethyl acetate was added thereto, followed by stirring at room temperature for 12 hours. The precipitated solid was collected by filtration to afford the entitled Compound 268 (267 mg, 73%) as pale yellow crystals.

$^1$H NMR (DMSO-$d_6$, δ ppm): 1.06 (t, J=7.0 Hz, 3H), 1.17 (t, J=6.8 Hz, 3H), 1.43-2.15 (m, 4H), 3.08-3.83 (m, 9H), 4.36 (s, 2H), 6.65 (dd, J=1.9, 3.5 Hz, 1H), 7.48 (d, J=3.5 Hz, 1H), 7.66-7.77 (m, 2H), 8.05-8.15 (m, 2H), 8.70-8.76 (m, 1H).

APCIMS m/z: [M+H]$^+$ 496.

m.p.: 180-185° C.

Example 269

2-(1,4-Dioxa-8-azaspiro[4.5]decan-8-yl)-N-[4-(2-furyl)-5-(pyridin-2-ylcarbonyl)thiazol-2-yl]acetamide (Compound 269)

In a manner similar to that in Example 264, by using 1,4-dioxa-8-azaspiro[4.5]decane in place of morpholine, the entitled Compound 269 (284 mg, 73%) was obtained as pale yellow crystals from Compound 262 (300 mg, 0.860 mmol) in place of Compound 263.

$^1$H NMR (DMSO-$d_6$, δ ppm): 1.62-1.70 (m, 4H), 2.58-2.66 (m, 4H), 3.39 (s, 2H), 3.86 (s, 4H), 6.62 (dd, J=1.6, 3.0 Hz, 1H), 7.42 (d, J=3.0 Hz, 1H), 7.64-7.71 (m, 2H), 8.03-8.10 (m, 2H), 8.67-8.71 (m, 1H).

APCIMS m/z: [M+H]$^+$ 455.

m.p.: 188-204° C.

Example 270

N-[4-(2-Furyl)-5-(pyridin-2-ylcarbonyl)thiazol-2-yl]-2-(4-piperidinopiperidino)acetamide (Compound 270)

In a manner similar to that in Example 264, by using 4-piperidinopiperidine (0.390 mL, 2.28 mmol) in place of morpholine, the entitled Compound 270 (362 mg, 99%) was obtained as pale yellow crystals from Compound 263 (300 mg, 0.760 mmol).

$^1$H NMR (DMSO-$d_6$, δ ppm): 1.22-2.01 (m, 14H), 2.16-2.42 (m, 2H), 2.91-3.12 (m, 3H), 3.39 (s, 2H), 6.62 (dd, J=1.9, 3.5 Hz, 1H), 7.41 (d, J=3.5 Hz, 1H), 7.63-7.71 (m, 2H), 8.05-8.12 (m, 2H), 8.65-8.70 (m, 1H).

APCIMS m/z: [M+H]$^+$ 480.

m.p.: 214-220° C. (decomposition).

Example 271

N-[4-(2-Furyl)-5-(pyridin-2-ylcarbonyl)thiazol-2-yl]-2-(4-morpholinopiperidino)acetamide (Compound 271)

In a manner similar to that in Example 264, by using 4-morpholinopiperidine (391 mg, 2.28 mmol) in place of morpholine, the entitled Compound 271 (349 mg, 95%) was obtained as pale yellow crystals from Compound 263 (300 mg, 0.760 mmol).

$^1$H NMR (DMSO-$d_6$, δ ppm): 1.35-1.63 (m, 2H), 1.63-1.90 (m, 2H), 2.06-2.35 (m, 3H), 2.35-2.67 (m, 1H), 2.79-3.02 (m, 2H), 3.22-3.49 (m, 5H), 3.49-3.73 (m, 4H), 6.62 (dd, J=1.6, 3.5 Hz, 1H), 7.42 (d, J=3.5 Hz, 1H), 7.63-7.70 (m, 2H), 8.03-8.11 (m, 2H), 8.66-8.70 (m, 1H).

APCIMS m/z: [M+H]$^+$ 482.

m.p.: 149-150° C.

Example 272

N-[4-(2-Furyl)-5-(pyridin-2-ylcarbonyl)thiazol-2-yl]-2-(4-methylpiperazin-1-yl)acetamide (Compound 272)

In a manner similar to that in Example 264, by using 1-methylpiperazine (0.0960 mg, 0.870 mmol) in place of morpholine, the entitled Compound 272 (128 mg, 100%) was obtained as pale yellow crystals from Compound 262 (100 mg, 0.290 mmol) in place of Compound 263.

$^1$H NMR (DMSO-$d_6$, δ ppm): 2.68 (s, 3H), 2.61-3.24 (m, 8H), 3.49 (s, 2H), 6.60-6.64 (m, 1H), 7.40-7.44 (m, 1H), 7.63-7.71 (m, 2H), 8.03-8.12 (m, 2H), 8.65-8.71 (m, 1H).

APCIMS m/z: [M+H]$^+$ 412.

m.p.: 136-145° C.

Example 273

2-(4-Ethylpiperazin-1-yl)-N-[4-(2-furyl)-5-(pyridin-2-ylcarbonyl)thiazol-2-yl]acetamide (Compound 273)

In a manner similar to that in Example 264, by using 1-ethylpiperazine (0.330 mg, 2.58 mmol) in place of morpholine, the entitled Compound 273 (360 mg, 98%) was obtained as pale yellow crystals from Compound 262 (300 mg, 0.860 mmol) in place of Compound 263.

$^1$H NMR (DMSO-$d_6$, δ ppm): 0.99 (t, J=7.0 Hz, 3H), 2.32 (q, J=7.0 Hz, 2H), 2.49-2.60 (m, 4H), 3.21-3.44 (m, 4H), 3.34 (s, 2H), 6.61 (dd, J=1.9, 4.1 Hz, 1H), 7.41 (d, J=4.1 Hz, 1H), 7.62-7.70 (m, 1H), 7.68 (d, J=1.9 Hz, 1H), 8.04-8.10 (m, 2H), 8.66-8.70 (m, 1H).

APCIMS m/z: [M+H]$^+$ 426.

m.p.: 142-144° C.

Example 274

N-[4-(2-Furyl)-5-(pyridin-2-ylcarbonyl)thiazol-2-yl]-2-(4-isopropylpiperazin-1-yl)acetamide (Compound 274)

In a manner similar to that in Example 264, by using 1-isopropylpiperazine (332 mg, 2.58 mmol) in place of morpholine, the entitled Compound 274 (316 mg, 84%) was obtained as pale yellow crystals from Compound 262 (300 mg, 0.860 mmol) in place of Compound 263.

$^1$H NMR (DMSO-$d_6$, δ ppm): 0.97 (d, J=6.5 Hz, 6H), 2.43-2.68 (m, 5H), 3.25-3.36 (m, 4H), 3.33 (s, 2H), 6.61 (dd, J=1.9, 3.5 Hz, 1H), 7.41 (d, J=3.5 Hz, 1H), 7.63-7.71 (m, 2H), 8.04-8.09 (m, 2H), 8.66-8.70 (m, 1H).

APCIMS m/z: [M+H]$^+$ 440.

m.p.: 154-155° C.

Example 275

2-(4-Acetylpiperazin-1-yl)-N-[4-(2-furyl)-5-(pyridin-2-ylcarbonyl)thiazol-2-yl]acetamide (Compound 275)

In a manner similar to that in Example 264, by using 1-acetylpiperazine (332 mg, 2.58 mmol) in place of morpholine, the entitled Compound 275 (335 mg, 89%) was obtained as pale yellow crystals from Compound 262 (300 mg, 0.860 mmol) in place of Compound 263.

$^1$H NMR (DMSO-$d_6$, δ ppm): 1.99 (s, 3H), 2.53-2.61 (m, 2H), 3.27-3.35 (m, 2H), 3.40-3.51 (m, 4H), 3.42 (s, 2H), 6.62 (dd, J=1.9, 3.5 Hz, 1H), 7.43 (d, J=3.5 Hz, 1H), 7.62-7.71 (m, 1H), 7.69 (d, J=1.9 Hz, 1H), 8.05-8.11 (m, 2H), 8.67-8.71 (m, 1H).

APCIMS m/z: [M+H]$^+$ 440.

m.p.: 170-171° C.

Example 276

N-[4-(2-Furyl)-5-(pyridin-2-ylcarbonyl)thiazol-2-yl]-2-(4-phenylpiperazin-1-yl)acetamide (Compound 276)

In a manner similar to that in Example 264, by using 1-phenylpiperazine (0.40 mL, 2.58 mmol) in place of morpholine, the entitled Compound 276 (320 mg, 79%) was obtained as pale yellow crystals from Compound 262 (300 mg, 0.860 mmol) in place of Compound 263.

$^1$H NMR (DMSO-$d_6$, δ ppm): 2.66-2.74 (m, 4H), 3.13-3.21° (m, 4H), 3.43 (s, 2H), 6.61 (dd, J=1.9, 3.2 Hz, 1H), 6.78 (t, J=7.6 Hz, 1H), 6.94 (d, J=8.9 Hz, 2H), 7.21 (dd, J=7.6, 8.9 Hz, 2H), 7.40 (d, J=3.2 Hz, 1H), 7.62-7.69 (m, 2H), 8.05-8.09 (m, 2H), 8.66-8.70 (m, 1H).

APCIMS m/z: [M+H]$^+$ 474.

m.p.: 203-204° C.

Example 277

N-[4-(2-Furyl)-5-(pyridin-2-ylcarbonyl)thiazol-2-yl]-2-[4-(2-pyridyl)piperazin-1-yl]acetamide (Compound 277)

In a manner similar to that in Example 264, by using 1-(2-pyridyl)piperazine in place of morpholine, the entitled Compound 277 (346 mg, 85%) was obtained as pale yellow crystals from Compound 262 (300 mg, 0.860 mmol) in place of Compound 263.

$^1$H NMR (DMSO-$d_6$, δ ppm): 2.61-2.69 (m, 4H), 3.43 (s, 2H), 3.49-3.57 (m, 4H), 6.60-6.70 (m, 2H), 6.82 (d, J=8.9 Hz, 1H), 7.42 (d, J=3.5 Hz, 1H), 7.48-7.57 (m, 1H), 7.63-7.71 (m, 2H), 8.05-8.13 (m, 3H), 8.67-8.72 (m, 1H).

APCIMS m/z: [M+H]$^+$ 475.

m.p.: 215-218° C.

Example 278

N-[4-(2-Furyl)-5-(pyridin-2-ylcarbonyl)thiazol-2-yl]-2-[4-(2-pyrimidinyl)piperazin-1-yl]acetamide (Compound 278)

Compound 262 (300 mg, 0.860 mmol) was dissolved in THF (5.0 mL), and 1-(2-pyrimidinyl)piperazine (0.370 mL, 2.58 mmol) was added thereto, followed by stirring at room temperature for 16 hours. Further, 1-(2-pyrimidinyl)piperazine (0.370 mL, 2.58 mmol) was added to the reaction mixture, followed by stirring at room temperature for 2 hours. Water and aqueous saturated sodium bicarbonate solution were added to the reaction mixture, and the precipitated solid was collected by filtration. The resulting solid was purified through silica gel column chromatography (hexane:ethyl acetate=1:2) to afford the entitled Compound 278 (345 mg, 84%) as pale yellow crystals.

$^1$H NMR (DMSO-$d_6$, δ ppm): 2.55-2.65 (m, 4H), 3.43 (s, 2H), 3.73-3.82 (m, 4H), 6.62 (t, J=4.9 Hz, 1H), 6.62 (dd, J=1.9, 3.5 Hz, 1H), 7.42 (d, J=3.5 Hz, 1H), 7.63-7.70 (m, 1H), 7.68 (d, J=1.9 Hz, 1H), 8.05-8.10 (m, 2H), 8.36 (d, J=4.9 Hz, 2H), 8.67-8.71 (m, 1H), 12.60 (br s, 1H).

APCIMS m/z: [M+H]$^+$ 476.

m.p.: 199-200° C.

Example 279

N-[4-(2-Furyl)-5-(pyridin-2-ylcarbonyl)thiazol-2-yl]-2-[4-(tetrahydropyran-4-yl)piperazin-1-yl]acetamide (Compound 279)

In a manner similar to that in Example 264, by using tetrahydropyran-4-ylpiperazine (391 mg, 2.28 mmol) in place of morpholine, the entitled Compound 279 (267 mg, 73%) was obtained as pale yellow crystals from Compound 263 (300 mg, 0.760 mmol).

$^1$H NMR (DMSO-$d_6$, δ ppm): 1.28-1.47 (m, 2H), 1.64-1.76 (m, 2H), 2.22-2.66 (m, 7H), 3.14-3.42 (m, 6H), 3.82-3.92 (m, 2H), 6.62 (dd, J=1.6, 3.2 Hz, 1H), 7.42 (d, J=3.2 Hz, 1H), 7.63-7.71 (m, 2H), 8.02-8.11 (m, 2H), 8.66-8.70 (m, 1H).

APCIMS m/z: [M+H]$^+$ 482.

m.p.: 172-188° C.

Example 280

N-[4-(2-Furyl)-5-(pyridin-2-ylcarbonyl)thiazol-2-yl]-2-(1-methyl-2-oxopiperazin-4-yl)acetamide hydrochloride (Compound 280)

In a manner similar to that in Example 264, by using 1-methyl-2-oxopiperazine in place of morpholine, a free form of the entitled Compound (307 mg, 95%) was obtained as pale yellow crystals from Compound 263 (300 mg, 0.760 mmol). The resulting free form (250 mg, 0.588 mmol) was dissolved in ethanol (2.5 mL), a 4 mol/L solution of hydrogen chloride (0.16 mL, 0.647 mmol) in ethyl acetate was added thereto, followed by stirring at room temperature for 30 minutes. The precipitated solid was collected by filtration to afford the entitled Compound 280 (177 mg, 65%) as pale yellow crystals.

$^1$H NMR (DMSO-$d_6$, δ ppm): 2.89 (s, 3H), 3.38-3.69 (m, 4H), 3.84-3.90 (m, 2H), 4.22-4.32 (m, 2H), 6.64 (dd, J=1.9, 3.5 Hz, 1H), 7.48 (d, J=3.5 Hz, 1H), 7.65-7.75 (m, 2H), 8.05-8.15 (m, 2H), 8.68-8.73 (m, 1H).

APCIMS m/z: [M+H]$^+$ 426.

m.p.: 170-188° C.

Example 281

N-[4-(2-Furyl)-5-(pyridin-2-ylcarbonyl)thiazol-2-yl]-2-(1,3-thiazolidin-3-yl)acetamide (Compound 281)

In a manner similar to that in Example 264, by using 1,3-thiazolidine in place of morpholine, the entitled Compound 281 (288 mg, 83%) was obtained as pale yellow crystals from Compound 262 (300 mg, 0.860 mmol) in place of Compound 263.

$^1$H NMR (DMSO-$d_6$, δ ppm): 2.82-2.90 (m, 2H), 3.07-3.15 (m, 2H), 3.36-3.48 (m, 2H), 4.11 (s, 2H), 6.62 (dd, J=1.9, 3.5 Hz, 1H), 7.42 (d, J=3.5 Hz, 1H), 7.62-7.72 (m, 2H), 8.05-8.12 (m, 2H), 8.67-8.71 (m, 1H).

APCIMS m/z: [M+H]$^+$ 401.

m.p.: 153-155° C.

Example 282

N-[4-(2-Furyl)-5-(pyridin-2-ylcarbonyl)thiazol-2-yl]-2-thiomorpholinoacetamide (Compound 282)

In a manner similar to that in Example 264, by using thiomorpholine (0.240 mL, 2.58 mmol) in place of morpholine, the entitled Compound 282 (326 mg, 92%) was obtained as pale yellow crystals from Compound 262 (300 mg, 0.860 mmol) in place of Compound 263.

$^1$H NMR (DMSO-$d_6$, δ ppm): 2.60-2.69 (m, 4H), 2.78-2.86 (m, 4H), 3.41 (s, 2H), 6.62 (dd, J=1.9, 3.5 Hz, 1H), 7.42 (d, J=3.5 Hz, 1H), 7.62-7.72 (m, 2H), 8.02-8.10 (m, 2H), 8.66-8.71 (m, 1H).

APCIMS m/z: [M+H]$^+$ 415.

m.p.: 148-149° C.

Example 283

N-[4-(2-Furyl)-5-(6-methoxypyridin-2-ylcarbonyl)thiazol-2-yl]pyridine-4-carboxamide (Compound 283)

2-Bromo-6-methoxypyridine (0.274 mL, 2.23 mmol) was dissolved in THF (1 mL), and a 1.58 mol/L solution of n-butyllithium in n-hexane (1.42 mL, 2.23 mmol) was added thereto in a stream of argon at −78° C., followed by stirring for 15 minutes at −78° C. A solution of Compound 98 (200 mg, 0.558 mmol) in THF (2 mL) was added dropwise to the reaction mixture, followed by stirring at room temperature for 1.5 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:9) to afford the entitled Compound 283 (77.0 mg, 34%).

$^1$H NMR (DMSO-$d_6$, δ ppm): 4.02 (s, 3H), 6.66 (dd, J=1.7, 3.5 Hz, 1H), 7.15 (d, J=8.3 Hz, 1H), 7.51 (d, J=3.5 Hz, 1H), 7.74-7.77 (m, 2H), 7.98 (dd, J=8.3, 8.3 Hz, 1H), 8.03 (d, J=6.1 Hz, 2H), 8.83 (d, J=6.1 Hz, 2H), 13.49 (br s, 1H).

APCIMS m/z: [M+H]$^+$ 407.

m.p.: 247-250° C.

Example 284

N-[4-(2-Furyl)-5-(6-methylpyridin-2-ylcarbonyl)thiazol-2-yl]pyridine-4-carboxamide (Compound 284)

In a manner similar to that in Example 283, by using 2-bromo-6-methylpyridine in place of 2-bromo-6-methoxypyridine, the entitled Compound 284 (70.0 mg, 32%) was obtained from Compound 98 (200 mg, 0.558 mmol).

$^1$H NMR (DMSO-$d_6$, δ ppm): 2.56 (s, 3H), 6.64 (dd, J=1.7, 3.6 Hz, 1H), 7.44 (d, J=3.6 Hz, 1H), 7.52-7.55 (m, 1H), 7.71 (d, J=1.7 Hz, 1H), 7.89-7.99 (m, 2H), 8.05 (d, J=5.9 Hz, 2H), 8.84 (d, J=5.9 Hz, 2H), 13.49 (br s, 1H).

APCIMS m/z: [M+H]$^+$ 391.

m.p.: 238-241° C.

Example 285 tert-Butyl N-[4-(2-furyl)-5-(6-methylpyridin-2-ylcarbonyl)thiazol-2-yl]carbamate (Compound 285)

In a manner similar to that in Example 283, by using 2-bromo-6-methylpyridine in place of 2-bromo-6-methoxypyridine, the entitled Compound 285 (765 mg, 99%) was obtained from Compound 134 (707 mg, 2.00 mmol) in place of Compound 98.

$^1$H NMR (CDCl$_3$, δ ppm): 1.48 (s, 9H), 2.68 (s, 3H), 6.54 (dd, J=1.7, 3.3 Hz, 1H), 7.31 (d, J=7.6 Hz, 1H), 7.49 (d, J=1.7 Hz, 1H), 7.75 (t, J=7.6 Hz, 1H), 7.82 (d, J=3.3 Hz, 1H), 7.95 (d, J=7.6 Hz, 1H), 9.33 (br s, 1H).

Example 286

2-Amino-4-(2-furyl)thiazol-5-yl 6-methylpyridin-2-yl ketone (Compound 286)

In a manner similar to that in Example 186, by using Compound 285 (765 mg, 1.98 mmol) in place of Compound 185, the entitled Compound 286 (553 mg, 98%) was obtained.

$^1$H NMR (DMSO-$d_6$, δ ppm): 2.45 (s, 3H), 6.53 (dd, J=1.8, 3.3 Hz, 1H), 7.36 (d, J=3.3 Hz, 1H), 7.39-7.42 (m, 1H), 7.54 (d, J=1.8 Hz, 1H), 7.73-7.89 (m, 2H), 8.00 (br s, 2H).

Example 287

N-[4-(2-Furyl)-5-(6-methylpyridin-2-ylcarbonyl)thiazol-2-yl]-2-morpholinoacetamide (Compound 287)

Compound 286 (150 mg, 0.526 mmol) and triethylamine (0.367 mL, 2.63 mmol) were dissolved in THF (4 mL), and bromoacetyl bromide (0.206 mL, 2.37 mmol) was added thereto at 0° C., followed by stirring for 1 hour at room temperature. Further, a solution (2 mL) of morpholine (0.689 mL, 7.89 mmol) and triethylamine (1.10 mL, 7.89 mmol) in THF was added thereto at 0° C., followed by stirring for 1 hour at room temperature. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography to afford the entitled Compound 287 (150 mg, 69%).

$^1$H NMR (DMSO-$d_6$, δ ppm): 2.51 (s, 3H), 2.54 (t, J=4.6 Hz, 4H), 3.36 (s, 2H), 3.62 (t, J=4.6 Hz, 4H), 6.61 (dd, J=1.7, 3.5 Hz, 1H), 7.38 (d, J=3.5 Hz, 1H), 7.51 (d, J=7.6 Hz, 1H), 7.66 (d, J=1.7 Hz, 1H), 7.85-7.97 (m, 2H), 12.5 (br s, 1H).

APCIMS m/z: [M+H]$^+$ 413.

Example 288

N-[4-(2-Furyl)-5-(6-methylpyridin-2-ylcarbonyl)thiazol-2-yl]-2-(4-hydroxypiperidino)acetamide (Compound 288)

In a manner similar to that in Example 287, by using 4-hydroxypiperidine in place of morpholine, the entitled Compound 288 (143 mg, 64%) was obtained from Compound 286 (150 mg, 0.526 mmol).

$^1$H NMR (CDCl$_3$, δ ppm): 1.65-1.78 (m, 2H), 1.95-2.05 (m, 2H), 2.41-2.50 (m, 2H), 2.69 (s, 3H), 2.80-2.88 (m, 2H), 3.29 (s, 2H), 3.79-3.85 (m, 1H), 6.58 (dd, J=1.7, 3.5 Hz, 1H), 7.33 (d, J=7.9 Hz, 1H), 7.56 (dd, J=0.7, 1.7 Hz, 1H), 7.77 (dd, J=7.9, 7.9 Hz, 1H), 7.85 (dd, J=0.7, 3.5 Hz, 1H), 7.98 (d, J=7.9 Hz, 1H).

APCIMS m/z: [M+H]$^+$ 427.

Example 289

N-[4-(2-Furyl)-5-(6-methylpyridin-2-ylcarbonyl)thiazol-2-yl]-2-(4-methylpiperazin-1-yl)acetamide dihydrochloride (Compound 289)

In a manner similar to that in Example 287, by using 1-methylpiperazine in place of morpholine, a free form of the entitled Compound 290 was obtained from Compound 286 (150 mg, 0.526 mmol). The resulting free form was dissolved in acetone (3 mL), and an ethyl acetate solution of 4 mol/L hydrogen chloride (0.394 mL, 1.58 mmol) was added thereto. The precipitated solid was collected by filtration to afford the entitled Compound 289 (163 mg, 62%).

$^1$H NMR (DMSO-$d_6$, δ ppm): 2.52 (s, 3H), 2.77 (s, 2H), 2.79 (s, 3H), 2.93-3.89 (m, 8H), 6.62 (dd, J=1.7, 3.3 Hz, 1H), 7.41 (d, J=3.3 Hz, 1H), 7.51-7.54 (m, 1H), 7.68 (d, J=1.7 Hz, 1H), 7.87-7.98 (m, 2H).

APCIMS m/z: [M+H]$^+$ 426.

Example 290

2-(4-Ethylpiperazin-1-yl)-N-[4-(2-furyl)-5-(6-methylpyridin-2-ylcarbonyl)thiazol-2-yl]acetamide dihydrochloride (Compound 290)

In a manner similar to that in Example 287, by using 1-ethylpiperazine in place of morpholine, a free form of the entitled Compound 289 was obtained from Compound 286 (100 mg, 0.350 mmol). The resulting free form was dissolved in acetone (3 mL), and a 4 mol/L solution of hydrogen chloride (0.263 mL, 1.05 mmol) in ethyl acetate was added thereto. The precipitated solid was collected by filtration to afford the entitled Compound 290 (89.0 mg, 49%).

$^1$H NMR (DMSO-$d_6$, δ ppm): 1.23-1.28 (m, 3H), 2.52 (s, 3H), 3.05-3.81 (m, 12H), 6.63 (dd, J=1.8, 3.3 Hz, 1H), 7.41 (d, J=3.3 Hz, 1H), 7.52-7.54 (m, 1H), 7.68 (d, J=1.8 Hz, 1H), 7.87-7.98 (m, 2H).

APCIMS m/z: [M+H]$^+$ 440.

Example 291

2-(4-Acetylpiperazin-1-yl)-N-[4-(2-furyl)-5-(6-methylpyridin-2-ylcarbonyl)thiazol-2-yl]acetamide (Compound 291)

In a manner similar to that in Example 287, by using 1-acetylpiperazine in place of morpholine, the entitled Compound 291 (136 mg, 86%) was obtained as pale yellow crystals from Compound 286 (100 mg, 0.350 mmol).

$^1$H NMR (CDCl$_3$, δ ppm): 2.12 (s, 3H), 2.70 (s, 3H), 2.59-2.64 (m, 4H), 3.33 (s, 2H), 3.56-3.74 (m, 4H), 6.58 (dd, J=1.7, 3.5 Hz, 1H), 7.34 (d, J=7.7 Hz, 1H), 7.57 (d, J=1.7 Hz, 1H), 7.78 (dd, J=7.7, 7.7 Hz, 1H), 7.88 (d, J=3.5 Hz, 1H), 7.99 (d, J=7.7 Hz, 1H), 10.39 (br s, 1H).

APCIMS m/z: [M+H]$^+$ 454.

Example 292

N-[4-(2-Furyl)-5-(6-methylpyridin-2-ylcarbonyl)thiazol-2-yl]-2-[4-(2-pyridyl)piperazin-1-yl]acetamide (Compound 292)

In a manner similar to that in Example 287, by using 1-(2-pyridyl)piperazine in place of morpholine, the entitled Compound 292 (104 mg, 61%) was obtained as pale yellow crystals from Compound 286 (100 mg, 0.350 mmol).

$^1$H NMR (DMSO-$d_6$, δ ppm): 2.70 (s, 3H), 2.74 (t, J=5.1 Hz, 4H), 3.36 (s, 2H), 3.66 (t, J=5.1 Hz, 4H), 6.57 (dd, J=1.7, 3.5 Hz, 1H), 6.65-6.68 (m, 2H), 7.34 (d, J=7.8 Hz, 1H), 7.48-7.54 (m, 1H), 7.55 (d, J=1.7 Hz, 1H), 7.77 (t, J=7.8 Hz, 1H), 7.85 (d, J=3.5 Hz, 1H), 7.99 (d, J=7.8 Hz, 1H), 8.20-8.22 (m, 1H), 10.45 (br s, 1H).

APCIMS m/z: [M+H]$^+$ 489.

Example 293

N-[4-(2-Furyl)-5-(6-methylpyridin-2-ylcarbonyl)thiazol-2-yl]-2-(4-morpholinopiperidino)acetamide (Compound 293)

In a manner similar to that in Example 287, by using 4-morpholinopiperidine in place of morpholine, the entitled Compound 293 (157 mg, 90%) was obtained as pale yellow crystals from Compound 286 (100 mg, 0.350 mmol).

$^1$H NMR (CDCl$_3$, δ ppm): 1.58-1.87 (m, 5H), 2.28-2.36 (m, 2H), 2.57 (t, J=4.5 Hz, 4H), 2.69 (s, 3H), 2.94-2.98 (m, 2H), 3.27 (s, 2H), 3.74 (t, J=4.5 Hz, 4H), 6.57 (dd, J=1.7, 3.5 Hz, 1H), 7.33 (d, J=7.8 Hz, 1H), 7.56 (d, J=1.7 Hz, 1H), 7.77 (dd, J=7.8, 7.8 Hz, 1H), 7.84 (d, J=3.5 Hz, 1H), 7.98 (d, J=7.8 Hz, 1H).

APCIMS m/z: [M+H]$^+$ 496.

Example 294

N-[4-(2-Furyl)-5-(5-methylpyridin-2-ylcarbonyl)thiazol-2-yl]pyridine-4-carboxamide (Compound 294)

In a manner similar to that in Example 283, by using 2-bromo-5-methylpyridine in place of 2-bromo-6-methoxypyridine, the entitled Compound 294 (128 mg, 59%) was obtained from Compound 98 (200 mg, 0.558 mmol).

¹H NMR (DMSO-d₆, δ ppm): 2.43 (s, 3H), 6.66 (dd, J=1.7, 3.5 Hz, 1H), 7.49 (dd, J=0.7, 3.5 Hz, 1H), 7.76 (dd, J=0.7, 1.7 Hz, 1H), 7.88-7.92 (m, 1H), 8.03-8.06 (m, 3H), 8.59-8.60 (m, 1H), 8.84 (d, J=6.1 Hz, 2H).
APCIMS m/z: [M+H]⁺ 391.
m.p.: 255-257° C.

Example 295

N-[4-(2-Furyl)-5-(4-methylpyridin-2-ylcarbonyl) thiazol-2-yl]pyridine-4-carboxamide (Compound 295)

In a manner similar to that in Example 283, by using 2-bromo-4-methylpyridine in place of 2-bromo-6-methoxypyridine, the entitled Compound 295 (50.0 mg, 23%) was obtained from Compound 98 (200 mg, 0.558 mmol).
¹H NMR (DMSO-d₆, δ ppm): 2.46 (s, 3H), 6.65 (dd, J=1.7, 3.5 Hz, 1H), 7.48 (dd, J=0.7, 3.5 Hz, 1H), 7.52 (d, J=4.8 Hz, 1H), 7.75 (dd, J=0.7, 1.7 Hz, 1H), 7.96 (s, 1H), 8.05 (d, J=6.1 Hz, 2H), 8.59 (d, J=4.8 Hz, 1H), 8.84 (d, J=6.1 Hz, 2H), 13.49 (br s, 1H).
APCIMS m/z: [M+H]⁺ 391.
m.p.: 240-245° C.

Example 296 tert-Butyl N-[4-(2-furyl)-5-[1-hydroxy-1-(5-methoxypyridin-2-yl)methyl]thiazol-2-yl]carbamate (Compound 296)

In a manner similar to that in Example 92, by using Compound z (1.11 g, 8.00 mmol) obtained in Reference Example 26 in place of DMF, the entitled Compound 296 (697 mg, 43%) was obtained from Compound h (1.38 g, 4.00 mmol).
¹H NMR (CDCl₃, δ ppm): 1.42 (s, 9H), 3.86 (s, 3H), 5.29 (d, J=4.3 Hz, 1H), 6.48 (dd, J=1.9, 3.5 Hz, 1H), 6.59 (d, J=4.3 Hz, 1H), 6.77 (dd, J=0.8, 3.5 Hz, 1H), 7.15 (dd, J=2.7, 8.7 Hz, 1H), 7.21 (d, J=8.7 Hz, 1H), 7.47 (dd, J=0.8, 1.9 Hz, 1H), 8.28 (d, J=2.7 Hz, 1H), 9.24 (br s, 1H).

Example 297 tert-Butyl N-[4-(2-furyl)-5-(5-methoxypyridin-2-ylcarbonyl)thiazol-2-yl]carbamate (Compound 297)

Compound 296 (697 mg, 1.73 mmol) was dissolved in dichloromethane (10 mL), and DMP (848 mg, 2.00 mmol) was added thereto, followed by stirring at room temperature for 1 hour. Methanol (10 mL) was added to the reaction mixture, followed by stirring for 10 minutes, and the solvent was distilled away under reduced pressure. The resulting residue was purified through silica gel column chromatography (hexane:ethyl acetate=1:1) to afford the entitled Compound 297 (632 mg, 91%).
¹H NMR (CDCl₃, δ ppm): 1.57 (s, 9H), 3.95 (s, 3H), 6.54 (dd, J=1.6, 3.4 Hz, 1H), 7.32 (dd, J=3.0, 8.8 Hz, 1H), 7.51 (dd, J=0.8, 1.6 Hz, 1H), 7.70 (dd, J=0.8, 3.4 Hz, 1H), 8.18 (dd, J=0.7, 8.8 Hz, 1H), 8.39 (dd, J=0.7, 3.0 Hz, 1H).

Example 298

2-Amino-4-(2-furyl)thiazol-5-yl 5-methoxypyridin-2-yl ketone (Compound 298)

In a manner similar to that in Example 186, the entitled Compound 298 (269 mg, 51%) was obtained from Compound 297 (697 mg, 1.74 mmol) in place of Compound 185.
¹H NMR (DMSO-d₆, δ ppm): 3.91 (s, 3H), 6.56 (dd, J=1.7, 3.5 Hz, 1H), 7.44 (dd, J=0.7, 3.5 Hz, 1H), 7.56 (dd, J=3.0, 8.7 Hz, 1H), 7.63 (dd, J=0.7, 1.7 Hz, 1H), 7.92 (br s, 2H), 8.02 (d, J=9.2 Hz, 1H), 8.26 (d, J=3.0 Hz, 1H).

Example 299

N-[4-(2-Furyl)-5-(5-methoxypyridin-2-ylcarbonyl) thiazol-2-yl]pyridine-4-carboxamide (Compound 299)

In a manner similar to that in Example 187, a crude Compound 299 was obtained from Compound 298 (250 mg, 0.831 mmol) in place of Compound 186. The resulting crude Compound 299 was recrystallized from ethanol to afford the entitled Compound 299 (133 mg, 40%).
¹H NMR (DMSO-d₆, δ ppm): 3.97 (s, 3H), 6.64 (dd, J=1.8, 3.5 Hz, 1H), 7.43 (d, J=3.5 Hz, 1H), 7.64 (dd, J=3.0, 8.8 Hz, 1H), 7.75 (d, J=1.8 Hz, 1H), 8.05 (dd, J=1.7, 4.5 Hz, 2H), 8.15 (d, J=8.8 Hz, 1H), 8.43 (d, J=3.0 Hz, 1H), 8.84 (dd, J=1.7, 4.5 Hz, 2H), 13.46 (br s, 1H).

Example 300

N-[5-(6-Bromopyridin-2-ylcarbonyl)-4-(2-furyl) thiazol-2-yl]pyridine-4-carboxamide (Compound 300)

A THF solution (10 mL) of 2,6-dibromopyridine (4.97 g, 21.0 mmol) was added to a 2.0 mol/L solution of isopropylmagnesium chloride in THF (9.56 mL, 10.1 mmol) at 0° C., followed by stirring for 3 hours at room temperature. A THF solution (5 mL) of Compound 98 (1.37 g, 3.82 mmol) was added dropwise to the reaction mixture, followed by stirring for 3 hours at room temperature. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=9:1) to afford the entitled Compound 300 (520 mg, 31%).

Example 301

N-[4-(2-Furyl)-5-(6-morpholinopyridin-2-ylcarbonyl)thiazol-2-yl]pyridin-4-ylcarboxamide (Compound 301)

Compound 300 (133 mg, 0.300 mmol) was suspended in 1,4-dioxane (2 mL), and morpholine (0.525 mL, 6.00 mmol) was added thereto, followed by stirring under heating and reflux for 5 hours. The reaction mixture was purified through silica gel column chromatography (chloroform:methanol=9:1) to afford the entitled Compound 301 (31.0 mg, 23%) as a brown solid.
¹H NMR (DMSO-d₆, δ ppm): 3.60-3.64 (m, 4H), 3.75-3.79 (m, 4H), 6.66 (dd, J=1.6, 3.5 Hz, 1H), 7.15 (d, J=8.6 Hz, 1H), 7.43 (d, J=7.3 Hz 1H), 7.55 (d, J=3.5 Hz, 1H), 7.78 (d, J=1.6 Hz, 1H), 7.81 (dd, J=7.3, 8.6 Hz, 1H), 8.04 (dd, J=0.8, 5.4 Hz, 2H), 8.83 (dd, J=0.8, 5.4 Hz, 2H), 13.47 (br s, 1H).
APCIMS m/z: [M+H]⁺ 450.
m.p.: 258-262° C.

Example 302 tert-Butyl N-[4-(2-furyl)-5-(pyridin-3-ylcarbonyl)thiazol-2-yl]carbamate (Compound 302)

In a manner similar to that in Example 185, by using nicotinic acid in place of picolinic acid, the entitled Compound 302 (102 mg, 19%) was obtained from Compound h (500 mg, 1.45 mmol) obtained in Reference Example 8.

$^1$H NMR (CDCl$_3$, δ ppm): 1.51 (s, 9H), 6.25 (dd, J=1.9, 3.4 Hz, 1H), 6.68 (d, J=3.4 Hz, 1H), 7.03 (d, J=1.9 Hz, 1H), 7.37 (dd, J=4.9, 7.9 Hz, 1H), 8.12 (dd, J=1.9, 7.9 Hz, 1H), 8.65 (dd, J=1.9, 4.9 Hz, 1H), 9.10 (s, 1H), 10.32 (br s, 1H).

Example 303

2-Amino-4-(2-furyl)thiazol-5-yl 3-pyridyl ketone (Compound 303)

In a manner similar to that in Example 186, the entitled Compound 303 (75.0 mg, 100%) was obtained from Compound 302 (102 mg, 0.275 mmol) in place of Compound 185.

$^1$H NMR (CDCl$_3$, δ ppm): 6.32 (dd, J=1.8, 3.3 Hz, 1H), 6.91 (d, J=3.3 Hz, 1H), 7.10 (d, J=1.8 Hz, 1H), 7.27-7.31 (m, 1H), 7.93-7.96 (m, 1H), 8.62-8.64 (m, 1H), 8.83-8.84 (m, 1H).

Example 304

N-[4-(2-Furyl)-5-(pyridin-3-ylcarbonyl)thiazol-2-yl]pyridine-4-carboxamide (Compound 304)

In a manner similar to that in Example 187, the entitled Compound 304 (69.0 mg, 57%) was obtained from Compound 303 (75.0 mg, 0.276 mmol) in place of Compound 186.

$^1$H NMR (DMSO-d$_6$, δ ppm): 6.50 (dd, J=1.8, 3.5 Hz, 1H), 6.97 (d, J=3.5 Hz, 1H), 7.46 (d, J=1.8 Hz, 1H), 7.44-7.48 (m, 1H), 8.01-8.06 (m, 1H), 8.02 (d, J=6.2 Hz, 2H), 8.04-8.07 (m, 1H), 8.70-8.72 (m, 1H), 8.80-8.81 (m, 1H), 8.83 (d, J=6.2 Hz, 2H).

APCIMS m/z: [M+H]$^+$ 377.

m.p.: 245-248° C.

Example 305

N-[4-(2-Furyl)-5-(pyridin-3-ylcarbonyl)thiazol-2-yl]cyclopropanecarboxamide (Compound 305)

In a manner similar to that in Example 188, by using cyclopropanecarbonyl chloride (109 mg, 1.04 mmol) in place of acetyl chloride, the entitled Compound 305 (33.2 mg, 20%) was obtained from Compound 303 (131 mg, 0.482 mmol) in place of Compound 186.

$^1$H NMR (CDCl$_3$, δ ppm): 0.92-0.98 (m, 2H), 1.15-1.19 (m, 2H), 1.50-1.59 (m, 1H), 6.30-6.31 (m, 1H), 6.80 (s, 1H), 7.12 (s, 1H), 7.41 (dd, J=4.8, 8.0 Hz, 1H), 8.17 (dd, J=1.5, 8.0 Hz, 1H), 8.70 (dd, J=1.5, 4.8 Hz, 1H), 9.14 (s, 1H).

ESIMS m/z: [M+H]$^+$ 340.

m.p.: 231-233° C.

Example 306

4-Cyano-N-[4-(2-furyl)-5-(pyridin-3-ylcarbonyl)thiazol-2-yl]benzamide (Compound 306)

In a manner similar to that in Example 187, by using 4-cyanobenzoic acid (344 mg, 2.34 mmol) in place of isonicotinic acid, the entitled Compound 306 (33.8 mg, 22%) was obtained from Compound 303 (106 mg, 0.390 mmol) in place of Compound 186.

$^1$H NMR (DMSO-d$_6$, δ ppm): 6.51 (dd, J=1.7, 3.2 Hz, 1H), 6.98 (d, J=3.2 Hz, 1H), 7.45-7.49 (m, 2H), 8.04-8.05 (m, 1H), 8.06 (d, J=8.1 Hz, 2H), 8.28 (d, J=8.1 Hz, 2H), 8.71 (d, J=4.8 Hz, 1H), 8.80-8.81 (m, 1H).

ESIMS m/z: [M+H]$^+$ 401.

m.p.: 288-290° C.

Example 307

N-[4-(2-Furyl)-5-(pyridin-3-ylcarbonyl)thiazol-2-yl]furan-2-carboxamide (Compound 307)

In a manner similar to that in Example 188, by using 2-furoyl chloride (75.5 mL, 0.766 mmol) in place of acetyl chloride, the entitled Compound 307 (20.7 mg, 13%) was obtained from Compound 303 (116 mg, 0.428 mmol) in place of Compound 186.

$^1$H NMR (DMSO-d$_6$, δ ppm): 6.50 (dd, J=2.0, 3.3 Hz, 1H), 6.78 (dd, J=1.6, 3.5 Hz, 1H), 6.96 (d, J=3.5 Hz, 1H), 7.43-7.48 (m, 2H), 7.79 (s, 1H), 8.03 (d, J=7.9 Hz, 1H), 8.07 (s, 1H), 8.70 (dd, J=1.6, 4.9 Hz, 1H), 8.80 (d, J=2.2 Hz, 1H), 13.34 (br s, 1H).

ESIMS m/z: [M+H]$^+$ 366.

m.p.: 234-236° C.

Example 308 tert-Butyl N-[4-(2-furyl)-5-(2-methylpyridin-3-ylcarbonyl)thiazol-2-yl]carbamate (Compound 308)

Compound h (500 mg, 1.45 mmol) obtained in Reference Example 8 was dissolved in THF (7.5 mL), and a 1.58 mol/L solution of n-butyllithium in n-hexane (2.02 mL, 3.19 mmol) was added thereto in a stream of argon at −78° C., followed by stirring at −78° C. for 15 minutes. Ethyl 2-methylnicotinate (723 mg, 4.35 mmol) was added dropwise to the reaction mixture, followed by stirring at room temperature for 1.5 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 308 (83.0 mg, 15%).

$^1$H NMR (CDCl$_3$, δ ppm): 1.43 (s, 9H), 2.61 (s, 3H), 6.41 (dd, J=1.8, 3.5 Hz, 1H), 7.05-7.10 (m, 1H), 7.24 (d, J=1.8 Hz, 1H), 7.40 (d, J=3.5 Hz, 1H), 7.57-7.60 (m, 1H), 8.52-8.54 (m, 1H).

Example 309

2-Amino-4-(2-furyl)thiazol-5-yl 2-methylpyridin-3-yl ketone (Compound 309)

Compound 308 (83.0 mg, 0.215 mmol) was dissolved in trifluoroacetic acid (1 mL), followed by stirring at room temperature for 1 hour. The reaction mixture was concentrated under reduced pressure, and ethyl acetate and a saturated aqueous solution of sodium hydrogencarbonate were added to the resulting residue, and the organic layer was separated. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:4) to afford the entitled Compound 309 (60.0 mg, 99%).

$^1$H NMR (CDCl$_3$, δ ppm): 2.53 (s, 3H), 6.12-6.14 (m, 1H), 6.93-7.05 (m, 2H), 7.44-7.47 (m, 1H), 8.19-8.21 (m, 1H), 8.51-8.54 (m, 1H).

Example 310

N-[4-(2-Furyl)-5-(2-methylpyridin-3-ylcarbonyl) thiazol-2-yl]pyridine-4-carboxamide (Compound 310)

In a manner similar to that in Example 187, the entitled Compound 310 (42.0 mg, 50%) was obtained from Compound 309 (60.0 mg, 0.215 mmol) in place of Compound 186.

$^1$H NMR (DMSO-d$_6$, δ ppm): 2.53 (s, 3H), 6.53 (dd, J=1.7, 3.5 Hz, 1H), 7.15 (dd, J=0.7, 3.5 Hz, 1H), 7.21 (dd, J=4.8, 7.7 Hz, 1H), 7.55 (dd, J=0.7, 1.7 Hz, 1H), 7.75 (dd, J=1.8, 7.7 Hz, 1H), 8.01 (d, J=6.1 Hz, 2H), 8.53 (dd, J=1.8, 4.8 Hz, 1H), 8.84 (d, J=6.1 Hz, 2H), 13.7 (br s, 1H).

APCIMS m/z: [M+H]$^+$ 391.

m.p.: 230-234° C.

Example 311 tert-Butyl N-[4-(2-furyl)-5-(2-methylpyridin-5-ylcarbonyl)thiazol-2-yl]carbamate (Compound 311)

In a manner similar to that in Example 185, by using 6-methylnicotinic acid in place of picolinic acid, the entitled Compound 311 (1.44 g, 73%) was obtained from Compound h (1.77 g, 5.13 mmol) obtained in Reference Example 8.

$^1$H NMR (CDCl$_3$, δ ppm): 1.49 (s, 9H), 3.31 (s, 3H), 6.48 (dd, J=1.7, 3.3 Hz, 1H), 6.91 (d, J=3.3 Hz, 1H), 7.29 (d, J=8.3 Hz, 1H), 7.46 (d, J=1.7 Hz, 1H), 7.89 (dd, J=2.3, 8.3 Hz, 1H), 8.65 (d, J=2.3 Hz, 1H), 12.2 (br s, 1H).

Example 312

2-Amino-4-(2-furyl)thiazol-5-yl 2-methylpyridin-5-yl ketone (Compound 312)

In a manner similar to that in Example 186, the entitled Compound 312 (1.04 g, 100%) was obtained from Compound 311 (1.41 g, 3.66 mmol) in place of Compound 185.

$^1$H NMR (DMSO-d$_6$, δ ppm): 2.45 (s, 3H), 6.41 (dd, J=1.7, 3.3 Hz, 1H), 6.79 (d, J=3.3 Hz, 1H), 7.20 (d, J=7.9 Hz, 1H), 7.32 (d, J=1.7 Hz, 1H), 7.75 (dd, J=2.3, 7.9 Hz, 1H), 8.51 (d, J=2.3 Hz, 1H).

Example 313

N-[4-(2-Furyl)-5-(2-methylpyridin-5-ylcarbonyl) thiazol-2-yl]pyridine-4-carboxamide (Compound 313)

Compound 312 (200 mg, 0.701 mmol) was dissolved in DMF (3.5 mL), and isonicotinic acid (259 mg, 2.10 mmol), EDC hydrochloride (403 mg, 2.10 mmol) and 1-hydroxybenzotriazole monohydrate (322 mg, 2.10 mmol) were added thereto, followed by stirring at 60° C. for 3 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was recrystallized from 2-propanol to afford the entitled Compound 313 (170 mg, 62%).

$^1$H NMR (DMSO-d$_6$, δ ppm): 2.51 (s, 3H), 6.52 (dd, J=1.8, 3.5 Hz, 1H), 6.97 (dd, J=0.7, 3.5 Hz, 1H), 7.32 (d, J=8.1 Hz, 1H), 7.50 (dd, J=0.7, 1.8 Hz, 1H), 7.95 (dd, J=2.3, 8.1 Hz, 1H), 8.02 (d, J=6.1 Hz, 2H), 8.70 (d, J=2.3 Hz, 1H), 8.83 (d, J=6.1 Hz, 2H), 13.6 (s, 1H).

APCIMS m/z: [M+H]$^+$ 391.

m.p.: 230-232° C. (decomposition)

Example 314

4-Cyano-N-[4-(2-furyl)-5-(2-methylpyridin-5-ylcarbonyl)thiazol-2-yl]benzamide (Compound 314)

In a manner similar to that in Example 313, by using 4-cyanobenzoic acid in place of isonicotinic acid, the entitled Compound 314 (253 mg, 72%) was obtained from Compound 312 (242 mg, 0.848 mmol).

$^1$H NMR (DMSO-d$_6$, δ ppm): 2.51 (s, 3H), 6.52 (dd, J=1.7, 3.5 Hz, 1H), 6.97 (dd, J=0.8, 3.5 Hz, 1H), 7.32 (d, J=8.1 Hz, 1H), 7.51 (dd, J=0.8, 1.7 Hz, 1H), 7.95 (dd, J=2.3, 8.1. Hz, 1H), 8.06 (d, J=8.4 Hz, 2H), 8.26 (d, J=8.4 Hz, 2H), 8.70 (d, J=2.3 Hz, 1H), 13.6 (br s, 1H).

APCIMS m/z: [M+H]$^+$ 415.

m.p.: 261-265° C.

Example 315

N-[4-(2-Furyl)-5-(2-methylpyridin-5-ylcarbonyl) thiazol-2-yl]furan-2-carboxamide (Compound 315)

In a manner similar to that in Example 313, by using 2-furancarboxylic acid in place of isonicotinic acid, the entitled Compound 315 (155 mg, 52. %) was obtained from Compound 312 (200 mg, 0.701 mmol).

$^1$H NMR (DMSO-d$_6$, δ ppm): 2.51 (s, 3H), 6.50 (dd, J=1.8, 3.3 Hz, 1H), 6.76 (dd, J=1.8, 3.5 Hz, 1H), 6.94 (d, J=3.3 Hz, 1H), 7.30 (d, J=8.1 Hz, 1H), 7.48 (d, J=1.8 Hz, 1H), 7.77 (d, J=3.5 Hz, 1H), 7.92 (dd, J=2.1, 8.1 Hz, 1H), 8.05 (d, J=1.8 Hz, 1H), 8.68 (d, J=2.1 Hz, 1H), 13.3 (br s, 1H).

APCIMS m/z: [M+H]$^+$ 380.

m.p.: 197-209° C.

Example 316

N-[4-(2-Furyl)-5-(2-methylpyridin-5-ylcarbonyl) thiazol-2-yl]furan-3-carboxamide (Compound 316)

In a manner similar to that in Example 313, by using 3-furancarboxylic acid in place of isonicotinic acid, the entitled Compound 316 (102 mg, 27%) was obtained from Compound 312 (200 mg, 0.701 mmol).

$^1$H NMR (DMSO-d$_6$, δ ppm): 2.47 (s, 3H), 6.50 (dd, J=1.8, 3.5 Hz, 1H), 6.94 (d, J=3.5 Hz, 1H), 7.11-7.12 (m, 1H), 7.30 (d, J=8.1 Hz, 1H), 7.47 (d, J=1.8 Hz, 1H), 7.84-7.86 (m, 1H), 7.92 (dd, J=2.3, 8.1 Hz, 1H), 8.63-8.64 (m, 1H), 8.67 (d, J=2.3 Hz, 1H).

APCIMS m/z: [M+H]$^+$ 380.

m.p.: 229-231° C.

Example 317 tert-Butyl N-[4-(2-furyl)-5-(2-methoxypyridin-5-ylcarbonyl)thiazol-2-yl]carbamate (Compound 317)

In a manner similar to that in Example 283, by using 5-bromo-2-methoxypyridine in place of 2-bromo-6-methoxypyridine, the entitled Compound 317 (2.09 g, 83%) was obtained from Compound 134 (2.49 g, 7.05 mmol) in place of Compound 98.

$^1$H NMR (CDCl$_3$, δ ppm): 1.47 (s, 9H), 3.99 (s, 3H), 6.39 (dd, J=1.8, 3.3 Hz, 1H), 6.74 (dd, J=0.9, 8.4 Hz, 1H), 6.98 (d, J=0.6, 3.3 Hz, 1H), 7.23 (dd, J=0.9, 2.4 Hz, 1H), 8.02 (dd, J=2.4, 8.4 Hz, 1H), 8.66 (dd, J=0.6, 1.8 Hz, 1H), 9.48 (br s, 1H).

APCIMS m/z: [M+H]$^+$ 402.

Example 318

2-Amino-4-(2-furyl)thiazol-5-yl 2-methoxypyridin-5-yl ketone (Compound 318)

In a manner similar to that in Example 186, the entitled Compound 318 (1.51 g, 86%) was obtained as a pale yellow solid from Compound 317 (2.09 g, 5.85 mmol) in place of Compound 185.

$^1$H NMR (DMSO-d$_6$, δ ppm): 3.85 (s, 3H), 6.43 (dd, J=1.6, 3.2 Hz, 1H), 6.74 (d, J=8.7 Hz, 1H), 6.77 (d, J=3.2 Hz, 1H), 7.37 (d, J=1.6 Hz, 1H), 7.81 (dd, J=2.4, 8.7 Hz, 1H), 8.03 (br s, 2H), 8.32 (d, J=2.4 Hz, 1H).

APCIMS m/z: [M+H]$^+$ 302.

Example 319

N-[4-(2-Furyl)-5-(2-methoxypyridin-5-ylcarbonyl)thiazol-2-yl]pyridine-4-carboxamide (Compound 319)

In a manner similar to that in Example 283, by using 5-bromo-2-methoxypyridine in place of 2-bromo-6-methoxypyridine, followed by reslurrying with methanol, the entitled Compound 319 (44.5 mg, 20%) was obtained as a brown solid from Compound 98 (200 mg, 0.558 mmol).

$^1$H NMR (DMSO-d$_6$, δ ppm): 3.91 (s, 3H), 6.54 (dd, J=1.9, 3.5 Hz, 1H), 6.87 (dd, J=0.8, 8.4 Hz, 1H), 6.95 (dd, J=0.8, 3.5 Hz, 1H), 7.54 (dd, J=0.8, 1.9 Hz, 1H), 8.01 (dd, J=2.7, 8.4 Hz, 1H), 8.03 (dd, J=1.3, 5.4 Hz, 2H), 8.52 (dd, J=0.8, 2.7 Hz, 1H), 8.81 (dd, J=1.3, 5.4 Hz, 2H), 13.60 (br s, 1H).

APCIMS m/z: [M+H]$^+$ 407.

m.p.: 246-257° C. (decomposition)

Example 320 tert-Butyl N-[5-(2-chloropyridin-5-ylcarbonyl)-4-(2-furyl)thiazol-2-yl]carbamate (Compound 320)

In a manner similar to that in Example 176, by using 6-chloronicotinic acid in place of 2-cyanobenzoic acid, the entitled Compound 320 (1.65 g, 41%) was obtained from Compound h (3.45 g, 10.0 mmol) obtained in Reference Example 8.

$^1$H NMR (CDCl$_3$, δ ppm): 1.53 (s, 9H), 6.41 (dd, J=1.9, 3.5 Hz, 1H), 7.02 (dd, J=0.5, 3.5 Hz, 1H), 7.21 (dd, J=0.5, 1.9 Hz, 1H), 7.34 (dd, 0.5, 8.1 Hz, 1H), 7.98 (dd, J=2.4, 8.1 Hz, 1H), 8.59 (br s, 1H), 8.71 (dd, J=0.5, 2.4 Hz, 1H).

Example 321

2-Amino-4-(2-furyl)thiazol-5-yl 2-chloropyridin-5-yl ketone (Compound 322)

In a manner similar to that in Example 186, the entitled Compound 321 (752 mg, 100%) was obtained from Compound 320 (1.00 g, 2.46 mmol) in place of Compound 185.

$^1$H NMR (DMSO-d$_6$, δ ppm): 6.45 (dd, J=1.6, 3.2 Hz, 1H), 6.79 (d, J=3.2 Hz, 1H), 7.35 (d, J=1.6 Hz, 1H), 7.47 (d, J=8.1 Hz, 1H), 7.90 (dd, J=2.2, 8.1 Hz, 1H), 8.22 (br s, 2H), 8.45 (d, J=2.2 Hz, 1H).

APCIMS m/z: [M+H]$^+$ 306.

Example 322

N-[5-(2-Chloropyridin-5-ylcarbonyl)-4-(2-furyl)thiazol-2-yl]pyridine-4-carboxamide (Compound 322)

In a manner similar to that in Example 187, the entitled Compound 322 (920 mg, 91%) was obtained as a yellow solid from Compound 321 (750 mg, 2.46 mmol) in place of Compound 186.

$^1$H NMR (DMSO-d$_6$, δ ppm): 6.54 (dd, J=1.6, 3.2 Hz, 1H), 6.93 (d, J=1.6 Hz, 1H), 7.50-7.56 (m, 2H), 7.67-7.69 (m, 1H), 8.02 (d, J=6.0 Hz, 2H), 8.33-8.35 (m, 1H), 8.83 (d, J=6.0 Hz, 2H), 13.65 (br s, 1H).

APCIMS m/z: [$^{35}$ClM–H]$^-$ 409, [$^{37}$ClM–H]$^-$ 411.

Example 323

N-(5-[2-(Dimethylaminopyridin-5-ylcarbonyl]-4-(2-furyl)thiazol-2-yl)pyridine-4-carboxamide (Compound 323)

Compound 322 (200 mg, 0.486 mmol) was suspended in 1,4-dioxane (1 mL), and a 2 mol/L solution of dimethylamine in THF (2.43 mL, 4.86 mmol) was added thereto, followed by stirring under heating and reflux for 4 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was reslurried with ethanol to afford the entitled Compound 323 (111 mg, 54%) as a brown solid.

$^1$H NMR (DMSO-d$_6$, δ ppm): 3.12 (s, 6H), 6.55 (dd, J=1.6, 3.2 Hz, 1H), 6.67 (d, J=8.6 Hz, 1H), 6.88 (d, J=3.2 Hz, 1H), 7.61 (d, J=1.6 Hz, 1H), 7.86 (dd, J=2.4, 8.6 Hz, 1H), 8.03 (dd, J=1.6, 4.6 Hz, 2H) 8.47 (d, J=2.4 Hz, 1H), 8.84 (dd, J=1.6, 4.6 Hz, 2H), 13.51 (br s, 1H).

APCIMS m/z: [M+H]$^+$ 420.

m.p.: 260-265° C. (decomposition)

Example 324

N-[4-(2-Furyl)-5-(2-morpholinopyridin-5-ylcarbonyl)thiazol-2-yl]pyridine-4-carboxamide (Compound 324)

In a manner similar to that in Example 323, by using morpholine in place of dimethylamine, the entitled Compound 324 (46.4 mg, 21%) was obtained as a pale yellow solid from Compound 322 (200 mg, 0.486 mmol).

$^1$H NMR (DMSO-d$_6$, δ ppm): 3.25-3.35 (m, 4H), 3.60-3.70 (m, 4H), 6.55 (dd, J=1.9, 3.2 Hz, 1H), 6.86 (d, J=9.2 Hz, 1H), 6.90 (dd, J=0.8, 3.2 Hz, 1H), 7.61 (dd, J=0.8, 1.9 Hz, 1H), 7.88 (dd, J=2.4, 9.2 Hz, 1H), 8.03 (dd, J=1.6, 6.2 Hz, 2H), 8.48 (d, J=2.4 Hz, 1H), 8.84 (dd, J=1.6, 6.2 Hz, 2H), 13.52 (br s, 1H).
APCIMS m/z: [M+H]$^+$ 462.
m.p.: 195-205° C.

Example 325

N-{4-(2-Furyl)-5-[2-(4-methylpiperazin-1-yl)pyridin-5-ylcarbonyl]thiazol-2-yl}pyridine-4-carboxamide (Compound 325)

In a manner similar to that in Example 323, by using 1-methylpiperazine in place of dimethylamine, the entitled Compound 325 (110 mg, 47%) was obtained from Compound 322 (200 mg, 0.486 mmol).
$^1$H NMR (DMSO-d$_6$, δ ppm): 2.28 (s, 3H), 2.47-2.50 (m, 4H), 3.65-3.75 (m, 4H), 6.55 (dd, J=1.6, 3.2 Hz, 1H), 6.87 (d, J=9.2 Hz, 1H), 6.90 (d, J=3.2 Hz, 1H), 7.60 (d, J=1.6 Hz, 1H), 7.86 (dd, J=2.4, 9.2 Hz, 1H), 8.02 (dd, J=1.4, 4.5 Hz, 2H), 8.47 (d, J=2.4 Hz, 1H), 8.81 (dd, J=1.4, 4.5 Hz, 2H).
APCIMS m/z: [M+H]$^+$ 475.
m.p.: 195-205° C.

Example 326

N-{4-(2-Furyl)-5-[2-(4-hydroxypiperidino)pyridin-5-ylcarbonyl]thiazol-2-yl}pyridine-4-carboxamide (Compound 326)

In a manner similar to that in Example 323, by using 4-hydroxypiperidine in place of dimethylamine, the entitled Compound 326 (95.0 mg, 41%) was obtained as a brown solid from Compound 322 (200 mg, 0.486 mmol).
$^1$H NMR (DMSO-d$_6$, δ ppm): 1.28-1.41 (m, 2H), 1.75-1.80 (m, 2H), 3.16-3.17 (m, 2H), 3.72-3.78 (m, 1H), 4.06-4.12 (m, 2H), 4.76 (d, J=4.0 Hz, 1H), 6.55 (dd, J=1.6, 3.5 Hz, 1H), 6.86 (d, J=9.2 Hz, 1H), 6.88 (dd, J=0.8, 3.5 Hz, 1H), 7.60 (dd, J=0.8, 1.6 Hz, 1H), 7.83 (dd, J=2.4, 9.2 Hz, 1H), 8.03 (dd, J=1.6, 4.6 Hz, 2H), 8.45 (d, J=2.4 Hz, 1H), 8.84 (dd, J=1.6, 4.6 Hz, 2H), 13.51 (br s, 1H).
APCIMS m/z: [M+H]$^+$ 476.
m.p.: 264-268° C.

Example 327 tert-Butyl N-[4-(2-furyl)-5-(pyridin-4-ylcarbonyl)thiazol-2-yl]carbamate (Compound 327)

In a manner similar to that in Example 185, by using isonicotinic acid in place of picolinic acid, the entitled Compound 327 (125 mg, 23%) was obtained from Compound h (500 mg, 1.45 mmol) obtained in Reference Example 8.
$^1$H NMR (CDCl$_3$, δ ppm): 1.51 (s, 9H), 6.40 (dd, J=1.7, 3.3 Hz, 1H), 7.14 (d, J=3.3 Hz, 1H), 7.16 (d, J=1.7 Hz, 1H), 7.55 (d, J=6.1 Hz, 2H), 8.67 (d, J=6.1 Hz, 2H).

Example 328

2-Amino-4-(2-furyl)thiazol-5-yl 4-pyridyl ketone (Compound 328)

In a manner similar to that in Example 186, the entitled Compound 328 (91.0 mg, 100%) was obtained from Compound 327 (125 mg, 0.337 mmol) in place of Compound 185.

$^1$H NMR (CDCl$_3$, δ ppm): 5.68 (br s, 2H), 6.35 (dd, J=1.8, 3.3 Hz, 1H), 6.98 (d, J=3.3 Hz, 1H), 7.04 (d, J=1.8 Hz, 1H), 7.51 (d, J=6.1 Hz, 2H), 8.62 (d, J=6.1 Hz, 2H).

Example 329

N-[4-(2-Furyl)-5-(pyridin-4-ylcarbonyl)thiazol-2-yl]pyridine-4-carboxamide (Compound 329)

In a manner similar to that in Example 187, the entitled Compound 329 (72.0 mg, 57%) was obtained from Compound 328 (91.0 mg, 0.335 mmol) in place of Compound 186.
$^1$H NMR (DMSO-d$_6$, δ ppm): 6.53 (dd, J=1.8, 3.5 Hz, 1H), 7.05 (dd, J=0.7, 3.5 Hz, 1H), 7.47 (dd, J=0.7, 1.8 Hz, 1H), 7.55 (d, J=5.8 Hz, 2H), 8.03 (d, J=6.1 Hz, 2H), 8.65 (d; J=5.8 Hz, 2H), 8.84 (d, J=6.1 Hz, 2H).
APCIMS m/z: [M+H]$^+$ 377.
m.p.: 276-285° C.

Example 330 tert-Butyl N-[4-(2-furyl)-5-(2-methylpyridin-4-ylcarbonyl)thiazol-2-yl]carbamate (Compound 330)

In a manner similar to that in Example 185, by using 2-methylisonicotinic acid in place of picolinic acid, the entitled Compound 330 (1.26 g, 61%) was obtained from Compound h (1.84 g, 5.33 mmol) obtained in Reference Example 8.
$^1$H NMR (CDCl$_3$, δ ppm): 1.53 (s, 9H), 2.57 (s, 3H), 6.42 (dd, J=1.7, 3.5 Hz, 1H), 7.20 (d, J=3.5 Hz, 1H), 7.24 (d, J=1.7 Hz, 1H), 7.30 (d, J=5.1 Hz, 1H), 7.35 (s, 1H), 8.56 (d, J=5.1 Hz, 1H).

Example 331

2-Amino-4-(2-furyl)thiazol-5-yl 2-methylpyridin-4-yl ketone (Compound 331)

In a manner similar to that in Example 186, the entitled Compound 331 (872 mg, 93%) was obtained from Compound 330 (1.26 g, 3.27 mmol) in place of Compound 185.
$^1$H NMR (CDCl$_3$, δ ppm): 2.53 (s, 3H), 5.67 (br s, 2H), 6.36 (dd, J=1.8, 3.5 Hz, 1H), 7.03 (d, J=3.5 Hz, 1H), 7.14 (d, J=1.8 Hz, 1H), 7.24 (d, J=5.1 Hz, 1H), 7.28 (s, 1H), 8.50 (d, J=5.1.Hz, 1H).

Example 332

N-[4-(2-Furyl)-5-(2-methylpyridin-4-ylcarbonyl)thiazol-2-yl]pyridine-4-carboxamide (Compound 332)

Compound 331 (150 mg, 0.526 mmol) was dissolved in DMF (2.mL), and isonicotinic acid (259 mg, 2.10 mmol), EDC hydrochloride (403 mg, 2.10 mmol) and 1-hydroxybenzotriazole monohydrate (322 mg, 2.10 mmol) were added thereto, followed by stirring at 60° C. for 3 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was recrystallized from 2-propanol to afford the entitled Compound 332 (78.0 mg, 38%).
$^1$H NMR (CDCl$_3$, δ ppm): 2.59 (s, 3H), 6.38 (dd, J=1.7, 3.5 Hz, 1H), 7.17 (d, J=3.5 Hz, 1H), 7.22 (d, J=1.7 Hz, 1H), 7.35

(d, J=5.1 Hz, 1H), 7.40 (s, 1H), 7.76 (d, J=6.1 Hz, 2H), 8.59 (d, J=5.1 Hz, 1H), 8.85 (d, J=6.1 Hz, 2H).
APCIMS m/z: [M+H]$^+$ 391.
m.p.: 223-225° C.

Example 333

N-[4-(2-Furyl)-5-(2-methylpyridin-4-ylcarbonyl)thiazol-2-yl]-2-methylpyridine-4-carboxamide (Compound 333)

In a manner-similar to that in Example 332, by using 2-methylisonicotinic acid in place of isonicotinic acid, the entitled Compound 333 (59.0 mg, 28%) was obtained from Compound 331 (150 mg, 0.526 mmol).

$^1$H NMR (DMSO-d$_6$, δ ppm): 2.47 (s, 3H), 2.59 (s, 3H), 6.54 (dd, J=1.8, 3.3 Hz, 1H), 7.05 (d, J=3.3 Hz, 1H), 7.35 (d, J=5.1 Hz, 1H), 7.40 (s, 1H), 7.48 (d, J=1.8 Hz, 1H), 7.83 (d, J=5.0 Hz, 1H), 7.92 (s, 1H), 8.54 (d, J=5.0 Hz, 1H), 8.69 (d, J=5.1 Hz, 1H), 13.6 (br s, 1H).
APCIMS m/z: [M+H]$^+$ 405.
m.p.: 205-229° C.

Example 334 tert-Butyl N-[4-(2-furyl)-5-(2-methoxypyridin-4-ylcarbonyl)thiazol-2-yl]carbamate (Compound 334)

In a manner similar to that in Example 176, by using Compound k obtained in Reference Example 11 in place of 2-cyanobenzoic acid, the entitled Compound 334 (2.34 g, 47%) was obtained from Compound h (4.45 g, 12.9 mmol) obtained in Reference Example 8.

$^1$H NMR (CDCl$_3$, δ ppm): 1.47 (s, 9H), 3.94 (s, 3H), 6.44 (dd, J=1.9, 3.5 Hz, 1H), 6.96 (dd, J=0.8, 1.4 Hz, 1H), 7.09 (dd, J=1.4, 5.1 Hz, 1H), 7.28-7.34 (m, 2H), 8.21 (dd, J=0.8, 5.1 Hz, 1H), 9.26 (br s, 1H).
APCIMS m/z: [M+H]$^+$ 402.

Example 335

2-Amino-4-(2-furyl)thiazol-5-yl 2-methoxypyridin-4-yl ketone (Compound 335)

In a manner similar to that in Example 186, the entitled Compound 335 (1.49 g, 76%) was obtained from Compound 334 (2.34 g, 6.55 mmol) in place of Compound 185.

$^1$H NMR (DMSO-d$_6$, δ ppm): 3.82 (s, 3H), 6.45 (dd, J=1.6, 3.2 Hz, 1H), 6.75 (dd, J=0.8, 1.4 Hz, 1H), 6.92 (dd, J=0.5, 3.2 Hz, 1H), 6.96 (dd, J=1.4, 5.1 Hz, 1H), 7.35 (dd, J=0.5, 1.6 Hz, 1H), 8.13 (dd, J=0.8, 5.1 Hz, 1H), 8.22 (br s, 2H).
APCIMS m/z: [M+H]$^+$ 302.

Example 336

N-[4-(2-Furyl)-5-(2-methoxypyridin-4-ylcarbonyl)thiazol-2-yl]pyridine-4-carboxamide (Compound 336)

In a manner similar to that in Example 187, a crude Compound 336 was obtained from Compound 335 (100 mg, 0.332 mmol) in place of Compound 186. The crude Compound 336 was reslurried with ethanol to afford the entitled Compound 336 (101 mg, 77%) as a yellow solid.

$^1$H NMR A(DMSO-d$_6$, δ ppm): 3.87 (s, 3H), 6.54-6.58 (m, 1H), 6.96 (s, 1H), 7.12 (d, J=3.2 Hz, 1H), 7.16 (d, J=5.1 Hz, 1H), 7.55 (s, 1H), 8.03 (d, J=4.9 Hz, 2H), 8.26 (d, J=5.1 Hz, 1H), 8.84 (d, J=4.9 Hz, 2H), 13.69 (br s, 1H).
APCIMS m/z: [M+H]$^+$ 407.
m.p.: 237-239° C.

Example 337 tert-Butyl N-[4-(2-furyl)-5-(2-morpholinopyridin-4-ylcarbonyl)thiazol-2-yl]carbamate (Compound 337)

In a manner similar to that in Example 176, by using 2-morpholinonicotinic acid in place of 2-cyanobenzoic acid, the entitled Compound 337 (672 mg, 43%) was obtained from Compound h (1.31 g, 3.80 mmol) obtained in Reference Example 8.

$^1$H NMR (CDCl$_3$, δ ppm): 1.49 (s, 9H), 3.49 (t, J=4.8 Hz, 4H), 3.80 (t, J=4.8 Hz, 4H), 6.44 (dd, J=1.8, 3.6 Hz, 1H), 6.82-6.84 (m, 1H), 6.86 (dd, J=1.8, 4.8 Hz, 1H), 7.24-7.27 (m, 1H), 7.30-7.32 (m, 1H), 8.23 (dd, J=0.6, 4.8 Hz, 1H), 9.11 (br s, 1H).
APCIMS m/z: [M+H]$^+$ 457.

Example 338

2-Amino-4-(2-furyl)thiazol-5-yl 2-morpholinopyridin-4-yl ketone (Compound 338)

In a manner similar to that in Example 186, the entitled Compound 338 (484 mg, 83%) was obtained from Compound 337 (672 mg, 1.63 mmol) in place of Compound 185.

$^1$H NMR (DMSO-d$_6$, δ ppm): 3.33 (t, J=5.1 Hz, 4H), 3.64 (t, J=5.1 Hz, 4H), 6.46 (dd, J=1.6, 3.5 Hz, 1H), 6.70 (dd, J=0.8, 3.5 Hz, 1H), 6.71-6.72 (m, 1H), 6.92 (d, J=3.5 Hz, 1H), 7.36-7.38 (m, 1H), 8.12 (d, J=5.1 Hz, 1H), 8.16 (br s, 2H).
APCIMS m/z: [M+H]$^+$ 357.

Example 339

N-[4-(2-Furyl)-5-(2-morpholinopyridin-4-ylcarbonyl)thiazol-2-yl]pyridine-4-carboxamide (Compound 339)

In a manner similar to that in Example 187, a crude Compound 339 was obtained from Compound 338 (485 mg, 1.36 mmol) in place of Compound 186. The crude Compound 339 was reslurried with ethanol to afford the entitled Compound 339 (447 mg, 71%).

$^1$H NMR (DMSO-d$_6$, δ ppm): 3.40 (dd, J=4.1, 5.1 Hz, 4H), 3.66 (dd, J=4.1, 5.1 Hz, 4H), 6.57 (dd, J=1.6, 3.2 Hz, 1H), 6.86 (d, J=4.9 Hz, 1H), 6.93 (s, 1H), 7.10 (d, J=3.2 Hz, 1H), 7.56 (d, J=1.6 Hz, 1H), 8.03 (dd. J=1.6, 4.4 Hz, 2H), 8.22 (d, J=4.9 Hz, 1H), 8.84 (dd, J=1.6, 4.4 Hz, 2H), 13.67 (br s, 1H).
APCIMS m/z: [M+H]$^+$ 462.
m.p.: 270-273° C.

Example 340 tert-Butyl N-[4-(2-furyl)-5-(furan-2-ylcarbonyl)thiazol-2-yl]carbamate (Compound 340)

In a manner similar to that in Example 185, by using 2-furancarboxylic acid in place of picolinic acid, the entitled Compound 340 (187 mg, 36%) was obtained from Compound h (500 mg, 1.45 mmol) obtained in Reference Example 8.

¹H NMR (CDCl₃, δ ppm): 1.51 (s, 9H), 6.47 (dd, J=1.8, 3.3 Hz, 1H), 6.53 (dd, J=1.7, 3.5 Hz, 1H), 7.28 (d, J=3.3 Hz, 1H), 7.45-7.46 (m, 2H), 7.60 (d, J=1.7 Hz, 1H).

Example 341

2-Amino-4-(2-furyl)thiazol-5-yl 2-furyl ketone (Compound 341)

In a manner similar to that in Example 186, the entitled Compound 341 (115 mg, 85%) was obtained from Compound 340 (187 mg, 0.519 mmol) in place of Compound 185.
¹H NMR (CDCl₃, δ ppm): 6.45-6.46 (m, 1H), 6.49-6.51 (m, 1H), 7.17-7.18 (m, 1H), 7.40-7.44 (m, 2H), 7.51-7.52 (m, 1H).

Example 342

N-[4-(2-Furyl)-5-(furan-2-ylcarbonyl)thiazol-2-yl]pyridine-4-carboxamide (Compound 342)

In a manner similar to that in Example 187, the entitled Compound 342 (112 mg, 70%) was obtained from Compound 341 (115 mg, 0.442 mmol) in place of Compound 186.
¹H NMR (DMSO-d₆, δ ppm): 6.60 (dd, J=1.8, 3.7 Hz, 1H), 6.73 (dd, J=1.5, 3.7 Hz, 1H), 7.09 (d, J=3.7 Hz, 1H), 7.32 (d, J=3.7 Hz, 1H), 7.68 (d, J=1.8 Hz, 1H), 8.00 (d, J=1.5 Hz, 1H), 8.01 (d, J=5.5 Hz, 2H), 8.82 (d, J=5.5 Hz, 2H).
APCIMS m/z: [M+H]⁺ 366.
m.p.: 245-248° C.

Example 343

N-[4-(2-Furyl)-5-(5-methylfuran-2-ylcarbonyl)thiazol-2-yl]pyridine-4-carboxamide (Compound 343)

In a manner similar to that in Example 283, by using 2-methylfuran in place of 2-bromo-6-methoxypyridine, the entitled Compound 343 (195 mg, 61%) was obtained from Compound 98 (300 mg, 0.837 mmol).
¹H NMR (DMSO-d₆, δ ppm): 2.41 (s, 3H), 6.21 (d, J=3.5 Hz, 1H), 6.44 (dd, J=1.8, 3.5 Hz, 1H), 7.26 (d, J=3.5 Hz, 1H), 7.32 (dd, J=0.7, 3.5 Hz, 1H), 7.41 (dd, J=0.7, 1.8 Hz, 1H), 7.75 (d, J=6.1 Hz, 2H), 8.85 (d, J=6.1 Hz, 2H).
APCIMS m/z: [M+H]⁺ 380.
m.p.: 185-189° C.

Example 344 tert-Butyl N-[4-(2-furyl)-5-(furan-3-ylcarbonyl)thiazol-2-yl]carbamate (Compound 344)

In a manner similar to that in Example 185, by using 3-furancarboxylic acid in place of picolinic acid, the entitled Compound 344 (79.0 mg, 15%) was obtained from Compound h (500 mg, 1.45 mmol) obtained in Reference Example 8.
¹H NMR (CDCl₃, δ ppm): 1.50 (s, 9H), 6.44-6.48 (m, 1H), 6.82-6.83 (m, 1H), 7.31-7.45 (m, 3H), 7.94-7.96 (m, 1H), 8.67 (br s, 1H).

Example 345

2-Amino-4-(2-furyl)thiazol-5-yl furan-3-yl ketone (Compound 345)

In a manner similar to that in Example 186, the entitled Compound 345 (40.0 mg, 70%) was obtained from Compound 344 (79.0 mg, 0.219 mmol) in place of Compound 185.
¹H NMR (CDCl₃, δ ppm): 6.39 (dd, J=1.8, 3.7 Hz, 1H), 6.67 (dd, J=0.7, 1.8 Hz, 1H), 7.21 (dd, J=0.7, 3.7 Hz, 1H), 7.32-7.33 (m, 1H), 7.34-7.35 (m, 1H), 7.78-7.79 (m, 1H).

Example 346

N-[4-(2-Furyl)-5-(furan-3-ylcarbonyl)thiazol-2-yl]pyridine-4-carboxamide (Compound 346)

In a manner similar to that in Example 187, the entitled Compound 346 (34.0 mg, 61%) was obtained from Compound 345 (40.0 mg, 0.154 mmol) in place of Compound 186.
¹H NMR (DMSO-d₆, δ ppm): 6.61 (dd, J=1.8, 3.5 Hz, 1H), 6.83-6.84 (m, 1H), 7.09 (dd, J=0.8, 3.5 Hz, 1H), 7.71 (dd, J=0.8, 1.8 Hz, 1H), 7.83-7.84 (m, 1H), 8.03 (d, J=5.9 Hz, 2H), 8.31-8.32 (m, 1H), 8.84 (d, J=5.9 Hz, 2H).
APCIMS m/z: [M+H]⁺ 366.
m.p.: 217-231° C.

Example 347

N-[4-(2-Furyl)-5-(thiophen-2-ylcarbonyl)thiazol-2-yl]pyridine-4-carboxamide (Compound 347)

In a manner similar to that in Example 283, by using thiophene in place of 2-bromo-6-methoxypyridine, the entitled Compound 347 (80.0 mg, 75%) was obtained from Compound 98 (100 mg, 0.279 mmol).
¹H NMR (DMSO-d₆, δ ppm): 6.59 (dd, J=1.8, 3.5 Hz, 1H), 7.02 (d, J=3.5 Hz, 1H), 7.20 (dd, J=3.9, 5.2 Hz, 1H), 7.67 (d, J=1.8 Hz, 1H), 7.68 (dd, J=1.1, 3.9 Hz, 1H), 8.03 (d, J=6.1 Hz, 2H), 8.09 (dd, J=1.1, 5.2 Hz, 1H), 8.84 (d, J=6.1 Hz, 2H), 13.6 (br s, 1H).
APCIMS m/z: [M+H]⁺ 382.
m.p.: 208-210° C.

Example 348

N-[4-(2-Furyl)-5-(thiazol-2-ylcarbonyl)thiazol-2-yl]pyridine-4-carboxamide (Compound 348)

In a manner similar to that in Example 283, by using thiazole in place of 2-bromo-6-methoxypyridine, the entitled Compound 348 (19.0 mg, 18%) was obtained from Compound 98 (100 mg, 0.279 mmol).
¹H NMR (DMSO-d₆, δ ppm): 6.72 (dd, J=1.7, 3.5 Hz, 1H), 7.73 (d, J=3.5 Hz, 1H), 7.89 (d, J=1.7 Hz, 1H), 8.06 (d, J=6.1 Hz, 2H), 8.26 (d, J=3.1 Hz, 1H), 8.30 (d, J=3.1 Hz, 1H), 8.85 (d, J=6.1 Hz, 2H), 13.7 (br s, 1H).
APCIMS m/z: [M+H]⁺ 383.
m.p.: 228-240° C.

Example 349

N-[4-(2-Furyl)-5-(5-methylthiazol-2-ylcarbonyl)thiazol-2-yl]pyridine-4-carboxamide (Compound 349)

In a manner similar to that in Example 283, by using 5-methylthiazole in place of 2-bromo-6-methoxypyridine, the entitled Compound 349 (150 mg, 68%) was obtained from Compound 98 (200 mg, 0.558 mmol).

¹H NMR (DMSO-d₆, δ ppm): 2.59 (s, 3H), 6.71 (dd, J=1.8, 3.5 Hz, 1H), 7.71 (d, J=3.5 Hz, 1H), 7.88 (d, J=1.8 Hz, 1H), 7.96 (s, 1H), 8.05 (d, J=6.1 Hz, 2H), 8.85 (d, J=6.1 Hz, 2H), 13.6 (br s, 1H).
APCIMS m/z: [M+H]⁺ 397.
m.p.: 275-277° C. (decomposition)

Example 350

N-[4-(2-Furyl)-5-(4-methylthiazol-2-ylcarbonyl) thiazol-2-yl]pyridine-4-carboxamide (Compound 350)

In a manner similar to that in Example 283, by using 4-methylthiazole in place of 2-bromo-6-methoxypyridine, the entitled Compound 350 (175 mg, 79%) was obtained from Compound 98 (200 mg, 0.558 mmol).
¹H NMR (DMSO-d₆, δ ppm): 2.50 (s, 3H), 6.69 (dd, J=1.8, 3.5 Hz, 1H), 7.64 (d, J=3.5 Hz, 1H), 7.83-7.85 (m, 2H), 8.04 (d, J=6.1 Hz, 2H), 8.83 (d, J=6.1 Hz, 2H), 13.6 (br s, 1H).
APCIMS m/z: [M+H]⁺ 397.
m.p.: 250-255° C.

Example 351

N-[5-(4,5-Dimethylthiazol-2-ylcarbonyl)-4-(2-furyl) thiazol-2-yl]pyridine-4-carboxamide (Compound 351)

In a manner similar to that in Example 283, by using 4,5-dimethylthiazole in place of 2-bromo-6-methoxypyridine, the entitled Compound 351 (131 mg, 57%) was obtained from Compound 98 (200 mg, 0.558 mmol).
¹H NMR (DMSO-d₆, δ ppm): 2.41 (s, 3H), 2.48 (s, 3H), 6.69 (dd, J=1.8, 3.5 Hz, 1H), 7.64 (dd, J=0.7, 3.5 Hz, 1H), 7.86 (dd, J=0.7, 1.8 Hz, 1H), 8.05 (d, J=6.1 Hz, 2H), 8.84 (d, J=6.1 Hz, 2H), 13.6 (br s, 1H).
APCIMS m/z: [M+H]⁺ 411.
m.p.: 270-272° C. (decomposition)

Example 352

N-{4-(2-Furyl)-5-[1-(triisopropylsilyl)pyrrol-3-ylcarbonyl]thiazol-2-yl}pyridine-4-carboxamide (Compound 352)

In a manner similar to that in Example 283, by using 3-bromo-1-(triisopropylsilyl)pyrrole in place of 2-bromo-6-methoxypyridine, the entitled Compound 352 (156 mg, 60%) was obtained from Compound 98 (179 mg, 0.500 mmol).
¹H NMR (DMSO-d₆, δ ppm): 0.96-1.03 (m, 18H), 1.41-1.49 (m, 3H), 6.52 (dd, J=1.8, 3.5 Hz, 1H), 6.64-6.65 (m, 1H), 6.91-6.92 (m, 2H), 7.31-7.32 (m, 1H), 7.80 (dd, J=0.7, 1.8 Hz, 1H), 8.00 (d, J=6.1 Hz, 2H), 8.80 (d, J=6.1 Hz, 2H).

Example 353

N-[4-(2-Furyl)-5-(pyrrol-3-ylcarbonyl)thiazol-2-yl] pyridine-4-carboxamide (Compound 353)

Compound 352 (155 mg, 0.298 mmol) and 0.1 mol/L hydrochloric acid (2.5 mL) were dissolved in ethanol (2.5 mL), followed by stirring at 90° C. for 2 hours. The reaction mixture was neutralized with a saturated aqueous solution of sodium hydrogencarbonate, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:4) to afford the entitled Compound 353 (89.0 mg, 82%).
¹H NMR (DMSO-d₆, δ ppm): 6.51-6.54 (m, 1H), 6.57 (dd, J=1.8, 3.3 Hz, 1H), 6.89-6.90 (m, 1H), 6.97 (d, J=3.3 Hz, 1H), 7.41-7.42 (m, 1H), 7.68 (d, J=1.8 Hz, 1H), 8.03 (d, J=6.1 Hz, 2H), 8.83 (d, J=6.1 Hz, 2H), 11.6 (br s, 1H), 13.5 (br s, 1H).
m.p.: 259-260° C.

Example 354

N-[4-(2-Furyl)-5-(1-methylpyrrol-3-ylcarbonyl)thiazol-2-yl]pyridine-4-carboxamide (Compound 354)

Compound 353 (105 mg, 0.288 mmol) was dissolved in DMF (1.4 mL), and 55% sodium hydride (25.3 mg, 0.576 mmol) and methyl iodide (0.0179 mL, 0.288 mmol) were added thereto, followed by stirring at room temperature for 2 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 354 (97.0 mg, 89%).
¹H NMR (DMSO-d₆, δ ppm): 3.69 (s, 3H), 6.36 (dd, J=1.8, 3.5 Hz, 1H), 6.61-6.62 (m, 1H), 6.71-6.72 (m, 1H), 7.16 (d, J=3.5 Hz, 1H), 7.29 (d, J=1.8 Hz, 1H), 7.33-7.34 (m, 1H), 7.74 (d, J=6.1 Hz, 2H), 8.82 (d, J=6.1 Hz, 2H), 10.7 (br s, 1H).
APCIMS m/z: [M+H]⁺ 379.
m.p.: 209-211° C.

Example 355

N-[5-(1-Ethylpyrrol-3-ylcarbonyl)-4-(2-furyl)thiazol-2-yl]pyridine-4-carboxamide (Compound 355)

In a manner similar to that in Example 354, by using ethyl iodide in place of methyl iodide, the entitled Compound 355 (99.0 mg, 88%) was obtained from Compound 353 (105 mg, 0.288 mmol).
¹H NMR (DMSO-d₆, δ ppm): 1.44 (t, J=7.3 Hz, 3H), 3.94 (q, J=7.3 Hz, 2H), 6.34 (dd, J=1.7, 3.3 Hz, 1H), 6.66-6.72 (m, 2H), 7.11 (d, J=3.3 Hz, 1H), 7.31 (d, J=1.7 Hz, 1H), 7.33-7.34 (m, 1H), 7.73 (d, J=6.1 Hz, 2H), 8.80 (d, J=6.1 Hz, 2H), 10.9 (br s, 1H).
APCIMS m/z: [M+H]⁺ 393.
m.p.: 127-134° C.

Example 356

N-[5-(1-Benzylpyrrol-3-ylcarbonyl)-4-(2-furyl)thiazol-2-yl]pyridine-4-carboxamide (Compound 356)

In a manner similar to that in Example 354, by using benzyl chloride in place of methyl iodide, the entitled Compound 356 (106 mg, 85%) was obtained from Compound 353 (100 mg, 0.274 mmol).
¹H NMR (DMSO-d₆, δ ppm): 5.06 (s, 2H), 6.35 (dd, J=1.8, 3.5 Hz, 1H), 6.65-6.75 (m, 2H), 7.11-7.14 (m, 3H), 7.31-7.37 (m, 5H), 7.73 (d, J=6.1 Hz, 2H), 8.81 (d, J=6.1 Hz, 2H), 10.6 (br s, 1H).
APCIMS m/z: [M+H]⁺ 455.
m.p.: 175-178° C.

Example 357

N-[5-(5-tert-Butyl-1,3,4-oxadiazol-2-ylcarbonyl)-4-(2-furyl)thiazol-2-yl]pyridine-4-carboxamide (Compound 357)

2-tert-Butyl-1,3,4-oxadiazole (116 mg, 0.919 mmol) obtained according to the method described in WO01/57004 was dissolved in THF (4 mL), and a 2.00 mol/L solution of lithium diisopropylamide (0.420 mL, 0.840 mmol) in THF was added thereto in a stream of argon at −78° C., followed by stirring for 15 minutes at −78° C. A solution of Compound 98 (100 mg, 0.279 mmol) in THF (2 mL) was added dropwise to the reaction mixture, followed by stirring at room temperature for 1.5 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was reslurried with ethanol to afford the entitled Compound 357 (80.7 mg, 68%).

$^1$H NMR (DMSO-$d_6$, δ ppm): 1.40 (s, 9H), 6.71 (dd, J=1.9, 3.5 Hz, 1H), 7.59 (d, J=3.5 Hz, 1H), 7.84 (d, J=1.9 Hz, 1H), 8.05 (dd, J=1.6, 6.2 Hz, 2H), 8.85 (dd, J=1.6, 6.2 Hz, 2H), 13.77 (br s, 1H).

ESIMS m/z: [M+H]$^+$ 424.

m.p.: 190-255° C. (decomposition).

Example 358

2-Amino-4-(2-furyl)thiazol-5-yl 2-oxo-1,2-dihydropyridin-5-yl ketone (Compound 358)

Compound 318 (1.36 g, 4.51 mmol) was dissolved in acetic acid (4 mL), and 48% hydrobromic acid (4 mL) was added thereto, followed by stirring at 100° C. for 1 hour. The reaction mixture was poured into aqueous saturated sodium carbonate solution, and the precipitated solid was collected by filtration to afford the entitled Compound 358 (1.20 g, 93%).

$^1$H NMR (DMSO-$d_6$, δ ppm): 6.18 (d, J=9.5 Hz, 1H), 6.50 (dd, J=1.6, 3.2 Hz, 1H), 6.73 (d, J=3.2 Hz, 1H), 7.54 (d, J=1.6 Hz, 1H), 7.60 (dd, J=2.4, 9.5 Hz, 1H), 7.74 (d, J=2.4 Hz, 1H), 7.83 (br s, 2H).

Example 359

2-Amino-4-(2-furyl)thiazol-5-yl 1-methyl-2-oxo-1,2-dihydropyridin-5-yl ketone (Compound 359)

In a manner similar to that in Example 126, the entitled Compound 359 (160 mg, 53%) was obtained as a yellow solid from Compound 358 (287 mg, 1.00 mmol) in place of Compound q.

$^1$H NMR (DMSO-$d_6$, δ ppm): 3.30 (s, 3H), 6.30 (d, J=9.7 Hz, 1H), 6.51 (dd, J=1.6, 3.2 Hz, 1H), 6.14 (dd, J=0.5, 3.2 Hz, 1H), 7.51 (dd, J=0.5, 1.6 Hz, 1H), 7.60 (dd, J=2.7, 9.7 Hz, 1H), 7.94 (br s, 2H), 8.11 (d, J=2.7 Hz, 1H).

ESIMS m/z: [M+H]$^+$ 302.

Example 360

N-[4-(2-Furyl)-5-(1-methyl-2-oxo-1,2-dihydropyridin-5-ylcarbonyl)thiazol-2-yl]pyridine-4-carboxamide (Compound 360)

In a manner similar to that in Example 187, a crude Compound 360 was obtained from Compound 359 (160 mg, 0.530 mmol) in place of Compound 186. The resulting crude Compound 360 was reslurried with methanol to afford the entitled Compound 360 (134 mg, 64%) as a yellow solid.

$^1$H NMR (DMSO-$d_6$, δ ppm): 3.33 (s, 3H), 6.41 (d, J=9.7 Hz, 1H), 6.59 (dd, J=2.2, 3.2 Hz, 1H), 6.88 (d, J=3.2 Hz, 1H), 7.65 (d, J=2.2 Hz, 1H), 7.77 (dd, J=2.4, 9.7 Hz 1H), 8.03 (dd, J=1.6, 4.6 Hz, 2H), 8.37 (d, J=2.4 Hz, 1H), 8.84 (dd, J=1.6, 4.6 Hz, 2H), 13.58 (br s, 1H).

APCIMS m/z: [M+H]$^+$ 407.

m.p.: 294-295° C.

Example 361

2-Amino-4-(2-furyl)thiazol-5-yl 1-ethyl-2-oxo-1,2-dihydropyridin-5-yl ketone (Compound 361)

In a manner similar to that in Example 126, by using ethyl iodide in place of methyl iodide, the entitled Compound 361 (160 mg, 51%) was obtained as a yellow solid from Compound 358 (287 mg, 1.00 mmol) in place of Compound q.

$^1$H NMR (DMSO-$d_6$, δ ppm): 1.01 (t, J=6.5 Hz, 3H), 3.79 (q, J=6.5 Hz, 2H), 6.34 (d, J=9.5 Hz, 1H), 6.50 (dd, J=1.6, 3.2 Hz, 1H), 6.74 (d, J=3.2 Hz, 1H), 7.51 (d, J=1.6 Hz, 1H), 7.64 (dd, J=2.4, 9.5 Hz, 1H), 7.93 (br s, 2H), 8.11 (d, J=2.4 Hz, 1H).

APCIMS m/z: [M+H]$^+$ 316.

Example 362

N-[5-(1-Ethyl-2-oxo-1,2-dihydropyridin-5-ylcarbonyl)-4-(2-furyl)thiazol-2-yl]pyridine-4-carboxamide (Compound 362)

In a manner similar to that in Example 187, a crude Compound 362 was obtained from Compound 361 (160 mg, 0.510 mmol) in place of Compound 186. The resulting crude Compound 362 was reslurried with methanol to afford the entitled Compound 362 (80.7 mg, 38%) as a yellow solid.

$^1$H NMR (DMSO-$d_6$, δ ppm): 1.04 (t, J=7.3 Hz, 3H), 3.85 (q, J=7.3 Hz, 2H), 6.43 (d, J=9.7 Hz, 1H), 6.58 (dd, J=1.6, 3.2 Hz, 1H), 6.88 (d, J=3.2 Hz, 1H), 7.64 (d, J=1.6 Hz, 1H), 7.98 (dd, J=2.7, 9.7 Hz, 1H), 8.04 (dd, J=1.6, 4.4 Hz, 2H), 8.32 (d, J=2.7 Hz, 1H), 8.85 (dd, J=1.6, 4.4 Hz 2H), 13.59 (br s, 1H).

APCIMS m/z: [M+H]$^+$ 421.

m.p.: 295-296° C.

Example 363

2-Amino-4-(2-furyl)thiazol-5-yl 1-benzyl-2-oxo-1,2-dihydropyridin-5-yl ketone (Compound 363)

In a manner similar to that in Example 126, by using benzyl bromide in place of methyl iodide, the entitled Compound 363 (130 mg, 34%) was obtained from Compound 362 (287 mg, 1.00 mmol) in place of Compound q.

$^1$H NMR (DMSO-$d_6$, δ ppm): 5.02 (s, 2H), 6.36 (d, J=9.7 Hz, 1H), 6.45 (dd, J=1.6, 3.2 Hz, 1H), 6.70 (dd, J=0.5, 3.2 Hz, 1H), 7.10 (dd, J=1.6, 7.5 Hz, 2H), 7.20-7.30 (m, 3H), 7.43 (dd, J=0.5, 1.6 Hz, 1H), 7.64 (dd, J=2.7, 9.7 Hz, 1H), 7.90 (br s, 2H), 8.29 (d, J=2.7 Hz, 1H).

APCIMS m/z: [M+H]$^+$ 378.

Example 364

N-[5-(1-Benzyl-2-oxo-1,2-dihydropyridin-5-ylcarbonyl)-4-(2-furyl)thiazol-2-yl]pyridine-4-carboxamide (Compound 364)

In a manner similar to that in Example 187, a crude Compound 364 was obtained from Compound 363 (130 mg, 0.340 mmol) in place of Compound 186. The resulting crude. Compound 364 was reslurried with methanol to afford the entitled Compound 364 (98.1 mg, 60%) as a yellow solid.

$^1$H NMR (DMSO-$d_6$, δ ppm): 5.05 (s, 2H), 6.45 (d, J=9.5 Hz, 1H), 6.54 (dd, J=1.9, 3.2 Hz, 1H), 6.83 (d, J=3.2 Hz, 1H), 7.04-7.12 (m, 2H), 7.24-7.30 (m, 3H), 7.58 (d, J=1.9 Hz, 1H), 7.82 (dd, J=2.7, 9.5 Hz, 1H), 8.02 (dd, J=1.6, 4.6 Hz, 2H), 8.51 (d, J=2.7 Hz, 1H), 8.83 (dd, J=1.6, 4.6 Hz, 2H), 13.57 (br s, 1H).

APCIMS m/z: [M+H]$^+$ 483.

m.p.: 265-282° C. (decomposition)

Example 365

2-Amino-4-(2-furyl)thiazol-5-yl 2-oxo-1,2-dihydropyridin-4-yl ketone (Compound 365)

In a manner similar to that in Example 358, the entitled Compound 365 (444 mg, 41%) was obtained from Compound 335 (1.14 g, 3.78 mmol) in place of Compound 318.

$^1$H NMR (DMSO-$d_6$, δ ppm): 6.15 (dd, J=1.6, 6.2 Hz, 1H), 6.22 (d, J=1.6 Hz, 1H), 6.51 (dd, J=1.9, 3.5 Hz, 1H), 6.98 (d, J=3.5 Hz, 1H), 7.33 (d, J=6.2 Hz, 1H), 7.52 (d, J=1.9 Hz, 1H), 11.65 (br s, 1H).

APCIMS m/z: [M+H]$^+$ 288.

Example 366

2-Amino-4-(2-furyl)thiazol-5-yl 1-methyl-2-oxo-1,2-dihydropyridin-4-yl ketone (Compound 366)

In a manner similar to that in Example 126, the entitled Compound 366 (114 mg, 77%) was obtained as a yellow solid from Compound 365 (140 mg, 0.487 mmol) in place of Compound q.

$^1$H NMR (DMSO-$d_6$, δ ppm): 3.39 (s, 3H), 6.19 (dd, J=1.9, 7.0 Hz, 1H), 6.30 (d, J=1.9 Hz, 1H), 6.51 (dd, J=1.9, 3.5 Hz, 1H), 7.00 (dd J=0.8, 3.5 Hz, 1H), 7.51 (dd, J=0.8, 1.9 Hz, 1H), 7.66 (d, J=7.0 Hz, 1H), 8.20 (br s, 2H).

APCIMS m/z: [M+H]$^+$ 302.

Example 367

N-[4-(2-Furyl)-5-(1-methyl-2-oxo-1,2-dihydropyridin-4-ylcarbonyl)thiazol-2-yl]pyridine-4-carboxamide (Compound 367)

In a manner similar to that in Example 187, a crude Compound 367 was obtained from Compound 366 (114 mg, 0.378 mmol) in place of Compound 186. The resulting crude Compound 367 was reslurried with methanol to afford the entitled Compound 367 (35.2 mg, 23%) as a yellow solid.

$^1$H NMR (DMSO-$d_6$, δ ppm): 3.44 (s, 3H), 6.38 (dd, J=1.9, 7.0 Hz, 1H), 6.53 (d, J=1.9 Hz, 1H), 6.62 (dd, J=1.6, 3.5 Hz, 1H), 7.19 (dd, J=0.5, 3.5 Hz, 1H), 7.70-7.77 (m, 2H), 8.03 (dd, J=1.6, 4.6 Hz, 2H), 8.84 (dd, J=1.6, 4.6 Hz, 2H), 13.69 (br s, 1H).

APCIMS m/z: [M+H]$^+$ 407.

m.p.: 243-255° C. (decomposition)

Example 368

2-Amino-4-(2-furyl)thiazol-5-yl 1-ethyl-2-oxo-1,2-dihydropyridin-4-yl ketone (Compound 368)

In a manner similar to that in Example 126, by using ethyl iodide in place of methyl iodide, the entitled Compound 368 (91.0 mg, 59%) was obtained as a yellow solid from Compound 365 (140 mg, 0.487 mmol) in place of Compound q.

$^1$H NMR (DMSO-$d_6$, δ ppm): 1.18 (t, J=7.3 Hz, 3H), 3.86 (q, J=7.3 Hz, 2H), 6.20 (dd, J=1.6, 4.9 Hz, 1H), 6.26 (d, J=1.6 Hz, 1H), 6.49 (dd, J=1.6, 3.2 Hz, 1H), 6.95 (dd, J=0.5, 3.2 Hz, 1H), 7.48 (dd, J=0.5, 1.6 Hz, 1H), 7.66 (d, J=4.9 Hz, 1H), 8.21 (br s, 2H)

APCIMS m/z: [M+H]$^+$ 316.

Example 369

N-[5-(1-Ethyl-2-oxo-1,2-dihydropyridin-4-ylcarbonyl)-4-(2-furyl)thiazol-2-yl]pyridine-4-carboxamide (Compound 369)

In a manner similar to that in Example 187, a crude Compound 369 was obtained from Compound 368 (81.5 mg, 0.258 mmol) in place of Compound 186. The resulting crude Compound 369 was reslurried with methanol to afford the entitled Compound 369 (31.4 mg, 29%) as a yellow solid.

$^1$H NMR (DMSO-$d_6$, δ ppm): 1.21 (t, J=7.0 Hz, 3H), 3.91 (q, J=7.0 Hz, 2H), 6.38 (dd, J=1.9, 7.3 Hz, 1H), 6.50 (d, J=1.9 Hz, 1H), 6.60 (dd, J=1.9, 3.2 Hz, 1H), 7.15 (dd, J=0.8, 3.2 Hz, 1H), 7.65 (dd, J=0.8, 1.9 Hz, 1H), 7.78 (d, J=7.3 Hz, 1H), 8.02 (dd, J=1.6, 4.4 Hz, 2H), 8.84 (dd, J=1.6, 4.4 Hz, 2H), 13.69 (br s, 1H).

APCIMS m/z: [M+H]$^+$ 421.

m.p.: 277-281° C.

Example 370

2-Amino-4-(2-furyl)thiazol-5-yl 1-benzyl-2-oxo-1,2-dihydropyridin-4-yl ketone (Compound 370)

In a manner similar to that in Example 126, by using benzyl bromide in place of methyl iodide, the entitled Compound 370 (142 mg, 77%) was obtained from Compound 365 (140 mg, 0.487 mmol) in place of Compound q.

$^1$H NMR (DMSO-$d_6$, δ ppm): 5.07 (s, 2H), 6.23 (dd, J=2.2, 7.0 Hz, 1H), 6.32 (d, J=2.2 Hz, 1H), 6.42 (dd, J=1.9, 3.5 Hz, 1H), 6.91 (dd, J=0.8, 3.5 Hz, 1H), 7.20-7.24 (m, 2H), 7.29-7.41 (m, 4H), 7.74 (d, J=7.0 Hz, 1H), 8.22 (br s, 2H)

APCIMS m/z: [M+H]$^+$ 378.

Example 371

N-[5-(1-Benzyl-2-oxo-1,2-dihydropyridin-4-ylcarbonyl)-4-(2-furyl)thiazol-2-yl]pyridine-4-carboxamide (Compound 371)

In a manner similar to that in Example 187, a crude Compound 371 was obtained from Compound 370 (121 mg, 0.319 mmol) in place of Compound 186. The resulting crude Compound 371 was reslurried with methanol to afford the entitled Compound 371 (25.1 mg, 16%) as a yellow solid.

$^1$H NMR (DMSO-$d_6$, δ ppm): 5.11 (s, 2H), 6.41 (dd, J=1.9, 6.7 Hz, 1H), 6.54 (d, J=1.9 Hz, 1H), 6.55 (dd, J=1.9, 3.5 Hz, 1H), 7.09 (dd, J=0.8, 3.5 Hz, 1H), 7.20-7.41 (m, 5H), 7.55

(dd, J=0.8, 1.9 Hz, 1H), 7.85 (d, J=6.7 Hz, 1H), 8.02 (dd, J=1.6, 4.3 Hz, 2H), 8.83 (dd, J=1.6, 4.3 Hz, 2H), 13.68 (br s, 1H).
APCIMS m/z: [M+H]$^+$ 483.
m.p.: 288-291° C.

Example 372 tert-Butyl N-[4-(2-furyl)-5-(pyrazin-2-ylcarbonyl)thiazol-2-yl]carbamate (Compound 372)

In a manner similar to that in Example 185, by using 2-pyrazinecarboxylic acid in place of picolinic acid, the entitled Compound 372 (60.0 mg, 11%) was obtained from Compound h (500 mg, 1.45 mmol) obtained in Reference Example 8.
$^1$H NMR (CDCl$_3$, δ ppm): 1.53 (s, 9H), 6.54 (dd, J=1.8, 3.7 Hz, 1H), 7.47 (d, J=1.8 Hz, 1H), 7.82 (d, J=3.7 Hz, 1H), 8.63-8.64 (m, 1H), 8.72-8.73 (m, 1H), 9.34-9.35 (m, 1H).

Example 373

2-Amino-4-(2-furyl)thiazol-5-yl pyrazin-2-yl ketone (Compound 373)

In a manner similar to that in Example 186, the entitled Compound 373 (44.0 mg, 100%) was obtained from Compound 372 (60.0 mg, 0.161 mmol) in place of Compound 185.
$^1$H NMR (CDCl$_3$, δ ppm): 6.48 (dd, J=1.8, 3.5 Hz, 1H), 7.42 (d, J=1.8 Hz, 1H), 7.84 (d, J=3.5 Hz, 1H), 8.49 (dd, J=1.5, 2.5 Hz, 1H), 8.66 (d, J=2.5 Hz, 1H), 9.29 (d, J=1.5 Hz, 1H).

Example 374

N-[4-(2-Furyl)-5-(pyrazin-2-ylcarbonyl)thiazol-2-yl]pyridine-4-carboxamide (Compound 374)

In a manner similar to that in Example 187, the entitled Compound 374 (50.0 mg, 82%) was obtained from Compound 373 (44.0 mg, 0.161 mmol) in place of Compound 186.
$^1$H NMR (DMSO-d$_6$, δ ppm): 6.63 (dd, J=1.8, 3.5 Hz, 1H), 7.40 (d, J=3.5 Hz, 1H), 7.66 (d, J=1.8 Hz, 1H), 8.05 (d, J=5.9 Hz, 2H), 8.74 (dd, J=1.3, 2.5 Hz, 1H), 8.85 (d, J=5.9 Hz, 2H), 8.89 (d, J=2.5 Hz, 1H), 9.23 (d, J=1.3 Hz, 1H).
APCIMS m/z: [M+H]$^+$ 378.
m.p.:>300° C.

Example 375

N-[4-(2-Furyl)-5-(pyrimidin-4-ylcarbonyl)thiazol-2-yl]pyridine-4-carboxamide (Compound 375)

2,2,6,6-Tetramethylpiperidine (0.233 mL, 1.38 mmol) was dissolved in THF (6 mL), and a 1.58 mol/L solution of n-butyllithium in n-hexane (0.880 mL, 1.38 mmol) was added thereto in a stream of argon at −78° C., followed by stirring at room temperature for 30 minutes. At −78° C., a solution of Compound 98 (150 mg, 0.419 mmol) and pyrimidine (0.0990 mL, 1.26 mmol) in THF (2 mL) was added to the reaction mixture, followed by stirring at room temperature for 2 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford the entitled Compound 375 (11.0 mg, 7%).
$^1$H NMR (DMSO-d$_6$, δ ppm): 6.64 (dd, J=1.8, 3.5 Hz, 1H), 7.42 (dd, J=0.7, 3.5 Hz, 1H), 7.66 (dd, J=0.7, 1.8 Hz, 1H), 8.02-8.03 (m, 1H), 8.05 (d, J=6.1 Hz, 2H), 8.85 (d, J=6.1 Hz, 2H), 9.12-9.14 (m, 1H), 9.33-9.34 (m, 1H), 13.6 (br s, 1H).
APCIMS m/z: [M+H]$^+$ 378.
m.p.: >300° C.

Example 376

N-[4-(2-Furyl)-5-(pyridazin-3-ylcarbonyl)thiazol-2-yl]pyridine-4-carboxamide (Compound 376)

In a manner similar to that in Example 375, by using pyridazine in place of pyrimidine, the entitled Compound 376 (117 mg, 75%) was obtained from Compound 98 (150 mg, 0.419 mmol).
$^1$H NMR (DMSO-d$_6$, δ ppm): 6.36 (d, J=9.6 Hz, 1H), 6.46 (dd, J=1.8, 3.3 Hz, 1H), 6.94 (dd, J=0.7, 3.3 Hz, 1H), 7.38-7.53 (m, 4H), 7.65 (d, J=6.1 Hz, 2H), 8.05 (dd, J=2.5, 9.6 Hz, 1H).
APCIMS m/z: [M+H]$^+$ 378.
m.p.: 280-281° C.

Example 377

N-[5-Acetyl-4-(2-furyl)thiazol-2-yl]pyridine-4-carboxamide (Compound 377)

Compound 98 (1.01 g, 2.82 mmol) was suspended in THF (20 mL), and a 0.93 mol/L solution of methylmagnesium bromide (12.0 mL, 11.2 mmol) in THF was added thereto under ice-cooling, followed by stirring at room temperature for 2.5 hours. A saturated aqueous solution of ammonium chloride was added to the reaction mixture, and the precipitated solid was collected by filtration to afford the entitled Compound 377 (609 mg, 69%) as a pale yellow solid.
$^1$H NMR (DMSO, δ ppm): 3.33 (s, 3H), 6.71 (dd, J=1.8, 3.5 Hz, 1H), 7.43 (dd, J=0.7, 3.5 Hz, 1H), 7.91 (dd, J=0.7, 1.8 Hz, 1H), 8.02 (d, J=4.4 Hz, 2H), 8.83 (d, J=4.4 Hz, 2H), 13.55 (br s, 1H).
ESIMS m/z: [M+H]$^+$ 314.
m.p.: 252-259° C. (decomposition).

Example 378 tert-Butyl N-[4-(2-furyl)-5-(trifluoroacetyl)thiazol-2-yl]carbamate (Compound 378)

In a manner similar to that in Step 2 of Example 176, by using phenyl trifluoroacetate in place of phenyl 2-cyanobenzoate, the entitled Compound 378 (366 mg, 67%) was obtained from Compound h (520 mg, 1.51 mmol) obtained in Reference Example 8.
$^1$H NMR (CDCl$_3$, δ ppm): 1.53 (s, 9H), 6.61 (dd, J=1.6, 3.5 Hz, 1H), 7.61 (dd, J=0.8, 1.6 Hz, 1H), 8.06 (dd, J=0.8, 3.5 Hz, 1H), 8.90 (br s, 1H)
ESIMS m/z: [M−H]$^-$ 361.

Example 379

2-Amino-4-(2-furyl)thiazol-5-yl trifluoromethyl ketone (Compound 379)

In a manner similar to that in Example 186, the entitled Compound 379 (172 mg, 65%) was obtained from Compound 378 (366 mg, 1.01 mmol) in place of Compound 185.

$^1$H NMR (DMSO-d$_6$, δ ppm): 6.71 (dd, J=1.6, 3.5 Hz, 1H), 7.83 (d, J=3.5 Hz, 1H), 7.92 (d, J=1.6 Hz, 1H), 8.75 (br s, 2H)
APCIMS m/z: [M+H]$^+$ 263.

Example 380

N-[4-(2-Furyl)-5-(trifluoroacetyl)thiazol-2-yl]pyridine-4-carboxamide (Compound 380)

In a manner similar to that in Example 187, the entitled Compound 380 (52.3 mg, 22%) was obtained from Compound 379 (172 mg, 0.656 mmol) in place of Compound 186.
$^1$H NMR (DMSO-d$_6$, δ ppm): 6.79 (dd, J=1.6, 3.5 Hz, 1H), 7.81 (dd, J=0.8, 3.5 Hz; 1H), 8.01 (dd, J=0.8, 1.6 Hz, 1H), 8.05 (dd, J=1.6, 4.3 Hz, 2H), 8.86 (dd, J=1.6, 4.3 Hz, 2H).
APCIMS m/z: [M−H]$^−$ 366.
m.p.: 268-270° C.

Example 381

N-[4-(2-Furyl)-5-propionylthiazol-2-yl]pyridine-4-carboxamide (Compound 381)

Compound 98 (200 mg, 0.559 mmol) was suspended in THF (2 mL), and a 0.89 mol/L solution of ethylmagnesium bromide (2.00 mL, 1.78 mmol) in THF was added thereto under ice-cooling, followed by stirring overnight at room temperature. A saturated aqueous solution of ammonium chloride was added to the reaction mixture, followed by extraction with a mixed solvent (4:1) of chloroform and 2-propanol. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=200:1) to afford the entitled Compound 381 (27.2 mg, 15%) as a pale yellow solid.
$^1$H NMR (DMSO, δ ppm): 1.08 (t, J=7.2 Hz, 3H), 2.88 (q, J=7.2 Hz, 2H), 6.70 (dd, J=1.8, 3.7 Hz, 1H), 7.46 (dd, J=0.7, 3.7 Hz, 1H), 7.89 (dd, J=0.7, 1.8 Hz, 1H), 8.02 (d, J=4.4 Hz, 2H), 8.83 (d, J=4.4 Hz, 2H), 13.52 (br s, 1H).
ESIMS m/z: [M+H]$^+$ 328.
m.p.: 225-240° C. (decomposition).

Example 382

N-[5-Butyryl-4-(2-furyl)thiazol-2-yl]pyridine-4-carboxamide (Compound 382)

Compound 98 (200 mg, 0.559 mmol) was suspended in THF (5 mL), and a 1.01 mol/L solution of propylmagnesium bromide (2.00 mL, 2.02 mmol) in THF was added thereto under ice-cooling, followed by stirring for 1 hour at room temperature. A saturated aqueous solution of ammonium chloride was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:4) to afford the entitled Compound 382 (76.3 mg, 40%) as a yellowish green solid.
$^1$H NMR (DMSO, δ ppm): 0.90 (t, J=7.3 Hz, 3H), 1.60-1.66 (m, 2H), 2.82 (t, J=7.3 Hz, 2H), 6.70 (dd, J=1.8, 3.5 Hz, 1H), 7.46 (dd, J=0.8, 3.5 Hz, 1H), 7.90 (dd, J=0.8, 1.8 Hz, 1H), 8.02 (d, J=4.5 Hz, 2H), 8.83 (d, J=4.5 Hz, 2H), 13.55 (br s, 1H).
ESIMS m/z: [M−H]$^−$ 340.
m.p.: 191-194° C.

Example 383 tert-Butyl N-[5-butyryl-4-(2-furyl)thiazol-2-yl]carbamate (Compound 383)

In a manner similar to that in Example 185, by using butyric acid in place of picolinic acid, the entitled Compound 383 (733 mg, 48%) was obtained from Compound h (1.57 g, 4.55 mmol) obtained in Reference Example 8.
$^1$H NMR (CDCl$_3$, δ ppm): 0.86 (t, J=7.3 Hz, 3H), 1.15-1.60 (m, 2H), 1.50 (s, 9H), 1.70-2.05 (m, 2H), 6.48 (dd, J=1.8 Hz, 3.3 Hz, 1H), 6.99 (dd, J=0.8, 1.8 Hz, 1H), 7.47 (dd, J=0.8, 3.3 Hz, 1H), 8.20 (br s, 1H).
ESIMS m/z: [M+H]$^+$ 337.

Example 384

2-Amino-4-(2-furyl)thiazol-5-yl propyl ketone (Compound 384)

In a manner similar to that in Example 186, the entitled Compound 384 (159 mg, 15%) was obtained from Compound 383 (618 mg, 1.84 mmol) in place of Compound 185.
$^1$H NMR (CDCl$_3$, δ ppm): 86 (t, J=7.3 Hz, 3H), 1.15-2.05 (m, 4H), 5.46 (br s, 2H), 6.53 (dd, J=1.8 Hz, 3.6 Hz, 1H), 7.54 (dd, J=0.7, 1.8 Hz, 1H), 7.66 (dd, J=0.7 Hz, 3.6 Hz, 1H).
ESIMS m/z: [M+H]$^+$ 237.

Example 385

N-[5-Butyryl-4-(2-furyl)thiazol-2-yl]cyclopropanecarboxamide (Compound 385)

Compound 384 (79.8 mg, 0.338 mmol) and N,N-dimethylaminopyridine (2.10 mg, 0.0172 mmol) were dissolved in pyridine (1.5 mL), and cyclopropanecarbonyl chloride (0.0521 mL, 0.570 mmol) was added thereto under ice-cooling, followed by stirring at room temperature for 5.5 hours. Aqueous saturated sodium hydrogencarbonate solution was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was recrystallized from ethanol to afford the entitled Compound 385 (57.1 mg, 55%) as a white solid.
$^1$H NMR (CDCl$_3$, δ ppm): 0.92-1.02 (m, 2H), 0.95 (t, J=7.3 Hz, 3H), 1.16-1.25 (m, 2H), 1.42-1.53 (m, 1H), 1.73-1.79 (m, 2H), 2.81 (t, J=7.3 Hz, 2H), 6.56 (dd, J=1.8, 3.7 Hz, 1H), 7.56 (dd, J=0.7, 1.8 Hz, 1H), 7.84 (dd, J=0.7, 3.7 Hz, 1H), 9.95 (br s, 1H).
ESIMS m/z: [M+H]$^+$ 305.
m.p.: 170-172° C.

Example 386

N-[5-Butyryl-4-(2-(furyl)thiazol-2-yl]furan-2-carboxamide (Compound 386)

In a manner similar to that in Example 385, by using 2-furoyl chloride (57.1 mL, 0.582 mmol) in place of cyclopropanecarbonyl chloride, the entitled Compound 386 (28.9 mg, 76%) was obtained as a white solid from Compound 384 (80.0 mg, 0.339 mmol).

¹H NMR (CDCl₃, δ ppm): 1.00 (t, J=7.3 Hz, 3H), 1.76-1.82 (m, 2H), 2.85 (t, J=7.3 Hz, 1H), 6.57 (dd, J=1.7 Hz, 3.3 Hz, 1H), 6.65 (dd, J=1.8, 3.7 Hz, 1H), 7.41 (dd, J=0.7, 3.7 Hz, 1H), 7.59 (dd, J=0.7, 1.8 Hz, 1H), 7.60 (dd, J=0.7, 1.8 Hz, 1H), 7.82 (dd, J=0.7 Hz, 3.3 Hz, 1H), 9.80 (br s, 1H).
ESIMS m/z: [M+H]⁺ 331.
m.p.: 172-176° C.

Example 387

N-[5-Butyryl-4-(2-furyl)thiazol-2-yl]-2-(chloromethyl)pyridine-4-carboxamide (Compound 387)

In a manner similar to that in Example 187, by using 2-(chloromethyl)isonicotinic acid obtained according to the method described in WO03/043636 in place of isonicotinic acid, the entitled Compound 387 (151 mg, 92%) was obtained from Compound 384 (100 mg, 0.423 mmol) in place of Compound 186.
¹H NMR (CDCl₃, δ ppm): 1.02 (t, J=7.4 Hz, 3H), 1.78-1.84 (m, 2H), 2.87 (t, J=7.4 Hz, 2H), 4.71 (s, 2H), 6.44 (dd, J=1.8, 3.6 Hz, 1H), 7.38 (dd, J=0.7, 1.8 Hz, 1H), 7.61-7.71 (m, 1H), 7.74 (dd, J=0.7, 3.6 Hz, 1H), 7.88 (s, 1H), 8.73 (d, J=5.1 Hz, 1H).

Example 388

N-[5-Butyryl-4-(2-furyl)thiazol-2-yl]-2-(methoxymethyl)pyridine-4-carboxamide (Compound 388)

Compound 387 (262 mg, 0.671 mmol) was dissolved in methanol (5 mL), and 55% sodium hydride (34.0 mg, 0.775 mmol) was added thereto, followed by stirring under heating and reflux for 4 hours. Water was added to the reaction mixture, followed by extraction with chloroform. The organic layer was dried over anhydrous magnesium sulfate, and then the solvent was distilled away under reduced pressure. The resulting residue was purified through silica gel column chromatography (chloroform:methanol=99:1) to afford the entitled Compound 388 (142 mg, 55%).
¹H NMR (CDCl₃, δ ppm): 1.01 (t, J=7.3 Hz, 3H), 1.77-1.83 (m, 2H), 2.87 (t, J=7.3 Hz, 2H), 4.60 (s, 2H), 6.43 (d, J=1.8, 3.5 Hz, 1H), 7.39 (d, J=1.8 Hz, 1H), 7.61-7.71 (m, 1H), 7.73 (d, J=3.5 Hz, 1H), 7.79 (s, 1H), 8.71 (d, J=5.0 Hz, 1H).
APCIMS m/z: [M+H]⁺ 386.

Example 389

N-[5-Butyryl-4-(2-furyl)thiazol-2-yl]-2-[2-(dimethylamino)ethoxymethyl]pyridine-4-carboxamide hydrochloride (Compound 389)

Compound 387 (247 mg, 0.635 mmol) was dissolved in 2-(dimethylamino)ethanol (3 mL), and 55% sodium hydride (55.0 mg, 1.27 mmol) was added thereto, followed by stirring at room temperature for 2 hours. The precipitated solid was collected by filtration to afford a free form of the entitled Compound. An ethyl acetate solution of 4 mol/L hydrogen chloride was added to the resulting free form, and the precipitated solid was collected by filtration to afford the entitled Compound 389 (248 mg, 82%).
¹H NMR (DMSO-d₆, δ ppm): 0.88 (t, J=7.4 Hz, 3H), 1.57-1.63(m, 2H), 2.64 (t, J=7.4 Hz, 2H), 3.16 (s, 6H), 3.53 (t, J=5.0 Hz, 2H), 3.95 (t, J=5.0 Hz, 2H), 4.76 (s, 2H), 6.60 (dd, J=1.8, 3.3 Hz, 1H), 7.34 (dd, J=0.8, 3.3 Hz, 1H), 7.77 (dd, J=0.8, 1.8 Hz, 1H), 8.05-8.15 (m, 1H), 8.35 (s, 1H), 8.77 (d, J=5.0 Hz, 1H).
APCIMS m/z: [M+H]⁺ 443.

Example 390

N-[5-Butyryl-4-(2-furyl)thiazol-2-yl]-2-morpholinoacetamide (Compound 390)

In a manner similar to that in Example 287, the entitled Compound 390 (150 mg, 69%) was obtained from Compound 384 (150 mg, 0.526 mmol) in place of Compound 286.
¹H NMR (CDCl₃, δ ppm): 0.987 (t, J=7.4 Hz, 3H), 1.74-1.80 (m, 2H), 2.67 (t, J=4.6 Hz, 4H), 2.82 (t, J=7.4 Hz, 2H), 3.79 (t, J=4.6 Hz, 4H), 6.57 (dd, J=1.7, 3.5 Hz, 1H), 7.59 (dd, J=0.7, 1.7 Hz, 1H), 7.80 (dd, J=0.7, 3.5 Hz, 1H).
APCIMS m/z: [M+H]⁺ 364.

Example 391 tert-Butyl N-[4-(2-furyl)-5-isobutyrylthiazol-2-yl]carbamate (Compound 391)

In a manner similar to that in Example 176, by using isobutyric acid in place of 2-cyanobenzoic acid, the entitled Compound 391 (618 mg, 55%) was obtained from Compound h (1.16 g, 3.36 mmol) obtained in Reference Example 8.
¹H NMR(CDCl₃, δ ppm): 1.22 (d, J=7.0 Hz, 6H), 1.54 (s, 9H), 3.16 (septet, J=7.0 Hz, 1H), 6.54 (dd, J=1.8, 3.7 Hz, 1H), 7.55 (dd, J=0.7, 1.8 Hz, 1H), 7.79 (dd, J=0.7, 3.7 Hz, 1H), 8.52 (br s, 1H).
ESIMS m/z: [M+H]⁺ 337.

Example 392

2-Amino-4-(2-furyl)thiazol-5-yl isopropyl ketone (Compound 392)

In a manner similar to that in Example 186, the entitled Compound 392 (217 mg, 27%) was obtained as a pale yellow solid from Compound 391 (618 mg, 1.80 mmol) in place of Compound 185.
¹H NMR (CDCl₃, δ ppm): 1.18 (d, J=6.8 Hz, 6H), 3.00 (septet, J=6.8 Hz, 2H), 5.46 (br s, 2H), 6.53 (dd, J=1.8, 3.6 Hz, 1H), 7.54 (dd, J=0.7, 1.8 Hz, 1H), 7.66 (dd, J=0.7, 3.6 Hz, 1H).
ESIMS m/z: [M+H]⁺ 237.
m.p.: 195-199° C.

Example 393

N-[4-(2-Furyl)-5-isobutyrylthiazol-2-yl]pyridine-4-carboxamide (Compound 393)

Compound 392 (100 mg, 0.424 mmol) was dissolved in DMF (5 mL), and isonicotinic acid (205 mg, 1.68 mmol), EDC hydrochloride (324 mg, 1.69 mmol) and 1-hydroxybenzotriazole monohydrate (259 mg, 1.69 mmol) were added thereto, followed by stirring at 60° C. for 3 hours. The reaction mixture was concentrated under reduced pressure, and a saturated aqueous solution of sodium hydrogencarbonate was added to the resulting residue, followed by extraction with ethyl acetate. The organic layer was washed with a saturated aqueous solution of sodium chloride and dried over anhydrous magnesium sulfate, and then the solvent was distilled away under reduced pressure. The resulting residue was recrystallized from ethanol to afford the entitled Compound 393 (103 mg, 71%) as a pale green solid.

¹H NMR (CDCl₃, δ ppm): 1.27 (d, J=6.6 Hz, 6H), 3.26 (septet, J=6.6 Hz, 1H), 6.53 (dd, J=1.8, 3.7 Hz, 1H), 7.52 (dd, J=0.8, 1.8 Hz, 1H), 7.74 (d, J=4.4 Hz, 2H), 7.82 (dd, J=0.8, 3.7 Hz, 1H), 8.87 (d, J=4.4 Hz, 2H), 10.17 (br s, 1H).
ESIMS m/z: [M+H]⁺ 342.
m.p.: 179-182° C.

Example 394

N-[4-(2-Furyl)-5-isobutyrylthiazol-2-yl]cyclopropane carboxamide (Compound 394)

In a manner similar to that in Example 385, the entitled Compound 394 (95.3 mg, 73%) was obtained as a pink solid from Compound 392 (100 mg, 0.424 mmol) in place of Compound 384.
¹H NMR (CDCl₃, δ ppm): 0.93-1.03 (m, 2H), 1.15-1.25 (m, 2H), 1.23 (d, J=7.0 Hz, 6H), 1.43-1.53 (m, 1H), 3.16 (septet, J=7.0 Hz, 1H), 6.55 (dd, J=1.8, 3.7 Hz, 1H), 7.56 (dd, J=0.7, 1.8 Hz, 1H), 7.85 (dd, J=0.7, 3.7 Hz, 1H), 10.07 (br s, 1H).
ESIMS m/z: [M+H]⁺ 305.
m.p.: 178-182° C.

Example 395 tert-Butyl N-[4-(2-furyl)-5-(1-hydroxypentyl)thiazol-2-yl]carbamate (Compound 395)

Compound 92 (298 mg, 1.01 mmol) was dissolved in THF (10 mL), and a 1.59 mol/L solution of n-butyllithium in n-hexane (5.70 mL, 9.06 mmol) was added thereto in a stream of argon at −78° C., followed by stirring at room temperature for 2 hours. A saturated aqueous solution of ammonium chloride was added to the reaction mixture, followed by extraction with chloroform. The organic layer was dried over anhydrous magnesium sulfate, and then the solvent was distilled away under reduced pressure. The resulting residue was purified through silica gel column chromatography (hexane:ethyl acetate=3:1) to afford the entitled Compound 395 (224 mg, 63%).
¹H NMR (CDCl₃, δ ppm): 0.90 (t, J=7.0 Hz, 3H), 1.34-1.45 (m, 13H), 1.79-1.97 (m, 2H), 5.43-5.49 (m, 1H), 5.46 (t, J=6.7 Hz, 1H), 6.47 (dd, J=1.8, 3.4 Hz, 1H), 6.68 (dd, J=0.8, 3.4 Hz, 1H), 7.4 6 (dd, J=0.8, 1.8 Hz, 1H).

Example 396 tert-Butyl N-[4-(2-furyl)-5-valerylthiazol-2-yl]carbamate (Compound 396)

In a manner similar to that in Example 297, the entitled Compound 396 (134 mg, 60%) was obtained as a pink solid from Compound 395 (224 mg, 0.635 mmol) in place of Compound 296.
¹H NMR (CDCl₃, δ ppm): 0.93 (t, J=7.3 Hz, 3H), 1.31-1.42 (m, 2H), 1.53 (s, 9H), 1.62-1.77 (m, 2H), 2.82 (t, J=7.3 Hz, 2H), 6.55 (dd, J=1.8, 3.4 Hz, 1H), 7.55 (dd, J=0.8, 1.8 Hz, 1H), 7.78 (d, J=0.8, 3.4 Hz, 1H), 8.62 (br s, 1H).

Example 397

2-Amino-4-(2-furyl)thiazol-5-yl butyl ketone (Compound 397)

In a manner similar to that in Example 186, the entitled Compound 397 (71.7 mg, 75%) was obtained from Compound 396 (134 mg, 0.384 mmol) in place of Compound 185.

¹H NMR (CDCl₃, δ ppm): 0.91 (t, J=7.3 Hz, 3H), 1.29-1.41 (m, 2H), 1.61-1.72 (m, 2H), 2.69 (t, J=7.3 Hz, 2H), 5.99 (br s, 2H), 6.55 (dd, J=1.8, 3.5 Hz, 1H), 7.56 (dd, J=1.0, 1.8 Hz, 1H), 7.62 (dd, J=1.0, 3.5 Hz, 1H).

Example 398 tert-Butyl N-[4-(2-furyl)-5-pivaloylthiazol-2-yl]carbamate (Compound 403)

In a manner similar to that in Example 176, by using pivalic acid in place of 2-cyanobenzoic acid, the entitled Compound 398 (286 mg, 12%) was obtained from Compound h (2.26 g, 6.55 mmol) obtained in Reference Example 8.
¹H NMR (CDCl₃, δ ppm): 1.33 (s, 9H), 1.51 (s, 9H), 6.47 (dd, J=1.8 Hz, 3.5 Hz, 1H), 7.10 (d, J=3.5 Hz, 1H), 7.46 (d, J=1.8 Hz, 1H), 8.631 (br s, 1H).
ESIMS m/z: [M+H]⁺ 351.

Example 399

2-Amino-4-(2-furyl)thiazol-5-yl tert-butyl ketone (Compound 399)

In a manner similar to that in Example 186, by using Compound 398 (286 mg, 0.817 mmol) in place of Compound 185, the entitled Compound 399 (205 mg, 100%) was obtained.
¹H NMR (CDCl₃, δ ppm): 1.30 (s, 9H), 5.26 (br s, 2H), 6.47 (dd, J=1.8 Hz, 3.5 Hz, 1H), 7.30 (d, J=3.5 Hz, 1H), 7.47 (d, J=1.8 Hz, 1H).
ESIMS m/z: [M+H]⁺ 251.

Example 400

N-[4-(2-Furyl)-5-pivaloylthiazol-2-yl]pyridine-4-carboxamide (Compound 400)

Compound 399 (102 mg, 0.408 mmol) was dissolved in DMF (5 mL), and isonicotinic acid (199 mg, 1.63 mmol), EDC hydrochloride (309 mg, 1.61 mmol) and 1-hydroxybenzotriazole monohydrate (245 mg, 1.60 mmol) were added thereto, followed by stirring at 60° C. for 1.5 hours. The reaction mixture was concentrated under reduced pressure, and a saturated aqueous solution of sodium hydrogencarbonate was added to the resulting residue, followed by extraction with ethyl acetate. The organic layer was washed with a saturated aqueous solution of sodium chloride and dried over anhydrous magnesium sulfate, and then the solvent was distilled away under reduced pressure. The resulting residue was recrystallized from ethanol to afford the entitled Compound 400 (115 mg, 79%) as a pale yellowish green solid.
¹H NMR (CDCl₃, δ ppm): 1.36 (s, 9H), 6.45 (dd, J=1.8 Hz, 3.5 Hz, 1H), 7.09 (dd, J=0.5, 3.5 Hz, 1H), 7.44 (dd, J=0.5 Hz, 1.8 Hz, 1H), 7.75 (d, J=4.5 Hz, 2H), 8.86 (d, J=4.5 Hz, 2H), 10.05 (br s, 1H).
ESIMS m/z: [M+H]⁺ 356.
m.p.: 240-245° C.

Example 401

N-[4-(2-Furyl)-5-pivaloylthiazol-2-yl]cyclopropanecarboxamide (Compound 401)

In a manner similar to that in Example 400, by using cyclopropanecarboxylic acid (0.130 mL, 1.61 mmol) in place of isonicotinic acid, the entitled Compound 401 (94.8 mg, 76%) was obtained as a white solid from Compound 399 (98.2 mg, 0.393 mmol).

$^1$H NMR (CDCl$_3$, δ ppm): 0.88-0.98 (m, 2H), 1.13-1.20 (m, 2H), 1.32 (s, 9H), 1.40-1.50 (m, 1H), 6.48 (dd, J=1.8, 3.7 Hz, 1H), 7.16 (dd, J=0.7, 3.7 Hz, 1H), 7.48 (dd, J=0.7, 1.8 Hz, 1H), 10.15 (br s, 1H).

ESIMS m/z: [M+H]$^+$ 319.

m.p.: 133-134° C.

Example 402 tert-Butyl N-[4-(2-furyl)-5-(methoxyacetyl)thiazol-2-yl]carbamate (Compound 402)

In a manner similar to that in Example 185, by using methoxyacetic acid in place of picolinic acid, the entitled Compound 402 (1.12 g, 42%) was obtained from Compound h (2.69 g, 7.79 mmol) obtained in Reference Example 8.

$^1$H NMR (CDCl$_3$, δ ppm): 1.46 (s, 9H), 3.47 (s, 3H), 4.41 (s, 2H), 6.54 (dd, J=1.7, 3.5 Hz, 1H), 7.53 (d, J=1.7 Hz, 1H), 7.80 (d, J=3.5 Hz, 1H).

Example 403

2-Amino-4-(2-furyl)thiazol-5-yl methoxymethyl ketone (Compound 403)

In a manner similar to that in Example 186, the entitled Compound 403 (296 mg, 98%) was obtained from Compound 402 (428 mg, 1.26 mmol) in place of Compound 185.

$^1$H NMR (CDCl$_3$, δ ppm): 3.43 (s, 3H), 4.29 (s, 2H), 6.54 (dd, J=1.8, 3.5 Hz, 1H), 7.55 (d, J=1.8 Hz, 1H), 7.69 (d, J=3.5 Hz, 1H).

Example 404

2-Chloro-N-[4-(2-furyl)-5-(methoxyacetyl)thiazol-2-yl]pyridine-5-carboxamide (Compound 404)

In a manner similar to that in Example 187, by using 6-chloronicotinic acid in place of isonicotinic acid, the entitled Compound 404 (129 mg, 81%) was obtained from Compound 403 (100 mg, 0.420 mmol) in place of Compound 186.

$^1$H NMR (CDCl$_3$, δ ppm): 3.51 (s, 3H), 4.44 (s, 2H), 6.48 (dd, J=1.8, 3.7 Hz, 1H), 7.44-7.46 (m, 2H), 7.77 (d, J=3.7 Hz, 1H), 8.18 (dd, J=2.2, 8.4 Hz, 1H), 8.92 (d, J=2.2 Hz, 1H).

APCIMS m/z: [M+H]$^+$ 378.

m.p.: 174-183° C.

Example 405

4-Fluoro-N-[4-(2-furyl)-5-(methoxyacetyl)thiazol-2-yl]benzamide (Compound 405)

In a manner similar to that in Example 187, by using 4-fluorobenzoic acid in place of isonicotinic acid, the entitled Compound 405 (138 mg, 91%) was obtained from Compound 403 (100 mg, 0.420 mmol) in place of Compound 186.

$^1$H NMR (CDCl$_3$, δ ppm): 3.50 (s, 3H), 4.45 (s, 2H), 6.51 (dd, J=1.8, 3.3 Hz, 1H), 7.15-7.21 (m, 2H), 7.50 (d, J=1.8 Hz, 1H), 7.82 (d, J=3.3 Hz, 1H), 7.93-7.97 (m, 2H).

APCIMS m/z: [M+H]$^+$ 361.

m.p.: 166-167° C.

Example 406 tert-Butyl N-[5-(ethoxyacetyl)-4-(2-furyl)thiazol-2-yl]carbamate (Compound 406)

In a manner similar to that in Example 185, by using ethoxyacetic acid in place of picolinic acid, the entitled Compound 406 (450 mg, 28%) was obtained from Compound h (1.59 g, 4.60 mmol) obtained in Reference Example 8.

$^1$H NMR (CDCl$_3$, δ ppm): 1.27 (t, J=6.9 Hz, 3H), 1.51 (s, 9H), 3.61 (q, J=6.9 Hz, 2H), 4.44 (s, 2H), 6.54 (dd, J=1.8, 3.5 Hz, 1H), 7.55 (d, J=1.8 Hz, 1H), 7.81 (d, J=3.5 Hz, 1H).

Example 407

2-Amino-4-(2-furyl)thiazol-5-yl ethoxymethyl ketone (Compound 407)

In a manner similar to that in Example 186, the entitled Compound 407 (247 mg, 77%) was obtained from Compound 406 (450 mg, 1.28 mmol) in place of Compound 185.

$^1$H NMR (CDCl$_3$, δ ppm): 1.24 (t, J=7.1 Hz, 3H), 3.57 (q, J=7.1 Hz, 2H), 4.31 (s, 2H), 6.54 (dd, J=1.8, 3.5 Hz, 1H), 7.56 (d, J=1.8 Hz, 1H), 7.75 (d, J=3.5 Hz, 1H).

Example 408 tert-Butyl N-[5-acryloyl-4-(2-furyl)thiazol-2-yl]carbamate (Compound 408)

Compound 98 (1.00 g, 2.83 mmol) was dissolved in THF (6 mL), and a 1.0 mol/L solution of vinylmagnesium bromide in THF (8.49 mL, 8.49 mmol) was added thereto in an atmosphere of argon at 0° C., followed by stirring at room temperature for 2 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=3:1) to afford the entitled Compound 408 (697 mg, 74%).

$^1$H NMR (CDCl$_3$, δ ppm): 1.45 (s, 9H), 5.76 (dd, J=1.7, 10.2 Hz, 1H), 6.42 (dd, J=1.7, 16.8 Hz, 1H), 6.53 (dd, J=1.8, 3.5 Hz, 1H), 6.83 (dd, J=10.2, 16.8 Hz, 1H), 7.53 (d, J=1.8 Hz, 1H), 7.56 (d, J=3.5 Hz, 1H).

Example 409 tert-Butyl N-[4-(2-furyl)-5-(2-methoxyethylcarbonyl)thiazol-2-yl]carbamate (Compound 409)

Compound 408 (110 mg, 0.343 mmol) was dissolved in methanol (10 mL), and potassium hydroxide (20.0 mg, 0.356 mmol) was added thereto, followed by stirring under heating and reflux for 2.5 hours. Water was added to the reaction mixture, followed by extraction with ethyl acetate. The organic layer was dried over anhydrous magnesium sulfate, and then the solvent was distilled away under reduced pressure. The resulting residue was purified through silica gel column chromatography (hexane:ethyl acetate=1:1) to afford the entitled Compound 409 (124 mg, 0.343 mmol).

$^1$H NMR (CDCl$_3$, δ ppm): 1.47 (s, 9H), 3.07 (t, J=6.1 Hz, 2H), 3.33 (s, 3H), 3.76 (t, J=6.1 Hz, 2H), 6.52 (dd, J=1.8, 3.5 Hz, 1H), 7.53 (d, J=1.8 Hz, 1H), 7.72 (d, J=3.5 Hz, 1H).

Example 410

2-Amino-4-(2-furyl)thiazol-5-yl 2-methoxyethyl ketone (Compound 410)

Compound 409 (124 mg, 0.343 mmol) was dissolved in trifluoroacetic acid (3 mL), followed by stirring at room temperature for 1 hour. The reaction mixture was concentrated under reduced pressure, and a saturated aqueous solution of sodium hydrogencarbonate was added to the residue, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford the entitled Compound 410 (79.0 mg, 87%).

$^1$H NMR (CDCl$_3$, δ ppm): 2.96 (t, J=6.2 Hz, 2H), 3.33 (s, 3H), 3.72 (t, J=6.2 Hz, 2H), 5.61 (br s, 2H), 6.52 (dd, J=1.8, 3.5 Hz, 1H), 7.53-7.54 (m, 2H).

Example 411 tert-Butyl N-[5-(2-ethoxyethylcarbonyl)-4-(2-furyl)thiazol-2-yl]carbamate (Compound 411)

In a manner similar to that in Example 409, by using ethanol in place of methanol, the entitled Compound 411 (126 mg, 100%) was obtained from Compound 408 (110 mg, 0.343 mmol).

$^1$H NMR (CDCl$_3$, δ ppm): 1.16 (t, J=6.9 Hz, 3H), 3.08 (t, J=6.4 Hz, 2H), 3.49 (q, J=6.9 Hz, 2H), 3.80 (t, J=6.4 Hz, 2H), 6.52 (dd, J=1.8, 3.6 Hz, 1H), 7.53 (d, J=1.8 Hz, 1H), 7.70 (d, J=3.6 Hz, 1H).

Example 412

2-Amino-4-(2-furyl)thiazol-5-yl 2-ethoxyethyl ketone (Compound 412)

In a manner similar to that in Example 410, the entitled Compound 412 (79.0 mg, 87%) was obtained from Compound 411 (126 mg, 0.343 mmol) in place of Compound 409.

$^1$H NMR (CDCl$_3$, δ ppm): 1.16 (t, J=7.0 Hz, 3H), 2.97 (t, J=6.6 Hz, 2H), 3.48 (q, J=7.0 Hz, 2H), 3.76 (t, J=6.6 Hz, 2H), 5.70 (br s, 2H), 6.51 (dd, J=1.8, 3.5 Hz, 1H), 7.53 (dd, J=0.7, 1.8 Hz, 1H), 7.56 (dd, J=0.7, 3.5 Hz, 1H).

Example 413

N-[4-(2-Furyl)-5-(3-methoxypropa-1-ynylcarbonyl)thiazol-2-yl]pyridine-4-carboxamide (Compound 413)

In a manner similar to that in Example 283, by using methyl propargyl ether (65.5 mg, 0.935 mmol) in place of 2-bromo-6-methoxypyridine, the entitled Compound 413 (86.3 mg, 80%) was obtained from Compound 98 (105 mg, 0.292 mmol).

$^1$H NMR (DMSO-d$_6$, δ ppm): 3.37 (s, 3H), 4.45 (s, 2H), 6.74 (dd, J=1.7, 3.5 Hz, 1H), 7.76 (dd, J=0.8, 3.5 Hz, 1H), 7.95 (dd, J=0.8, 1.7 Hz, 1H), 8.04 (dd, J=1.6, 4.5 Hz, 2H), 8.84 (dd, J=1.6, 4.5 Hz, 2H), 13.80 (br s, 1H).

ESIMS m/z: [M+H]$^+$ 368.

m.p.: 198-200° C.

Example 414 tert-Butyl N-[4-(2-furyl)-5-(3-methoxypropa-1-ynylcarbonyl)thiazol-2-yl]carbamate (Compound 414)

In a manner similar to that in Example 283, by using methyl propargyl ether (380 mg, 5.42 mmol) in place of 2-bromo-6-methoxypyridine, the entitled Compound 414 (479 mg, 78%) was obtained from Compound 134 (602 mg, 1.70 mmol) in place of Compound 98.

$^1$H NMR (CDCl$_3$, δ ppm): 1.55 (s, 9H), 3.47 (s, 3H), 4.34 (s, 2H), 6.58 (dd, J=1.8, 3.0 Hz, 1H), 7.59 (dd, J=1.2, 1.8 Hz, 1H), 8.02 (dd, J=1.2, 3.0 Hz, 1H), 8.67 (br s, 1H).

Example 415 tert-Butyl N-[4-(2-furyl)-5-(3-methoxypropylcarbonyl)thiazol-2-yl]carbamate (Compound 415)

Compound 414 (92.3 mg, 0.255 mmol) was dissolved in ethanol (5 mL), and 10% palladium-carbon (15.8 mg) was added thereto, followed by stirring in an atmosphere of hydrogen at room temperature for 1.5 hours. The reaction mixture was filtered, and the filtrate was concentrated under reduced pressure to afford the entitled Compound 415 (93.3 mg, 100%).

$^1$H NMR (CDCl$_3$, δ ppm): 1.48 (s, 9H), 1.98-2.03 (m, 2H), 2.93 (t, J=7.0 Hz, 2H), 3.32 (s, 3H), 3.43 (t, J=7.0 Hz, 2H), 6.55 (dd, J=1.0, 3.3 Hz, 1H), 7.54 (d, J=1.0 Hz, 1H), 7.79 (d, J=3.3 Hz, 1H), 9.28 (br s, 1H).

Example 416

2-Amino-4-(2-furyl)thiazol-5-yl 3-methoxypropyl ketone (Compound 416)

In a manner similar to that in Example 186, the entitled Compound 416 (67.4 mg, 99%) was obtained from Compound 415 (93.3 mg, 0.263 mmol) in place of Compound 185.

$^1$H NMR (CDCl$_3$, δ ppm): 1.96 (t, J=7.0 Hz, 2H), 2.76-2.81 (m, 2H), 3.31 (s, 3H), 3.42 (t, J=7.0 Hz, 2H), 6.00 (br s, 2H), 6.54 (dd, J=1.8, 3.3 Hz, 1H), 7.55 (d, J=1.8 Hz, 1H), 7.63 (d, J=3.3 Hz, 1H).

Example 417

N-[5-(Cyclopropylcarbonyl)-4-(2-furyl)thiazol-2-yl]pyridine-4-carboxamide (Compound 417)

Compound 98 (127 mg, 0.355 mmol) was suspended in THF (2.5 mL), and a 0.5 mol/L solution of cyclopropylmagnesium bromide in THF (4.00 mL, 2.00 mmol) was added thereto under ice-cooling, followed by stirring at room temperature for 2.5 hours. A saturated aqueous solution of ammonium chloride was added to the reaction mixture, followed by extraction with a mixed solvent (4:1) of chloroform and 2-propanol. The organic layer was washed with a saturated aqueous solution of sodium chloride and dried, over anhydrous magnesium sulfate, and then the solvent was distilled away under reduced pressure. The resulting residue was purified through silica gel column chromatography (ethyl acetate) to afford the entitled Compound 417 (94.1 mg, 78%) as a pale yellow solid.

$^1$H NMR (CDCl$_3$, δ ppm): 1.03-1.10 (m, 2H), 1.29-1.34 (m, 2H), 2.35-2.43 (m, 1H), 6.50 (dd, J=1.7, 3.5 Hz, 1H), 7.50 (dd, J=0.7, 3.5 Hz, 1H), 7.61 (dd, J=0.7, 1.7 Hz, 1H), 7.76 (d, J=4.4 Hz, 2H), 8.85 (d, J=4.4 Hz, 2H), 10.34 (br s, 1H).

Example 418 tert-Butyl N-[5-(cyclopropylcarbonyl)-4-(2-furyl)thiazol-2-yl]carbamate (Compound 418)

In a manner similar to that in Example 176, by using cyclopropanecarboxylic acid in place of 2-cyanobenzoic acid, the entitled Compound 418 (884 mg, 67%) was obtained from Compound h (1.36 g, 3.94 mmol) obtained in Reference Example 8.

$^1$H NMR (CDCl$_3$, δ ppm): 0.90-1.03 (m, 2H), 1.16-1.36 (m, 2H), 1.52 (s, 9H), 1.78-1.99 (m, 1H), 6.53 (dd, J=1.7 Hz, 3.3 Hz, 1H), 6.74 (d, J=3.3 Hz, 1H), 7.55 (d, J=1.7 Hz, 1H), 8.30 (br s, 1H).

ESIMS m/z: [M+H]$^+$ 335.

Example 419

2-Amino-4-(2-furyl)thiazol-5-yl cyclopropyl ketone (Compound 419)

In a manner similar to that in Example 186, the entitled Compound 419 (352 mg, 57%) was obtained from Compound 418 (884 mg, 2.65 mmol) in place of Compound 185.

$^1$H NMR (CDCl$_3$, δ ppm): 1.03-1.10 (m, 2H), 1.28-1.35 (m, 2H), 2.35-2.45 (m, 1H), 5.46 (br s, 2H), 6.53 (dd, J=1.8, 3.6 Hz, 1H), 7.54 (dd, J=0.7, 1.8 Hz, 1H), 7.66 (dd, J=0.7, 3.6 Hz, 1H).

ESIMS m/z: [M+H]$^+$ 235.

Example 420

N-[5-(Cyclopropylcarbonyl)-4-(2-furyl)thiazol-2-yl]-2-methoxybenzamide (Compound 420)

In a manner similar to that in Example 187, by using 2-methoxybenzoic acid (208 mg, 1.37 mmol) in place of isonicotinic acid, the entitled Compound 420 (73.3 mg, 58%) was obtained as a pink solid from Compound 419 (79.1 mg, 0.338 mmol) in place of Compound 186.

$^1$H NMR (CDCl$_3$, δ ppm): 0.80-1.07 (m, 2H), 1.24-1.32 (m, 2H), 2.37-2.42 (m, 1H), 4.12 (s, 3H), 6.55 (dd, J=1.8, 3.5 Hz, 1H), 7.08 (d, J=8.4 Hz, 1H), 7.18 (ddd, J=1.0 Hz, 7.4 Hz, 7.8 Hz, 1H), 7.55-7.65 (m, 3H), 8.32 (dd, J=1.8, 7.8 Hz, 1H), 11.23 (br s, 1H).

ESIMS m/z: [M+H]$^+$ 369.

m.p.: 150-154° C.

Example 421

N-[5-(Cyclopropylcarbonyl)-4-(2-furyl)thiazol-2-yl]-2-morpholinoacetamide (Compound 421)

Compound 419 (192 mg, 0.824 mmol) and triethylamine (0.379 mL, 2.72 mmol) were dissolved in THF (4 mL), and bromoacetyl bromide (0.215 mL, 2.47 mmol) was added thereto at 0° C., followed by stirring at room temperature for 1 hour. At 0° C., a solution (2 mL) of morpholine (1.08 mL, 12.4 mmol) in THF and triethylamine (1.73 mL, 12.4 mmol) was added to the reaction mixture, followed by stirring at room temperature for 1 hour. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography to afford the entitled Compound 421 (229 mg, 77%).

$^1$H NMR (CDCl$_3$, δ ppm): 1.00-1.03 (m, 2H), 1.22-1.18 (m, 2H), 2.30-2.38 (m, 1H), 2.61 (t, J=4.6 Hz, 4H), 3.77 (t, J=4.6 Hz, 4H), 6.53 (dd, J=1.8, 3.5 Hz, 1H), 7.56 (dd, J=0.7, 1.8 Hz, 1H), 7.60 (J=0.7, 3.5 Hz, 1H).

APCIMS m/z: [M+H]$^+$ 362.

Example 422 tert-Butyl N-[5-(cyclobutylcarbonyl)-4-(2-furyl)thiazol-2-yl]carbamate (Compound 422)

In a manner similar to that in Example 176, by using cyclobutanecarboxylic acid in place of 2-cyanobenzoic acid, the entitled Compound 422 (628 mg, 44%) was obtained from Compound h (1.41 g, 4.09 mmol) obtained in Reference Example 8.

$^1$H NMR (CDCl$_3$, δ ppm): 1.48 (s, 9H), 1.80-2.10 (m, 2H), 2.15-2.33 (m, 2H), 2.35-2.48 (m, 2H), 3.70-3.77 (m, 1H), 6.55 (dd, J=1.8, 3.5 Hz, 1H), 7.55 (dd, J=0.7 Hz, 1.8 Hz, 1H), 7.87 (dd, J=0.7, 3.5 Hz, 1H), 9.28 (br s, 1H).

Example 423

2-Amino-4-(2-furyl)thiazol-5-yl cyclobutyl ketone (Compound 423)

In a manner similar to that in Example 186, the entitled Compound 423 (448 mg, 100%) was obtained from Compound 422 (628 mg, 1.81 mmol) in place of Compound 185.

$^1$H NMR (CDCl$_3$, δ ppm): 1.80-2.05 (m, 2H), 2.10-2.22 (m, 2H), 2.30-2.45 (m, 2H), 3.55-3.61 (m, 1H), 5.56 (br s, 2H), 6.55 (dd, J=1.8, 3.5 Hz, 1H), 7.55 (dd, J=0.8, 1.8 Hz, 1H), 7.70 (dd, J=0.8, 3.5 Hz, 1H).

ESIMS m/z: [M+H]$^+$ 249.

m.p.: 125-160° C. (decomposition)

Example 424

N-[5-(Cyclobutylcarbonyl)-4-(2-furyl)thiazol-2-yl]pyridine-4-carboxamide (Compound 442)

In a manner similar to that in Example 187, the entitled Compound 424 (106 mg, 72%) was obtained as a pale brown solid from Compound 423 (103 mg, 0.415 mmol) in place of Compound 186.

$^1$H NMR (CDCl$_3$, δ ppm): 1.85-2.18 (m, 2H), 2.25-2.40 (m, 2H), 2.40-2.55 (m, 2H), 3.76-3.82 (m, 1H), 6.53 (dd, J=1.8, 3.5 Hz, 1H), 7.50 (dd, J=0.8, 1.8 Hz, 1H), 7.73 (d, J=4.5 Hz, 2H), 7.85 (dd, J=0.8, 3.5 Hz, 1H), 8.84 (d, J=4.5 Hz, 1H), 8.85 (d, J=4.5 Hz, 1H), 10.27 (br s, 1H).

ESIMS m/z: [M+H]$^+$ 354.

m.p.: 227-235° C. (decomposition)

Example 425

N-[5-(Cyclobutylcarbonyl)-4-(2-furyl)thiazol-2-yl]furan-2-carboxamide (Compound 425)

In a manner similar to that in Example 385, by using 2-furoyl chloride (0.0702 mL, 0.721 mmol) in place of cyclopropanecarbonyl chloride, the entitled Compound 425 (106 mg, 76%) was obtained from Compound 423 (100 mg, 0.403 mmol) in place of Compound 384.

¹H NMR (CDCl₃, δ ppm): 1.93-2.13 (m, 2H), 2.23-2.50 (m, 4H), 3.74-3.80 (m, 1H), 6.58 (dd, J=1.8, 3.7 Hz, 1H), 6.64 (dd, J=1.8, 3.7 Hz, 1H), 7.39-7.41 (m, 3H), 7.90 (dd, J=0.7, 3.7 Hz, 1H), 9.81 (br s, 1H).
ESIMS m/z: [M+H]⁺ 343.
m.p.: 188-192° C.

Example 426

4-Cyano-N-[5-(cyclobutylcarbonyl)-4-(2-furyl)thiazol-2-yl]benzamide (Compound 426)

In a manner similar to that in Example 385, by using 4-cyanobenzoyl chloride (127 mg, 0.767 mmol) in place of cyclopropanecarbonyl chloride, the entitled Compound 426 (122 mg, 75%) was obtained from Compound 423 (106 mg, 0.427 mmol) in place of Compound 384.
¹H NMR (CDCl₃, δ ppm): 1.85-2.14 (m, 2H), 2.24-2.50 (m, 4H), 3.76-3.82 (m, 1H), 6.51 (dd, J=1.8, 3.7 Hz, 1H), 7.47 (dd, J=0.7, 1.8 Hz, 1H), 7.80 (d, J=8.8 Hz, 2H), 7.85 (dd, J=0.7, 3.7 Hz, 1H), 8.01 (d, J=8.8 Hz, 2H), 10.41 (br s, 1H).
ESIMS m/z: [M−H]⁻ 376.
m.p.: 220-225° C.

Example 427

N-[5-(Cyclobutylcarbonyl)-4-(2-furyl)thiazol-2-yl]cyclopropanecarboxamide (Compound 427)

In a manner similar to that in Example 385, the entitled Compound 427 (109 mg, 84%) was obtained from Compound 423 (102 mg, 0.411 mmol) in place of Compound 384.
¹H NMR (CDCl₃, δ ppm): 0.91-0.99 (m, 2H), 1.15-1.25 (m, 2H), 1.80-2.10 (m, 2H), 2.20-2.49 (m, 5H), 3.69-3.75 (m, 1H), 6.56 (dd, J=1.7, 3.5 Hz, 1H), 7.56 (dd, J=0.7, 1.7 Hz, 1H), 7.91 (dd, J=0.7, 3.5 Hz, 1H), 10.09 (br s, 1H).
ESIMS m/z: [M+H]⁺ 317.
m.p.: 200-205° C.

Example 428 tert-Butyl N-{4-(2-furyl)-5-[1-hydroxy-1-(3-methyloxetan-3-yl)methyl]thiazol-2-yl}carbamate (Compound 428)

Step 1:
(3-Methyloxetan-3-yl)methanol (1.00 g, 9.79 mmol) and a 2.0 mol/L solution (5.4 mL) of oxalyl chloride in dichloromethane were dissolved in dichloromethane (200 mL), followed by stirring at −60° C. for 10 minutes. DMSO (1.67 mL, 23.5 mmol) was added to the reaction mixture, followed by stirring for 15 minutes. Triethylamine (6.82 mL, 49.0 mmol) was added thereto, and followed by further stirring at room temperature for 30 minutes. Water was added to the reaction mixture, followed by extraction with ethyl acetate. The organic layer was dried over anhydrous magnesium sulfate, and then the solvent was distilled away under reduced pressure to afford 3-methyloxetane-3-carbaldehyde (340 mg, 35%).
¹H NMR (CDCl₃, δ ppm): 1.45 (s, 3H), 4.47 (d, J=6.3 Hz, 2H), 4.84 (d, J=6.3 Hz, 2H), 9.92 (s, 1H).

Step 2:
Compound h (500 mg, 1.45 mmol) obtained in Reference Example 8 was dissolved in THF (14 mL), and a 1.58 mol/L solution of n-butyllithium in n-hexane (2.03 mL, 3.21 mmol) was added thereto in a stream of argon at −78° C., followed by stirring at −78° C. for 15 minutes. 3-Methyloxetane-3-carbaldehyde (436 mg, 4.35 mmol) obtained in Step 1 was added dropwise to the reaction mixture, followed by stirring at room temperature for 1.5 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 428 (141 mg, 27%).
7¹H NMR (CDCl₃, δ ppm): 1.27-1.35 (m, 3H), 1.50 (s, 9H), 4.27-4.38 (m, 2H), 4.84-4.98, (m, 2H), 5.67 (m, 1H), 6.47 (dd, J=1.8, 3.5 Hz, 1H), 6.73 (d, J=3.5 Hz, 1H), 7.45 (d, J=1.8 Hz, 1H).

Example 429 tert-Butyl N-[4-(2-furyl)-5-(3-methyloxetan-3-ylcarbonyl)-thiazol-2-yl]carbamate (Compound 429)

In a manner similar to that in Example 297, the entitled Compound 429 (85.0 mg, 61%) was obtained from Compound 428 (140 mg, 0.382 mmol) in place of Compound 296.
¹H NMR (CDCl₃, δ ppm): 1.38 (s, 9H), 1.77 (s, 3H), 4.44 (d, J=6.1 Hz, 2H), 5.05 (d, J=6.1 Hz, 2H), 6.50 (dd, J=1.8, 3.6 Hz, 1H), 7.48 (dd, J=0.8, 1.8 Hz, 1H), 7.84 (dd, J=0.8, 3.6 Hz, 1H).

Example 430

2-Amino-4-(2-furyl)thiazol-5-yl 3-methyloxetan-3-yl ketone (Compound 430)

In a manner similar to that in Example 186, the entitled Compound 430 (62.0 mg, 100%) was obtained from Compound 429 (85.0 mg, 0.233 mmol) in place of Compound 185.
¹H NMR (CDCl₃, δ ppm): 1.75 (s, 3H), 4.37 (d, J=6.1 Hz, 2H), 5.02 (d, J=6.1 Hz, 2H), 6.56 (dd, J=1.8, 3.6 Hz, 1H), 7.57 (d, J=1.8 Hz, 1H), 7.88 (d, J=3.6 Hz, 1H).

Example 431

N-[5-(Cycolopentylcarbonyl)-4-(2-furyl)thiazol-2-yl]-pyridine-4-carboxamide (Compound 431)

Compound 98 (74.0 mg, 0.207 mmol) was dissolved in THF (1.5 mL), and a 2 mol/L solution of cyclopentylmagnesium bromide in diethyl ether (0.500 mL, 1.00 mmol) was added thereto under ice-cooling, followed by stirring at room temperature for 1.5 hours. A saturated aqueous solution of ammonium chloride was added to the reaction mixture, followed by extraction with chloroform. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 431 (5.60 mg, 7%) as a pale brown solid.
¹H NMR (CDCl₃, δ ppm): 1.62-1.84 (m, 4H), 1.90-2.03 (m, 4H), 3.42-3.48 (m, 1H), 6.53 (dd, J=1.8, 3.5 Hz, 1H), 7.52 (dd, J=0.7, 3.5 Hz, 1H), 7.74 (d, J=4.4 Hz, 2H), 7.85 (dd, J=0.7, 1.8 Hz, 1H), 8.86 (d, J=4.4 Hz, 2H), 8.88 (d, J=4.4 Hz, 1H), 10.16 (br s, 1H).
ESIMS m/z: [M+H]⁺ 368.
m.p.: 168-181° C.

Example 432 tert-Butyl N-[5-(cyclopentylcarbonyl)-4-(2-furyl)thiazol-2-yl]carbamate (Compound 432)

In a manner similar to that in Example 176, by using cyclopentanecarboxylic acid in place of 2-cyanobenzoic acid, the entitled Compound 432 (251 mg, 17%) was obtained from Compound h (1.44 g, 4.17 mmol) obtained in Reference Example 8.
$^1$H NMR (CDCl$_3$, δ ppm): 1.20-2.10 (m, 8H), 1.51 (s, 9H), 2.96-3.02 (m, 1H), 6.45 (dd, J=1.8 Hz, 3.3 Hz, 1H), 6.65 (d, J=3.3 Hz, 1H), 7.41 (d, J=1.8 Hz, 1H), 8.45 (br s, 1H).
ESIMS m/z: [M+H]$^+$ 363.

Example 433

2-Amino-4-(2-furyl)thiazol-5-yl cyclopentyl ketone (Compound 433)

In a manner similar to that in Example 186, the entitled Compound 433 (246 mg, 79%) was obtained from Compound 432 (433 mg, 1.20 mmol) in place of Compound 185.
$^1$H NMR (CDCl$_3$, δ ppm): 1.20-2.10 (m, 8H), 2.96-3.02 (m, 1H), 5.46 (br s, 2H), 6.53 (dd, J=1.8, 3.6 Hz, 1H), 7.54 (dd, J=0.7, 1.8 Hz, 1H), 7.66 (dd, J=0.7, 3.6 Hz, 1H).
ESIMS m/z: [M+H]$^+$ 263.

Example 434

N-[5-(Cyclopentylcarbonyl)-4-(2-furyl)thiazol-2-yl]cyclopropanecarboxamide (Compound 434)

In a manner similar to that in Example 385, the entitled Compound 434 (28.2 mg, 44%) was obtained as a white solid from Compound 433 (49.6 mg, 0.189 mmol) in place of Compound 384.
$^1$H NMR (CDCl$_3$, δ ppm): 0.94-1.04 (m, 2H), 1.16-1.25 (m, 2H), 1.46-1.82 (m, 6H), 1.86-1.99 (m, 3H), 3.32-3.41 (m, 1H), 6.55 (dd, J=1.8, 3.5 Hz, 1H), 7.56 (dd, J=0.7, 1.8 Hz, 1H), 7.87 (dd, J=0.7, 3.5 Hz, 1H), 9.83 (br s, 1H).
ESIMS m/z: [M+H]$^+$ 331.
m.p.: 182-187° C.

Example 435

N-[5-(Cyclopentylcarbonyl)-4-(2-furyl)thiazol-2-yl]-morpholine-4-carboxamide (Compound 435)

Compound 432 (251 mg, 0.693 mmol) was dissolved in 1,4-dioxane (5 mL), and morpholine (6.19 mL, 70.9 mmol) was added thereto, followed by stirring overnight under heating and reflux. The reaction mixture was concentrated under reduced pressure, and water was added to the resulting residue, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=3:1) to afford the entitled Compound 435 (168 mg, 64%) as a pale brown solid.
$^1$H NMR (CDCl$_3$, δ ppm): 1.55-1.80 (m, 4H), 1.85-2.00 (m, 4H), 3.35-3.41 (m, 1H), 3.45-3.53 (m, 4H), 3.65-3.73 (m, 4H), 6.56 (dd, J=1.8, 3.5 Hz, 1H), 7.52 (dd, J=0.7, 1.8 Hz, 1H), 7.93 (dd, J=0.7, 3.5 Hz, 1H), 9.23 (br s, 1H).
ESIMS m/z: [M+H]$^+$ 376.
m.p.: 108-110° C.

Example 436 tert-Butyl N-[5-(1-cyclohexyl-1-hydroxymethyl)-4-(2-furyl)thiazol-2-yl]carbamate (Compound 436)

In a manner similar to that in Example 92, by using cyclohexanecarbaldehyde in place of DMF, the entitled Compound 436 (173 mg, 46%) was obtained from Compound h (3.45 g, 1.00 mmol) obtained in Reference Example 8.
$^1$H NMR (CDCl$_3$, δ ppm): 0.86-1.40 (m, 6H), 1.45 (s, 9H), 1.50-1.80 (m, 4H), 2.05-2.15 (m, 1H), 5.21 (d, J=8.1 Hz, 1H), 6.46 (dd, J=1.9, 3.5 Hz, 1H), 6.65 (dd, J=0.8, 3.5 Hz, 1H), 7.45 (dd, J=0.8, 1.9 Hz, 1H), 8.55 (br s, 1H).

Example 437 tert-Butyl N-[5-(cyclohexylcarbonyl)-4-(2-furyl)thiazol-2-yl]carbamate (Compound 437)

In a manner similar to that in Example 297, the entitled Compound 437 (109 mg, 63%) was obtained from Compound 436 (173 mg, 0.458 mmol) in place of Compound 296.
$^1$H NMR (CDCl$_3$, δ ppm): 1.15-1.35 (m, 4H), 1.56 (s, 9H), 1.65-1.95 (m, 6H), 2.85 (tt, J=3.4, 11.0 Hz, 1H), 6.53 (dd, J=0.9, 1.8 Hz, 1H), 7.54 (dd, J=0.9, 3.3 Hz, 1H), 7.75 (dd, J=1.7, 3.3 Hz, 1H).

Example 438

2-Amino-4-(2-furyl)thiazol-5-yl cyclohexyl ketone (Compound 438)

In a manner similar to that in Example 186, the entitled Compound 438 (55.8 mg, 70%) was obtained from Compound 437 (109 mg, 0.290 mmol) in place of Compound 185.
$^1$H NMR (DMSO-d$_6$, δ ppm): 1.10-1.45 (m, 4H), 1.50-1.80 (m, 6H), 2.80-2.95 (m, 1H), 6.64 (dd, J=1.8, 3.5 Hz, 1H), 7.21 (d, J=3.5 Hz, 1H), 7.82 (d, J=1.8 Hz, 1H), 7.87 (br s, 1H).

Example 439

N-[5-(Cyclohexylcarbonyl)-4-(2-furyl)thiazol-2-yl]-pyridine-4-carboxamide (Compound 439)

In a manner similar to that in Example 187, a crude Compound 439 was obtained from Compound 438 in place of Compound 186. The crude Compound 439 was reslurried with a mixed solvent of ethanol and diethyl ether to afford the entitled Compound 439 (41.6 mg, 55%) as a white solid.
$^1$H NMR (DMSO-d$_6$, δ ppm): 1.05-1.45 (m, 4H), 1.55-1.90 (m, 6H), 2.86-2.94 (m, 1H), 6.70 (dd, J=1.6, 3.2 Hz, 1H), 7.40 (d, J=3.2 Hz, 1H), 7.89 (d, J=1.6 Hz 1H), 8.02 (dd, J=1.9, 4.3 Hz, 2H), 8.83 (dd, J=1.9, 4.3 Hz, 2H), 13.54 (br s, 1H).
m.p.: 197-199° C.

Example 440 tert-Butyl N-[4-(2-furyl)-5-(4-methoxycyclohexylcarbonyl)thiazol-2-yl]carbamate (Compound 440)

In a manner similar to that in Example 185, by using 4-methoxycyclohexanecarboxylic acid in place of picolinic acid, the entitled Compound 440 (149 mg, 18%) was obtained from Compound h (500 mg, 2.04 mmol) obtained in Reference Example 8.

$^1$H NMR (CDCl$_3$, δ ppm): 1.23-2.17 (m, 19H), 3.30-3.36 (m, 4H), 6.53 (dd, J=1.7, 3.5 Hz, 1H), 7.54 (d, J=1.7, Hz, 1H), 7.76 (d, J=3.5 Hz, 1H).

Example 441

2-Amino-4-(2-furyl)thiazol-5-yl 4-methoxycyclohexyl ketone (Compound 441)

In a manner similar to that in Example 186, the entitled Compound 441 (90.0 mg, 80%) was obtained from Compound 440 (149 mg, 0.367 mmol) in place of Compound 185.
$^1$H NMR (CDCl$_3$, δ ppm): 1.26-2.02 (m, 8H), 2.70-2.78 (m, 1H), 3.29-3.36 (m, 3H), 5.57-5.60 (m, 2H), 6.52-6.55 (m, 1H), 7.53-7.54 (m, 1H), 7.59-7.60 (m, 1H).

Example 442

N-[4-(2-Furyl)-5-(4-methoxycyclohexylcarbonyl)thiazol-2-yl]pyridine-4-carboxamide (Compound 442)

Compound 441 (579 mg, 1.89 mmol) was dissolved in THF (9.0 mL), and isonicotinic acid (931 mg, 7.57 mmol), EDC hydrochloride (1.45 g, 7.57 mmol) and 1-hydroxybenzotriazole monohydrate (1.16 g, 7.57 mmol) were added thereto, followed by stirring at 60° C. for 3 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was recrystallized from 2-propanol to afford the entitled Compound 442 (664 mg, 85%).
$^1$H NMR (DMSO-d$_6$, δ ppm): 1.08-2.08 (m, 8H), 2.84-3.01 (m, 1H), 3.20-3.23 (m, 3H), 6.68-6.71 (m, 1H), 7.39-7.42 (m, 1H), 7.89-7.90 (m, 1H), 8.02 (d, J=5.9 Hz, 2H), 8.82 (d, J=5.9 Hz, 2H), 13.6 (br s, 1H).
APCIMS m/z: [M+H]$^+$ 412.
m.p.: 180-187° C.

Example 443

4-Cyano-N-[4-(2-furyl)-5-(4-methoxycyclohexylcarbonyl)thiazol-2-yl]benzamide (Compound 443)

In a manner similar to that in Example 442, by using 4-cyanobenzoic acid in place of isonicotinic acid, the entitled Compound (199 mg, 62%) was obtained from Compound 441 (226 mg, 0.738 mmol).
$^1$H NMR (DMSO-d$_6$, δ ppm): 1.10-2.17 (m, 9H), 2.88-2.97 (m, 1H), 3.20-3.23 (m, 3H), 6.69-6.71 (m, 1H), 7.40-7.43 (m, 1H), 7.88-7.91 (m, 1H), 8.06 (d, J=8.3 Hz, 2H), 8.26 (d, J=8.3 Hz, 2H), 13.5 (br s, 1H).
APCIMS m/z: [M+H]$^+$ 436.
m.p.: 105-109° C.

Example 444

2-Amino-4-(2-furyl)thiazol-5-yl 4-hydroxycyclohexyl ketone (Compound 444)

Step 1:
Ethyl 4-hydroxycyclohexanecaboxylate (3.44 g, 20.0 mmol) was dissolved in DMF (7 mL), and imidazole (3.40 g, 50.0 mmol) and tert-butyldimethylsilyl chloride (3.62 g, 24 mmol) were added thereto, followed by stirring overnight at room temperature. Water was added to the reaction mixture, followed by extraction with ethyl acetate. The organic layer was dried over anhydrous magnesium sulfate, and then the solvent was distilled away under reduced pressure. The resulting residue was purified through silica gel column chromatography (hexane:ethyl acetate=10:1) to afford ethyl 4-(tert-butyldimethylsilyloxy)cyclohexanecarboxylate (5.73 g, 100%).
$^1$H NMR (CDCl$_3$, δ ppm): 0.00-0.03 (m, 6H), 0.85-0.86 (m, 9H), 1.19-1.25 (m, 3H), 1.42-2.26 (m, 10H), 4.05-4.13 (m, 2H).

Step 2:
Ethyl 4-(tert-butyldimethylsilyloxy)cyclohexane-carboxylate (5.73 g, 20.0 mmol) obtained in Step 1 and N,O-dimethylhydroxylamine hydrochloride (2.93 g, 30.0 mmol) were suspended in THF (40 mL), and a 2.0 mol/L solution of isopropylmagnesium chloride in THF (30.0 mL, 60.0 mmol) was added dropwise thereto in a atmosphere of argon at −20° C., followed by stirring at 0° C. for 1 hour. A saturated aqueous solution of ammonium chloride and ethyl acetate were added to the reaction mixture for extraction. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:4) to afford 4-(tert-butyldimethylsilyloxy)-N-methoxy-N-methylcyclo-hexanecarboxamide (6.03 g, 100%).
$^1$H NMR (CDCl$_3$, δ ppm): 0.00-0.03 (m, 6H), 0.85-0.86 (m, 9H), 1.45-1.97 (m, 10H), 3.14-3.15 (m, 3H), 3.66-3.67 (m, 3H).

Step 3:
Compound h (690 mg, 2.00 mmol) obtained in Reference Example 8 was dissolved in THF (20 mL), and a 1.57 mol/L solution of n-butyllithium in n-hexane (2.80 mL, 4.40 mmol) was added thereto in a stream of argon at −78° C., followed by stirring at −78° C. for 15 minutes. 4-(tert-Butyldimethylsilyloxy)-N-methoxy-N-methylcyclohexane-carboxamide (1.21 g, 4.00 mmol) obtained in Step 2 was added dropwise to the reaction mixture, followed by stirring overnight at room temperature. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue dissolved in trifluoroacetic acid (2 mL), followed by stirring for 1 hour. The reaction mixture was concentrated under reduced pressure, and a saturated aqueous solution of sodium hydrogencarbonate was added to the resulting residue, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford the entitled Compound 444 (76.0 mg, 13%).
$^1$H NMR (CDCl$_3$, δ ppm): 1.55-2.15 (m, 10H), 5.82-5.92 (m, 2H), 6.52-6.54 (m, 1H), 7.54-7.59 (m, 2H).

Example 445 tert-Butyl N-[5-(1,4-dioxaspiro[4,5]undecan-8-ylcarbonyl)-4-(2-furyl)thiazol-2-yl]carbamate (Compound 445)

Step 1:

Ethyl 4-oxocyclohexanecarboxylate (5.00 g, 29.4 mmol) was dissolved in toluene (200 mL), and ethylene glycol (15 mL) and oxalic acid (500 mg) were added thereto, followed by stirring under heating and reflux for 5 hours. The reaction mixture was poured into a saturated aqueous solution of sodium hydrogencarbonate, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=8:2) to afford ethyl 1,4-dioxaspiro[4,5]decane-8-carboxylate (6.28 g, 99%).

Step 2:

Ethyl 1,4-dioxaspiro[4,5]decane-8-carboxylate (6.28 g, 29.3 mmol) obtained in Step 1 was dissolved in THF, and N,O-dimethylhydroxylamine hydrochloride (4.30 g, 44.1 mmol) was added thereto, followed by stirring. In an atmosphere of argon at −30° C., a 2.0 mol/L solution of isopropylmagnesium chloride in THF (44.1 mL, 88.2 mmol) was added dropwise to the reaction mixture, followed by stirring at −5° C. for 1 hour. Water was added to the reaction mixture, followed by extraction with chloroform. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford N-methoxy-N-methyl-1,4-dioxaspiro[4,5]decane-8-carboxamide (6.61 g, 99%).

$^1$H NMR (CDCl$_3$, δ ppm): 1.51-1.62 (m, 2H), 1.76-1.90 (m, 6H), 2.68-2.71 (m, 1H), 3.18 (s, 3H), 3.71 (s, 3H), 3.95 (s, 4H).

Step 3:

Compound h (1.50 g, 4.34 mmol) obtained in Reference Example 8 was dissolved in THF (30 mL), and a 1.58 mol/L solution of n-butyllithium in n-hexane (8.58 mL, 13.5 mmol) was added thereto in a stream of argon at −78° C., followed by stirring at −78° C. for 15 minutes. N-methoxy-N-methyl-1,4-dioxaspiro[4,5]decane-8-carboxamide (2.80 g, 12.2 mmol) obtained in Step 2 was added dropwise to the reaction mixture, followed by stirring at room temperature for 1.5 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 445 (1.79 g, 95%).

$^1$H NMR (CDCl$_3$, δ ppm): 1.52 (s, 9H), 1.57-1.64 (m, 2H), 1.82-1.95 (m, 6H), 2.85-3.00 (m, 1H), 3.95 (s, 4H), 6.54 (dd, J=1.8, 3.3 Hz, 1H), 7.53 (d, J=1.8 Hz, 1H), 7.73 (d, J=3.3 Hz, 1H).

Example 446

2-Amino-4-(2-furyl)thiazol-5-yl 1,4-dioxaspiro[4,5]decan-8-yl ketone (Compound 446)

Compound 445 (500 mg, 1.15 mmol) was dissolved in diphenyl ether (5 mL), followed by stirring at 170° C. for 2 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:3) to afford the entitled Compound 446 (223 mg, 58%).

$^1$H NMR (DMSO-d$_6$, δ ppm): 1.35-1.73 (m. 8H), 2.67-2.74 (m, 1H), 3.84 (s, 3H), 6.65 (dd, J=1.8, 3.5 Hz, 1H), 7.22 (dd, J=0.7, 3.5 Hz, 1H), 7.84 (dd, J=0.7, 1.8 Hz, 1H), 7.97 (br s, 2H).

Example 447

2-Amino-4-(2-furyl)thiazol-5-yl 4-oxocyclohexyl ketone (Compound 447)

Compound 445 (1.00 g, 2.30 mmol) was dissolved in THF (14 mL), and 2 mol/L hydrochloric acid (7 mL) was added thereto, followed by stirring under heating and reflux for 8 hours. The reaction mixture was neutralized with a saturated aqueous solution of sodium hydrogencarbonate added thereto, followed by extraction with ethyl acetate. The organic layer was washed with a saturated aqueous solution of sodium chloride and dried over anhydrous magnesium sulfate, and then the solvent was distilled away under reduced pressure. The resulting residue was crystallized from diethyl ether to afford the entitled Compound 447 (399 mg, 60%).

$^1$H NMR (DMSO-d$_6$, δ ppm): 1.70-1.79 (m, 2H), 2.01-2.08 (m, 2H), 2.20-2.36 (m, 4H), 3.18-3.26 (m, 1H), 6.64 (dd, J=1.8, 3.5 Hz, 1H), 7.28 (dd, J=0.8, 3.5 Hz, 1H), 7.85 (dd, J=0.8, 1.8 Hz, 1H), 8.01 (br s, 2H).

Example 448

N-[4-(2-Furyl)-5-(4-oxocyclohexylcarbonyl)thiazol-2-yl]pyridine-4-carboxamide (Compound 448)

Compound 447 (150 mg, 0.517 mmol) was dissolved in DMF (2.5 mL), and isonicotinic acid (191 mg, 1.55 mmol), EDC hydrochloride (298 mg, 1.55 mmol) and 1-hydroxybenzotriazole monohydrate (237 mg, 1.55 mmol) were added thereto, followed by stirring at 60° C. for 3 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was recrystallized from 2-propanol to afford the entitled Compound 448 (115 mg, 66%).

$^1$H NMR (DMSO-d$_6$, δ ppm): 2.07-2.60 (m, 8H), 3.36-3.23 (m, 1H), 6.56 (dd, J=1.8, 3.5 Hz, 1H), 7.54 (dd, J=0.7, 1.8 Hz, 1H), 7.75 (dd, J=0.7, 3.5 Hz, 1H), 7.80 (d, J=6.1 Hz, 2H), 8.88 (d, J=6.1 Hz, 2H).

Example 449

N-[4-(2-Furyl)-5-(4-oxocyclohexylcarbonyl)thiazol-2-yl]-2-methylpyridine-4-carboxamide (Compound 449)

In a manner similar to that in Example 448, by using 2-methylisonicotinic acid in place of isonicotinic acid, the entitled Compound 449 (73.0 mg, 43%) was obtained from Compound 447 (120 mg, 0.413 mmol).

$^1$H NMR (CDCl$_3$, δ ppm): 2.04-2.60 (m, 8H), 2.66 (s, 3H), 3.35-3.43 (m, 1H), 6.54 (dd, J=1.8, 3.6 Hz, 1H), 7.52 (dd, J=0.7, 1.8 Hz, 1H), 7.57 (d, J=5.1 Hz, 1H), 7.62 (s, 1H), 7.75 (dd, J=0.7, 3.6 Hz, 1H), 8.72 (d, J=5.1 Hz, 1H).

APCIMS m/z: [M+H]$^+$ 410.

m.p.: 108-115° C.

Example 450

N-[4-(2-Furyl)-5-(4-oxocyclohexylcarbonyl)thiazol-2-yl]furan-2-carboxamide (Compound 450)

In a manner similar to that in Example 448, by using furan-2-carboxylic acid in place of isonicotinic acid, the entitled Compound 450 (124 mg, 62%) was obtained from Compound 447 (150 mg, 0.517 mmol).

$^1$H NMR (CDCl$_3$, δ ppm): 2.03-2.57 (m, 8H), 3.30-3.39 (m, 1H), 6.57 (dd, J=1.8, 3.5 Hz, 1H), 6.64 (dd, J=1.7, 3.6 Hz, 1H), 7.42 (d, J=3.6 Hz, 1H), 7.59-7.60 (m, 2H), 7.79 (d, J=3.5 Hz, 1H).

APCIMS m/z: [M+H]$^+$ 385.

m.p.: 232-235° C.

Example 451

N-[4-(2-Furyl)-5-(4-oxocyclohexylcarbonyl)thiazol-2-yl]-3-methoxybenzamide (Compound 451)

In a manner similar to that in Example 448, by using 3-methoxybenzoic acid in place of isonicotinic acid, the entitled Compound 451 (72.0 mg, 33%) was obtained from Compound 447 (150 mg, 0.517 mmol).

$^1$H NMR (CDCl$_3$, δ ppm): 2.06-2.58 (m, 8H), 3.33-3.41 (m, 1H), 3.88 (s, 3H), 6.56 (dd, J=1.7, 3.6 Hz, 1H), 7.16-7.20 (m, 1H), 7.41-7.51 (m, 3H), 7.58 (d, J=1.7 Hz, 1H), 7.82 (d, J=3.6 Hz, 1H).

APCIMS m/z: [M+H]$^+$ 425.

m.p.: 176-183° C.

Example 452

4-Cyano-N-[4-(2-furyl)-5-(4-oxocyclohexylcarbonyl)thiazol-2-yl]benzamide (Compound 452)

In a manner similar to that in Example 448, by using 4-cyanobenzoic acid in place of isonicotinic acid, the entitled Compound 452 (164 mg, 76%) was obtained from Compound 447 (150 mg, 0.517 mmol).

$^1$H NMR (CDCl$_3$, δ ppm): 2.06-2.58 (m, 8H), 3.32-3.40 (m, 1H), 6.51 (dd, J=1.8, 3.5 Hz, 1H), 7.48 (dd, J=0.7, 1.8 Hz, 1H), 7.74 (dd, J=0.7, 3.5 Hz, 1H), 7.81 (d, J=8.6 Hz, 2H), 8.06 (d, J=8.6 Hz, 2H).

APCIMS m/z: [M−H]$^−$ 418.

m.p.: 211-212° C.

Example 453 tert-Butyl N-[4-(2-furyl)-5-(tetrahydropyran-4-ylcarbonyl)thiazol-2-yl]carbamate (Compound 453)

In a manner similar to that in Example 176, by using tetrahydropyran-4-carboxylic acid in place of 2-cyanobenzoic acid, the entitled Compound 453 (350 mg, 35%) was obtained from Compound h (1.04 g, 3.00 mmol) obtained in Reference Example 8.

$^1$H NMR (CDCl$_3$, δ ppm): 1.53 (s, 9H), 1.76-1.94 (m, 4H), 3.06-3.18 (m, 1H), 3.46 (ddd, J=2.7, 11.6, 11.6 Hz, 2H), 4.03 (ddd, J=2.7, 4.0, 11.6 Hz, 2H), 6.55 (dd, J=1.9, 3.5 Hz, 1H), 7.55 (dd, J=0.8, 1.9 Hz, 1H), 7.76 (dd, J=0.8, 3.5 Hz, 1H), 8.68 (br s, 1H).

APCIMS m/z: [M+H]$^+$ 379.

Example 454

2-Amino-4-(2-furyl)thiazol-5-yl tetrahydropyran-4-yl ketone (Compound 454)

In a manner similar to that in Example 186, the entitled Compound 454 (212 mg, 72%) was obtained from Compound 453 (350 mg, 1.05 mmol) in place of Compound 185.

$^1$H NMR (DMSO-d$_6$, δ ppm): 1.52-1.64 (m, 4H), 2.89-3.03 (m, 1H), 3.24 (ddd, J=3.8, 11.3, 11.3 Hz, 2H), 3.85 (ddd, J=2.7, 3.8, 11.3 Hz, 2H), 6.65 (dd, J=1.9, 3.5 Hz, 1H), 7.24 (d, J=3.5 Hz, 1H), 7.84 (d, J=1.9 Hz, 1H), 7.96 (br s, 2H).

APCIMS m/z: [M+H]$^+$ 279.

Example 455

N-[4-(2-Furyl)-5-(tetrahydropyran-4-ylcarbonyl)thiazol-2-yl]pyridine-4-carboxamide (Compound 455)

Compound 454 (6.95 g, 25.0 mmol) was dissolved in DMF (100 mL), and isonicotinic acid (36.9 g, 300 mmol), EDC hydrochloride (57.6 g, 300 mmol) and 1-hydroxybenzotriazole monohydrate (45.9 g, 300 mmol) were added thereto, followed by stirring at 80° C. for 6 hours. The reaction mixture was poured into a mixture of a saturated aqueous solution of sodium hydrogencarbonate (600 mL) and water (200 mL), and the precipitated solid was collected by filtration. The resulting solid was recrystallized from ethanol to afford the entitled Compound 455 (4.41 g, 48%) as a grayish white solid.

$^1$H NMR (DMSO-d$_6$, δ ppm): 1.50-1.90 (m, 4H), 3.15-3.25 (m, 1H), 3.35 (ddd, J=2.7, 11.6, 11.6 Hz, 2H), 3.89 (ddd, J=2.7, 4.0, 11.6 Hz, 2H), 6.71 (dd, J=1.9, 3.5 Hz, 1H), 7.43 (dd, J=0.8, 3.5 Hz, 1H), 7.91 (dd, J=0.8, 1.9 Hz, 1H), 8.02 (dd, J=1.6, 4.6 Hz, 2H), 8.84 (dd, J=1.6, 4.6 Hz, 2H), 13.56 (br s, 1H).

APCIMS m/z: [M+H]$^+$ 384.

m.p.: 202-209° C.

Example 456

N-[4-(2-Furyl)-5-(tetrahydropyran-4-ylcarbonyl)thiazol-2-yl]cyclopropanecarboxamide (Compound 456)

Compound 454 (1.67 g, 6.00 mmol) and DMAP (36.7 mg, 0.300 mmol) were suspended in pyridine (24 mL), and cyclopropanecarbonyl chloride (1.09 mL, 12.0 mmol) was added thereto, followed by stirring at 60° C. for 90 minutes. The reaction mixture was poured into water, and the precipitated solid was collected by filtration. The resulting solid was purified through silica gel column chromatography (chloroform: methanol=99:1), followed by recrystallizing from ethanol to afford the entitled Compound 456 (1.35 g, 65%) as a white solid.

$^1$H NMR (DMSO-d$_6$, δ ppm): 0.90-1.04 (m, 4H), 1.50-1.76 (m, 4H), 1.92-2.03 (m, 1H), 3.07-3.21 (m, 1H), 3.25-3.40 (m, 2H), 3.83-3.91 (m, 2H), 6.69 (dd, J=1.9, 3.5 Hz, 1H), 7.41 (d, J=3.5 Hz, 1H), 7.88 (d, J=1.9 Hz, 1H), 13.04 (br s, 1H).

APCIMS m/z: [M+H]$^+$ 347.

m.p.: 182-183° C.

Example 457

N-[4-(2-Furyl)-5-(tetrahydropyran-4-ylcarbonyl) thiazol-2-yl]benzamide (Compound 457)

In a manner similar to that in Example 456, by using benzoyl chloride in place of cyclopropanecarbonyl chloride, the entitled Compound 457 (151 mg, 88%) was obtained as a white solid from Compound 454 (125 mg, 0.450 mmol).

$^1$H NMR (DMSO-d$_6$, δ ppm): 1.50-1.80 (m, 4H), 3.13-3.26 (m, 1H), 3.36 (ddd, J=2.2, 11.3, 11.3 Hz, 2H), 3.84-3.93 (m, 2H), 6.70 (dd, J=1.6, 3.5 Hz, 1H), 7.44 (d, J=3.5 Hz, 1H), 7.53-7.61 (m, 2H), 7.64-7.72 (m. 1H), 7.91 (d, J=1.6 Hz, 1H), 8.11-8.18 (m, 2H), 13.27 (br s, 1H).

APCIMS m/z: [M+H]$^+$ 383.

m.p.: 221-222° C.

Example 458

N-[4-(2-Furyl)-5-(tetrahydropyran-4-ylcarbonyl) thiazol-2-yl]-2-methylbenzamide (Compound 458)

In a manner similar to that in Example 456, by using 2-methylbenzoyl chloride in place of cyclopropanecarbonyl chloride, the entitled Compound 458 (159 mg, 88%) was obtained as a grayish white solid from Compound 454 (125 mg, 0.450 mmol).

$^1$H NMR (DMSO-d$_6$, δ ppm): 1.55-1.85 (m, 4H), 2.44 (s, 3H), 3.14-3.26 (m, 1H), 3.36 (ddd, J=2.2, 11.9, 11.9 Hz, 2H), 3.84-3.92 (m, 2H), 6.69 (dd, J=1.9, 3.5 Hz, 1H), 7.27-7.51 (m, 4H), 7.60-7.66 (m, 1H), 7.89 (d, J=1.9 Hz, 1H), 13.14 (br s, 1H).

APCIMS m/z: [M+H]$^+$ 397.

m.p.: 204-206° C.

Example 459

N-[4-(2-Furyl)-5-(tetrahydropyran-4-ylcarbonyl) thiazol-2-yl]-3-methylbenzamide (Compound 459)

In a manner similar to that in Example 456, by using 3-methylbenzoyl chloride in place of cyclopropanecarbonyl chloride, the entitled Compound 459 (151 mg, 89%) was obtained as a white solid from Compound 454 (125 mg, 0.450 mmol).

$^1$H NMR (DMSO-d$_6$, δ ppm): 1.52-1.74 (m, 4H), 2.38 (s, 3H), 3.03-3.16 (m, 1H), 3.34 (ddd, J=2.4, 11.3, 11.3 Hz, 2H), 3.84-3.94 (m, 2H), 6.62 (dd, J=1.9, 3.5 Hz, 1H), 7.20-7.37 (m, 2H), 7.40 (dd, J=0.5, 3.5 Hz, 1H), 7.80 (dd, J=0.5, 1.9 Hz, 1H), 7.90-7.95 (m, 1H), 7.97-8.01 (m, 1H), 13.17 (br s, 1H).

APCIMS m/z: [M+H]$^+$ 397.

m.p.: 197-201° C.

Example 460

N-[4-(2-Furyl)-5-(tetrahydropyran-4-ylcarbonyl) thiazol-2-yl]-4-methylbenzamide (Compound 460)

In a manner similar to that in Example 456, by using 4-methylbenzoyl chloride in place of cyclopropanecarbonyl chloride, the entitled Compound 460 (128 mg, 72%) was obtained as a grayish white solid from Compound 454 (125 mg, 0.450 mmol).

$^1$H NMR (DMSO-d$_6$, δ ppm): 1.54-1.76 (m, 4H), 2.40 (s, 3H), 3.13-3.26 (m, 1H), 3.36 (ddd, J=2.2, 11.3, 11.3 Hz, 2H), 3.84-3.94 (m, 2H), 6.70 (dd, J=1.9, 3.5 Hz, 1H), 7.38 (d, J=8.4 Hz, 2H), 7.44 (d, J=3.5 Hz, 1H), 7.91 (d, J=1.9 Hz, 1H), 8.06 (d, J=8.4 Hz, 2H), 13.18 (br s, 1H).

APCIMS m/z: [M+H]$^+$ 397.

m.p.: 190-192° C.

Example 461

N-[4-(2-Furyl)-5-(tetrahydropyran-4-ylcarbonyl) thiazol-2-yl]-2-methoxybenzamide (Compound 461)

In a manner similar to that in Example 456, by using 2-methoxybenzoyl chloride in place of cyclopropanecarbonyl chloride, the entitled Compound 461 (152 mg, 82%) was obtained as a grayish white solid from Compound 454 (125 mg, 0.450 mmol).

$^1$H NMR (DMSO-d$_6$, δ ppm): 1.55-1.80 (m, 4H), 3.15-3.25 (m, 1H), 3.35 (ddd, J=2.2, 11.6, 11.6 Hz, 2H), 3.80-3.95 (m, 2H), 3.92 (s, 3H), 6.69 (dd, J=1.6, 3.2 Hz, 1H), 7.05-7.15 (m, 1H), 7.16-7.24 (m, 1H), 7.41 (d, J=3.2 Hz, 1H), 7.55-7.63 (m, 1H), 7.70 (dd, J=1.3, 8.6 Hz, 1H), 7.90 (d, J=1.6 Hz, 1H), 12.47 (br s, 1H).

APCIMS m/z: [M+H]$^+$ 413.

m.p.: 181-184° C.

Example 462

N-[4-(2-Furyl)-5-(tetrahydropyran-4-ylcarbonyl) thiazol-2-yl]-3-methoxybenzamide (Compound 462)

In a manner similar to that in Example 456, by using 3-methoxybenzoyl chloride in place of cyclopropanecarbonyl chloride, the entitled Compound 462 (1.91 g, 77%) was obtained as a grayish white solid from Compound 454 (1.67 g, 6.00 mmol).

$^1$H NMR (DMSO-d$_6$, δ ppm): 1.55-1.80 (m, 4H), 3.14-3.24 (m, 1H), 3.36 (ddd, J=2.4, 11.3, 11.3 Hz, 2H), 3.86 (s, 3H), 3.87-3.92 (m, 2H), 6.70 (dd, J=1.6, 3.5 Hz, 1H), 7.20-7.26 (m, 1H), 7.45 (dd, J=0.8, 3.5 Hz, 1H), 7.43-7.53 (m, 1H), 7.69-7.77 (m, 2H), 7.91 (dd, J=0.8, 1.6 Hz, 1H), 13.27 (br s, 1H).

APCIMS m/z: [M+H]$^+$ 413.

m.p.: 198-200° C.

Example 463

N-[4-(2-Furyl)-5-(tetrahydropyran-4-ylcarbonyl) thiazol-2-yl]-4-methoxybenzamide (Compound 463)

In a manner similar to that in Example 456, by using 4-methoxybenzoyl chloride in place of cyclopropanecarbonyl chloride, the entitled Compound 463 (152 mg, 82%) was obtained as a grayish white solid from Compound 454 (125 mg, 0.450 mmol).

¹H NMR (DMSO-d₆, δ ppm): 1.54-1.76 (m, 4H), 3.13-3.24 (m, 1H), 3.36 (ddd, J=2.2, 11.3, 11.3 Hz, 2H), 3.86 (s, 3H), 3.89-3.91 (m, 2H), 6.70 (dd, J=1.6, 3.2 Hz, 1H), 7.10 (dd, J=1.9, 8.9 Hz, 2H), 7.45 (dd, J=0.5, 3.2 Hz, 1H), 7.90 (dd, J=0.5, 1.6 Hz, 1H), 8.15 (dd, J=1.9, 8.9 Hz), 13.10 (br s, 1H).

APCIMS m/z: [M+H]⁺ 413.

m.p.: 184-188° C.

Example 464

3-(Dimethylamino)-N-[4-(2-furyl)-5-(tetrahydropyran-4-ylcarbonyl)thiazol-2-yl]benzamide (Compound 464)

Compound 454 (125 mg, 0.450 mmol) was dissolved in DMF (2 mL), and 3-(dimethylamino)benzoic acid (296 mg, 1.80 mmol), EDC hydrochloride (344 mg, 1.80 mmol) and 1-hydroxybenzotriazole monohydrate (276 mg, 1.80 mmol) were added thereto, followed by stirring at 80° C. for 2 hours. The reaction mixture was poured into water (200 mL), followed by extraction with chloroform. The organic layer was washed with water and a saturated aqueous solution of sodium chloride and dried over anhydrous magnesium sulfate, and then the solvent was distilled away under reduced pressure. The resulting residue was purified through silica gel column chromatography (chloroform:methanol=19:1), followed by reslurrying with methanol to afford the entitled Compound 464 (78.5 mg, 41%) as a pale yellow solid.

¹H NMR (DMSO-d₆, δ ppm): 1.55-1.75 (m, 4H), 2.99 (s, 6H), 3.13-3.23 (m, 1H), 3.35 (ddd, J=2.2, 11.6, 11.6 Hz, 2H), 3.89 (ddd, J=2.2, 3.8, 11.6 Hz, 2H), 6.70 (dd, J=1.9, 3.5 Hz, 1H), 6.99 (ddd, J=1.4, 2.7, 8.1 Hz, 1H), 7.31-7.48 (m, 4H), 7.90 (dd, J=0.8, 1.9 Hz, 1H), 13.19 (br s, 1H).

APCIMS m/z: [M+H]⁺ 426.

m.p.: 239-243° C.

Example 465

4-(Dimethylamino)-N-[4-(2-furyl)-5-(tetrahydropyran-4-ylcarbonyl)thiazol-2-yl]benzamide (Compound 465)

Compound 454 (125 mg, 0.450 mmol) was dissolved in DMF (2 mL), and 4-(dimethylamino)benzoic acid (296 mg, 1.80 mmol), EDC hydrochloride (344 mg, 1.80 mmol) and 1-hydroxybenzotriazole monohydrate (276 mg, 1.80 mmol) were added thereto, followed by stirring at 80° C. for 2 hours. Water (200 mL) was added to the reaction mixture, and the precipitated solid was collected by filtration. The resulting solid was purified through silica gel column chromatography (chloroform:methanol=9:1), followed by reslurrying with ethanol to afford the entitled Compound 465 (5.30 mg, 3%) as a pale brown solid.

¹H NMR (DMSO-d₆, δ ppm): 1.55-1.80 (m, 4H), 3.03 (s, 6H), 3.11-3.2 (m, 1H), 3.35 (ddd, J=2.2, 11.6, 11.6 Hz, 2H), 3.85-3.93 (m, 2H), 6.69 (dd, J=1.6, 3.5 Hz, 1H), 6.77 (d, J=9.2 Hz, 2H), 7.45 (dd, J=0.8, 3.5 Hz, 1H), 7.89 (dd, J=0.8, 1.6 Hz, 1H), 8.05 (d, J=9.2 Hz, 2H), 12.81 (br s, 1H).

APCIMS m/z: [M+H]⁺ 426.

m.p.: 238-240° C.

Example 466

2-Fluoro-N-[4-(2-furyl)-5-(tetrahydropyran-4-ylcarbonyl)thiazol-2-yl]benzamide (Compound 466)

In a manner similar to that in Example 456, by using 2-fluorobenzoyl chloride in place of cyclopropanecarbonyl chloride, the entitled Compound 466 (155 mg, 86%) was obtained as a pale brown solid from Compound 454 (125 mg, 0.450 mmol).

¹H NMR (DMSO-d₆, δ ppm): 1.54-1.76 (m, 4H), 3.15-3.25 (m, 1H), 3.36 (ddd, J=2.2, 11.3, 11.3 Hz, 2H), 3.84-3.93 (m, 2H), 6.69 (dd, J=1.9, 3.5 Hz, 1H), 7.35-7.50 (m, 3H) 7.61-7.71 (m, 1H), 7.75-7.83 (m, 1H), 7.89 (d, J=1.9 Hz, 1H), 13.23 (br s, 1H).

APCIMS m/z: [M+H]⁺ 401.

m.p.: 172-176° C.

Example 467

3-Fluoro-N-[4-(2-furyl)-5-(tetrahydropyran-4-ylcarbonyl)thiazol-2-yl]benzamide (Compound 467)

In a manner similar to that in Example 456, by using 3-fluorobenzoyl chloride in place of cyclopropanecarbonyl chloride, the entitled Compound 467 (160 mg, 89%) was obtained as a grayish white solid from Compound 454 (125 mg, 0.450 mmol).

¹H NMR (DMSO-d₆, δ ppm): 1.50-1.80 (m, 4H), 3.15-3.25 (m, 1H), 3.36 (ddd, J=2.2, 11.6, 11.6 Hz, 2H), 3.89 (ddd, J=2.2, 4.0, 11.6 Hz, 2H), 6.70 (dd, J=1.6, 3.2 Hz, 1H), 7.44 (d, J=3.2 Hz, 1H), 7.49-7.68 (m, 2H), 7.90 (dd, J=0.8, 1.6 Hz, 1H), 7.94-8.02 (m, 2H), 13.34 (br s, 1H).

APCIMS m/z: [M+H]⁺ 401.

m.p.: 229-231° C.

Example 468

4-Fluoro-N-[4-(2-furyl)-5-(tetrahydropyran-4-ylcarbonyl)thiazol-2-yl]benzamide (Compound 468)

Compound 454 (834 mg, 3.00 mmol) was dissolved in DMF (12 mL), and 4-fluorobenzoic acid (3.36 g, 24.0 mmol), EDC hydrochloride (4.12 g, 24.0 mmol) and 1-hydroxybenzotriazole monohydrate (3.68 g, 24.0 mmol) were added thereto, followed by stirring at 80° C. for 2 hours. The reaction mixture was poured into a mixture of a saturated aqueous solution of sodium hydrogencarbonate (30 mL) and water (30 mL), and the precipitated solid was collected by filtration. The resulting solid was purified through silica gel column chromatography (chloroform:methanol=19:1), followed by recrystallizing from ethanol to afford the entitled Compound 468 (270 mg, 23%) as a white solid.

¹H NMR (DMSO-d₆, δ ppm): 1.58-1.78 (m, 4H), 3.15-3.25 (m, 1H), 3.35-3.55 (m, 2H), 3.88 (ddd, J=1.9, 3.8, 11.3 Hz, 2H), 6.70 (dd, J=1.6, 3.2 Hz, 1H), 7.37-7.46 (m, 3H), 7.90 (dd, J=0.8, 1.6 Hz, 1H), 8.20-8.26 (m, 2H), 13.27 (br s, 1H).

APCIMS m/z: [M+H]⁺ 401.

m.p.: 131-132° C.

Example 469

2-Chloro-N-[4-(2-furyl)-5-(tetrahydropyran-4-ylcarbonyl)thiazol-2-yl]benzamide (Compound 469)

In a manner similar to that in Example 456, by using 2-chlorobenzoyl chloride in place of cyclopropanecarbonyl chloride, the entitled Compound 469 (140 mg, 75%) was obtained as a white solid from Compound 454 (125 mg, 0.450 mmol).

¹H NMR (DMSO-d₆, δ ppm): 1.55-1.85 (m, 4H), 3.15-3.25 (m, 1H), 336 (ddd, J=2.4, 11.3, 11.3 Hz, 2H), 3.88 (ddd, J=2.4, 3.8, 11.3 Hz, 2H), 6.69 (dd, J=1.6, 3.5 Hz, 1H), 7.39 (d, J=3.5 Hz, 1H), 7.45-7.70 (m, 5H), 7.89 (dd, J=0.8, 1.6 Hz, 1H), 13.34 (br s, 1H).
APCIMS m/z: [$^{35}$ClM+H]$^+$ 417, [$^{37}$ClM+H]$^+$ 419.
m.p.: 160-162° C.

Example 470

3-Chloro-N-[4-(2-furyl)-5-(tetrahydropyran-4-ylcarbonyl)thiazol-2-yl]benzamide (Compound 470)

In a manner similar to that in Example 456, by using 3-chlorobenzoyl chloride in place of cyclopropanecarbonyl chloride, the entitled Compound 470 (131 mg, 70%) was obtained from Compound 454 (125 mg, 0.450 mmol).
$^1$H NMR (DMSO-d$_6$, δ ppm): 1.55-1.80 (m, 4H), 3.12-3.25 (m, 1H), 3.36 (ddd, J=2.2, 12.1, 12.1 Hz, 2H), 3.86-3.92 (m, 2H), 6.70 (dd, J=1.9, 3.5 Hz, 1H), 7.43 (d, J=3.5 Hz, 1H), 7.60 (dd, J=7.8, 7.8 Hz, 1H), 7.72-7.76 (m, 1H), 7.90 (d, J=1.9 Hz, 1H), 8.09 (dd, J=1.1, 7.8 Hz, 1H), 8.19-8.20 (m, 1H), 13.36 (br s, 1H).
APCIMS m/z: [$^{35}$ClM+H]$^+$ 417, [$^{37}$ClM+H]$^+$ 419.
m.p.: 210-212° C.

Example 471

4-Chloro-N-[4-(2-furyl)-5-(tetrahydropyran-4-ylcarbonyl)thiazol-2-yl]benzamide (Compound 471)

In a manner similar to that in Example 456, by using 4-chlorobenzoyl chloride in place of cyclopropanecarbonyl chloride, the entitled Compound 471 (129 mg, 69%) was obtained as a white solid from Compound 454 (125 mg, 0.450 mmol).
$^1$H NMR (DMSO-d$_6$, δ ppm): 1.55-1.85 (m, 4H), 3.15-3.25 (m, 1H), 3.34-3.42 (m, 2H), 3.84-3.93 (m, 2H), 6.70 (dd, J=1.9, 3.5 Hz, 1H), 7.44 (dd, J=0.8, 3.5 Hz, 1H), 7.65 (dd, J=1.6, 8.4 Hz, 2H), 7.90 (dd, J=0.8, 1.9 Hz, 1H), 8.15 (dd, J=1.6, 8.4 Hz, 2H), 13.35 (br s, 1H).
APCIMS m/z: [$^{35}$ClM+H]$^+$ 417, [$^{37}$ClM+H]$^+$ 419.
m.p.: 204-206° C.

Example 472

2-Cyano-N-[4-(2-furyl)-5-(tetrahydropyran-4-ylcarbonyl)thiazol-2-yl]benzamide (Compound 472)

In a manner similar to that in Example 465, by using 2-cyanobenzoic acid in place of 3-(dimethylamino)benzoic acid, the entitled Compound 472 (35.3 mg, 19%) was obtained as a yellow solid from Compound 454 (125 mg, 0.450 mmol).
$^1$H NMR (DMSO-d$_6$, δ ppm): 1.50-1.80 (m, 4H), 3.12-3.22 (m, 1H), 3.28-3.38 (m, 2H), 3.88 (ddd. J=2.2, 11.3, 11.3 Hz, 2H), 6.73 (dd, J=1.9, 3.5 Hz, 1H), 7.50 (d, J=3.5 Hz, 1H), 7.80-8.20 (m, 5H), 11.27 (br s, 1H).
APCIMS m/z: [M+H]$^+$ 408.
m.p.: 221-224° C.

Example 473

3-Cyano-N-[4-(2-furyl)-5-(tetrahydropyran-4-ylcarbonyl)thiazol-2-yl]benzamide (Compound 473)

In a manner similar to that in Example 465, by using 3-cyanobenzoic acid in place of 3-(dimethylamino)benzoic acid, the entitled Compound 473 (166 mg, 90%) was obtained as a pink solid from Compound 454 (125 mg, 0.450 mmol).
$^1$H NMR (DMSO-d$_6$, δ ppm): 1.55-1.76 (m, 4H), 3.15-3.25 (m, 1H), 3.37 (ddd, J=1.6, 11.6, 11.6 Hz, 2H), 3.80-3.91 (m, 2H), 6.71 (dd, J=1.6, 3.2 Hz, 1H), 7.45 (d, J=3.2 Hz, 1H), 7.79 (dd, J=7.8, 7.8 Hz, 1H), 7.92 (d, J=1.6 Hz, 1H), 8.14 (d, J=7.8 Hz, 1H), 8.40 (d, J=7.8 Hz, 1H), 8.58 (s, 1H), 13.47 (br s, 1H).
APCIMS m/z: [M+H]$^+$ 408.
m.p.: 257-260° C.

Example 474

4-Cyano-N-[4-(2-furyl)-5-(tetrahydropyran-4-ylcarbonyl)thiazol-2-yl]benzamide (Compound 474)

In a manner similar to that in Example 465, by using 4-cyanobenzoic acid in place of 3-(dimethylamino)benzoic acid, the entitled Compound 474 (35.3 mg, 19%) was obtained from Compound 454 (125 mg, 0.450 mmol).
$^1$H NMR (DMSO-d$_6$, δ ppm): 1.50-1.80 (m, 4H), 3.10-3.30 (m, 1H), 3.35-3.50 (m, 2H), 3.84-3.93 (m, 2H), 6.70 (dd, J=1.9, 3.5 Hz, 1H), 7.44 (d, J=3.5 Hz, 1H), 7.90 (d, J=1.9 Hz, 1H), 8.05 (d, J=8.4 Hz, 2H), 8.26 (d, J=8.4 Hz, 2H), 13.53 (br s, 1H).
APCIMS m/z: [M−H]$^−$ 406.
m.p.: 231-234° C.

Example 475

N-[4-(2-Furyl)-5-(tetrahydropyran-4-ylcarbonyl)thiazol-2-yl]-2-(trifluoromethoxy)benzamide (Compound 475)

Compound 454 (125 mg, 0.450 mmol) and DMAP (0.022 mmol) were suspended in pyridine (2 mL), and 2-(trifluoromethoxy)benzoyl chloride (202 mg, 0.900 mmol) was added thereto, followed by stirring at 80° C. for 6 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was recrystallized from ethanol to afford the entitled Compound 475 (111 mg, 53%) as a pale yellow solid.
$^1$H NMR (DMSO-d$_6$, δ ppm): 1.50-1.80 (m, 4H), 3.10-3.22 (m, 1H), 3.36 (ddd, J=2.2, 11.3, 11.3 Hz, 2H), 3.85-3.92 (m, 2H), 6.70 (dd, J=1.6, 3.5 Hz, 1H), 7.41 (d, J=3.5 Hz, 1H), 7.52-7.60 (m, 2H), 7.73 (ddd, J=1.6, 7.6, 7.6 Hz 1H), 7.83 (dd, J=1.6, 7.6 Hz, 1H), 7.89 (d, J=1.6 Hz, 1H), 13.41 (br s, 1H).
APCIMS m/z: [M+H]$^+$ 467.
m.p.: 131-134° C.

Example 476

N-[4-(2-Furyl)-5-(tetrahydropyran-4-ylcarbonyl)thiazol-2-yl]-3-(trifluoromethoxy)benzamide (Compound 476)

In a manner similar to that in Example 456, by using 3-(trifluoromethoxy)benzoyl chloride in place of cyclopropanecarbonyl chloride, the entitled Compound 476 (170 mg, 81%) was obtained as a brown solid from Compound 454 (125 mg, 0.450 mmol).
$^1$H NMR (DMSO-d$_6$, δ ppm): 1.50-1.80 (m, 4H), 3.10-3.25 (m, 1H), 3.36 (ddd, J=2.2, 11.6, 11.6 Hz, 2H), 3.85-3.93 (m, 2H); 6.71 (dd, J=1.6, 3.2 Hz, 1H), 7.45 (d, J=3.2 Hz, 1H), 7.68-7.75 (m, 2H), 7.90 (d, J=1.6 Hz, 1H), 8.12-8.21 (m, 2H), 13.49 (br s, 1H).
APCIMS m/z: [M+H]$^+$ 467.
m.p.: 197-198° C.

Example 477

N-[4-(2-Furyl)-5-(tetrahydropyran-4-ylcarbonyl) thiazol-2-yl]-4-(trifluoromethoxy)benzamide (Compound 477)

In a manner similar to that in Example 456, by using 4-(trifluoromethoxy)benzoyl chloride in place of cyclopropanecarbonyl chloride, the entitled Compound 477 (156 mg, 74%) was obtained as a pale brown solid from Compound 454 (125 mg, 0.450 mmol).
$^1$H NMR (DMSO-d$_6$, δ ppm): 1.50-1.80 (m, 4H), 3.15-3.25 (m, 1H), 3.36 (ddd, J=2.2, 11.6, 11.6 Hz, 2H), 3.85-3.94 (m, 2H), 6.70 (dd, J=1.6, 3.2 Hz, 1H), 7.44 (d, J=3.2 Hz, 1H), 7.57 (d, J=8.1 Hz, 2H), 7.90 (d, J=1.6 Hz, 1H), 8.27 (d, J=8.1 Hz, 2H), 13.39 (br s, 1H).
APCIMS m/z: [M+H]$^+$ 467.
m.p.: 177-180° C.

Example 478

4-(Chloromethyl)-N-[4-(2-furyl)-5-(tetrahydropyran-4-ylcarbonyl)thiazol-2-yl]benzamide (Compound 478)

4-(Chloromethyl)benzoyl chloride (942 mg, 4.99 mmol) was dissolved in THF (16 mL), and Compound 454 (1.11 g, 3.99 mmol), triethylamine (0.840 mL, 5.98 mmol) and DMAP (50.0 mg, 0.400 mmol) were added thereto, followed by stirring under heating and reflux for 2 hours. The reaction mixture was concentrated under reduced pressure, and water was added to the resulting residue, followed by extraction with chloroform. The organic layer was washed successively with a saturated aqueous solution of sodium hydrogencarbonate and a saturated aqueous solution of sodium chloride and dried over anhydrous magnesium sulfate, and then the solvent was distilled away under reduced pressure. The resulting residue was purified through silica gel column chromatography (chloroform:methanol=99:1), followed by reslurrying with methanol to afford the entitled Compound 476 (1.42 g, 83%) as an ocher solid.
$^1$H NMR (DMSO-d$_6$, δ ppm): 1.55-1.78 (m, 4H), 3.13-3.27 (m, 1H), 3.36 (ddd, J=2.4, 11.3, 11.3 Hz, 2H), 3.89 (ddd, J=2.4, 3.8, 11.3 Hz, 2H), 4.86 (s, 2H), 6.70 (dd, J=1.9, 3.5 Hz, 1H), 7.44 (dd, J=0.5, 3.5 Hz, 1H), 7.63 (d, J=8.4 Hz, 2H), 7.90 (dd, J=0.5, 1.9 Hz, 1H), 8.14 (d, J=8.4 Hz, 2H), 13.30 (br s, 1H).
APCIMS m/z: [$^{35}$ClM+H]$^+$ 431, [$^{37}$ClM+H]$^+$ 433.

Example 479

4-(Dimethylaminomethyl)-N-[4-(2-furyl)-5-(tetrahydropyran-4-ylcarbonyl)thiazol-2-yl]benzamide (Compound 479)

Compound 478 (340 mg, 0.789 mmol) was added to a 2 mol/L solution of dimethylamine in THF (20 mL, 39.5 mmol), followed by stirring overnight at 60° C. The solvent was distilled away under reduced pressure, and the resulting residue was purified through silica gel column chromatography (chloroform:methanol=19:1), followed by reslurrying with a mixed solvent of ethanol and diethyl ether to afford the entitled Compound 479 (153 mg, 44%) as a yellow solid.
$^1$H NMR (DMSO-d$_6$, δ ppm): 1.55-1.80 (m, 4H), 2.20 (s, 6H), 3.10-3.20 (m, 1H), 3.36 (ddd, J=2.4, 11.6, 11.6 Hz, 2H), 3.52 (s, 2H), 3.85-3.93 (m, 2H), 6.70 (dd, J=1.9, 3.5 Hz, 1H), 7.44 (d, J=3.5 Hz, 1H), 7.48 (d, J=8.1 Hz, 2H), 7.90 (d, J=1.9 Hz, 1H), 8.12 (d, J=8.1 Hz, 2H), 13.06 (br s, 1H).
APCIMS m/z: [M+H]$^+$ 440.
m.p.: 109-112° C.

Example 480

N-[4-(2-Furyl)-5-(tetrahydropyran-4-ylcarbonyl) thiazol-2-yl]-4-(piperidinomethyl)benzamide (Compound 480)

Compound 478 (340 mg, 0.789 mmol) was suspended in THF (3 mL), and piperidine (0.390 mmol, 3.95 mmol) was added thereto, followed by stirring under heating and reflux for 1.5 hours. The solvent was distilled away under reduced pressure, and the resulting residue was purified through silica gel column chromatography (chloroform:methanol=4:1), followed by reslurrying with diethyl ether to afford the entitled Compound 480 (262 mg, 69%) as a white solid.
$^1$H NMR (DMSO-d$_6$, δ ppm): 1.20-1.50 (m, 6H), 1.50-1.80 (m, 6H), 2.30-2.45 (m, 2H), 3.10-3.25 (m, 1H), 3.30-3.45 (m, 2H), 3.55 (s, 2H), 3.85-3.93 (m, 2H), 6.69 (dd, J=1.6, 3.2 Hz, 1H), 7.44 (d, J=3.2 Hz, 1H), 7.48 (d, J=8.1 Hz, 2H), 7.90 (d, J=1.6 Hz, 1H), 8.11 (d, J=8.1 Hz, 2H), 13.07 (br s, 1H).
APCIMS m/z: [M+H]$^+$ 480.
m.p.: 160-162° C.

Example 481

N-[4-(2-Furyl)-5-(tetrahydropyran-4-ylcarbonyl) thiazol-2-yl]-4-(4-hydroxypiperidinomethyl)benzamide (Compound 481)

In a manner similar to that in Example 480, by using 4-hydroxypiperidine in place of piperidine, the entitled Compound 481 (380 mg, 97%) was obtained as a pale yellow solid from Compound 478 (340 mg, 0.789 mmol).
$^1$H NMR (DMSO-d$_6$, δ ppm): 1.40-1.50 (m, 2H), 1.65-1.85 (m, 4H), 2.00-2.10 (m, 2H), 2.85-2.90 (m, 2H), 2.84 (ddd, J=3.5, 9.4, 11.3 Hz, 2H), 3.05-3.20 (m, 1H), 3.20-3.40 (m, 3H), 3.45 (s, 2H), 3.70-3.80 (m, 1H), 3.85-3.95 (m, 2H), 4.45-4.50 (m, 1H), 6.63 (dd, J=1.6, 3.5 Hz, 1H), 7.35 (d, J=8.4 Hz, 2H), 7.41 (d, J=3.5 Hz, 1H), 7.80 (d, J=1.6 Hz, 1H), 8.09 (d, J=8.4 Hz, 2H).
APCIMS m/z: [M+H]$^+$ 496.
m.p.: 194-195° C.

Example 482

N-[4-(2-Furyl)-5-(tetrahydropyran-4-ylcarbonyl) thiazol-2-yl]-4-(morpholinomethyl)benzamide (Compound 482)

In a manner similar to that in Example 480, by using morpholine in place of piperidine, the entitled Compound 482 (322 mg, 85%) was obtained as a pale yellow solid from Compound 478 (340 mg, 0.789 mmol).
$^1$H NMR (DMSO-d$_6$, δ ppm): 1.50-1.80 (m, 4H), 2.38 (t, J=4.3 Hz, 4H), 3.10-3.25 (m, 1H), 3.36 (ddd, J=2.4, 11.3, 11.3 Hz, 2H), 3.56 (s, 2H), 3.59 (t, J=4.3 Hz, 4H), 3.85-3.93 (m, 2H), 6.69 (dd, J=1.9, 3.5 Hz, 1H), 7.44 (dd, J=0.8, 3.5 Hz, 1H), 7.49 (d, J=8.4 Hz, 2H), 7.89 (dd, J=0.8, 1.9 Hz, 1H), 8.12 (d, J=8.4 Hz, 2H), 12.67 (br s, 1H).
APCIMS m/z: [M+H]$^+$ 482.
m.p.: 92-96° C.

Example 483

N-[4-(2-Furyl)-5-(tetrahydropyran-4-ylcarbonyl) thiazol-2-yl]-2,3-dimethoxybenzamide (Compound 483)

In a manner similar to that in Example 465, by using 2,3-dimethoxybenzoic acid in place of 4-(dimethylamino) benzoic acid, the entitled Compound 483 (158 mg, 79%) was obtained as a pale yellow solid from Compound 454 (125 mg, 0.450 mmol).
$^1$H NMR (DMSO-d$_6$, δ ppm): 1.50-1.75 (m, 4H), 3.15-3.25 (m, 1H), 3.36 (ddd, J=2.4, 11.3, 11.3 Hz, 2H), 3.83 (s, 3H), 3.84-3.94 (m, 2H), 3.87 (s, 3H), 6.69 (dd, J=1.9, 3.5 Hz, 1H), 7.17-7.21 (m, 2H), 7.23-7.30 (m, 1H), 7.41 (dd, J=0.5, 3.5 Hz, 1H), 7.89 (dd, J=0.5, 1.9 Hz, 1H), 12.80 (br s, 1H).
APCIMS m/z: [M+H]$^+$ 443.
m.p.: 198-200° C.

Example 484

N-[4-(2-Furyl)-5-(tetrahydropyran-4-ylcarbonyl) thiazol-2-yl]-2,4-dimethoxybenzamide (Compound 484)

In a manner similar to that in Example 456, by using 2,4-dimethoxybenzoyl chloride in place of cyclopropanecarbonyl chloride, followed by reslurrying with methanol, the entitled Compound 484 (156 mg, 78%) was obtained as a brown solid from Compound 454 (125 mg, 0.150 mmol).
$^1$H NMR (DMSO-d$_6$, δ ppm): 1.54-1.75 (m, 4H), 3.12-3.22 (m, 1H), 3.34 (ddd, J=2.4, 11.3, 11.3 Hz, 2H), 3.89 (s, 3H), 3.90-3.95 (m, 2H), 3.97 (s, 3H), 6.69 (dd, J=1.9, 3.2 Hz, 1H), 6.72-6.77 (m, 2H), 7.41 (d, J=3.2 Hz, 1H), 7.80 (dd, J=3.0, 8.4 Hz, 1H), 7.89 (d, J=1.9 Hz, 1H), 11.94 (br s, 1H).
APCIMS m/z: [M+H]$^+$ 443.
m.p.: 219-222° C.

Example 485

N-[4-(2-Furyl)-5-(tetrahydropyran-4-ylcarbonyl) thiazol-2-yl]-2,5-dimethoxybenzamide (Compound 485)

In a manner similar to that in Example 465, by using 2,5-dimethoxybenzoic acid in place of 4-(dimethylamino) benzoic acid, followed by reslurrying with ethanol, the entitled Compound 485 (172 mg, 86%) was obtained as a pale yellow solid from Compound 454 (125 mg, 0.450 mmol).
$^1$H NMR (DMSO-d$_6$, δ ppm): 1.50-1.80 (m, 4H), 3.10-3.25 (m, 1H), 3.35 (ddd, J=2.2, 11.3, 11.3 Hz, 2H), 3.77 (s, 3H), 3.80-3.92 (m, 2H), 3.88 (s, 3H), 6.69 (dd, J=1.9, 3.5 Hz, 1H), 7.15-7.24 (m, 2H), 7.25-7.31 (m, 1H), 7.41 (d, J=3.5 Hz, 1H), 7.90 (d, J=1.9 Hz, 1H), 12.44 (br s, 1H).
APCIMS m/z: [M+H]$^+$ 443.
m.p.: 107-110° C.

Example 486

N-[4-(2-Furyl)-5-(tetrahydropyran-4-ylcarbonyl) thiazol-2-yl]-2,6-dimethoxybenzamide (Compound 486)

In a manner similar to that in Example 456, by using 2,6-dimethoxybenzoyl chloride in place of cyclopropanecarbonyl chloride, followed by recrystallizing from a mixed solvent of ethanol, diethyl ether and ethyl acetate, the entitled Compound 486 (91.1 mg, 46%) was obtained as a pink solid from Compound 454 (125 mg, 0.450 mmol).
$^1$H NMR (DMSO-d$_6$, δ ppm): 1.54-1.76 (m, 4H), 3.12-3.24 (m, 1H), 3.32-3.42 (m, 2H), 3.76 (s, 6H), 3.84-3.92 (m, 2H), 6.68 (dd, J=1.6, 3.0 Hz, 1H), 6.75 (d, J=8.4 Hz, 2H), 7.37 (d, J=3.0 Hz, 1H), 7.42 (t, J=8.4 Hz, 1H), 7.88 (d, J=1.6 Hz, 1H), 12.93 (br s, 1H).
APCIMS m/z: [M+H]$^+$ 443.
m.p.: 152-156° C.

Example 487

N-[4-(2-Furyl)-5-(tetrahydropyran-4-ylcarbonyl) thiazol-2-yl]-3,4-dimethoxybenzamide (Compound 487)

In a manner similar to that in Example 456, by using 3,4-dimethoxybenzoyl chloride in place of cyclopropanecarbonyl chloride followed by reslurrying with ethanol, the entitled Compound 487 (150 mg, 75%) was obtained as a brown solid from Compound 454 (125 mg, 0.450 mmol).
$^1$H NMR (DMSO-d$_6$, δ ppm): 1.55-1.80 (m, 4H), 3.10-3.25 (m, 1H), 3.35 (ddd, J=2.2, 11.3, 11.3 Hz, 2H), 3.86 (s, 3H), 3.87 (s, 3H), 3.88-3.92 (m, 2H), 6.70 (dd, J=1.6, 3.2 Hz, 1H), 7.13 (d, J=8.4 Hz, 1H), 7.45 (d, J=3.2 Hz, 1H), 7.78-7.82 (m, 2H), 7.84 (d, J=1.6 Hz, 1H), 13.11 (br s, 1H).
APCIMS m/z: [M+H]$^+$ 443.
m.p.: 289-292° C.

Example 488

N-[4-(2-Furyl)-5-(tetrahydropyran-4-ylcarbonyl) thiazol-2-yl]-3,5-dimethoxybenzamide (Compound 488)

In a manner similar to that in Example 456, by using 3,5-dimethoxybenzoyl chloride in place of cyclopropanecarbonyl chloride, followed by reslurrying with methanol, the entitled Compound 488 (179 mg, 93%) was obtained as a pale brown solid from Compound 454 (125 mg, 0.450 mmol).
$^1$H NMR (DMSO-d$_6$, δ ppm): 1.50-1.80 (m, 4H), 3.10-3.25 (m, 1H), 3.36 (ddd, J=2.2, 11.3, 11.3 Hz, 2H), 3.84 (s, 6H), 3.80-3.92 (m, 2H), 6.70 (dd, J=1.9, 3.5 Hz, 1H), 6.78 (t, J=2.7 Hz, 1H), 7.35 (d, J=2.7 Hz, 2H), 7.45 (dd, J=0.8, 3.5 Hz, 1H), 7.91 (dd, J=0.8, 1.9 Hz, 1H), 13.25 (br s, 1H).
APCIMS m/z: [M+H]$^+$ 443.
m.p.: 278-280° C.

Example 489

2,3-Difluoro-N-[4-(2-furyl)-5-(tetrahydropyran-4-ylcarbonyl)thiazol-2-yl]benzamide (Compound 489)

In a manner similar to that in Example 456, by using 2,3-difluorobenzoyl chloride in place of cyclopropanecarbonyl chloride, followed by recrystallizing from a mixed solvent of ethanol and diethyl ether, the entitled Compound 489 (116 mg, 62%) was obtained as a brown solid from Compound 454 (125 mg, 0.450 mmol).
$^1$H NMR (DMSO-d$_6$, δ ppm): 1.50-1.80 (m, 4H), 3.15-3.25 (m, 1H), 3.36 (ddd, J=2.4, 11.3, 11.3 Hz, 2H), 3.84-3.93 (m, 2H), 6.70 (dd, J=1.6, 3.5 Hz, 1H), 7.34-7.41 (m, 1H), 7.42 (dd, J=0.8, 3.5 Hz, 1H), 7.57-7.77 (m, 2H), 7.90 (dd, J=0.8, 1.6 Hz, 1H), 13.42 (br s, 1H).
APCIMS m/z: [M+H]$^+$ 419.
m.p.: 154-160° C.

Example 490

2,4-Difluoro-N-[4-(2-furyl)-5-(tetrahydropyran-4-ylcarbonyl)thiazol-2-yl]benzamide (Compound 490)

In a manner similar to that in Example 456, by using 2,4-difluorobenzoyl chloride in place of cyclopropanecarbonyl chloride, followed by reslurrying with ethanol, the entitled Compound 490 (170 mg, 90%) was obtained as a brown solid from Compound 454 (125 mg, 0.450 mmol).
$^1$H NMR (DMSO-d$_6$, δ ppm): 1.50-1.80 (m, 4H), 3.15-3.25 (m, 1H), 3.36 (ddd, J=2.2, 11.3, 11.3 Hz, 2H), 3.84-3.93 (m, 2H), 6.70 (dd, J=1.6, 3.5 Hz, 1H), 7.22-7.32 (m, 1H), 7.42 (dd, J=0.8, 3.5 Hz, 1H), 7.44-7.52 (m, 1H), 7.85-7.92 (m, 2H), 13.28 (br s, 1H).
APCIMS m/z: [M+H]$^+$ 419.
m.p.: 213-215° C.

Example 491

2,5-Difluoro-N-[4-(2-furyl)-5-(tetrahydropyran-4-ylcarbonyl)thiazol-2-yl]benzamide (Compound 491)

In a manner similar to that in Example 456, by using 2,5-difluorobenzoyl chloride in place of cyclopropanecarbonyl chloride, followed by reslurrying with diethyl ether, the entitled Compound 491 (164 mg, 87%) was obtained as a brown solid from Compound 454 (125 mg, 0.450 mmol).
$^1$H NMR (DMSO-d$_6$, δ ppm): 1.50-1.80 (m, 4H), 3.15-3.25 (m, 1H), 3.36 (ddd, J=2.2, 11.3, 11.3 Hz, 2H), 3.88 (ddd, J=2.2, 4.3, 11.3 Hz, 2H), 6.70 (dd, J=1.9, 3.5 Hz, 1H), 7.41 (dd, J=0.8, 3.5 Hz, 1H), 7.43-7.58 (m, 2H), 7.68 (ddd, J=3.0, 5.4, 8.4 Hz, 1H), 7.90 (dd, J=0.8, 1.9 Hz, 1H), 13.37 (br s, 1H).
APCIMS m/z: [M+H]$^+$ 419.
m.p.: 172-174° C.

Example 492

2,6-Difluoro-N-[4-(2-furyl)-5-(tetrahydropyran-4-ylcarbonyl)thiazol-2-yl]benzamide (Compound 492)

In a manner similar to that in Example 456, by using 2,6-difluorobenzoyl chloride in place of cyclopropanecarbonyl chloride, followed by reslurrying with a mixed solvent of ethanol and diethyl ether, the entitled Compound 492 (120 mg, 69%) was obtained as a brown solid from Compound 454 (125 mg, 0.450 mmol).
$^1$H NMR (DMSO-d$_6$, δ ppm): 1.50-1.80 (m, 4H), 3.15-3.25 (m, 1H), 3.36 (ddd, J=2.4, 11.6, 11.6 Hz, 2H), 3.83-3.92 (m, 2H), 6.70 (dd, J=1.6, 3.5 Hz, 1H), 7.29 (t, J=8.1 Hz, 1H), 7.40 (d, J=3.5 Hz, 1H), 7.60-7.73 (m, 2H), 7.90 (d, J=1.9 Hz, 1H), 13.60 (br s, 1H).
APCIMS m/z: [M+H]$^+$ 419.
m.p.: 168-170° C.

Example 493

3,4-Difluoro-N-[4-(2-furyl)-5-(tetrahydropyran-4-ylcarbonyl)thiazol-2-yl]benzamide (Compound 493)

In a manner similar to that in Example 456, by using 3,4-difluorobenzoyl chloride in place of cyclopropanecarbonyl chloride, followed by reslurrying with diethyl ether, the entitled Compound 493 (145 mg, 77%) was obtained as a brown solid from Compound 454 (125 mg, 0.450 mmol).
$^1$H NMR (DMSO-d$_6$, δ ppm): 1.50-1.80 (m, 4H), 3.15-3.25 (m, 1H), 3.36 (ddd, J=2.4, 11.6, 11.6 Hz, 2H), 3.83-3.92 (m, 2H), 6.70 (dd, J=1.9, 3.5 Hz, 1H), 7.45 (d, J=3.5 Hz, 1H), 7.63-7.73 (m, 1H), 7.90 (d, J=1.9 Hz, 1H), 8.02-8.08 (m, 1H), 8.24 (ddd, J=2.2, 7.5, 11.3 Hz, 1H), 13.37 (br s, 1H).
APCIMS m/z: [M+H]$^+$ 419.
m.p.: 208-210° C.

Example 494

3,5-Difluoro-N-[4-(2-furyl)-5-(tetrahydropyran-4-ylcarbonyl)thiazol-2-yl]benzamide (Compound 494)

In a manner similar to that in Example 456, by using 3,5-difluorobenzoyl chloride in place of cyclopropanecarbonyl chloride, followed by reslurrying with a mixed solvent of ethanol and diethyl ether, the entitled Compound 494 (165 mg, 88%) was obtained as a brown solid from Compound 454 (125 mg, 0.450 mmol).
$^1$H NMR (DMSO-d$_6$, δ ppm): 1.50-1.80 (m, 4H), 3.15-3.25 (m, 1H), 3.36 (ddd, J=2.4, 11.3, 11.3 Hz, 2H), 3.83-3.93 (m, 2H), 6.71 (dd, J=1.9, 3.5 Hz, 1H), 7.44 (dd, J=0.8, 3.5 Hz, 1H), 7.58-7.67 (m, 1H), 7.84-7.90 (m, 2H), 7.91 (dd, J=0.8, 1.9 Hz, 1H), 13.43 (br s, 1H).
APCIMS m/z: [M+H]$^+$ 419.
m.p.: 259-265° C.

Example 495

N-[4-(2-Furyl)-5-(tetrahydropyran-4-ylcarbonyl) thiazol-2-yl]-1,4-benzodioxane-5-carboxamide (Compound 495)

In a manner similar to that in Example 455, by using 1,4-benzodioxane-5-carboxylic acid in place of isonicotinic acid, the entitled Compound 495 (145 mg, 73%) was obtained as a brown solid from Compound 454 (125 mg, 0.450 mmol).
$^1$H NMR (DMSO-d$_6$, δ ppm): 1.50-1.80 (m, 4H), 3.10-3.22 (m, 1H), 3.35 (ddd, J=2.4, 11.6, 11.6 Hz, 2H), 3.83-3.93 (m, 2H), 4.29-4.34 (m, 2H), 4.39-4.43 (m, 2H), 6.69 (dd, J=1.6, 3.2 Hz, 1H), 6.96 (dd, J=7.8, 7.8 Hz, 1H), 7.09 (dd, J=1.6, 7.8 Hz, 1H), 7.23 (dd, J=1.6, 7.8 Hz, 1H), 7.42 (d, J=3.2 Hz, 1H), 7.89 (d, J=1.6 Hz, 1H), 12.52 (br s, 1H).
APCIMS m/z: [M+H]$^+$ 441.
m.p.: 188-190° C.

Example 496

N-[4-(2-Furyl)-5-(tetrahydropyran-4-ylcarbonyl) thiazol-2-yl]-1,3-benzodioxole-5-carboxamide (Compound 496)

In a manner similar to that in Example 456, by using 1,3-benzodioxole-5-carbonyl chloride in place of cyclopropanecarbonyl chloride, followed by reslurrying with ethanol, the entitled Compound 496 (143 mg, 75%) was obtained as a brown solid from Compound 454 (125 mg, 0.450 mmol).
$^1$H NMR (DMSO-d$_6$, δ ppm): 1.50-1.80 (m, 4H), 3.15-3.25 (m, 1H), 3.36 (ddd, J=2.4, 11.6, 11.6 Hz, 2H), 3.83-3.93 (m, 2H), 6.16 (s, 2H), 6.70 (dd, J=1.6, 3.2 Hz, 1H), 7.09 (d, J=8.1

Hz, 1H), 7.45 (d, J=3.2 Hz, 1H), 7.70 (d, J=1.9 Hz, 1H), 7.79 (dd, J=1.9, 8.1 Hz, 1H), 7.90 (d, J=1.6 Hz, 1H), 13.07 (br s, 1H).

APCIMS m/z: [M+H]+ 427.

m.p.: 194-196° C.

Example 497

2,2-Difluoro-N-[4-(2-furyl)-5-(tetrahydropyran-4-ylcarbonyl)thiazol-2-yl]-1,3-benzodioxole-4-carboxamide (Compound 497)

In a manner similar to that in Example 456, by using 2,2-difluoro-1,3-benzodioxole-4-carbonyl chloride in place of cyclopropanecarbonyl chloride, followed by reslurrying with ethanol, the entitled Compound 497 (161 mg, 77%) was obtained as a brown solid from Compound 454 (125 mg, 0.450 mmol).

$^1$H NMR (DMSO-d$_6$, δ ppm): 1.50-1.80 (m, 4H), 3.10-3.30 (m, 1H), 3.36 (ddd, J=2.2, 11.6, 11.6 Hz, 2H), 3.85-3.92 (m, 2H), 6.70 (dd, J=1.6, 3.2 Hz, 1H), 7.37 (dd, J=8.1, 8.1 Hz, 1H), 7.45 (d, J=3.2 Hz, 1H), 7.69 (dd, J=0.8, 8.1 Hz, 1H), 7.82 (dd, J=0.8, 8.1 Hz, 1H), 7.90 (d, J=1.6 Hz, 1H), 13.43 (br s, 1H).

APCIMS m/z: [M+H]+ 463.

m.p.: 206-207° C.

Example 498

2,2-Difluoro-N-[4-(2-furyl)-5-(tetrahydropyran-4-ylcarbonyl)thiazol-2-yl]-1,3-benzodioxole-5-carboxamide (Compound 498)

In a manner similar to that in Example 456, by using 2,2-difluoro-1,3-benzodioxole-5-carbonyl chloride in place of cyclopropanecarbonyl chloride, followed by reslurrying with ethanol, the entitled Compound 498 (98.5 mg, 47%) was obtained from Compound 454 (125 mg, 0.450 mmol).

$^1$H NMR (DMSO-d$_6$, δ ppm): 1.50-1.80 (m, 4H), 3.15-3.25 (m, 1H), 3.36 (ddd, J=2.4, 11.6, 11.6 Hz, 2H), 3.85-3.92 (m, 2H), 6.70 (dd, J=1.6, 3.5 Hz, 1H), 7.45 (d, J=3.5 Hz, 1H), 7.63 (d, J=8.6 Hz, 1H), 7.90 (d, J=1.6 Hz, 1H), 8.08 (dd, J=1.6, 8.6 Hz, 1H), 8.18 (d, J=1.6 Hz, 1H), 13.33 (br s, 1H).

APCIMS m/z: [M+H]+ 463.

m.p.: 124-129° C.

Example 499

2-Chloro-N-(4-(2-furyl)-5-(tetrahydropyran-4-ylcarbonyl)thiazol-2-yl]pyridine-4-carboxamide (Compound 499)

Step 1:

2-Chloroisonicotinic acid (707 mg, 4.49 mmol) was suspended in thionyl chloride (10 mL), followed by stirring under heating and reflux for 7 hours. The reaction mixture was concentrated under reduced pressure to afford 2-chloroisonicotinoyl chloride.

Step 2:

In a manner similar to that in Example 456, by using 2-chloroisonicotinoyl chloride obtained in Step 1, in place of cyclopropanecarbonyl chloride, and crystallizing the product from ethanol, the entitled Compound 499 (90.3 mg, 48%) was obtained from Compound 454 (125 mg, 0.450 mmol).

$^1$H NMR (DMSO-d$_6$, δ ppm): 1.50-1.80 (m, 4H), 3.15-3.25 (m, 1H), 3.36 (ddd, J=2.7, 11.3, 11.3 Hz, 2H), 3.85-3.92 (m, 2H), 6.71 (dd, J=1.6, 3.5 Hz, 1H), 7.44 (dd, J=0.8, 3.5 Hz, 1H), 7.92 (dd, J=0.8, 1.6 Hz, 1H), 8.01 (dd, J=1.4, 5.1 Hz, 1H), 8.17 (dd, J=0.8, 1.4 Hz, 1H), 8.67 (dd, J=0.8, 5.1 Hz, 1H), 13.64 (br s, 1H).

APCIMS m/z: [$^{35}$ClM+H]+ 418, [$^{37}$ClM+H]+ 420.

m.p.: 185-186° C.

Example 500

N-[4-(2-Furyl)-5-(tetrahydropyran-4-ylcarbonyl)thiazol-2-yl]-2-methylpyridine-4-carboxamide (Compound 500)

In a manner similar to that in Example 465, by using 2-methylisonicotinic acid in place of 3-(dimethylamino)benzoic acid, followed by reslurrying with diethyl ether, the entitled Compound 500 (22.0 mg, 12%) was obtained from Compound 454 (125 mg, 0.450 mmol).

$^1$H NMR (DMSO-d$_6$, δ ppm): 1.50-1.80 (m, 4H), 2.58 (s, 3H), 3.15-3.25 (m, 1H), 3.35-3.38 (m, 2H), 3.83-3.93 (m, 2H), 6.71 (dd, J=1.9, 3.5 Hz, 1H), 7.43 (dd, J=0.8, 3.5 Hz, 1H), 7.81 (dd, J=1.1, 5.1 Hz, 1H), 7.89-7.92 (m, 2H), 8.68 (d, J=5.1 Hz, 1H), 13.48 (br s, 1H).

APCIMS m/z: [M+H]+ 398.

m.p.: 169-173° C.

Example 501

N-[4-(2-Furyl)-5-(tetrahydropyran-4-ylcarbonyl)thiazol-2-yl]pyridine-3-carboxamide (Compound 501)

In a manner similar to that in Example 464, by using nicotinic acid in place of 3-(dimethylamino)benzoic acid, followed by recrystallizing from ethanol, the entitled Compound 501 (1.72 g, 75%) was obtained as a pale yellow solid from Compound 454 (1.67 g, 6.00 mmol).

$^1$H NMR (DMSO-d$_6$, δ ppm): 1.54-1.76 (m, 4H), 3.15-3.25 (m, 1H), 3.36 (ddd, J=2.2, 11.3, 11.3 Hz, 2H), 3.84-3.93 (m, 2H), 6.71 (dd, J=1.9, 3.5 Hz, 1H), 7.45 (d, J=3.5 Hz, 1H), 7.61 (dd, J=4.9, 8.4 Hz, 1H), 7.90 (d, J=1.9 Hz, 1H), 8.46 (ddd, J=2.2, 2.2, 8.4 Hz, 1H), 8.80 (dd, J=2.2, 4.9 Hz, 1H), 9.25 (d, J=2.2 Hz, 1H), 13.50 (br s, 1H).

APCIMS m/z: [M+H]+ 384.

m.p.: 209-212° C.

Example 502

2-Chloro-N-[4-(2-furyl)-5-(tetrahydropyran-4-ylcarbonyl)thiazol-2-yl]pyridine-5-carboxamide (Compound 502)

Compound 454 (125 mg, 0.450 mmol) and DMAP (3.0 mg, 0.022 mmol) were suspended in pyridine (2 mL), and 6-chloronicotinoyl chloride (158 mg, 0.897 mmol) was added thereto, followed by stirring at 80° C. for 1 hour. Water was added to the reaction mixture, followed by extraction with chloroform. The organic layer was washed with a saturated aqueous solution of sodium chloride and dried over anhydrous magnesium sulfate, and then the solvent was distilled away under reduced pressure. The resulting residue was reslurried with ethanol to afford the entitled Compound 502 (138 mg, 73%) as a pale brown solid.

$^1$H NMR (DMSO-d$_6$, δ ppm): 1.50-1.80 (m, 4H), 3.15-3.27 (m, 1H), 3.36 (ddd, J=2.2, 11.6, 11.6 Hz, 2H), 3.89 (ddd, J=2.2, 4.0, 11.6 Hz, 2H), 6.71 (dd, J=1.9, 3.5 Hz, 1H), 7.44 (dd, J=0.5, 3.5 Hz, 1H), 7.76 (dd, J=0.5, 8.6 Hz, 1H), 7.91 (dd, J=0.5, 1.9 Hz, 1H), 8.49 (dd, J=2.7, 8.6 Hz, 1H), 9.90 (dd, J=0.5, 2.7 Hz, 1H), 13.55 (br s, 1H).
APCIMS m/z: [$^{35}$ClM+H]$^+$ 416, [$^{37}$ClM+H]$^+$ 418.
m.p.: 233-235° C.

Example 503

N-[4-(2-Furyl)-5-(tetrahydropyran-4-ylcarbonyl)thiazol-2-yl]-2-morpholinopyridine-5-carboxamide (Compound 503)

Compound 502 (100 mg, 0.239 mmol) was suspended in 1,4-dioxane (1 mL), and morpholine (0.063 mL, 0.72 mmol) was added thereto, followed by stirring overnight at 100° C. The reaction mixture was concentrated under reduced pressure, and the resulting residue was reslurried with ethanol to afford the entitled Compound 503 (109 mg, 97 mmol) as a pale brown solid.
$^1$H NMR (DMSO-d$_6$, δ ppm): 1.50-1.75 (m, 4H), 3.12-3.23 (m, 1H), 3.35 (ddd, J=2.4, 11.6, 11.6 Hz, 2H), 3.60-3.70 (m, 8H), 3.83-3.93 (m, 2H), 6.69 (dd, J=1.6, 3.2 Hz, 1H), 6.94 (d, J=9.4 Hz, 1H), 7.45 (d, J=3.2 Hz, 1H), 7.89 (d, J=1.6, Hz, 1H), 8.24 (dd, J=2.4, 9.4 Hz, 1H), 8.90 (d, J=2.4 Hz, 1H), 12.98 (br s, 1H).
APCIMS m/z: [M+H]$^+$ 469.
m.p.: 166-170° C.

Example 504

N-[4-(2-Furyl)-5-(tetrahydropyran-4-ylcarbonyl)thiazol-2-yl]-2-methylpyridine-5-carboxamide (Compound 504)

In a manner similar to that in Example 455, by using 6-methylnicotinic acid (247 mg, 1.80 mmol) in place of isonicotinic acid, followed by recrystallizing from ethanol, the entitled Compound 504 (97.5 mg, 55%) was obtained as a pale brown solid from Compound 454 (125 mg, 0.450 mmol).
$^1$H NMR (DMSO-d$_6$, δ ppm): 1.54-1.78 (m, 4H), 2.57 (s, 3H), 3.16-3.25 (m, 1H), 3.32-3.48 (m, 2H), 3.84-3.93 (m, 2H), 6.70 (dd, J=1.9, 3.5 Hz, 1H), 7.43-7.49 (m, 2H), 7.91 (d, J=1.9 Hz, 1H), 8.35 (dd, J=2.4, 8.1 Hz, 1H), 9.14 (d, J=2.4 Hz, 1H), 13.40 (br s, 1H).
APCIMS m/z: [M+H]$^+$ 398.
m.p.: 209-211° C.

Example 505

N-[4-(2-Furyl)-5-(tetrahydropyran-4-ylcarbonyl)thiazol-2-yl]-2-(trifluoromethyl)pyridine-5-carboxamide (Compound 505)

In a manner similar to that in Example 464, by using 6-(trifluoromethyl)nicotinic acid in place of 3-(dimethylamino)benzoic acid, the entitled Compound 505 (168 mg, 82%) was obtained from Compound 454 (125 mg, 0.450 mmol).
$^1$H NMR (DMSO-d$_6$, δ ppm): 1.50-1.80 (m, 4H), 3.15-3.25 (m, 1H), 3.37 (ddd, J=2.4, 11.3, 11.3 Hz, 2H), 3.89 (ddd, J=2.4, 4.3, 11.3 Hz, 2H), 6.72 (dd, J=1.9, 3.5 Hz, 1H), 7.45 (dd, J=0.8, 3.5 Hz, 1H), 7.92 (dd, J=0.8, 1.9 Hz, 1H), 8.15 (dd, J=0.8, 8.1 Hz, 1H), 8.72 (dd, J=1.6, 8.1 Hz, 1H), 9.39 (dd, J=0.8, 1.6 Hz, 1H), 13.71 (br s, 1H).
APCIMS m/z: [M+H]$^+$ 452.
m.p.: 217-222° C.

Example 506

N-[4-(2-Furyl)-5-(tetrahydropyran-4-ylcarbonyl)thiazol-2-yl]-5-methylpyridine-3-carboxamide (Compound 506)

In a manner similar to that in Example 464, by using 5-methylnicotinic acid in place of 3-(dimethylamino)benzoic acid, followed by reslurrying with ethanol, the entitled Compound 506 (147 mg, 82%) was obtained as a pale brown solid from Compound 454 (125 mg, 0.450 mmol).
$^1$H NMR (DMSO-d$_6$, δ ppm): 1.50-1.80 (m, 4H), 2.40 (s, 3H), 3.15-3.25 (m, 1H), 3.36 (ddd, J=2.4, 11.6, 11.6 Hz, 2H), 3.89 (ddd, J=2.2, 4.4, 11.6 Hz, 2H), 6.71 (dd, J=1.9, 3.2 Hz, 1H), 7.43 (dd, J=0.8, 3.2 Hz, 1H), 7.91 (dd, J=0.8, 1.9 Hz, 1H), 8.28-8.31 (m, 1H), 8.67 (d, J=1.6 Hz, 1H), 9.05 (d, J=1.6 Hz, 1H), 13.42 (br s, 1H).
APCIMS m/z: [M+H]$^+$ 398.
m.p.: 239-243° C.

Example 507

N-[4-(2-Furyl)-5-(tetrahydropyran-4-ylcarbonyl)thiazol-2-yl]pyridine-2-carboxamide (Compound 507)

In a manner similar to that in Example 464, by using picolinic acid in place of 3-(dimethylamino)benzoic acid, followed by reslurrying with ethanol, the entitled Compound 507 (105 mg, 61%) was obtained as a pale brown solid from Compound 454 (125 mg, 0.450 mmol).
$^1$H NMR (DMSO-d$_6$, δ ppm): 1.53-1.78 (m, 4H), 3.15-3.27 (m, 1H), 3.35 (ddd, J=2.4, 11.6, 11.6 Hz, 2H), 3.88 (ddd, J=2.4, 4.3, 11.6 Hz, 2H), 6.71 (dd, J=1.6, 3.2 Hz, 1H), 7.37 (dd, J=0.8, 3.2 Hz, 1H), 7.74 (ddd, J=1.3, 4.9, 7.5 Hz, 1H), 7.92 (dd, J=0.8, 1.6 Hz, 1H), 8.11 (ddd, J=1.6, 7.5, 7.5 Hz, 1H), 8.20 (ddd, J=1.3, 1.3, 7.5 Hz, 1H), 8.78 (ddd, J=1.3, 1.6, 4.9 Hz, 1H), 12.62 (br s, 1H).
APCIMS m/z: [M+H]$^+$ 384.
m.p.: 185-186° C.

Example 508

N-[4-(2-Furyl)-5-(tetrahydropyran-4-ylcarbonyl)thiazol-2-yl]-2-methylpyrimidine-5-carboxamide (Compound 508)

In a manner similar to that in Example 228, a crude Compound 508 was obtained from Compound 454 (200 mg, 0.719 mmol) in place of Compound 186. The crude Compound 508 was recrystallized from a mixed solvent of ethanol and water to afford the entitled Compound 508 (118 mg, 41%) as a pale brown solid.
$^1$H NMR (DMSO-d$_6$, δ ppm): 1.55-176 (m, 4H), 2.73 (s, 3H), 3.16-3.30 (m, 1H), 3.30-3.50 (m, 2H), 3.80-3.93 (m, 2H), 6.71 (dd, J=1.6, 3.2 Hz, 1H), 7.44 (d, J=3.2 Hz, 1H), 7.92 (d, J=1.6 Hz, 1H), 9.29 (s, 2H), 13.58 (br s, 1H).
APCIMS m/z: [M+H]$^+$ 399.

Example 509

N-[4-(2-Furyl)-5-(tetrahydropyran-4-ylcarbonyl)thiazol-2-yl]pyrazine-2-carboxamide (Compound 509)

In a manner similar to that in Example 455, by using pyrazine-2-carboxylic acid in place of isonicotinic acid, followed by reslurrying with ethanol, the entitled Compound 509 (111 mg, 64%) was obtained as a brown solid from Compound 454 (125 mg, 0.450 mmol).

$^1$H NMR (DMSO-d$_6$, δ ppm): 1.50-1.80 (m, 4H), 3.10-3.30 (m, 1H), 3.35 (ddd, J=2.2, 11.3, 11.3 Hz, 2H), 3.85-3.94 (m, 2H), 6.71 (dd, J=1.9, 3.5 Hz, 1H), 7.39 (d, J=3.5 Hz, 1H), 7.92 (d, J=1.9 Hz, 1H), 8.85 (dd, J=1.3, 2.4 Hz, 1H), 8.96 (d, J=2.4 Hz, 1H), 9.33 (d, J=1.3 Hz, 1H), 13.18 (br s, 1H).

APCIMS m/z: [M+H]$^+$ 385.

m.p.: 200-205° C.

Example 510

N-[4-(2-Furyl)-5-(tetrahydropyran-4-ylcarbonyl) thiazol-2-yl]-5-methylpyrazine-2-carboxamide (Compound 510)

In a manner similar to that in Example 455, by using 5-methylpyrazine-2-carboxylic acid in place of isonicotinic acid, followed by reslurrying with ethanol, the entitled Compound 510 (118 mg, 66%) was obtained as a brown solid from Compound 454 (125 mg, 0.450 mmol).

$^1$H NMR (DMSO-d$_6$, δ ppm): 1.50-1.80 (m, 4H), 2.65 (s, 3H), 3.15-3.25 (m, 1H), 3.35 (ddd, J=2.2, 11.3, 11.3 Hz, 2H), 3.85-3.93 (m, 2H), 6.71 (dd, J=1.9, 3.5 Hz, 1H), 7.38 (dd, J=0.5, 3.5 Hz, 1H), 7.92 (dd, J=0.5, 1.9 Hz, 1H), 8.74 (d, J=1.1 Hz, 1H), 9.20 (d, J=1.1 Hz, 1H), 13.07 (br s, 1H).

APCIMS m/z: [M+H]$^+$ 399.

m.p.: 130-131° C.

Example 511

N-[4-(2-Furyl)-5-(tetrahydropyran-4-ylcarbonyl) thiazol-2-yl]furan-2-carboxamide (Compound 511)

Compound 454 (556 mg, 2.00 mmol) and DMAP (24.4 mg, 0.200 mmol) were suspended in pyridine (8 mL), and 2-furoyl chloride (0.394 mL, 4.00 mmol) was added thereto, followed by stirring at 50° C. for 2 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=19:1), followed by recrystallizing from ethanol to afford the entitled Compound 511 (491 mg, 66%) as a white solid.

$^1$H NMR (DMSO-d$_6$, δ ppm): 1.54-1.74 (m, 4H), 3.13-3.24 (m, 1H), 3.26-3.40 (m, 2H), 3.84-3.92 (m, 2H), 6.70 (dd, J=1.6, 3.5 Hz, 1H), 6.77 (dd, J=1.6, 3.5 Hz, 1H), 7.42 (d, J=3.5 Hz, 1H), 7.78 (d, J=3.5 Hz, 1H), 7.90 (d, J=1.6 Hz, 1H), 8.06 (d, J=1.6 Hz, 1H), 13.22 (br s, 1H).

APCIMS m/z: [M+H]$^+$ 373.

m.p.: 196-198° C.

Example 512

N-[4-(2-Furyl)-5-(tetrahydropyran-4-ylcarbonyl) thiazol-2-yl]-5-methylfuran-2-carboxamide (Compound 512)

Step 1:

2-Methylfuran (9.02 mL, 100 mmol) and N,N,N',N'-tetramethylethylenediamine (12.1 mL, 80.0 mmol) were dissolved in THF (200 mL), and a 1.59 mol/L solution of n-butyllithium in n-hexane (50.3 mL, 80.0 mmol) was added thereto in a stream of argon at −78° C., followed by stirring at room temperature for 1 hour. At −78° C., DMF (31.0 mL, 400 mmol) was added dropwise to the reaction mixture, followed by stirring at room temperature for 1.5 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=7:3) to afford 5-methylfuran-2-carbaldehyde (7.46 g, 68%).

$^1$H NMR (CDCl$_3$, δ ppm): 2.42 (s, 3H), 6.23 (d, J=3.6 Hz, 1H), 7.22 (d, J=3.6 Hz, 1H), 9.51 (s, 1H).

Step 2:

5-Methylfuran-2-carbaldehyde (2.20 g, 20.0 mmol) obtained in Step 1 was dissolved in a mixed solvent of 2-methyl-2-propanol (150 mL) and water (40 mL), and 2-methyl-2-butene (10.6 mL, 100 mmol) and sodium dihydrogenphosphate (2.40 g, 20.0 mmol) were added thereto, followed by stirring at room temperature for 15 minutes. 79% sodium chlorite (8.01 g, 70.0 mmol) was added to the reaction mixture little by little, followed by stirring at room temperature for 1 hour. 4 mol/L hydrochloric acid was added to the reaction mixture to adjust the pH to 3, followed by extraction with chloroform. The organic layer was dried over anhydrous magnesium sulfate, and then the solvent was distilled away under reduced pressure. The resulting residue was purified through silica gel column chromatography (chloroform:methanol=17:3) to afford 5-methylfuran-2-carboxylic acid (606 mg, 24%).

$^1$H NMR (CDCl$_3$, δ ppm): 2.41 (s, 3H), 6.17 (d, J=3.5 Hz, 1H), 7.26 (d, J=3.5 Hz, 1H).

Step 3:

In a manner similar to that in Example 455, by using 5-methylfuran-2-carboxylic acid obtained in Step 3, in place of isonicotinic acid, followed by reslurrying with ethanol, the entitled Compound 512 (123 mg, 71%) was obtained as a brown solid from Compound 454 (125 mg, 0.450 mmol).

$^1$H NMR (DMSO-d$_6$, δ ppm): 1.50-1.80 (m, 4H), 2.40 (s, 3H), 3.13-3.24 (m, 1H), 3.34 (ddd, J=2.4, 11.6, 11.6 Hz, 2H), 3.84-3.91 (m, 2H), 6.41 (d, J=3.5 Hz, 1H), 6.70 (dd, J=1.6, 3.5 Hz, 1H), 7.41 (dd, J=0.8, 3.5 Hz, 1H), 7.70 (d, J=3.5 Hz, 1H), 7.90 (dd, J=0.8, 1.9 Hz, 1H), 13.08 (br s, 1H).

APCIMS m/z: [M+H]$^+$ 387.

m.p.: 209-212° C.

Example 513

5-Formyl-N-[4-(2-furyl)-5-(tetrahydropyran-4-ylcarbonyl)thiazol-2-yl]furan-2-carboxamide (Compound 513)

In a manner similar to that in Example 465, by using 5-formylfuran-2-carboxylic acid in place of 4-(dimethylamino)benzoic acid, followed by reslurrying with ethanol, the entitled Compound 513 (2.43 g, 61%) was obtained as a yellow solid from Compound 454 (2.78 g, 10.0 mmol).

$^1$H NMR (DMSO-d$_6$, δ ppm): 1.50-1.80 (m, 4H), 3.10-3.22 (m, 1H), 3.35 (ddd, J=2.2, 11.6, 11.6 Hz, 2H), 3.82-3.92 (m, 2H), 6.70 (dd, J=1.6, 3.5 Hz, 1H), 7.41 (d, J=3.5 Hz, 1H), 7.67 (d, J=3.8 Hz 1H), 7.87 (d, J=3.8 Hz, 1H), 7.90 (d, J=1.6 Hz, 1H), 9.78 (s, 1H), 13.63 (br s, 1H)

APCIMS m/z: [M+H]$^+$ 401. .

Example 514

N-[4-(2-Furyl)-5-(tetrahydropyran-4-ylcarbonyl)thiazol-2-yl]-5-(hydroxyimino)furan-2-carboxamide (Compound 514)

Compound 513 (2.40 g, 6.00 mmol) was suspended in ethanol (24 mL), and hydroxylamine hydrochloride (438 mg, 6.30 mmol) was added thereto, followed by stirring at 60° C. for 1 hour. The precipitated solid was collected by filtration to afford the entitled Compound 514 (2.09 g, 84%) as a pale brown solid.

Example 515

5-Cyano-N-[4-(2-furyl)-5-(tetrahydropyran-4-ylcarbonyl)thiazol-2-yl]furan-2-carboxamide (Compound 515)

Compound 514 (2.08 g, 5.00 mmol) and triethylamine (0.836 mL, 6.00 mmol) were suspended in dichloromethane (20 mL), and 2-chloro-1,3-dimethylimidazolinium chloride (2.03 g, 12.0 mmol) was added thereto at 0° C. This was stirred at 0° C. for 30 minutes, and then triethylamine (0.836 mL, 6.00 mmol) was added thereto, followed by stirring at 0° C. for 5 minutes. Aqueous saturated sodium hydrogencarbonate solution was added to the reaction mixture, followed by extraction with chloroform. The organic layer was dried over anhydrous magnesium sulfate, and then the solvent was distilled away under reduced pressure. The resulting residue was purified through silica gel column chromatography (chloroform:methanol=49:1), followed by recrystallizing from a mixed solvent (3:1) of ethanol and water to afford the entitled Compound 515 (1.26 g, 63%) as a pale brown solid.

$^1$H NMR (DMSO-d$_6$, δ ppm): 1.50-1.75 (m, 4H), 3.15-3.35 (m, 3H), 3.85-3.92 (m, 2H), 6.71 (dd, J=1.6, 3.2 Hz, 1H), 7.43 (d, J=3.2 Hz, 1H), 7.82 (d, J=4.1 Hz, 1H), 7.86 (d, J=4.1 Hz, 1H), 7.91 (d, J=1.6 Hz, 1H), 13.66 (br s, 1H).

APCIMS m/z: [M+H]$^+$ 398.

m.p.: 222-223° C.

Example 516

N-[4-(2-Furyl)-5-(tetrahydropyran-4-ylcarbonyl)thiazol-2-yl]furan-3-carboxamide (Compound 516)

In a manner similar to that in Example 464, by using furan-3-carboxylic acid in place of 3-(dimethylamino)benzoic acid, followed by reslurrying with ethanol, the entitled Compound 516 (111 mg, 66%) was obtained as a pale pink solid from Compound 454 (125 mg, 0.450 mmol).

$^1$H NMR (DMSO-d$_6$, δ ppm): 1.53-1.73 (m, 4H), 3.13-3.24 (m, 1H), 3.40 (ddd, J=2.4, 11.3, 11.3 Hz, 2H), 3.88 (ddd, J=2.4, 4.0, 11.3 Hz, 2H), 6.70 (dd, J=1.9, 3.5 Hz, 1H), 7.12-7.14 (m, 1H), 7.43 (dd, J=0.8, 3.5 Hz, 1H), 7.85-7.89 (m, 1H), 7.90 (dd, J=0.8, 1.9 Hz, 1H), 8.65-8.69 (m, 1H), 13.08 (br s, 1H).

APCIMS m/z: [M+H]$^+$ 373.

m.p.: 236-238° C.

Example 517

N-[4-(2-Furyl)-5-(tetrahydropyran-4-ylcarbonyl)thiazol-2-yl]thiophene-2-carboxamide (Compound 517)

In a manner similar to that in Example 455, by using thiophene-2-carboxylic acid in place of isonicotinic acid, followed by reslurrying with ethanol, the entitled Compound 517 (158 mg, 90%) was obtained as a pale brown solid from Compound 454 (125 mg, 0.450 mmol).

$^1$H NMR (DMSO-d$_6$, δ ppm): 1.53-1.77 (m, 4H), 3.12-3.24 (m, 1H), 3.35 (ddd, J=2.4, 11.3, 11.3 Hz, 2H), 3.89 (ddd, J=2.4, 3.8, 11.3 Hz, 2H), 6.70 (dd, J=1.9, 3.5 Hz, 1H), 7.28 (dd, J=1.4, 4.9 Hz, 1H), 7.45 (dd, J=0.5, 3.5 Hz 1H), 7.90 (dd, J=0.5, 1.9 Hz, 1H), 8.04 (dd, J=0.8, 4.9 Hz, 1H), 8.34 (dd, J=0.8, 1.4 Hz, 1H), 13.35 (br s, 1H).

APCIMS m/z: [M+H]$^+$ 389.

m.p.: 231-232° C.

Example 518

N-[4-(2-Furyl)-5-(tetrahydropyran-4-ylcarbonyl)thiazol-2-yl]thiophene-3-carboxamide (Compound 518)

In a manner similar to that in Example 455, by using thiophene-3-carboxylic acid in place of isonicotinic acid, followed by reslurrying with ethanol, the entitled Compound 518 (148 mg, 85%) was obtained as a pale brown solid from Compound 454 (125 mg, 0.450 mmol).

$^1$H NMR (DMSO-d$_6$, δ ppm): 1.54-1.76 (m, 4H), 3.13-3.25 (m, 1H), 3.35 (ddd, J=2.2, 11.6, 11.6 Hz, 2H), 3.84-3.93 (m, 2H), 6.70 (dd, J=1.6, 3.2 Hz, 1H), 7.44 (d, J=3.2 Hz, 1H), 7.72 (dd, J=2.7, 5.1Hz, 1H), 7.78 (dd, J=1.3, 2.7 Hz, 1H), 7.90 (d, J=1.6 Hz, 1H), 8.70 (dd, J=1.3, 2.7 Hz, 1H), 13.13 (br s, 1H).

APCIMS m/z: [M+H]$^+$ 389.

m.p.: 227-229° C.

Example 519

N-[4-(2-Furyl)-5-(tetrahydropyran-4-ylcarbonyl)thiazol-2-yl]-1-methylpyrazole-4-carboxamide (Compound 519)

In a manner similar to that in Example 499, by using 1-methylpyrazole-4-carboxylic acid in place of 2-chloroisonicotinic acid, followed by reslurrying with ethanol, the entitled Compound 519 (67.2 mg, 39%) was obtained as a pale yellow solid from Compound 454 (125 mg, 0.450 mmol).

$^1$H NMR (DMSO-d$_6$, δ ppm): 1.50-1.75 (m, 4H), 3.10-3.20 (m, 1H), 3.35 (ddd, J=2.2, 11.3, 11.3 Hz, 2H), 3.88 (ddd, J=2.2, 4.1, 11.3 Hz, 2H), 3.92 (s, 3H), 6.70 (dd, J=1.6, 3.5 Hz, 1H), 7.44 (dd, J=0.8, 1.6 Hz, 1H), 7.90 (dd, J=0.8, 3.5 Hz, 1H), 8.22 (s, 1H), 8.53 (s, 1H), 12.94 (br s, 1H).

APCIMS m/z: [M+H]$^+$ 387.

m.p.: 243-247° C.

Example 520

1-Ethyl-N-[4-(2-furyl)-5-(tetrahydropyran-4-ylcarbonyl)thiazol-2-yl]pyrazole-4-carboxamide (Compound 520)

In a manner similar to that in Example 499, by using 1-ethylpyrazole-4-carboxylic acid in place of 2-chloroisonicotinic acid, followed by reslurrying with diethyl ether, the entitled Compound 520 (74.9 mg, 42%) was obtained as a pale yellow solid from Compound 454 (125 mg, 0.450 mmol).

$^1$H NMR (DMSO-d$_6$, δ ppm): 1.41 (t, J=7.0 Hz, 3H), 1.50-1.80 (m, 4H), 3.10-3.25 (m, 1H), 3.30-3.45 (m, 2H), 3.83-3.92 (m, 2H), 4.21 (q, J=7.0 Hz, 2H), 6.70 (dd, J=1.6, 3.5 Hz, 1H), 7.43 (d, J=3.5 Hz, 1H), 7.90 (d, J=1.6 Hz, 1H), 8.23 (s, 1H), 8.58 (s, 1H). 12.93 (br s, 1H).

APCIMS m/z: [M+H]$^+$ 401.

m.p.: 170-174° C.

Example 521

N-[4-(2-Furyl)-5-(tetrahydropyran-4-ylcarbonyl) thiazol-2-yl]-1-phenylpyrazole-4-carboxamide (Compound 521)

In a manner similar to that in Example 499, by using 1-phenylpyrazole-4-carboxylic acid in place of 2-chloroisonicotinic acid, followed by reslurrying with ethanol, the entitled Compound 521 (131 mg, 65%) was obtained as a pale yellow solid from Compound 454 (125 mg, 0.450 mmol).

$^1$H NMR (DMSO-d$_6$, δ ppm): 1.50-1.80 (m, 4H), 3.20-3.30 (m, 1H), 3.30-3.45 (m, 2H), 3.82-3.92 (m, 2H), 6.71 (dd, J=1.6, 3.2 Hz, 1H), 7.38-7.44 (m, 2H), 7.43 (d, J=3.2 Hz, 1H), 7.55-7.62 (m, 2H), 7.85-7.93 (m, 2H), 8.50 (s, 1H), 9.30 (s, 1H), 13.08 (br s, 1H).

APCIMS m/z: [M+H]$^+$ 449.

m.p.: 217-220° C.

Example 522

N-[4-(2-Furyl)-5-(tetrahydropyran-4-ylcarbonyl) thiazol-2-yl]isoxazole-5-carboxamide (Compound 522)

In a manner similar to that in Example 456, by using isoxazole-5-carbonyl chloride in place of cyclopropanecarbonyl chloride, followed by reslurrying with a mixed solvent of ethanol and diethyl ether, the entitled Compound 522 (118 mg, 70%) was obtained as a yellow solid from Compound 454 (125 mg, 0.450 mmol).

$^1$H NMR (DMSO-d$_6$, δ ppm): 1.53-1.79 (m, 4H), 3.15-3.26 (m, 1H), 3.36 (ddd, J=2.2, 11.6, 11.6 Hz, 2H), 3.83-3.92 (m, 2H), 6.71 (dd, J=1.6, 3.5 Hz, 1H), 7.42 (d, J=3.5 Hz, 1H), 7.59 (d, J=1.9 Hz, 1H), 7.91 (d, J=1.6 Hz, 1H) 8.87 (d, J=1.9 Hz, 1H), 13.78 (br s, 1H).

APCIMS m/z: [M+H]$^+$ 372.

Example 523

N-[4-(2-Furyl)-5-(tetrahydropyran-4-ylcarbonyl) thiazol-2-yl]tetrahydrofuran-2-carboxamide (Compound 523)

In a manner similar to that in Example 465, by using tetrahydrofuran-2-carboxylic acid in place of 4-(dimethylamino)benzoic acid, followed by reslurrying with diethyl ether, the entitled Compound 523 (111 mg, 66%) was obtained from Compound 454 (125 mg, 0.450 mmol).

$^1$H NMR (DMSO-d$_6$, δ ppm): 1.50-1.75 (m, 4H), 1.80-2.20 (m, 3H), 2.20-2.30 (m, 1H), 3.10-3.25 (m, 1H), 3.33 (ddd, J=2.2, 11.3, 11.3 Hz, 2H), 3.77-4.02 (m, 4H), 4.58 (dd, J=5.4, 8.1 Hz, 1H), 6.69 (dd, J=1.9, 3.5 Hz, 1H), 7.38 (dd, J=0.8, 3.5 Hz, 1H), 7.89 (dd, J=0.8, 1.9 Hz, 1H), 12.66 (br s, 1H).

APCIMS m/z: [M+H]$^+$ 377.

m.p.: 115-117° C.

Example 524

N-[4-(2-Furyl)-5-(tetrahydropyran-4-ylcarbonyl) thiazol-2-yl]tetrahydrofuran-3-carboxamide (Compound 524)

Tetrahydrofuran-3-carboxylic acid (1.72 mL, 1.8 mmol), EDC hydrochloride (344 mg, 1.80 mmol) and 1-hydroxybenzotriazole monohydrate (276 mg, 1.80 mmol) were added to Compound 454 (125 mg, 0.450 mmol), followed by stirring at 60° C. for 3.5 hours. The reaction mixture was poured into a saturated aqueous solution of sodium hydrogencarbonate, followed by extraction with ethyl acetate. The organic layer was washed with a saturated aqueous solution of sodium chloride and dried over anhydrous magnesium sulfate, and then the solvent was distilled away under reduced pressure. The resulting residue was reslurried with diethyl ether to afford the entitled Compound 524 (142 mg, 84%).

$^1$H NMR (DMSO-d$_6$, δ ppm): 1.50-1.80 (m, 4H), 2.05-2.15 (m, 2H), 3.10-3.25 (m, 1H), 3.30-3.45 (m, 3H), 3.70-4.00 (m, 6H), 6.69 (dd, J=1.9, 3.5 Hz, 1H), 7.40 (dd, J=0.8, 3.5 Hz, 1H), 7.89 (dd, J=0.8, 1.9 Hz, 1H), 12.90 (br s, 1H).

APCIMS m/z: [M+H]$^+$ 377.

m.p.: 164-166° C.

Example 525

N-[4-(2-Furyl)-5-(tetrahydropyran-4-ylcarbonyl) thiazol-2-yl]-2-(tetrahydropyran-4-yl)acetamide (Compound 525)

In a manner similar to that in Example 465, by using tetrahydropyran-4-ylacetic acid in place of 4-(dimethylamino)benzoic acid, followed by reslurrying with diethyl ether, the entitled Compound 525 (139 mg, 76%) was obtained as a pale brown solid from Compound 454 (125 mg, 0.450 mmol).

$^1$H NMR (DMSO-d$_6$, δ ppm): 1.20-1.40 (m, 2H), 1.50-1.75 (m, 8H), 1.95-2.10 (m, 1H), 2.43 (d, J=7.0 Hz, 2H), 3.15-3.30 (m, 1H), 3.33 (ddd, J=2.2, 11.6, 11.6 Hz, 2H), 3.80-3.90 (m, 4H), 6.69 (dd, J=1.9, 3.5 Hz, 1H), 7.39 (dd, J=0.8, 3.5 Hz, 1H), 7.88 (dd, J=0.8, 1.9 Hz, 1H), 12.77 (br s, 1H).

APCIMS m/z: [M+H]$^+$ 405.

m.p.: 206-209° C.

Example 526

N-[4-(2-Furyl)-5-(tetrahydropyran-4-ylcarbonyl) thiazol-2-yl]-2-phenylacetamide (Compound 526)

In a manner similar to that in Example 511, by using phenylacetyl chloride in place of 2-furoyl chloride, followed by reslurrying with a mixed solvent of ethanol and hexane, the entitled Compound 526 (81.4 mg, 46%) was obtained as an orange solid from Compound 454 (125 mg, 0.450 mmol).

$^1$H NMR (DMSO-d$_6$, δ ppm): 1.49-1.75 (m, 4H), 3.08-3.20 (m, 1H), 3.36-3.50 (m, 2H), 3.82 (s, 2H), 3.83-3.90 (m, 2H), 6.69 (dd, J=1.9, 3.5 Hz, 1H), 7.20-7.35 (m, 5H), 7.40 (d, J=3.5 Hz, 1H), 7.89 (d, J=1.9 Hz, 1H), 13.02 (br s, 1H).

APCIMS m/z: [M+H]$^+$ 397.

m.p.: 140-142° C.

Example 527

N-[4-(2-Furyl)-5-(tetrahydropyran-4-ylcarbonyl)thiazol-2-yl]-3-phenylpropanamide (Compound 527)

In a manner similar to that in Example 502, by using 3-phenylpropionyl chloride in place of 6-chloronicotinoyl chloride, followed by reslurrying with ethanol, the entitled Compound 527 (96.4 mg, 52%) was obtained as a pale brown solid from Compound 454 (125 mg, 0.450 mmol).

$^1$H NMR (DMSO-d$_6$, δ ppm): 1.50-1.67 (m, 4H), 2.81 (t, J=6.7 Hz, 2H), 2.94 (t, J=6.7 Hz, 2H), 3.10-3.22 (m, 1H), 3.34 (ddd, J=2.4, 10.8, 10.8 Hz, 2H), 3.83-3.93 (m, 2H), 6.68 (dd, J=1.9, 3.5 Hz, 1H), 7.15-7.29 (m, 5H), 7.38 (d, J=3.5 Hz, 1H), 7.88 (d, J=1.9 Hz, 1H), 12.78 (br s, 1H).

APCIMS m/z: [M+H]$^+$ 411.

m.p.: 161-164° C.

Example 528

N-[4-(2-Furyl)-5-(tetrahydropyran-4-ylcarbonyl)thiazol-2-yl]-3-phenylacrylamide (Compound 528)

In a manner similar to that in Example 456, by using cinnamoyl chloride in place of cyclopropanecarbonyl chloride, followed by reslurrying with methanol, the entitled Compound 528 (146 mg, 79%) was obtained as a pale orange solid from Compound 454 (125 mg, 0.450 mmol).

$^1$H NMR (DMSO-d$_6$, δ ppm): 1.50-1.75 (m, 4H), 3.10-3.30 (m, 1H), 3.35-3.45 (m, 2H), 3.83-3.93 (m, 2H), 6.70 (dd, J=1.6, 3.2 Hz, 1H), 6.92 (d, J=15.6 Hz, 1H), 7.40 (d, J=3.2 Hz, 1H), 7.45-7.51 (m, 3H), 7.63-7.69 (m, 2H), 7.80 (d, J=15.6 Hz, 1H), 7.91 (d, J=1.6 Hz, 1H), 13.04 (br s, 1H).

APCIMS m/z: [M+H]$^+$ 409.

m.p.: 253-256° C.

Example 529

N-[4-(2-Furyl)-5-(tetrahydropyran-4-ylcarbonyl)thiazol-2-yl]-2-phenoxyacetamide (Compound 529)

In a manner similar to that in Example 455, by using phenoxyacetic acid in place of isonicotinic acid, followed by reslurrying with methanol, the entitled Compound 529 (140 mg, 75%) was obtained as a pale brown solid from Compound 454 (125 mg, 0.450 mmol).

$^1$H NMR (DMSO-d$_6$, δ ppm): 1.50-1.78 (m, 4H), 3.11-3.23 (m, 1H), 3.32-3.38 (m, 2H), 3.82-3.88 (m, 2H), 4.92 (s, 2H), 6.70 (dd, J=1.9, 3.5 Hz, 1H), 6.95-7.02 (m, 3H), 7.31 (dd, J=7.8, 7.8 Hz, 2H), 7.39 (d, J=3.5 Hz, 1H), 7.90 (d, J=1.9 Hz, 1H), 13.05 (br s, 1H).

APCIMS m/z: [M+H]$^+$ 413.

m.p.: 148-150° C.

Example 530

N-[4-(2-Furyl)-5-(tetrahydropyran-4-ylcarbonyl)thiazol-2-yl]-2-methoxyacetamide (Compound 530)

In a manner similar to that in Example 456, by using methoxyacetyl chloride in place of cyclopropanecarbonyl chloride, followed by reslurrying with ethanol, the entitled Compound 530 (81.2 mg, 51%) was obtained as a reddish violet solid from Compound 454 (125 mg, 0.450 mmol).

$^1$H NMR (DMSO-d$_6$, δ ppm): 1.50-1.80 (m, 4H), 3.10-3.22 (m, 1H), 3.34 (ddd, J=2.2, 11.3, 11.3 Hz, 2H), 3.36 (s, 3H), 3.87 (ddd, J=2.2, 4.3, 11.3 Hz, 2H), 4.20 (s, 2H), 6.69 (dd, J=1.6, 3.2 Hz, 1H), 7.38 (dd, J=0.8, 3.2 Hz, 1H), 7.89 (dd, J=0.8, 1.6 Hz, 1H), 12.75 (br s, 1H).

APCIMS m/z: [M+H]$^+$ 351.

m.p.: 148-149° C.

Example 531

2-Bromo-N-[4-(2-furyl)-5-(tetrahydropyran-4-ylcarbonyl)thiazol-2-yl]acetamide (Compound 531)

Compound 454 (1.39 g, 5.00 mmol), triethylamine (3.06 mL, 22.0 mmol) and DMAP (61.0 mg, 0.500 mmol) were suspended in THF (30 mL), and bromoacetyl bromide (1.64 mL, 20.0 mmol) was added dropwise thereto at 0° C., followed by stirring at room temperature for 2 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=99:1), followed by reslurrying with diethyl ether to afford the entitled Compound 531 (1.59 g, 80%) as a pale brown solid.

$^1$H NMR (CDCl$_3$, δ ppm): 1.65-2.00 (m, 4H), 3.15 (tt, J=4.3, 10.7 Hz, 1H), 3.49 (ddd, J=2.8, 11.4, 11.4 Hz, 2H), 4.00-4.08 (m, 2H), 4.05 (s, 2H), 6.58 (dd, J=1.8, 3.6 Hz, 1H), 7.58 (dd, J=0.8, 1.8 Hz, 1H), 7.74 (dd, J=0.8, 3.6 Hz, 1H).

Example 532

2-Ethoxy-N-[4-(2-furyl)-5-(tetrahydropyran-4-ylcarbonyl)thiazol-2-yl]acetamide (Compound 532)

Sodium ethoxide (62.0 mg, 0.900 mmol) was dissolved in ethanol (2 mL), and Compound 531 (120 mg, 0.300 mmol) was added thereto, followed by stirring at 60° C. for 3 hours. The reaction mixture was concentrated under reduced pressure, and the resulting residue was purified through silica gel column chromatography (chloroform:methanol=99:1) and crystallized from 2-propanol to afford the entitled Compound 532 (53.4 mg, 49%).

$^1$H NMR (DMSO-d$_6$, δ ppm): 1.16 (t, J=7.0 Hz, 3H), 1.50-1.75 (m, 4H), 3.10-3.25 (m, 1H), 3.34 (ddd, J=2.7, 11.6, 11.6 Hz, 2H), 3.56 (q, J=7.0 Hz, 2H), 3.87 (ddd, J=2.7, 4.3, 11.6 Hz, 2H), 4.23 (s, 2H), 6.69 (dd, J=1.9, 3.5 Hz, 1H), 7.38 (dd, J=0.8, 3.5 Hz, 1H), 7.89 (dd, J=0.8, 1.9 Hz, 1H), 12.70 (br s, 1H).

APCIMS m/z: [M+H]$^+$ 365.

m.p.: 121-126° C.

Example 533

2-(Dimethylamino)-N-[4-(2-furyl)-5-(tetrahydropyran-4-ylcarbonyl)thiazol-2-yl]acetamide (Compound 533)

Compound 531 (120 mg, 0.300 mmol) was dissolved in THF (2 mL), and a 2 mol/L solution of dimethylamine in THF (0.054 mL, 1.80 mmol) was added thereto, followed by stirring at room temperature for 4.5 hours. The reaction mixture was concentrated under reduced pressure, and the resulting residue was purified through silica gel column chromatography (chloroform), followed by reslurrying with a mixed solvent of 2-propanol and diethyl ether to afford the entitled Compound 533 (64.1 mg, 10%).

¹H NMR (DMSO-d₆, δ ppm): 1.50-1.75 (m, 4H), 2.32 (s, 6H), 3.10-3.22 (m, 1H), 3.30 (s, 2H), 3.30-3.45 (m, 2H), 3.83-3.92 (m, 2H), 6.68 (dd, J=1.6, 3.5 Hz, 1H), 7.38 (d, J=3.5 Hz, 1H), 7.88 (d, J=1.6 Hz, 1H).
APCIMS m/z: [M+H]⁺ 364.
m.p.: 129-130° C.

Example 534

N-[4-(2-Furyl)-5-(tetrahydropyran-4-ylcarbonyl)thiazol-2-yl]-2-[N-(2-methoxyethyl)-N-methylamino].acetamide (Compound 534)

In a manner similar to that in Example 533, by using N-(2-methoxyethyl)-N-methylamine in place of the solution of dimethylamine in THF, the entitled Compound 534 (78.1 mg, 64%) was obtained from Compound 531 (120 mg, 0.300 mmol).
¹H NMR (DMSO-d₆, δ ppm): 1.50-1.75 (m, 4H), 2.37 (s, 3H), 2.69 (t, J=5.4 Hz, 2H), 3.10-3.20 (m, 1H), 3.26 (s, 3H), 3.34 (ddd, J=2.4, 11.3, 11.3 Hz, 2H), 3.44 (s, 2H), 3.44 (q, J=5.4 Hz, 2H), 3.87 (ddd, J=2.4, 3.8, 11.3 Hz, 2H), 6.69 (dd, J=1.9, 3.5 Hz, 1H), 7.38 (d, J=3.5 Hz, 1H), 7.89 (d, J=1.9 Hz, 1H).
APCIMS m/z: [M+H]⁺ 408.
m.p.: 103-105° C.

Example 535

2-[N,N-Bis(2-methoxyethyl)amino]-N-[4-(2-furyl)-5-(tetrahydropyran-4-ylcarbonyl)thiazol-2-yl]acetamide (Compound 535)

In a manner similar to that in Example 533, by using N,N-bis(2-methoxyethyl)amine in place of the solution of dimethylamine in THF, followed by recrystallizing from 2-propanol, the entitled Compound 535 (51.0 mg, 38%) was obtained as a white solid from Compound 531 (120 mg, 0.300 mmol).
¹H NMR (CDCl₃, δ ppm): 1.70-2.00 (m, 4H), 2.88 (t, J=5.1 Hz, 4H), 3.10-3.20 (m, 1H), 3.23 (s, 6H), 3.30-3.40 (m, 2H), 3.49 (t, J=5.1 Hz, 4H), 3.58 (s, 2H), 4.03 (ddd, J=2.7, 3.8, 11.3 Hz, 2H), 6.55 (dd, J=1.6, 3.5 Hz, 1H), 7.56 (dd, J=0.8, 1.6 Hz, 1H), 7.64 (dd, J=0.8, 3.5 Hz, 1H), 11.55 (br s, 1H).
APCIMS m/z: [M+H]⁺ 452.

Example 536

N-[4-(2-Furyl)-5-(tetrahydropyran-4-ylcarbonyl)thiazol-2-yl]-2-(1-pyrrolidinyl)acetamide (Compound 536)

In a manner similar to that in Example 533, by using pyrrolidine (0.076 mL, 0.90 mmol) in place of the solution of dimethylamine in THF, followed by reslurrying with diethyl ether, the entitled Compound 536 (66.1 mg, 57%) was obtained as a white solid from Compound 531 (120 mg, 0.300 mmol).
¹H NMR (DMSO-d₆, δ ppm): 1.50-1.80 (m, 6H), 2.63-2.71 (m, 4H), 3.10-3.22 (m, 1H), 3.25-3.40 (m, 4H), 3.51 (s, 2H), 3.87 (ddd, J=2.2, 4.0, 12.1 Hz, 2H), 6.68 (dd, J=1.9, 3.5 Hz, 1H), 7.38 (dd, J=0.8, 3.5 Hz, 1H), 7.87 (dd, J=0.8, 1.9 Hz, 1H).
APCIMS m/z: [M+H]⁺ 390.
m.p.: 115-117° C.

Example 537

N-[4-(2-Furyl)-5-(tetrahydropyran-4-ylcarbonyl)thiazol-2-yl]-2-[(2R)-2-(methoxymethyl)pyrrolidin-1-yl]acetamide (Compound 537)

In a manner similar to that in Example 533, by using (R)-2-methoxymethylpyrrolidine (104 mg, 0.900 mmol) in place of the solution of dimethylamine in THF, followed by reslurrying with a mixed solvent of 2-propanol and hexane, the entitled Compound 537 (100 mg, 77%) was obtained as a white solid from Compound 531 (120 mg, 0.300 mmol).
¹H NMR (DMSO-d₆, δ ppm): 1.45-1.95 (m, 8H), 2.84-2.89 (m, 1H), 3.00-3.05 (m, 1H), 3.10-3.40 (m, 6H), 3.20 (s, 3H), 3.48 (d, J=16.7 Hz, 1H), 3.72 (d, J=16.7 Hz, 1H), 3.87 (ddd, J=2.4, 4.0, 11.6 Hz, 2H), 6.69 (dd, J=1.9, 3.5 Hz, 1H), 7.39 (dd, J=0.8, 3.5 Hz, 1H), 7.89 (dd, J=0.8, 1.9 Hz, 1H).
APCIMS m/z: [M+H]⁺ 434.
m.p.: 103-104° C.

Example 538

N-[4-(2-Furyl)-5-(tetrahydropyran-4-ylcarbonyl)thiazol-2-yl]-2-[(2S)-2-(methoxymethyl)pyrrolidin-1-yl]acetamide (Compound 538)

In a manner similar to that in Example 533, by using (S)-2-methoxymethylpyrrolidine (104 mg, 0.900 mmol) in place of the solution of dimethylamine in THF, followed by reslurrying with a mixed solvent of 2-propanol and hexane, the entitled Compound 538 (92.6 mg, 71%) was obtained as a white solid from Compound 531 (120 mg, 0.300 mmol).
¹H NMR (DMSO-d₆, δ ppm): 1.45-1.95 (m, 8H), 2.84-2.89 (m, 1H), 3.00-3.05 (m, 1H), 3.10-3.40 (m, 6H), 3.20 (s, 3H), 3.48 (d, J=16.7 Hz, 1H), 3.72 (d, J=16.7 Hz, 1H), 3.87 (ddd, J=2.4, 4.0, 11.6 Hz, 2H), 6.69 (dd, J=1.9, 3.5 Hz, 1H), 7.39 (dd, J=0.8, 3.5 Hz, 1H), 7.89 (dd, J=0.8, 1.9 Hz, 1H).
APCIMS m/z: [M+H]⁺ 434.
m.p.: 102-103° C.

Example 539

N-[4-(2-Furyl)-5-(tetrahydropyran-4-ylcarbonyl)thiazol-2-yl]-2-[3-(dimethylamino)pyrrolidin-1-yl]acetamide (Compound 539)

In a manner similar to that in Example 533, by using 3-(dimethylamino)pyrrolidine (103 mg, 0.900 mmol) in place of the solution of dimethylamine in THF, followed by recrystallizing from diethyl ether, the entitled Compound 539 (73.9 mg, 57%) was obtained as a pale brown solid from Compound 531 (120 mg, 0.300 mmol).
¹H NMR (CDCl₃, δ ppm): 1.70-2.15 (m, 6H), 2.26 (m, 6H), 2.45-2.55 (m, 1H), 2.55-2.80 (m, 2H), 2.85-3.05 (m, 2H), 3.10-3.20 (m, 1H), 3.40-3.60 (m, 4H), 4.00-4.09 (m, 2H), 6.58 (dd, J=1.6, 3.2 Hz, 1H), 7.59 (d, J=1.6 Hz, 1H), 7.78 (d, J=3.2 Hz, 1H).
APCIMS m/z: [M+H]⁺ 433.

Example 540

N-[4-(2-Furyl)-5-(tetrahydropyran-4-ylcarbonyl)thiazol-2-yl]-2-(isoindolin-2-yl)acetamide (Compound 540)

In a manner similar to that in Example 533, by using isoindoline (110 mg, 0.900 mmol) in place of the solution of di-methylamine in THF, followed by reslurrying with a mixed solvent of ethanol and diethyl ether, the entitled Compound 540 (87.2 mg, 66%) was obtained as a brown solid from Compound 531 (120 mg, 0.300 mmol).

$^1$H NMR (CDCl$_3$, δ ppm): 1.70-2.00 (m, 4H), 3.10-3.20 (m, 1H), 3.49 (ddd, J=2.7, 11.3, 11.3 Hz, 2H), 3.73 (s, 2H), 4.04 (ddd, J=2.7, 3.5, 11.3 Hz, 2H), 4.16 (s, 4H), 6.55 (dd, J=1.9, 3.8 Hz, 1H), 7.20-7.30 (m, 4H), 7.54 (dd, J=0.8, 1.9 Hz, 1H), 7.77 (dd, J=0.8, 3.8 Hz, 1H).

APCIMS m/z: [M+H]$^+$ 438.

Example 541

N-[4-(2-Furyl)-5-(tetrahydropyran-4-ylcarbonyl)thiazol-2-yl]-2-(thiazolidin-3-yl)acetamide (Compound 541)

In a manner similar to that in Example 533, by using thiazolidine (0.071 mL, 0.90 mmol) in place of the solution of dimethylamine in THF, followed by reslurrying with diethyl ether, the entitled Compound 541 (70.7 mg, 58%) was obtained as a white solid from Compound 531 (120 mg, 0.300 mmol).

$^1$H NMR (CDCl$_3$, δ ppm): 1.75-2.00 (m, 4H), 2.96-3.03 (m, 2H), 3.10-3.20 (m, 3H), 3.37 (s, 2H), 3.49 (ddd, J=3.0, 11.6, 11.6 Hz, 2H), 4.04 (ddd, J=3.0, 4.0, 11.6 Hz, 2H), 4.04 (s, 2H), 6.58 (dd, J=1.9, 3.5 Hz, 1H), 7.59 (dd, J=0.8, 1.9 Hz, 1H), 7.82 (dd, J=0.8, 3.5 Hz, 1H), 10.71 (br s, 1H).

APCIMS m/z: [M+H]$^+$ 408.

[Compound 542]

N-[4-(2-Furyl)-5-(tetrahydropyran-4-ylcarbonyl)thiazol-2-yl]-2-piperidinoacetamide (Compound 542)

In a manner similar to that in Example 533, by using piperidine (0.09 mL, 0.9 mmol) in place of the solution of dimethylamine in THF, followed by reslurrying with diethyl ether, the entitled Compound 542 (78.5 mg, 65%) was obtained as a pale yellow solid from Compound 531 (120 mg, 0.300 mmol).

$^1$H NMR (DMSO-d$_6$, δ ppm): 1.35-1.45 (m, 2H), 1.50-1.80 (m, 8H), 3.05-3.20 (m, 1H), 3.29 (s, 2H), 3.30-3.50 (m, 6H), 3.87 (ddd, J=2.4, 3.8, 11.6 Hz, 2H), 6.68 (dd, J=1.9, 3.5 Hz, 1H), 7.39 (dd, J=0.5, 3.5 Hz, 1H), 7.88 (dd, J=0.5, 1.9 Hz, 1H).

APCIMS m/z: [M+H]$^+$ 404.
m.p.: 146-147° C.

Example 543

N-[4-(2-Furyl)-5-(tetrahydropyran-4-ylcarbonyl)thiazol-2-yl]-2-(4-hydroxypiperidino)acetamide (Compound 543)

In a manner similar to that in Example 533, by using 4-hydroxypiperidine (92 mg, 0.90 mmol) in place of the solution of dimethylamine in THF, followed by recrystallizing from diethyl ether, the entitled Compound 543 (79.2 mg, 63%) was obtained as a white solid from Compound 531 (120 mg, 0.300 mmol).

$^1$H NMR (DMSO-d$_6$, δ ppm): 1.30-1.50 (m, 2H), 1.50-1.75 (m, 6H), 2.28 (ddd, J=2.4, 9.7, 12.1 Hz, 2H), 2.80-2.90 (m, 2H), 3.10-3.22 (m, 1H), 3.30-3.50 (m, 4H), 3.33 (s, 2H), 3.83-3.92 (m, 2H), 6.69 (dd, J=1.9, 3.5 Hz, 1H), 7.39 (dd, J=0.8, 3.5 Hz, 1H), 7.88 (dd, J=0.8, 1.9 Hz, 1H).

APCIMS m/z: [M+H]$^+$ 420.
m.p.: 178-180° C.

Example 544

N-[4-(2-Furyl)-5-(tetrahydropyran-4-ylcarbonyl)thiazol-2-yl]-2-(3-hydroxypiperidino)acetamide (Compound 544)

In a manner similar to that in Example 533, by using 3-hydroxypiperidine in place of the solution of dimethylamine in THF, followed by recrystallizing from diisopropyl ether, the entitled Compound 544 (78.5 mg, 65%) was obtained as a white solid from Compound 531 (120 mg, 0.300 mmol).

$^1$H NMR (CDCl$_3$, δ ppm): 1.75-2.00 (m, 8H), 2.45-2.60 (m, 2H), 2.55-2.70 (m, 1H), 2.82 (dd, J=2.4, 8.1 Hz, 1H), 3.10-3.20 (m, 1H), 3.31 (s, 2H), 3.48 (ddd, J=2.7, 11.3, 11.3 Hz, 2H), 3.80-3.95 (m, 1H), 4.03 (ddd, J=2.4, 4.0, 11.3 Hz, 2H), 6.57 (dd, J=1.6, 3.2 Hz, 1H), 7.58 (d, J=1.6 Hz, 1H), 7.74 (d, J=3.2 Hz, 1H).

APCIMS m/z: [M+H]$^+$ 420.

Example 545

N-[4-(2-Furyl)-5-(tetrahydropyran-4-ylcarbonyl)thiazol-2-yl]-2-(4-methoxypiperidino)acetamide (Compound 545)

Compound 531 (120 mg, 0.300 mmol) and 4-methoxypiperidine hydrochloride (139 mg, 0.900 mmol) were suspended in THF (4 mL), and triethylamine (0.140 mL, 0.990 mmol) was added dropwise thereto, followed by stirring at room temperature for 1.5 hours. The reaction mixture was concentrated under reduced pressure, and the resulting residue was purified through silica gel column chromatography (chloroform:methanol=49:1), followed by reslurrying with a mixed solvent of diisopropyl ether and diethyl ether to afford the entitled Compound 545 (96.0 mg, 74%) as a white solid.

$^1$H NMR (DMSO-d$_6$, δ ppm): 1.40-1.85 (m, 8H), 2.32 (ddd, J=2.7, 9.2, 11.6 Hz, 2H), 2.70-2.80 (m, 2H), 3.22 (s, 3H), 3.30-3.80 (m, 4H), 3.34 (s, 2H), 3.87 (ddd, J=2.2, 4.3, 11.3 Hz, 2H), 6.69 (dd, J=1.6, 3.5 Hz, 1H), 7.39 (dd, J=0.8, 3.5 Hz, 1H), 7.88 (dd, J=0.8, 1.6 Hz, 1H).

APCIMS m/z: [M+H]$^+$ 434.
m.p.: 109-111° C.

Example 546

N-[4-(2-Furyl)-5-(tetrahydropyran-4-ylcarbonyl)thiazol-2-yl]-2-(4-hydroxy-4-methylpiperidino)acetamide (Compound 546)

In a manner similar to that in Example 533, by using 4-hydroxy-4-methylpiperidine in place of the solution of dimethylamine in THF, followed by reslurrying with diisopropyl ether, the entitled Compound 546 (105 mg, 81%) was obtained as a white solid from Compound 531 (120 mg, 0.300 mmol).

$^1$H NMR (CDCl$_3$, δ ppm): 1.11 (s, 3H), 1.45-1.75 (m, 8H), 2.50-2.55 (m, 4H), 3.10-3.20 (m, 1H), 3.34 (ddd, J=2.7, 11.3, 11.3 Hz, 2H), 3.34 (s, 2H), 3.87 (ddd, J=2.7, 4.3, 11.3 Hz, 2H), 6.68 (dd, J=1.6, 3.5 Hz, 1H), 7.39 (dd, J=0.5, 3.5 Hz, 1H), 7.88 (dd, J=0.5, 1.6 Hz, 1H).

APCIMS m/z: [M+H]$^+$ 434.
m.p.: 151-153° C.

Example 547

N-[4-(2-Furyl)-5-(tetrahydropyran-4-ylcarbonyl)thiazol-2-yl]-2-(3-hydroxymethylpiperidino)acetamide (Compound 547)

In a manner similar to that in Example 533, by using 3-hydroxymethylpiperidine (104 mg, 0.900 mmol) in place of the solution of dimethylamine in THF, followed by recrystallizing from diisopropyl ether, the entitled Compound 547 (79.8 mg, 61%) was obtained as a pale brown solid from Compound 531 (120 mg, 0.300 mmol).

$^1$H NMR (CDCl$_3$, δ ppm): 1.60-2.00 (m, 9H), 2.08-2.18 (m, 1H), 2.18-2.38 (m, 1H), 2.71-2.91(m, 1H), 2.94 (dd, J=1.6, 10.8 Hz, 1H), 3.10-3.20 (m, 1H), 3.28 (s, 2H), 3.48 (ddd, J=3.0, 11.3, 11.3 Hz, 2H), 3.50-3.64 (m, 2H), 4.04 (ddd, J=3.0, 4.0, 11.3 Hz, 2H), 6.57 (dd, J=1.6, 3.5 Hz, 1H), 7.59 (dd, J=0.8, 1.6 Hz, 1H), 7.76 (dd, J=0.8, 3.5 Hz, 1H).

APCIMS m/z: [M+H]$^+$ 434.

Example 548

N-[4-(2-Furyl)-5-(tetrahydropyran-4-ylcarbonyl)thiazol-2-yl]-2-(4-hydroxymethylpiperidino)acetamide (Compound 548)

In a manner similar to that in Example 533, by using 4-hydroxymethylpiperidine (104 mg, 0.900 mmol) in place of the solution of dimethylamine in THF, followed by recrystallizing from diethyl ether, the entitled Compound 548 (104 mg, 80%) was obtained as a white solid from Compound 531 (120 mg, 0.300 mmol).

$^1$H NMR (CDCl$_3$, δ ppm): 1.30-1.60 (m, 3H), 1.70-2.00 (m, 8H), 2.31 (ddd, J=2.4, 11.9, 11.9 Hz, 2H), 2.86-2.96 (m, 2H), 3.10-3.20 (m, 1H), 3.28 (s, 2H), 3.48 (ddd, J=3.0, 11.6, 11.6 Hz, 2H), 3.55 (d, J=3.5 Hz, 2H), 4.04 (ddd, J=3.0, 4.0, 11.6 Hz, 2H), 6.58 (dd, J=1.6, 3.5 Hz, 1H), 7.59 (dd, J=0.8, 1.6 Hz, 1H), 7.77 (dd, J=0.8, 3.5 Hz, 1H).

APCIMS m/z: [M+H]$^+$ 434.

Example 549

N-[4-(2-Furyl)-5-(tetrahydropyran-4-ylcarbonyl)thiazol-2-yl]-2-[4-(2-hydroxypropan-2-yl)piperidino]acetamide (Compound 549)

In a manner similar to that in Example 533, by using 4-(2-hydroxypropan-2-yl)piperidine (130 mg, 0.900 mmol) in place of the solution of dimethylamine in THF, followed by reslurrying with a mixed solvent of ethanol and diethyl ether, the entitled Compound 549 (121 mg, 87%) was obtained as a white solid from Compound 531 (120 mg, 0.300 mmol).

$^1$H NMR (CDCl$_3$, δ ppm): 1.22 (s, 6H), 1.40-1.60 (m, 4H), 1.70-2.00 (m, 6H), 2.26 (ddd, J=2.2, 11.3, 11.3 Hz, 2H) 2.93-3.00 (m, 2H), 3.05-3.15 (m, 1H), 3.27 (s, 2H), 3.49 (ddd, J=2.7, 11.3, 11.3 Hz, 2H), 4.03 (ddd, J=2.7, 3.8, 11.3 Hz, 2H), 6.57 (dd, J=1.6, 3.5 Hz, 1H), 7.59 (dd, J=0.8, 1.6 Hz, 1H), 7.79 (dd, J=0.8, 3.5 Hz, 1H).

APCIMS m/z: [M+H]$^+$ 462.

Example 550

N-[4-(2-Furyl)-5-(tetrahydropyran-4-ylcarbonyl)thiazol-2-yl]-2-[4-(2-hydroxy-2-methylpropyl)piperidino]acetamide (Compound 550)

In a manner similar to that in Example 533, by using 4-(2-hydroxy-2-methylpropyl)piperidine (142 mg, 0.900 mmol) in place of the solution of dimethylamine in THF, followed by recrystallizing from diethyl ether, the entitled Compound 550 (108 mg, 76%) was obtained as a grayish white solid from Compound 531 (120 mg, 0.300 mmol).

$^1$H NMR (CDCl$_3$, δ ppm): 1.26 (s, 6H), 1.40-1.70 (m, 3H), 1.70-2.00 (m, 8H), 2.27-2.34 (m, 2H), 2.80-2.90 (m, 2H), 3.10-3.20 (m, 1H), 3.25 (s, 2H), 3.42-3.54 (m, 3H), 3.99-4.09 (m, 2H), 6.57 (dd, J=1.6, 3.5 Hz, 1H), 7.59 (d, J=1.6 Hz, 1H), 7.78 (d, J=3.5 Hz, 1H).

APCIMS m/z: [M+H]$^+$ 476.

Example 551

N-[4-(2-Furyl)-5-(tetrahydropyran-4-ylcarbonyl)thiazol-2-yl]-2-[4-(1-pyrrolidinyl)piperidino]acetamide (Compound 551)

In a manner similar to that in Example 533, by using 4-(1-pyrrolidinyl)piperidine (140 mg, 0.900 mmol) in place of the solution of dimethylamine in THF, followed by reslurrying with diethyl ether, the entitled Compound 551 (55.1 mg, 39%) was obtained as a pale orange solid from Compound 531 (120 mg, 0.300 mmol).

$^1$H NMR (DMSO-d$_6$, δ ppm): 1.30-1.75 (m, 12H), 1.95-2.05 (m, 1H), 2.10-2.20 (m, 2H), 2.70-2.85 (m, 2H), 3.10-3.20 (m, 1H), 3.25-3.40 (m, 8H), 3.83-3.93 (m, 2H), 6.68 (dd, J=1.6, 3.2 Hz, 1H), 7.39 (d, J=3.2 Hz, 1H), 7.88 (d, J=1.6 Hz, 1H).

ESIMS m/z: [M+H]$^+$ 473.

m.p.: 183-184° C.

Example 552

N-[4-(2-Furyl)-5-(tetrahydropyran-4-ylcarbonyl)thiazol-2-yl]-2-(4-piperidinopiperidino)acetamide (Compound 552)

In a manner similar to that in Example 533, by using 4-piperidinopiperidine (152 mg, 0.900 mmol) in place of the solution of dimethylamine in THF, followed by reslurrying with a mixed solvent of ethanol and diethyl ether, the entitled Compound 552 (82.7 mg, 57%) was obtained as a pale brown solid from Compound 531 (120 mg, 0.300 mmol).

$^1$H NMR (DMSO-d$_6$, δ ppm): 1.30-1.75 (m, 12H), 2.13-2.20 (m, 2H), 2.50-2.60 (m, 3H), 2.80-2.95 (m, 2H), 3.15-3.25 (m, 1H), 3.25-3.40 (m, 6H), 3.33 (s, 2H), 3.83-3.93 (m, 2H), 6.69 (dd, J=1.6, 3.5 Hz, 1H), 7.39 (dd, J=0.8, 3.5 Hz, 1H), 7.88 (dd, J=0.8, 1.6 Hz, 1H).

APCIMS m/z: [M+H]$^+$ 487.

m.p.: 177-179° C.

Example 553

N-[4-(2-Furyl)-5-(tetrahydropyran-4-ylcarbonyl)thiazol-2-yl]-2-(4-morpholinopiperidino)acetamide (Compound 553)

In a manner similar to that in Example 533, by using 4-morpholinopiperidine (153 mg, 0.900 mmol) in place of the solution of dimethylamine in THF, followed by reslurrying with diethyl ether, the entitled Compound 553 (109 mg, 75%) was obtained as a pale yellowish green solid from Compound 531 (120 mg, 0.300 mmol).

$^1$H NMR (DMSO-d$_6$, δ ppm): 1.30-1.55 (m, 2H), 1.55-1.80 (m, 6H), 2.05-2.30 (m, 3H), 2.44 (t, J=4.3 Hz, 4H), 2.90 (d, J=11.6 Hz, 2H), 3.10-3.25 (m, 1H), 3.34 (ddd, J=2.2, 11.3, 11.3 Hz, 2H), 3.34 (s, 2H), 3.56 (t, J=4.3 Hz, 4H), 3.87 (ddd, J=2.2, 3.8, 11.3 Hz, 2H), 6.69 (dd, J=11.9, 3.5 Hz, 1H), 7.39 (dd, J=0.5, 3.5 Hz, 1H), 7.88 (dd, J=0.5, 1.9 Hz, 1H).
APCIMS m/z: [M+H]$^+$ 489.
m.p.: 193-195° C.

Example 554

2-(1,4-Dioxa-8-azaspiro[4.5]decan-8-yl)-N-[4-(2-furyl)-5-(tetrahydropyran-4-ylcarbonyl)thiazol-2-yl]acetamide (Compound 554)

In a manner similar to that in Example 533, by using 1,4-dioxa-8-azaspiro[4.5]decane (0.240 mL, 1.80 mmol) in place of the solution of dimethylamine in THF, followed by reslurrying with diethyl ether, the entitled Compound 554 (122 mg; 88%) was obtained as a white solid from Compound 531 (120 mg, 0.300 mmol).
$^1$H NMR (DMSO-d$_6$, δ ppm): 1.52-1.75 (m, 8H), 2.55-2.70 (m, 4H), 3.15-3.25 (m, 1H), 3.25-3.35 (m, 2H), 3.37 (s, 2H), 3.86 (s, 4H), 3.86-3.93 (m, 2H), 6.69 (dd, J=1.9, 3.5 Hz, 1H), 7.39 (d, J=3.5 Hz, 1H), 7.89 (d, J=1.9 Hz, 1H).
APCIMS m/z: [M+H]$^+$ 462.
m.p.: 186-187° C.

Example 555

2-(4-Cyanopiperidino)-N-[4-(2-furyl)-5-(tetrahydropyran-4-ylcarbonyl)thiazol-2-yl]acetamide (Compound 555)

In a manner similar to that in Example 533, by using 4-cyanopiperidine (99.0 mg, 0.900 mmol) in place of the solution of dimethylamine in THF, followed by reslurrying with diethyl ether, the entitled Compound 555 (88.9 mg, 69%) was obtained as a pale brown solid from Compound 531 (120 mg, 0.300 mmol).
$^1$H NMR (DMSO-d$_6$, δ ppm): 1.50-1.80 (m, 6H), 2.65-2.75 (m, 2H), 2.85-3.00 (m, 1H), 3.10-3.20 (m, 1H), 3.30-3.50 (m, 6H), 3.40 (s, 2H), 3.83-3.93 (m, 2H), 6.69 (dd, J=1.9, 3.5 Hz, 1H), 7.40 (d, J=3.5 Hz, 1H), 7.89 (d, J=1.9 Hz, 1H), 12.59 (br s, 1H).
APCIMS m/z: [M+H]$^+$ 429.

Example 556

2-(4,4-Difluoropiperidino)-N-[4-(2-furyl)-5-(tetrahydropyran-4-ylcarbonyl)thiazol-2-yl]acetamide (Compound 556)

In a manner similar to that in Example 545, by using 4,4-difluoropiperidine hydrochloride (142 mg, 0.900 mmol) in place of 4-methoxypiperldine hydrochloride, followed by reslurrying with diethyl ether, the entitled Compound 556 (104 mg, 79%) was obtained as a white solid from Compound 531 (120 mg, 0.300 mmol).
$^1$H NMR (CDCl$_3$, δ ppm): 1.70-2.00 (m, 4H), 2.00-2.20 (m, 4H), 2.70-2.80 (m, 4H), 3.05-3.20 (m, 1H), 3.37 (s, 2H), 3.47 (ddd, J=2.7, 11.3, 11.3 Hz, 2H), 4.04 (ddd, J=2.7, 4.0, 11.3 Hz, 2H), 6.58 (dd, J=1.9, 3.8 Hz, 1H), 7.59 (d, J=1.9 Hz, 1H), 7.77 (d, J=3.8 Hz, 1H), 10.43 (br s, 1H).
APCIMS m/z: [M+H]$^+$ 440.

Example 557

N-[4-(2-Furyl)-5-(tetrahydropyran-4-ylcarbonyl)thiazol-2-yl]-2-(1,2,3,6-tetrahydropyridin-1-yl)acetamide (Compound 557)

In a manner similar to that in Example 533, by using 1,2,3,6-tetrahydropyridine (0.825 mL, 0.900 mmol) in place of the solution of dimethylamine in THF, followed by reslurrying with a mixed solvent of ethanol and diethyl ether, the entitled Compound 557 (63.0 mg, 52%) was obtained from Compound 531 (120 mg, 0.300 mmol).
$^1$H NMR (CDCl$_3$, δ ppm): 1.70-1.95 (m, 4H), 2.20-2.35 (m, 2H), 2.73-2.77 (m, 1H), 3.05-3.20 (m, 3H), 3.37 (s, 2H), 3.49 (ddd, J=2.7, 11.6, 11.6 Hz, 2H), 4.04 (ddd, J=2.7, 4.0, 11.6 Hz, 2H), 5.60-5.70 (m, 1H), 5.75-5.85 (m, 1H), 6.57 (dd, J=1.9, 3.5 Hz, 1H), 7.59 (d, J=1.9 Hz, 1H), 7.79 (d, J=3.5 Hz, 1H).
APCIMS m/z: [M+H]$^+$ 402.

Example 558

N-[4-(2-Furyl)-5-(tetrahydropyran-4-ylcarbonyl)thiazol-2-yl]-2-morpholinoacetamide (Compound 558)

Compound 454 (13.9 g, 50.0 mmol) and triethylamine (15.3 mL, 110 mmol) were suspended in THF (200 mL), and a solution (50 mL) of bromoacetyl bromide (8.80 mL, 100 mmol) in THF was added dropwise thereto at 0° C., followed by stirring at room temperature for 1 hour. At 0° C., a solution (100 mL) of bromoacetyl bromide (17.6 mL, 200 mmol) in THF was added to the reaction mixture, followed by stirring at room temperature for 2 hours. At 0° C., a solution (100 mL) of morpholine (61.2 mL, 700 mmol) and triethylamine (97.6 mL, 700 mmol) in THF was added dropwise to the reaction mixture, followed by stirring at room temperature for 30 minutes. The reaction mixture was poured into a mixture of water (500 mL) and ethyl acetate (500 mL), followed by filtration, and the resulting filtrate was subjected to liquid-liquid separation. The organic layer was washed successively with a saturated aqueous solution of sodium hydrogencarbonate and a saturated aqueous solution of sodium chloride and dried over anhydrous magnesium sulfate, and then the solvent was distilled away under reduced pressure. The resulting residue was purified through silica gel column chromatography (chloroform:methanol=97:3), followed by recrystallizing from ethanol to afford the entitled Compound 558 (8.17 g, 40%) as a pale brown solid.
$^1$H NMR (DMSO-d$_6$, δ ppm): 1.50-1.80 (m, 4H), 3.15-3.25 (m, 1H), 3.33-3.38 (m, 6H), 3.39 (s, 2H), 3.60 (t, J=4.6 Hz, 4H), 3.87 (ddd, J=2.4, 4.0, 11.6 Hz, 2H), 6.71 (dd, J=1.6, 3.5 Hz, 1H), 7.39 (dd, J=0.8, 3.5 Hz, 1H), 7.89 (dd, J=0.8, 1.6 Hz, 1H), 12.63 (br s, 1H).
APCIMS m/z: [M+H]$^+$ 406.
m.p.: 110-104° C.

Example 559

2-(cis-2,6-Dimethylmorpholino)-N-[4-(2-furyl)-5-(tetrahydropyran-4-ylcarbonyl)thiazol-2-yl]acetamide (Compound 559)

In a manner similar to that in Example 533, by using cis-2,6-dimethylmorpholine (0.110 mL, 0.900 mmol) in place of the solution of dimethylamine in THF, followed by recrystallizing from a mixed solvent of ethanol and diethyl ether, the entitled Compound 559 (76.7 mg, 59%) was obtained as a grayish white solid from Compound 531 (120 mg, 0.300 mmol).
$^1$H NMR (CDCl$_3$, δ ppm): 1.18 (d, J=6.2 Hz, 6H), 1.70-2.00 (m, 4H), 2.00-2.10 (m, 2H), 2.65-2.80 (m, 4H), 3.05-3.20 (m, 1H), 3.28 (s, 2H), 3.49 (ddd, J=3.0, 11.3, 11.3 Hz, 2H), 4.04 (ddd, J=3.0, 4.0, 11.3 Hz, 2H), 6.58 (dd, J=1.9, 3.8 Hz, 1H), 7.60 (dd, J=0.8, 1.9 Hz, 1H), 7.78 (dd, J=0.8, 3.8 Hz, 1H), 10.45 (br s, 1H).
APCIMS m/z: [M+H]$^+$ 434.

Example 560

2-[4-(tert-Butoxycarbonyl)piperazin-1-yl]-N-[4-(2-furyl)-5-(tetrahydropyran-4-ylcarbonyl)thiazol-2-yl]acetamide (Compound 560)

In a manner similar to that in Example 533, by using 1-(tert-butoxycarbonyl)piperazine (504 mg, 2.70 mmol) in place of the solution of dimethylamine in THF, the entitled Compound 560 (428 mg, 94%) was obtained from Compound 531 (360 mg, 504 mmol).
$^1$H NMR (CDCl$_3$, δ ppm): 1.44 (s, 9H), 1.70-2.00 (m, 4H), 2.57 (t, J=4.9 Hz, 4H), 3.05-3.20 (m, 1H), 3.32 (s, 2H), 3.49 (ddd, J=2.7, 11.6, 11.6 Hz, 2H), 3.53 (t, J=4.9 Hz, 4H), 4.04 (ddd, J=2.7, 4.0, 11.6 Hz, 2H), 6.58 (dd, J=1.9, 3.8 Hz, 1H), 7.59 (dd, J=0.8, 1.9 Hz, 1H), 7.78 (dd, J=0.8, 3.8 Hz, 1H), 10.46 (br s, 1H).
APCIMS m/z: [M+H]$^+$ 505.

Example 561

N-[4-(2-Furyl)-5-(tetrahydropyran-4-ylcarbonyl)thiazol-2-yl]-2-(1-piperazinyl)acetamide (Compound 561)

Compound 560 (428 mg, 0.849 mmol) was dissolved in dichloromethane (3 mL), and trifluoroacetic acid (3 mL) was added thereto at 0° C., followed by stirring at room temperature for 3 hours. The reaction mixture was concentrated under reduced pressure, and a saturated aqueous solution of sodium hydrogencarbonate was added to the resulting residue, followed by extraction with chloroform. The organic layer was dried over anhydrous magnesium sulfate, and then the solvent was distilled away under reduced pressure. The resulting residue was reslurried with diethyl ether to afford the entitled Compound 561 (263 mg, 77%).
$^1$H NMR (CDCl$_3$, δ ppm): 1.50-1.80 (m, 4H), 2.74-2.80 (m, 4H), 3.10-3.20 (m, 1H), 3.34 (s, 2H), 3.35-3.45 (m, 8H), 3.87 (ddd, J=2.2, 4.3, 11.1 Hz, 2H), 6.67 (dd, J=1.9, 3.5 Hz, 1H), 7.38 (dd, J=0.5, 3.5 Hz, 1H), 7.87 (dd, J=0.5, 1.9 Hz, 1H).
APCIMS m/z: [M+H]$^+$ 405.

Example 562

N-[4-(2-Furyl)-5-(tetrahydropyran-4-ylcarbonyl)thiazol-2-yl]-2-(4-methylpiperazin-1-yl)acetamide (Compound 562)

In a manner similar to that in Example 533, by using 1-methylpiperazine (0.100 mL, 9.00 mmol) in place of the solution of dimethylamine in THF, followed by recrystallizing from diethyl ether, the entitled Compound 562 (43.4 mg, 35%) was obtained as a pale orange solid from Compound 531 (120 mg, 0.300 mmol).
$^1$H NMR (DMSO-d$_6$, δ ppm): 1.40-1.75 (m, 4H), 2.30-2.45 (m, 4H), 3.10-3.22 (m, 1H), 3.33 (s, 3H), 3.34-3.50 (m, 8H), 3.87 (ddd, J=2.2, 12.1, 12.1 Hz, 2H), 6.69 (dd, J=1.9, 3.5 Hz, 1H), 7.39 (dd, J=0.8, 3.5 Hz, 1H), 7.89 (dd, J=0.8, 1.9 Hz, 1H).
APCIMS m/z: [M+H]$^+$ 419.
m.p.: 106-112° C.

Example 563

N-[4-(2-Furyl)-5-(tetrahydropyran-4-ylcarbonyl)thiazol-2-yl]-2-(4-isopropylpiperazin-1-yl)acetamide (Compound 563)

In a manner similar to that in Example 533, by using 1-isopropylpiperazine (115 mg, 9.00 mmol) in place of the solution of dimethylamine in THF, followed by reslurrying with a mixed solvent of ethanol and diethyl ether, the entitled Compound 563 (85.5 mg, 64%) was obtained as a gray solid from Compound 531 (120 mg, 0.300 mmol).
$^1$H NMR (DMSO-d$_6$, δ ppm): 1.08 (d, J=6.5 Hz, 6H), 1.70-2.00 (m, 4H), 2.65-2.80 (m, 9H), 3.05-3.20 (m, 1H), 3.30 (s, 2H), 3.49 (ddd, J=2.7, 11.3, 11.3 Hz, 2H), 3.95-4.05 (m, 2H), 6.58 (dd, J=1.6, 3.2 Hz, 1H), 7.59 (d, J=1.6 Hz, 1H), 7.79 (d, J=3.2 Hz, 1H).
APCIMS m/z: [M+H]$^+$ 447.

Example 564

2-[4-(Ethoxycarbonyl)piperazin-1-yl]-N-[4-(2-furyl)-5-(tetrahydropyran-4-ylcarbonyl)thiazol-2-yl]acetamide (Compound 564)

In a manner similar to that in Example 533, by using 1-ethoxycarbonylpiperazine (0.266 mL, 18.0 mmol) in place of the solution of dimethylamine in THF, followed by recrystallizing from ethanol, the entitled Compound 564 (58.7 mg, 41%) was obtained as a white solid from Compound 531 (120 mg, 0.300 mmol).
$^1$H NMR (DMSO-d$_6$, δ ppm): 1.28 (t, J=7.0 Hz, 3H), 1.75-2.00 (m, 4H), 2.59 (dd, J=7.5, 7.8 Hz, 4H), 3.05-3.20 (m, 1H), 3.33 (s, 2H), 3.48 (ddd, J=3.0, 11.6, 11.6. Hz, 2H), 3.59 (dd, J=7.5, 7.8 Hz, 4H), 4.04 (ddd, J=3.0, 4.0, 11.6 Hz, 2H), 4.16 (q, J=7.0 Hz, 2H), 6.58 (dd, J=1.9, 3.8 Hz, 1H), 7.59 (dd, J=0.5, 1.9 Hz, 1H), 7.78 (dd, J=0.5, 3.8 Hz, 1H), 10.44 (br s, 1H).
APCIMS m/z: [M+H]$^+$ 477.

Example 565

N-[4-(2-Furyl)-5-(tetrahydropyran-4-ylcarbonyl)thiazol-2-yl]-2-[4-(2-hydroxy-2-methylpropyl)piperazin-1-yl]acetamide (Compound 565)

In a manner similar to that in Example 533, by using 2-hydroxy-2-methylpropylpiperazine (143 mg, 9.00 mmol) in place of the solution of dimethylamine in THF, followed by reslurrying with a mixed solvent of diisopropyl ether and hexane, the entitled Compound 565 (112 mg, 78%) was obtained as a pale orange solid from Compound 531 (120 mg, 0.300 mmol).
$^1$H NMR (DMSO-d$_6$, δ ppm): 1.07 (s, 6H), 1.50-1.80 (m, 4H), 2.48-2.58 (m, 4H), 3.10-3.40 (m, 10H), 3.38 (s, 2H), 3.83-3.92 (m, 2H), 6.69 (dd, J=1.9, 3.5 Hz, 1H), 7.39 (d, J=3.5 Hz, 1H), 7.88 (d, J=1.9 Hz, 1H).
APCIMS m/z: [M+H]$^+$ 477.
m.p.: 106-108° C.

Example 566

N-[4-(2-Furyl)-5-(tetrahydropyran-4-ylcarbonyl) thiazol-2-yl]-2-[4-(2-hydroxy-2-methylpropyl)piperazin-1-yl]acetamide (Compound 566)

In a manner similar to that in Example 533, by using 2-methoxy-2-methylpropylpiperazine (155 mg, 9.00 mmol) in place of the solution of dimethylamine in THF, followed by reslurrying with a mixed solvent of diisopropyl ether and hexane, the entitled Compound 566 (66.5 mg, 45%) was obtained as a pale orange solid from Compound 531 (120 mg, 0.300 mmol).

$^1$H NMR (DMSO-d$_6$, δ ppm): 1.08 (s, 6H), 1.50-1.80 (m, 4H), 2.51-2.53 (m, 4H), 3.07 (s, 3H), 3.10-3.22 (m, 3H), 3.30-3.45 (m, 6H), 3.32 (s, 2H), 3.83-3.92 (m, 2H), 6.69 (dd, J=1.9, 3.5 Hz, 1H), 7.39 (d, J=3.5 Hz, 1H), 7.88 (d, J=1.9 Hz, 1H).

APCIMS m/z: [M+H]$^+$ 491.

m.p.: 105-107° C.

Example 567

N-[4-(2-Furyl)-5-(tetrahydropyran-4-ylcarbonyl) thiazol-2-yl]-2-{4-[(1-methoxycyclopropyl)methyl]piperazin-1-yl}acetamide (Compound 567)

In a manner similar to that in Example 533, by using 1-[(1-methoxycyclopropyl)methyl]piperazine (154 mg, 9.00 mmol) in place of the solution of dimethylamine in THF, followed by reslurrying with a mixed solvent of ethanol and diethyl ether, the entitled Compound 567 (56.0 mg, 38%) was obtained as a pale brown solid from Compound 531 (120 mg, 0.300 mmol).

$^1$H NMR (DMSO-d$_6$, δ ppm): 0.40-0.44 (m, 2H), 0.65-0.69 (m, 2H), 1.50-1.80 (m, 4H), 2.46 (s, 2H), 2.49-2.55 (m, 4H), 3.10-3.20 (m, 1H), 3.20 (s, 3H), 3.30-3.80 (m, 6H), 3.33 (s, 2H), 3.83-3.92 (m, 2H), 6.69 (dd, J=1.9, 3.5 Hz, 1H), 7.39 (d, J=3.5 Hz, 1H), 7.88 (d, J=1.9 Hz, 1H).

APCIMS m/z: [M+H]$^+$ 489.

m.p.: 155-157° C.

Example 568

N-[4-(2-Furyl)-5-(tetrahydropyran-4-ylcarbonyl) thiazol-2-yl]-2-[(7R,8aS)-7-methoxyoctahydropyrrolo[1,2-a]pyrazin-2-yl]acetamide (Compound 568)

In a manner similar to that in Example 533, by using (7R,8aS)-7-methoxyoctahydropyrrolo[1,2-a]pyrazine (141 mg, 9.00 mmol) in place of the solution of dimethylamine in THF, followed by recrystallizing from diethyl ether, the entitled Compound 568 (63.2 mg, 44%) was obtained as a white solid from Compound 531 (120 mg, 0.300 mmol).

$^1$H NMR (DMSO-d$_6$, δ ppm): 1.40-1.80 (m, 7H), 1.95-2.05 (m, 2H), 2.20-2.35 (m, 2H), 2.70-2.97 (m, 4H), 3.15-3.20 (m, 1H), 3.16 (s, 3H), 3.25-3.40 (m, 1H), 3.38 (s, 2H), 3.83-3.93 (m, 4H), 6.69 (dd, J=1.9, 3.5 Hz, 1H), 7.39 (d, J=3.5 Hz, 1H), 7.88 (d, J=1.9 Hz, 1H).

APCIMS m/z: [M+H]$^+$ 475.

Example 569

N-[4-(2-Furyl)-5-(tetrahydropyran-4-ylcarbonyl) thiazol-2-yl]-2-[(7S,8aS)-7-hydroxyoctahydropyrrolo[1,2-a]pyrazin-2-yl]acetamide (Compound 569)

Compound 531 (120 mg, 0.300 mmol) was dissolved in THF (2 mL), and (7S,8aS)-7-(tetrahydropyran-2-yl)oxyoctahydropyrrolo[1,2-a]pyrazine (204 mg, 0.900 mmol) was added thereto, followed by stirring at room temperature for 2.5 hours. The reaction mixture was concentrated under reduced pressure, and the resulting residue was dissolved in ethanol (3 mL), and 2 mol/L hydrochloric acid (3 mL) was added thereto, followed by stirring overnight at room temperature. The reaction mixture was concentrated under reduced pressure, and the resulting residue was poured into water. A 2 mol/L sodium hydroxide solution added thereto to adjust the pH to 8, followed by extraction with chloroform. The organic layer was washed with a solution of sodium chloride and dried over anhydrous magnesium sulfate, and then the solvent was distilled away under reduced pressure. The resulting residue was purified through silica gel column chromatography (chloroform:methanol=23:2), followed by recrystallizing from a mixed solvent of ethanol and diethyl ether to afford the entitled Compound 569 (46.5 mg, 34%).

$^1$H NMR (DMSO-d$_6$, δ ppm): 1.50-1.80 (m, 6H), 1.90-2.00 (m, 2H), 2.10-2.20 (m, 3H), 2.35-2.45 (m, 2H), 2.45-2.50 (m, 1H), 3.10-3.20 (m, 1H), 3.30-3.50 (m, 3H), 3.34 (s, 2H), 3.83-3.92 (m, 2H), 4.14-4.20 (m, 1H), 6.69 (dd, J=1.9, 3.5 Hz, 1H), 7.39 (d, J=3.5 Hz, 1H), 7.89 (d, J=1.9 Hz, 1H).

APCIMS m/z: [M+H]$^+$ 461.

Example 5701

N-[4-(2-Furyl)-5-(tetrahydropyran-4-ylcarbonyl) thiazol-2-yl]-2-[octahydropyrazino[2,1-c][1,4]thiazin-8-yl]acetamide (Compound 570)

In a manner similar to that in Example 533, by using octahydropyrazino[2,1-c][1,4]thiazine (143 mg, 9.00 mmol) in place of the solution of dimethylamine in THF, followed by recrystallizing from diethyl ether, the entitled Compound 570 (113 mg, 79%) was obtained from Compound 531 (120 mg, 0.300 mmol).

$^1$H NMR (DMSO-d$_6$, δ ppm): 1.50-1.80 (m, 4H), 1.95-2.00 (m, 1H), 2.05-2.40 (m, 6H), 2.55-2.80 (m, 4H), 2.95-3.05 (m, 1H), 3.10-3.20 (m, 1H), 3.30-3.50 (m, 5H), 3.83-3.93 (m, 2H), 6.69 (dd, J=1.6, 3.2 Hz, 1H), 7.39 (d, J=3.2 Hz, 1H), 7.88 (d, J=1.6 Hz, 1H), 12.60 (br s, 1H).

APCIMS m/z: [M+H]$^+$ 477.

Example 571

N-[4-(2-Furyl)-5-(tetrahydropyran-4-ylcarbonyl) thiazol-2-yl]-2-[4-(tetrahydropyran-4-yl)piperazin-1-yl]acetamide (Compound 571)

In a manner similar to that in Example 533, by using 1-(tetrahydropyran-4-yl)piperazine (154 mg, 9.00 mmol) in place of the solution of dimethylamine in THF, followed by reslurrying with a mixed solvent of ethanol and diethyl ether, the entitled Compound 571 (79.8 mg, 54%) was obtained from Compound 531 (120 mg, 0.300 mmol).

$^1$H NMR (CDCl$_3$, δ ppm): 1.75-2.00 (m, 6H), 2.75-2.85 (m, 45H), 3.05-3.20 (m, 1H), 3.31 (s, 2H), 3.36-3.54 (m, 6H), 4.00-4.10 (m, 8H), 6.58 (dd, J=1.9, 3.5 Hz, 1H), 7.60 (dd, J=0.8, 1.9 Hz, 1H), 7.79 (dd, J=0.8, 3.5 Hz, 1H).

APCIMS m/z: [M+H]$^+$ 489.

Example 572

N-[4-(2-Furyl)-5-(tetrahydropyran-4-ylcarbonyl)
thiazol-2-yl]-2-(4-oxooctahydropyrazino[2,1-c][1,4]
oxazin-8-yl)acetamide (Compound 572)

In a manner similar to that in Example 533, by using 4-oxooctahydropyrazino[2,1-c][1,4]oxazine (141 mg, 9.00 mmol) in place of the solution of dimethylamine in THF, followed by recrystallizing from ethanol, the entitled Compound 572 (127 mg, 89%) was obtained as a pale pink solid from Compound 531 (120 mg, 0.300 mmol).

$^1$H NMR (CDCl$_3$, δ ppm): 1.75-2.00 (m, 4H), 2.29 (dd, J=11.0, 11.0 Hz, 1H), 2.41 (ddd, J=3.6, 11.0, 11.0 Hz, 1H), 2.75-2.88 (m, 1H), 2.88-3.00 (m, 2H), 3.05-3.20 (m, 1H), 3.37 (s, 2H), 3.49 (ddd, J=2.7, 11.0, 11.0 Hz, 2H), 3.55 (dd, J=7.0, 11.0 Hz, 1H), 3.65-3.80 (m, 1H), 3.96-4.08 (m, 3H), 4.18 (d, J=7.0 Hz, 2H), 4.66 (dd, J=2.7, 11.9 Hz, 1H), 6.59 (dd, J=1.9, 3.8 Hz, 1H), 7.60 (d, J=1.9 Hz, 1H), 7.78 (d, J=3.8 Hz, 1H), 10.35 (br s, 1H).

APCIMS m/z: [M+H]$^+$ 475.

Example 573

N-[4-(2-Furyl)-5-(tetrahydropyran-4-ylcarbonyl)
thiazol-2-yl]-2-(octahydropyrazino[2,1-c][1,4]ox-
azin-8-yl)acetamide (Compound 573)

In a manner similar to that in Example 533, by using octahydropyrazino[2,1-c][1,4]oxazine (128 mg, 9.00 mmol) in place of the solution of dimethylamine in THF, followed by recrystallizing from ethanol, the entitled Compound 573 (75.8 mg, 55%) was obtained from Compound 531 (120.mg, 0.300 mmol).

$^1$H NMR (CDCl$_3$, δ ppm): 1.70-2.00 (m, 4H), 2.11 (dd, J=13.2, 13.2 Hz, 1H), 2.35-2.85 (m, 8H), 3.05-3.20 (m, 1H), 3.23 (dd, J=13.2, 13.2 Hz, 1H), 3.30 (s, 2H), 3.48 (ddd, J=2.7, 11.3, 11.3 Hz, 2H), 3.60-3.72 (m, 2H), 3.88 (dd, J=3.5, 11.1 Hz, 1H), 4.04 (ddd, J=2.7, 4.0, 11.3 Hz, 2H), 6.58 (dd, J=1.6, 3.5 Hz, 1H), 7.60 (dd, J=0.8, 1.6 Hz, 1H), 7.78 (dd, J=0.8, 3.5 Hz, 1H), 10.46 (br s, 1H).

APCIMS m/z: [M+H]$^+$ 461.

Example 574

N-[4-(2-Furyl)-5-(tetrahydropyran-4-ylcarbonyl)
thiazol-2-yl]-2-(1-methyl-2-oxopiperazin-4-yl)aceta-
mide (Compound 574)

In a manner similar to that in Example 533, by using 1-methyl-2-oxopiperazine (103 mg, 0.900 mmol) in place of the solution of dimethylamine in THF, followed by recrystallizing from a mixed solvent of ethanol and diethyl ether, the entitled Compound 574 (86.1 mg, 66%) was obtained as a brown solid from Compound 531 (120 mg, 0.300 mmol).

$^1$H NMR (CDCl$_3$, δ ppm): 1.75-2.00 (m, 4H), 2.92 (dd, J=5.1, 5.6 Hz, 2H), 3.02 (s, 3H), 3.10-3.20 (m, 1H), 3.32 (s, 2H), 3.41 (s, 2H), 3.45 (dd, J=5.1, 5.6 Hz, 2H), 3.48 (ddd, J=2.7, 11.3, 11.3 Hz, 2H), 4.04 (ddd, J=2.7, 4.0, 11.3 Hz, 2H), 6.57 (dd, J=1.9, 3.8 Hz, 1H), 7.59 (dd, J=0.8, 1.9 Hz, 1H), 7.79 (dd, J=0.8, 3.8 Hz, 1H), 10.40 (br s, 1H).

APCIMS m/z: [M+H]$^+$ 433.

Example 575

N-[4-(2-Furyl)-5-(tetrahydropyran-4-ylcarbonyl)
thiazol-2-yl]-2-(1,4-perhydroxazepin-4-yl)acetamide
(Compound 575)

In a manner similar to that in Example 545, by using 1,4-diazepane hydrochloride (125 mg, 0.900 mmol) in place of 4-methoxypiperidine hydrochloride, followed by reslurrying with diethyl ether, the entitled Compound 575 (83.5 mg, 66%) was obtained as a white solid from Compound 531 (120 mg, 0.300 mmol).

$^1$H NMR (CDCl$_3$, δ ppm): 1.70-2.00 (m, 6H), 2.86-2.93 (m, 4H), 3.10-3.20 (m, 1H), 3.47 (s, 2H), 3.48 (ddd, J=2.7, 11.1, 11.1 Hz, 2H), 3.75-3.87 (m, 4H), 4.03 (ddd, J=2.7, 3.7, 11.1 Hz, 2H), 6.57 (dd, J=1.9, 3.5 Hz, 1H), 7.59 (d, J=1.9 Hz, 1H), 7.78 (d, J=3.5 Hz, 1H).

APCIMS m/z: [M+H]$^+$ 420.

Example 576

N-[4-(2-Furyl)-5-(tetrahydropyran-4-ylcarbonyl)
thiazol-2-yl]-2-(4-methyl-1,4-diazepan-1-yl)aceta-
mide (Compound 576)

In a manner similar to that in Example 533, by using 1-methyl-1,4-diazepane (143 mg, 9.00 mmol) in place of the solution of dimethylamine in THF, followed by recrystallizing from a mixed solvent of ethanol and diethyl ether, the entitled Compound 576 (50.3 mg, 39%) was obtained from Compound 531 (120 mg, 0.300 mmol).

$^1$H NMR (DMSO-d$_6$, δ ppm): 1.50-1.80 (m, 4H), 1.85-2.00 (m, 2H), 2.78 (s, 3H), 2.80-2.90 (m, 2H), 2.95-3.05 (m, 2H), 3.10-3.20 (m, 1H), 3.30-3.45 (m, 6H), 3.62 (s, 2H), 3.83-3.93 (m, 2H), 6.69 (dd, J=1.6, 3.5 Hz, 1H), 7.40 (d, J=3.5 Hz, 1H), 7.89 (d, J=1.6 Hz, 1H).

APCIMS m/z: [M+H]$^+$ 433.

m.p.: 94-96° C.

Example 577

N-[4-(2-Furyl)-5-(tetrahydropyran-4-ylcarbonyl)
thiazol-2-yl]-2-(adamantan-1-ylamino)acetamide
(Compound 577)

In a manner similar to that in Example 533, by using 1-adamantylamine (136 mg, 9.00 mmol) in place of the solution of dimethylamine in THF, followed by reslurrying with diethyl ether, the entitled Compound 577 (92.6 mg, 66%) was obtained as a pale brown solid from Compound 531 (120 mg, 0.300 mmol).

$^1$H NMR (DMSO-d$_6$, δ ppm): 1.50-1.80 (m, 16H), 2.00-2.05 (m, 3H), 3.10-3.25 (m, 1H), 3.35-3.50 (m, 2H), 3.53 (s, 2H), 3.87 (ddd, J=2.4, 4.0, 12.1 Hz, 2H), 6.66 (dd, J=1.6, 3.2 Hz, 1H), 7.33 (dd, J=0.8, 3.2 Hz, 1H), 7.84 (dd, J=0.8, 1.6 Hz, 1H).

APCIMS m/z: [M+H]$^+$ 470.

m.p.: 168-170° C.

Example 578

N-[4-(2-Furyl)-5-(tetrahydropyran-4-ylcarbonyl)
thiazol-2-yl]-2-(3-hydroxyadamantan-1-ylamino)
acetamide (Compound 578)

In a manner similar to that in Example 533, by using 1-amino-3-hydroxyadamantane (151 mg, 9.00 mmol) in place of the solution of dimethylamine in THF, followed by reslurrying with diethyl ether, the entitled Compound 578 (102 mg, 70%) was obtained from Compound 531 (120 mg, 0.300 mmol).

$^1$H NMR (DMSO-d$_6$, δ ppm): 1.25-1.75 (m, 16H), 2.10-2.15 (m, 2H), 3.05-3.20 (m, 1H), 3.30-3.40 (m, 2H), 3.51 (s, 2H), 3.84-3.90 (m, 2H), 6.66 (dd, J=1.9, 3.5 Hz, 1H), 7.34 (dd, J=0.5, 3.5 Hz, 1H), 7.85 (dd, J=0.5, 1.9 Hz, 1H).

APCIMS m/z: [M+H]$^+$ 486.

mp.: 176-178° C.

Example 579

N-[4-(2-Furyl)-5-(tetrahydropyran-4-ylcarbonyl)thiazol-2-yl]-2-(1-imidazolyl)acetamide (Compound 579)

In a manner similar to that in Example 533, by using imidazole (62.0 mg, 9.00 mmol) in place of the solution of dimethylamine in THF, followed by recrystallizing from a mixed solvent of ethanol and diethyl ether, the entitled Compound 579 (43.2 mg, 37%) was obtained from Compound 531 (120 mg, 0.300 mmol).

$^1$H NMR (CDCl$_3$, δ ppm): 1.70-2.00 (m, 4H), 3.05-3.20 (m, 1H), 3.40-3.50 (m, 2H), 3.90-4.10 (m, 2H), 4.98 (s, 2H), 6.54 (dd, J=1.6, 3.2 Hz, 1H), 7.07 (s, 1H), 7.18 (s, 1H), 7.53 (d, J=1.6 Hz, 1H), 7.65 (d, J=3.2 Hz, 1H), 7.73 (s, 1H).

APCIMS m/z: [M+H]$^+$ 387.

Example 580

N-[4-(2-Furyl)-5-(tetrahydropyran-4-ylcarbonyl)thiazol-2-yl]-2-(2-methylimidazol-1-yl)acetamide (Compound 580)

In a manner similar to that in Example 533, by using 2-methylimidazole (74.0 mg, 9.00 mmol) in place of the solution of dimethylamine in THF, followed by recrystallizing from a mixed solvent of ethanol and diethyl ether, the entitled Compound 580 (9.1 mg, 8%) was obtained from Compound 531 (120 mg, 0.300 mmol).

$^1$H NMR (DMSO-d$_6$, δ ppm): 1.70-1.95 (m, 4H), 2.43 (s, 3H), 3.10-3.20 (m, 1H), 3.45 (ddd, J=2.7, 11.3, 11.3 Hz, 2H), 4.00-4.05 (m, 2H), 4.93 (s, 2H), 6.53 (dd, J=1.6, 3.2 Hz, 1H), 6.96 (d, J=0.5 Hz, 1H), 7.03 (d, J=0.5 Hz, 1H), 7.43 (d, J=1.6 Hz, 1H), 7.66 (d, J=3.2 Hz, 1H).

APCIMS m/z: [M+H]$^+$ 401.

Example 581

Ethyl N-[4-(2-furyl)-5-(tetrahydropyran-4-ylcarbonyl)thiazol-2-yl]carbamate (Compound 581)

In a manner similar to that in Example 456, by using ethyl chloroformate in place of cyclopropanecarbonyl chloride, the entitled Compound 581 (73.6 mg, 47%) was obtained from Compound 454 (125 mg, 0.450 mmol).

$^1$H NMR (DMSO-d$_6$, δ ppm): 1.27 (t, J=7.0 Hz, 3H), 1.50-1.76 (m, 4H), 3.05-3.18 (m, 1H), 3.22-3.40 (m, 2H), 3.82-3.92 (m, 2H), 4.25 (q, J=7.0 Hz, 2H), 6.68 (dd, J=1.6, 3.2 Hz, 1H), 7.36 (d, J=3.2 Hz, 1H), 7.88 (d, J=1.6 Hz, 1H), 12.39 (br s, 1H).

APCIMS m/z: [M+H]$^+$ 351.

m.p.: 152-153° C.

Example 582 tert-Butyl N-[4-(2-furyl)-5-(4-methyltetrahydropyran-4-ylcarbonyl)thiazol-2-yl]carbamate (Compound 582)

Step 1:

Methyl tetrahydropyran-4-carboxylate (2.88 g, 20.0 mmol) was dissolved in THF (100 mL), and a 2.0 mol/L solution of lithium diisopropylamide in THF (22.0 ml, 44.0 mmol) was added thereto at 0° C., followed by stirring at room temperature for 30 minutes. Methyl iodide (4.98 ml, 40.0 mmol) was added dropwise to the reaction mixture, followed by stirring for 1 hour. The reaction mixture was poured into water, followed by extraction with ethyl acetate. The organic layer was dried over anhydrous magnesium sulfate, and then the solvent was distilled away under reduced pressure, and the resulting residue was purified through silica gel column chromatography (hexane:ethyl acetate=1:1) to afford methyl 4-methyltetrahydropyran-4-carboxylate (1.93 g, 61%).

$^1$H NMR (CDCl$_3$, δ ppm): 1.20 (s, 3H), 1.42-1.52 (m, 2H), 2.01-2.08 (m, 2H), 3.40-3.49 (m, 2H), 3.9 (s, 3H), 3.73-3.81 (m, 2H).

Step 2:

In a manner similar to that in Step 2 of Example 445, N-methoxy-4,N-dimethyltetrahydropyran-4-carboxamide (886 mg, 32%) was obtained from methyl 4-methyltetrahydropyran-4-carboxylate (2.32 g, 14.6 mmol) obtained in Step 1, in place of ethyl 1,4-dioxaspiro[4,5]decane-8-carboxylate.

Step 3:

Compound h (817 mg, 2.37 mmol) obtained in Reference Example 8 was dissolved in THF (17 mL), and a 1.57 mol/L solution of n-butyllithium in n-hexane (3.32 mL, 5.21 mmol) was added thereto in a stream of argon at −78° C., followed by stirring at −78° C. for 15 minutes. N-methoxy-4,N-dimethyltetrahydropyran-4-carboxamide (886 mg, 4.73 mmol) obtained in Step 2 was added dropwise to the reaction mixture, followed by stirring overnight at room temperature. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 582 (449 mg, 48%).

$^1$H NMR (CDCl$_3$, δ ppm): 1.40 (s, 3H), 1.52 (s, 9H), 1.60-1.68 (m, 2H), 3.55-3.71 (m, 4H), 6.46 (dd, J=1.8, 3.5 Hz, 1H), 7.14 (d, J=3.5 Hz, 1H), 7.46 (d, J=1.8 Hz, 1H).

Example 583

2-Amino-4-(2-furyl)thiazol-5-yl 4-methyltetrahydropyran-4-yl ketone (Compound 583)

Compound 582 (210 mg, 0.535 mmol) was dissolved in trifluoroacetic acid (2 mL), followed by stirring at room temperature for 1 hour. The solvent was distilled away under reduced pressure, and a saturated aqueous solution of sodium hydrogencarbonate was added to the resulting residue, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford the entitled Compound 583 (156 mg, 100%).

$^1$H NMR (CDCl$_3$, δ ppm): 1.25 (s, 3H), 1.48-1.54 (m, 2H), 1.98-2.09 (m, 2H), 3.30-3.62 (m, 4H), 6.54 (dd, J=1.8, 3.5 Hz, 1H), 6.98 (dd, J=0.8, 3.5 Hz, 1H), 7.68 (dd; J=0.8, 1.8 Hz, 1H), 7.72 (br s, 2H).

Example 584 tert-Butyl N-[4-(2-furyl)-5-(4-methoxytetrahydropyran-4-ylcarbonyl)thiazol-2-yl]carbamate (Compound 584)

In a manner similar to that in Example 185, by using 4-methoxytetrahydrofuran-4-carboxylic acid in place of picolinic acid, the entitled Compound 584 (167 mg, 20%) was obtained from Compound h (690 mg, 2.00 mmol) obtained in Reference Example 8.

$^1$H NMR (CDCl$_3$, δ ppm): 1.52 (s, 9H), 1.93-2.11 (m, 4H), 3.23 (s, 3H), 3.76-3.79 (m, 4H), 6.53 (dd, J=1.8, 3.3 Hz, 1H), 7.55 (d, J=1.8 Hz, 1H), 7.80 (d, J=3.3 Hz, 1H).

Example 585

2-Amino-4-(2-furyl)thiazol-5-yl 4-methoxytetrahydropyran-4-yl ketone (Compound 585)

In a manner similar to that in Example 583, the entitled Compound 585 (124 mg, 98%) was obtained from Compound 584 (167 mg, 0.409 mmol) in place of Compound 582.

$^1$H NMR (CDCl$_3$, δ ppm): 1.85-2.09 (m, 4H), 3.22 (s, 3H), 3.73-3.78 (m, 4H), 5.64 (br s, 2H), 6.52 (dd, J=1.8, 3.6 Hz, 1H), 7.54 (dd, J=0.8, 1.8 Hz, 1H), 7.91 (dd, J=0.8, 3.6 Hz, 1H).

Example 586 tert-Butyl N-{4-(2-furyl)-5-[1-hydroxy-1-(tetrahydrothiopyran-4-yl)methyl]thiazol-2-yl}carbamate (Compound 586)

In a manner similar to that in Example 92, by using tetrahydrothiopyran-4-carbaldehyde in place of DMF, the entitled Compound 586 (2.17 g, 65%) was obtained from Compound h (2.92 g, 8.45 mmol) obtained in Reference Example 8.

$^1$H NMR (CDCl$_3$, δ ppm): 1.46 (s, 9H), 1.66-1.86 (m, 4H), 2.50-2.67 (m, 5H), 5.26-5.29 (m, 1H), 6.45 (dd, J=1.8, 3.3 Hz, 1H), 6.66 (dd, J=0.8, 3.3 Hz, 1H), 7.43 (dd, J=0.8, 1.8 Hz, 1H).

Example 587 tert-Butyl N-[4-(2-furyl)-5-(tetrahydrothiopyran-4-ylcarbonyl)thiazol-2-yl]carbamate (Compound 587)

In a manner similar to that in Example 297, the entitled Compound 587 (444 mg, 66%) was obtained from Compound 586 (680 mg, 1.71 mmol) in place of Compound 296.

$^1$H NMR (CDCl$_3$, δ ppm): 1.42 (s, 9H), 1.95-2.26 (m, 4H), 2.69-2.94 (m, 5H), 6.55 (dd, J=1.8, 3.5 Hz, 1H), 7.52 (d, 1.8 Hz, 1H), 7.77 (d, J=3.5 Hz, 1H).

Example 588

2-Amino-4-(2-furyl)thiazol-5-yl tetrahydrothiopyran-4-yl ketone (Compound 588)

In a manner similar to that in Example 583, the entitled Compound 588 (241 mg, 62%) was obtained from Compound 587 (497 mg, 1.26 mmol) in place of Compound 582.

$^1$H NMR (CDCl$_3$, δ ppm): 1.84-1.93 (m, 2H), 2.13-2.20 (m, 2H), 2.65-2.83 (m, 5H), 6.56 (dd, J=1.7, 3.3 Hz, 1H), 7.52 (d, J=3.3 Hz, 1H), 7.56 (d, J=1.7 Hz, 1H).

Example 589

N-[4-(2-Furyl)-5-(tetrahydrothiopyran-4-ylcarbonyl)thiazol-2-yl]pyridine-4-carboxamide (Compound 589)

Compound 588 (120 mg, 0.408 mmol) was dissolved in DMF (2 mL), and isonicotinic acid (150 mg, 1.22 mmol), EDC hydrochloride (234 mg, 1.22 mmol) and 1-hydroxybenzotriazole monohydrate (187 mg, 1.22 mmol) were added thereto, followed by stirring at 60° C. for 3 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was recrystallized from 2-propanol to afford the entitled Compound 589 (106 mg, 65%).

$^1$H NMR (CDCl$_3$, δ ppm): 1.88-2.05 (m, 2H), 2.22-2.29 (m, 2H), 2.68-2.84 (m, 4H), 2.94-3.03 (m, 1H), 6.51 (dd, J=1.8, 3.6 Hz, 1H), 7.48 (dd, J=0.7, 3.6 Hz, 1H), 7.71-7.48 (m, 3H), 8.85 (d, J=6.3 Hz, 2H), 10.6 (br s, 1H).

APCIMS m/z: [M+H]$^-$ 398.

m.p.: 203-210° C.

Example 590

N-[4-(2-Furyl)-5-(tetrahydrothiopyran-4-ylcarbonyl)thiazol-2-yl]-2-methylpyridine-5-carboxamide (Compound 590)

In a manner similar to that in Example 228, the entitled Compound 590 (40.0 mg, 28%) was obtained from Compound 588 (100 mg, 0.340 mmol) in place of Compound 186.

$^1$H NMR (DMSO-d$_6$, δ ppm): 1.65-1.69 (m, 2H), 2.13-2.17 (m, 2H), 2.65-2.73 (m, 4H), 2.73 (s, 3H), 3.04-3.20 (m, 1H), 6.71 (dd, J=1.7, 3.5 Hz, 1H), 7.43 (d, J=3.5 Hz, 1H), 7.92 (d, J=1.7 Hz, 1H), 9.29 (s, 2H).

APCIMS m/z: [M+H]$^+$ 415.

m.p.: 238-240° C.

Example 591 tert-Butyl N-[4-(2-furyl)-5-(1-oxotetrahydrothiopyran-4-ylcarbonyl)thiazol-2-yl]carbamate (Compound 591)

Compound 587 (500 mg, 1.27 mmol) was dissolved in chloroform (13 mL), and m-chloroperbenzoic acid (219 mg, 1.27 mmol) was added thereto, followed by stirring at room temperature for 3 hours. The reaction mixture was poured into water, followed by extraction with chloroform. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford the entitled Compound 591 (359 mg, 69%).

$^1$H NMR (CDCl$_3$, δ ppm): 1.51 (s, 9H), 1.93-2.09 (m, 2H), 2.41-2.76 (m, 4H), 3.08-3.30 (m, 3H), 6.56 (dd, J=1.8, 3.3 Hz, 1H), 7.56 (d, J=1.8 Hz, 1H), 7.60 (d, J=3.3 Hz, 1H).

Example 592

2-Amino-4-(2-furyl)thiazol-5-yl 1-oxotetrahydrothiopyran-4-yl ketone (Compound 592)

In a manner similar to that in Example 583, the entitled Compound 592 (234 mg, 86%) was obtained from Compound 591 (359 mg, 0.874 mmol) in place of Compound 582.

$^1$H NMR (DMSO-d$_6$, δ ppm): 1.62-1.75 (m, 2H), 2.01-2.26 (m, 2H), 2.51-2.68 (m, 2H), 2.85-3.24 (m, 3H), 6.64-6.67 (m, 1H), 7.26-7.32 (m, 1H), 7.84-7.89 (m, 1H), 8.02-8.04 (m, 2H).

Example 593 tert-Butyl N-[4-(2-furyl)-5-(1,1-dioxotetrahydrothiopyran-4-ylcarbonyl)thiazol-2-yl]carbamate (Compound 593)

In a manner similar to that in Example 591, by using m-chloroperbenzoic acid (870 mg, 5.04 mmol), the entitled Compound 593 (242 mg, 22%) was obtained from Compound 587 (995 mg, 2.52 mmol).

$^1$H NMR (CDCl$_3$, δ ppm): 1.51 (s, 9H), 2.29-2.48 (m, 4H), 2.96-3.01 (m, 2H), 3.15-3.28 (m, 3H), 6.56 (dd, J=1.7, 3.5 Hz, 1H), 7.55 (d, J=1.7 Hz, 1H), 7.63 (d, J=3.5 Hz, 1H).

Example 594

2-Amino-4-(2-furyl)thiazol-5-yl 1,1-dioxotetrahydrothiopyran-4-yl ketone (Compound 594)

In a manner similar to that in Example 583, the entitled Compound 594 (167 mg, 90%) was obtained from Compound 593 (242 mg, 0.567 mmol) in place of Compound 582.

$^1$H NMR (DMSO-d$_6$, δ ppm): 1.96-2.15 (m, 4H), 3.05-3.20 (m, 5H), 6.66 (dd, J=1.8, 3.5 Hz, 1H), 7.33 (d, J=3.5 Hz, 1H), 7.88 (d, J=1.8 Hz, 1H).

Example 595 tert-Butyl N-[4-(2-furyl)-5-(1-hydroxy-2-phenylethyl)thiazol-2-yl]carbamate (Compound 595)

In a manner similar to that in Example 99, by using a 1.03 mol/L solution of benzylmagnesium chloride in THF (2.60 mL, 2.68 mmol) in place of phenylmagnesium bromide, the entitled Compound 595 (255 mg, 100%) was obtained from Compound 92 (194 mg, 0.660 mmol) in place of Compound 98.

$^1$H NMR (CDCl$_3$, δ ppm): 1.47 (s, 9H), 2.44-2.46 (m, 1H), 2.92 (s, 1H), 6.46 (dd, J=1.8, 3.3. Hz, 1H), 6.60 (d, J=3.3 Hz, 1H), 7.01-7.40 (m, 7H), 8.95 (br s, 1H).

ESIMS m/z: [M+H]$^+$ 387.

Example 596 tert-Butyl N-[4-(2-furyl)-5-phenylacetylthiazol-2-yl]carbamate (Compound 596)

In a manner similar to that in Example 297, the entitled Compound 596 (130 mg, 51%) was obtained from Compound 595 (255 mg, 0.66 mmol) in place of Compound 296.

$^1$H NMR (CDCl$_3$, δ ppm): 1.54 (s, 9H), 4.13 (s, 2H), 6.53 (dd, J=1.8, 3.3 Hz, 1H), 7.20-7.40 (m, 5H), 7.56 (d, J=1.8 Hz, 1H), 7.79 (d, J=3.3 Hz, 1H), 8.60 (brs, 1H).

ESIMS m/z: [M+H]$^+$ 385.

Example 597

2-Amino-4-(2-furyl)thiazol-5-yl benzyl ketone (Compound 597)

In a manner similar to that in Example 583, the entitled Compound 597 (91.2 mg, 97. %) was obtained from Compound 596 (126 mg, 0.330 mmol) in place of Compound 582.

$^1$H NMR (CDCl$_3$, δ ppm): 4.01 (s, 2H), 5.68 (br s, 2H), 6.53 (dd, J=1.7 Hz, 3.6 Hz, 1H), 7.18-7.35 (m, 5H), 7.55 (dd, J=0.7, 1.8 Hz, 1H), 7.68 (dd, J=0.7 Hz, 3.6 Hz, 1H).

ESIMS m/z: [M+H]$^+$ 285.

Example 598 tert-Butyl N-[4-(2-furyl)-5-[1-hydroxy-2-(2-methoxyphenyl)ethyl]thiazol-2-yl]carbamate (Compound 598)

In a manner similar to that in Example 99, by using a 0.25 mol/L solution of (2-methoxy)benzylmagnesium chloride in THF (25.0 mL, 6.25 mmol) in place of phenylmagnesiium bromide, the entitled Compound 598 (716 mg, 100%) was obtained from Compound 92 (506 mg, 1.72 mmol) in place of Compound 98.

$^1$H NMR (CDCl$_3$, δ ppm): 1.50 (s, 9H), 3.75 (s, 3H), 4.69 (s, 2H), 5.65 (brs, 1H), 6.46 (dd, J=1.8, 3.5 Hz, 1H), 6.70 (dd, J=0.7 Hz, 1.8 Hz, 1H), 6.75-7.00 (m, 2H), 7.10-7.35 (m, 2H), 7.46 (dd, J=0.7 Hz, 3.5 Hz, 1H), 8.45 (br s, 1H).

ESIMS m/z: [M+H]$^+$ 417.

Example 599 tert-Butyl N-[4-(2-furyl)-5-[2-(2-methoxyphenyl)acetyl]thiazol-2-yl]carbamate (Compound 599)

In a manner similar to that in Example 297, the entitled Compound 599 (218 mg, 31%) was obtained from Compound 598 (716 mg, 1.72 mmol) in place of Compound 296.

$^1$H NMR (CDCl$_3$, δ ppm): 1.54 (s, 9H), 3.77 (s, 3H), 4.13 (s, 2H), 6.50 (dd, J=1.8, 3.7 Hz, 1H), 6.88 (dd, J=1.1 Hz, 8.4 Hz, 1H), 6.93 (ddd, J=1.1 Hz, 7.3 Hz, 7.4 Hz, 1H), 7.15 (dd, J=1.6 Hz, 7.3 Hz, 1H), 7.25 (ddd, J=1.6 Hz, 7.4 Hz, 7.5 Hz, 1H), 7.54 (dd, J=0.7 Hz, 1.8 Hz, 1H), 7.79 (dd, J=0.7 Hz, 3.7 Hz, 1H), 8.58 (brs, 1H).

ESIMS m/z: [M+H]$^+$ 415.

Example 600

2-Amino-4-(2-furyl)thiazol-5-yl 2-methoxybenzyl ketone (Compound 600)

In a manner similar to that in Example 583, the entitled Compound 600 (162 mg, 98%) was obtained from Compound 599 (218 mg, 0.527 mmol) in place of Compound 582.

$^1$H NMR (CDCl$_3$, δ ppm): 3.77 (s, 3H), 4.01 (s, 2H), 5.51 (brs, 2H), 6.49 (dd, J=1.8, 3.5 Hz, 1H), 6.82-6.95 (m, 2H), 7.10-7.29 (m, 2H), 7.59 (dd, J=0.7, 1.8 Hz, 1H), 7.75 (dd, J=0.7, 3.5 Hz, 1H).

ESIMS m/z: [M+H]$^+$ 315.

Example 601

N-[4-(5-Methylfuran-2-yl)-5-(4-pyridyl)thiazol-2-yl]pyridine-4-carboxamide (Compound 601)

In a manner similar to that in Example 1, by using Compound aa (46.1 mg, 0.179 mmol) obtained in Reference Example 27 in place of Compound a, the entitled Compound 601 (31.1 mg, 48%) was obtained.

$^1$H NMR (DMSO-d$_6$, δ ppm): 2.23 (s, 3H), 6.21 (s, 1H), 6.58 (s, 1H), 7.51 (d, J=6.0 Hz, 2H), 8.03 (d, J=6.0 Hz, 2H), 8.64 (d, J=6.0 Hz, 2H), 8.84 (d, J=6.0 Hz, 2H).

ESIMS m/z: [M+H]$^+$ 363.

m.p.: 274-276° C.

Example 602

N-[4-(3-Methylfuran-2-yl)-5-(4-pyridyl)thiazol-2-yl]pyridine-4-carboxamide (Compound 602)

In a manner similar to that in Example 1, by using Compound ab (106 mg, 0.413 mmol) obtained in Reference Example 28 in place of Compound a, the entitled Compound 602 (61.1 mg, 41%) was obtained.

$^1$H NMR (DMSO-d$_6$, δ ppm): 1.99 (s, 3H), 6.50 (s, 1H), 7.27 (dd, J=1.6, 6.1 Hz, 2H), 7.63 (s, 1H), 8.02 (dd, J=1.6, 6.1 Hz, 2H), 8.57 (dd, J=1.6, 6.1 Hz, 2H), 8.84 (dd, J=1.6, 6.1 Hz, 2H).

ESIMS m/z: [M+H]$^+$ 363.

m.p.: 254-257° C.

Example 603

N-[4-(3-Phenylfuran-2-yl)-5-(4-pyridyl)thiazol-2-yl]pyridine-4-carboxamide (Compound 603)

In a manner similar to that in Example 1, by using Compound ac (22.5 mg, 0.070 mmol) obtained in Reference Example 29 in place of Compound a, the entitled Compound 603 (14.5 mg, 49%) was obtained.

$^1$H NMR (CD$_3$OD, δ ppm): 6.70 (d, J=1.5 Hz, 1H), 7.07-7.14 (m, 5H), 7.29 (d, J=5.8 Hz, 2H), 7.61 (d, J=1.5 Hz, 1H), 7.89 (d, J=5.8 Hz, 2H), 8.32-8.35 (m, 2H), 8.65-8.72 (m, 2H).

ESIMS m/z: [M+H]$^+$ 425.

m.p.: 190-192° C.

Example 604

N-{5-(4-Pyridyl)-4-[3-(4-pyridyl)furan-2-yl]thiazol-2-yl}pyridine-4-carboxamide (Compound 604)

In a manner similar to that in Example 1, by using Compound ad (35.2 mg, 0.110 mmol) obtained in Reference Example 30 in place of Compound a, the entitled Compound 604 (9.90 mg, 21%) was obtained. H NMR (CD$_3$OD, δ ppm): 6.92 (d, J=2.0 Hz, 1H), 7.17 (dd, J=1.3, 4.8 Hz, 2H), 7.33 (d, J=4.8 Hz, 2H), 7.72 (d, J=2.0 Hz, 1H), 7.98 (dd, J=1.3, 4.8 Hz, 2H), 8.34-8.37 (m, 4H), 8.78 (d, J=4.8 Hz, 2H).

ESIMS m/z: [M+H]$^+$ 426.

Example 605

N-[4-(3-Furyl)-5-(4-pyridyl)thiazol-2-yl]pyridine-4-carboxamide (Compound 605)

In a manner similar to that in Example 1, by using Compound ae (109 mg, 0.450 mmol) obtained in Reference Example 31 in place of Compound a, the entitled Compound 605 (155 mg, 99%) was obtained.

$^1$H NMR (DMSO-d$_6$, δ ppm): 6.43 (dd, J=0.8, 2.0 Hz, 1H), 7.48 (dd, J=1.6, 4.5 Hz, 2H), 7.72 (dd, J=1.5, 2.0 Hz, 1H), 7.88 (dd, J=0.8, 1.5 Hz, 1H), 8.02 (dd, J=1.6, 4.4 Hz, 2H), 8.63 (dd, J=1.6, 4.5 Hz, 2H), 8.83 (dd, J=1.6, 4.4 Hz, 2H), 13.31 (br s, 1H).

ESIMS m/z: [M+H]$^+$ 349.

m.p.: 251-254° C.

Example 606 tert-Butyl N-[4-(3-furyl)-5-(pyridin-2-ylcarbonyl)thiazol-2-yl]carbamate (Compound 606)

In a manner similar to that in Example 185, by using Compound af (508 mg, 1.47 mmol) obtained in Reference Example 32 in place of Compound h, the entitled Compound 606 (310 mg, 57%) was obtained.

Example 607

2-Amino-4-(3-furyl)thiazol-5-yl 2-pyridyl ketone (Compound 607)

In a manner similar to that in Example 186, by using Compound 606 (331 mg, 0.892 mmol) in place of Compound 185, the entitled Compound 607 (199 mg, 88%) was obtained.

$^1$H NMR (CDCl$_3$, δ ppm): 5.66 (br s, 2H), 7.07 (dd, J=0.6, 1.8 Hz, 1H), 7.44-7.46 (m, 1H), 7.45-7.51 (m, 1H), 7.85-7.91 (m, 1H), 8.16-8.22 (m, 1H), 8.64-8.67 (m, 1H), 8.72-8.73 (m, 1H).

Example 608

N-[4-(3-Furyl)-5-(pyridin-2-ylcarbonyl)thiazol-2-yl]pyridine-4-carboxamide (Compound 608)

In a manner similar to that in Example 1, by using Compound 607 (87.4 mg, 0.322 mmol) in place of Compound a, the entitled Compound 608 (96.8 mg, 80%) was obtained.

$^1$H NMR (DMSO-d$_6$, δ ppm): 7.07-7.08 (m, 1H), 7.70-7.76 (m, 1H), 7.78-7.79 (m, 1H), 8.05 (d, J=5.9 Hz, 2H), 8.07-8.17 (m, 2H), 8.66-8.70 (m, 1H), 8.82-8.86 (m, 3H), 13.4 (br s, 1H).

ESIMS m/z: [M+H]$^+$ 377.

m.p.: 264-266° C.

Example 609 tert-Butyl N-[4-(3-furyl)-5-(tetrahydropyran-4-ylcarbonyl)thiazol-2-yl]carbamate (Compound 609)

In a manner similar to that in Example 185, by using tetrahydropyran-4-carboxylic acid in place of picolinic acid, the entitled Compound 609 (2.66 g, 66%) was obtained from Compound af (3.68 g, 10.7 mmol) obtained in Reference Example 32 in place of Compound h.

$^1$H NMR (CDCl$_3$, δ ppm): 1.49 (s, 9H), 1.76-1.97 (m, 4H), 3.09 (tt, J=4.0, 11.0 Hz, 1H), 3.49 (ddd, J=2.6, 11.4, 11.4 Hz, 2H), 4.06 (ddd, J=2.6, 4.0, 11.4 Hz, 2H), 7.01 (dd, J=0.7, 1.8 Hz, 1H), 7.44 (dd, J=1.5, 1.8 Hz, 1H), 8.69 (dd, J=0.7, 1.5 Hz, 1H), 9.24 (br s, 1H).

APCIMS m/z: [M+H]$^+$ 379.

Example 610

2-Amino-4-(3-furyl)thiazol-5-yl tetrahydropyran-4-yl ketone (Compound 610)

In a manner similar to that in Example 186, by using Compound 609 (1.92 g, 5.07 mmol) in place of Compound 185, the entitled Compound 610 (1.41 g, 99%) was obtained.

$^1$H NMR (CDCl$_3$, δ ppm): 1.69-1.95 (m, 4H), 2.88 (tt, J=3.9, 11.0 Hz, 1H), 3.41 (ddd, J=2.4, 11.6, 11.6 Hz, 2H), 4.02 (ddd, J=2.4, 4.2, 11.6 Hz, 2H), 5.34 (br s, 2H), 6.95 (dd, J=0.7, 1.8 Hz, 1H), 7.45 (dd, J=1.6, 1.8 Hz, 1H), 8.52 (dd, J=0.7, 1.6 Hz, 1H).

APCIMS m/z: [M+H]$^+$ 279.

Example 611

N-[4-(3-Furyl)-5-(tetrahydropyran-4-ylcarbonyl)thiazol-2-yl]cyclopropanecarboxamide (Compound 611)

In a manner similar to that in Example 187, by using cyclopropanecarboxylic acid in place of isonicotinic acid, followed by recrystallizing from a mixed solvent of ethanol and water, the entitled Compound 611 (98.6 mg, 66%) was obtained as a white solid from Compound 610 (150 mg, 0.435 mmol) in place of Compound 186.

$^1$H NMR (CDCl$_3$, δ ppm): 0.90-1.00 (m, 2H), 1.14-1.22 (m, 2H), 1.42-1.52 (m, 1H), 1.76-1.98 (m, 4H), 3.08 (tt, J=4.4, 10.6 Hz, 1H), 3.48 (ddd, J=2.6, 11.4, 11.4 Hz, 2H), 4.04 (ddd, J=2.6, 4.0, 11.4 Hz, 2H), 7.02 (dd, J=0.7, 1.8 Hz, 1H), 7.47 (dd, J=1.5, 1.8 Hz, 1H), 8.66 (dd, J=0.7, 1.5 Hz, 1H), 10.11 (br s, 1H).

APCIMS m/z: [M+H]$^+$ 347.

m.p.: 231-232° C.

Example 612

2-Chloro-N-[4-(3-furyl)-5-(tetrahydropyran-4-ylcarbonyl)thiazol-2-yl]pyridine-5-carboxamide (Compound 612)

In a manner similar to that in Example 188, by using 6-chloronicotinoyl chloride in place of acetyl chloride, followed by reslurrying with ethanol, the entitled Compound 612 (110 mg, 73%) was obtained as a white solid from Compound 610 (100 mg, 0.359 mmol) in place of Compound 186.

$^1$H NMR (CDCl$_3$, δ ppm): 1.74-2.00 (m, 4H), 3.13 (tt, J=4.2, 10.6 Hz, 1H), 3.50 (ddd, J=2.8, 11.4, 11.4 Hz, 2H), 4.04 (ddd, J=2.8, 4.3, 11.4 Hz, 2H), 6.97 (dd, J=0.8, 1.8 Hz, 1H), 7.43 (dd, J=1.6, 1.8 Hz, 1H), 7.51 (dd, J=0.7, 8.4 Hz, 1H), 8.21 (dd, J=2.5, 8.4 Hz, 1H), 8.57 (dd, J=0.8, 1.6 Hz, 1H), 8.95 (dd, J=0.7, 2.5 Hz, 1H).

APCIMS m/z: [$^{35}$ClM–H]$^-$ 416, [$^{37}$ClM–H]$^-$ 418.

m.p.: 237-239° C.

Example 613

N-[4-(3-Furyl)-5-(tetrahydropyran-4-ylcarbonyl)thiazol-2-yl]-5-methylpyridine-3-carboxamide (Compound 613)

In a manner similar to that in Example 187, by using 5-methylnicotinic acid in place of isonicotinic acid, followed by recrystallizing from a mixed solvent of ethanol and water, the entitled Compound 613 (46.5 mg, 53%) was obtained as a white solid from Compound 610 (59.8 mg, 0.215 mmol) in place of Compound 186.

$^1$H NMR (CDCl$_3$, δ ppm): 1.79-2.01 (m, 4H), 2.48 (s, 3H), 3.15 (tt, J=4.0, 10.6 Hz, 1H), 3.52 (ddd, J=2.7, 11.4, 11.4 Hz, 2H), 4.06 (ddd, J=2.7, 4.0, 11.4 Hz, 2H), 7.01 (dd, J=0.7, 1.8 Hz, 1H), 7.46 (dd, J=1.6, 1.8 Hz, 1H), 8.06-8.10 (m, 1H), 8.66 (dd, J=0.7, 1.6 Hz, 1H), 8.71 (d, J=2.2 Hz, 1H), 9.01 (d, J=2.2 Hz, 1H).

APCIMS m/z: [M+H]$^+$ 398.

m.p.: 244-246° C.

Example 614

N-[4-(3-Furyl)-5-(tetrahydropyran-4-ylcarbonyl)thiazol-2-yl]-2-methylpyridine-5-carboxamide (Compound 614)

In a manner similar to that in Example 187, by using 6-methylnicotinic acid (290 mg, 2.11 mmol) in place of isonicotinic acid, the entitled Compound 614 (120 mg, 87%) was obtained from Compound 610 (96.0 mg, 0.345 mmol) in place of Compound 186.

$^1$H NMR (DMSO-d$_6$, δ ppm): 1.56-1.78 (m, 4H), 2.58 (s, 3H), 3.16-3.24 (m, 1H), 3.36-3.44 (m, 2H), 3.88-3.92 (m, 2H), 7.05 (dd, J=0.8, 1.5 Hz, 1H), 7.47 (d, J=8.3 Hz, 1H), 7.80 (dd, J=1.0, 1.5 Hz, 1H), 8.35 (dd, J=2.4, 8.3 Hz, 1H), 8.62 (dd, J=0.8, 1.0 Hz, 1H), 9.14 (d, J=2.4 Hz, 1H), 13.30 (br s, 1H).

ESIMS m/z: [M+H]$^+$ 398.

m.p.: 217-219° C.

Example 615

N-[4-(3-Furyl)-5-(tetrahydropyran-4-ylcarbonyl)thiazol-2-yl]-2-methylpyridine-4-carboxamide (Compound 615)

Compound 610 (100 mg, 0.359 mmol) was dissolved in DMF (3 mL), and 2-methylisonicotinic acid hydrochloride (249 mg, 1.44 mmol), EDC hydrochloride (558 mg, 2.91 mmol), 1-hydroxybenzotriazole monohydrate (463 mg, 3.02 mmol) and triethylamine (0.400 mL, 2.87 mmol) were added thereto, followed by stirring overnight at 80° C. The reaction mixture was poured into aqueous sodium hydrogencarbonate solution, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=3:1), followed by recrystallizing from a mixed solvent of ethanol and water to afford the entitled Compound 615 (73.1 mg, 51%) as a white solid.

$^1$H NMR (CDCl$_3$, δ ppm): 1.76-2.01 (m, 4H), 2.71 (s, 3H), 3.15 (tt, J=4.0, 10.6 Hz, 1H), 3.52 (ddd, J=2.8, 11.4, 11.4 Hz, 2H), 4.02-4.12 (m, 2H), 7.02 (dd, J=0.7, 1.8 Hz, 1H), 7.48 (dd, J=1.6, 1.8 Hz, 1H), 7.57-7.63 (m, 1H), 7.67 (m, 1H), 8.67, (dd, J=0.7, 1.6 Hz, 1H), 8.78 (d, J=5.1 Hz, 1H), 9.74 (br s, 1H).

APCIMS m/z: [M−H]$^−$ 396.

m.p.: 202-204° C.

Example 616

2-Chloro-N-[4-(3-furyl)-5-(tetrahydropyran-4-ylcarbonyl)thiazol-2-yl]pyridine-4-carboxamide (Compound 616)

Compound 610 (100 mg, 0.359 mmol) was dissolved in pyridine (3 mL), and 6-chloroisonicotinoyl chloride (560 mg, 3.18 mmol) and DMAP (4.40 mg, 0.0360 mmol) were added thereto, followed by stirring at 80° C. for 3 hours. The reaction mixture was concentrated under reduced pressure, and the resulting residue was poured into a saturated aqueous solution of sodium hydrogencarbonate, and the precipitated solid was collected by filtration. The resulting solid was purified through silica gel column chromatography (hexane:ethyl acetate=3:1), followed by recrystallizing from a mixed solvent of ethanol and water to afford the entitled Compound 616 (54.5 mg, 36%) as a white solid.

$^1$H NMR (CDCl$_3$, δ ppm): 1.79-2.01 (m, 4H), 3.14 (tt, J=4.0, 10.8 Hz, 1H), 3.53 (ddd, J=2.5, 11.6, 11.6 Hz, 2H), 4.07 (ddd, J=2.5, 4.0, 11.6 Hz, 2H), 6.99 (dd, J=0.7, 1.8 Hz, 1H), 7.47 (dd, J=1.6, 1.8 Hz, 1H), 7.70 (dd, J=1.6, 5.1 Hz, 1H), 7.82 (dd, J=0.7, 1.6 Hz, 1H), 8.65 (dd, J=0.6, 1.6 Hz, 1H), 8.67 (dd, J=0.6, 5.1 Hz, 1H), 9.73 (br s, 1H).

APCIMS m/z: [$^{35}$ClM−H]$^−$ 416, [$^{37}$ClM−H]$^−$ 418.

m.p.: 202-204° C.

Example 617

N-[4-(3-Furyl)-5-(tetrahydropyran-4-ylcarbonyl)thiazol-2-yl]-2-methylpyridine-5-carboxamide (Compound 617)

In a manner similar to that in Example 228, the entitled Compound 617 (42.6 mg, 29%) was obtained from Compound 610 (104 mg, 0.372 mmol) in place of Compound 186.

$^1$H NMR (CDCl$_3$, δ ppm): 1.80-2.00 (m, 4H), 2.86 (s, 3H), 3.14 (tt, J=4.4, 10.5 Hz, 1H), 3.52 (ddd, J=2.8, 11.4, 11.4 Hz, 2H), 4.02-4.12 (m, 2H), 6.92 (dd, J=0.7, 1.8 Hz, 1H), 7.41 (dd, J=1.5, 1.8 Hz, 1H), 8.56 (dd, J=0.7, 1.5 Hz, 1H), 9.15 (s, 2H), 10.39 (br s, 1H).

ESIMS m/z: [M+H]$^+$ 399.

m.p.: 225-227° C.

Example 618

N-[4-(3-Furyl)-5-(tetrahydropyran-4-ylcarbonyl)thiazol-2-yl]-2-(3-pyridyl)acetamide (Compound 618)

Compound 610 (102 mg, 0.366 mmol) was dissolved in DMF (3 mL), and 3-pyridylacetic acid hydrochloride (635 mg, 3.66 mmol), EDC hydrochloride (702 mg, 3.66 mmol), 1-hydroxybenzotriazole monohydrate (561 mg, 3.66 mmol) and triethylamine (0.510 mL, 3.66 mmol) were added thereto, followed by stirring at 80° C. for 10 hours. The reaction mixture was poured into a saturated aqueous solution of sodium hydrogencarbonate, and the precipitated solid was collected by filtration. The resulting solid was purified through silica gel column chromatography (hexane:ethyl acetate=2:1), followed by recrystallizing from a mixed solvent of ethanol and water to afford the entitled Compound 618 (74.6 mg, 52%) as a white solid.

$^1$H NMR (CDCl$_3$, δ ppm): 1.75-1.94 (m, 4H), 3.08 (tt, J=4.4, 10.5 Hz, 1H), 3.48 (ddd, J=2.5, 11.4, 11.4 Hz, 2H), 3.82 (s, 2H), 4.04 (ddd, J=2.5, 4.1, 11.4 Hz, 2H), 6.92 (dd, J=0.8, 1.8 Hz, 1H), 7.36 (ddd, J=0.7, 4.8, 7.7 Hz, 1H), 7.47 (dd, J=1.6, 1.8 Hz, 1H), 7.67-7.73 (m, 1H), 8.55-8.67 (m, 3H), 9.41 (br s, 1H).

APCIMS m/z: [M+H]$^+$ 398.

m.p.: 195-197° C.

Example 619

N-[4-(3-Furyl)-5-(tetrahydropyran-4-ylcarbonyl)thiazol-2-yl]-3-methoxybenzamide (Compound 619)

In a manner similar to that in Example 188, by using 3-methoxybenzoyl chloride in place of acetyl chloride, followed by recrystallizing from a mixed solvent of ethanol and water, the entitled Compound 619 (90.0 mg, 61%) was obtained as a white solid from Compound 610 (100 mg, 0.359 mmol) in place of Compound 186.

$^1$H NMR (CDCl$_3$, δ ppm): 1.79-2.01 (m, 4H), 3.15 (tt, J=4.6, 10.7 Hz, 1H), 3.52 (ddd, J=2.6, 11.6, 11.6 Hz, 2H), 3.90 (s, 3H), 4.0.6 (ddd, J=2.6, 3.9, 11.6 Hz, 2H), 7.04 (dd, J=0.7, 1.8 Hz, 1H), 7.20 (ddd, J=2.6, 2.6, 6.6 Hz, 1H), 7.46-7.54 (m, 4H), 8.68 (dd, J=0.7, 1.5 Hz, 1H), 9.52 (br s, 1H).

APCIMS m/z: [M+H]$^+$ 413.

m.p.: 194-196° C.

Example 620

4-Fluoro-N-[4-(3-furyl)-5-(tetrahydropyran-4-ylcarbonyl)thiazol-2-yl]benzamide (Compound 620)

In a manner similar to that in Example 188, by using 4-fluorobenzoyl chloride in place of acetyl chloride, followed by recrystallizing from a mixed solvent of ethanol and water, the entitled Compound 620 (68.3 mg, 47%) was obtained as a white solid from Compound 610 (100 mg, 0.359 mmol) in place of Compound 186.

$^1$H NMR (CDCl$_3$, δ ppm): 1.79-2.01 (m, 4H), 3.15 (tt, J=4.4, 10.6 Hz, 1H), 3.52 (ddd, J=2.6, 11.4, 11.4 Hz, 2H), 4.06 (ddd, J=2.6, 4.0, 11.4 Hz, 2H), 7.02 (dd, J=0.7, 1.8 Hz, 1H), 7.20-7.30 (m, 2H), 7.46 (dd, J=1.5, 1.8 Hz, 1H), 7.96-8.04 (m, 2H), 8.67 (0.7, 1.5 Hz, 1H), 9.63 (br s, 1H).

APCIMS m/z: [M+H]$^+$ 401.

m.p.: 231-232° C.

Example 621

N-[4-(3-Furyl)-5-(tetrahydropyran-4-ylcarbonyl)thiazol-2-yl]-2-morpholinoacetamide (Compound 621)

In a manner similar to that in Example 287, by using Compound 610 (204 mg, 0.745 mmol) in place of Compound 286, the entitled Compound (68.4 mg, 23%) was obtained.

$^1$H NMR (CDCl$_3$, δ ppm): 1.76-1.97 (m, 4H), 2.62-2.69 (m, 4H), 3.10 (tt, J=4.2, 10.8 Hz, 1H), 3.31 (s, 2H), 3.49 (ddd, J=2.8, 11.6, 11.6 Hz, 2H), 3.80-3.86 (m, 4H), 4.04 (ddd, J=2.4, 4.4, 11.6 Hz, 2H), 7.04 (dd, J=0.7, 1.8 Hz, 1H), 7.48 (dd, J=1.5, 1.8 Hz, 1H), 8.64 (dd, J=0.7, 1.5 Hz, 1H), 10.35 (br s, 1H).

Example 622

N-[5-(Cyclopentylcarbonyl)-4-(2-furyl)thiazol-2-yl] dicyclopropanecarboxamide (Compound 622)

Compound 452 (88.9 mg, 0.339 mmol) was dissolved in THF (5 mL), and cyclopropanecarbonyl chloride (0.188 mL, 1.98 mmol) and triethylamine (0.279 mL, 2.00 mmol) were added thereto, followed by stirring overnight at 50° C. Aqueous saturated sodium hydrogencarbonate solution was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=3:1) to afford the entitled Compound 622 (135 mg, 100%) as pale brown crystals.

$^1$H NMR (CDCl$_3$, δ ppm): 1.06-1.14 (m, 4H), 1.30-1.36 (m, 4H), 1.56-1.80 (m, 4H), 1.87-1.96 (m, 4H), 2.08-2.18 (m, 1H), 3.38-3.44 (m, 2H), 6.53 (dd, J=1.7 Hz, 3.5 Hz, 1H), 7.50 (dd, J=0.7 Hz, 3.5 Hz, 1H), 7.55 (dd, J=0.7 Hz, 1.7 Hz, 1H).

ESIMS m/z: [M+H]$^+$ 331.

m.p.: 87-88° C.

Example 623 tert-Butyl N-[5-(2-ethoxyacetyl)-4-(2-furyl)thiazol-2-yl]-N-methylcarbamate (Compound 623)

Step 1:

Compound h (2.00 g, 5.79 mmol) obtained in Reference Example 8 was dissolved in DMF (29 mL), and 55% sodium hydride (278 mg, 6.37 mmol) was added thereto, followed by stirring at room temperature for 30 minutes. Methyl iodide (0.793 mL, 12.7 mmol) was added dropwise to the reaction mixture, followed by stirring at room temperature for 1 hour. The reaction mixture was poured into water, followed by extraction with ethyl acetate. The organic layer was dried over anhydrous magnesium sulfate, and then the solvent was distilled away under reduced pressure. The resulting residue was purified through silica gel column chromatography (hexane:ethyl acetate=1:1) to afford tert-butyl N-[5-bromo-4-(2-furyl)thiazol-2-yl]-N-methylcarbamate (2.08 g, 100%).

$^1$H NMR (CDCl$_3$, δ ppm): 1.57 (s, 9H), 3.54 (s, 3H), 6.48 (dd, J=1.8, 3.5 Hz, 1H), 6.97 (dd, J=0.7, 3.5 Hz, 1H), 7.50 (dd, J=0.7, 1.8 Hz, 1H).

Step 2:

tert-Butyl N-[5-bromo-4-(2-furyl)thiazol-2-yl]-N-methylcarbamate (1.41 g, 3.93 mmol) obtained in Step 1 was dissolved in THF (19 mL), and a 1.57 mol/L solution of n-butyllithium in n-hexane (2.75 mL, 4.32 mmol) was added thereto in a stream of argon at −78° C., followed by stirring at −78° C. for 15 minutes. 2-Ethoxy-N-methoxy-N-methylacetamide (1.74 g, 11.8 mmol) was added to the reaction mixture, followed by stirring at room temperature for 2 hours. The reaction mixture was poured into a saturated aqueous solution of ammonium chloride, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford the entitled Compound 623 (550 mg, 38%).

$^1$H NMR (CDCl$_3$, δ ppm): 1.24 (t, J=6.9 Hz, 3H), 1.59 (s, 9H), 3.58 (q, J=6.9 Hz, 2H), 3.61 (s, 3H), 4.46 (s, 2H), 6.52 (dd, J=1.8, 3.5 Hz, 1H), 7.55 (d, J=1.8 Hz, 1H), 7.59 (d, J=3.5 Hz, 1H).

Example 624

Ethoxymethyl 4-(2-furyl)-2-(methylamino)thiazol-5-yl ketone (Compound 624)

Compound 623 (550 mg, 1.50 mmol) was dissolved in trifluoroacetic acid (2 mL), followed by stirring for 1 hour. The reaction mixture was concentrated under reduced pressure, and saturated sodium hydrogencarbonate was added to the resulting residue, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford the entitled Compound 624 (344 mg, 86%).

$^1$H NMR (CDCl$_3$, δ ppm): 1.24 (t, J=6.9 Hz, 3H), 3.00 (d, J=4.3 Hz, 3H), 3.57 (q, J=6.9 Hz, 2H), 4.45 (s, 2H), 6.53 (dd, J=1.8, 3.5 Hz, 1H), 6.72-6.74 (m, 1H), 7.54 (d, J=1.8 Hz, 1H), 7.69 (d, J=3.5 Hz, 1H).

Example 625

2-(Benzylamino)-4-(2-furyl)thiazol-5-yl tetrahydropyran-4-yl ketone (Compound 625)

In a manner similar to that in Example 623, by using benzyl bromide in place of methyl iodide and using N-methoxy-N-methyltetrahydropyran-4-carboxamide in place of 2-ethoxy-N-methoxy-N-methylacetamide, tert-butyl N-benzyl-N-[4-(2-furyl)-5-(tetrahydropyran-4-ylcarbonyl)thiazol-2-yl] carbamate was obtained from Compound h obtained in Reference Example 8. In a manner similar to that in Example 624, the entitled Compound 625 was obtained from tert-butyl N-benzyl-N-[4-(2-furyl)-5-(tetrahydropyran-4-ylcarbonyl) thiazol-2-yl]carbamate obtained herein in place of Compound 623.

$^1$H NMR (CDCl$_3$, δ ppm): 1.65-1.90 (m, 4H), 2.98 (tt, J=3.8, 10.9 Hz, 1H), 3.38 (ddd, J=2.4, 10.9, 10.9 Hz, 2H), 4.00 (ddd, J=2.4, 4.8, 10.9 Hz, 2H), 4.50 (d, J=4.4 Hz, 2H), 6.53 (dd, J=1.8, 3.5 Hz, 1H), 7.33-7.41 (m, 5H), 7.49 (dd, J=0.8, 1.8 Hz, 1H), 7.52 (dd, J=0.8, 3.5 Hz, 1H).

Example 626

4-(2-Furyl)-2-(methylamino)thiazol-5-yl tetrahydropyran-4-yl ketone (Compound 626)

In a manner similar to that in Example 623, by using N-methoxy-N-methyltetrahydropyran-4-carboxamide in place of 2-ethoxy-N-methoxy-N-methylacetamide, tert-butyl N-[4-(2-furyl)-5-(tetrahydropyran-4-ylcarbonyl)thiazol-2-yl]-N-methylcarbamate was obtained from Compound h obtained in Reference Example 8. In a manner similar to that in Example 624, the entitled Compound 626 was obtained from tert-butyl 1N-[4-(2-furyl)-5-(tetrahydropyran-4-ylcarbonyl)thiazol-2-yl]-N-methylcarbamate obtained herein in place of Compound 623.

¹H NMR (CDCl₃, δ ppm): 1.65-1.90 (m, 4H), 2.95-3.10 (m, 1H), 3.11-3.20 (m, 3H), 3.38 (ddd, J=2.4, 10.9, 10.9 Hz, 2H), 4.00 (ddd, J=2.4, 4.8, 10.9 Hz, 2H), 4.50 (d, J=4.4 Hz, 2H), 6.53 (dd, J=1.8, 3.5 Hz, 1H), 7.49 (dd, J=0.8, 1.8 Hz, 1H), 7.52 (dd, J=0.8, 3.5 Hz, 1H).

Example 627

2-(tert-Butylamino)-4-(2-furyl)thiazol-5-yl tetrahydropyran-4-yl ketone (Compound 627)

In a manner similar to that in Example 623, by using 2-iodo-2-methylpropane in place of methyl iodide and using N-methoxy-N-methyltetrahydropyran-4-carboxamide in place of 2-ethoxy-N-methoxy-N-methylacetamide, tert-butyl N-(tert-butyl)-N-[4-(2-furyl)-5-(tetrahydropyran-4-ylcarbonyl)thiazol-2-yl]carbamate was obtained from Compound h obtained in Reference Example 8. In a manner similar to that in Example 624, the entitled Compound 627 was obtained from tert-butyl N-(tert-butyl)-N-[4-(2-furyl)-5-(tetrahydropyran-4-ylcarbonyl)thiazol-2-yl]carbamate obtained herein in place of Compound 623.
¹H NMR (CDCl₃, δ ppm): 1.49 (s, 9H), 1.72-1.96 (m, 4H), 3.05 (tt, J=3.8, 11.1 Hz, 1H), 3.41 (ddd, J=2.3, 11.1, 11.1 Hz, 2H), 4.02 (ddd, J=2.3, 4.0, 11.1 Hz, 2H), 5.84 (br s, 1H), 6.55 (dd, J=1.8, 3.5 Hz, 1H), 7.48 (d, J=3.5 Hz, 1H), 7.54 (d, J=1.8 Hz, 1H).

Example 628

4-(2-Furyl)-2-(2,2,4,4-tetramethylbutylamino)thiazol-5-yl tetrahydropyran-4-yl ketone (Compound 628)

In a manner similar to that in Example 623, by using 2-chloro-2,2,4,4-tetramethylbutane in place of methyl iodide and using N-methoxy-N-methyltetrahydropyran-4-carboxamide in place of 2-ethoxy-N-methoxy-N-methylacetamide, tert-butyl N-[4-(2-furyl)-5-(tetrahydropyran-4-ylcarbonyl)thiazol-2-yl]-N-(2,2,4,4-tetramethylbutylamino)carbamate was obtained from Compound h obtained in Reference Example 8. In a manner similar to that in Example 624, the entitled Compound 628 was obtained from tert-butyl N-[4-(2-furyl)-5-(tetrahydropyran-4-ylcarbonyl)thiazol-2-yl]-N-(2,2,4,4-tetramethylbutylamino)carbamate obtained herein in place of Compound 623.
¹H NMR (CDCl₃, δ ppm): 1.03 (s, 9H), 1.50 (s, 6H), 1.71-1.80 (m, 4H), 1.80 (s, 2H), 3.05 (tt, J=3.9, 11.2 Hz, 1H), 3.40 ddd, J=1.6, 11.6, 11.6 Hz, 2H), 3.95-4.10 (m, 2H), 5.87 br s, 1H), 6.55 (dd, J=1.8, 3.5 Hz, 1H), 7.45 (d, J=3.5 Hz, 1H), 7.54 (d, J=1.8 Hz, 1H).

Example 629

N-[4-(2-Furyl)-5-(4-hydroxy-1-methylpiperidin-4-yl)thiazol-2-yl]benzamide (Compound 629)

In a manner similar to that in Example 92, by using 1-methyl-4-piperidone (1.39 mL, 113 mmol) in place of DMF, the entitled Compound 629 (48.5 mg, 4%) was obtained from N-[5-bromo-4-(2-furyl)thiazol-2-yl]benzamide (1.13 g, 3.23 mmol) obtained in Step 1 of Reference Example 14 in place of Compound h.
¹H NMR (CDCl₃, δ ppm): 2.03-2.39 (m, 4H), 2.37 (s, 3H), 2.59-2.67 (m, 2H), 2.70-2.83 (m, 2H), 6.44 (dd, J=1.9, 3.5 Hz, 1H), 6.75 (dd, J=0.5, 3.5 Hz, 1H), 7.41-7.50 (m, 2H), 7.45 (dd, J=0.5, 1.9 Hz, 1H), 7.52-7.60 (m, 1H), 7.84-7.91 (m, 2H).

Example 630

2-Amino-4-(2-pyridyl)thiazol-5-yl 2-pyridyl ketone (Compound 630)

1,3-Di(2-pyridyl)propane-1,3-dione (1.17 g, 5.15 mmol) was dissolved in acetic acid (20 mL), and bromine (856 mg, 5.35 mmol) was added thereto, followed by stirring at 80° C. for 1 hour. The reaction mixture was concentrated under reduced pressure, and the resulting residue was suspended in ethanol (30 mL), and triethylamine (0.750 mL, 5.38 mmol) and thiourea (416 mg, 5.47 mmol) were added thereto, followed by stirring under heating and reflux for 30 minutes. Aqueous saturated sodium hydrogencarbonate solution was added to the reaction mixture, followed by extraction with chloroform. The solvent was distilled away under reduced pressure, and the resulting residue was purified through silica gel column chromatography (chloroform:methanol=9:1) to afford the entitled Compound 630 (739 mg, 51%).
¹H NMR (DMSO-d₆, δ ppm): 7.09-7.27 (m, 2H), 7.32-7.37 (m, 1H), 7.58 (d, J=0.9, 7.8 Hz, 1H), 7.70-7.75 (m, 2H), 7.80-7.88 (m, 1H), 8.01 (br s, 2H), 8.15 (d, J=4.8 Hz, 1H).

Example 631

N-[4-(2-Pyridyl)-5-(pyridin-2-ylcarbonyl)thiazol-2-yl]pyridine-4-carboxamide (Compound 631)

In a manner similar to that in Example 1, by using Compound 630 (739 mg, 2.62 mmol) in place of Compound a, the entitled Compound 631 (680 mg, 67%) was obtained.
¹H NMR (DMSO-d₆, δ ppm): 7.19-7.24 (m, 1H), 7.45-7.50 (m, 1H), 7.82-7.85 (m, 2H), 7.96-7.98 (m, 2H), 8.05 (d, J=6.0 Hz, 2H), 8.12 (d, J=4.6 Hz, 1H), 8.32 (d, J=4.6 Hz, 1H), 8.85 (d, J=6.0 Hz, 2H), 13.5 (br s, 1H).
ESIMS m/z: [M+H]⁺ 388.
m.p.: 232-234° C.

Example 632 tert-Butyl N-[4-phenyl-5-(pyridin-2-ylcarbonyl)thiazol-2-yl]carbamate (Compound 632)

Step 1:

In a manner similar to that in Reference Example 7, by using acetophenone (3.18 g, 26.5 mmol) in place of 2-acetylfuran, 2-amino-5-bromo-4-phenylthiazole (3.56 g, 53%) was obtained.
¹H NMR (CDCl₃, δ ppm): 5.03 (br s, 2H), 7.31-7.44 (m, 3H), 7.84 (dd, J=1.6, 8.4 Hz, 2H).

Step 2:

In a manner similar to that in Step 1 of Example 92, by using 2-amino-5-bromo-4-phenylthiazole (691 mg, 2.71 mmol) obtained in Step 1 in place of Compound g, tert-butyl N-[5-bromo-4-phenylthiazol-2-yl]carbamate (499 mg, 52%) was obtained.
¹H NMR (DMSO-d₆, δ ppm): 1.50 (s, 9H), 7.37-7.50 (m, 3H), 7.83 (d, J=6.7 Hz, 2H).

Step 3:

In a manner similar to that in Example 185, by using tert-butyl N-[5-bromo-4-phenylthiazol-2-yl]carbamate (499 mg, 1.41 mmol) obtained in Step 2 in place of Compound h, the entitled Compound 632 (355 mg, 66%) was obtained.

¹H NMR (CDCl₃, δ ppm): 1.55 (s, 9H), 7.35-7.46 (m, 4H), 7.55-7.59 (m, 2H), 7.76-7.86 (m, 1H), 8.00-8.06 (m, 1H), 8.31 (br s, 1H), 8.63-8.67 (m, 1H).

Example 633

2-Amino-4-phenylthiazol-5-yl 2-pyridyl ketone (Compound 633)

In a manner similar to that in Example 186, by using Compound 632 (355 mg, 0.931 mmol) in place of Compound 185, the entitled Compound 633 (256 mg, 98%) was obtained.

¹H NMR (DMSO-d₆, δ ppm): 7.28-7.21 (m, 3H), 7.40 (d, J=7.4 Hz, 2H), 7.47 (dd, J=7.0, 7.7 Hz, 1H), 7.79 (d, J=7.7 Hz, 1H), 7.89 (dd, J=7.0, 7.7 Hz, 1H), 8.03 (br s, 2H), 8.45 (d, J=7.0 Hz, 1H).

Example 634

N-[4-Phenyl-5-(pyridin-2-ylcarbonyl)thiazol-2-yl] pyridine-4-carboxamide (Compound 634)

In a manner similar to that in Example 187, by using Compound 633 (256 mg, 0.911 mmol) in place of Compound 186, the entitled Compound 634 (247 mg, 70%) was obtained.

¹H NMR (DMSO-d₆, δ ppm): 7.35-7.38 (m, 3H), 7.54-7.57 (m, 2H), 7.61-7.66 (m, 1H), 8.00-8.03 (m, 2H), 8.04 (dd, J=1.3, 4.6 Hz, 2H), 8.67 (d, J=4.8 Hz, 1H), 8.84 (dd, J=1.3, 4.6 Hz, 2H), 13.39 (br s, 1H).
ESIMS m/z: [M+H]⁺ 387.
m.p.: 231-235° C.

Reference Example 1

2-Amino-4-(2-furyl)-5-(4-pyridyl)thiazole (Compound a)

Step 1:
1-(2-Furyl)-2-(4-pyridyl)ethane (4.15 g, 22.2 mmol) obtained according to the method described in WO03/35639 was dissolved in acetic acid (22 mL), and bromine (3.54 g, 22.2 mmol) was added thereto, followed by stirring at 80° C. for 1 hour. The reaction mixture was cooled with ice in water, and then ethyl acetate was added thereto. The precipitated crystals were collected by filtration to afford 2-bromo-1-(2-furyl)-2-(4-pyridyl)ethanone hydrobromide (7.59 g, 99%).

¹H NMR (DMSO-d₆, δ ppm): 6.58 (dd, J=1.7, 3.7 Hz, 1H), 7.01 (1H, s), 7.91 (dd, J=0.8, 3.7 Hz, 1H), 8.19 (dd, J=0.8, 1.7 Hz, 1H), 8.21 (d, J=5.6 Hz, 2H), 8.97 (d, J=5.6 Hz, 2H).

Step 2:
2-Bromo-1-(2-furyl)-2-(4-pyridyl)ethanone hydrobromide (7.59 g, 21.9 mmol) was suspended in ethanol (110 mL), and triethylamine (3.35 mL, 24.1 mmol) was added thereto, followed by stirring at room temperature for 30 minutes. Thiourea (1.83 g, 24.1 mmol) was added to the reaction mixture, followed by stirring under heating and reflux for 30 minutes. The reaction mixture was allowed to cool down to room temperature, and then a saturated aqueous solution of sodium hydrogencarbonate was added thereto, followed by extraction with chloroform. The organic layer was washed with a saturated aqueous solution of sodium chloride and dried over anhydrous magnesium sulfate, and then the solvent was distilled away under reduced pressure. The resulting residue was purified through silica gel column chromatography (chloroform:methanol=10:1) to afford the entitled Compound a (5.10 g, 96%) as pale yellow crystals.

¹H NMR (DMSO-d₆, δ ppm): 6.55 (dd, J=1.7, 3.3 Hz, 1H), 6.63 (dd, J=0.7, 3.3 Hz, 1H), 7.34 (dd, J=1.7, 6.3 Hz, 2H), 7.43 (br s, 2H), 7.60 (dd, J=0.7, 1.7 Hz, 1H), 8.50 (dd, J=1.7, 6.3 Hz, 2H).

Reference Example 2

2-Amino-4-(2-furyl)-5-(2-pyridyl)thiazole (Compound b)

In a manner similar to that in Reference Example 1, the entitled Compound b (155 mg, 13%, 2 steps) was obtained from 1-(2-furyl)-2-(2-pyridyl)ethanone (936 mg, 5.00 mmol) in place of 1-(2-furyl)-2-(4-pyridyl)ethanone.

¹H NMR (DMSO-d₆, δ ppm): 6.56 (dd, J=1.8, 3.3 Hz, 1H), 6.62 (dd, J=0.7, 3.3 Hz, 1H), 7.26 (dd, J=1.7, 4.4 Hz, 2H), 7.44 (br s, 2H), 7.60 (dd, J=0.7, 1.8 Hz, 1H), 8.50 (dd, J=1.7, 4.4 Hz, 2H).

Reference Example 3

2-Amino-4-(2-furyl)-5-phenylthiazole (Compound c)

In a manner similar to that in Reference Example 1, the entitled Compound c (1.47 g, 41%, 2 steps) was obtained from 1-(2-furyl)-2-phenylethanone (2.75 g, 14.8 mmol) in place of 1-(2-furyl)-2-(4-pyridyl)ethanone.

¹H NMR (DMSO-d₆, δ ppm): 6.43-6.47 (m, 2H), 7.14 (br s, 2H), 7.28-7.35 (m, 5H), 7.49 (d, J=1.7 Hz, 1H).

Reference Example 4

2-Amino-5-benzyl-4-(2-furyl)thiazole hydrobromide (Compound d)

In a manner similar to that in Step 1 of Reference Example 1, by using 1-(2-furyl)-3-phenylpropanone (1.19 g, 5.94 mmol) in place of 1-(2-furyl)-2-(4-pyridyl)ethanone, 2-bromo-1-(2-furyl)-3-phenylpropanone (1.66 g, 5.94 mmol) was obtained. The resulting Compound was dissolved in acetonitrile (15 mL), thiourea (0.49 g, 6.44 mmol) was added thereto, followed by stirring under heating and reflux for 1 hour. The reaction mixture was allowed to cool down to room temperature, and the precipitated solid was collected by filtration to afford the entitled Compound d (1.21 g, 60

¹H NMR (DMSO-d₆, δ ppm): 4.25 (s, 2H), 6.70 (dd, J=1.7, 3.3 Hz, 1H), 6.91 (dd, J=3.3 Hz, 1H), 7.27-7.35 (m, 5H), 7.90 (d, J=1.7 Hz, 1H), 9.05 (br s, 2H).

Reference Example 5

2-Amino-5-(ethoxycarbonyl)-4-(2-furyl)thiazole hydrobromide (Compound e)

In a manner similar to that in Reference Example 4, the entitled Compound e (2.91 g, 61%) was obtained from ethyl froylacetate (2.73 g, 15 mmol) in place of 1-(2-furyl)-2-(4-pyridyl)ethanone.

$^1$H NMR (DMSO-$d_6$, δ ppm): 1.25 (t, J=7.2 Hz, 3H), 4.19 (q, J=7.2 Hz, 2H), 6.63 (dd, J=1.7, 3.5 Hz, 1H), 7.50 (dd, J=0.7, 3.5 Hz, 1H), 7.67 (br s, 2H), 7.79 (dd, J=0.7, 1.7 Hz, 1H).

Reference Example 6

2-Amino-4-(2-furyl)-5-methylthiazole (Compound f)

In a manner similar to that in Reference Example 1, the entitled Compound f (245 mg, 34%) was obtained from 1-(2-furyl)propanoe (500 mg, 4.03 mmol) in place of 1-(2-furyl)-2-(4-pyridyl)ethanone.

$^1$H NMR (CDCl$_3$, δ ppm): 2.48 (s, 3H), 4.82 (br s, 2H), 6.45 (dd, J=1.8, 3.3 Hz, 1H), 6.53 (dd, J=0.7, 3.3 Hz, 1H), 7.43 (dd, J=0.7, 1.8 Hz, 1H)

Reference Example 7

2-Amino-5-bromo-4-(2-furyl)thiazole (Compound g)

Step 1:

2-Acetylfuran (5.1 g, 4.6.0 mmol) was dissolved in a mixed solvent of dichloromethane (50 mL) and methanol (50 mL), and tetra(n-butyl)ammonium bromide (22.3 g, 46.0 mmol) was added thereto, followed by stirring at room temperature for 1 hour. The reaction mixture was concentrated under reduced pressure, water was added to the resulting residue, followed by extraction with ethyl acetate. The organic layer was washed with a saturated aqueous solution of sodium chloride and dried over anhydrous magnesium sulfate, and then the solvent was distilled away under reduced pressure. The resulting residue was dissolved in acetonitrile (60 mL), thiourea (3.5 g, 46.0 mmol) was added thereto, followed by stirring at room temperature for 30 minutes. The precipitated solid was collected by filtration, and the resulting solid was dissolved in a mixed solvent of a saturated aqueous solution of sodium hydrogencarbonate and ethyl acetate, and subjected to liquid-liquid separation. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=3:1) to afford 2-amino-4-(2-furyl)thiazole (1.53 g, 20%).

$^1$H NMR (CDCl$_3$, δ ppm): 5.17 (br s, 2H), 6.43 (dd, J=2.0, 3.3 Hz, 1H), 6.61 (d, J=3.3 Hz, 1H), 6.69 (s, 1H), 7.49 (d, J=2.0 Hz, 1H).

Step 2:

2-Amino-4-(2-furyl)thiazole (330 mg, 1.99 mmol) obtained in Step 1 was suspended in chloroform (4 mL), and N-bromosuccinimide (360 mg, 2.02 mmol) was added thereto, followed by stirring at room temperature for 1 hour. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure to afford the entitled Compound g (438 mg, 90%).

$^1$H NMR (CDCl$_3$, δ ppm): 5.08 (br s, 2H), 6.48 (dd, J=2.0, 3.3 Hz, 1H), 6.96 (d, J=3.3 Hz, 1H), 7.48 (d, J=2.0 Hz, 1H).

Reference Example 8 tert-Butyl N-[5-bromo-4-(2-furyl)thiazol-2-yl]carbamate (Compound h)

Compound g (12.0 g, 49.0 mmol) obtained in Reference Example 7, di-tert-butyl dicarbonate (21.3 g, 97.9 mmol), triethylamine (17.1 mL, 122 mmol) and N,N-dimethylaminopyridine (0.60 g, 4.91 mmol) were dissolved in DMI (200 mL), followed by stirring overnight at room temperature. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=5:1) to afford the entitled Compound h (14.2 g, 84%).

$^1$H NMR (DMSO-$d_6$, δ ppm): 1.49 (s, 9H), 6.64 (dd, J=2.0, 3.3 Hz, 1H), 6.91 (dd, J=0.7, 3.3 Hz, 1H), 7.80 (dd, J=0.7, 2.0 Hz, 1H).

Reference Example 9

2-Amino-5-bromo-4-(5-bromo-2-furyl)thiazole (Compound i)

Compound g (500 mg, 2.04 mmol) obtained in Reference Example 7 was dissolved in DMF (10 mL), and N-bromosuccinimide (363 mg, 2.04 mmol) was added thereto, followed by stirring at room temperature for 1 hour. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=4:1) to afford the entitled Compound j (379 mg, 57%).

$^1$H NMR (CDCl$_3$, δ ppm): 5.16 (br s, 2H), 6.44 (d, J=3.3 Hz, 1H), 6.91 (d, J=3.3 Hz, 1H)

Reference Example 10

N-[5-Bromo-4-(2-furyl)thiazol-2-yl]pyridine-4-carboxamide (Compound j)

In a manner similar to that in Example 1, by using Compound g (332 mg, 1.36 mmol) obtained in Reference Example 7 in place of Compound a, the entitled Compound k (382 mg, 81%) was obtained.

$^1$H NMR (DMSO-$d_6$, δ ppm): 6.68 (dd, J=1.8, 3.5 Hz, 1H), 7.01 (d, J=3.5 Hz, 1H), 7.85 (d, J=1.8 Hz, 1H), 8.01 (d, J=4.8 Hz, 2H), 8.82 (d, J=4.8 Hz, 2H), 13.48 (br s, 1H).

ESIMS m/z: [$^{79}$BrM−H]$^-$ 348, [$^{81}$BrM−H]$^-$ 350.

Reference Example 11

2-Methoxyisonicotinic acid (Compound k)

Methyl 2-methoxyisonicotinate (6.35 g, 38.0 mmol) obtained according to the method described in U.S. Pat. No. 6,509,361 was dissolved in a mixed solvent of methanol (39 mL) and water (13 mL), and lithium hydroxide monohydrate (7.97 g, 190 mmol) was added thereto, followed by stirring at room temperature for 2 hours. Methanol was distilled away under reduced pressure, and 4 mol/L hydrochloric acid added to the resulting aqueous solution adjust the pH to 3. The precipitated solid was collected by filtration to afford the entitled Compound k (4.72 g, 81%) as a white solid.

$^1$H NMR (DMSO-d$_6$, δ ppm): 3.90 (s, 3H), 7.19 (d, J=1.3 Hz, 1H), 7.39 (dd, J=5.3, 1.9 Hz, 1H), 8.dd (d, J=5.3 Hz, 1H).

APCIMS m/z: [M+H]$^+$ 154.

Reference Example 12

2-(4-Methoxybenzyloxy)isonicotinic acid (Compound 1)

55% sodium hydride (2.49 g, 0.0570 mmol) was suspended in DMF (19 mL), and under ice-cooling, 4-methoxybenzyl alcohol (7.12 mL, 0.057 mmol) was added thereto, followed by stirring at room temperature for 1 hour. 2-Chloroisonicotinic acid (3.00 g, 0.0190 mmol) was added to the reaction mixture, followed by stirring at 80° C. for 2 hours. The reaction mixture was poured into a mixture of a saturated aqueous solution of sodium chloride (60 mL) and water (60 mL), and 10% hydrochloric acid was added to the resulting solution to adjust the pH to 5, followed by stirring under ice-cooling for 1 hour. The precipitated solid was collected by filtration to afford the entitled Compound 1 (5.26 g, quantitative) as a white solid.

$^1$H NMR (DMSO-d$_6$, δ ppm): 3.75 (s, 3H), 5.31 (s, 2H), 6.94 (d, J=8.1 Hz, 2H), 7.21 (s, 1H), 7.39 (d, J=5.4 Hz, 1H), 7.40 (d, J=8.1 Hz, 2H), 8.34 (d, J=5.4 Hz, 1H).

APCIMS m/z: [M+H]$^+$ 260.

Reference Example 13

2-Amino-4-(2-furyl)-5-(2-methylpyridin-4-yl)thiazole (Compound m)

Step 1:

3,4-Dimethylpyridine (2.25 mL, 20.0 mmol) and ethyl furan-2-carboxylate (5.02 mL, 40.0 mmol) were dissolved in THF (20 mL), and at 0° C., a 1.0 mol/L solution of lithium hexamethyldisilazide in THF (40.0 mL, 40.0 mmol) was added dropwise thereto, followed by stirring at room temperature for 1.5 hours. The reaction mixture was poured into a saturated aqueous solution of ammonium chloride, followed by extraction with ethyl acetate. The organic layer was washed successively with a saturated aqueous solution of ammonium chloride and a saturated aqueous solution of sodium chloride and dried over anhydrous magnesium sulfate, and then the solvent was distilled away under reduced pressure. The resulting residue was purified through silica gel column chromatography (hexane:ethyl acetate=1:2) to afford 1-(2-furyl)-2-(3-methylpyridin-4-yl)ethanone (3.34 g, 16.6 mmol).

$^1$H NMR (CDCl$_3$, δ ppm): 2.32 (s, 3H), 4.18 (s, 2H), 6.58 (dd, J=1.8, 3.6 Hz, 1H), 7.11 (d, J=5.0 Hz, 1H), 7.26 (dd, J=0.7, 3.6 Hz, 1H), 7.62 (dd, J=0.7, 1.8 Hz, 1H), 8.38 (d, J=5.0 Hz, 1H), 8.41 (s, 1H).

APCIMS m/z: [M+H]$^+$ 260.

Step 2:

In a manner similar to that in Reference Example 1, by using 1-(2-furyl)-2-(3-methylpyridin-4-yl)ethanone (1.61 g, 8.00 mmol) obtained in Step 1 in place of 1-(2-furyl)-2-(4-pyridyl)ethanone, the entitled Compound m (1.67 g, 81%) was obtained.

$^1$H NMR (DMSO-d$_6$, δ ppm): 2.05 (s, 3H), 6.39 (dd, J=0.8, 3.5 Hz, 1H), 6.45 (dd, J=1.7, 3.5 Hz, 1H), 7.25 (d, J=5.0 Hz, 1H), 7.29 (br s, 2H), 7.46 (dd, J=0.8, 1.7 Hz, 1H), 8.39 (d, J=5.0 Hz, 1H), 8.48 (s, 1H).

Reference Example 14

N-[4-(2-Furyl)-5-iodothiazol-2-yl]benzamide (Compound n)

Step 1:

Compound g (10.0 g, 40.8 mmol) obtained in Reference Example 7 was dissolved in pyridine (136 mL), and under ice-cooling, 4-dimethylaminopyridine (250 mg, 2.04 mmol) and benzoyl chloride (8.05 mL, 69.4 mmol) were added thereto, followed by stirring at room temperature for 30 minutes. Water was added to the reaction mixture, followed by extraction with ethyl acetate. The organic layer was dried over anhydrous magnesium sulfate, and then the solvent was distilled away under reduced pressure. The resulting residue was purified through silica gel column chromatography (hexane: ethyl acetate=10:1) to afford N-[5-bromo-4-(2-furyl)thiazol-2-yl]benzamide (12.0 g, 84%) as a white solid.

$^1$H NMR (CDCl$_3$, δ ppm): 6.67 (dd, J=1.6, 3.5 Hz, 1H), 7.01 (d, J=3.5 Hz, 1H), 7.46-7.71 (m, 3H), 7.84 (d, J=1.6 Hz, 1H), 8.09-8.17 (m, 2H).

Step 2:

In a manner similar to that in Example 92, by using iodine (26.3 g, 104 mmol) in place of DMF and using N-[5-bromo-4-(2-furyl)thiazol-2-yl]benzamide (10.3 g, 29.6 mmol) obtained in Step 1 in place of Compound h, the entitled Compound n (6.56 g, 56%) was obtained as a white solid.

$^1$H NMR (CDCl$_3$, δ ppm): 6.48 (dd, J=1.8, 3.3 Hz, 1H), 7.15 (d, J=3.3 Hz, 1H), 7.42-7.65 (m, 3H), 7.45 (d, J=1.8 Hz, 1H), 7.85-7.93 (m, 2H), 10.04 (br s, 1H).

Reference Example 15

2-Amino-4-(2-furyl)-5-(2-methylphenyl)thiazole (Compound o)

Step 1:

At 0° C., trimethylsilylcyanide (3.52 mL, 26.4 mmol) was added to a mixture of dried zinc iodide (100 mg) and furfural (1.99 mL, 24.0 mmol), followed by stirring at 0° C. for 30 minutes. THF (20 mL) was added to the reaction mixture, and at −78° C., a 1.0 mol/L solution of lithium hexamethyldisilazide in THF (24.0 mL, 24.0 mmol) was added dropwise thereto, followed by stirring at the same temperature for 15 minutes. A solution (10 mL) of 2-methylbenzyl bromide (2.68 mL, 20.0 mmol) in THF was added to the reaction mixture, followed by stirring at room temperature for 1 hour. 1.0 mol/L tetra(n-butyl)ammonium fluoride (26.4 mL, 26.4 mmol) was added to the reaction mixture, followed by stirring at room temperature for 30 minutes. A saturated aqueous solution of ammonium chloride was added to the reaction mixture, followed by extraction with ethyl acetate. The organic layer was washed successively with a saturated aqueous solution of ammonium chloride and a saturated aqueous solution of sodium chloride and dried over anhydrous magnesium sulfate, and then the solvent was distilled away under reduced pressure. The resulting residue was purified through silica gel column chromatography (hexane:ethyl acetate=4:1) to afford 1-(2-furyl)-2-(2-methylphenyl)ethanone (3.33 g, 83%).

$^1$H NMR (CDCl$_3$, δ ppm): 2.31 (s, 3H), 4.16 (s, 2H), 6.53 (dd, J=1.8, 3.6 Hz, 1H), 7.15-7.21 (,m, 5H), 7.59 (dd, J=0.8, 1.8 Hz, 1H)

Step 2:

In a manner similar to that in Reference Example 1, by using 1-(2-furyl)-2-(2-methylphenyl)ethanone (3.33 g, 16.6 mmol) obtained in Step 1 in place of 1-(2-furyl)-2-(4-pyridyl)ethanone, the entitled Compound o (1.62 g, 38%) was obtained.

Reference Example 16

2-Amino-4-(2-furyl)-5-(2-oxo-1,2-dihydropyridin-4-yl)thiazole (Compound p)

Step 1:

In a manner similar to that in Reference Example 1, by using 2-(2-fluoropyridin-4-yl)-1-(2-furyl)ethanone (6.16 g, 30.0 mmol) obtained according to the method described in WO03/35639, in place of 1-(2-furyl)-2-(4-pyridyl)ethanone, 2-amino-5-(2-fluoropyridin-4-yl)-4-(2-furyl)thiazole (4.86 g, 62%) was obtained.

APCIMS m/z: [M+H]$^+$ 262.

Step 2:

2-Amino-5-(2-fluoropyridin-4-yl)-4-(2-furyl)thiazole (2.00 g, 7.65 mmol) obtained in Step 1 was suspended in 6 mol/L hydrochloric acid (20 mL), followed by stirring under heating and reflux for 1 hour. The reaction mixture was neutralized with aqueous 10 mol/L sodium hydroxide solution added thereto, and the precipitated solid was collected by filtration. The resulting solid was purified through silica gel column chromatography (chloroform:methanol=17:3) to afford the entitled Compound p (1.01 g, 51%) as a yellow solid.

$^1$H NMR (DMSO-$d_6$, δ ppm): 5.98 (dd, J=1.8, 6.9 Hz, 1H), 6.18 (d, J=1.8 Hz, 1H), 6.56 (dd, J=1.7, 3.5 Hz, 1H), 6.62 (d, J=3.5 Hz, 1H), 7.28 (d, J=6.9 Hz, 1H), 7.42 (br s, 2H), 7.65 (d, J=1.7 Hz, 1H), 11.44 (br s, 1H).

APCIMS m/z: [M+H]$^+$ 260.

Reference Example 17

2-Amino-4-(2-furyl)-5-(2-oxo-1,2-dihydropyridin-5-yl)thiazole (Compound q)

Step 1:

In a manner similar to that in Reference Example 1, by using 2-(2-chloropyridin-5-yl)-1-(2-furyl)ethanone (13.8 g, 62.0 mmol) obtained according to the method described in WO03/35639, in place of 1-(2-furyl)-2-(4-pyridyl)ethanone, 2-amino-5-(2-chloropyridin-5-yl)-4-(2-furyl)thiazole (11.6 g, 67%) was obtained.

$^1$H NMR (DMSO-$d_6$, δ ppm): 6.52 (dd, J=1.7, 3.5 Hz, 1H), 6.57 (d, J=3.5 Hz, 1H), 7.36 (br s, 2H), 7.50-7.52 (m, 2H), 7.80 (dd, J=2.6, 8.3 Hz, 1H), 8.37 (d, J=2.6 Hz, 1H).

APCIMS m/z: [$^{35}$ClM+H]$^+$ 278, [$^{37}$ClM+H]$^+$ 280.

Step 2:

2-Amino-5-(2-chloropyridin-5-yl)-4-(2-furyl)thiazole (2.22 g, 80.0 mmol) obtained in Step 1 and a methanol solution of 28% sodium methoxide (4.63 g, 24.0 mmol) were suspended in 1,4-dioxane (8 mL), followed by stirring at 95° C. for 2 hours. The reaction mixture was concentrated under reduced pressure, and the resulting residue was purified through silica gel column chromatography (chloroform:methanol=9:1) to afford 2-amino-4-(2-furyl)-5-(2-methoxypyridin-5-yl)thiazole (1.32 g, 60%).

$^1$H NMR (DMSO-$d_6$, δ ppm): 3.88 (s, 3H), 6.47-6.49 (m, 2H), 6.84 (d, J=8.4 Hz, 1H), 7.20 (br s, 2H), 7.51 (d, J=1.2 Hz, 1H), 7.66 (dd, J=2.5, 8.6 Hz, 1H), 8.16 (d, J=2.5 Hz, 1H).

APCIMS m/z: [M+H]$^+$ 274.

Step 3:

2-Amino-4-(2-furyl)-5-(2-methoxypyridin-5-yl)thiazole (1.32 g, 4.83 mmol) obtained in Step 2 was suspended in a mixture of 48% hydrobromic acid (4 mL) and acetic acid (4 mL), followed by stirring at 100° C. for 2 hours. The reaction mixture was neutralized with a 10 mol/L aqueous solution of sodium hydroxide added thereto, and the precipitated solid was collected by filtration. The resulting solid was purified through silica gel column chromatography (chloroform:methanol=4:1) to afford the entitled Compound q (870 mg, 70%).

$^1$H NMR (DMSO-$d_6$, δ ppm): 6.33 (d, J=9.2 Hz, 1H), 6.47-6.49 (m, 2H), 7.14 (br s, 2H), 7.35-7.39 (m, 2H), 7.56 (dd, J=0.8, 1.7 Hz, 1H), 11.78 (br s, 1H).

APCIMS m/z: [M+H]$^+$ 260.

Reference Example 18

2-Amino-5-(1-ethyl-6-oxo-1,6-dihydropyridin-2-yl)-4-(2-furyl)thiazole (Compound r)

Step 1:

Ethyl 6-oxo-1,6-dihydropyridine-2-carboxylate (16.7 g, 100 mmol) obtained according to the method described in *Heterocycles*, Vol. 24, p. 2169, 1986, was dissolved in DMF (200 mL), and potassium carbonate (20.7 g, 150 mmol) was added thereto, followed by stirring at room temperature for 1 hour. Ethyl iodide (16.0 mL, 200 mmol) was added to the reaction mixture, followed by stirring at 60° C. for 3 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford ethyl 1-ethyl-6-oxo-1,6-dihydropyridine-2-carboxylate (3.17 g, 16%).

Step 2:

Ethyl 1-ethyl-6-oxo-1,6-dihydropyridine-2-carboxylate (2.25 g, 11.5 mmol) obtained in Step 1 was dissolved in ethanol (50 mL), and at 0° C., calcium chloride (2.56 g, 23.1 mmol) and sodium borohydride (2.18 g, 57.6 mmol) were added thereto, followed by stirring at 0° C. for 2 hours. The reaction mixture was concentrated under reduced pressure, and a saturated aqueous solution of ammonium chloride was added to the resulting residue, followed by stirring at room temperature for 30 minutes. The reaction mixture was extracted with chloroform. The organic layer was dried over anhydrous magnesium sulfate, and then the solvent was distilled away under reduced pressure. The resulting residue was purified through silica gel column chromatography (chloroform:methanol=49:1) to afford 1-ethyl-6-(hydroxymethyl)-2-oxo-1,2-dihydropyridine (1.51 g, 76%).

$^1$H NMR (CDCl$_3$, δ ppm): 1.31 (t, J=7.0 Hz, 3H), 4.14 (q, J=7.0 Hz, 2H), 3.22 (t, J=5.7 Hz, 1H), 4.60 (d, J=5.7 Hz, 1H), 6.27 (dd, J=1.4, 7.0 Hz, 1H), 6.49 (dd, J=1.4, 9.2 Hz, 1H), 7.27 (dd, J=7.0, 9.2 Hz, 1H).

APCIMS m/z: [M+H]$^+$ 154.

Step 3:

1-Ethyl-6-(hydroxymethyl)-2-oxo-1,2-dihydropyridine (1.51 g, 9.86 mmol) obtained in Step 2 and triethylamine (2.06 mL, 14.8 mmol) were dissolved in dichloromethane (40 mL), and at 0° C., methanesulfonyl chloride (0.920 mL, 11.8 mmol) was added dropwise thereto, followed by stirring at 0° C. for 30 minutes. Water was added to the reaction mixture, followed by extraction with chloroform. The organic layer was washed with a saturated aqueous solution of sodium chloride and dried over anhydrous magnesium sulfate, and then the solvent was distilled away under reduced pressure to afford 1-ethyl-6-(methanesulfonyloxymethyl)-2-oxo-1,2-dihydropyridine (2.29 g, 100%).

$^1$H NMR (CDCl$_3$, δ ppm): 1.36 (t, J=7.5 Hz, 3H), 3.07 (s, 3H), 4.12 (q, J=7.5 Hz, 2H), 5.13 (s, 2H), 6.32 (dd, J=1.5, 6.6 Hz, 1H), 6.65 (dd, J=1.5, 9.3 Hz, 1H), 7.29 (dd, J=6.6, 9.3 Hz, 1H).

APCIMS m/z: [M+H]$^+$ 232.

Step 4:

In a manner similar to that Reference Example 15, by using 1-ethyl-6-(methanesulfonyloxymethyl)-2-oxo-1,2-dihydropyridine (2.23 g, 9.86 mmol) obtained in Step 3 in place of 2-methylbenzyl bromide, the entitled Compound r (913 mg, 32%) was obtained.

$^1$H NMR (DMSO-d$_6$, δ ppm): 1.01 (t, J=6.9 Hz, 3H), 3.30-3.50 (m. 2H), 6.29 (dd, J=1.5, 6.9 Hz, 1H), 6.43-6.49 (m, 3H), 7.39 (dd, J=6.9, 9.0 Hz, 1H), 7.44-7.46 (br s, 2H), 7.54-7.56 (m, 1H).

APCIMS m/z: [M+H]$^+$ 288.

Reference Example 19

2-Amino-5-(1-ethyl-6-oxo-1,6-dihydropyridazin-3-yl)-4-(2-furyl)thiazole (Compound s)

Step 1:

2-Acetylfuran (3.30 g, 30.0 mmol) was dissolved in THF (30 mL), and cooled to −78° C. A 1.0 mol/L solution of lithium hexamethyldisilazide in THF (33.3 mL, 33.0 mmol) was added thereto, and heated up to room temperature, and then stirred at room temperature for 15 minutes. The reaction mixture was cooled to −78° C., and a solution of 1-ethyl-6-oxo-3-(trifluoromethanesulfonyloxy)-1,6-dihydropyridazine (4.08 g, 15.0 mmol) in THF (5 mL) obtained according to the method described in WO03/039451 was added dropwise thereto, followed by stirring at room temperature for 1.5 hours. The reaction mixture was poured into water, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=1:1) to afford 2-(1-ethyl-6-oxo-1,6-dihydro-3-pyridazinyl)-1-(2-furyl)ethanone (1.01 g, 29%).

$^1$H NMR (CDCl$_3$, δ ppm): 1.33 (t, J=7.3 Hz, 3H), 4.13 (s, 2H), 4.16 (q, J=7.3 Hz, 2H), 6.57 (dd, J=1.8, 3.6 Hz, 1H), 6.88 (d, J=9.6 Hz, 1H), 7.21 (d, J=9.6 Hz, 1H), 7.29 (d, J=3.6 Hz, 1H), 7.62 (d, J=1.8 Hz, 1H).

Step 2:

In a manner similar to that in Reference Example 1, by using 2-(1-ethyl-6-oxo-1,6-dihydropyridazin-3-yl)-1-(2-furyl)ethanone (1.00 g, 4.31 mmol) obtained in Step 1, in place of 1-(2-furyl)-2-(4-pyridyl)ethanone, the entitled Compound s (191 mg, 14%) was obtained.

$^1$H NMR (CDCl$_3$, δ ppm): 1.38 (t, J=7.0 Hz, 3H), 4.20 (q, J=7.0 Hz, 2H), 5.41 (br s, 2H), 6.47 (dd, J=1.8, 3.3 Hz, 1H), 6.71 (d, J=3.3 Hz, 1H), 6.81 (d, J=9.9 Hz, 1H) 7.33 (d, J=9.9 Hz, 1H), 7.41 (d, J=1.8 Hz, 1H).

Reference Example 20

2-Amino-5-(1-isopropyl-6-oxo-1,6-dihydropyridazin-3-yl)-4-(2-furyl)thiazole (Compound t)

Step 1:

In a manner similar to that in Step 1 of Reference Example 19, by using 1-isopropyl-6-oxo-3-(trifluoromethanesulfonyloxy)-1,6-dihydropyridazine (2.86 g, 10.0 mmol) obtained according to the method described in WO03/039451, in place of 1-ethyl-6-oxo-3-(trifluoromethanesulfonyloxy)-1,6-dihydropyridazine, 1-(2-furyl)-2-(1-isopropyl-6-oxo-1,6-dihydropyridazin-3-yl)ethanone (961 mg, 39%) was obtained.

$^1$H NMR (CDCl$_3$, δ ppm): 1.28-1.30 (m, 6H), 4.14 (s, 2H), 5.20-5.30 (m, 1H), 6.56 (dd, J=1.8, 3.6 Hz, 1H), 6.85 (d, J=9.4 Hz, 1H), 7.17 (d, J=9.4 Hz, 1H), 7.29 (d, J=3.6 Hz, 1H), 7.61 (d, J=1.8 Hz, 1H).

Step 2:

In a manner similar to that in Reference Example 1, by using 1-(2-furyl)-2-(1-isopropyl-6-oxo-1,6-dihydropyridazin-3-yl)ethanone (960 mg, 3.90 mmol) obtained in Step 1, in place of 1-(2-furyl)-2-(4-pyridyl)ethanone, the entitled Compound t (331 mg, 28%) was obtained.

$^1$H NMR (CDCl$_3$, δ ppm): 1.36-1.39 (m, 6H), 5.27-5.36 (m, 1H), 6.49 (dd, J=1.8, 3.3 Hz, 1H), 6.69 (dd, J=0.8, 3.3 Hz, 1H), 6.82 (d, J=9.7 Hz, 1H), 7.34 (d, J=9.7 Hz, 1H), 7.44 (dd, J=0.8, 1.8 Hz, 1H).

Reference Example 21

1-Ethyl-2-oxo-1,2-dihydropyridine-5-carboxylic acid (Compound u)

Step 1:

4-Methoxybenzyl alcohol (11.9 mL, 95.2 mmol) was dissolved in DMF (150 mL), and at 0° C., 55% sodium hydride (4.15 g, 95.2 mmol) was added thereto, followed by stirring at room temperature for 1 hour. A DMF (10 mL) solution of 6-chloronicotinic acid (5.00 g, 31.7 mmol) was added to the reaction mixture, followed by stirring at 80° C. for 2 hours. Water (200 mL) was added to the reaction mixture, and 4 mol/L hydrochloric acid (30 mL) was added dropwise thereto, and the precipitated solid was collected by filtration to afford 6-(4-methoxybenzyloxy)nicotinic acid (8.15 g, 99%).

$^1$H NMR (DMSO-d$_6$, δ ppm): 3.75 (s, 3H), 5.35 (s, 2H), 6.92 (d, J=8.6 Hz, 1H), 6.94 (d, J=8.6 Hz, 2H), 7.40 (d, J=8.6 Hz, 2H), 8.15 (dd, J=2.4, 8.6 Hz, 1H), 8.74 (d, J=2.4 Hz, 1H).

Step 2:

6-(4-Methoxybenzyloxy)nicotinic acid (8.10 g, 31.2 mmol) obtained in Step 1 was dissolved in DMF (250 ml), and potassium carbonate (8.64 g, 62.5 mmol) and methyl iodide (3.89 mL, 62.5 mmol) were added thereto, followed by stirring at room temperature for 1 hour. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford methyl 6-(4-methoxybenzyloxy)nicotinate (3.78 g, 44%).

¹H NMR (CDCl₃, δ ppm): 3.81 (s, 3H), 3.91 (s, 3H), 5.37 (s, 2H), 6.78 (dd, J=0.7, 8.6 Hz, 1H), 6.91 (d, J=8.8 Hz, 2H), 7.39 (d, J=8.8 Hz, 2H), 8.15 (dd, J=2.4, 8.6 Hz, 1H), 8.84 (dd, J=0.7, 2.4 Hz, 1H).

Step 3:

Methyl 6-(4-methoxybenzyloxy)nicotinate (2.66 g, 9.73 mmol) obtained in Step 2 and anisole (10.6 mL) were dissolved in trifluoroacetic acid (15 mL), followed by stirring at room temperature for 30 minutes. The reaction mixture was concentrated under reduced pressure, and saturated sodium hydrogencarbonate was added to the resulting residue, followed by extraction with chloroform. The organic layer was dried over anhydrous magnesium sulfate, and then the solvent was distilled away under reduced pressure. The precipitated solid was collected by filtration to afford methyl 2-oxo-1,2-dihydropyridine-5-carboxylate (1.33 g, 89%).

¹H NMR (CDCl₃, δ ppm): 3.87 (s, 3H), 6.58 (dd, J=0.7, 9.5 Hz, 1H), 8.00 (dd, J=2.6, 9.5 Hz, 1H), 8.20 (dd, J=0.7, 2.6 Hz, 1H).

Step 4:

Methyl 2-oxo-1,2-dihydropyridinecarboxylate-5- (400 mg, 2.61 mmol) obtained in Step 3 was dissolved in DMF (3 mL), and 55% sodium hydride (125 mg, 2.87 mmol) and ethyl iodide (0.230 mL, 2.87 mmol) were added thereto, followed by stirring at room temperature for 2 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (ethyl acetate) to afford methyl 1-ethyl-2-oxo-1,2-dihydropyridine-5-carboxylate (375 mg, 79%).

¹H NMR (CDCl₃, δ ppm): 1.39 (t, J=7.2 Hz, 3H), 3.86 (s, 3H), 4.03 (q, J=7.2 Hz, 2H), 6.53 (d, J=9.5 Hz, 1H), 7.83 (dd, J=2.6, 9.5 Hz, 1H), 8.18 (d, J=2.6 Hz, 1H).

Step 5:

Methyl 1-ethyl-2-oxo-1,2-dihydropyridine-5-carboxylate (375 mg, 2.07 mmol) obtained in Step 4 was dissolved in a mixed solvent (1:1) (20 mL) of water and methanol, and lithium hydroxide monohydrate (191 mg, 4.55 mmol) was added thereto, followed by stirring at room temperature for 1 hour. The reaction mixture was neutralized with 3 mol/L hydrochloric acid added thereto, and the precipitated solid was collected by filtration to afford the entitled Compound u (224 mg, 65%).

¹H NMR (DMSO-d₆, δ ppm): 1.21 (t, J=7.1 Hz, 3H), 3.97 (q, J=7.1 Hz, 2H), 6.39 (d, J=9.4 Hz, 1H), 7.76 (dd, J=2.5, 9.4 Hz, 1H), 8.43 (d, J=2.5 Hz, 1H).

Reference Example 22

2-Oxo-1-(4-pyridylmethyl)-1,2-dihydropyridine-5-carboxylic acid (Compound v)

In a manner similar to that in Steps 4 and 5 of Reference Example 21, by using 4-chloromethylpyridine hydrochloride in place of ethyl iodide, the entitled Compound v (490 mg, 82%) was obtained from Methyl 2-oxo-1,2-dihydropyridine-5-carboxylate (400 mg, 2.61 mmol) obtained in Step 3 of Reference Example 21.

¹H NMR (DMSO-d₆, δ ppm): 5.16 (s, 2H), 6.30 (d, J=9.2 Hz, 1H), 7.15 (d, J=5.9 Hz, 2H), 7.89 (dd, J=2.3, 9.2 Hz, 1H), 8.15 (d, J=2.3 Hz, 1H), 8.50 (d, J=5.9 Hz, 2H).

Reference Example 23

1-Benzyl-2-oxo-1,2-dihydropyridine-4-carboxylic acid (Compound w)

Step 1:

Compound 1 (20.4 g, 84.0 mmol) obtained in Reference Example 12 was dissolved in trifluoroacetic acid (168 mL), and anisole (91.1 mL, 0.840 mol) was added thereto, followed by stirring at room temperature for 3 hours. The reaction mixture was concentrated under reduced pressure, and the resulting residue was reslurried with ethyl acetate to afford 2-oxo-1,2-dihydropyridine-4-carboxylic acid (6.99 g, 60%) as a white solid.

¹H NMR (DMSO-d₆, δ ppm): 6.51 (d, J=6.8 Hz, 1H), 6.80 (d, 1H), 7.49 (d, J=6.8 Hz, 1H).

Step 2:

2-Oxo-1,2-dihydropyridine-4-carboxylic acid (2.00 g, 14.4 mmol) obtained in Step 1 was dissolved in DMF (29 mL), and potassium carbonate (7.95 g, 57.6 mmol) and benzyl bromide (5.13 mL, 43.2 mmol) were added thereto, followed by stirring at 50° C. for 2 hours. Water was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=2:1) to afford benzyl 1-benzyl-2-oxo-1,2-dihydropyridine-4-carboxylate (1.58 g, 34%) as a white solid.

¹H NMR (CDCl₃, δ ppm): 5.14 (s, 2H), 5.31 (s, 2H), 7.23-7.41 (m, 13H).

Step 3:

Benzyl 1-benzyl-2-oxo-1,2-dihydropyridine-4-carboxylate (1.08 g, 3.38 mmol) obtained in Step 2 was dissolved in a mixed solvent of methanol (7 mL) and water (7 mL), and sodium hydroxide (0.680 g, 16.9 mmol) was added thereto, followed by stirring under heating and reflux for 30 minutes. The reaction mixture was poured into water (50 mL), and 10% hydrochloric acid was added thereto to adjust the pH to 4.5, followed by stirring at room temperature for 1 hour. The precipitated solid was collected by filtration to afford the entitled Compound w (151 mg, 20%) as a white solid.

¹H NMR (DMSO-d₆, δ ppm): 5.10 (s, 2H), 6.57 (dd, J=1.9, 7.0 Hz, 1H), 6.78 (d, J=1.9 Hz, 1H), 7.23-7.39 (m, 5H), 7.76 (d, J=7.0 Hz, 1H).

Reference Example 24

1-Methyl-2-oxo-1,2-dihydropyridine-4-carboxylic acid (Compound x)

In a manner similar to that in Steps 2 and 3 of Reference Example 23, by using methyl iodide in place of benzyl bromide, the entitled Compound x (1.20 g, 50%) was obtained as a colorless oily substance from 2-oxo-1,2-dihydropyridine-4-carboxylic acid (2.00 g, 14.4 mmol) obtained in Step 1 of Reference Example 23.

¹H NMR (CDCl₃, δ ppm): 3.55 (s, 3H), 3.89 (s, 3H), 6.64 (dd, J=1.9 Hz, 1H), 7.19 (d, J=1.9 Hz, 1H), 7.33 (d, J=7.0 Hz, 1H).

Reference Example 25

4-(2-Furyl)-5-(pyridin-2-ylcarbonyl)thiazol-2-yl isocyanate (Compound y)

Compound 186 (200 mg, 0.737 mmol) was suspended in dichloromethane (15 mL), and carbonyldiimidazole (179 mg, 1.11 mmol) was added thereto at room temperature, followed by stirring at room temperature for 2 hours. Hexane (7.5 mL) was added to the reaction mixture, and the precipitated solid was collected by filtration to afford the entitled Compound y (133 mg, 61%) as a brown solid.

Reference Example 26

2-Formyl-5-methoxypyridine (Compound z)

2-Methoxy-5-(methoxymethyl)pyridine (11.6 g, 83.5 mmol) obtained according to the method described in *Tetrahedron Asymmetry*, Vol. 12, p. 1047, 2001 was dissolved in chloroform (160 mL), and manganese dioxide (14.5 g, 167 mmol) was added thereto, followed by stirring under heating and reflux for 1 hour. The reaction mixture was filtered, and the filtrate was concentrated under reduced pressure. The resulting residue was purified through silica gel column chromatography (hexane:ethyl acetate=3:2).to afford the entitled Compound z (4.32 g, 37%) as a white solid.

$^1$H NMR (CDCl$_3$, δ ppm): 3.96 (s, 3H), 7.31 (dd, J=2.8, 8.7 Hz, 1H), 7.97 (d, J=2.8 Hz, 1H), 8.44 (d, J=8.7 Hz, 1H), 9.99 (s, 1H).

Reference Example 27

2-Amino-4-(5-methylfuran-2-yl)-5-(4-pyridyl)thiazole (Compound aa)

In a manner similar to that in Reference Example 13, by using 4-methylpyridine in place of 3,4-dimethylpyridine and using ethyl 5-methylfuran-2-carboxylate (163 mg, 1.06 mmol) in place of ethyl furan-2-carboxylate, the entitled Compound aa (80.0 mg, 30%) was obtained.

$^1$H NMR (CDCl$_3$, δ ppm): 2.28 (s, 3H), 5.28 (br s, 2H), 6.04 (d, J=3.2 Hz, 1H), 6.53 (d, J=3.2 Hz, 1H), 7.43 (d, J=6.5 Hz, 2H), 8.53 (d, J=6.2 Hz, 2H).

Reference Example 28

2-Amino-4-(3-methylfuran-2-yl)-5-(4-pyridyl)thiazole (Compound ab)

In a manner similar to that in Reference Example 13, by using 4-methylpyridine in place of 3,4-dimethylpyridine and using ethyl 3-methylfuran-2-carboxylate (572 mg, 3.71 mmol) in place of ethyl furan-2-carboxylate, the entitled Compound ab (536 mg, 71%) was obtained.

$^1$H NMR (CD$_3$OD, δ ppm): 1.81 (s, 3H), 6.28 (d, J=1.9 Hz, 1H), 6.99 (d, J=6.3 Hz, 2H), 7.35 (d, J=1.9 Hz, 1H), 8.26 (d, J=6.3 Hz, 2H).

Reference Example 29

2-Amino-4-(3-phenylfuran-2-yl)-5-(4-pyridyl)thiazole (Compound ac)

Step 1:

3-Bromofuran-2-carboxylic acid (1.86 g, 9.75 mmol), ethyl iodide (3.1 mL, 38.8 mol) and cesium carbonate (4.80 g, 14.7 mmol) were suspended in acetonitrile (50 mL), followed by stirring at 80° C. for 3 hours. Aqueous saturated sodium hydrogencarbonate solution was added to the reaction mixture, followed by extraction with ethyl acetate. The organic layer was dried over anhydrous magnesium sulfate, and then the solvent was distilled away under reduced pressure. The resulting residue was purified through silica gel column chromatography (hexane:ethyl acetate=9:1) to afford ethyl 3-bromofuran-2-carboxylate (1.16 g, 54%).

$^1$H NMR (CDCl$_3$, δ ppm): 1.40 (t, J=7.1 Hz, 3H), 4.39 (q, J=7.1 Hz, 2H), 6.59 (d, J=1.8 Hz, 1H), 7.49 (d, J=1.8 Hz, 1H).

Step 2:

Ethyl 3-bromofuran-2-carboxylate (307 mg, 1.40 mmol) obtained in Step 1, phenylboronic acid (208 mg, 1.71 mmol), dichlorobis(tri-O-tolylphosphine)palladium(II) (60.3 mg, 0.008 mmol) and potassium carbonate (387 mg, 2.80 mmol) were dissolved in a mixed solvent of toluene (13 mL), ethanol (0.65 mL) and water (1.4 mL), followed by stirring at 90° C. for 6 hours. Aqueous saturated sodium hydrogencarbonate solution was added to the reaction mixture, followed by extraction with ethyl acetate. The organic layer was washed with a saturated aqueous solution of sodium chloride and dried over anhydrous magnesium sulfate, and then the solvent was distilled away under reduced pressure. The resulting residue was purified through silica gel column chromatography (hexane:ethyl acetate=6:6) to afford ethyl 3-phenyl-2-carboxylate (290 mg, 96%).

$^1$H NMR (CDCl$_3$, δ ppm): 1.30 (t, J=7.3 Hz, 3H), 4.31 (q, J=7.3 Hz, 2H), 6.61-6.62 (m, 1H), 7.35-7.44 (m, 3H), 7.54-7.60 (m, 3H).

Step 3:

In a manner similar to that in Reference Example 13, by using 4-methylpyridine in place of 3,4-dimethylpyridine and using ethyl 3-phenyl-2-carboxylate (277 mg, 1.28 mmol) obtained in Step 2 in place of ethyl furan-2-carboxylate, 2-(3-phenylfuran-2-yl)-1-(4-pyridyl)ethanone (230 mg, 75%) was obtained.

$^1$H NMR (CDCl$_3$, δ ppm): 4.20 (s, 2H), 6.71-6.72 (m, 1H), 7.23 (d, J=6.0 Hz, 2H), 7.37-7.44 (m, 3H), 7.61-7.65 (m, 3H), 8.54 (d, J=6.0 Hz, 2H).

Step 4:

In a manner similar to that in Reference Example 1, by using 1-(2-furyl)-2-(3-phenylfuran-2-yl)ethanone (292 mg, 0.850 mmol) obtained in Step 3 in place of 1-(2-furyl)-2-(4-pyridyl)ethanone, the entitled Compound ac (22.5 mg, 8%) was obtained.

$^1$H NMR (CD$_3$OD, δ ppm): 5.47 (br s, 2H), 6.64 (d, J=1.9 Hz, 1H), 6.84 (d, J=6.2 Hz, 2H), 7.11-7.22 (m, 5H), 7.51 (d, J=1.9 Hz, 1H), 8.28 (d, J=5.9 Hz, 2H).

Reference Example 30

2-Amino-5-(4-pyridyl)-4-[3-(4-pyridyl)furan-2-yl]thiazole (Compound ad)

Step 1:

Ethyl 3-bromofuran-2-carboxylate (296 mg, 1.35 mmol) obtained in Step 1 of Reference Example 29, 4-(tri-n-butylstannyl)pyridine (550 mg, 1.51 mmol) and tetrakis(triphenylphosphine)palladium(0) (157 mg, 0.136 mmol) were dissolved in THF (10 mL), followed by stirring under heating and reflux for 4 hours. Aqueous ammonium fluoride solution was added to the reaction mixture, followed by extraction with ethyl acetate. The organic layer was dried over anhydrous magnesium sulfate, and then the solvent was distilled away under reduced pressure. The resulting residue was purified through silica gel column chromatography (hexane:ethyl acetate=2:3) to afford ethyl 3-(4-pyridyl)furan-2-carboxylate (133 mg, 45%).

$^1$H NMR (CDCl$_3$, δ ppm): 1.33 (t, J=7.2 Hz, 3H), 4.34 (q, J=7.2 Hz, 2H), 6.66 (d, J=1.8 Hz, 1H), 7.51 (d, J=6.2 Hz, 2H), 7.63 (d, J=1.8 Hz, 1H), 8.66 (d, J=6.2 Hz, 2H).

Step 2:

In a manner similar to that in Reference Example 13, by using 4-methylpyridine in place of 3,4-dimethylpyridine and using ethyl 3-(4-pyridyl)furan-2-carboxylate (133 mg, 0.612 mmol) obtained in Step 1, in place of ethyl furan-2-carboxylate, the entitled Compound ad (35.3 mg, 18%) was obtained.

$^1$H NMR (CDCl$_3$, δ ppm): 5.21 (br s, 2H), 6.69 (d, J=1.9 Hz, 1H), 6.87 (d, J=6.1 Hz, 2H), 7.18-7.21 (m, 2H), 7.55 (d, J=1.9 Hz, 1H), 8.36 (d, J=6.1 Hz, 2H), 8.43 (d, J=6.1 Hz, 2H).

Reference Example 31

2-Amino-4-(3-furyl)-5-(4-pyridyl)thiazole (Compound ae)

In a manner similar to that in Reference Example 13, by using 4-methylpyridine in place of 3,4-dimethylpyridine, the entitled Compound ae (216 mg, 25%) was obtained from ethyl 3-furan-2-carboxylate (502 mg, 3.58 mmol).

$^1$H NMR (CD$_3$OD, δ ppm): 6.38 (d, J=2.8 Hz, 1H), 7.36 (d, J=6.3 Hz, 2H), 7.50 (dd, J=2.3, 2.8 Hz, 1H), 7.67 (d, J=2.3 Hz, 1H), 8.41 (d, J=6.3 Hz, 2H).

Reference Example 32 tert-Butyl N-[5-bromo-4-(3-furyl)thiazol-2-yl]carbamate (Compound af)

In a manner similar to that in Reference Example 7, by using 3-acetylfuran (1.00 g, 8.82 mmol) in place of 2-acetylfuran, 2-amino-5-bromo-4-(3-furyl)thiazole was obtained. In a manner similar to that in Reference Example 8, the entitled Compound af (845 mg, 28%) was obtained from 2-amino-5-bromo-4-(3-furyl)thiazole in place of 2-amino-5-bromo-4-(2-furyl)thiazole.

$^1$H NMR (CDCl$_3$, δ ppm): 1.54 (s, 9H), 6.97 (dd, J=0.9, 1.7 Hz, 1H), 7.46 (dd, J=1.7, 1.7 Hz, 1H), 8.07 (0.9, 1.7 Hz, 1H).

Preparation Example 1

Tablets (Compound 1)

In an ordinary method, tablets having the composition mentioned below were prepared. Compound 1 (40 g), lactose (286.8 g) and potato starch (60 g) were mixed, and 10% aqueous solution (120 g) of hydroxypropyl cellulose was added thereto. The mixture was kneaded in an ordinary manner, granulated and dried, and dressed to give granules for tabletting. Magnesium stearate (1.2 g) was added thereto and mixed, and tabletted, using a tabletting machine with a pestle having a diameter of 8 mm (Kikusui-sha's RT-15 Model), into tablets (containing 20 mg/tablet of the active ingredient).

Formulation:

| | |
|---|---|
| Compound 1 | 20 mg |
| Lactose | 143.4 mg |
| Potato starch | 30 mg |
| Hydroxypropyl cellulose | 6 mg |
| Magnesium stearate | 0.6 mg |
| | 200 mg |

Preparation Example 2

Tablets (Compound 86)

In a manner similar to that in Preparation Example 1, by using Compound 86 (40 g), the entitled tablets (containing 20 mg/tablet of the active ingredient) were prepared.

Formulation:

| | |
|---|---|
| Compound 86 | 20 mg |
| Lactose | 143.4 mg |
| Potato starch | 30 mg |
| Hydroxypropyl cellulose | 6 mg |
| Magnesium stearate | 0.6 mg |
| | 200 mg |

Preparation Example 3

Injection Preparation (Compound 99)

In an ordinary method, an injection preparation having the composition mentioned below was prepared. Compound 99 (1 g) and D-mannitol (5 g) were added to distilled water for injection, and hydrochloric acid and aqueous sodium hydroxide solution were added thereto to adjust the pH to 6. Then distilled water for injection was added thereto to be 1000 mL in total. In a germ-free condition, the resulting mixture was filled into glass vials in an amount of 2 mL/vial to prepare injection vials (containing 2 mg/vial of the active ingredient).

Formulation:

| | |
|---|---|
| Compound 99 | 2 mg |
| D-mannitol | 10 mg |
| Hydrochloric acid | ad lib. |
| Aqueous sodium hydroxide solution | ad lib. |
| Distilled water for injection | ad lib. |
| | 2.00 mL |

INDUSTRIAL APPLICABILITY

The present invention provides adenosine $A_{2A}$ receptor antagonists comprising a thiazole derivative or a pharmaceutically acceptable salt thereof as the active ingredient; thiazole derivatives or pharmaceutically acceptable salts thereof which have an adenosine $A_{2A}$ receptor antagonism and are useful for agents for preventing and/or treating diseases associated with adenosine $A_{2A}$ receptor; and the like.

The invention claimed is:

1. A thiazole derivative represented by formula (IA):

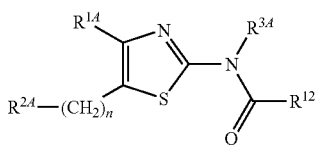

wherein
- $R^{1A}$ represents a 5-membered aromatic heterocyclic group containing at least one oxygen atom;
- n represents an integer of from 0 to 3;
- $R^{12}$ represents substituted or unsubstituted cycloalkyl, substituted or unsubstituted aryl, substituted or unsubstituted aralkyl, a substituted or unsubstituted alicyclic heterocyclic group, a substituted or unsubstituted aromatic heterocyclic group, substituted or unsubstituted alicyclic heterocyclic-alkyl, or substituted or unsubstituted aromatic heterocyclic-alkyl;
- $R^{3A}$ represents a hydrogen atom, or substituted or unsubstituted lower alkyl; and
- $R^{2A}$ represents —$COR^8$ (wherein $R^8$ represents a substituted or unsubstituted aromatic heterocyclic group);

or a pharmaceutically acceptable salt thereof.

2. The thiazole derivative according to claim 1, wherein $R^{1A}$ is substituted or unsubstituted furyl, or a pharmaceutically acceptable salt thereof.

3. The thiazole derivative according to claim 1, wherein n is 0, or a pharmaceutically acceptable salt thereof.

4. The thiazole derivative according to claim 1, wherein $R^{3A}$ is a hydrogen atom, or a pharmaceutically acceptable salt thereof.

5. The thiazole derivative according to claim 1, wherein $R^{3A}$ is lower alkyl, or a pharmaceutically acceptable salt thereof.

6. The thiazole derivative according to claim 1, wherein $R^{1A}$ is furyl, or a pharmaceutically acceptable salt thereof.

7. The thiazole derivative according to claim 6, wherein n is 0, or a pharmaceutically acceptable salt thereof.

8. The thiazole derivative according to claim 7, wherein $R^{3A}$ is a hydrogen atom, or a pharmaceutically acceptable salt thereof.

9. The thiazole derivative according to claim 8, wherein $R^{12}$ is substituted or unsubstituted phenyl, or said substituted or unsubstituted aromatic heterocyclic group, or a pharmaceutically acceptable salt thereof.

10. The thiazole derivative according to claim 8, wherein $R^{12}$ is substituted or unsubstituted alicyclic heterocyclic-methyl, or a pharmaceutically acceptable salt thereof.

11. The thiazole derivative according to claim 8, wherein $R^{12}$ is substituted or unsubstituted aromatic heterocyclic group, or a pharmaceutically acceptable salt thereof.

12. The thiazole derivative according to claim 9, wherein $R^8$ is pyridyl, or a pharmaceutically acceptable salt thereof.

13. The thiazole derivative according to claim 10, wherein $R^8$ is pyridyl, or a pharmaceutically acceptable salt thereof.

14. The thiazole derivative according to claim 11, wherein $R^8$ is pyridyl, or a pharmaceutically acceptable salt thereof.

15. A thiazole derivative represented by any of the following formulae (206), (228), (234) or (348), or a pharmaceutically acceptable salt thereof

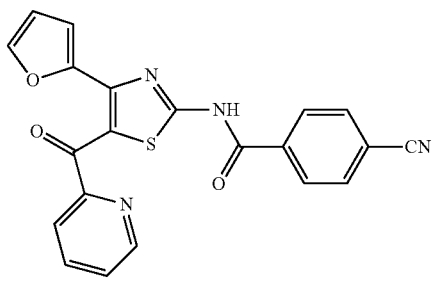

206

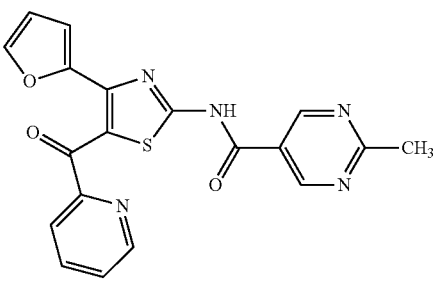

228

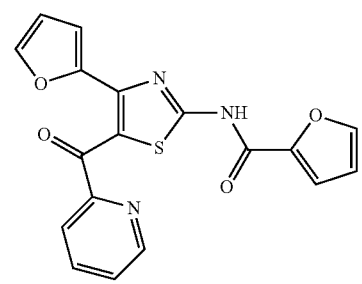

234

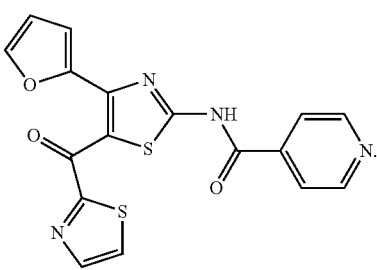

348

* * * * *

UNITED STATES PATENT AND TRADEMARK OFFICE
CERTIFICATE OF CORRECTION

PATENT NO. : 7,880,013 B2
APPLICATION NO. : 12/766986
DATED : February 1, 2011
INVENTOR(S) : Takao Nakajima et al.

It is certified that error appears in the above-identified patent and that said Letters Patent is hereby corrected as shown below:

ON COVER PAGE AT (57) ABSTRACT

Line 1, "(Wherein" should read --Provided are adenosine $A_{2A}$ receptor antagonists comprising, as the active ingredient, a thiazole derivative represented by a general formula (I), or a pharmaceutically acceptable salt thereof, and the like.

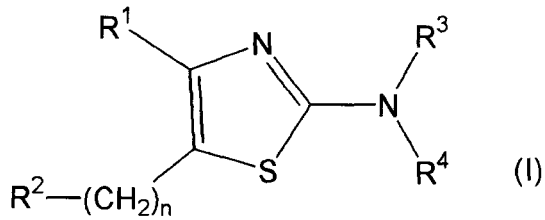

(wherein n--; and

Lines 12-16, delete "For example, provided are adenosine $A_{2A}$ receptor antagonists comprising, as the active ingredient, a thiazole derivative represented by a general formula (I), or a pharmaceutically acceptable salt thereof, and the like.

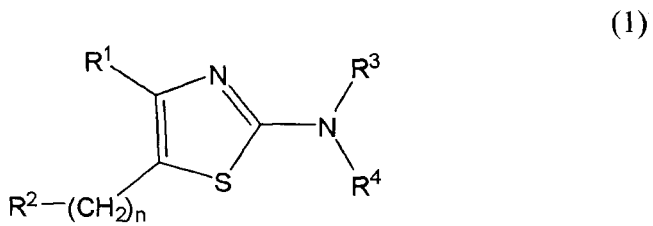

".

COLUMN 2

Line 27, "represented" should read --represented by--.

Signed and Sealed this
Twenty-third Day of August, 2011

David J. Kappos
*Director of the United States Patent and Trademark Office*

COLUMN 3

Line 27, "substituted" should read --¶ substituted--.

COLUMN 9

Line 11, "have" should read --has--.

COLUMN 11

Line 46, "—COR$^{12A}$")" should read -- —COR$^{12A}$"),--.

COLUMN 12

Line 13, "(-52)" should read --(52)--, and
Line 36, "NR$^{13}$R$^{14}$" should read -- —NR$^{13}$R$^{14}$--.

COLUMN 13

Line 1, "derivatives" should read --derivative--.

COLUMN 19

Line 38, "alkanoyl the" should read --alkanoyl, the--; and
Line 43, "alkoxycarbonyl the" should read --alkoxycarbonyl, the--.

COLUMN 20

Line 6, "aromatic the" should read --aromatic--.

COLUMN 21

Line 3, "(1999)] If" should read --(1999)]. If--.

COLUMN 23

Line 52, "eridine;" should read --eridine,--.

COLUMN 29

Line 15, "R$^{1a}$" should read --R$^{4a}$--.

COLUMN 30

Line 1, "R$^{1}$, R$^{3}$, R$^{4}$, R$^{3}$" should read --R$^{1}$, R$^{3}$, R$^{4}$, R$^{8b}$--.

COLUMN 31

Line 37, "1,2-dimethoxyethanea" should read --1,2-dimethoxyethane--.

COLUMN 32

Line 43, "more can be used a" should read --more in a mixture.--; and
Line 44, "mixture with" should be deleted.

COLUMN 41

Compound No. 43,

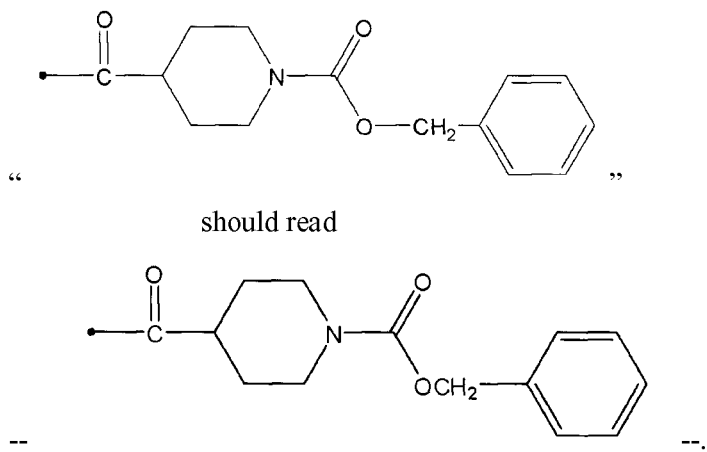

should read --.

COLUMN 162

Line 21, "adopt" should read --adapt--;
Line 24, "orally" should read --oral--; and
Line 25, "As," should read --As--.

COLUMN 169

Line 45, "6.74;" should read --6.74.--.

COLUMN 170

Line 32, "N-(5-(Ethoxycarbonyl)-" should read --N-[5-(Ethoxycarbonyl)- --.

COLUMN 174

Line 19, "6-chlo-" should read --6-(chlo- --;
Line 20, "romethylnicotinic acid" should read --romethyl)nicotinic acid--;
Line 25, "6-Chloromethylnicotinic acid" should read --6-(Chloromethyl)nicotinic acid--;

Line 26, "Step 1,2-amino-4-" should read --Step 1, 2-amino-4- --; and
Line 66, "9.09 (d, J=2.2 Hz, 1H)" should read --9.09 (d, J=2.2 Hz, 1H).--.

COLUMN 175

Line 31, "(48.8 mmol, 0.400 mmol)" should read --(48.8 mg, 0.400 mmol)--; and
Line 35, "(1.05.g, 66%)" should read --(1.05 g, 66%).--.

COLUMN 176

Line 59, "by 178," should read --by--.

COLUMN 180

Line 49, "2.41-2.8.5 (m, 1H)," should read --2.41-2.85 (m, 1H),--.

COLUMN 181

Line 26, "-2-yl]-1-mor-" should read -- -2-yl]-1-(mor- --; and
Line 27, "pholinocarbonylpiperidine-4-" should read --pholinocarbonyl)piperidine-4- --.

COLUMN 182

Line 14, "4-Bromomethyl-N-" should read --4-(Bromomethyl)-N- --; and
Line 18, "4-Bromomethylbenzoic acid" should read --4-(Bromomethyl)benzoic acid--.

COLUMN 184

Line 22, "(629 mg. 27%)." should read --(629 mg, 27%).--; and
Line 66, "(br s, 1H)" should read --(br s, 1H).--.

COLUMN 186

Line 7, "10.2 (br-s, 1H)." should read --10.2 (br s, 1H).--;
Line 30, "(752 mg, 76-%)" should read --752 mg, 76%)--; and
Line 66, "8.67 (d, J=6.1 Hz, 2H)" should read --8.67 (d, J=6.1 Hz, 2H).--.

COLUMN 189

Line 22, "-2-amino-" should read --2-amino- --;
Line 39, "Compound 79;" should read --Compound 79--; and
Line 45, "10.9 (br-s," should read --10.9 (br s,--.

COLUMN 191

Line 48, "1H)" should read --1H).--.

COLUMN 192

Line 33, "N-[4-(2-Furyl)-" should read --N-{4-(2-Furyl)- --; and
Line 34, "-2yl]pyridine-4-" should read -- -2yl}pyridine-4- --.

COLUMN 197

Line 17, "APCIMS m/z;" should read --APCIMS m/z:--.

COLUMN 200

Line 27, "Compound 114" should read --Compound 115--;
Line 42, "Compound 115" should read --Compound 116--; and
Line 45, "$^1$H NMR," should read --$^1$H NMR--.

COLUMN 204

Line 46, "Compound 111" should read --Compound 126--.

COLUMN 205

Line 3, "7.34 (dd, J=2.6, 9.4 Hz, 1H)" should read --7.34 (dd, J=2.6, 9.4 Hz, 1H).--.

COLUMN 206

Line 25, "8.88 (dd, J=1.6, 4.6 Hz, 2H)" should read --8.88 (dd, J=1.6, 4.6 Hz, 2H).--.

COLUMN 207

Line 38, "dimethylhydroxyamine" should read --dimethylhydroxylamine--.

COLUMN 209

Line 46, "2-Chloromethyl-5-" should read --2-(Chloromethyl)-5- --; and
Line 50, "2-chloromethylisonicotinic" should read --2-(chloromethyl)isonicotinic--.

COLUMN 213

Line 2, "Compound-136" should read --Compound 136--.

COLUMN 215

Line 16, "(180 mg, 0.468 mmol" should read --(180 mg, 0.468 mmol)--.

COLUMN 218

Line 66, "s, 1H)" should read --s, 1H).--.

COLUMN 219

Line 15, "13.63 (br s, 1H)" should read --13.63 (br s, 1H).--.

COLUMN 224

Line 31, "7.48 (dd, J=4.9, 7.6 Hz; 1H)," should read --7.48 (dd, J=4.9, 7.6 Hz, 1H),--.

COLUMN 235

Line 56, "Synthesis," should read --*Synthesis*,--.

COLUMN 236

Line 34, "δ 8.68-8.77 (m," should read --8.68-8.77 (m,--.

COLUMN 240

Line 62, "Tetrahedron Letters," should read --*Tetrahedron Letters*,--.

COLUMN 246

Line 65, "Compound" should read --Compound 267--.

COLUMN 247

Line 8, "6.65 (dd, J=1.6, 3.5 Hz, —1H)," should read --6.65 (dd, J=1.6, 3.5 Hz, 1H),--; and
Line 22, "Compound" should read --Compound 268--.

COLUMN 249

Line 49, "3.21° (m, 4H)," should read --3.21 (m, 4H),--.

COLUMN 250

Line 62, "Compound" should read --Compound 280--.

COLUMN 253

Line 38, "Compound 290" should read --Compound 289--; and
Line 57, "Compound 289" should read --Compound 290--.

COLUMN 260

Line 39, "52.%)" should read --52%)--.

COLUMN 261

Line 66, "7.34 (dd, 0.5, 8.1 Hz, 1H)," should read --7.34 (dd, J=0.5, 8.1 Hz, 1H),--.

COLUMN 267

Line 7, "-5-yl2-furyl" should read -- -5-yl 2-furyl--.

COLUMN 271

Line 54, "6.14 (dd, J=0.5, 3.2 Hz," should read --6.74 (dd, J=0.5, 3.2 Hz,--.

COLUMN 272

Line 47, "8.85 (dd, J=1.6, 4.4 Hz 2H)," should read --8.85 (dd, J=1.6, 4.4 Hz, 2H),--.

COLUMN 273

Line 9, "crude." should read --crude--.

COLUMN 274

Line 12, "6.49 (dd, J=1.6, 3.2.Hz, 1H)," should read --6.49 (dd, J=1.6, 3.2 Hz, 1H),--;
Line 14, "(br s, 2H)" should read --(br s, 2H).--; and
Line 50, "8.22 (br s, 2H)" should read --8.22 (br s, 2H).--.

COLUMN 276

Line 57, "8.90 (br s, 1H)" should read --8.90 (br s, 1H).--.

COLUMN 277

Line 2, "8.75 (br s, 2H)" should read --8.75 (br s, 2H).--; and
Line 14, "7.81 (dd, J=0.8, 3.5 Hz; 1H)," should read --7.81 (dd, J=0.8, 3.5 Hz, 1H),--.

COLUMN 279

Line 57, "Compound." should read --Compound 389.--.

COLUMN 281

Line 44, "7.4 6 (dd, J=0.8, 1.8 Hz, 1H)." should read --7.46 (dd, J=0.8, 1.8 Hz, 1H).--.

COLUMN 282

Line 9, "(Compound 403)" should read --(Compound 398)--.

COLUMN 286

Line 57, "dried," should read --dried--.

COLUMN 288

Line 44, "(Compound 442)" should read --Compound (424)--.

COLUMN 290

Line 13, "7$^1$H NMR (CDCL$_3$, δ ppm):" should read -- $^1$H NMR (CDCL$_3$, δ ppm):--.

COLUMN 294

Line 54, "dissolved" should read --was dissolved--.

COLUMN 302

Line 67, "336 (ddd, J=2.4, 11.3, 11.3 Hz, 2H)," should read --3.36 (ddd, J=2.4, 11.3, 11.3 Hz, 2H),--.

COLUMN 305

Line 1, "2H); 6.71" should read --2H), 6.71--.

COLUMN 316

Line 39, "Step 3," should read --Step 2,--; and
Line 66, "13.63 (br s, 1H)" should read --13.63 (br s, 1H).--.

COLUMN 319

Line 46, "7.91 (d, J=1.6 Hz, 1H)" should read --7.91 (d, J=1.6 Hz, 1H),--.

COLUMN 325

Line 1, "di-methylamine" should read --dimethylamine--; and
Line 30, "[Compound 542]" should read --¶Example 542--.

COLUMN 329

Line 15, "(122 mg; 88%)" should read --(122 mg, 88%)--.

COLUMN 334

Line 28, "Example 5701" should read --Example 570--.

COLUMN 335

Line 35, "(120.mg," should read --(120 mg,--.

COLUMN 339

Line 8, "7.68 (dd; J=0.8, 1.8 Hz," should read --7.68 (dd, J=0.8, 1.8 Hz,--.

COLUMN 344

Line 2, "$^1$H NMR (CD$_3$OD, δ ppm):" should read --¶$^1$H NMR (CD$_3$OD, δ ppm):--.

COLUMN 347

Line 8, "8.67," should read --8.67--.

COLUMN 350

Line 65, "1N-[4-(2-furyl)-" should read --N-[4-(2-furyl)- --.

COLUMN 351

Line 48, "3.40 ddd, J=1.6, 11.6, 11.6 Hz 2H)," should read --3.40 (ddd, J=1.6, 11.6, 11.6 Hz, 2H),--; and
Line 49, "br s, 1H)," should read --(br s, 1H),--.

COLUMN 354

Line 52, "(1.21 g, 60" should read --(1.21 g, 60%).--; and
Line 66, "froylacetate" should read --furylacetate--.

COLUMN 355

Line 13, "furyl)propanoe" should read --furyl)propanone--;
Line 17, "7.43 (dd, J=0.7, 1.8 Hz, 1H" should read --7.43 (dd, J=0.7, 1.8 Hz, 1H).--; and
Line 26, "(5.1 g, 4.6.0 mmol)" should read --(5.1 g, 46.0 mmol)--.

COLUMN 357

Line 1, "adjust" should read --to adjust--.

COLUMN 358

Line 67, "1.8 Hz, 1H)" should read --1.8 Hz, 1H).--.

COLUMN 361

Line 17, "Reference Example 15," should read --in Reference Example 15,--.

COLUMN 363

Line 22, "Methyl 2-oxo-1,2-dihydropyridinecarboxylate-5-" should read --Methyl 2-oxo-1,2-dihydropyridine-5-carboxylate--.

COLUMN 365

Line 42, "7.43 (d, J= = 6.5" should read --7.43 (d, J=6.5--.